US009388510B2

(12) United States Patent
Ladner

(10) Patent No.: US 9,388,510 B2
(45) Date of Patent: Jul. 12, 2016

(54) LIBRARIES OF GENETIC PACKAGES COMPRISING NOVEL HC CDR1, CDR2, AND CDR3 AND NOVEL LC CDR1, CDR2, AND CDR3 DESIGNS

(75) Inventor: Robert C. Ladner, Ijamsville, MD (US)

(73) Assignee: Dyax Corp., Burlington, MA (US)

( * ) Notice: Subject to any disclaimer, the term of this patent is extended or adjusted under 35 U.S.C. 154(b) by 621 days.

(21) Appl. No.: 12/989,307

(22) PCT Filed: Apr. 24, 2009

(86) PCT No.: PCT/US2009/041688
§ 371 (c)(1),
(2), (4) Date: Mar. 10, 2011

(87) PCT Pub. No.: WO2009/132287
PCT Pub. Date: Oct. 29, 2009

(65) Prior Publication Data
US 2011/0172125 A1    Jul. 14, 2011

Related U.S. Application Data

(60) Provisional application No. 61/047,529, filed on Apr. 24, 2008.

(51) Int. Cl.
*C40B 40/08* (2006.01)
*C40B 40/02* (2006.01)
*C07K 16/00* (2006.01)

(52) U.S. Cl.
CPC .............. *C40B 40/02* (2013.01); *C07K 16/005* (2013.01); *C07K 2317/565* (2013.01); *C40B 40/08* (2013.01)

(58) Field of Classification Search
None
See application file for complete search history.

(56) References Cited

U.S. PATENT DOCUMENTS

| | | | |
|---|---|---|---|
| 5,118,605 A | 6/1992 | Urdea | |
| 5,223,409 A | 6/1993 | Ladner et al. | |
| 5,380,833 A | 1/1995 | Urdea | |
| 5,565,332 A | 10/1996 | Hoogenboom et al. | |
| 5,618,920 A | 4/1997 | Robinson et al. | |
| 5,641,640 A | 6/1997 | Hanning | |
| 5,658,727 A | 8/1997 | Barbas et al. | |
| 5,688,666 A | 11/1997 | Bass et al. | |
| 5,723,323 A | 3/1998 | Kauffman et al. | |
| 5,733,743 A | 3/1998 | Johnson et al. | |
| 5,739,281 A | 4/1998 | Thøgersen et al. | |
| 5,750,373 A | 5/1998 | Garrard et al. | |
| 5,780,279 A | 7/1998 | Matthews et al. | |
| 5,798,208 A | 8/1998 | Crea | |
| 5,814,476 A | 9/1998 | Kauffman et al. | |
| 5,817,483 A | 10/1998 | Kauffman et al. | |
| 5,821,047 A | 10/1998 | Garrard et al. | |
| 5,824,514 A | 10/1998 | Kauffman et al. | |
| 5,830,663 A | 11/1998 | Embleton et al. | |
| 5,837,242 A | 11/1998 | Holliger et al. | |
| 5,840,479 A | 11/1998 | Little et al. | |
| 5,846,765 A | 12/1998 | Matthews et al. | |
| 5,858,657 A | 1/1999 | Winter et al. | |
| 5,858,671 A | 1/1999 | Jones | |
| 5,871,907 A | 2/1999 | Winter et al. | |
| 5,872,215 A | 2/1999 | Osbourne et al. | |
| 5,874,214 A | 2/1999 | Nova et al. | |
| 5,885,793 A | 3/1999 | Griffiths et al. | |
| 5,917,018 A | 6/1999 | Thogersen et al. | |
| 5,935,831 A | 8/1999 | Quax et al. | |
| 5,962,255 A | 10/1999 | Griffiths et al. | |
| 5,969,108 A | 10/1999 | McCafferty et al. | |
| 5,976,862 A | 11/1999 | Kauffman et al. | |
| 5,994,519 A | 11/1999 | Osbourn et al. | |
| 6,010,884 A | 1/2000 | Griffiths et al. | |
| 6,017,732 A | 1/2000 | Jespers et al. | |
| 6,040,136 A | 3/2000 | Garrard et al. | |
| 6,057,098 A | 5/2000 | Buechler et al. | |
| 6,140,471 A | 10/2000 | Johnson et al. | |
| 6,172,197 B1 | 1/2001 | McCafferty et al. | |
| 6,180,336 B1 | 1/2001 | Osbourn et al. | |
| 6,207,446 B1 | 3/2001 | Szostak et al. | |
| 6,225,447 B1 | 5/2001 | Winter et al. | |
| 6,248,516 B1 | 6/2001 | Winter et al. | |
| 6,291,158 B1 | 9/2001 | Winter et al. | |
| 6,291,159 B1 | 9/2001 | Winter et al. | |
| 6,291,160 B1 | 9/2001 | Lerner et al. | |
| 6,291,161 B1 | 9/2001 | Lerner et al. | |
| 6,291,650 B1 | 9/2001 | Winter et al. | |

(Continued)

FOREIGN PATENT DOCUMENTS

| | | | |
|---|---|---|---|
| DE | 19624562 A1 | 1/1998 | |
| WO | 94/07922 A1 | 4/1994 | |

(Continued)

OTHER PUBLICATIONS

Rickles et al. (Nov. 1995) Proceedings of the National Academy of Sciences USA vol. 92 pp. 10909 to 10913.*
Alves et al., "Accuracy of the EcoRV restriction endonuclease: binding and cleavage studies with oligodeoxynucleotide substrates containing degenerate recognition sequences," Biochemistry, 34(35):11191-11197 (1995).
Arden, "Conserved motifs in T-cell receptor CDR1 and CDR2: implications for ligand and CD8 co-receptor binding" Current Opinion in Immunology, Current Biology LTD., 10(1):74-81, 1998, XP004313624.
Aujame et al., "High affinity human antibodies by phage display," Human Antibodies, 8(4): 155-168, 1997.

(Continued)

*Primary Examiner* — Christian Boesen
(74) *Attorney, Agent, or Firm* — Wolf, Greenfield & Sacks, P.C.

(57) ABSTRACT

Provided are compositions and methods for preparing and identifying antibodies having CDR3s that vary in sequence and in length from very short to very long which in certain embodiments may bind to a carbohydrate moiety or the active site of an enzyme. Libraries coding for antibodies with the CDR3s are also provided. The libraries can be provided by modifying a pre-existing nucleic acid library.

25 Claims, No Drawings

(56) References Cited

U.S. PATENT DOCUMENTS

| | | | |
|---|---|---|---|
| 6,300,064 | B1 | 10/2001 | Knappik et al. |
| 6,319,690 | B1 | 11/2001 | Little et al. |
| 6,342,588 | B1 | 1/2002 | Osbourn et al. |
| 6,420,113 | B1 | 7/2002 | Buechler et al. |
| 6,489,123 | B2 | 12/2002 | Osbourn et al. |
| 6,492,107 | B1 | 12/2002 | Kauffman et al. |
| 6,492,123 | B1 | 12/2002 | Holliger et al. |
| 6,492,160 | B1 | 12/2002 | Griffiths et al. |
| 6,521,404 | B1 | 2/2003 | Griffiths et al. |
| 6,531,580 | B1 | 3/2003 | Huse et al. |
| 6,544,731 | B1 | 4/2003 | Griffiths et al. |
| 6,545,142 | B1 | 4/2003 | Winter et al. |
| 6,555,313 | B1 | 4/2003 | Griffiths et al. |
| 6,569,641 | B1 | 5/2003 | Kauffman et al. |
| 6,582,915 | B1 | 6/2003 | Griffiths et al. |
| 6,589,527 | B1 | 7/2003 | Winter et al. |
| 6,593,081 | B1 | 7/2003 | Griffiths et al. |
| 6,680,192 | B1 | 1/2004 | Lerner et al. |
| 6,696,245 | B2 | 2/2004 | Winter et al. |
| 6,696,248 | B1 | 2/2004 | Knappik et al. |
| 6,706,484 | B1 | 3/2004 | Knappik et al. |
| 6,753,136 | B2 | 6/2004 | Lohning |
| 6,806,079 | B1 | 10/2004 | McCafferty et al. |
| 6,828,422 | B1 | 12/2004 | Achim et al. |
| 6,846,634 | B1 | 1/2005 | Tomlinson et al. |
| 6,916,605 | B1 | 7/2005 | McCafferty et al. |
| 6,969,586 | B1 | 11/2005 | Lerner et al. |
| 7,063,943 | B1 | 6/2006 | McCafferty et al. |
| 7,189,841 | B2 | 3/2007 | Lerner et al. |
| 2002/0004215 | A1 | 1/2002 | Osbourn et al. |
| 2003/0114659 | A1 | 6/2003 | Winter et al. |
| 2003/0130496 | A1 | 7/2003 | Winter et al. |
| 2003/0148372 | A1 | 8/2003 | Tomlinson et al. |
| 2003/0190674 | A1 | 10/2003 | Griffiths et al. |
| 2003/0224408 | A1 | 12/2003 | Hoogenboom et al. |
| 2003/0232333 | A1 | 12/2003 | Ladner et al. |
| 2004/0038921 | A1 | 2/2004 | Kreutzer et al. |
| 2004/0110941 | A2 | 6/2004 | Winter et al. |
| 2004/0157214 | A1 | 8/2004 | McCafferty et al. |
| 2004/0157215 | A1 | 8/2004 | McCafferty et al. |
| 2005/0119455 | A1 | 6/2005 | Fuh et al. |
| 2005/0202512 | A1 | 9/2005 | Tomlinson et al. |
| 2006/0003334 | A1 | 1/2006 | Achim et al. |
| 2006/0019260 | A1 | 1/2006 | Lerner et al. |
| 2006/0166252 | A1 | 7/2006 | Ladner et al. |
| 2006/0234302 | A1* | 10/2006 | Hoet et al. ............... 435/7.1 |
| 2006/0257937 | A1 | 11/2006 | Ladner |
| 2007/0031879 | A1 | 2/2007 | Ley et al. |
| 2009/0088346 | A1 | 4/2009 | Enzelberger et al. |
| 2009/0181855 | A1 | 7/2009 | Vasquez et al. |

FOREIGN PATENT DOCUMENTS

| | | | |
|---|---|---|---|
| WO | 9708320 | A1 | 3/1997 |
| WO | 97/20923 | A1 | 6/1997 |
| WO | 97/49809 | A1 | 12/1997 |
| WO | 99/06834 | A2 | 2/1999 |
| WO | 99/51773 | A1 | 10/1999 |
| WO | 9955367 | A1 | 11/1999 |
| WO | 00/18905 | A1 | 4/2000 |
| WO | 01/40803 | A1 | 6/2001 |
| WO | 01/79481 | A2 | 10/2001 |
| WO | 03/029456 | A1 | 4/2003 |
| WO | WO 2006/084050 | | 8/2006 |
| WO | 2008053275 | A2 | 5/2008 |

OTHER PUBLICATIONS

Balint et al., "Antibody engineering by parsimonious mutagenesis," Gene, 1993, vol. 137, pp. 109-118.
Barbas et al. "Semisynthetic combinatorial antibody libraries: a chemical solution to the diversity problem," Proc. Natl. Acad. Sci. USA, 89:4457-4461 (1992).
Barbas et al., "Human Autoantibody Recognition of DNA" Proc. Natl. Acad. Sci. 92:2529-2533, 1995, XP002927212.
Barbas, C.F., "Assembly of Combinatorial antibody libraries on phage surfaces: The gene III site", Proc. Natl. Acad. Sci., vol. 88, pp. 7978-7982, Sep. 1991.
Blakesley et al., "Duplex Regions in "Single-Stranded" øX174 DNA Are Cleaved by a Restriction Endonuclease from Haemophilus Aegyptius," The Journal of Biological Chemistry, 252:7300-7306 (1977).
Brezinschek, Journal of Clinical Investigation, 99:2488-2501 (1997).
Chothia et al., Structural Repertoire of the Human VH Segments, J. Mol. Biol. (1992) 227:799-817.
Clackson, T., "In Vitro Selection from Protein and Peptide Libraries," Elsevier Science Ltd. vol. 12, pp. 173-184, May 1, 1994.
Coco et al., "DNA shuffling method for generating highly recombined genes and evolved enzymes," Nature Biotechnology (2001) 19:354-359.
Cook et al., "The human immunoglobulin VH repertoire," Immunology Today (1995) 16(5):237-242.
Corbett et al., "Sequence of the human immunoglobulin diversity (D) segment locus: a systematic analysis provides no evidence for the use of DIR segments, inverted D segments, "minor" D segments or D-D recombination," J. Mol. Biol. 270(4):587-597 (1997).
Courtney, B.C., "A phage display vector with improved stability, applicability and ease of manipulation," Gene, vol. 165, No. 1, pp. 139-140, Nov. 7, 1995.
Davies et al., "Affinity improvement of single antibody VH domains: residues in all three hypervariable regions affect antigen binding," Immunotechnology 2(3):169-179, 1996, XP004070292.
De Haard et al., "A Large Non-immunized Human Fab Fragment Phage Library That Permits Rapid Isolation and Kinetic Analysis of High Affinity Antibodies," Journal of Biological Chemistry, 274(26):18218-18230, 1999, XP002128301.
De Wildt et al., "Antibody arrays for high-throughput screening of antibody-antigen interactions," Nature Biotechnology (2000) 18:989-994.
De Wildt et al., Eur. J. Immunol. (1996) 26(3):629-39.
Extended European Search Report dated May 26, 2010 from European Application No. 10156326.0.
Fan, Z-C, "Three-dimensional structure of an Fv from a Human IgM Immunoglobulin," J. Mol. Biol. vol. 228, No. 1, pp. 188-207, Nov. 5, 1992.
Fellhouse et al., "High-throughput Generation of Synthetic Antibodies from Highly Functional Minimalist Phage-displayed Libraries," Journal of Molecular Biology, (2007) 373(4):924-940.
Fellhouse et al., "Synthetic antibodies from a four-amino-acid code: A dominant role for tyrosine in antigen recognition," Proceedings of the National Academy of Sciences, (2004) 101(34):12467-12472.
Ge, "UPA, a universal protein array system for quantitative detection of protein-protein, protein-DNA, protein-RNA and protein-ligand interactions," Nucleic Acids Research (2000) 28(2):e3, I-VII.
Griffiths et al., "Isolation of high affinity human antibodies directly from large synthetic repertoires," The EMBO Journal (1994) 13(14):3245-3260.
Grimes et al., "Achilles' heel cleavage: creation of rare restriction sites in I phage genomes and evaluation of additional operators, repressors and restriction/modification systems," Gene 90(1):1-7 (1990).
Gushiken et al., "Polymorphism of ?2-Glycoprotein I at codons 306 and 316 in Patients with Systemic Lupus Erythematosus and Antiphospholipid Syndrome", Arthritis & Rheumatism, Jun. 1999, 42(6): 1189-1193.
Hanes et al., Picomolar affinity antibodies from a fully synthetic naive library selected and evolved by ribosome display, Nature Biotechnology (2000) 18:1287-1292.
Hasan et al., "Control of cloned gene expression by promoter inversion in vivo: construction of improved vectors with a multiple cloning site and the Ptac promoter," Gene,56(1):145-151 (1987).
Heddle et al., "Dog immunoglobulins. I. Immunochemical characterization of dog serum, parotid saliva, colostrum, milk and small bowel fluid," Immunology, 29(1):185-195 (1975).
Hoet et al., "The Importance of the Light Chain for the Epitope Specificity of Human Anti-U1 Small Nuclear RNA Autoantibodies Present in Systemic Lupus Erythematosus Patients," Journal of Immunology, 163(6):3304-3312 (1999).

(56) References Cited

OTHER PUBLICATIONS

Hoet, R.M., "Generation of high-affinity human antibodies by combining donor-derived and synthetic complementarity-determining-region diversity", Nature Biotechnology, vol. 23, No. 3, pp. 344-348, Mar. 2005.
Hoogenboom et al., "Antibody phage display technology and its applications," Immunotechnology, 4(1):1-20 (1998).
Hoogenboom et al., "By-passing Immunisation Human Antibodies from Synthetic Repertoires of Germline VH Gene Segments Rearranges in Vitro," J. Mol. Biol. (1992) 227:381-388.
Hoogenboom et al., "Natural and designer binding sites made by phage display technology," Immunology Today (2000) 21:371-378.
Hoogenboom, H.R., "Multi-subunit proteins on the surface of filamentous phage: methodologies for displaying antibody (Fab) heavy and light chains", Nucleic Acids Research, vol. 19, No. 15, pp. 4133-4137, Jan. 1, 1991.
Hrncir et al., "Anticardiolipin antibodies in diffuse connective tissue diseases in the IgG, IgM and IgA isotypes," Vnitmi Lekarstvi. 36(11):1041-1049, translation (provided by the USPTO), pp. 1-13 (1999).
Jirholt et al., "Exploiting sequence space: shuffling in vivo formed complementarity determining regions into a master framework," Gene, 1998, vol. 215, No. 2, pp. 471-476.
Kaczorowski et al., "Genomic DNA sequencing by SPEL-6 primer walking using hexamer ligation," Gene 223 (1-2):83-91 (1998).
Kadirvelraj et al., "Understanding the bacterial polysaccharide antigenicity of Streptococcus agalactiae versus Streptococcus pneumoniae," Proc. Natl. Acad. Sci. USA (2006) 103(21):8149-8154.
Kim et al., "Cleaving DNA at any predetermined site with adapter-primers and class-IIS restriction enzymes," Science 240(4851):504-506 (1988).
Kim et al., "Structural requirements for FokI-DNA interaction and oligodeoxyribonucleotide-instructed cleavage," J. Mol. Biol. 258(4):638-649 (1996).
Knappik et al., "Fully Synthetic Human Combinatorial Antibody Libraries (HuCAL) Based on Modular Consensus Frameworks and CDRs Randomized with Trinucleotides," J. Mol. Biol. 296:57-86, 2000.
Koichi Nishigaki et al., "Type II Restriction Endonucleases Cleave Single-Stranded DNAs in General," Nucleic Acids Research, 13:5747-5760 (1985).
Koob et al., "Cleaving yeast and Escherichia coli genomes at a single site," Science, 250(4978):271-273 (1990).
Koob et al., "Conferring new specificity upon restriction endonucleases by combining repressor-operator interaction and methylation," Gene 74(1):165-167 (1988).
Koob et al., "Conferring operator specificity on restriction endonucleases," Science, 241(4869):1084-1086 (1988).
Koob et al., "RecA-AC: single-site cleavage of plasmids and chromosomes at any predetermined restriction site," Nucleic Acids Res. 20(21):5831-5836 (1992).
Kruif et al., "Selection and application of human single chain Fv antibody fragments from a semi-synthetic phage antibody display library with designed CDR3 regions," J. Mol. Biol. 248(1):97-105 (1995).
Kur et al., "A novel method for converting common restriction enzymes into rare cutters: integration host factor-mediated Achilles' cleavage (IHF-AC)," Gene, 110(1):1-7 (1992).
Lee et al., High-affinity human antibodies from phage-displayed synthetic Fab libraries with a single framework scaffold. J Mol Biol. Jul. 23, 2004;340(5):1073-93.
Sidhu et al., Synthetic therapeutic antibodies. Nat Chem Biol. Dec. 2006;2(12):682-8.
Leuking et al., "Protein Microarrays for Gene Expression and Antibody Screening," Analytical Biochemistry (1999) 270:103-111.
Zucconi et al., "Domain repertoires as a tool to derive protein recognition rules," 2000, FEBS Letters, vol. 480, No. 1, pp. 49-54.
Lowman, "Affinity Maturation of Human Growth Hormone by Monovalent Phage Display," J. Mol. Biol. 234:564-578 (1993).
MacBeath et al., "Printing Problems as Microarrays for High-Throughput Function Determination," Science (2000) 289:1760-1763.
Mattheakis et al., "An in vitro polysome display system for identifying ligands from very large peptide libraries," Proc. Natl. Acad. Sci. USA (1994) 91:9022-9026.
Pini, Journal of Biological Chemistry, 273:21769-21776 (Aug. 21, 1998).
Podhajska et al., "Conferring new specificities on restriction enzymes: cleavage at any predetermined site by combining adapter oligodeoxynucleotide and class-IIS enzyme, Methods Enzymol. 216(G):303-309 (1992).
Podhajska et al., "Conversion of the Fok-I endonuclease to a universal restriction enzyme: cleavage of phage M13mp7 DNA at predetermined sites," Gene, 40(1):175-182 (1985).
Posfai et al., "A simple method for locating methylated bases in DNA using class-IIS restriction enzymes," Gene, 74 (1):179-181 (1988).
Powell et al., "Construction, assembly and selection of combinatorial antibody libraries," pp. 155-172 in Genetic Engineering with PCR (Horton and Tait, Eds. 1998), vol. 5 of the Current Innovations in Molecular Biology series, Horizon Scientific Press.
Pritchard et al., "A general model of error-prone PCR," Journal of Theoretical Biology (2005) 234:497-509.
Qi et al., "Restriction of Single-Stranded M13 DNA Using Synthetic Oligonucleotides: The Structural Requirement of Restriction Enzymes," Cell Biol. 65:50-55 (1986).
Reidhaar-Olson et al., "Random Mutagenesis of Protein Sequences Using Oligonucleotide Cassettes," Methods in Enzymology (1991) 208:564-586.
Roitt et al., Male D., Immunology Sixth Edition, New York: Mosby pp. 67-70 and 80 (2001).
Ryu et al., "Recent Progress in Biomolecular Engineering," Biotechnology Progress, 2000, vol. 15, No. 1, pp. 2-16.
Saviranta et al., "Engineering the steroid-specificity of an anti-17B-estradiol Fab by random mutagenesis and competitive phage panning," Protein Engineering, 1998, vol. 11, No. 2, pp. 143-152.
Schoonbroodt et al., "Engineering Antibody Heave Chain CDR3 to Create a Phage Display Fab Library Rich in Antibodies That Bind Charged Carbohydrates," Journal of Immunology, (2008) 181(9):6213-6221.
Schoonbroodt, S., "Oligonucleotide-assisted cleavage and ligation: a novel directional DNA cloning technology to capture cDNAs. Application in the construction of a human immune antibody phage-display library", Nucleic Acids Research, vol. 33, No. 9, p. E81, 2005.
Seed, "Developments in expression cloning," Current Opinion in Biotechnology, 6:567-573, (1995).
Sheets et al., "Efficient construction of a large nonimmune phage antibody library: The production of high-affinity human single-chain antibodies to protein antigens," Proc. Natl. Acad. Sci. USA, 1998, vol. 95, pp. 6157-6162.
Short et al., "Contribution of Antibody Heavy Chain CDR1 to Digoxin Binding Analyzed by Random Mutagenesis of Phage-displayed Fab 26-10", J. Biol. Chem., vol. 270(1):28541-28550 (1995).
Sidhu et al., "Phage-displayed Antibody Libraries of Synthetic Heavy Chain Complementarity Determining Regions," J. Mol. Biol. (2004) 338:299-310.
Sjolander et al., "Integrated Fluid Handling System for Biomolecular Interaction Analysis," Anal. Chem. (1991) 63:2338-2345.
Smith, G.P., "Phage Display", Chem. Rev. vol. 97, No. 2, pp. 391-410, Mar. 1, 1997.
Solderind et al., "Domain libraries: Synthetic diversity for de novo design of antibody V-regions," Gene, 1995, vol. 160, No. 2, pp. 269-272.
Solderlind et al., "The Immune Diversity in a Test Tube—Non-Immunised Antibody Libraries and Functional Variability in Defined Protein Scaffolds," Combinotorial Chemistry & High Throughput Screening, 4:409-416, 2001.
Stemmer, "Rapid evolution of a protein in vitro by DNa shuffling," Nature (1994) 370:389-391.
Stewart, Journal of Experimental Medicine, 177:409-418 (Feb. 1, 1993).
Supplementary European Search Report from European Application No. EP09735791, dated Jun. 8, 2011.

(56) References Cited

OTHER PUBLICATIONS

Suzuki et al., "Light Chain Determines the Binding Property of Human Anti-dsDNA IgG Autoantibodies," Biochem. Biophys. Res. Commun., 271:240-243 (Apr. 29, 2000).

Szabo et al., "Surface plasmon resonance and its use in biomolecular interaction analysis (BIA)," Curr. Opin. Struct. Biol. (1995) 5:699-705.

Szybalski et al., "Class-IIS restriction enzymes-a review," Gene, 100:13-26 (1991).

Szybalski et al., "Nobel prizes and restriction to enzymes," Gene 4(3):181-182 (1978).

Szybalski, "Reasons and risks to study restriction/modification enzymes form extreme thermophiles: chilly coldrooms, 13th sample, and 13-codon overlap," Gene, 112(1):1-2 (1992).

Szybalski, "Universal restriction endonucleases: designing novel cleavage specificities by combining adapter oligodeoxynucleotide and enzyme moieties," Gene 40(2-3):169-173 (1985).

Thielking et al., "Accuracy of the EcoRI restriction endonuclease: binding and cleavage studies iwth oligodeoxynucleotide substrates containing degenerate recognition sequences," Biochemistry, 29(19):4682-4691 (1990).

Tomlinson et al., "The Repertoire of Human Germline VH Sequences Reveals about Fifty Groups of VH Segments with Different Hypervariable Loops," J. Mol. Biol. 227:776-798, 1992, XP000990787.

U.S. Appl. No. 12/371,000, filed Feb. 13, 2009.

U.S. Appl. No. 61/028,265, filed Feb. 13, 2008.

U.S. Appl. No. 61/043,938, filed Apr. 10, 2008.

Van Den Brulle et al., "A novel solid phase technology for high-throughput gene synthesis," BioTechniques (2008) 45(3):340-343.

Yang, Journal of Molecular Biology, 254:392-403 (1995).

Zhu, "Oligodeoxynucleotide-directed cleavage and repair of a single-stranded vector: a method of site-specific mutagenesis," Analytical Biochemistry, 177(1):120-124 (1989).

Zoller et al., "Oligonucleotide-directed mutagenesis using M13-derived vectors: an efficient and general procedure for the production of point mutations in any fragment of DNA," Nucleic Acids Research 10(20):6487-6504 (1982).

* cited by examiner

LIBRARIES OF GENETIC PACKAGES COMPRISING NOVEL HC CDR1, CDR2, AND CDR3 AND NOVEL LC CDR1, CDR2, AND CDR3 DESIGNS

CROSS REFERENCE TO RELATED APPLICATIONS

This application is a national phase application under 35 U.S.C. §371 of International Application No. PCT/US2009/041688 filed Apr. 24, 2009, which claims priority to U.S. Application Ser. No. 61/047,529, filed on Apr. 24, 2008. The disclosure of the prior application is considered part of (and is incorporated by reference in) the disclosure of this application.

BACKGROUND

It is now common practice in the art to prepare libraries of genetic packages that individually display, display and express, or comprise a member of a diverse family of peptides, polypeptides or proteins and collectively display, display and express, or comprise at least a portion of the amino acid diversity of the family. In many common libraries, the peptides, polypeptides or proteins are related to antibodies (e.g., single chain Fv (scFv), Fv, Fab, whole antibodies or minibodies (i.e., dimers that consist of $V_H$ linked to $V_L$)). Often, they comprise one or more of the CDRs and framework regions of the heavy and light chains of human antibodies.

Peptide, polypeptide or protein libraries have been produced in several ways. See, e.g., Knappik et al., *J. Mol. Biol.*, 296, pp. 57-86 (2000), which is incorporated herein by reference. One method is to capture the diversity of native donors, either naive or immunized. Another way is to generate libraries having synthetic diversity. A third method is a combination of the first two. Typically, the diversity produced by these methods is limited to sequence diversity, i.e., each member of the library has the same length but differs from the other members of the family by having different amino acids or variegation at a given position in the peptide, polypeptide or protein chain. Naturally diverse peptides, polypeptides or proteins, however, are not limited to diversity only in their amino acid sequences. For example, human antibodies are not limited to sequence diversity in their amino acids, they are also diverse in the lengths of their amino acid chains.

SUMMARY

For antibodies, heavy chain diversity in length occurs, for example, during variable region rearrangements. See e.g., Corbett et al., *J. Mol. Biol.*, 270, pp. 587-97 (1997). The joining of V genes to J genes, for example, results in the inclusion of a recognizable D segment in CDR3 in about half of the heavy chain antibody sequences, thus creating regions encoding varying lengths of amino acids. D segments are more common in antibodies having long HC CDR3s. The following also may occur during joining of antibody gene segments: (i) the end of the V gene may have zero to several bases deleted or changed; (ii) the end of the D segment may have zero to many bases removed or changed; (iii) a number of approximately random bases may be inserted between V and D or between D and J; and (iv) the 5' end of J may be edited to remove or to change several bases. These rearrangements result in antibodies that are diverse both in amino acid sequence and in length. HC CDR3s of different lengths may fold into different shapes, giving the antibodies novel shapes with which to bind antigens. The conformations depend on both the length and the sequence of the CDR3. It should be remembered that a HC CDR3 of length 8, for example, and of any sequence cannot adequately mimic the behavior of a CDR3 of length 22, for example.

Libraries that contain only amino acid sequence diversity are, thus, disadvantaged in that they do not reflect the natural diversity of the peptide, polypeptide or protein that the library is intended to mimic. Further, diversity in length may be important to the ultimate functioning of the protein, peptide or polypeptide. For example, with regard to a library comprising antibody regions, many of the peptides, polypeptides, proteins displayed, displayed and expressed, or comprised by the genetic packages of the library may not fold properly or their binding to an antigen may be disadvantaged, if diversity both in sequence and length are not represented in the library.

An additional disadvantage of such libraries of genetic packages that display, display and express, or comprise peptides, polypeptides and proteins is that they are not focused on those members that are based on natural occurring diversity and thus on members that are most likely to be functional and least likely to be immunogenic. Rather, the libraries, typically, attempt to include as much diversity or variegation as possible at every CDR position. This makes library construction time-consuming and less efficient than necessary. The large number of members that are produced by trying to capture complete diversity also makes screening more cumbersome than it needs to be. This is particularly true given that many members of the library will not be functional or will be non-specifically sticky.

In addition to the labor of constructing synthetic libraries is the question of immunogenicity. For example, there are libraries in which all CDR residues are either Tyr (Y) or Ser (S). Although antibodies (Abs) selected from these libraries show high affinity and specificity, their very unusual composition may make them immunogenic. The present invention is directed toward making Abs that could well have come from the human immune system and so are less likely to be immunogenic. The libraries of the present invention retain as many residues from V-D-J or V-J fusions as possible. To reduce the risk of immunogenicity, it may be prudent to change each non-germline amino acid in both framework and CDRs back to germline to determine whether the change from germline is needed to retain binding affinity. Thus, a library that is biased at each varied position toward germline will reduce the likelihood of isolating Abs that have unneeded non-germline amino acids.

Abs are large proteins and are subject to various forms of degradation. One form of degradation is the deamidation of Asn and Gln residues (especially in Asn-Gly or Gln-Gly) and the isomerization of Asp residues. Another form of degration is the oxidation of methionines, tryptophan, and cysteine. Another form of degradation is the cleavage of Asp-Pro dipeptides. Another form of degradation is the formation of pyroglutamate from N-terminal Glu or Gln. It is advantageous to provide a library in which the occurance of problematic sequences is minimized.

Provided are libraries of vectors or packages that encode members of a diverse family of human antibodies comprising heavy chain (HC) CDR3s that are between about 3 amino acids in length to about 35 amino acids in length. The HC CDR3s may also, in certain embodiments, may be rich in Tyr (Y) and Ser (S) and/or comprise diversified D regions and/or comprise extended JH regions. For example, the HC CDR3s may contain greater than about 40% (e.g., between about 43% and about 80%; e.g., greater than about 40% but less than about 100%) Y and/or S residues, e.g., as provided in the examples herein. Also provided are focused libraries comprising such HC CDR3s. Also provided are designs for HC CDR1, HC CDR2, and a library of VKIII A27 with diversity in the CDRs. A library of vectors or packages that encode members of a diverse family of human antibodies comprising HC CDR3s described herein can further have diversity at one or more (e.g., at one, two or three) of HC CDR1, HC CDR2, LC CDR1, LC CDR2, and LC CDR3. For example, the library can have diversity at one or more (e.g., at one, two or three) of HC CDR1, HC CDR2, LC CDR1, LC CDR2, and LC CDR3 as described herein.

A diversified D region is a D region into which one or more amino acid changes have been introduced (e.g., as compared to the sequence of a nautrally occurring D region; for example, a stop codon can be changed to a Tyr residue).

An extended JH region is a JH region that has one or more amino acid residues present at the amino terminus of the framework sequence of the JH region (e.g., amino terminal to FR4 sequences, e.g., which commence with WGQ . . . ). For example, JH1 is an extended JH region. As other examples, JH2, JH3, JH4, JH5, and JH6 are extended JH regions.

Provided also are methods of making and screening the above libraries and the HC CDR3s and antibodies obtained in such screening. Compositions and kits for the practice of these methods are also described herein.

In some aspects, the disclosure features a focused library of vectors or genetic packages that display, display and express, or comprise a member of a diverse family of human antibody related peptides, polypeptides and proteins (e.g., a diverse family of antibodies) and collectively display, display and express, or comprise at least a portion of the diversity of the family, wherein the vectors or genetic packages comprise variegated DNA sequences that encode a heavy chain (HC) CDR3 selected from the group consisting of:
  (a) a HC CDR3 that is about 3 or about 4 or about 5 amino acids in length;
  (b) a HC CDR3 that is about 23, about 24, about 25, about 26, about 27, about 28, about 29, about 30, about 31, about 32, about 33, about 34 or about 35 amino acids in length (e.g., about 23 to about 35 amino acids in length); and
  c) a HC CDR3 that is from about 6 to about 20 amino acids in length (e.g., about 6, about 7, about 8, about 9, about 10, about 11, about 12, about 13, about 14, about 15, about 16, about 17, about 18, about 19, or about 20 amino acids in length);
  wherein the HC CDR3 comprises amino acids from a D region (e.g., a diversified D region) (or fragment thereof (e.g., 3 or more amino acids of the D region, e.g., diversified D region)) or a JH region (e.g., an extended JH region).

In some embodiments, the HC CDR3 is enriched in Tyr (Y) and Ser (S) (e.g., greater than 40% of the residues of the HC CDR3 are Y and/or S).

In some embodiments, the library (e.g., the vectors or genetic packages thereof) comprises a D region or a fragment of a D region (e.g., wherein the D region is adjacent to a JH region).

In some embodiments, the library comprises a JH region, e.g., an extended JH region.

In some embodiments, the HC CDR3 comprises amino acids from a D region or a fragment of a D region (e.g., wherein the D region is adjacent to a JH region).

In some embodiments, the D region is selected from the group consisting of D2-2 (RF 2), D2-8(RF 2), D2-15(RF 2), D2-21(RF 2), D3-16(RF 2), D3-22 (RF 2), D3-3 (RF-2), D3-9 (RF 2), D3-10 (RF 2), D1-26 (RF 3), D4-11 (RF 2), D4-4 (RF 2), D5-5 (RF 3), D5-12 (RF 3), D5-18 (RF 3), D6-6 (RF1), D6-13 (RF 1), and D6-19 (RF 1).

In some embodiments, the HC CDR3 comprises amino acids from a JH region. The JH region may be an extended JH region. In some embodiments, the extended JH region is selected from the group consisting of JH1, JH2, JH3, JH4, JH5, and JH6. In some embodiments, the JH region may be enriched in Y and/or S residues, for example, it may contain greater than about 40% (e.g., between about 43% and about 80%; e.g., greater than about 40% but less than about 100%) Y and/or S residues.

In some embodiments, the D region comprises one or more cysteine (Cys) residues and in some embodiments, the one or more Cys residues are held constant (e.g., are not varied).

In some embodiments, the HC CDR3 (e.g., the DNA encoding the HC CDR3) comprises one or more filling codons between FR3 and the D region and each filling codon is individually NNK, TMY, TMT, or TMC (TMY, TMT, or TMC encode S or Y).

In some embodiments, the HC CDR3 (e.g., the DNA encoding the HC CDR3) comprises one or more filling codons between the D region and JH and each filling codon is individually NNK, TMY, TMT, or TMC.

In some embodiments, the library (e.g., the vectors or genetic packages of the library) further comprises a HC CDR1, HC CDR2, and/or a light chain and also comprises diversity in the HC CDR1, HC CDR2, or light chain comprises diversity in HC CDR1 and/or HC CDR2, and/or a light chain (e.g., kappa or lambda light chain) (respectively). For example, HC CDR3 diversity can be constructed in the background of diversity in HC CDR1, HC CDR2, and/or light chains. For example, the light-chain diversity may be encoded in the same DNA molecule as the HC diversity or the LC and HC diversities may be encoded in separate DNA molecules.

In some aspects, the disclosure features a library comprising a HC CDR3 that is 3, 4, or 5 amino acids in length, wherein the CDR3 comprises amino acids from a JH region (e.g., extended JH region) or from a D region (e.g., a diversified D region) (or fragment thereof (e.g., 3 or more amino acids of the D region, e.g., diversified D region)) joined to the FR4 portion of a JH region.

In some embodiments, the HC CDR3 is from a D region joined to the FR4 portion of a JH region and comprises a trimer, a tetramer, or a pentamer, wherein the trimer, tetramer, or pentamer does not comprise a cysteine residue.

In some embodiments, the HC CDR3 is from a D region joined to the FR4 portion of a JH region and comprises a trimer, a tetramer, or a pentamer, wherein the trimer, tetramer, or pentamer does not comprise a stop codon.

In some embodiments, the D region (e.g., the DNA encoding the D region) comprises a TAG codon and the TAG codon is replaced by a codon selected from the group consisting of TCG, TTG, TGG, CAG, AAG, TAT, and GAG.

In some embodiments, the D region (e.g., the DNA encoding the D region) comprises a TAA codon and the TAA codon is replaced by a codon selected from the group consisting of TCA, TTA, CAA, AAA, TAT, and GAA.

In some embodiments, the D region (e.g., the DNA encoding the D region) comprises a TGA codon and the TGA codon is replaced by a codon selected from the group consisting of TGG, TCA, TTA, AGA, and GGA.

In some embodiments, the library further comprises diversity in HC CDR1 and/or HC CDR2, and/or a light chain (e.g., kappa or lambda light chain). For example, HC CDR3 diversity can be constructed in the background of diversity in HC CDR1, HC CDR2, and/or light chains. For example, the light-chain diversity may be encoded in the same DNA molecule as the HC diversity or the LC and HC diversities may be encoded in separate DNA molecules.

In some aspects, the disclosure provides a method of diversifying a library, the method comprising mutagenizing a library described herein.

In some embodiments, the mutagenizing comprises error-prone PCR.

In some embodiments, the mutagenizing comprises wobbling.

In some embodiments, the mutagenizing comprises dobbling.

In some embodiments, the mutagenizing introduces on average about 1 to about 10 mutations (e.g., about 1, about 2, about 3, about 4, about 5, about 6, about 7, about 8, about 9, about 10 mutations; e.g., base changes) per HC CDR3.

"Wobbling" is a method of making variegated DNA so that an original sequence is favored. If the original sequence had, for example, an Ala that could be encoded with GCT the mixture (0.7 G, 0.1 A, 0.1 T, 0.1 C) can be used for the first position, (0.7 C, 0.1 A, 0.1 T, 0.1 G) at the second position, and (0.7 T, 0.1 A, 0.1 G, 0.1 C) at the third. Other ratios of "doping" can be used. This allows Ala to appear about 50% of the time while V, D, G, T, P, and S occur about 7% of the time. Other AA types occur at lower frequency.

In some aspects, the present disclosure is drawn, e.g., to keeping a (purified) HC CDR1-2 repertoire, and building synthetic HC CDR3 and LC diversity.

In some embodiments, the dislocsure provides a cassette for displaying a wobbled heavy chain (HC) CDR3, for example, wherein the cassette comprises the cassette shown in Table 400.

In some aspects, the present disclosure features a library in which Tyr levels are controlled in the HC CDR3. In some embodiments, the HC CDR3 regions contain about 15% or greater (e.g., about 16%, about 18%, about 20%, or greater) Tyr residues. In some embodiments, high levels (e.g., more than about 20%) of Tyr are inserted into the HC CDR3 of library members, e.g., at D regions and J stumps (or synthetic sequences corresponding thereto) that contain Tyr. In some embodiments, at leadin or DJ filler positions (or synthetic sequences corresponding thereto), Tyr is allowed, but at no more than 20%. In some embodiments, the HC CDR3 regions contain less than about 15% (e.g., about 14%, about 12%, about 10%, about 8%, about 6% or less) Tyr residues. In some embodiments, the HC leadin or DJ filler positions (or synthetic sequences corresponding thereto) contain less than about 15% (e.g., about 14%, about 12%, about 10%, about 8%, about 6% or less) Tyr residues.

In some aspects, the disclosure features a library of genetic packages that encode a human antibody heavy chain in which a parent amino-acid sequence comprises a VH sequence followed by zero to ten amino acids selected from the group consisting of (Y, S, D, L, R), followed by a human D-region or fragment of a D-region, followed by zero to ten amino acids selected from the group consisting of (Y,S,R,D,L), followed by a JH segment that comprises at least W103 onward wherein the variable DNA encoding this sequence is synthesized in a way that the parental amino-acid sequence is the most likely one (e.g., by wobbling).

In some aspects, the disclosure features a library of light chains having germline framework regions and wherein the CDRs are varied such that residues remote from the combining site or having buried side groups are held constant. In some embodiments, a method of variable DNA synthesis is used so that germline sequence is the most likely one (e.g., by wobbling).

In some aspects, the disclosure features a library of diverse members encoding antigen binding variable regions as disclosed herein.

In some aspects, the disclosure features a library of diverse members encoding HC CDR3 regions as disclosed herein. In some embodiments, the library is a library of Table 1097.

In some aspects, the disclosure features a library of diverse members, each member encoding comprising a HC CDR 3, wherein
at least 1, 2, 3, 4, 5, 6, 7, or 8 positions in the HDCR3, respectively, is occupied by G, S, R, D, L, and Y in the library in the following proportions [1.0G, 0.57S, 0.46R, 0.42D, 0.36L, 0.35Y] and optionally,
the last 4 positions of HC CDR3 are represented as follows:
the parental amino acid is present at 3, 4, 5, 6, 7, 8, 10 times as likely as other amino-acid types, wherein the other amino-acid types comprise Y, S, D, R, G.

In some aspects, the disclosure features a library of diverse members, each member encoding comprising a HC CDR 3, wherein
at least one and preferably all of the first 1, 2, 3, 4, 5, 6, 7, or 8 positions in the HC CDR3, is occupied by G, S, R, D, L, and Y, in the library in the following proportions [1.0G, 0.57S, 0.46R, 0.42D, 0.36L, 0.35Y] and optionally
the last 4 positions of HCDR3 are represented as follows:
the parental amino acid is present at 3, 4, 5, 6, 7, 8, 10 times as likely as other amino-acid types, wherein the other amino-acid types comprise Y, S, D, R, G.

In some aspects, the disclosure features a library of diverse members, each member encoding a HC CDR 3, wherein
the length of HC CDR3 is 10, 11, or 12 positions;
each of the first 6, 7, or 8 positions in the HC CDR3, respectively, is occupied by G, S, R, D, L, and Y in the library in the following proportions [1.0G, 0.57S, 0.46R, 0.42D, 0.36L, 0.35Y];
the last 4 positions of HCDR3 are represented as follows:
the parental amino acid is present at 3, 4, 5, 6, 7, 8, 10 times as likely as other amino-acid types, wherein the other amino-acid types comprise Y, S, D, R, G.

In some embodiments, each of the last 4 HC CDR3 positions is represented in the library as 7/12 parental, plus 1/12 each of Y, S, D, R, and G.

In some embodiments, each of the last 4 HC CDR3 positions is represented in the library as A6=7/12 A, plus 1/12 each of Y, S, D, R, and G; F7=7/12 F plus 1/12 each of Y, S, D, R, and G; D8=7/11 D plus 1/11 of Y, S, R, and G; I9=7/12 I plus 1/12 Y, S, R, D, G.

In some embodiments, the members further encode HC CDR1, HC CDR2.

In some embodiments, the members further encode F framework (FR) regions 1-4.

In some embodiments, the members encode HC CDR1, HC CDR2 and FR regions 1-4.

In some embodiments, the members comprise a 3-23 HC framework.

In some embodiments, the library further comprises a LC variable region.

In some embodiments, the library comprises members encoding diverse LC variable regions.

In some embodiments, the members comprising a LC variable region comprise an A27 LC framework.

In some embodiments, the library is a display library, e.g., a phage display library.

In some embodiments, the library has at least $10^4$, $10^5$ $10^6$, $10^7$, $10^8$, $10^9$ $10^{10}$, $10^{11}$ diverse members.

In some aspects, the disclosure features a method of selecting a library member, comprising, contacting a library described herein with a target, allowing a member to bind to said target, and recovering the member which binds the target.

These embodiments of the present invention, other embodiments, and their features and characteristics will be apparent from the description, drawings, and claims that follow.

DETAILED DESCRIPTION

Antibodies ("Ab") concentrate their diversity into those regions that are involved in determining affinity and specificity of the Ab for particular targets. These regions may be diverse in sequence or in length. Generally, they are diverse in both ways. However, within families of human antibodies the diversities, both in sequence and in length, are not truly random. Rather, some amino acid residues are preferred at certain positions of the CDRs and some CDR lengths are preferred. These preferred diversities account for the natural diversity of the antibody family.

According to this invention, and as more fully described below, libraries of vectors and genetic packages that encode members of a diverse family of human antibodies comprising heavy chain (HC) CDR3s that are between about 3 to about 35 amino acids in length may be prepared and used. The HC CDR3s may also, in certain embodiments, may be rich in Y and S and/or comprise diversified D regions. Also provided are focused libraries comprising such HC CDR3s.

When an immune cell constructs an antibody heavy chain, it connects a V segment to a D segment and that to a J segment. The D segment is optional and about 50% of human Abs have recognizable Ds. The cell may perform considerable editing at the junction sites (V-to-D, D-to-J, or V-to-J) both removing and adding bases, but not exactly randomly. The initially rearranged antibody is presented on the surface of the cell and if it binds an antigen (Ag), the cell is stimulated to perform somatic mutations to improve the affinity. There are hot spots encoded in the immunoglobulin germline genes so that certain places in the Ab gene are very likely to go through a particular set of mutations in search of a better binder to a persistent Ag. In nature, some of the mutations are in framework positions but most are in the complementarity determining regions (CDRs). Of particular interest is the CDR3 of the heavy chain (HC) because it shows not only a high degree of sequence diversity but also length diversity. Antibody (Ab) libraries have been built in which the CDRs are replaced with random DNA, and useful Abs have been obtained. However, some therapeutic Abs show a significant degree of antigenicity. It is possible that Abs that are closer to human germline would be less antigenic.

Definitions

For convenience, before further description of the present invention, certain terms employed in the specification, examples and appended claims are defined here.

The singular forms "a", "an", and "the" include plural references unless the context clearly dictates otherwise.

The term "affinity" or "binding affinity" refers to the apparent association constant or $K_a$. The $K_a$ is the reciprocal of the dissociation constant ($K_d$). A binding protein may, for example, have a binding affinity of at least $10^5$, $10^6$, $10^7$, $10^8$, $10^9$, $10^{10}$ and $10^{11}$ M$^{-1}$ for a particular target molecule. Higher affinity binding of a binding protein to a first target relative to a second target can be indicated by a higher $K_A$ (or a smaller numerical value $K_D$) for binding the first target than the $K_A$ (or numerical value $K_D$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in TRIS-buffer (50 mM TRIS, 150 mM NaCl, 5 mM CaCl$_2$ at pH7.5). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[\text{Bound}] = N \cdot [\text{Free}]/((1/K_A) + [\text{Free}]).$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. Heavy chain and light chain may also be abbreviated as HC and LC, respectively. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., *Eur J. Immunol.* 1996; 26(3):629-39.)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types, kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, CL), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the $NH_2$-terminus (about 110 amino acids) and a kappa or lambda constant region gene at the COOH—terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

Herein, the terms "D segment" and "D region" are used interchangeably and are identical. It is to be understood that these items have both DNA and amino-acid representations and that which is meant is clear from the context.

A "library" or "display library" refers to a collection of nucleotide, e.g., DNA, sequences within clones; or a genetically diverse collection of polypeptides displayed on replicable display packages capable of selection or screening to provide an individual polypeptide or a mixed population of polypeptides.

The term "package" as used herein refers to a replicable genetic display package in which the particle is displaying a polypeptide at its surface. The package may be a bacteriophage which displays an antigen binding domain at its surface. This type of package has been called a phage antibody (pAb).

A "pre-determined target" refers to a target molecule whose identity is known prior to using it in any of the disclosed methods.

The term "replicable display package" as used herein refers to a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed polypeptide may be any member of a specific binding pair e.g., heavy or light chain domains based on an immunoglobulin molecule, an enzyme or a receptor etc. The particle may be, for example, a virus e.g., a bacteriophage such as fd or M13.

The term "vector" refers to a DNA molecule, capable of replication in a host organism, into which a gene is inserted to construct a recombinant DNA molecule. A "phage vector" is a vector derived by modification of a phage genome, containing an origin of replication for a bacteriophage, but not one for a plasmid. A "phagemid vector" is a vector derived by modification of a plasmid genome, containing an origin of replication for a bacteriophage as well as the plasmid origin of replication.

In discussing oligonucleotides, the notation "[RC]" indicates that the Reverse Complement of the oligonucleotide shown is the one to be used.

Human Antibody Heavy Chain CDR3s

The heavy chain ("HC") Germ-Line Gene (GLG) 3-23 (also known as VP-47) accounts for about 12% of all human Abs and is preferred as the framework in the preferred embodiment of the invention. It should, however, be understood that other well-known frameworks, such as 4-34, 3-30, 3-30.3 and 4-30.1, may also be used without departing from the principles of the focused diversities of this invention.

In addition, JH4 (<u>YFDY</u>W$_{103}$GQGTLVTVSS (SEQ ID NO:1)) occurs more often than JH3 in native antibodies. Hence, it is preferred for the focused libraries of this invention. However, JH3 (<u>AFDI</u>W$_{103}$GQGTMVTVSS (SEQ ID NO:2)), JH6 (<u>YYYYYGMDV</u>W$_{103}$GQGTTVTVSS (SEQ ID NO:3)), JH1, JH2, or JH5 could be used as well. JH2 has the advantage of having RG at 105-106 instead of QG in all the other human JHs. JH3 has the disadvantage of $M_{108}$. In a collection of 1419 Abs that were ELISA positive for at least one target, we saw 17 JH1s, 31 JH2s, 452 JH3s, 636 JH4s, 32 JH5s, and 251 JH6s. If present, the double underscored portions of the JHs are considered to be part of CDR3. In Table 3, the FR4 parts of the JHs are underscored.

The frequency at which each amino-acid appeared in the HC CDR3s of these 1419 Abs was tabulated and recorded in Table 75. Note that the most common amino acid is Tyr with Gly, Asp, Ser, and Arg following in that order. Rel. Up is the relative abundance of each type compared to Cys, the least common. Rel. Down is the abundance of each type compared to Tyr, the most common. Hence the preferred amino-acid types to substitute into HC CDR3s are Y, G, D, S, and R.

Naturally, HC CDR3s vary in length. About half of human HCs consist of the components: V::nz::D::ny::JHn where V is a V gene, nz is a series of bases that are essentially random, D is a D segment, often with heavy editing at both ends, ny is a series of bases that are essentially random, and JHn is one of the six JH segments, often with heavy editing at the 5' end. The D segments appear to provide spacer segments that allow folding of the IgG. The greatest diversity is at the junctions of V with D and of D with JH.

Corbett et al. (Corbett S J, Tomlinson I M, Sonnhammer E L, Buck D, Winter G. J Mol. Biol. 1997 V270:587-97.) showed that the human immune system does not insert multiple D segments and recombing D segments. Nevertheless, D segments have been selected to be good components of HC CDR3s and the present invention comprises HC CDR3 that contain more than one D segment.

Human D segments have some very strong biases. The tally of the 522 amino-acids in human D segments is Y 70 (13.4%), L 63 (12.1%), V 52 (10%), G 49 (9.4%), 141 (7.9%), T 40 (7.7%), S 33 (6.3%), W 27 (5.2%), D 21 (4%), A 19 (3.6%), R 16 (3.1%), TAG 15 (2.9%), N 14 2.7%), Q 11 (2.1%), C 9 (1.7%), E 9 (1.7%), F 8 (1.5%), M 8 (1.5%), TGA 8 (1.5%), TAA 7 (1.3%), P 1 (0.2%), H 1 (0.2%), and K 0 (0%). There is one D (2-8 RF 1) that has an unpaired Cys but also a TGA stop codon, so it is little used. Thus, D segments are primarily hydrophobic. The frequencies of amino acids in human HC CDR3s are shown in Table 75. There are both similarities and differences in the frequencies. In HC CDR3s overall, Tyr is the most common and only Gly comes close (96% as common as Tyr). Asp (75% as common as Tyr), Ser (53% as common as Tyr). Leu, Val, and Ile are relatively common in the D segments if all the D segments are counted as equal. The immune system does not use the D segments with equal frequency. Table 77 shows the frequency of utilization of D segments. The D segments that are often used are very rich in Tyr, Gly, Ser, and Asp. Arg is not found in the most often used D segments nor is Arg encoded in any of the CDR portions of JH segments. Arg comes to prominence either by mutation of V, D, and J or in the filler regions between V and D, D and J, or V and J. In this sample, 50% of all the amino acids are Tyr, Gly, Asp, Ser, or Arg. In one embodiment of the present invention, substitutions of "parental" HC CDR3 sequences is limited to the set of amino acids consisting of Tyr, Gly, Ser, Asp, and Arg. In one embodiment of the present invention, Arg is made common in the filler regions between V and D, between D and J, or between V and J.

In the preferred libraries of this invention, both types of HC CDR3s are used. In HC CDR3s that have no identifiable D segment, the structure is V::nz::JHn (n=1,6) where JH is usually edited at the 5 end. In HC CDR3s that have an identifiable D segment, the structure is V::nz::D::ny::JHn.

Provided herein are HC CDR3s that are between about 3 to a about 35 amino acids in length. The HC CDR3s may also, in certain embodiments, be rich in Y and S and/or comprise diversified D regions, where a D region is present. For example, the HC CDR3s may contain between about 43% and about 80% Y and/or S residues, e.g., about 43%, about 48%, about 69%, about 63%, about 71%, about 62%, about 58%, about 68%, about 80%, about 77%, or greater than about 40%, or about 40% to less than about 100%, of the residues are Y and/or S. For example, not all of the residues in the CDR3 are Y and/or S. The HC CDR3s may, in certain embodiments, comprise an extended JH region. Exemplary HC CDR3 component designs of the preferred libraries of this invention are shown and described in Examples 1, 2, and 3.

In some embodiments, diversity (e.g., in a CDR, e.g., HC CDR3, or framework region (e.g., framework region near or adjacent to a CDR, e.g., CDR3, e.g., HC CDR3) is generated to create on average about 1, about 2, about 3, about 4, about 5, about 6, about 7, about 8, about 9, about 10, or about 1 to about 10 mutations (e.g., base change), e.g., per CDR (e.g., HC CDR3) or framework region (e.g., framework region near or adjacent to a CDR, e.g., CDR3, e.g., HC CDR3). In some implementations, the mutagenesis is targeted to regions known or likely to be at the binding interface. Further, mutagenesis can be directed to framework regions near or adjacent to the CDRs. In the case of antibodies, mutagenesis can also be limited to one or a few of the CDRs, e.g., to make precise step-wise improvements. Likewise, if the identified ligands are enzymes, mutagenesis can provide antibodies that are able to bind to the active site and vicinity. The CDR or framework region (e.g., an HC CDR3 described herein) may be, in certain embodiments, subjected to error-prone PCR to generate the diversity. This approach uses a "sloppy" version of PCR, in which the polymerase has a fairly high error rate (up to 2%), to amplify the wild-type sequence, and is generally described in Pritchard, et al. (2005) *J. Theor. Biol.* 234: 497-509 and Leung et al. (1989) *Technique* 1:11-15. Other exemplary mutagenesis techniques include DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zoller et al. (1987) *Nucl Acids Res* 10:6487-6504), cassette mutagenesis (Reidhaar-Olson (1991) *Methods Enzymol.* 208: 564-586) and incorporation of degenerate oligonucleotides (Griffiths et al. (1994) *EMBO J.* 13:3245).

In some embodiments of the invention, D segments in which a majority of the residues are either Ser or Tyr are picked. In some embodiments, when the DNA encoding the D region is synthesized, each Ser or Tyr residue is encoded by TMT, TMC, or TMY so that the encoded amino acid is either Ser or Tyr.

In some embodiments, the HC CDR3 sequences described herein may be subjected to selection for open reading frames by fusing the sequence encoding the HC CDR3 of interest in frame to an antibiotic resistance gene, such as $Kan^R$ gene and selecting for kanamycin resistance. Cells in which the potential CDR3 has a stop codon or a frame shift will not have the antibiotic resistance and that sequence will be eliminated.

Methods of Construction of Libraries comprising Human Antibody Heavy Chain CDR3s and Libraries comprising Human Antibody Heavy Chain CDR3s An antibody library is a collection of proteins that include proteins that have at least one immunoglobulin variable domain sequence. For example, camelized variable domains (e.g., VH domains) can be used as a scaffold for a library of proteins that include only one immunoglobulin variable domain sequence. In another example, the proteins include two variable domains sequences, e.g., a VH and VL domain, that are able to pair. An antibody library can be prepared from a nucleic acid library (an antibody-coding library) that includes antibody-coding sequences, e.g., comprising the sequences encoding the HC CDR3s provided herein.

In cases where a display library is used, each member of the antibody-coding library can be associated with the antibody that it encodes. In the case of phage display, the antibody protein is physically associated (directly or indirectly) with a phage coat protein. A typical antibody display library member displays a polypeptide that includes a VH domain and a VL domain. The display library member can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are included. It is also possible to add one or more constant regions to a molecule after it is identified as having useful antigen binding site. See, e.g., US 2003-0224408.

Antibody libraries can be constructed by a number of processes (see, e.g., de Haard et al. (1999) *J. Biol. Chem.* 274: 18218-30; Hoogenboom et al. (1998) *Immunotechnology* 4:1-20, Hoogenboom et al. (2000) *Immunol Today* 21:371-8, and Hoet et al. (2005) *Nat. Biotechnol.* 23(3):344-8.

In certain embodiments for constructing libraries, the heavy chains comprising the CDR3s described herein and the kappa and lambda light chains are best constructed in separate vectors. First, a synthetic gene is designed to embody each of the synthetic variable domains. The light chains may be bounded by restriction sites for ApaLI (positioned at the very end of the signal sequence) and AscI (positioned after the stop codon). The heavy chain may be bounded by StiI (positioned within the Pe1B signal sequence) and NotI (positioned in the linker between CH1 and the anchor protein). Signal sequences other than Pe1B may also be used, e.g., a M13 pIII signal sequence.

The initial genes may be made with "stuffer" sequences in place of the desired CDRs. A "stuffer" is a sequence that is to be cut away and replaced by diverse DNA, but which does not allow expression of a functional antibody gene. For example, the stuffer may contain several stop codons and restriction sites that will not occur in the correct finished library vector. Stuffers are used to avoid have any one CDR sequence highly represented.

In another embodiment of the present invention, the heavy chain and the kappa or lambda light chains are constructed in a single vector or genetic packages (e.g., for display or display and expression) having appropriate restriction sites that allow cloning of these chains. The processes to construct such vectors are well known and widely used in the art. Preferably, a heavy chain and kappa light chain library and a heavy chain and lambda light chain library would be prepared separately.

Most preferably, the display is on the surface of a derivative of M13 phage. The most preferred vector contains all the genes of M13, an antibiotic resistance gene, and the display cassette. The preferred vector is provided with restriction sites that allow introduction and excision of members of the diverse family of genes, as cassettes. The preferred vector is stable against rearrangement under the growth conditions used to amplify phage.

In another embodiment of this invention, the diversity captured by the methods of the present invention may be displayed and/or expressed in a phagemid vector (e.g., pMID21 (DNA sequence shown in Table 35)) that displays and/or expresses the peptide, polypeptide or protein. Such vectors may also be used to store the diversity for subsequent display and/or expression using other vectors or phage.

In still other embodiments, a method termed the Rapid Optimization of LIght Chains or "ROLIC", described in U.S. Ser. No. 61/028,265 filed Feb. 13, 2008, U.S. Ser. No. 61/043, 938 filed Apr. 10, 2008, and U.S. Ser. No. 12/371,000 filed Feb. 13, 2009, a large population of LCs is placed in a phage vector that causes them to be displayed on phage. A small population (e.g., 3, 10, or 25) of HCs are cloned into *E. coli* so that the HCs are secreted into the periplasm, e.g., those HCs having the CDR3s described herein. The *E. coli* are then infected with the phage vectors encoding the large population of LCs to produce the HC/LC protein pairings on the phage. The phage particles carry only a LC gene.

In another aspect, in a method termed the Economical Selection of Heavy Chains or "ESCH", also described in U.S. Ser. No. 61/028,265 filed Feb. 13, 2008, U.S. Ser. No. 61/043, 938 filed Apr. 10, 2008, and U.S. Ser. No. 12/371,000 filed Feb. 13, 2009, a small population of LCs may be placed in a vector that causes them to be secreted. A new library of HCs in phage is constructed, such as those provided herein comprising the CDR3s. The LCs and HCs can then be combined by the much more efficient method of infection. Once a small set of effective HC are selected, these can be used as is, fed into ROLIC to obtain an optimal HC/LC pairing, or cloned into a Fab library of LCs for classical selection.

In another embodiment of this invention, the diversity captured by the methods of the present invention may be displayed and/or expressed using a vector suitable for expression in a eukaryotic cell, e.g., a yeast vector, e.g., for expression in a yeast cell.

Other types of protein display include cell-based display (see, e.g., WO 03/029,456); ribosome display (see, e.g., Mattheakis et al. (1994) *Proc. Natl. Acad. Sci. USA* 91:9022 and Hanes et al. (2000) *Nat. Biotechnol.* 18:1287-92); protein-nucleic acid fusions (see, e.g., U.S. Pat. No. 6,207,446); and immobilization to a non-biological tag (see, e.g., U.S. Pat. No. 5,874,214).

Antibodies isolated from the libraries of the present disclosure may be analyzed to determine the type of the LC and the closest germline gene. In a preferred embodiment, non-germline framework residues are changed back to the germline amino acid so long as binding affinity and specificity are not adversely affected to an unacceptable extent. The substitutions may be done as a group or singly. Human germline sequences are disclosed in Tomlinson, I. A. et al., 1992, *J. Mol. Biol.* 227:776-798; Cook, G. P. et al., 1995, *Immunol. Today* 16 (5): 237-242; Chothia, D. et al., 1992, *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). Antibodies are "germlined" by reverting one or more non-germline amino acids in framework regions to corresponding germline amino acids of the antibody, so long as binding properties are substantially retained. Similar methods can also be used in the constant region, e.g., in constant immunoglobulin domains.

For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) are then made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

CDR1, CDR2, and Light-Chain Diversity

It is to be understood that the libraries of HC CDR3 are constructed in the background of diversity in HC CDR1, HC CDR2, and light chains. The light-chain diversity may be encoded in the same DNA molecule as the HC diversity or the LC and HC diversities may be encoded in separate DNA molecules. In Table 22 the fusion of a signal sequence::VH::CH1::His6::Myc::IIIstump (His6 is disclosed as SEQ ID NO: 934). CDR1 comprises residues 31-35; there is diversity at residues 31, 33, and 35. In one embodiment, residues 31, 33, and 35 can be any amino-acid type except cysteine. CDR2 comprises residues 50 through 65. There is diversity at positions 50, 52, 52a, 56, and 58. In one embodiment, residues 50, and 52 can be any of the types Ser, Gly, Val, Trp, Arg, Tyr; residue 52a can be Pro or Ser and residues 56 and 58 can be any amino-acid type except Cys. The diversity of HC CDR3 is cloned into a diversity of HC CDR1 and 2 that is at least 1. E 4, 1. E 5, 1. E 6, 1.E 7, 5. E 7, or 1. E 8.

In one embodiment, residues 31, 33, 35, 50, 52, 56, and 58 can be any amino-acid type except Cys or Met and residue 52a can be Gly, Ser, Pro, or Tyr. The diversity of HC CDR3 is cloned into a diversity of HC CDR1 and 2 that is at least 1. E 4, 1. E 5, 1. E 6, 1. E 7, 5. E 7, or 1. E 8.

In one embodiment, the diversity of the HC is cloned into a vector (phage or phagemid) that contains a diversity of light chains. This diversity is at least 25, 50, 100, 500, 1. E 3, 1. E 4, 1. E 5, 1. E 6, or 1. E7. The diversity of HC CDR3 is at least 221, 272, 500, 1000, 1. E 4, 1. E 5, 1. E 6, 1. E7, 1. E 8, or 1. E 9.

In one embodiment, the diversity of the HC is cloned into a phage vector that displays the HC on a phage protein such as III, VIII, VII, VI, or IX or a fragment of one of these sufficient to cause display and light chains are combined with the HC by infecting a cell collection wherein each cell secrets a light chain. The diversity of the light chains in the cells is at least 5, 10, 15, 20, 25, 30, 35, 40, 50, 75, or 100. The diversity of HC CDR3 is at least 221, 272, 500, 1000, 1. E 4, 1. E 5, 1. E 6, 1. E7, 1. E 8, or 1. E 9.

Table 30 shows the sequence of the phage vector DY3FHC87 (SEQ ID NO:894) which carries a bla gene, a display cassette for heavy chains under control of a $P_{lac}$ promoter. DY3FHC87 contains all the genes of M13 as well. Infecting F+ E. coli cells that harbor a diversity of light chains in a vector such as pLCSK23 (Sequence in Table 40) (SEQ ID NO:896). The vector pLCSK23 carries a $Kan^R$ gene. Under the control of Plac promoter, there is a gene beginning at base 2215 having a signal sequence (bases 2215-2277), a VL (in this sequence the VL encodes the sequence shown in (SEQ ID NO:897) from base 2278 to base 2598, Ckappa from base 2599 to 2922, a linker that allows an NotI site from 2923 to 2931, and a V5 tag (bases 2932-2973). There are an SfiI site at 2259-2271 and a KpnI site at 2602-2605 to allow easy replacement of Vkappas. (SEQ ID NO:897) is an example of the proteins that are secreted. It is to be understood that CKappa and the V5 tag are constant. All of the proteins shown in Table 19 (VK1O2gl-JK3, VK1O2var1, VK1O2var2, VK1O2var3, VK1O2var4, VK1O2var5, VK3L6gl-JK4, VK3L6var1, VK3L6var2, VK3L6var3, VK3L6var4, VK3L6var5, VK3L6var6, VK3L6var7, VK3L6var8, VK3A27gl-JK3, VK3A27var1, VK3A27var2, VK3A27var3, VK3A27var4, VK3A27var5, VK3A27var6, VK3A27var7, VK3L2gl-JK3, and VK1glL8-JK5) will have these sequences attached at the carboxy end.

Light Chain Diversity

Table 800 shows a kappa LC (light chain) that is known to pair well with 3-23 and with five CDR mutations with one HC based on 3-23, LC K1(O12)::JK1 makes a high affinity Ab to a protein target. O12 is a frequently used VKI. The gene has been designed to have useful, distinct restriction sites in the signal sequence (ApaLI), FR1 (XhoI, SgfI), FR2 (KpnI), FR3(XbaI), and Fr4::Ckappa (BsiWI) so that each CDR and be replaced with a varied population.

In human LCs, CDR3 is most important and CDR1 is next most important. CDR2 seldom makes contact with the Ag. Diversity is introduced into the CDRs as shown in Table 900 and Table 1000 (CDR1), Table 1100 and Table 1200 (CDR2), Tables 1300, 1400, and 1500 (CDR3). For Economical Selection of Heavy Chains (ESHC), a small number, for example, 50 LCs with diversity in CDR3 as in Table 1200 are picked for expression in pLCSK24 for secretion into the periplasm. More LCs can be used if several cell lines are maintained so that each cell line contains, for example, 50 or fewer LC.

Table 900 shows diversity for LC CDR1. The library can contain the O12 residue with the added diversity of the AA types shown as "allowed"; reading "allowed" as "additional allowed types" in Tables 900, 1000, 1100, 1200, 1300, 1400. O12 has $R_{24}ASQSISSYLN_{34}$ (SEQ ID NO: 935). Other VK1 loci have Q at 24. Other loci have M at 25. $S_{26}$ and $Q_{27}$ are invariant in VKI. Other VKI loci have D or G at 28. $I_{29}$ and $L_{33}$ are invariant in VKI and the side groups are oriented inward. Other VKI loci allow the diversity shown in Table 900 at positions 30, 31, 32, and 34. In Table 900, only seven of the eleven positions are varied and the total diversity is 576.

Table 1000 shows a higher level of diversity for LC CDR1. Here 8 of 11 positions have been varied. Those that are constant are either far from the combining site or have buried side groups.

Table 1100 shows a low level variegation for CDR2. CDR2 is far from the antigen combining site and diversity here may not be very useful. Indeed, the GL diversity is very limited. Table 1100 includes the GL diversity. Table 1200 contains a higher level of diversity, 1920 sequences allowed.

Table 1300 shows a low level of diversity for LC CDR3, 2160 sequences. Table 1400 shows a higher level which allows 105,840 sequences.

For ROLIC, about $3 \times 10^7$ LC are produced having the diversity shown in Tables 900, 1100, and 1300.

Heavy Chain Diversity

Ab HC (heavy chain) have diversity in CDR1, CDR2, and CDR3. The diversity in CDR3 is especially complex because there is both sequence and length diversity. The sequence diversity is not random. Cells making Ab genes join a V segment to a D segment to a JH segment. The D segment is optional; about half of natural human Abs have a recognizable D. There can be extensive editing at the V-D, D-J, or V-J boundaries with none to many bases added or removed. An Ab that has a germline V::D::JH could be viewed as a germline Ab.

Human D segments are shown in Table 21. Each germline (GL) D segment may appear in an Ab gene in any of the three forward reading frames. In some reading frames, some of the D segments encode stop codons. These D segments do occur rarely with the stop codon modified. Table 600 shows the frequency of each D segment as a percent of all observed D segments. Most of the examples herein that contain D segments use Ds that are fairly common (>2% of all observed Ds).

In one aspect, the present invention involves composing Ab HC genes by fusing 3-23 (or another VH, such as 4-34) to one of a) a number of amino acids picked from the set comprising (S, Y, D, R, N), b) a D region, c) a JH region, and d) the FR4 portion of a JH region. These fusions can be a GL 3-23 or a 3-23 that has synthetic diversity in CDR1 and/or CDR2. The lengths of the HC CDR3 and be any number from about 3 to about 24. Preferably, the library would contain member with HC CDR3 of lengths 6, 8, 10, 12, 14, 16, 18, and 20. Alternatively, the lengths could be 5, 8, 11, 14, 17, and 20 or any other combination.

Table 21 shows a number of examples of designs of suitable CDR3s with lengths from 6 to 20. The codons that specify the uppercase letters in column 2 are to be synthesized with wobbling. Column 3 shows the level of doping. Table 100 shows ratios in which the various lengths of HC CDR3 could be combined to form a library that is expected to contain Abs that bind almost all protein targets.

TABLE 100

| Length | 6 | 8 | 10 | 12 | 14 | 16 | 20 |
|---|---|---|---|---|---|---|---|
| Diversity | $1. \times 10^5$ | $2. \times 10^5$ | $4. \times 10^5$ | $8. \times 10^5$ | $8. \times 10^5$ | $8. \times 10^5$ | $4. \times 10^5$ |

For length 6, Table 21 four examples are given. For example, 6a has VH(3-23) joined directly to JH1 with the first six AAs wobbled, 6b has Tyr joined to D4-17 in second reading frame joined to the FR4 AAs of JH1, and 6c has D5-5(3) joined to the FR residues of JH1. Since these give different kinds of diversity, including all is preferred, but a library containing only one of these should give useful Abs.

For length 8, Table 21 shows three examples. 8a has YY fused to all of JH1 while 8b has one Y fused to D6-13(1) fused to the FR region of JH1. Lengths 10, 12, 14, 16, and 20 are also shown in Table 21. The HC CDR3 diversity could be built in a germline 3-23 or 3-23 containing synthetic diversity. Alternatively, a different VH, such as 4-34 could be used.

ROLIC is a method in which a small population of HCs are expressed in $F^+$ E. coli as soluble proteins. The population is infected with phage that carry LC::III$_{stump}$ fusions. The phage produced obtain a HC from the periplasm of the cell that produces them. These phage can be bound to immobilized target and the binder are separated from the non-binders. The size of the population is important because when the recovered phage are propagated, the recovered phage must find the same type of cell as it came from to continue the association between LC and HC. Thus it is desirable that the number of HC be small in each cell line. Thus it may be desirable to maintain a number of cell lines with up to 10, 20, 30, or 40 different HC in each cell line. Thus we may have 1, 2, 4, 6, 8, 10, 24, 48, or 96 cell lines and we perform the same number of parallel phage productions, selections, and amplifications. After one or two rounds, we test colonies for production of phage that bind the target by an ELISA assay. Each ELISA colony contains a useful LC and a useful HC, but they are not on the same piece of DNA. Nevertheless, we know the start and end of each LC and each HC and can therefore use PCR on the colony to produce a Fab display or Fab secretion cassette that can be put into a display phage or phagemid or into a Fab-production plasmid.

In Efficient Selection of HCs (ESHC), we reverse the roles of LC and HC in ROLIC and have LCs in a plasmid so that they are produced as soluble proteins in the periplasm of $F^+$ E. coli. We produce the HC diversity in a phage vector that has no LC gene. We infect the LC-producing $F^+$ E. coli with the HC-carrying phage. We obtain phage that carry an HC gene and both HC and LC proteins. We select these phage for binding to the target. In many Abs, the LC is permissive and does not contribute greatly to binding affinity. Picking the best LC can greatly increase affinity, but it is usually possible to select a Fab with a very limited repertoire of LCs. Thus, we place a small set of LCs, preferable germline in the framework regions in the LC-producing $F^+$ E. coli. If there are, for example, 25 LC in the LC cell line, then we obtain a 25-fold reduction in the number of cell transformants that need to be made.

The libraries described have a range of HC CDR3 lengths. To favor proper folding, the HC CDR3 have either a D segment or no D segment joined to most, all, or the framework portion of a JH segment. The sequences are diversified by using wobble DNA synthesis. Although this theoretically allows any amino-acid type at any position, in practice, the actual sequences are strongly biased toward the parental sequences and AA types that are close in the genetic code table.

By using ESHC, we can sample new designs of synthetic HC CDR3 diversity. In the examples given, we use a pool of, for example, 50 LCs. A library of $5 \times 10^8$ HC should perform as well as an old-style library of $2.5 \times 10^{10}$ but require far less effort.

When wobbling a sequence, picking the initial codons affects the actual mixture of AAs seen in the library. Table 300 shows which amino-acid substitutions require 1, 2, or 3 base changes from each starting parental codon. For example, if we start with gct or gcc for Ala, all three stop codons require three base changes and so are rare. If using 76:8:8:8 mixtures, Ala will appear in 57% of the cases (0.76*0.76). V, G, T, P, S will each appear in about 6% and D about 3%. E, I, L, F, Y, H, N, C, and R will be down about 10-fold. M, W, Q, K, Am, Oc, and Op will be even rarer. If we started with gca, then E would replace D in needing only one base change, but opal and ochre stops require only two base changes, which is undesirable. The preferred codons are marked with a star (*). The choice for serine is complicate our desire to have Y substitute for S with high frequency. This brings Op and Oc into the group that differ from the parent by only two bases. This problem can be overcome by cloning the HC CDR3 repertoire before an antibiotic resistance gene such as KanR or AmpR and selecting for resistance, thus eliminating the members that contain stop codons. In addition, the library can be produced in supE E. coli which insert Q instead of stopping.

TABLE 300

| Amino acid | Parental codon | 1 base change | 2 base changes | 3 base changes |
|---|---|---|---|---|
| A* | gct, gcc | V, D, G, T, P, S | E, I, L, F, Y, H, N, C, R | M, W, Q, K, Am, Oc, Op |
| A | gca | V, E, G, T, P, S | D, I, L, Oc, Q, K, Op, R | M, W, H, N, C, Am, F, Y |

TABLE 300-continued

| Amino acid | Parental codon | 1 base change | 2 base changes | 3 base changes |
|---|---|---|---|---|
| A | gcg | V, E, G, T, P, S | D, M, L, Am, Q, K, R, W | I, F, Y, Oc, Op, H, N, C |
| C | tgt, tgc | Y, S, F, W, Op, R, G | L, H, N, D, P, T, A, V, I | Am, Oc, Q, K, E, M |
| D | gat, gac | E, G, A, V, N, H, Y | F, S, C, L, P, Q, K, R, Oc, Am, I, T | M, W, Op |
| E | gaa | D, G, A, V, K, Q, Oc | Am, L, I, S, P, T, R, Op, Y, H, N | M, F, C, W |
| E* | gag | D, G, A, V, K, Q, Am | M, L, S, P, T, Y, H, N, Oc, R, W | F, C, I, Op |
| F | ttt, ttc | L, I, V, S, Y, C | M, Am, Op, Oc, W, P, T, A, H, N, D, R, G | Q, K, E |
| G* | ggt, ggc | D, A, V, S, R, C | E, W, F, L, I, T, P, Y, H, N | Am, Oc, Op, M, Q, K |
| G | gga | E, A, V, R, Oc | D, W, L, I, S, P, T, Op, Q, K | Am, Oc, M, F, Y, H, N |
| G | ggg | E, A, V, R, W | D, Oc, L, M, S, P, T, Am, Op, Q, K | Oc, I, F, Y, H, N |
| H | cat, cac | Q, Y, N, D, L, P, R | F, S, C, I, T, V, A, D, G, Am, Oc | Op, W, M, E |
| I* | att, atc | M, L, F, V, T, N, S | Y, C, P, H, R, A, D, G | Am, Op, Oc, W, Q, K, E |
| I | ata | M, L, V, T, K, R | Op, Oc, S, P, Q, A, E, G, F, N | Am, C, D, H, W, Y |
| K | aaa | N, Q, Oc, E, P, I, R | H, Y, D, M, L, V, S, T, A, Am, Op, G | C, F, W |
| K* | aag | N, Q, Am, E, P, M, R | H, Y, D, I, L, V, S, T, A, Oc, G, W | C, F, Op |
| L | tta | F, S, Oc, Op, I, V | Y, C, W, M, P, T, A, Q, K, E, R, G, Am | D, H, N |
| L | ttg | F, S, Am, W, M, V | Y, C, Oc, Op, P, T, A, Q, K, E, R, G, I | D, H, N |
| L* | ctt, ctc | F, I, V, P, H, R | M, S, Y, C, T, N, A, D, G | Am, Oc, Op, W, E, K, Q |
| L | cta | I, V, P, Q, R | F, M, S, Oc, Op, T, K, A, E, G, H | Am, W, D, N, C, Y |
| L | ctg | M, V, P, Q, R | F, I, S, Am, T, K, A, E, G, H, W | Oc, Op, D, N, C, Y |
| M | atg | L, V, T, K, R, I | F, N, S, P, A, Am, Q, E, W, G | Oc, Op, Y, C, H, D |
| N | aat, aac | K, Y, H, D, I, T, S | F, C, L, P, R, V, A, G, M, Q, E, Am, Oc | Op, W |
| P* | cct, ccc | S, T, A, L, H, R | F, Y, C, I, N, V, D, G, Q | Am, Oc, Op, W, M, E, K |
| P | cca | S, T, A, L, Q, R | Oc, Op, I, K, V, E, G, H | Am, W, M, D, N, C, F, Y |
| P | ccg | S, T, A, L, Q, R | Am, M, K, V, E, G, H | C, D, F, I, N, W, Y, Oc, Op |
| Q | caa | Oc, K, E, R, P, L, H | Y, Am, N, D, S, T, A, I, V, G, Op | F, C, W, M |
| Q* | cag | H, Am, K, E, R, P, L | N, D, Y, M, T, V, A, G, W, Oc, S | C, F, Op, I |
| R* | cgt, cgc | C, S, G, H, P, L | Op, W, Q, F, Y, I, T, N, V, A, D | Am, Oc, M, E, K |
| R | cga | G, Op, Q, P, L | Oc, S, C, W, H, I, V, T, A, E, K | Am, M, C, D, N, F, Y |
| R | cgg | G, W, Q, P, L | Am, Op, S, M, V, T, A, K, E, H, C | F, Y, I, Oc, D, N |
| R | aga | G, Op, S, K, T, I | C, W, N, M, L, V, P, A, Oc, Q, E | F, Y, H, D, Am |
| R | agg | G, W, S, K, T, M | C, Op, Am, L, I, V, A, Q, P, E, N | F, Y, H, D, Oc |
| S* | tct, tcc | F, Y, C, P, T, A | L, Oc, Op, Am, W, I, V, N, D, R, G, H | E, K, M, Q |
| S | tca | L, Oc, Op, P, T, A | F, Y, C, W, Q, R, I, K, V, E, G, Am | M, W, D, N, H |
| S | tcg | L, Am, W, P, T, A | F, Y, C, Op, Oc, Q, R, M, K, V, E, G | I, D, N, H |
| S | agt, agc | C, R, G, N, T, I | F, Y, L, P, H, V, A, D, K, W, Op | Am, Oc, M, E, Q |
| T* | act, acc | S, P, A, I, N | F, Y, C, L, H, R, M, K, V, D, G | Am, Oc, Op, W, E, Q |
| T | aca | S, P, A, I, K, R | L, Oc, Op, Q, M, E, G, V, N | F, Y, C, Am, W, D, H |
| T | acg | S, P, A, M, K, R | I, N, L, Am, W, Q, V, E, G | C, F, Y, Oc, Op, D, H |
| V* | gtt, gtc | F, L, I, A, D, G | S, P, T, Y, H, N, E, C, R, M | Am, Oc, Op, W, Q, K |
| V | gta | L, I, A, E, G | F, M, D, S, P, T, Oc, Op, Q, R, K | Am, W, C, Y, H, N |
| V | gtg | L, M, A, E, G | F, I, D, S, P, T, Am, Q, R, K, W | Oc, Op, C, Y, H, N |
| W | tgg | C, R, G, Am, S, L, Op | P, Q, F, M, T, K, V, A, E, Oc, Y | D, N, H, I |
| Y | tat, tac | C, S, F, N, H, D, Oc, Am | L, W, Q, K, E, P, I, T, V, A, G, Op, R | M |

Am is TAG stop,
Op is TGA,
Oc is TAA

Methods of Using the Libraries

Off-Rate Selection. Since a slow dissociation rate can be predictive of high affinity, particularly with respect to interactions between polypeptides and their targets, the methods described herein can be used to isolate ligands with a desired kinetic dissociation rate (i.e., reduced) for a binding interaction to a target.

To select for slow dissociating antibodies from a display library, the library is contacted to an immobilized target. The immobilized target is then washed with a first solution that removes non-specifically or weakly bound antibodies. Then the bound antibodies are eluted with a second solution that includes a saturating amount of free target, i.e., replicates of the target that are not attached to the particle. The free target binds to antibodies that dissociate from the target. Rebinding of the eluted antibodies is effectively prevented by the saturating amount of free target relative to the much lower concentration of immobilized target.

The second solution can have solution conditions that are substantially physiological or that are stringent (e.g., low pH, high pH, or high salt). Typically, the solution conditions of the second solution are identical to the solution conditions of the first solution. Fractions of the second solution are collected in temporal order to distinguish early from late fractions. Later fractions include antibodies that dissociate at a slower rate from the target than biomolecules in the early fractions. Further, it is also possible to recover antibodies that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards antibodies that bind to a non-target molecule. Examples of non-target molecules include, e.g., a carbohydrate molecule that differs structurally from the target molecule, e.g., a carbohydrate molecule that has a different biological property from the target molecule. In the case of a sulfated carbohydrate, a non-target may be the same carbohydrate without the sulfate or with the sulfate in a different position. In the case of a phosphopeptide, the non-target may be the same peptide without the phosphate or a different phosphopeptide.

In one implementation, a so-called "negative selection" step is used to discriminate between the target and related non-target molecule and a related, but distinct non-target molecules. The display library or a pool thereof is contacted to the non-target molecule. Members that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to the target.

In certain embodiments, the antibodies comprising the CDR3s of the invention may be able to bind carbohydrates. Methods for evaluating antibodies for carbohydrate binding include ELISA, immunohistochemistry, immunoblotting, and fluorescence-activated cell sorting. These methods can be used to identify antibodies which have a $K_D$ of better than a threshold, e.g., better than 100 nM, 50 nM, 10 nM, 5 nM, 1 nM, 500 pM, 100 pM, or 10 pM.

ELISA. Proteins encoded by a display library can also be screened for a binding property using an ELISA assay. For example, each protein is contacted to a microtitre plate whose bottom surface has been coated with the target, e.g., a limiting amount of the target. The plate is washed with buffer to remove non-specifically bound polypeptides. Then the amount of the protein bound to the plate is determined by probing the plate with an antibody that can recognize the polypeptide, e.g., a tag or constant portion of the polypeptide. The antibody is linked to an enzyme such as alkaline phosphatase, which produces a calorimetric product when appropriate substrates are provided. The protein can be purified from cells or assayed in a display library format, e.g., as a fusion to a filamentous bacteriophage coat. Alternatively, cells (e.g., live or fixed) that express the target molecule, e.g., a target that contains a carbohydrate moiety, can be plated in a microtitre plate and used to test the affinity of the peptides/ antibodies present in the display library or obtained by selection from the display library.

In another version of the ELISA assay, each polypeptide of a diversity strand library is used to coat a different well of a microtitre plate. The ELISA then proceeds using a constant target molecule to query each well.

Cell Binding Assays. Antibodies can be evaluated for their ability to interact with one or more cell types, e.g., a hematopoietic cell. Fluorescent activated cell sorting (FACS) is one exemplary method for testing an interaction between a protein and a cell. The antibody is labeled directly or indirectly with a fluorophore, before or after, binding to the cells, and then cells are counted in a FACS sorter.

Other cell types can be prepared for FACS by methods known in the art.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate polypeptide is attached to the display library vehicle, e.g., a bacteriophage.

Surface Plasmon Resonance (SPR). The binding interaction of a molecule isolated from a display library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden).

Information from SPR can be used to provide an accurate and quantitative measure of the equilibrium dissociation constant ($K_D$), and kinetic parameters, including $k_{on}$ and $k_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $k_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $k_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Protein Arrays. Proteins identified from the display library can be immobilized on a solid support, for example, on a bead or an array. For a protein array, each of the polypeptides is immobilized at a unique address on a support. Typically, the address is a two-dimensional address. Methods of producing polypeptide arrays are described, e.g., in De Wildt et al. (2000) Nat. Biotechnol. 18:989-994; Lueking et al. (1999) Anal. Biochem. 270:103-111; Ge (2000) Nucleic Acids Res. 28, e3, 1-VII; MacBeath and Schreiber (2000) Science 289: 1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

Kits

Also provided are kits for use in carrying out a method according to any aspect of the invention. The kits may include the necessary vectors. One such vector will typically have an origin of replication for single stranded bacteriophage and either contain the sbp member nucleic acid or have a restriction site for its insertion in the 5' end region of the mature coding sequence of a phage capsid protein, and with a secretory leader coding sequence upstream of said site which directs a fusion of the capsid protein exogenous polypeptide to the periplasmic space.

Also provided are packages encoding the HC CDR3s as defined above and polypeptides comprising the HC CDR3s and fragments and derivatives thereof, obtainable by use of any of the above defined methods. The derivatives may comprise polypeptides fused to another molecule such as an enzyme or a Fc tail.

The kit may include a phage vector (e.g., DY3F87HC) which has a site for insertion of HC CDR3s for expression of the encoded polypeptide in free form. The kit may also include a plasmid vector for expression of soluble light chains, e.g., pLCSK23. The kit may also include a suitable cell line (e.g., TG1). The diversity of light chains encoded by pLCSK23 may be 10, 15, 20, 25, 30, or 50. The LCs in the diversity may be constructed or picked to have certain desirable properties, such as, being germline in the framework regions and having diversity in CDR3 and/or CDR1. The germlines may be of highly utilized ones, e.g., VK1_2-O2, VK3_1-A27, VK3_5-L6, VK3_3-L2 for kappa and VL2_2a2, VL1_1c, VL1_1g, VL3_3r for lambda.

For example, one could clone genes for

VK1O2gl-JK3, VK1O2var1, VK1O2var2, VK1O2var3, VK1O2var4, VK1O2var5, VK3L6gl-JK4, VK3L6var1, VK3L6var2, VK3L6var3, VK3L6var4, VK3L6var5, VK3L6var6, VK3L6var7, VK3L6var8, VK3A27gl-JK3, VK3A27var1, VK3A27var2, VK3A27var3, VK3A27var4, VK3A27var5, VK3A27var6, VK3A27var7, VK3L2gl-JK3, VK1glL8-JK5, and VK1GLO12-JK3 (amino-acid sequences shown in Table 19) into pLCSK23.

TABLE 19

26 VL to be used in pLCSK23.

```
VK1O2gl-JK3 (SEQ ID NO: 4)
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPFTFGP GTKVDIK               107

VK1O2var1 (SEQ ID NO: 5) S28D
DIQMTQSPSS LSASVGDRVT ITCRASQDIS SYLNWYQQKP GKAPKLLIYA ASSLQSGVPS   60
RFSGSGSGTD FTLTISSLQP EDFATYYCQQ SYSTPFTFGP GTKVDIK               107

VK1O2var2 (SEQ ID NO: 6) S91R
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ RYSTPFTFGP GTKVDIK               107

VK1O2var3 (SEQ ID NO: 7) S91E
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ EYSTPFTFGP GTKVDIK               107

VK1O2var4 (SEQ ID NO: 8) S31R
DIQMTQSPSS LSASVGDRVT ITCRASQSIS RYLNWYQQKP GKAPKLLIYA ASSLQSGVPS   60
RFSGSGSGTD FTLTISSLQP EDFATYYCQQ SYSTPFTFGP GTKVDIK               107

VK1O2var5 (SEQ ID NO: 9) S31E, S93R
DIQMTQSPSS LSASVGDRVT ITCRASQSIS EYLNWYQQKP GKAPKLLIYA ASSLQSGVPS   60
RFSGSGSGTD FTLTISSLQP EDFATYYCQQ SYRTPFTFGP GTKVDIK               107

VK3L6gl-JK4 (SEQ ID NO: 10)
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPLTFGG GTKVEIK               107

VK3L6var1 (SEQ ID NO: 11) S31R
EIVLTQSPAT LSLSPGERAT LSCRASQSVS RYLAWYQQKP GQAPRLLIYD ASNRATGIPA   60
RFSGSGSGTD FTLTISSLEP EDFAVYYCQQ RSNWPLTFGG GTKVEIK               107

VK3L6var2 (SEQ ID NO: 12) S92R
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RRNWPLTFGG GTKVEIK               107

VK3L6var3 (SEQ ID NO: 13) S92G
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RGNWPLTFGG GTKVEIK               107

VK3L6var4 (SEQ ID NO: 14) S92Y
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RYNWPLTFGG GTKVEIK               107
```

TABLE 19-continued

26 VL to be used in pLCSK23.

```
VK3L6var5 (SEQ ID NO: 15) S92E
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RENWPLTFGG GTKVEIK                107

VK3L6var6 (SEQ ID NO: 16) Y32F
EIVLTQSPAT LSLSPGERAT LSCRASQSVS SFLAWYQQKP GQAPRLLIYD ASNRATGIPA    60
RFSGSGSGTD FTLTISSLEP EDFAVYYCQQ RSNWPLTFGG GTKVEIK                107

VK3L6var7 (SEQ ID NO: 17) Y32D
EIVLTQSPAT LSLSPGERAT LSCRASQSVS SDLAWYQQKP GQAPRLLIYD ASNRATGIPA    60
RFSGSGSGTD FTLTISSLEP EDFAVYYCQQ RSNWPLTFGG GTKVEIK                107

VK3L6var8 (SEQ ID NO: 18) N93G
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSGWPLTFGG GTKVEIK                107

VK3A27g1-JK3 (SEQ ID NO: 19)
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPFTFG PGTKVDIK                108

VK3A27var1 (SEQ ID NO: 20) S31R
EIVLTQSPGT LSLSPGERAT LSCRASQSVS RSYLAWYQQK PGQAPRLLIY GASSRATGIP    60
DRFSGSGSGT DFTLTISRLE PEDFAVYYCQ QYGSSPFTFG PGTKVDIK                108

VK3A27var2 (SEQ ID NO: 21) S32R
EIVLTQSPGT LSLSPGERAT LSCRASQSVS SRYLAWYQQK PGQAPRLLIY GASSRATGIP    60
DRFSGSGSGT DFTLTISRLE PEDFAVYYCQ QYGSSPFTFG PGTKVDIK                108

VK3A27var3 (SEQ ID NO: 22) S32D
EIVLTQSPGT LSLSPGERAT LSCRASQSVS SDYLAWYQQK PGQAPRLLIY GASSRATGIP    60
DRFSGSGSGT DFTLTISRLE PEDFAVYYCQ QYGSSPFTFG PGTKVDIK                108

VK3A27var4 (SEQ ID NO: 23) G93E
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYESSPFTFG PGTKVDIK                108

VK3A27var5 (SEQ ID NO: 24) G93R
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYRSSPFTFG PGTKVDIK                108

VK3A27var6 (SEQ ID NO: 25) S30D, G93E
EIVLTQSPGT LSLSPGERAT LSCRASQSVD SSYLAWYQQK PGQAPRLLIY GASSRATGIP    60
DRFSGSGSGT DFTLTISRLE PEDFAVYYCQ QYESSPFTFG PGTKVDIK                108

VK3A27var7 (SEQ ID NO: 26) S94R
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGRSPFTFG PGTKVDIK                108

VK3L2g1-JK3 (SEQ ID NO: 27)
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPFTFGP GTKVDIK                107

VK1g1L8-JK5 (SEQ ID NO: 28)
DIQLTQSPSF LSASVGDRVT ITCRASQGIS SYLAWYQQKP GKAPKLLIYA ASTLQSGVPS    60
RFSGSGSGTE FTLTISSLQP EDFATYYCQQ LNSYPITFGQ GTRLEIK                107

VK1GLO12-JK3 (SEQ ID NO: 897)
DIQMTQSPSS LSASVGDRV TITCRASQSI SSYLNWYQQK PGKAPKLLIY AASSLQSGVP     60
SRFSGSGSGT DFTLTISSL QPEDFATYYC QQSYSTPFTF GPGTKVDIKR GTVAAPSVFI   120
FPPSDEQLKS GTASVVCLL NNFYPREAKV QWKVDNALQS GNSQESVTEQ DSKDSTYSLS   180
STLTLSKADY EKHKVYACE VTHQGLSSPV TKSFNRGECA AAGKPIPNPL LGLDST       236
```

The kits may include ancillary components required for carrying out the method, the nature of such components depending of course on the particular method employed. Useful ancillary components may comprise helper phage, PCR primers, buffers, and/or enzymes of various kinds. Buffers and enzymes are typically used to enable preparation of nucleotide sequences encoding Fv, scFv or Fab fragments derived from rearranged or unrearranged immunoglobulin genes according to the strategies described herein.

Methods of Introducing Diversity

There are many ways of generating DNA that is variable. One way is to use mixed-nucleotide synthesis (MNS). One version of MNS uses equimolar mixtures of nucleotides as shown in Table 5. For example, using NNK codons gives all twenty amino acids and one TAG stop codon. The distribution is 3(R/S/L): 2(A/G/V/T/P): 1(C/D/E/F/H/I/K/M/N/Q/W/Y) (e.g., 3 of each of Arg, Ser, and Leu, and so forth). An alternative, herein termed "wobbling", uses mixed nucleotides but not in equimolar amounts. For example, if a parental codon were TTC (encoding Phe), we could use a mixture of (0.082 T, 0.06 C, 0.06 A, and 0.06 G) in place of T and a mixture of (0.082 C, 0.06 T, 0.06 A, and 0.06 G) in place of C. This would give TTC or TTT (encoding Phe) 59% of the time and Leu 13%, S/V/I/C/Y ~5%, and other amino-acid types less often.

Van den Brulle et al. (*Biotechniques* 45:340-3 (2008)) describe a method of synthesis of variable DNA in which type IIs restriction enzymes are used to transfer trinucleotides from an anchored hair-pin oligonucleotide (PHONs) to a so called "splinker". See also EP patents 1 181 395, EP 1 411 122, EP 1 314 783 and EP applications EP 01127864.5, EP 04001462.3, EP 08006472.8. By using mixtures of anchored PHONs and splinkers, one can build libraries in which desired amino-acid types are allowed in designer-determined ratios. Thus, one can direct that one amino-acid type is present, for example 82% of the time and 18 other amino-acid types (all non-parental amino-acid types except Cys) are present at 2% each. Herein, we will refer to such a synthesis as "dobbling" (digital wobbling). In some aspects, dobbling is preferred to wobbling, but wobbling provides useful embodiments, partly because the structure of the genetic code table causes wobbling to make mostly conservative substitutions. Dobbling does offer the possibility to exclude unwanted amino-acid types. In CDRs, unpaired cysteines are known, even in Abs approved as therapeutics, but in some embodiments, one would like to avoid them. In some embodiments, when diversifying a D region that contains a pair of cysteines, the cysteines are not allowed to vary because the disulfide-closed loop is an important structural element and because one does not want unpaired cysteines.

In addition, one can synthesize a DNA molecule that encodes a parental amino-acid sequence and subject that DNA to error-prone PCR using primers that cover the framework regions so that mutations in the framework regions are avoided.

TABLE 5

Standard codes for mixed nucleotides

| | |
|---|---|
| N is equimolar A, C, G, T | |
| B is equimolar C, G, T | (not A) |
| D is equimolar A, G, T | (not C) |
| H is equimolar A, C, T | (not G) |
| V is equimolar A, C, G | (not T) |
| K is equimolar G, T | (Keto) |
| M is equimolar A, C | (aMino) |
| R is equimolar A, G | (puRine) |
| S is equimolar C, G | (Strong) |
| W is equimolar A, T | (weak) |
| Y is equimolar C, T | (pYrimidine) |

TABLE 6

Example of mixed nucleotides for wobbling

| | | | | |
|---|---|---|---|---|
| e = 0.82 | A + 0.06 | C + 0.06 | G + 0.06 | T |
| q = 0.06 | A + 0.82 | C + 0.06 | G + 0.06 | T |
| j = 0.06 | A + 0.06 | C + 0.82 | G + 0.06 | T |
| z = 0.06 | A + 0.06 | C + 0.06 | G + 0.82 | T |

EXEMPLIFICATION

The present invention is further illustrated by the following examples which should not be construed as limiting in any way. The contents of all references, pending patent applications and published patents, cited throughout this application are hereby expressly incorporated by reference.

Prophetic Example 1

Libraries with Very Short HC CDR3s

Very short HC CDR3s have been described in the art. Kadirvelraj et al. (2006) *Proc. Natl. Acad. Sci. USA* 103: 8149-54 have described a four amino-acid HC CDR3 sequence in an antibody that binds *Streptococcus* Type B III Ag (GBS-Ag) but not to *Streptococcus pneumoniae* capsular Ag. GBS-Ag is sialylated at regular intervals. *S. pneumoniae* capsular Ag (SPC-Ag) is very similar but lacks the sialic acid groups. Such a short HC CDR3 creates a wide groove into which a carbohydrate could bind, and such Abs are very, very rare in existing antibody libraries. Thus, current libraries do not afford a large variety of potential binders to carbohydrates.

Ab 1B1 is the murine mAb that binds GBS-Ag; Ab 1QFU is the mAb having a known 3D structure and the closest sequence; and 1NSN is an antibody of known 3D structure having a HC CDR3 of length 4. Examination of a 3-23 HC structure gives a distance from C$\alpha$ of $R_{94}$ (which ends FR3) to the C$\alpha$ of the $W_{104}$ (which begins FR4) of ~10 Å. The CDR3 of 1B1 (NWDY (SEQ ID NO:29)) shows that the AAs need not have only small side groups or be mostly of glycine. Three amino acids (AAs) can bridge 10 Å, although PPP might not work. Indeed, we have obtained a few Fabs with CDR3s as short as 3 AAs, but they are very rare.

Although short and very short HC CDR3s have been described, no one has suggested making an Ab library having many members (e.g., greater than about 50%, about 60%, about 70%, about 80%, about 90%, or about 95% of members) with short HC CDR3s (e.g., HC CDR3s of 3 to 5 amino acids). One approach to building an effective library is to first design amino-acid sequences that could arise from V-J or V-D-J coupling. For CDR3 length 3, 4, or 5, we start with the amino-acid sequences shown in Table 7. For example, Sequence V-3JH1 shows the C-terminal end of 3-23 FR3 (TAVYYCAK (SEQ ID NO:30)) followed by JH1 which has been trimmed from the N-terminal end until three amino-acids before the Trp-Gly that starts FR4. V-3JH2 shows the end of FR3 followed by the trimmed JH2. The sequence following V-3JH6 are constructed by joining FR4 to a trimer taken from a human D segment followed by the FR4 region of a human JH segment. 3D3-3.3.2 would be a trimer from segment D3-3, third reading frame starting at the second amino acid. 5D5-12.2.3 is a pentamer from D5-12 in reading frame 2 starting at amino acid 3. Some of the germ-line D segments contain stop codons, yet they appear in natural antibodies when the stop codons are edited away. Here we assume that the most likely change fro TAA and TAG codons is to Tyr (Y) and that TGA stops are most likely mutated to Trp (W). Table 20 shows the amino-acid sequences of the human D segments; the types of stop codons is indicated by the use of * for TAG, @ for TAA, and $ for TGA. In Table 11 are 266 distinct trimers that can be constructed from human D segments. The TAA and TAG stops have been changed to Tyr shown as "y" (i.e., lowercase). These could also be changed to Ser, Cys, Phe, Gln, Lys, or Glu by single base changes. TAG could be changed by single base changes to Trp as well as Tyr, Gln, Lys, Glu, Ser, and Leu. Table 12 shows the 266 distinct tetramers that can be obtained by trimming human D segments. Table 13 shows the 215 pentamers that can be obtained from trimming human D segments. Table 14 shows the 155 hexamers that can be obtained by trimming human D segments. The libraries to be built have substantial diversity in HC CDR1 and HC CDR2. The sequence diversity of HC CDR3 may be less important than having a short, but acceptable sequence. The diversity of JH segments or fragments (e.g., 3 or more amino acids) of D segments provides sequences that could be built by the human immune system and so are less likely to be immunogenic.

In one embodiment, the trimers, tetramers, and pentamers that contain a Cys are eliminated.

In one embodiment, the trimers, tetramers, and pentamers that contain a Cys or the came from a D fragment containing a stop are eliminated.

The short libraries constructed using the trimers of Table 11, tetramers of Table 12, pentamers of Table 13 have substantial diversity: 266, 266, and 215 respectively. This is to be compared to the number of peptides of these lengths: 8000, 160000, and 3200000 respectively.

V-3D1-1.1.1-JH1 contains the final portion of FR3 followed by three amino acids from D1-1 (RF1), viz. GTT (SEQ ID NO:257). V-3D1-1.2-JH1 uses amino acids 2-4 of D1-1 (RF1) as the parental CDR3. V-3D3-3.3.3-JH2 shows the end of FR3 followed by amino acids 3-5 of D3-3 (RF 3). The invention comprises any amino-acid sequence comprising FR3::(three, four, or five stop-free AAs of a human D segment)::FR4 from a human JH. Fragments of D regions containing unpaired Cys residues are less preferred than those that are free of unpaired Cys residues. In V-5JH3, there is a Tyr shown as 'y' because JH3 has only 4 codons before the codons for Trp-Gly that define the beginning of FR4. V-5JH4 has a Ser shown as 's' for the same reason. If wobbling is used, the preferred level of purity is between 0.75 and 0.90. The invention comprises the sequences V-3JH1 through V-3JH6, V-4JH1 through V-4JH6, and V-5JH1 through V-5JH6, and libraries containing the same The invention also comprises the sequences in which the CDR region is replaced by a 3, 4, or 5 amino-acid segment from a human D region, and libraries containing the same. The invention further comprises DNA in which the parental sequence has been mutated in the CDR3 region, and libraries containing the same. A preferred embodiment is one in which the average number of base changes per CDR3 is one, two, or three. The methods of mutagenesis include error-prone PCR, wobbling, and dobbling.

TABLE 7

Amino-acid sequences of parental CDR3s of lengths 3, 4, 5

...FR3----- CDR3- FR4--------

Length 3

| | | | |
|---|---|---|---|
| V-3JH1 | TAVYYCAK | FQH | WGQGTLVTVSS (SEQ ID NO: 31) |
| V-3JH2 | TAVYYCAK | FDL | WGRGTLVTVSS (SEQ ID NO: 32) |
| V-3JH3 | TAVYYCAK | FDI | WGQGTMVTVSS (SEQ ID NO: 33) |
| V-3JH4 | TAVYYCAK | FDY | WGQGTLVTVSS (SEQ ID NO: 34) |
| V-3JH5 | TAVYYCAK | FDP | WGQGTLVTVSS (SEQ ID NO: 35) |
| V-3JH6 | TAVYYCAK | MDV | WGQGTTVTVSS (SEQ ID NO: 36) |
| V-3D1-1.1.1-JH1 | TAVYYCAK | GTT | WGQGTLVTVSS (SEQ ID NO: 37) |
| V-3D1-1.1.2-JH1 | TAVYYCAK | TTG | WGQGTLVTVSS (SEQ ID NO: 38) |
| V-3D3-3.3.3-JH2 | TAVYYCAK | IFG | WGRGTLVTVSS (SEQ ID NO: 39) |

Length 4

| | | | |
|---|---|---|---|
| V-4JH1 | TAVYYCAK | YFQH | WGQGTLVTVSS (SEQ ID NO: 40) |
| V-4JH2 | TAVYYCAK | YFDL | WGRGTLVTVSS (SEQ ID NO: 41) |
| V-4JH3 | TAVYYCAK | AFDI | WGQGTMVTVSS (SEQ ID NO: 42) |
| V-4JH4 | TAVYYCAK | YFDY | WGQGTLVTVSS (SEQ ID NO: 43) |
| V-4JH5 | TAVYYCAK | WFDP | WGQGTLVTVSS (SEQ ID NO: 44) |
| V-4JH6 | TAVYYCAK | GMDV | WGQGTTVTVSS (SEQ ID NO: 45) |
| V-4D3-10.1a-JH2 | TAVYYCAK | LLWF | WGRGTLVTVSS (SEQ ID NO: 46) |

Length 5

| | | | |
|---|---|---|---|
| V-5JH1 | TAVYYCAK | EYFQH | WGQGTLVTVSS (SEQ ID NO: 47) |
| V-5JH2 | TAVYYCAK | WYFDL | WGRGTLVTVSS (SEQ ID NO: 48) |
| V-5JH3 | TAVYYCAK | yAFDI | WGQGTMVTVSS (SEQ ID NO: 49) |
| V-5JH4 | TAVYYCAK | sYFDY | WGQGTLVTVSS (SEQ ID NO: 50) |
| V-5JH5 | TAVYYCAK | NWFDP | WGQGTLVTVSS (SEQ ID NO: 51) |
| V-5JH6 | TAVYYCAK | YGMDV | WGQGTTVTVSS (SEQ ID NO: 52) |
| V-5D2-8.2a-JH2 | TAVYYCAK | DIVLM | WGRGTLVTVSS (SEQ ID NO: 53) |

TABLE 8

DNA encoding V-5D2-8.2a-JH2 for wobbling

```
!                                      CDR3.......
!  A   E   D   T   A   V   Y   Y   C   A   K   D   I   V   L   M
  |gct|gag|gaT|aCT|GCA|GtT|taT|taC|tgc|gct aag jez ezq jzz qzz ezj
!
!    W   G   Q   G   T   T   V   T   V   S   S                          (SEQ ID NO: 54)
    tgg ggc cag ggt act acG GTC ACC gtc tcc agt-3'                       (SEQ ID NO: 55)
!               BstEII...
```

Alternatively, one could synthesize three fragments of DNA that correspond to the region from XbaI to BstEII and having residue 94 being K or R followed by 3, 4, or 5 NNK codons, followed by WG . . . of FR4. The allowed variation is $20^3+20^4+20^5=3,368,000$. After amplification, these DNA molecules would be mixed in the ratio 1:10:100 (so that shorter sequences are relatively oversampled) and cloned into the phagemid encoding the kappa library with HC CDR1/2 diversity. A library of $1\times10^9$ would give significant diversity and will allow isolation of antibodies that bind to targets that have small to medium protrusions. For example, various carbohydrates, loops of proteins that are not well ordered (such as GPCRs) may benefit from a groove in the antibody created by having a very short HC CDR3. We can also build a lambda library. The ratio of AA sequences is 1:20:400, and it may be important to sample the shorter sequences more densely. Getting a big, wide gulley in the Ab may require exactly one 3 AA CDR3, but with a 4 AA CDR3, one probably has more leeway and with 5 AAs, even more leeway. In this Example, we use the JH6 version of FR4 from the WG motif onward.

We can select from our current kappa library a collection of, for example, 25 kappa light chains that are a) germline in the framework regions, b) show suitable diversity in CDRs, and c) are of types that produce well and pair well with 3-23. These $LC_s$ will be made in *E. coli* from a vector that carries $Kan^R$ and no phage packaging signal. We would then build our HC library in a phage vector that has no LC. HC and LC will be crossed by infecting the LC producing cells with the HC phage. HC phage that are selected can be combined with the LC of the cell that produces $ELISA^+$ phage or the HCs can be cloned into pMID21 that have the whole LC diversity. Alternatively, the selected HC can be moved into pHCSK85 and used with ROLIC to combine with all the LCs of our collection. Lambda LCs could also be used. Thus, a library of $1\times10^9$ HC in phage can be expanded into a Fab library of $1.2\times10^{11}$ ($1.\times10^9\times117$). If we combined $1\times10^7$ CDR1-2s with $10^6$ HC CDR3s, we could make a library of $5\times10^7$ in which each CDR3 is coupled with 50 CDR1-2s. A library of $5\times10^7$ HCs in phage could give results similar to an old-style library of $6\times10^9$.

TABLE 1

Designs of very short exemplary HC CDR3s

```
C3XXX
! scab DNA      S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!              XbaI...
!
!                                             CDR3.......
!   L   R   A   E   D   T   A   V   Y   Y   C   A   K|R any any any   W   G
  |TTA|AGg|gct|gag|gaT|aCT|GCA|GtT|taT|taC|tgc|gct aRg nnk nnk nnk tgg ggc-
!
!   Q   G   T   T   V   T   V   S   S                                     (SEQ ID NO: 56)
    cag ggt act acG GTC ACC gtc tcc agt-3'                                 (SEQ ID NO: 57)
!              BstEII...
!
(C3XXX)5'-T|GCA|GtT|taT|taC|tgc|gct aRg nnk nnk nnk tgg ggc cag ggt act ac-3'  (SEQ ID NO: 58)
(ON_5)  5'-AcTggAgAcggTgAccgTAgTAcccTggccccA-3'  ! 33 bases                    (SEQ ID NO: 256)
(ON_5 is reverse complement of 5'-tgg ggc cag ggt act acG GTC ACC gtc tcc
agt-3'                                                                         (SEQ ID NO: 59))
! Use ON-1 and ON-3 shown below
!--------------------------------------------------
!
C3X4
! scab DNA      S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!              XbaI...
!
!                                             CDR3...........
!   L   R   A   E   D   T   A   V   Y   Y   C   A   K|R any any any any   W
  |TTA|AGg|gct|gag|gaT|aCT|GCA|GtT|taT|taC|tgc|gct aRg nnk nnk nnk nnk tgg-
!
!   G   Q   G   T   T   V   T   V   S   S                                  (SEQ ID NO: 60)
    ggc cag ggt act acG GTC ACC gtc tcc agt-3'                              (SEQ ID NO: 61)
!               BstEII...
!
(C3X4)5'-GCA|GtT|taT|taC|tgc|gct aRg nnk nnk nnk nnk tgg-
          ggc cag ggt act ac-3'                                             (SEQ ID NO: 62)
! Use ON-1, ON-3, and ON-5
!--------------------------------------------------
C3X5
```

TABLE 1-continued

Designs of very short exemplary HC CDR3s

```
!  scab DNA     S    R    D    N    S    K    N    T    L    Y    L    Q    M    N    S
5'-ttc|act|atc|TCT|AGA|gac|aac|tct|aag|aat|act|ctc|tac|ttg|cag|atg|aac|agC-
!             XbaI...
!
!                                                                  CDR3...............
!  L    R    E    D    T    A    V    Y    Y    C    A    K|R any any any any any
   |TTA|AGg|gct|gag|gaT|aCT|GCA|GtT|taT|taC|tgc|gct aRg nnk nnk nnk nnk nnk-
!
!  W    G    Q    G    T    T    V    T    V    S    S                    (SEQ ID NO: 63)
   tgg ggc cag ggt act acG GTC ACC gtc tcc agt-3'                         (SEQ ID NO: 64)
!                    BstEII...
(C3X5) 5'-GCA|GtT|taT|taC|tgc|gct aRg nnk nnk nnk nnk nnk tgg-
       ggc cag ggt act ac-3'                                              (SEQ ID NO: 65)
!-------------------------------------------------
aRg encodes K or R
```

Alternatively, the current HC diversity can be cloned into DY3F87HC and the CDR3 diversity described above is cloned into that diversity as XbaI-BstEII fragments. A library of, for example, 25 LC are cloned into pLCSK23 and used to create a cell line in TG1 *E. coli*. These cells are infected with the DY3F87HC phage which harbor the novel HC CDR3 (and CDR1-2) diversity. The phage obtained from this infection are selected for binding to a desired target. After two to four rounds of selection, the selected HCs are transferred to pHCSK22 and used to create a cell line which can be used with ROLIC to combine the selected HC with all the LCs in the ROLIC LC library. In this way, a library of 1. E 9 can be give Abs that normally would require construction of a library of 1. E 16 (assuming a LC diversity of 1. E 7).

Prophetic Example 2

Libraries with Very Long HC CDR3s

Sidhu et al. (*J Mol. Biol.* 2004 338:299-310. and US application 20050119455A1) report high-affinity Abs selected from a library in which only Y and S were allowed in the CDRs which were limited in length to 20 amino acids. It may be possible to generate high affinity Abs from a library that has HC CDR3s with one or more of the following forms of diversity: a) several (but not all) sites allowing Y or S, b) including 4-6 NNK codons, c) introducing D segments (with or without diversification in the D), and/or d) using error-prone PCR. We have already sampled the Ab space in which HC CDR3 is in the range ~8 to ~22 with a median length of 13. Thus, libraries in which HC CDR3 is either ~23 AAs or ~35 AAs are possible and may have advantages with certain types of targets. For example, GPCRs are integral membrane proteins with seven helical segments transversing the lipid bilayer of the call that are thought to have multiple states. An antibody having a very long HC CDR3 could form a protuberance that fits into the channel formed by the seven strands. Finding Abs that bind GPCRs has been difficult and intentionally building libraries in which all the members have very long HC CDR3s may ameliorate this problem. The lengths may be made somewhat variable, say 23, 24, or 25 in one library and 33, 34, or 35 in a second.

Below are a number of representative designs. The CDR3 have been broken up and diversity generated that lets the various parts have differing relationships depending on the value of X. A full-length JH1 has been used, and in some designs diversity allowed diversity in the CDR3 part of JH1. Other JHs could be used. In the designs, the D segments are either rich in Y or have an S-rich disulfide loop. The amino-acid sequences of human D segments are shown in Table 3. The places where the D region has either S or Y or allowed other combinations have in particular been varied. Table 4 shows the amino-acid sequences of human J regions.

Each of the libraries could be built in at least four ways: 1) DNA encoding a particular amino acid sequence is first synthesized and subjected to error-prone PCR, 2) the library can be synthesized by wobbling or with mixtures of nucleotides, 3) the library can be built using dobbling, and 4) routes (2) or (3) could be followed by error-prone PCR. As an example of route (1), in Design 12, DNA encoding SEQ ID NO:908 could be synthesized, as shown in SEQ ID NO:911. This DNA could be subjected to error-prone PCR using the primers shown in SEQ ID NO:909 and SEQ ID NO:910. Because these primers cover the framework regions, the errors will occur only in the CDR3.

A library of HCs with CDR3 with length 23 of, for example, $2 \times 10^9$ members and a second library with HC CDR3s of length ~35 also having $2 \times 10^9$ members could be built. Alternatively, the DNA could be mixed to build one library of $4 \times 10^9$.

TABLE 4

Human JH amino-acid sequences

```
             H3
          ------
           CDR3
        --------
        100      110
          |        |
JH1   ---AEYFQHWGQGTLVTVSS   (SEQ ID NO: 66)
JH2   ---YWYFDLWGRGTLVTVSS   (SEQ ID NO: 67)
JH3   -----AFDIWGQGTMVTVSS   (SEQ ID NO: 2)
JH4   -----YFDYWGQGTLVTVSS   (SEQ ID NO: 1)
JH5   ----NWFDPWGQGTLVTVSS   (SEQ ID NO: 68)
JH6   YYYYYGMDVWGQGTTVTVSS   (SEQ ID NO: 3)
```

In each of the following designs, the amino-acid sequence begins with YYCA(K/R) (SEQ ID NO: 936) which is the end of FR3. FR4 starts with WG and is shown bold.

Design 1

SEQ ID NO:898 comprises the end of FR3 joined to two residues (DY) of types often found in the filler sequence that the immune system places between V and D. These are followed by D2-2.2, preferred because it has a disulfide loop and is rich in Ser and Tyr residues. This is followed by YGYSY (SEQ ID NO: 937), which is rich in Tyr and Ser residues, which is followed by full-length JH1.

```
XX::D2-2.2::XX::JH1

1     1     2     2
     FR3 1     5     0     5     0  3FR4
     YYCAK DYGYCSSTSCYTYGYSYAEYFQHWGQGTLVTVSS              (SEQ ID NO: 898)

YYCAK XXGYCSXXSCYTXXYSYAEYFQHWGQGTLVTVSS              (SEQ ID NO: 69)
         R   GYCSSTSCYT       AEYFQHWGQGTLVTVSS  (JH1)
             (SEQ ID NO: 70)      (SEQ ID NO: 66)
                 1 1                  1       1
      9 9       0 0                   0       1
      4 5       0 2abcdefghijklmnp3           0

Amino-acid diversity     = 1.28 E 8
DNA diversity            = 2.15 E 9
Stop-free                = 83%
Gratuitous Cys-free      = 83%
Free of stop and Cys     = 68%
```

Design 1 (C23D222) has 94 being R or K, then 2 Xs, D2-2insecondreadingframewithtwoXsintheloop, followed by two Xs, and JH1. D2-2 $2^{nd}$ reading frame has a disulfide-closed loop into which diversity at two points has been introduced. This CDR3 is 23 long. Using primers that include DNA up to . . . YYCA (SEQ ID NO: 938) and from WGQG (SEQ ID NO: 939) . . . , error-prone PCR on the CDR3 could be performed before amplifying out to XbaI and BstEII for cloning into the library of kappa LC and HC CDR1/2. Thus, the AAs that are shown as fixed will be allowed to vary some. The AAs that are part of the PCR overlap region will be reinforced by the final non-error prone PCR. Error-prone PCR is not a necessary part of the design.

```
        C23D222JH1
        ! scab DNA  S   R   D   N   S   K   N   T   L   Y   L   Q   M   N   S
        5'-ttc|act|atc|TCT|AGA|gac|aac|tct|aag|aat|act|ctc|tac|ttg|cag|atg|aac|agC-
        !           XbaI...
        !
        !         L   R   A   E   D   T   A   V   Y   Y   C   A   K|R
           |TTA|AGg|gct|gag|gaT|aCT|GCA|GtT|taT|taC|tgc|gct aRg -
        !
        ! CDR3------------------------------------------------------------
        !   X    X         D2-2 RF2...........          X    X             JH1..
        !  any  any  G   Y   C   S   any any  S   C   Y   T   any any  Y   S   Y   A
           nnk  nnk  ggt tat tgt tcc nnk nnk  tct tgc tat act nnk nnk  tat tcc tac gct-
        !
        ! CDR3---------------
        !   E   Y   F   Q   H
           gaa tat ttc cag cac-
        !
        !  W   G   Q   G   T   L   V   T   V   S   S                      (SEQ ID NO: 71)
           tgg ggc cag ggt act ctG GTC ACC gtc tcc agt-3'                  (SEQ ID NO: 72)
        !                         BstEII...

(ON_C23D222)  5'-GCA|GtT|taT|taC|tgc|gct aRg nnk nnk ggt tat tgt tcc nnk-  (SEQ ID NO: 73)
                nnk tct tgc tat act nnk nnk tat tcc tac gct gaa tat ttc cag cac-
                tgg ggc cag ggt act ct-3'  ! 107 bases (ON_1)    5'-GCA|GtT|taT|taC|tgc|gct-3'                            (SEQ ID NO: 74)

(ON_2)    5'-AgAgTAcccTggccccAgAcgTccATAccgTAATAgT-3'  ! 37 bases   (SEQ ID NO: 75)

(ON_2 is reverse complement of 5'-ac tat tac ggt atg gac gtc tgg   (SEQ ID NO: 76)
         ggc cag ggt act ct-3')

(ON_3)    5'-ttc|act|atc|TCT|AGA|gac|aac|tct|aag|aat|act|ctc|tac|ttg|cag|atg|- (SEQ ID NO: 77)
                aac|agC|TTA|AGg|gct|gag|gaT|aCT|GCA|GtT|taT|taC|tgc|gct-3'

(ON_4)    5'-AcTggAgAcggTgAccAgAgTAcccTggccccA-3'  ! 33 bases       (SEQ ID NO: 78)

(5'-tgg ggc cag ggt act ctG GTC ACC gtc tcc agt-3' [RC]             (SEQ ID NO: 79))
```

Design 2

```
                            1     1     2     2
                      1     5     0     5     0  3
              YYCAK GSYYYGSGSYYNVDSYYAEYFQHWGQGTLVTVSS       (SEQ ID NO: 899)

YYCAK XXYYYGXGSXYNXXSYYAEYFQHWGQGTLVTVSS       (SEQ ID NO: 80)
                  R   YYYGSGSYYN     AEYFQHWGQGTLVTVSS       (JH1)
```

(SEQ ID NO: 81) (SEQ ID NO: 66)

Amino-acid diversity = 1.28E8
DNA diversity = 2.15E9
Stop-free = 83%
Gratuitous Cys-free = 83%
Free of stop and Cys = 68%

Design 2 (C23D310) has 94 as R or K, two Xs, D3-10(RF2) with 5th and 8th residues changed to X, 2 Xs, SYY, and JH1. The CDR3 is 23 AA long and could be further diversified by use of error-prone PCR.

```
C23D310JH1
! scab DNA     S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!             XbaI...
!
!   L   R   A   E   D   T   A   V   Y   Y   C   A   K|R
   |TTA|AGg|gct|gag|gaT|aCT|GCA|GtT|taT|taC|tgc|gct aRg -
!
! CDR3-----------------------------------------------------------------
!
! any any  Y   Y   Y   G  any  G   S  any  Y   N  any any  S   Y   Y
  nnk nnk tac tac tat ggt nnk ggc tct nnk tac aat nnk nnk tct tat tac
!
!   A   E   Y   F   Q   H
   gct gag tac ttt caa cat
!
!   JH1.....................................
!   W   G   Q   G   T   L   V   T   V   S   S                              (SEQ ID NO: 82)

tgg ggc cag ggt act ctG GTC ACC gtc tcc agt-3'                          (SEQ ID NO: 83)
!                          BstEII...

(C23D310) 5'-GCA|GtT|taT|taC|tgc|gct aRg nnk nnk tac tac tat ggt nnk ggc-  (SEQ ID NO: 84)
 tct nnk tac aat nnk nnk tct tat tac gct gag tac ttt caa cat tgg ggc cag-
 ggt act ct-3'
```

ON_1, ON_2, ON_3, and ON_4 as above.

Design 3

```
               1   1   2   2
       1   5   0   5   0   3
YYCAK DYYYYGSGSYYNSDSYSAEYFQHWGQGTLVTVSS    (SEQ ID NO: 900)

YYCAK XZYZZGZGZXYNZXZYZAXZFQHWGQGTLVTVSS    (SEQ ID NO: 940)
    R    YYYGSGSYYN     AEYFQHWGQGTLVTVSS    (JH1)
         (SEQ ID        (SEQ ID NO: 66)
         NO: 81)
```

Amino-acid diversity = 1.64E8
DNA diversity = 1.07E9
Stop-free = 88%
Gratuitous Cys-free = 88%
Free of stop and Cys = 77%

Design 3 (C23D310B) has 94 as R or K, XZ, D3-10(RF2) with 2nd, 3rd, 5th, and 7th as Z(YIS) and 8th residue changed to X, ZXZYZ (SEQ ID NO:992), and JH1 (with the E changed to X). Z is either Y or S. The CDR3 is 23 AA long and could be further diversified by use of error-prone PCR.

Design 4

```
                       A   V   Y   Y   C   A   R|K any Y|S  Y   Y|S Y|S  G   Y|S  G
(C23D310b)  5'-GCA|GtT|taT|taC|tgc|gct aRg nnk tmc tac tmc tmt ggt tmc ggc-
               Y|S any  Y   N  Y|S any Y|S  Y  Y|S  A  any Y|S  F   Q   H   W   G   Q
               tmt nnk tac aat tmt nnk tmc tat tmc gct nnk tmc ttt caa cat tgg ggc cag-
                G   T   L                                                                  (SEQ ID NO: 85)

ggt act ct-3'                                                                (SEQ ID NO: 86)

ON_1, ON_2, ON_3, and ON_4 as above.
```

Design 4

```
                1   1   2 2   3   3
         1  5   0   5   0 3 5 0   5
YYCAK YYSFSYYPYYYDSSGYYYGYYSDYSYSYYAEYFQHWGQGTLVTVSS        (SEQ ID NO: 901)

YYCAK YYSXSYYXYZYDSZGYZYXYYSXYZYZZZAZZFQHWGQGTLVTVSS        (SEQ ID NO: 87)
  R       YYYDSSGYYY            AEYFQHWGQGTLVTVSS (JH1)
             (SEQ ID NO: 88)         (SEQ ID NO: 66)
            1 1                      1      1
   9 9      0 0                      0      1
   4 5      0 2abcdefghijklmnoopqrstuvwxyab3 0
                                             ''

Amino-acid diversity     = 1.64 E 8
DNA diversity            = 1.07 E 9
Stop-free                = 88%
Gratuitous Cys-free      = 88%
Free of stop and Cys     = 77%
```

Design 4 has CDR3 of length 35. Residue 94 can be K or R, then YYS::X::SYY::X::D3-22 ($2^{nd}$ RF with one S as X and 3 Zs)::X::YYS::X::YZZZ(SEQ ID NO:993)::JH1 (with 2 Zs). Error-prone PCR could be used to add more diversity.

```
C35D322JH1
!  scab DNA         S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!             XbaI...
!
!   L   R   A   E   D   T   A   V   Y   Y   C   A   K|R
   |TTA|AGg|gct|gag|gaT|aCT|GCA|GtT|taT|taC|tgc|gct aRg -
!
!  CDR3---------------------------------------------------------------
!
!   Y   Y   S  any  S   Y   Y  any  Y  Y|S  Y   D   S  Y|S  G   Y  Y|S  Y
    tac tat tcc nnk tct tac tat nnk tat tmt tac gat agt tmt ggt tac tmc tat
!
    any  Y   Y   S  any  Y  Y|S  Y  Y|S Y|S Y|S  A  Y|S Y|S  F   Q   H
    nnk tac tat agc nnk tat tmc tac tmc tmt tmc gct tmt tmc ttc caa cac
!
!   W   G   Q   G   T   L   V   T   V   S   S                        (SEQ ID NO: 89)

tgg ggc cag ggt act ctG GTC ACC gtc tcc agt-3'                    (SEQ ID NO: 90)
!                           BstEII...

(c35d322B) 5'-GCA|GtT|taT|taC|tgc|gct aRg tac tat tcc nnk tct tac tat nnk-    (SEQ ID NO: 91)
   tat tmt tac gat agt tmt ggt tac tmc tat nnk tac tat agc nnk tat tmc tac-
   tmc tmt tmc gct tmt tmc ttc caa cac tgg ggc cag ggt act ct-3'

ON_1, ON_2, ON_3, and ON_4 as above.
```

Design 5

```
                1   1   2 2
         1  5   0   5   0 3
YYCAK SSGYCSSTSCYTGVYYYAEYFQHWGQGTLVTVSS        (SEQ ID NO: 902)

YYCAK ZZGZCZZXZCZTXXYZYXZYFQHWGQGTLVTVSS        (SEQ ID NO: 92)
  R    GYCSSTSCYT         AEYFQHWGQGTLVTVSS (JH1)
       (SEQ ID NO: 70)       (SEQ ID NO: 66)

Amino-acid diversity     = 1.64 E 8
DNA diversity            = 1.07 E 9
```

```
                                        -continued
Stop-free              = 88%
Gratuitous Cys-free    = 88%
Free of stop and Cys   = 77%
```

Design 5 (C23D222b) is like design 1 but uses many Z(Y or S) variable codons. This CDR3 is 23 long.

```
C23D222JH1b
!  scab DNA       S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!              XbaI...
!
!  L   R   A   E   D   T   A   V   Y   Y   C   A   K|R
  |TTA|AGg|gct|gag|gaT|aCT|GCA|GtT|taT|taC|tgc|gct aRg -
!
! CDR3-------------------------------------------------------------
! Y|S Y|S  G  Y|S  C  Y|S Y|S any Y|S  C  Y|S  T  any any  Y  Y|S  Y  any
   tmc tmt ggt tmt tgc tmc tmt nnk tmt tgt tmc acc nnk nnk tat tmt tac nnk
!
! Y|S  Y   F   Q   H
  tmt tat ttc cag cac
!
!  W   G   Q   G   T   L   V   T   V   S   S                    (SEQ ID NO: 93)
   tgg ggc cag ggt act ctG GTC ACC gtc tcc agt-3'                (SEQ ID NO: 94)
!                     BstEII...

(C23D222JH1b) 5'-GCA|GtT|taT|taC|tgc|gct aRg tmc tmt ggt tmt tgc tmc tmt-  (SEQ ID NO: 95)
 nnk tmt tgt tmc acc nnk nnk tat tmt tac nnk tmt tat ttc cag cac tgg ggc-
 cag ggt act ct-3'
```

Design 6

```
                    1   1   2 2     3   3
          1    5    0   5   0 3 5   0   5
YYCAK SYDYYGYCSSTSCYTYYSYVSYSSYYSYYAEYFQHWGQGTLVTVSS                       (SEQ ID NO: 903)

YYCAK ZYXZYGZCZZXSCZTYZSZXXZYSZYZSZYAEZFQHWGQGTLVTVSS                      (SEQ ID NO: 96)

R       GYCSSTSCYT D2-2.2       AEYFQHWGQGTLVTVSS (JH1)
                  (SEQ ID NO: 70)         (SEQ ID NO: 66)
Amino-acid diversity   = 2.00 E 8
DNA diversity          = 5.37 E 8
Stop-free              = 91%
Gratuitous Cys-free    = 91%
Free of stop and Cys   = 83%

C35D222JH1
!
!  scab DNA       S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!              XbaI...
!
!  L   R   A   E   D   T   A   V   Y   Y   C   A   K|R
  |TTA|AGg|gct|gag|gaT|aCT|GCA|GtT|taT|taC|tgc|gct aRg -
!
! CDR3-------------------------------------------------------------
! Y|S  Y  any Y|S  Y   G  Y|S  C  Y|S Y|S any  S   C  Y|S  T   Y  Y|S  S
   tmt tac nnk tmc tac ggc tMt tgc tmt tmc nnk tCt tgt tmc acc tat tmt tcc
!
! Y|S any Y|S  Y   S  any  Y  Y|S  S  Y|S  Y   A   E   Y   F   Q   H
   tmt nnk tmc tat tct nnk tac tmc agt tmt tat gct gag tat ttc cag cac
!
!  W   G   Q   G   T   L   V   T   V   S   S                    (SEQ ID NO: 97)
   tgg ggc cag ggt act ctG GTC ACC gtc tcc agt-3'                (SEQ ID NO: 98)
!                     BstEII...

(C35D222JH1) 5'-GCA|GtT|taT|taC|tgc|gct aRg tmt tac nnk tmc tac ggc tat- tgc tmt tmc  (SEQ ID NO: 99)
nnk tmt tgt tmc acc tat tmt tcc tmt nnk tmc tat tct nnk tac-
tmc agt tmt tat gct gag tat ttc cag cac tgg ggc cag ggt act ct-3'
```

Design 7

```
                1   1       2 2 2       3   3
        1   5   0   5       0 3 5       0   5
YYCAK YSYYGYCSSTSCYTYSSSVSYSYYSSYYAEYFQHWGQGTLVTVSS                      (SEQ ID NO: 904)

YYCAK ZYZZYGZCZZXZCZTYZSZXZYSZYZSZYAψZJQBWGQGTLVTVSS                     (SEQ ID NO: 100)
      R      GYCSSTSCYT  D2-2.2       AEYFQHWGQGTLVTVSS (JH1)
             (SEQ ID NO: 70)          (SEQ ID NO: 66)
(J = FSY, B = YHND, ψ = EKQ)

Amino-acid diversity   = 9.44 E 8
DNA diversity          = 2.42 E 9
Stop-free              = 93%
Gratuitous Cys-free    = 93%
Free of stop and Cys   = 88%
C35D222JH1B
!
! scab DNA       S     R    D    N    S    K    N    T    L    Y    L    Q    M    N    S
5'-ttc|act|atc|TCT|AGA|gac|aac|tct|aag|aat|act|ctc|tac|ttg|cag|atg|aac|agC-
!              XbaI...
!
!    L    R    A    E    D    T    A    V    Y    Y    C    A    K|R
    |TTA|AGg|gct|gag|gaT|aCT|GCA|GtT|taT|taC|tgc|gct|aRg  -
!
! CDR3-----------------------------------------------------------------
!  Y|S   Y   Y|S Y|S   Y   G   Y|S   C   Y|S Y|S any Y|S   C   Y|S   T    Y   Y|S   S
   tmt  tac  tmc tmc  tac  ggc  tMt  tgc  tmt tmc  nnk tmt  tgt tmc  acc  tat tmt  tcc
!
!                                                         Q         Y          N|D
!  Y|S any Y|S   Y    S   Y|S  Y   Y|S   S    Y|S   Y    A    E|K Y|S   F|S    Q    H|Y
   tmt nnk tmc  tat  tct  tmt tac  tmc  agt   tmt  tat  gct  Vag  tmt  tHc   cag   Nac
!
!    W    G    Q    G    T    L    V    T    V    S    S                 (SEQ ID NO: 101)

tgg  ggc  cag  ggt  act  ctG  GTC  ACC  gtc  tcc  agt-3'             (SEQ ID NO: 102)
!                            BstEII...
```

Design 8

```
                1   1       2 2 2       3   3
        1   5   0   5       0 3 5       0   5
YYCAK SRSYYDYVWGSYRYTSSYSYYSYSYSSYYAEYFQHWGQGTLVTVSS                     (SEQ ID NO: 905)

YYCAK ZXZYZBZVWGZZRZTZSZXZYZZZYZSZAψZFQHWGQGTLVTVSS                      (SEQ ID NO: 103)
      R    YYDYVWGSYRYT   D3-16.2      AEYFQHWGQGTLVTVSS (JH1)
           (SEQ ID NO: 104)            (SEQ ID NO: 66)
(J =FSY, B =YHND, ψ=EKQ)

Amino-acid diversity   = 9.44 E 8
DNA diversity          = 1.61 E 9
Stop-free              = 93%
Gratuitous Cys-free    = 93%
Free of stop and Cys   = 88%
C34D316JH1A
!
! scab DNA       S     R    D    N    S    K    N    T    L    Y    L    Q    M    N    S
5'-ttc|act|atc|TCT|AGA|gac|aac|tct|aag|aat|act|ctc|tac|ttg|cag|atg|aac|agC-
!              XbaI...
!
!    L    R    A    E    D    T    A    V    Y    Y    C    A    K|R
    |TTA|AGg|gct|gag|gaT|aCT|GCA|GtT|taT|taC|tgc|gct|aRg  -
!
! CDR3-----------------------------------------------------------------
!                          N|D
!  Y|S any Y|S   Y   Y|S Y|H Y|S   V    W    G    Y|S Y|S   R    Y|S   T    Y|S
   tmt nnk tmc  tac  tmt Nat tmt  gtt  tgg  ggt  tmt tmc  cgt  tmt   act   tmt
!
!   S   Y|S any Y|S   Y   Y|S Y|S Y|S   Y   Y|S   S   Y|S
   agt tmc  nnk tmt  tac tmc tmt tmc  tat  tmc  agt  tmt
!
!           Q
!     A    E|K  Y|S  F    Q    H
     GCT   vag  tmc  ttc  cag  cat
!
!    W    G    Q    G    T    L    V    T    V    S    S                 (SEQ ID NO: 105)

tgg  ggc  cag  ggt  act  ctG  GTC  ACC  gtc  tcc  agt-3'             (SEQ ID NO: 106)
!                            BstEII...
```

```
(C34D316JH1A) 5'-GCA|GtT|taT|taC|tgc|gct aRg tmt nnk tmc tac tmt Nat tmt-    (SEQ ID NO: 107)
gtt tgg ggt tmt tmc cgt tmt act tmt agt tmc nnk tmt tac tmc tmt tat-
tmc agt tmt GCT vag tmc ttc cag cat tgg ggc cag ggt act ct-3'
```

Design 9

Design 9 is like 8 except the D segment is moved to the right

```
                  1   1    2 2 2    3   3
        1    5    0   5    0 3 5    0   5
YYCAK YGYSSDSYYSSYYDYVWGSYRYTYSSYYAEYFQHWGQGTLVTVSS                            (SEQ ID NO: 906)

YYCAK ZXZZZXZYZZZYZBZVWGZZRZTYZSZYAψZFQHWGQGTLVTVSS                           (SEQ ID NO: 108)
      R  D3-16.2  YYDYVWGSYRYT     AEYFQHWGQGTLVTVSS (JH1)
               (SEQ ID NO: 104)    (SEQ ID NO: 66)
(J =FSY, B =YHND, ψ=EKQ)
```

```
Amino-acid diversity   = 1.31 E 8
DNA diversity          = 5.37 E 8
Stop-free              = 91%
Gratuitous Cys-free    = 91%
Free of stop and Cys   = 83%
C34D316JH1B
!
!  scab DNA      S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!               XbaI...
!
!   L   R   A   E   D   T   A   Y   Y   C   A   K|R
   |TTA|AGg|gct|gag|gaT|aCT|GCA|GtT|taT|taC|tgc|gct aRg -
!
!  CDR3-----------------------------------------------------------------
!   Y|S any Y|S Y|S Y|S any Y|S  Y  Y|S Y|S Y|S
    tmt nnk  tmc tmt tmc nnk  tmt tac tmc tmt tmc
!
!            N|D
!   Y  Y|S Y|H Y|S  V   W   G  Y|S Y|S R  Y|S T
    tac tmt Nat tmt gtt tgg ggt tmt tmc cgt tmt act
!
!   Y  Y|S  S  Y|S  Y
    tat tmc agt tmt tac
!
!        Q
!   A  E|K Y|S  F   Q   H
    GCT vag tmc ttc cag cat
!
!   W   G   Q   G   T   L   V   T   V   S   S                                  (SEQ ID NO: 109)

tgg ggc cag ggt act ctG GTC ACC gtc tcc agt-3'                             (SEQ ID NO: 110)
!                           BstEII...

(C35D316JH1B)
5'-GCA|GtT|taT|taC|tgc|gct aRg tmt nnk tmc tmt tmc nnk tmt tac tmc tmt tmc    (SEQ ID NO: 111)
tac tmt Nat tmt gtt tgg ggt tmt tmc cgt tmt act tat tmc agt tmt tac GCT vag
tmc ttc cag cat tgg ggc cag ggt act ct-3'
```

Design 10

```
                  1   1   2   2
        1    5    0   5   0   4
YYCAK GSSYYYGSGSYYNSDYYSAEYFQHWGQGTLVTVSS            (SEQ ID NO: 907)

YYCAK XZZYZZGZGZXYNZXZYZAXZFQHWGQGTLVTVSS            (SEQ ID NO: 112)
      R    YYYGSGSYYN      AEYFQHWGQGTLVTVSS (JH1)
        (SEQ ID NO: 81)    (SEQ ID NO: 66)
```

Design 10 (C24D310B) is like Design 3, but the CDR3 is of length 24. Design 10 has 94 as R or K, XZZ, D3-10(RF2) with 2nd, 3rd, 5th, and 7th as Z(YIS) and 8th residue changed to X, ZXZYZ (SEQ ID NO:994), and JH1 (with the E changed to X). Z is either Y or S. The CDR3 is 24 AA long and could be further diversified by use of error-prone PCR.

```
(C24D310b) 5'-GCA|GtT|taT|taC|tgc|gct aRg nnk tmc tmc tac tmc tmt ggt tmc-    (SEQ ID NO: 113)
  ggc tmt nnk tac aat tmt nnk tmc tat tmc gct nnk tmc ttt caa cat tgg ggc-
  cag ggt act ct-3'
```

ON_1, ON_2, ON_3, and ON_4 as above.

Design 11

```
                  1   1   2   2
           1  5   0   5   0   5
YYCAR SSRSGYCTNGVCYRSGSYWYFDLWGRGTLVTVSS                       (SEQ ID NO: 991)

YYCAR ZZXZGZC32GVCZ3ZXZZ4Z12LWGRGTLVTVSS                       (SEQ ID NO: 114)
  K       GYCTNGVCYT    YWYFDLWGRGTLVTVSS  D2-8.2 JH2
       (SEQ ID NO: 115)   (SEQ ID NO: 67)
(1 = FYS(THT), 2 = YHND(NAT), 3 = ITKR(ANA), 4 = LSW(TBG))
(C24D282) 5'-GCA|GtT|taT|taC|tgc|gct aRg tmc tmt nnk tmt ggt   (SEQ ID NO: 116)
 tmc tgt ana nat ggt gtc tgc tmt ana tmc nnk tmt tmt
  tbg tmt tht nat ctg tgg ggc cag ggt act ct-3'

(C24D282.1) 5'-GCA|GtT|taT|taC|tgc|gct aRg tmc tmt nnk tmc ggt (SEQ ID NO: 117)
 tmc tgc ana nat ggc gtc tgc tmt ana tmc nnk tmt tmt tbg
  tmt tht nat ctg tgg ggc cag ggt act ct-3'

(C24D282.1) 5'-GCA|GtT|taT|taC|tgc|gct aRg tmc tmt nnk tmc ggt (SEQ ID NO: 118) (needs R, M, N, K)
 tmc tgc ana nat ggc gtc tgc t-3'

(C24D282.2) 5'-Ag AgT Acc cTg gcc ccA cAg ATN ADA AKA cVA AKA  (SEQ ID NO: 119) ! 75 bases
AKA MNN gKA TNT AKA gcA gAc gcc ATN TNT gcA gKA Acc g-3'

(5'-c ggt tmc tgc ana-                                         (SEQ ID NO: 120) (needs N, M, K, B, H))
 nat ggc gtc tgc tmt ana tmc nnk tmt tmt tbg tmt tht nat ctg
 tgg ggc cag ggt act ct-3' [RC]
```

Design 12

```
                  1   1   2   2   3   3
           1  5   0   5   0   5   0   5
YYCAR SSYYSYGYCTNGVCYTYSYSYYSYSYSYWYFDLWGRGTLVTVSS  (SEQ ID NO: 908)

YYCAR ZZZZZZGZC32GVCZ3ZZZZYZZYZYZZ4Z12LWGRGTLVTVSS  (SEQ ID NO: 121)
  K       GYCTNGVCYT         YWYFDLWGRGTLVTVSS  D2-8.2 JH2
         (SEQ ID NO: 115)    (SEQ ID NO: 67)
(1 = FYS, 2 = YHND, 3 = ITKR, 4 = LSW, Z = YS)

(C33D282TP) 5'-GCA|GtT|taT|taC|tgc|gct-3'           (SEQ ID NO: 909)

(C33D282BP) 5'-ag agt acc ctg gcc cca-3'            (SEQ ID NO: 910)

(C33D282) 5'-GCA|GtT|taT|taC|tgc|gct aRg tmt tmc tmc tmt tmc tmc ggt-  (SEQ ID NO: 122)
tmt tgt ana nat ggc gtg tgc tmt ana tmc tmc tmc tat tmt tmc tat tmt-
tac tmt tmc tbg tmc tht nat ctg tgg ggc cag ggt act ct-3'

(C33D282F) 5'-GCA|GtT|taT|taC|tgc|gct agg tct tcc tac tat tcc tac ggt-  (SEQ ID NO: 911)
tat tgt aca aat ggc gtg tgc tat aca tac tcc tac tct tat tcc tat tct-
tac tct tac tgg tac ttt gat ctg tgg ggc cag ggt act ct-3'
```

Design 13

Design 13 places a germ-line D segment in the middle of a sea of Zs so that one can make two pieces of DNA that overlap throughout the constant region. HC CDR3 is 34 long and diversity is $2^{23} \sim 8 \times 10^6$.

```
                  1   1   2   2   3   3
           1  5   0   5   0   5   0   5
YYCAR SSSYYSYYSSGYCTNGVCYTSSYYSSYYWYFDLWGRGTLVTVSS       (SEQ ID NO: 912)

YYCAR ZZZZZZZZZZGYCTNGVCYTZZZZZZZZZZWZF2LWGRGTLVTVSS    (SEQ ID NO: 123)
  K            GYCTNGVCYT           YWYFDLWGRGTLVTVSS   D2-8.2 JH2
              (SEQ ID NO: 115)      (SEQ ID NO: 67)
(2 = YHND)

(C34D282.2A) 5'-GCA|GtT|taT|taC|tgc|gct aRg tmt tmc tmc tmt tmt tmc tmc   (SEQ ID NO: 124)
```

```
tmt tmc tmc ggt tat tgt act aac ggc gtt tgc tat act-3'

(C34D282.2B) 5'-Ag AgT Acc cTg gcc ccA cAg gTN gAA AKA ccA AKA AKA AKA gKA-    (SEQ ID NO: 125) ! 86 bases
gKA gKA gKA AKA AKA AgT ATA gcA AAc gcc gTT AgT AcA ATA-3'!

(5'-tat tgt act aac ggc gtt tgc tat act tmt tmt tmc tmc tmc tmc-              (SEQ ID NO: 126) [RC])
tmt tmt tmt tgg tmt ttc Nac ctg tgg ggc cag ggt act ct-3'
```

Design 14

Design 14 is like 9 except the D segment is mostly germline.

```
            1   1   2 2   3   3
      1 5   0   5   0 3 5 0   5
YYCAK YSYYSGSYYYSDYVWGSYRYTSYDSYYYAEYFQHWGQGTLVTVSS      (SEQ ID NO: 913)

YYCAK ZZZZZZZZZZDYVWGSYRZTZZZZZZZZAEZFQHWGQGTLVTVSS      (SEQ ID NO: 127)
    R D3-16.2 YYDYVWGSYRYT         AEYFQHWGQGTLVTVSS      (JH1)
          (SEQ ID NO: 104)       (SEQ ID NO: 66)

(C34D316.2A) 5'-GCA|GtT|taT|taC|tgc|gct aRg tmt tmc tmc tmt tmt tmc tmc        (SEQ ID NO: 128)
tmt tmc tmc tmc gat tat gtc tgg ggt act tat cgt-3'

(C34D316.2B) 5'-Ag AgT Acc cTg gcc ccA ATg cTg gAA AKA cTc Agc gKA gKA gKA-    (SEQ ID NO: 129) ! 86 bases
gKA gKA gKA AKA AgT gKA Acg ATA AgT Acc ccA gAc ATA ATC-3'

(5'-gat tat gtc tgg ggt act tat cgt tmc act tmt tmc tmc tmc-                  (SEQ ID NO: 130) [RC])
tmc tmc gct gag tmt ttc cag cat tgg ggc cag ggt act ct-3'
```

Design 15

Design 15 allows some diversity in the overlap, 5 two-way
flip-flops. There are only 32 overlap sequences and even if
there are mismatches, they will not change the allowed diversity.

```
            1   1   2 2   3   3
      1 5   0   5   0 3 5 0   5
YYCAK SYDYSSYSYYYDYVWGSYRYTSYSGDSYYAEYFQHWGQGTLVTVSS      (SEQ ID NO: 914)

YYCAK ZZZZZZZZZZDZVWGZZRZTZZZZZZZZAEZFQHWGQGTLVTVSS      (SEQ ID NO: 131)
           YYDYVWGSYRYT         AEYFQHWGQGTLVTVSS
         (SEQ ID NO: 104)       (SEQ ID NO: 66)

(C35D316.2A) 5'-GCA|GtT|taT|taC|tgc|gct aRg tmt tmc tmc tmt tmt tmc tmc        (SEQID NO: 132)
tmt tmc tmc tmc gac tmt gtc tgg ggt tmc tmc cgt tmc acc t-3'

(C35D316.2B) 5'-Ag AgT Acc cTg gcc ccA ATg cTg gAA AKA cTc Agc gKA gKA-        (SEQ ID NO: 133)
gKA gKA gKA gKA gKA AKA ggT gKA Acg gKA gKA Acc ccA gAc AKA gTc gKA g-3'

(5'-c tmc gac tmt gtc tgg ggt tmc tmc cgt tmc acc tmt tmc tmc-                (SEQ ID NO: 134) [RC])
tmc tmc tmc tmc tmc gct gag tmt ttc cag cat tgg ggc cag ggt act ct-3'
```

Design 16

Design 16 provides a CDR3 of 35. There are 4 two-way
flip-flops in the overlap, thus 16 sequences.

```
            1   1   2 2   3   3
      1 5   0   5   0 3 5 0   5
YYCAK SSSYYSYSYSGYCSGGSCYSSYYYSSYYSAEYFQGWGQGTLVTVSS      (SEQ ID NO: 915)

YYCAK ZZZZZZZZZZGZCZGGZCZSZZZZZZZZZAEZFQHWGQGTLVTVSS     (SEQ ID NO: 135)
    R          GYCSGGSCYS    2-25.2 AEYFQHWGQGTLVTVSS     JH1
             (SEQ ID NO: 136)      (SEQ ID NO: 66)

(C35D225.2A) 5'-GCA|GtT|taT|taC|tgc|gct aRg tmt tmt tmt tmt tmt tmt tmt        (SEQ ID NO: 137)
tmt tmc tmc ggc tmc tgt tmc ggt ggc tmc tgc tmc tcc t-3'

(C35D225.2B) 5'-Ag AgT Acc cTg gcc ccA ATg TTg gAA AKA TTc Agc gKA gKA-        (SEQ ID NO: 138) !
gKA gKA gKA gKA gKA gKA gKA gKA gga gcA gKA gcc Acc gKA AcA gKA gcc           96 bases
gKA g-3'
```

If we add C34D225.2A and C34D225.2B to the mixture, then we get CDR3s of lengths 33, 34, and 35.

(C34D225.2A) (SEQ ID NO: 139)
5'-GCA|GtT|taT|taC|tgc|gct aRg tmt tmt tmt tmt t-
mt tmt
tmt-tmc tmc ggc tmc tgt tmc ggt ggc tmc tgc tmc
tcc t-3'

(C34D225.2B) (SEQ ID NO: 140)
5'-Ag AgT Acc cTg gcc ccA ATg TTg gAA AKA TTc Agc
gKA gKA-gKA gKA gKA gKA gKA gKA gKA ggA gcA gKA
gcc Acc gKA AcA gKA gcc gKA g-3'!
93 bases Design 17

```
                1     1   2 2 2   3   3
          1  5  0     5   0 3 5   0   5
YYCAK YSSYSYYDYVWGSYRYTSSSYSYYSYYYAEYFQGWGQGTLVTVSS   (SEQ ID NO: 916)

YYCAK ZZZZZZZDZVWGZZRZTZZZZZZZZZZZAEZFQHWGQGTLVTVSS   (SEQ ID NO: 141)
    R         YYDYVWGSYRYT D3-16.2  AEYFQHWGQGTLVTVSS   (JH1)
              (SEQ ID NO: 104)      (SEQ ID NO: 66)
```

(C35D3162A) 5'-GCA|GtT|taT|taC|tgc|gct aRg tmt tmt tmt tmt tmt tmt tmc gac- (SEQ ID NO: 142)
tmc gtc tgg ggt tmt tmc cgt tmt acc t-3'

(C35D3162B) 5'-Ag AgT Acc cTg gcc ccA gTg cTg gAA gKA cTc Agc gKA gKA gKA- (SEQ ID NO: 143)
gKA gKA gKA gKA gKA gKA gKA gKA gKA gKA ggT AKA Acg gKA AKA Acc ccA gAc-
gKA gTc g-3'

Design 18

```
                1     1   2 2 2   3   3
          1  5  0     5   0 3 5   0   5
YYCAK SSYYYSSSYYDYVWGSYRYTSSYYSYSYAEYFQGWGQGTLVTVSS   (SEQ ID NO: 917)

YYCAK ZZZZZZZZZDZVWGZZRZTZZZZZZZZAEZFQHWGQGTLVTVSS    (SEQ ID NO: 144)
    R           YYDYVWGSYRYT D3-16.2AEYFQHWGQGTLVTVSS   (JH1)
                (SEQ ID NO: 104)    (SEQ ID NO: 66)
```

(C35D3162C) 5'- GCA|GtT|taT|taC|tgc|gct aRg tmt tmt tmt tmt tmt (SEQ ID NO: 145) 82 bases
tmc tmc tmc tmc gac tmc gtc tgg ggt tmc tmc cgt tmc acc t-3'

(C35D3162B) 5'-Ag AgT Acc cTg gcc ccA gTg cTg gAA gKA cTc Agc gKA   (SEQ ID NO: 146)
gKA gKA gKA gKA gKA gKA gKA gKA gKA ggT gKA Acg gKA gKA Acc ccA gAc
gKA gTc g-3'

Design 19

```
                    1     1   2 2 2   3   3
              1  5  0     5   0 3 5   0   5
YYCAK YSGDSYSYYYYDSSGYYYSYYSSSYYSYYAEYFQGWGQGTLVTVSS   (SEQ ID NO: 918)

YYCAK ZZZZZZZZZZZDSSGZZZZZZZZZZZZZZAEZFQHWGQGTLVTVSS   (SEQ ID NO: 147)
    R            YYYDSSGYYY           AEYFQHWGQGTLVTVSS   (JH1)
                 (SEQ ID NO: 88)      (SEQ ID NO: 66)
                      1 1                  1       1
                   9  9 0 0                0       1
                   4  5 0 2abcdefghijklmnopqrstuvwxyab3  0
```

Amino-acid diversity = 6.7 E 7
DNA diversity       = 6.7 E 7
Stop-free           = 100
Gratuitous Cys-free = 100
Free of stop and Cys = 100%

Design 19 has CDR3 of length 35. Residue 94 can be K or R, The ZZZZZZZZZ::D3-22($2^{nd}$ RF with six Ys as Z):: ZZZZZZZZZZZ(SEQ ID NO:995)(::JH1 with 1 Z). Error-prone PCR could be used to add more diversity.

```
C35D322AJH1
! scab DNA    S   R   D   N   S   K   N   T   L   Y   L   Q   M   N   S
5'-ttc|act|atc|TCT|AGA|gac|aac|tct|aag|aat|act|ctc|tac|ttg|cag|atg|aac|agC-
!           XbaI...
!
```

```
                                     -continued
!  L   R   E   D   T   A   V   Y   Y   C   A   K|R
 |TTA|AGg|gct|gag|gaT|aCT|GCA|GtT|taT|taC|tgc|gct aRg -
!
! CDR3-----------------------------------------------------------------
!
! Y|S Y|S Y|S Y|S Y|S Y|S Y|S Y|S Y|S Y|S Y|S  D   S   S   G  Y|S Y|S Y|S
   tmc tmt tmc tmc tmt tmc tmt tmc tmc tmc tmc gac agc tcc ggc tmc tmc tmt
!
   Y|S Y|S Y|S Y|S Y|S Y|S Y|S Y|S Y|S Y|S Y|S  A   E  Y|S  F   Q   H
   tmc tmt tmc tmc tmt tmc tmt tmc tmc tmc tmc gct gaa tmc ttc caa cac
!
! W   G   Q   G   T   L   V   T   V   S   S        (SEQ ID NO: 148)

tgg ggc cag ggt act ctG GTC ACC gtc tcc agt-3' (SEQ ID NO: 149)
!                               BstEII...
```

(C35D322AJH1_T)5'-`GCA|GtT|taT|taC|tgc|gct` aRg tmc tmt tmc tmc tmt-    (SEQ ID NO: 150)
 tmc tmt tmc tmc tmc tmc gac agc tcc ggc tmc tmc t-3'

(C35D322AJH1_B) 5'-cAg AgT Acc cTg gcc ccA gTg TTg gAA gKA TTc Agc gKA-  (SEQ ID NO: 151)
   gKA gKA gKA AKA gKA AKA gKA gKA AKA gKA AKA gKA gKA gcc ggA gcT gTc-
   gKA gKA g-3'

ON_1, ON_2, ON_3, and ON_4 as above.

Design 20

1   1       2  2       3       3
       1   5  0   5       0  5       0       5
YYCAK  YSSYSS   YYYYDSSGYYYSSYSSYS   YYYAEYFQGWGQGTLVTVSS   (SEQ ID NO: 919)

YYCAK  ZZZZZZ(Z)ZZZZDSSGZZZZZZZZZZZ(Z)ZZZAEZFQHWGQGTLVTVSS   (SEQ ID NO: 152)
    R          YYYDSSGYYY          AEYFQHWGQGTLVTVSS    (JH1)
               (SEQ ID NO: 88)     (SEQ ID NO: 66)
             1  1                              1    1
        9    1  1                              1    1
        4 5  0  3abcdefghijklmnop q rstuvwxya4  0
                                              '

Amino-acid diversity =   6.7 E 7
DNA diversity =          6.7 E 7
Stop-free =              100
Gratuitous Cys-free =    100
Free of stop and Cys =   100%

Design 20 has CDR3s of length 33, 34, or 35. Residue 94 can be K or R, The ZZZZZZ(Z)ZZ::D3-22 (2$^{nd}$ RF with six Ys as Z)::ZZZZZZZ(Z)ZZZ::JH1 (with 1 Z). PCR combining (C35D322AJH1_T), (C34D322AJH1_T), (C35D322AJH1_B), and (C34D322AJH1_B) allows length as well as sequence diversity.

(C35D322AJH1_T)5'-`GCA|GtT|taT|taC|tgc|gct` aRg tmc tmt tmc tmc-        (SEQ ID NO: 153)
tmt tmc tmt tmc tmc tmc tmc gac agc tcc ggc tmc tmc t-3'

(C34D322AJH1_T)5'-`GCA|GtT|taT|taC|tgc|gct` aRg tmc tmt tmc tmc tmt-    (SEQ ID NO: 154)
tmc tmt tmc tmc tmc tmc gac agc tcc ggc tmc tmc t-3'

(C35D322AJH1_B) 5'-cAg AgT Acc cTg gcc ccA gTg TTg gAA gKA TTc Agc gKA- (SEQ ID NO: 920)
gKA gKA gKA AKA gKA AKA gKA gKA AKA gKA AKA gKA gKA gcc ggA gcT gTc-
gKA gKA g-3'

(C34D322AJH1_B) 5'-cAg AgT Acc cTg gcc ccA gTg TTg gAA gKA TTc Agc gKA- (SEQ ID NO: 155)
gKA gKA gKA AKA gKA AKA gKA gKA AKA AKA gKA gKA gcc ggA gcT gTc-
gKA gKA g-3'

Selection Against Stop Codons:

Because some of these libraries have NNK codons, they will have some TAG stop codons. We could remove the clones with TAG by cloning the amplified DNA into an XbaI-BstEII site between the signal sequence for a bla gene and the actual bla protein and express in Sup⁰ cells. Bla^R colonies do not contain TAG stops. Alternatively, we could clone the XbaI-BstEII fragments ahead of a kanamycin-resistance gene and select for Kan^R. We would then move the XbaI-BstEII cassette into the phage library.

Also, because wobbling allows some stop codons, we can improve the library by removing the clones with stops by cloning the amplified DNA into an XbaI-BstEII site between the signal sequence for a bla gene and the actual bla protein and express in Sup⁰ cells. Bla^R colonies do not contain stops. Alternatively, we can clone the XbaI-BstEII fragments ahead of a kanamycin-resistance gene and select for Kan^R. We can then move the XbaI-BstEII cassette into the phage library.

TABLE 20

| | | RF 1 | RF 2 | RF 3 | Used in designs |
|---|---|---|---|---|---|
| | | (SEQ ID NO: 156) | (SEQ ID NO: 157) | (SEQ ID NO: 158) | |
| D1 | 1-1 | GTTGT | VQLER | YNWND | |
| | | (SEQ ID NO: 159) | (SEQ ID NO: 160) | (SEQ ID NO: 161) | |
| | 1-7 | GITGT | V*LEL | YNWNY | |
| | | (SEQ ID NO: 159) | (SEQ ID NO: 162) | (SEQ ID NO: 163) | |
| | 1-20 | GITGT | V*LER | YNWND | |
| | | (SEQ ID NO: 164) | (SEQ ID NO: 165) | (SEQ ID NO: 166) | |
| | 1-26 | GIVGAT | V*WELL | YSGSYY | |
| | | (SEQ ID NOS 171 & 167) | (SEQ ID NO: 70) | (SEQ ID NO: 168) | |
| D2 | 2-2 | RILYQLLY | GYCSSTSCYT** | DIVVVPAAI | 1, 5, 6, 7, |
| | | (SEQ ID NOS 169 & 392) | (SEQ ID NO: 115) | (SEQ ID NO: 170) | |
| | 2-8 | RILY@WCMLY | GYCTNGVCYT | DIVLMVYAI | 20, 21, 22, |
| | | (SEQ ID NO: 171) | (SEQ ID NO: 136) | (SEQ ID NO: 172) | |
| | 2-15 | RIL*WW*LLL | GYCSGGSCYS | DIVVVAAT | 25, |
| | | (SEQ ID NO: 173) | (SEQ ID NO: 174) | (SEQ ID NO: 175) | |
| | 2-21 | SILWW$LLF | AYCGGDCYS | HIVVVTAI | |
| | | (SEQ ID NO: 176) | (SEQ ID NO: 177) | (SEQ ID NO: 178) | |
| D3 | 3-3 | VLRFLEWLLY | YYDFWSGYYT | ITIFGVVII | |
| | | (SEQ ID NO: 179) | (SEQ ID NO: 180) | (SEQ ID NOS 181 & 579) | |
| | 3-9 | VLRYFDWLL@ | YYDILTGYYN | ITIF*LVII | |
| | | (SEQ ID NO: 182) | (SEQ ID NO: 81) | (SEQ ID NO: 183) | |
| | 3-10 | VLLWFGELL@ | YYYGSGSYYN | ITMVRGVII | |
| | | (SEQ ID NO: 184) | (SEQ ID NO: 104) | (SEQ ID NO: 185) | |
| | 3-16 | VL$LRLGELSLY | YYDYVWGSYRYT | IMITFGGVIVI | 8, 9, 14, 15, 17, 18 |
| | | (SEQ ID NO: 186) | (SEQ ID NO: 187) | (SEQ ID NO: 188) | |
| | 3-22 | VLL*WLLL | YYYDSSGYYY** | ITMIVVVIT | 4, 19, 20 |
| | | (SEQ ID NO: 189) | (SEQ ID NO: 192) | (SEQ ID NO: 190) | |
| D4 | 4-4 | $LQ@L | DYSNY | TTVT | |
| | | (SEQ ID NO: 191) | (SEQ ID NO: 192) | (SEQ ID NO: 193) | |
| | 4-11 | $LQ@L | DYSNY | TTVT | |
| | | (SEQ ID NO: 194) | (SEQ ID NO: 195) | (SEQ ID NO: 196) | |
| | 4-17 | $LR@L | DYGDY | TTVT | |
| | | (SEQ ID NO: 197) | (SEQ ID NO: 198) | (SEQ ID NO: 199) | |
| | 4-23 | $LRW@L | DYGGNS | TTVVT | |
| | | (SEQ ID NO: 200) | (SEQ ID NO: 201) | (SEQ ID NO: 202) | |
| D5 | 5-5 | VDTAMV | WIQLWL | GYSYGY | |
| | | (SEQ ID NO: 203) | (SEQ ID NO: 204) | (SEQ ID NO: 205) | |
| | 5-12 | VDIVATI | WI*WLRL | GYSGYDY | |
| | | (SEQ ID NO: 206) | (SEQ ID NO: 207) | (SEQ ID NO: 208) | |
| | 5-18 | VDTAMV | WIQLWL | GYSYGY | |
| | | (SEQ ID NO: 209) | (SEQ ID NO: 210) | (SEQ ID NO: 211) | |
| | 5-24 | VEMATI | *RWLQL | RDGYNY | |
| | | (SEQ ID NO: 212) | (SEQ ID NO: 213) | (SEQ ID NO: 214) | |
| D6 | 6-6 | EYSSSS | SIAAR | V*QLV | |
| | | (SEQ ID NO: 215) | (SEQ ID NO: 216) | (SEQ ID NO: 217) | |
| | 6-13 | GYSSSWY | GIAAAG | V*QQLV | |
| | | (SEQ ID NO: 218) | (SEQ ID NO: 219) | (SEQ ID NO: 220) | |
| | 6-19 | GYSSGWY | GIAVAG | V*QWLV | |
| | | (SEQ ID NO: 221) | (SEQ ID NO: 222) | (SEQ ID NO: 223) | |
| D7 | 7-27 | LTG | @LG | NWG | |

! for TAG;
@ for TAA;
$ for TGA
D - Amino acid sequence alignment (RF: reading frame)

TABLE 3

Human JH segments
JH - Amino acid sequence alignment

```
              H3
              ------
              CDR3
              --------
           100         110
            |   FR4--------   Used in designs
JH1   ---AEYFQHWGQGTLVTVSS 1-8,    (SEQ ID NO: 66)
JH2   ---YWYFDLWGRGTLVTVSS         (SEQ ID NO: 67)
JH3   -----AFDIWGQGTMVTVSS         (SEQ ID NO: 2)
JH4   -----YFDYWGQGTLVTVSS         (SEQ ID NO: 1)
JH5   ----NWFDPWGQGTLVTVSS         (SEQ ID NO: 68)
JH6   YYYYYGMDVWGQGTTVTVSS         (SEQ ID NO: 3)
           123456789
```

Table 10: DNA Encoding V-5D2-8.2a-JH2 for Wobbling

```
!                                       CDR3.......
!  A   E   D   T   A   V   Y   Y   C   A   K   D   I   V   L   M
  |gct|gag|gaT|aCT|GCA|GtT|taT|taC|tgc|gct aag jez ezq jzz qzz ezj
!
!  W   G   Q   G   T   T   V   T   V   S   S   (SEQ ID NO: 224)

tgg ggc cag ggt act acG GTC ACC gtc tcc agt- (SEQ ID NO: 225)
3'
!                              BstEII...
```

TABLE 11

Trimers that can be extracted from human D segments
In Tables 11-14, the use of a lower case letter in an amino acid sequence indicates that a stop codon was changed to the residue listed as the lower case letter. For example, in the amino acid sequence "yLE", a Tyr residue was introduced in place of a stop codon.

| | | | |
|---|---|---|---|
| GTT | D1-1.1.1 | 1 | |
| VQL | D1-1.2.1 | 2 | |
| YNW | D1-1.3.1 | 3 | |
| TTG | D1-1.1.2 | 4 | |
| QLE | D1-1.2.2 | 5 | |
| NWN | D1-1.3.2 | 6 | |
| TGT | D1-1.1.3 | 7 | |
| LER | D1-1.2.3 | 8 | (SEQ ID NO: 162) |
| WND | D1-1.3.3 | 9 | |
| GIT | D1-7.1.1 | 10 | |
| VyL | D1-7.2.1 | 11 | * |
| ITG | D1-7.1.2 | 12 | |
| yLE | D1-7.2.2 | 13 | * |
| LEL | D1-7.2.3 | 14 | (SEQ ID NO: 160) |
| WNY | D1-7.3.3 | 15 | |
| GIV | D1-26.1.1 | 16 | |
| VyW | D1-26.2.1 | 17 | * |
| YSG | D1-26.3.1 | 18 | |
| IVG | D1-26.1.2 | 19 | |
| yWE | D1-26.2.2 | 20 | * |
| SGS | D1-26.3.2 | 21 | |
| VGA | D1-26.1.3 | 22 | |
| WEL | D1-26.2.3 | 23 | |
| GSY | D1-26.3.3 | 24 | |
| GAT | D1-26.1.4 | 25 | |
| ELL | D1-26.2.4 | 26 | |
| SYY | D1-26.3.4 | 27 | |
| RIL | D2-2.1.1 | 28 | (SEQ ID NO: 171) |
| GYC | D2-2.2.1 | 29 | # |
| DIV | D2-2.3.1 | 30 | |
| ILy | D2-2.1.2 | 31 | * |
| YCS | D2-2.2.2 | 32 | # |
| IVV | D2-2.3.2 | 33 | |
| Lyy | D2-2.1.3 | 34 | * |
| CSS | D2-2.2.3 | 35 | # |
| VVV | D2-2.3.3 | 36 | |
| yyY | D2-2.1.4 | 37 | * |
| SST | D2-2.2.4 | 38 | |

TABLE 11-continued

Trimers that can be extracted from human D segments
In Tables 11-14, the use of a lower case letter in an amino acid sequence indicates that a stop codon was changed to the residue listed as the lower case letter. For example, in the amino acid sequence "yLE", a Tyr residue was introduced in place of a stop codon.

| | | | |
|---|---|---|---|
| VVP | D2-2.3.4 | 39 | |
| yYQ | D2-2.1.5 | 40 | * |
| STS | D2-2.2.5 | 41 | |
| VPA | D2-2.3.5 | 42 | |
| YQL | D2-2.1.6 | 43 | |
| TSC | D2-2.2.6 | 44 | # |
| PAA | D2-2.3.6 | 45 | |
| QLL | D2-2.1.7 | 46 | |
| SCY | D2-2.2.7 | 47 | # |
| AAI | D2-2.3.7 | 48 | |
| LLY | D2-2.1.8 | 49 | |
| CYT | D2-2.2.8 | 50 | # |
| ILY | D2-8.1.2 | 51 | |
| YCT | D2-8.2.2 | 52 | # |
| IVL | D2-8.3.2 | 53 | |
| LYy | D2-8.1.3 | 54 | * |
| CTN | D2-8.2.3 | 55 | # |
| VLM | D2-8.3.3 | 56 | |
| YyW | D2-8.1.4 | 57 | * |
| TNG | D2-8.2.4 | 58 | |
| LMV | D2-8.3.4 | 59 | |
| yWC | D2-8.1.5 | 60 | *# |
| NGV | D2-8.2.5 | 61 | |
| MVY | D2-8.3.5 | 62 | |
| WCM | D2-8.1.6 | 63 | # |
| GVC | D2-8.2.6 | 64 | # |
| VYA | D2-8.3.6 | 65 | |
| CML | D2-8.1.7 | 66 | # |
| VCY | D2-8.2.7 | 67 | # |
| YAI | D2-8.3.7 | 68 | |
| MLY | D2-8.1.8 | 69 | |
| LyW | D2-15.1.3 | 70 | * |
| CSG | D2-15.2.3 | 71 | # |
| yWW | D2-15.1.4 | 72 | * |
| SGG | D2-15.2.4 | 73 | |
| WWy | D2-15.1.5 | 74 | * |
| GGS | D2-15.2.5 | 75 | |
| VVA | D2-15.3.5 | 76 | |
| WyL | D2-15.1.6 | 77 | * |
| GSC | D2-15.2.6 | 78 | # |
| VAA | D2-15.3.6 | 79 | |
| yLL | D2-15.1.7 | 80 | * |
| AAT | D2-15.3.7 | 81 | |
| LLL | D2-15.1.8 | 82 | |
| CYS | D2-15.2.8 | 83 | # |
| SIL | D2-21.1.1 | 84 | |
| AYC | D2-21.2.1 | 85 | # |
| HIV | D2-21.3.1 | 86 | |
| ILW | D2-21.1.2 | 87 | |
| YCG | D2-21.2.2 | 88 | # |
| LWW | D2-21.1.3 | 89 | |
| CGG | D2-21.2.3 | 90 | # |
| WWw | D2-21.1.4 | 91 | * |
| GGD | D2-21.2.4 | 92 | |
| VVT | D2-21.3.4 | 93 | |
| WwL | D2-21.1.5 | 94 | * |
| GDC | D2-21.2.5 | 95 | # |
| VTA | D2-21.3.5 | 96 | |
| wLL | D2-21.1.6 | 97 | * |
| DCY | D2-21.2.6 | 98 | # |
| TAI | D2-21.3.6 | 99 | |
| LLF | D2-21.1.7 | 100 | |
| VLR | D3-3.1.1 | 101 | |
| YYD | D3-3.2.1 | 102 | |
| ITI | D3-3.3.1 | 103 | |
| LRF | D3-3.1.2 | 104 | |
| YDF | D3-3.2.2 | 105 | |
| TIF | D3-3.3.2 | 106 | |
| RFL | D3-3.1.3 | 107 | |
| DFW | D3-3.2.3 | 108 | |
| IFG | D3-3.3.3 | 109 | |

TABLE 11-continued

Trimers that can be extracted from human D segments
In Tables 11-14, the use of a lower case letter in an amino acid sequence indicates that a stop codon was changed to the residue listed as the lower case letter. For example, in the amino acid sequence "yLE", a Tyr residue was introduced in place of a stop codon.

| | | | | |
|---|---|---|---|---|
| FLE | D3-3.1.4 | 110 | | |
| FWS | D3-3.2.4 | 111 | | |
| FGV | D3-3.3.4 | 112 | | |
| LEW | D3-3.1.5 | 113 | | |
| WSG | D3-3.2.5 | 114 | | |
| GVV | D3-3.3.5 | 115 | | |
| EWL | D3-3.1.6 | 116 | | |
| SGY | D3-3.2.6 | 117 | | |
| VVI | D3-3.3.6 | 118 | | |
| WLL | D3-3.1.7 | 119 | | |
| GYY | D3-3.2.7 | 120 | | |
| VII | D3-3.3.7 | 121 | | |
| YYT | D3-3.2.8 | 122 | | |
| LRY | D3-9.1.2 | 123 | | |
| YDI | D3-9.2.2 | 124 | | |
| RYF | D3-9.1.3 | 125 | | |
| DIL | D3-9.2.3 | 126 | | |
| IFy | D3-9.3.3 | 127 | * | |
| YFD | D3-9.1.4 | 128 | | |
| ILT | D3-9.2.4 | 129 | | |
| FyL | D3-9.3.4 | 130 | * | |
| FDW | D3-9.1.5 | 131 | | |
| LTG | D3-9.2.5 | 132 | (SEQ ID NO: 221) | |
| yLV | D3-9.3.5 | 133 | * | |
| DWL | D3-9.1.6 | 134 | | |
| TGY | D3-9.2.6 | 135 | | |
| LVI | D3-9.3.6 | 136 | | |
| LLy | D3-9.1.8 | 137 | * | |
| YYN | D3-9.2.8 | 138 | | |
| VLL | D3-10.1.1 | 139 | | |
| YYY | D3-10.2.1 | 140 | | |
| ITM | D3-10.3.1 | 141 | | |
| LLW | D3-10.1.2 | 142 | | |
| YYG | D3-10.2.2 | 143 | | |
| TMV | D3-10.3.2 | 144 | | |
| LWF | D3-10.1.3 | 145 | | |
| YGS | D3-10.2.3 | 146 | | |
| MVR | D3-10.3.3 | 147 | | |
| WFG | D3-10.1.4 | 148 | | |
| GSG | D3-10.2.4 | 149 | | |
| VRG | D3-10.3.4 | 150 | | |
| FGE | D3-10.1.5 | 151 | | |
| RGV | D3-10.3.5 | 152 | | |
| GEL | D3-10.1.6 | 153 | | |
| GVI | D3-10.3.6 | 154 | | |
| VLw | D3-16.1.1 | 155 | * | |
| IMI | D3-16.3.1 | 156 | | |
| LwL | D3-16.1.2 | 157 | * | |
| YDY | D3-16.2.2 | 158 | | |
| MIT | D3-16.3.2 | 159 | | |
| wLR | D3-16.1.3 | 160 | * | |
| DYV | D3-16.2.3 | 161 | | |
| ITF | D3-16.3.3 | 162 | | |
| LRL | D3-16.1.4 | 163 | | |
| YVW | D3-16.2.4 | 164 | | |
| TFG | D3-16.3.4 | 165 | | |
| RLG | D3-16.1.5 | 166 | | |
| VWG | D3-16.2.5 | 167 | | |
| FGG | D3-16.3.5 | 168 | | |
| LGE | D3-16.1.6 | 169 | | |
| WGS | D3-16.2.6 | 170 | | |
| GGV | D3-16.3.6 | 171 | | |
| ELS | D3-16.1.8 | 172 | | |
| SYR | D3-16.2.8 | 173 | | |
| VIV | D3-16.3.8 | 174 | | |
| LSL | D3-16.1.9 | 175 | | |
| YRY | D3-16.2.9 | 176 | | |
| IVI | D3-16.3.9 | 177 | | |
| SLY | D3-16.1.10 | 178 | | |
| RYT | D3-16.2.10 | 179 | | |
| LLw | D3-22.1.2 | 180 | * | |

TABLE 11-continued

Trimers that can be extracted from human D segments
In Tables 11-14, the use of a lower case letter in an amino acid sequence indicates that a stop codon was changed to the residue listed as the lower case letter. For example, in the amino acid sequence "yLE", a Tyr residue was introduced in place of a stop codon.

| | | | |
|---|---|---|---|
| TMI | D3-22.3.2 | 181 | |
| Lwy | D3-22.1.3 | 182 | * |
| YDS | D3-22.2.3 | 183 | |
| MIV | D3-22.3.3 | 184 | |
| wyy | D3-22.1.4 | 185 | * |
| DSS | D3-22.2.4 | 186 | |
| yyW | D3-22.1.5 | 187 | * |
| SSG | D3-22.2.5 | 188 | |
| yWL | D3-22.1.6 | 189 | * |
| VIT | D3-22.3.7 | 190 | |
| wLQ | D4-4.1.1 | 191 | * |
| DYS | D4-4.2.1 | 192 | |
| TTV | D4-4.3.1 | 193 | |
| LQy | D4-4.1.2 | 194 | * |
| YSN | D4-4.2.2 | 195 | |
| TVT | D4-4.3.2 | 196 | |
| QyL | D4-4.1.3 | 197 | * |
| SNY | D4-4.2.3 | 198 | |
| DYG | D4-17.2.1 | 199 | |
| LRw | D4-17.1.2 | 200 | * (SEQ ID NO: 197) |
| YGD | D4-17.2.2 | 201 | |
| RwL | D4-17.1.3 | 202 | * |
| GDY | D4-17.2.3 | 203 | |
| LRW | D4-23.1.2 | 204 | (SEQ ID NO: 197) |
| YGG | D4-23.2.2 | 205 | |
| TVV | D4-23.3.2 | 206 | |
| RWy | D4-23.1.3 | 207 | * |
| GGN | D4-23.2.3 | 208 | |
| GNS | D4-23.2.4 | 209 | |
| VDT | D5-5.1.1 | 210 | |
| WIQ | D5-5.2.1 | 211 | |
| GYS | D5-5.3.1 | 212 | |
| DTA | D5-5.1.2 | 213 | |
| IQL | D5-5.2.2 | 214 | |
| YSY | D5-5.3.2 | 215 | |
| TAM | D5-5.1.3 | 216 | |
| QLW | D5-5.2.3 | 217 | |
| SYG | D5-5.3.3 | 218 | |
| AMV | D5-5.1.4 | 219 | |
| LWL | D5-5.2.4 | 220 | |
| YGY | D5-5.3.4 | 221 | |
| VDI | D5-12.1.1 | 222 | |
| WIy | D5-12.2.1 | 223 | * |
| IyW | D5-12.2.2 | 224 | * |
| IVA | D5-12.1.3 | 225 | |
| VAT | D5-12.1.4 | 226 | |
| WLR | D5-12.2.4 | 227 | |
| GYD | D5-12.3.4 | 228 | |
| ATI | D5-12.1.5 | 229 | |
| VEM | D5-24.1.1 | 230 | |
| yRW | D5-24.2.1 | 231 | * |
| RDG | D5-24.3.1 | 232 | |
| EMA | D5-24.1.2 | 233 | |
| RWL | D5-24.2.2 | 234 | |
| DGY | D5-24.3.2 | 235 | |
| MAT | D5-24.1.3 | 236 | |
| WLQ | D5-24.2.3 | 237 | |
| GYN | D5-24.3.3 | 238 | |
| LQL | D5-24.2.4 | 239 | |
| YNY | D5-24.3.4 | 240 | |
| EYS | D6-6.1.1 | 241 | |
| SIA | D6-6.2.1 | 242 | |
| VyQ | D6-6.3.1 | 243 | * |
| YSS | D6-6.1.2 | 244 | |
| IAA | D6-6.2.2 | 245 | |
| yQL | D6-6.3.2 | 246 | * |
| SSS | D6-6.1.3 | 247 | |
| AAR | D6-6.2.3 | 248 | |
| QLV | D6-6.3.3 | 249 | (SEQ ID NO: 214) |
| GIA | D6-13.2.1 | 250 | |
| yQQ | D6-13.3.2 | 251 | * |

TABLE 11-continued

Trimers that can be extracted from human D segments

In Tables 11-14, the use of a lower case letter in an amino acid sequence indicates that a stop codon was changed to the residue listed as the lower case letter. For example, in the amino acid sequence "yLE", a Tyr residue was introduced in place of a stop codon.

| | | | |
|---|---|---|---|
| AAA | D6-13.2.3 | 252 | |
| QQL | D6-13.3.3 | 253 | |
| SSW | D6-13.1.4 | 254 | |
| AAG | D6-13.2.4 | 255 | |
| SWY | D6-13.1.5 | 256 | |
| IAV | D6-19.2.2 | 257 | |
| yQW | D6-19.3.2 | 258 | * |
| AVA | D6-19.2.3 | 259 | |
| QWL | D6-19.3.3 | 260 | |
| SGW | D6-19.1.4 | 261 | |
| VAG | D6-19.2.4 | 262 | |
| WLV | D6-19.3.4 | 263 | |
| GWY | D6-19.1.5 | 264 | |
| yLG | D7-27.2.1 | 265 | * |
| NWG | D7-27.3.1 | 266 | (SEQ ID NO: 223) |

TABLE 12

Distinct tetramers that can be extracted from human D segments

| | | | |
|---|---|---|---|
| GTTG | D1-1.1.1 | (SEQ ID NO: 257) | 1 |
| VQLE | D1-1.2.1 | (SEQ ID NO: 258) | 2 |
| YNWN | D1-1.3.1 | (SEQ ID NO: 259) | 3 |
| TTGT | D1-1.1.2 | (SEQ ID NO: 263) | 4 |
| QLER | D1-1.2.2 | (SEQ ID NO: 264) | 5 |
| NWND | D1-1.3.2 | (SEQ ID NO: 265) | 6 |
| GITG | D1-7.1.1 | (SEQ ID NO: 266) | 7 |
| VyLE | D1-7.2.1 | (SEQ ID NO: 267) | 8 |
| ITGT | D1-7.1.2 | (SEQ ID NO: 271) | 9 |
| yLEL | D1-7.2.2 | (SEQ ID NO: 272) | 10 |
| NWNY | D1-7.3.2 | (SEQ ID NO: 273) | 11 |
| yLER | D1-20.2.2 | (SEQ ID NO: 275) | 12 |
| GIVG | D1-26.1.1 | (SEQ ID NO: 276) | 13 |
| VyWE | D1-26.2.1 | (SEQ ID NO: 277) | 14 |
| YSGS | D1-26.3.1 | (SEQ ID NO: 278) | 15 |
| IVGA | D1-26.1.2 | (SEQ ID NO: 285) | 16 |
| yWEL | D1-26.2.2 | (SEQ ID NO: 286) | 17 |

TABLE 12-continued

Distinct tetramers that can be extracted from human D segments

| | | | |
|---|---|---|---|
| SGSY | D1-26.3.2 | (SEQ ID NO: 287) | 18 |
| VGAT | D1-26.1.3 | (SEQ ID NO: 291) | 19 |
| WELL | D1-26.2.3 | (SEQ ID NO: 292) | 20 |
| GSYY | D1-26.3.3 | (SEQ ID NO: 293) | 21 |
| RILy | D2-2.1.1 | (SEQ ID NO: 294) | 22 |
| GYCS | D2-2.2.1 | (SEQ ID NO: 295) | 23 |
| DIVV | D2-2.3.1 | (SEQ ID NO: 296) | 24 |
| ILyy | D2-2.1.2 | (SEQ ID NO: 303) | 25 |
| YCSS | D2-2.2.2 | (SEQ ID NO: 304) | 26 |
| IVVV | D2-2.3.2 | (SEQ ID NO: 305) | 27 |
| LyyY | D2-2.1.3 | (SEQ ID NO: 312) | 28 |
| CSST | D2-2.2.3 | (SEQ ID NO: 313) | 29 |
| VVVP | D2-2.3.3 | (SEQ ID NO: 314) | 30 |
| yyYQ | D2-2.1.4 | (SEQ ID NO: 321) | 31 |
| SSTS | D2-2.2.4 | (SEQ ID NO: 322) | 32 |
| VVPA | D2-2.3.4 | (SEQ ID NO: 323) | 33 |
| yYQL | D2-2.1.5 | (SEQ ID NO: 330) | 34 |
| STSC | D2-2.2.5 | (SEQ ID NO: 331) | 35 |
| VPAA | D2-2.3.5 | (SEQ ID NO: 332) | 36 |
| YQLL | D2-2.1.6 | (SEQ ID NO: 338) | 37 |
| TSCY | D2-2.2.6 | (SEQ ID NO: 339) | 38 |
| PAAI | D2-2.3.6 | (SEQ ID NO: 340) | 39 |
| QLLY | D2-2.1.7 | (SEQ ID NO: 343) | 40 |
| SCYT | D2-2.2.7 | (SEQ ID NO: 344) | 41 |
| RILY | D2-8.1.1 | (SEQ ID NO: 345) | 42 |
| GYCT | D2-8.2.1 | (SEQ ID NO: 346) | 43 |
| DIVL | D2-8.3.1 | (SEQ ID NO: 347) | 44 |
| ILYy | D2-8.1.2 | (SEQ ID NO: 354) | 45 |
| YCTN | D2-8.2.2 | (SEQ ID NO: 355) | 46 |
| IVLM | D2-8.3.2 | (SEQ ID NO: 356) | 47 |
| LYyW | D2-8.1.3 | (SEQ ID NO: 363) | 48 |
| CTNG | D2-8.2.3 | (SEQ ID NO: 364) | 49 |
| VLMV | D2-8.3.3 | (SEQ ID NO: 365) | 50 |
| YyWC | D2-8.1.4 | (SEQ ID NO: 372) | 51 |
| TNGV | D2-8.2.4 | (SEQ ID NO: 373) | 52 |
| LMVY | D2-8.3.4 | (SEQ ID NO: 374) | 53 |
| yWCM | D2-8.1.5 | (SEQ ID NO: 381) | 54 |
| NGVC | D2-8.2.5 | (SEQ ID NO: 382) | 55 |

TABLE 12-continued

Distinct tetramers that can be extracted from human D segments

| | | | |
|---|---|---|---|
| MVYA | D2-8.3.5 | (SEQ ID NO: 383) | 56 |
| WCML | D2-8.1.6 | (SEQ ID NO: 389) | 57 |
| GVCY | D2-8.2.6 | (SEQ ID NO: 390) | 58 |
| VYAI | D2-8.3.6 | (SEQ ID NO: 391) | 59 |
| CMLY | D2-8.1.7 | (SEQ ID NO: 394) | 60 |
| VCYT | D2-8.2.7 | (SEQ ID NO: 395) | 61 |
| ILyW | D2-15.1.2 | (SEQ ID NO: 401) | 62 |
| YCSG | D2-15.2.2 | (SEQ ID NO: 402) | 63 |
| LyWW | D2-15.1.3 | (SEQ ID NO: 409) | 64 |
| CSGG | D2-15.2.3 | (SEQ ID NO: 410) | 65 |
| VVVV | D2-15.3.3 | (SEQ ID NO: 411) | 66 |
| yWWy | D2-15.1.4 | (SEQ ID NO: 418) | 67 |
| SGGS | D2-15.2.4 | (SEQ ID NO: 419) | 68 |
| VVVA | D2-15.3.4 | (SEQ ID NO: 420) | 69 |
| WWyL | D2-15.1.5 | (SEQ ID NO: 427) | 70 |
| GGSC | D2-15.2.5 | (SEQ ID NO: 428) | 71 |
| VVAA | D2-15.3.5 | (SEQ ID NO: 429) | 72 |
| WyLL | D2-15.1.6 | (SEQ ID NO: 435) | 73 |
| GSCY | D2-15.2.6 | (SEQ ID NO: 436) | 74 |
| VAAT | D2-15.3.6 | (SEQ ID NO: 437) | 75 |
| yLLL | D2-15.1.7 | (SEQ ID NO: 440) | 76 |
| SCYS | D2-15.2.7 | (SEQ ID NO: 441) | 77 |
| SILW | D2-21.1.1 | (SEQ ID NO: 442) | 78 |
| AYCG | D2-21.2.1 | (SEQ ID NO: 443) | 79 |
| HIVV | D2-21.3.1 | (SEQ ID NO: 444) | 80 |
| ILWW | D2-21.1.2 | (SEQ ID NO: 451) | 81 |
| YCGG | D2-21.2.2 | (SEQ ID NO: 452) | 82 |
| LWWw | D2-21.1.3 | (SEQ ID NO: 459) | 83 |
| CGGD | D2-21.2.3 | (SEQ ID NO: 460) | 84 |
| VVVT | D2-21.3.3 | (SEQ ID NO: 461) | 85 |
| WWwL | D2-21.1.4 | (SEQ ID NO: 468) | 86 |
| GGDC | D2-21.2.4 | (SEQ ID NO: 469) | 87 |
| VVTA | D2-21.3.4 | (SEQ ID NO: 470) | 88 |
| WwLL | D2-21.1.5 | (SEQ ID NO: 476) | 89 |
| GDCY | D2-21.2.5 | (SEQ ID NO: 477) | 90 |
| VTAI | D2-21.3.5 | (SEQ ID NO: 478) | 91 |
| wLLF | D2-21.1.6 | (SEQ ID NO: 481) | 92 |
| DCYS | D2-21.2.6 | (SEQ ID NO: 482) | 93 |
| VLRF | D3-3.1.1 | (SEQ ID NO: 483) | 94 |
| YYDF | D3-3.2.1 | (SEQ ID NO: 484) | 95 |
| ITIF | D3-3.3.1 | (SEQ ID NO: 485) | 96 |
| LRFL | D3-3.1.2 | (SEQ ID NO: 492) | 97 |
| YDFW | D3-3.2.2 | (SEQ ID NO: 493) | 98 |
| TIFG | D3-3.3.2 | (SEQ ID NO: 494) | 99 |
| RFLE | D3-3.1.3 | (SEQ ID NO: 501) | 100 |
| DFWS | D3-3.2.3 | (SEQ ID NO: 502) | 101 |
| IFGV | D3-3.3.3 | (SEQ ID NO: 503) | 102 |
| FLEW | D3-3.1.4 | (SEQ ID NO: 510) | 103 |
| FWSG | D3-3.2.4 | (SEQ ID NO: 511) | 104 |
| FGVV | D3-3.3.4 | (SEQ ID NO: 512) | 105 |
| LEWL | D3-3.1.5 | (SEQ ID NO: 519) | 106 |
| WSGY | D3-3.2.5 | (SEQ ID NO: 520) | 107 |
| GVVI | D3-3.3.5 | (SEQ ID NO: 521) | 108 |
| EWLL | D3-3.1.6 | (SEQ ID NO: 527) | 109 |
| SGYY | D3-3.2.6 | (SEQ ID NO: 528) | 110 |
| VVII | D3-3.3.6 | (SEQ ID NO: 529) | 111 |
| WLLY | D3-3.1.7 | (SEQ ID NO: 532) | 112 |
| GYYT | D3-3.2.7 | (SEQ ID NO: 533) | 113 |
| VLRY | D3-9.1.1 | (SEQ ID NO: 534) | 114 |
| YYDI | D3-9.2.1 | (SEQ ID NO: 535) | 115 |
| LRYF | D3-9.1.2 | (SEQ ID NO: 542) | 116 |
| YDIL | D3-9.2.2 | (SEQ ID NO: 543) | 117 |
| TIFy | D3-9.3.2 | (SEQ ID NO: 544) | 118 |
| RYFD | D3-9.1.3 | (SEQ ID NO: 551) | 119 |
| DILT | D3-9.2.3 | (SEQ ID NO: 552) | 120 |
| IFyL | D3-9.3.3 | (SEQ ID NO: 553) | 121 |
| YFDW | D3-9.1.4 | (SEQ ID NO: 560) | 122 |
| ILTG | D3-9.2.4 | (SEQ ID NO: 561) | 123 |
| FyLV | D3-9.3.4 | (SEQ ID NO: 562) | 124 |
| FDWL | D3-9.1.5 | (SEQ ID NO: 569) | 125 |
| LTGY | D3-9.2.5 | (SEQ ID NO: 570) | 126 |
| yLVI | D3-9.3.5 | (SEQ ID NO: 571) | 127 |
| DWLL | D3-9.1.6 | (SEQ ID NO: 577) | 128 |
| TGYY | D3-9.2.6 | (SEQ ID NO: 578) | 129 |
| LVII | D3-9.3.6 | (SEQ ID NO: 579) | 130 |
| WLLy | D3-9.1.7 | (SEQ ID NO: 582) | 131 |
| GYYN | D3-9.2.7 | (SEQ ID NO: 583) | 132 |

TABLE 12-continued

Distinct tetramers that can be extracted from human D segments

| | | | |
|---|---|---|---|
| VLLW | D3-10.1.1 | (SEQ ID NO: 584) | 133 |
| YYYG | D3-10.2.1 | (SEQ ID NO: 585) | 134 |
| ITMV | D3-10.3.1 | (SEQ ID NO: 586) | 135 |
| LLWF | D3-10.1.2 | (SEQ ID NO: 593) | 136 |
| YYGS | D3-10.2.2 | (SEQ ID NO: 594) | 137 |
| TMVR | D3-10.3.2 | (SEQ ID NO: 595) | 138 |
| LWFG | D3-10.1.3 | (SEQ ID NO: 602) | 139 |
| YGSG | D3-10.2.3 | (SEQ ID NO: 603) | 140 |
| MVRG | D3-10.3.3 | (SEQ ID NO: 604) | 141 |
| WFGE | D3-10.1.4 | (SEQ ID NO: 611) | 142 |
| GSGS | D3-10.2.4 | (SEQ ID NO: 612) | 143 |
| VRGV | D3-10.3.4 | (SEQ ID NO: 613) | 144 |
| FGEL | D3-10.1.5 | (SEQ ID NO: 620) | 145 |
| RGVI | D3-10.3.5 | (SEQ ID NO: 621) | 146 |
| GELL | D3-10.1.6 | (SEQ ID NO: 626) | 147 |
| GVII | D3-10.3.6 | (SEQ ID NO: 627) | 148 |
| ELLy | D3-10.1.7 | (SEQ ID NO: 630) | 149 |
| SYYN | D3-10.2.7 | (SEQ ID NO: 631) | 150 |
| VLwL | D3-16.1.1 | (SEQ ID NO: 632) | 151 |
| YYDY | D3-16.2.1 | (SEQ ID NO: 633) | 152 |
| IMIT | D3-16.3.1 | (SEQ ID NO: 634) | 153 |
| LwLR | D3-16.1.2 | (SEQ ID NO: 641) | 154 |
| YDYV | D3-16.2.2 | (SEQ ID NO: 642) | 155 |
| MITF | D3-16.3.2 | (SEQ ID NO: 643) | 156 |
| wLRL | D3-16.1.3 | (SEQ ID NO: 650) | 157 |
| DYVW | D3-16.2.3 | (SEQ ID NO: 651) | 158 |
| ITFG | D3-16.3.3 | (SEQ ID NO: 652) | 159 |
| LRLG | D3-16.1.4 | (SEQ ID NO: 659) | 160 |
| YVWG | D3-16.2.4 | (SEQ ID NO: 660) | 161 |
| TFGG | D3-16.3.4 | (SEQ ID NO: 661) | 162 |
| RLGE | D3-16.1.5 | (SEQ ID NO: 668) | 163 |
| VWGS | D3-16.2.5 | (SEQ ID NO: 669) | 164 |
| FGGV | D3-16.3.5 | (SEQ ID NO: 670) | 165 |
| LGEL | D3-16.1.6 | (SEQ ID NO: 677) | 166 |
| WGSY | D3-16.2.6 | (SEQ ID NO: 678) | 167 |
| GGVI | D3-16.3.6 | (SEQ ID NO: 679) | 168 |
| GELS | D3-16.1.7 | (SEQ ID NO: 686) | 169 |
| GSYR | D3-16.2.7 | (SEQ ID NO: 687) | 170 |
| GVIV | D3-16.3.7 | (SEQ ID NO: 688) | 171 |
| ELSL | D3-16.1.8 | (SEQ ID NO: 694) | 172 |
| SYRY | D3-16.2.8 | (SEQ ID NO: 695) | 173 |
| VIVI | D3-16.3.8 | (SEQ ID NO: 696) | 174 |
| LSLY | D3-16.1.9 | (SEQ ID NO: 699) | 175 |
| YRYT | D3-16.2.9 | (SEQ ID NO: 700) | 176 |
| VLLw | D3-22.1.1 | (SEQ ID NO: 701) | 177 |
| YYYD | D3-22.2.1 | (SEQ ID NO: 702) | 178 |
| ITMI | D3-22.3.1 | (SEQ ID NO: 703) | 179 |
| LLwy | D3-22.1.2 | (SEQ ID NO: 710) | 180 |
| YYDS | D3-22.2.2 | (SEQ ID NO: 711) | 181 |
| TMIV | D3-22.3.2 | (SEQ ID NO: 712) | 182 |
| Lwyy | D3-22.1.3 | (SEQ ID NO: 719) | 183 |
| YDSS | D3-22.2.3 | (SEQ ID NO: 720) | 184 |
| MIVV | D3-22.3.3 | (SEQ ID NO: 721) | 185 |
| wyyW | D3-22.1.4 | (SEQ ID NO: 728) | 186 |
| DSSG | D3-22.2.4 | (SEQ ID NO: 729) | 187 |
| yyWL | D3-22.1.5 | (SEQ ID NO: 736) | 188 |
| SSGY | D3-22.2.5 | (SEQ ID NO: 737) | 189 |
| VVVI | D3-22.3.5 | (SEQ ID NO: 738) | 190 |
| yWLL | D3-22.1.6 | (SEQ ID NO: 744) | 191 |
| VVIT | D3-22.3.6 | (SEQ ID NO: 745) | 192 |
| WLLL | D3-22.1.7 | (SEQ ID NO: 748) | 193 |
| GYYY | D3-22.2.7 | (SEQ ID NO: 749) | 194 |
| wLQy | D4-4.1.1 | (SEQ ID NO: 750) | 195 |
| DYSN | D4-4.2.1 | (SEQ ID NO: 751) | 196 |
| TTVT | D4-4.3.1 | (SEQ ID NO: 752) | 197 |
| LQyL | D4-4.1.2 | (SEQ ID NO: 755) | 198 |
| YSNY | D4-4.2.2 | (SEQ ID NO: 756) | 199 |
| wLRw | D4-17.1.1 | (SEQ ID NO: 757) | 200 |
| DYGD | D4-17.2.1 | (SEQ ID NO: 758) | 201 |
| LRwL | D4-17.1.2 | (SEQ ID NO: 761) | 202 |
| YGDY | D4-17.2.2 | (SEQ ID NO: 762) | 203 |
| wLRW | D4-23.1.1 | (SEQ ID NO: 763) | 204 |
| DYGG | D4-23.2.1 | (SEQ ID NO: 764) | 205 |
| TTVV | D4-23.3.1 | (SEQ ID NO: 765) | 206 |
| LRWy | D4-23.1.2 | (SEQ ID NO: 771) | 207 |
| YGGN | D4-23.2.2 | (SEQ ID NO: 772) | 208 |
| TVVT | D4-23.3.2 | (SEQ ID NO: 773) | 209 |

TABLE 12-continued

Distinct tetramers that can be extracted from human D segments

| | | | |
|---|---|---|---|
| RWyL | D4-23.1.3 | (SEQ ID NO: 776) | 210 |
| GGNS | D4-23.2.3 | (SEQ ID NO: 777) | 211 |
| VDTA | D5-5.1.1 | (SEQ ID NO: 778) | 212 |
| WIQL | D5-5.2.1 | (SEQ ID NO: 779) | 213 |
| GYSY | D5-5.3.1 | (SEQ ID NO: 780) | 214 |
| DTAM | D5-5.1.2 | (SEQ ID NO: 787) | 215 |
| IQLW | D5-5.2.2 | (SEQ ID NO: 788) | 216 |
| YSYG | D5-5.3.2 | (SEQ ID NO: 789) | 217 |
| TAMV | D5-5.1.3 | (SEQ ID NO: 793) | 218 |
| QLWL | D5-5.2.3 | (SEQ ID NO: 794) | 219 |
| SYGY | D5-5.3.3 | (SEQ ID NO: 795) | 220 |
| VDIV | D5-12.1.1 | (SEQ ID NO: 796) | 221 |
| WIyW | D5-12.2.1 | (SEQ ID NO: 797) | 222 |
| GYSG | D5-12.3.1 | (SEQ ID NO: 798) | 223 |
| DIVA | D5-12.1.2 | (SEQ ID NO: 805) | 224 |
| IyWL | D5-12.2.2 | (SEQ ID NO: 806) | 225 |
| YSGY | D5-12.3.2 | (SEQ ID NO: 807) | 226 |
| IVAT | D5-12.1.3 | (SEQ ID NO: 814) | 227 |
| yWLR | D5-12.2.3 | (SEQ ID NO: 815) | 228 |
| SGYD | D5-12.3.3 | (SEQ ID NO: 816) | 229 |
| VATI | D5-12.1.4 | (SEQ ID NO: 820) | 230 |
| WLRL | D5-12.2.4 | (SEQ ID NO: 821) | 231 |
| GYDY | D5-12.3.4 | (SEQ ID NO: 822) | 232 |
| VEMA | D5-24.1.1 | (SEQ ID NO: 823) | 233 |
| yRWL | D5-24.2.1 | (SEQ ID NO: 824) | 234 |
| RDGY | D5-24.3.1 | (SEQ ID NO: 825) | 235 |
| EMAT | D5-24.1.2 | (SEQ ID NO: 832) | 236 |
| RWLQ | D5-24.2.2 | (SEQ ID NO: 833) | 237 |
| DGYN | D5-24.3.2 | (SEQ ID NO: 834) | 238 |
| MATI | D5-24.1.3 | (SEQ ID NO: 838) | 239 |
| WLQL | D5-24.2.3 | (SEQ ID NO: 839) | 240 |
| GYNY | D5-24.3.3 | (SEQ ID NO: 840) | 241 |
| EYSS | D6-6.1.1 | (SEQ ID NO: 841) | 242 |
| SIAA | D6-6.2.1 | (SEQ ID NO: 842) | 243 |
| VyQL | D6-6.3.1 | (SEQ ID NO: 843) | 244 |
| YSSS | D6-6.1.2 | (SEQ ID NO: 848) | 245 |
| IAAR | D6-6.2.2 | (SEQ ID NO: 849) | 246 |
| yQLV | D6-6.3.2 | (SEQ ID NO: 850) | 247 |
| SSSS | D6-6.1.3 | (SEQ ID NO: 852) | 248 |
| GYSS | D6-13.1.1 | (SEQ ID NO: 853) | 249 |
| GIAA | D6-13.2.1 | (SEQ ID NO: 854) | 250 |
| VyQQ | D6-13.3.1 | (SEQ ID NO: 855) | 251 |
| IAAA | D6-13.2.2 | (SEQ ID NO: 862) | 252 |
| yQQL | D6-13.3.2 | (SEQ ID NO: 863) | 253 |
| SSSW | D6-13.1.3 | (SEQ ID NO: 868) | 254 |
| AAAG | D6-13.2.3 | (SEQ ID NO: 869) | 255 |
| QQLV | D6-13.3.3 | (SEQ ID NO: 870) | 256 |
| SSWY | D6-13.1.4 | (SEQ ID NO: 872) | 257 |
| GIAV | D6-19.2.1 | (SEQ ID NO: 873) | 258 |
| VyQW | D6-19.3.1 | (SEQ ID NO: 874) | 259 |
| YSSG | D6-19.1.2 | (SEQ ID NO: 881) | 260 |
| IAVA | D6-19.2.2 | (SEQ ID NO: 882) | 261 |
| yQWL | D6-19.3.2 | (SEQ ID NO: 883) | 262 |
| SSGW | D6-19.1.3 | (SEQ ID NO: 888) | 263 |
| AVAG | D6-19.2.3 | (SEQ ID NO: 889) | 264 |
| QWLV | D6-19.3.3 | (SEQ ID NO: 890) | 265 |
| SGWY | D6-19.1.4 | (SEQ ID NO: 941) | 266 |

TABLE 13

Pentamers that can be extracted from human D segments

| | | | |
|---|---|---|---|
| GTTGT | D1-1.1.1 | (SEQ ID NO: 260) | 1 |
| VQLER | D1-1.2.1 | (SEQ ID NO: 261) | 2 |
| YNWND | D1-1.3.1 | (SEQ ID NO: 262) | 3 |
| GITGT | D1-7.1.1 | (SEQ ID NO: 268) | 4 |
| VyLEL | D1-7.2.1 | (SEQ ID NO: 269) | 5 |
| YNWNY | D1-7.3.1 | (SEQ ID NO: 270) | 6 |
| VyLER | D1-20.2.1 | (SEQ ID NO: 274) | 7 |
| GIVGA | D1-26.1.1 | (SEQ ID NO: 279) | 8 |
| VyWEL | D1-26.2.1 | (SEQ ID NO: 280) | 9 |
| YSGSY | D1-26.3.1 | (SEQ ID NO: 281) | 10 |
| IVGAT | D1-26.1.2 | (SEQ ID NO: 288) | 11 |
| yWELL | D1-26.2.2 | (SEQ ID NO: 289) | 12 |
| SGSYY | D1-26.3.2 | (SEQ ID NO: 290) | 13 |
| RILyy | D2-2.1.1 | (SEQ ID NO: 297) | 14 |
| GYCSS | D2-2.2.1 | (SEQ ID NO: 298) | 15 |
| DIVVV | D2-2.3.1 | (SEQ ID NO: 299) | 16 |

TABLE 13-continued

Pentamers that can be extracted from human D segments

| | | | |
|---|---|---|---|
| ILyyY | D2-2.1.2 | (SEQ ID NO: 306) | 17 |
| YCSST | D2-2.2.2 | (SEQ ID NO: 307) | 18 |
| IVVVP | D2-2.3.2 | (SEQ ID NO: 308) | 19 |
| LyyYQ | D2-2.1.3 | (SEQ ID NO: 315) | 20 |
| CSSTS | D2-2.2.3 | (SEQ ID NO: 316) | 21 |
| VVVPA | D2-2.3.3 | (SEQ ID NO: 317) | 22 |
| yyYQL | D2-2.1.4 | (SEQ ID NO: 324) | 23 |
| SSTSC | D2-2.2.4 | (SEQ ID NO: 325) | 24 |
| VVPAA | D2-2.3.4 | (SEQ ID NO: 326) | 25 |
| yYQLL | D2-2.1.5 | (SEQ ID NO: 333) | 26 |
| STSCY | D2-2.2.5 | (SEQ ID NO: 334) | 27 |
| VPAAI | D2-2.3.5 | (SEQ ID NO: 335) | 28 |
| YQLLY | D2-2.1.6 | (SEQ ID NO: 341) | 29 |
| TSCYT | D2-2.2.6 | (SEQ ID NO: 342) | 30 |
| RILYy | D2-8.1.1 | (SEQ ID NO: 348) | 31 |
| GYCTN | D2-8.2.1 | (SEQ ID NO: 349) | 32 |
| DIVLM | D2-8.3.1 | (SEQ ID NO: 350) | 33 |
| ILYyW | D2-8.1.2 | (SEQ ID NO: 357) | 34 |
| YCTNG | D2-8.2.2 | (SEQ ID NO: 358) | 35 |
| IVLMV | D2-8.3.2 | (SEQ ID NO: 359) | 36 |
| LYyWC | D2-8.1.3 | (SEQ ID NO: 366) | 37 |
| CTNGV | D2-8.2.3 | (SEQ ID NO: 367) | 38 |
| VLMVY | D2-8.3.3 | (SEQ ID NO: 368) | 39 |
| YyWCM | D2-8.1.4 | (SEQ ID NO: 375) | 40 |
| TNGVC | D2-8.2.4 | (SEQ ID NO: 376) | 41 |
| LMVYA | D2-8.3.4 | (SEQ ID NO: 377) | 42 |
| yWCML | D2-8.1.5 | (SEQ ID NO: 384) | 43 |
| NGVCY | D2-8.2.5 | (SEQ ID NO: 385) | 44 |
| MVYAI | D2-8.3.5 | (SEQ ID NO: 386) | 45 |
| WCMLY | D2-8.1.6 | (SEQ ID NO: 392) | 46 |
| GVCYT | D2-8.2.6 | (SEQ ID NO: 393) | 47 |
| RILyW | D2-15.1.1 | (SEQ ID NO: 396) | 48 |
| GYCSG | D2-15.2.1 | (SEQ ID NO: 397) | 49 |
| ILyWW | D2-15.1.2 | (SEQ ID NO: 403) | 50 |
| YCSGG | D2-15.2.2 | (SEQ ID NO: 404) | 51 |
| IVVVV | D2-15.3.2 | (SEQ ID NO: 405) | 52 |
| LyWWy | D2-15.1.3 | (SEQ ID NO: 412) | 53 |
| CSGGS | D2-15.2.3 | (SEQ ID NO: 413) | 54 |
| VVVVA | D2-15.3.3 | (SEQ ID NO: 414) | 55 |
| yWWyL | D2-15.1.4 | (SEQ ID NO: 421) | 56 |
| SGGSC | D2-15.2.4 | (SEQ ID NO: 422) | 57 |
| VVVAA | D2-15.3.4 | (SEQ ID NO: 423) | 58 |
| WWyLL | D2-15.1.5 | (SEQ ID NO: 430) | 59 |
| GGSCY | D2-15.2.5 | (SEQ ID NO: 431) | 60 |
| VVAAT | D2-15.3.5 | (SEQ ID NO: 432) | 61 |
| WyLLL | D2-15.1.6 | (SEQ ID NO: 438) | 62 |
| GSCYS | D2-15.2.6 | (SEQ ID NO: 439) | 63 |
| SILWW | D2-21.1.1 | (SEQ ID NO: 445) | 64 |
| AYCGG | D2-21.2.1 | (SEQ ID NO: 446) | 65 |
| HIVVV | D2-21.3.1 | (SEQ ID NO: 447) | 66 |
| ILWWw | D2-21.1.2 | (SEQ ID NO: 453) | 67 |
| YCGGD | D2-21.2.2 | (SEQ ID NO: 454) | 68 |
| IVVVT | D2-21.3.2 | (SEQ ID NO: 455) | 69 |
| LWWwL | D2-21.1.3 | (SEQ ID NO: 462) | 70 |
| CGGDC | D2-21.2.3 | (SEQ ID NO: 463) | 71 |
| VVVTA | D2-21.3.3 | (SEQ ID NO: 464) | 72 |
| WWwLL | D2-21.1.4 | (SEQ ID NO: 471) | 73 |
| GGDCY | D2-21.2.4 | (SEQ ID NO: 472) | 74 |
| VVTAI | D2-21.3.4 | (SEQ ID NO: 473) | 75 |
| WwLLF | D2-21.1.5 | (SEQ ID NO: 479) | 76 |
| GDCYS | D2-21.2.5 | (SEQ ID NO: 480) | 77 |
| VLRFL | D3-3.1.1 | (SEQ ID NO: 486) | 78 |
| YYDFW | D3-3.2.1 | (SEQ ID NO: 487) | 79 |
| ITIFG | D3-3.3.1 | (SEQ ID NO: 488) | 80 |
| LRFLE | D3-3.1.2 | (SEQ ID NO: 495) | 81 |
| YDFWS | D3-3.2.2 | (SEQ ID NO: 496) | 82 |
| TIFGV | D3-3.3.2 | (SEQ ID NO: 497) | 83 |
| RFLEW | D3-3.1.3 | (SEQ ID NO: 504) | 84 |
| DFWSG | D3-3.2.3 | (SEQ ID NO: 505) | 85 |
| IFGVV | D3-3.3.3 | (SEQ ID NO: 506) | 86 |
| FLEWL | D3-3.1.4 | (SEQ ID NO: 513) | 87 |
| FWSGY | D3-3.2.4 | (SEQ ID NO: 514) | 88 |
| FGVVI | D3-3.3.4 | (SEQ ID NO: 515) | 89 |
| LEWLL | D3-3.1.5 | (SEQ ID NO: 522) | 90 |
| WSGYY | D3-3.2.5 | (SEQ ID NO: 523) | 91 |
| GVVII | D3-3.3.5 | (SEQ ID NO: 524) | 92 |
| EWLLY | D3-3.1.6 | (SEQ ID NO: 530) | 93 |

TABLE 13-continued

Pentamers that can be extracted from human D segments

| | | | |
|---|---|---|---|
| SGYYT | D3-3.2.6 | (SEQ ID NO: 531) | 94 |
| VLRYF | D3-9.1.1 | (SEQ ID NO: 536) | 95 |
| YYDIL | D3-9.2.1 | (SEQ ID NO: 537) | 96 |
| ITIFy | D3-9.3.1 | (SEQ ID NO: 538) | 97 |
| LRYFD | D3-9.1.2 | (SEQ ID NO: 545) | 98 |
| YDILT | D3-9.2.2 | (SEQ ID NO: 546) | 99 |
| TIFyL | D3-9.3.2 | (SEQ ID NO: 547) | 100 |
| RYFDW | D3-9.1.3 | (SEQ ID NO: 554) | 101 |
| DILTG | D3-9.2.3 | (SEQ ID NO: 555) | 102 |
| IFyLV | D3-9.3.3 | (SEQ ID NO: 556) | 103 |
| YFDWL | D3-9.1.4 | (SEQ ID NO: 563) | 104 |
| ILTGY | D3-9.2.4 | (SEQ ID NO: 564) | 105 |
| FyLVI | D3-9.3.4 | (SEQ ID NO: 565) | 106 |
| FDWLL | D3-9.1.5 | (SEQ ID NO: 572) | 107 |
| LTGYY | D3-9.2.5 | (SEQ ID NO: 573) | 108 |
| yLVII | D3-9.3.5 | (SEQ ID NO: 574) | 109 |
| DWLLy | D3-9.1.6 | (SEQ ID NO: 580) | 110 |
| TGYYN | D3-9.2.6 | (SEQ ID NO: 581) | 111 |
| VLLWF | D3-10.1.1 | (SEQ ID NO: 587) | 112 |
| YYYGS | D3-10.2.1 | (SEQ ID NO: 588) | 113 |
| ITMVR | D3-10.3.1 | (SEQ ID NO: 589) | 114 |
| LLWFG | D3-10.1.2 | (SEQ ID NO: 596) | 115 |
| YYGSG | D3-10.2.2 | (SEQ ID NO: 597) | 116 |
| TMVRG | D3-10.3.2 | (SEQ ID NO: 598) | 117 |
| LWFGE | D3-10.1.3 | (SEQ ID NO: 605) | 118 |
| YGSGS | D3-10.2.3 | (SEQ ID NO: 606) | 119 |
| MVRGV | D3-10.3.3 | (SEQ ID NO: 607) | 120 |
| WFGEL | D3-10.1.4 | (SEQ ID NO: 614) | 121 |
| GSGSY | D3-10.2.4 | (SEQ ID NO: 615) | 122 |
| VRGVI | D3-10.3.4 | (SEQ ID NO: 616) | 123 |
| FGELL | D3-10.1.5 | (SEQ ID NO: 622) | 124 |
| RGVII | D3-10.3.5 | (SEQ ID NO: 623) | 125 |
| GELLy | D3-10.1.6 | (SEQ ID NO: 628) | 126 |
| GSYYN | D3-10.2.6 | (SEQ ID NO: 629) | 127 |
| VLwLR | D3-16.1.1 | (SEQ ID NO: 635) | 128 |
| YYDYV | D3-16.2.1 | (SEQ ID NO: 636) | 129 |
| IMITF | D3-16.3.1 | (SEQ ID NO: 637) | 130 |
| LwLRL | D3-16.1.2 | (SEQ ID NO: 644) | 131 |
| YDYVW | D3-16.2.2 | (SEQ ID NO: 645) | 132 |
| MITFG | D3-16.3.2 | (SEQ ID NO: 646) | 133 |
| wLRLG | D3-16.1.3 | (SEQ ID NO: 653) | 134 |
| DYVWG | D3-16.2.3 | (SEQ ID NO: 654) | 135 |
| ITFGG | D3-16.3.3 | (SEQ ID NO: 655) | 136 |
| LRLGE | D3-16.1.4 | (SEQ ID NO: 662) | 137 |
| YVWGS | D3-16.2.4 | (SEQ ID NO: 663) | 138 |
| TFGGV | D3-16.3.4 | (SEQ ID NO: 664) | 139 |
| RLGEL | D3-16.1.5 | (SEQ ID NO: 671) | 140 |
| VWGSY | D3-16.2.5 | (SEQ ID NO: 672) | 141 |
| FGGVI | D3-16.3.5 | (SEQ ID NO: 673) | 142 |
| LGELS | D3-16.1.6 | (SEQ ID NO: 680) | 143 |
| WGSYR | D3-16.2.6 | (SEQ ID NO: 681) | 144 |
| GGVIV | D3-16.3.6 | (SEQ ID NO: 682) | 145 |
| GELSL | D3-16.1.7 | (SEQ ID NO: 689) | 146 |
| GSYRY | D3-16.2.7 | (SEQ ID NO: 690) | 147 |
| GVIVI | D3-16.3.7 | (SEQ ID NO: 691) | 148 |
| ELSLY | D3-16.1.8 | (SEQ ID NO: 697) | 149 |
| SYRYT | D3-16.2.8 | (SEQ ID NO: 698) | 150 |
| VLLwy | D3-22.1.1 | (SEQ ID NO: 704) | 151 |
| YYYDS | D3-22.2.1 | (SEQ ID NO: 705) | 152 |
| ITMIV | D3-22.3.1 | (SEQ ID NO: 706) | 153 |
| LLwyy | D3-22.1.2 | (SEQ ID NO: 713) | 154 |
| YYDSS | D3-22.2.2 | (SEQ ID NO: 714) | 155 |
| TMIVV | D3-22.3.2 | (SEQ ID NO: 715) | 156 |
| LwyyW | D3-22.1.3 | (SEQ ID NO: 722) | 157 |
| YDSSG | D3-22.2.3 | (SEQ ID NO: 723) | 158 |
| MIVVV | D3-22.3.3 | (SEQ ID NO: 724) | 159 |
| wyyWL | D3-22.1.4 | (SEQ ID NO: 730) | 160 |
| DSSGY | D3-22.2.4 | (SEQ ID NO: 731) | 161 |
| IVVVI | D3-22.3.4 | (SEQ ID NO: 732) | 162 |
| yyWLL | D3-22.1.5 | (SEQ ID NO: 739) | 163 |
| SSGYY | D3-22.2.5 | (SEQ ID NO: 740) | 164 |
| VVVIT | D3-22.3.5 | (SEQ ID NO: 741) | 165 |
| yWLLL | D3-22.1.6 | (SEQ ID NO: 746) | 166 |
| SGYYY | D3-22.2.6 | (SEQ ID NO: 747) | 167 |
| wLQyL | D4-4.1.1 | (SEQ ID NO: 753) | 168 |
| DYSNY | D4-4.2.1 | (SEQ ID NO: 754) | 169 |
| wLRwL | D4-17.1.1 | (SEQ ID NO: 759) | 170 |

TABLE 13-continued

Pentamers that can be extracted from human D segments

| | | | |
|---|---|---|---|
| DYGDY | D4-17.2.1 | (SEQ ID NO: 760) | 171 |
| wLRWy | D4-23.1.1 | (SEQ ID NO: 766) | 172 |
| DYGGN | D4-23.2.1 | (SEQ ID NO: 767) | 173 |
| TTVVT | D4-23.3.1 | (SEQ ID NO: 768) | 174 |
| LRWyL | D4-23.1.2 | (SEQ ID NO: 774) | 175 |
| YGGNS | D4-23.2.2 | (SEQ ID NO: 775) | 176 |
| VDTAM | D5-5.1.1 | (SEQ ID NO: 781) | 177 |
| WIQLW | D5-5.2.1 | (SEQ ID NO: 782) | 178 |
| GYSYG | D5-5.3.1 | (SEQ ID NO: 783) | 179 |
| DTAMV | D5-5.1.2 | (SEQ ID NO: 790) | 180 |
| IQLWL | D5-5.2.2 | (SEQ ID NO: 791) | 181 |
| YSYGY | D5-5.3.2 | (SEQ ID NO: 792) | 182 |
| VDIVA | D5-12.1.1 | (SEQ ID NO: 799) | 183 |
| WIyWL | D5-12.2.1 | (SEQ ID NO: 800) | 184 |
| GYSGY | D5-12.3.1 | (SEQ ID NO: 801) | 185 |
| DIVAT | D5-12.1.2 | (SEQ ID NO: 808) | 186 |
| IyWLR | D5-12.2.2 | (SEQ ID NO: 809) | 187 |
| YSGYD | D5-12.3.2 | (SEQ ID NO: 810) | 188 |
| IVATI | D5-12.1.3 | (SEQ ID NO: 817) | 189 |
| yWLRL | D5-12.2.3 | (SEQ ID NO: 818) | 190 |
| SGYDY | D5-12.3.3 | (SEQ ID NO: 819) | 191 |
| VEMAT | D5-24.1.1 | (SEQ ID NO: 826) | 192 |
| yRWLQ | D5-24.2.1 | (SEQ ID NO: 827) | 193 |
| RDGYN | D5-24.3.1 | (SEQ ID NO: 828) | 194 |
| EMATI | D5-24.1.2 | (SEQ ID NO: 835) | 195 |
| RWLQL | D5-24.2.2 | (SEQ ID NO: 836) | 196 |
| DGYNY | D5-24.3.2 | (SEQ ID NO: 837) | 197 |
| EYSSS | D6-6.1.1 | (SEQ ID NO: 844) | 198 |
| SIAAR | D6-6.2.1 | (SEQ ID NO: 845) | 199 |
| VyQLV | D6-6.3.1 | (SEQ ID NO: 846) | 200 |
| YSSSS | D6-6.1.2 | (SEQ ID NO: 851) | 201 |
| GYSSS | D6-13.1.1 | (SEQ ID NO: 856) | 202 |
| GIAAA | D6-13.2.1 | (SEQ ID NO: 857) | 203 |
| VyQQL | D6-13.3.1 | (SEQ ID NO: 858) | 204 |
| YSSSW | D6-13.1.2 | (SEQ ID NO: 864) | 205 |
| IAAAG | D6-13.2.2 | (SEQ ID NO: 865) | 206 |
| yQQLV | D6-13.3.2 | (SEQ ID NO: 866) | 207 |
| SSSWY | D6-13.1.3 | (SEQ ID NO: 871) | 208 |
| GYSSG | D6-19.1.1 | (SEQ ID NO: 875) | 209 |
| GIAVA | D6-19.2.1 | (SEQ ID NO: 876) | 210 |
| VyQWL | D6-19.3.1 | (SEQ ID NO: 877) | 211 |
| YSSGW | D6-19.1.2 | (SEQ ID NO: 884) | 212 |
| IAVAG | D6-19.2.2 | (SEQ ID NO: 885) | 213 |
| yQWLV | D6-19.3.2 | (SEQ ID NO: 886) | 214 |
| SSGWY | D6-19.1.3 | (SEQ ID NO: 891) | 215 |

TABLE 14

All hexamers that can be extracted from human D segments

| | | | |
|---|---|---|---|
| GIVGAT | D1-26.1.1 | (SEQ ID NO: 282) | 1 |
| VyWELL | D1-26.2.1 | (SEQ ID NO: 283) | 2 |
| YSGSYY | D1-26.3.1 | (SEQ ID NO: 284) | 3 |
| RILyyY | D2-2.1.1 | (SEQ ID NO: 300) | 4 |
| GYCSST | D2-2.2.1 | (SEQ ID NO: 301) | 5 |
| DIVVVP | D2-2.3.1 | (SEQ ID NO: 302) | 6 |
| ILyyYQ | D2-2.1.2 | (SEQ ID NO: 309) | 7 |
| YCSSTS | D2-2.2.2 | (SEQ ID NO: 310) | 8 |
| IVVVPA | D2-2.3.2 | (SEQ ID NO: 311) | 9 |
| LyyYQL | D2-2.1.3 | (SEQ ID NO: 318) | 10 |
| CSSTSC | D2-2.2.3 | (SEQ ID NO: 319) | 11 |
| VVVPAA | D2-2.3.3 | (SEQ ID NO: 320) | 12 |
| yyYQLL | D2-2.1.4 | (SEQ ID NO: 327) | 13 |
| SSTSCY | D2-2.2.4 | (SEQ ID NO: 328) | 14 |
| VVPAAI | D2-2.3.4 | (SEQ ID NO: 329) | 15 |
| yYQLLY | D2-2.1.5 | (SEQ ID NO: 336) | 16 |
| STSCYT | D2-2.2.5 | (SEQ ID NO: 337) | 17 |
| RILYyW | D2-8.1.1 | (SEQ ID NO: 351) | 18 |
| GYCTNG | D2-8.2.1 | (SEQ ID NO: 352) | 19 |
| DIVLMV | D2-8.3.1 | (SEQ ID NO: 353) | 20 |
| ILYyWC | D2-8.1.2 | (SEQ ID NO: 360) | 21 |
| YCTNGV | D2-8.2.2 | (SEQ ID NO: 361) | 22 |
| IVLMVY | D2-8.3.2 | (SEQ ID NO: 362) | 23 |
| LYyWCM | D2-8.1.3 | (SEQ ID NO: 369) | 24 |
| CTNGVC | D2-8.2.3 | (SEQ ID NO: 370) | 25 |
| VLMVYA | D2-8.3.3 | (SEQ ID NO: 371) | 26 |
| YyWCML | D2-8.1.4 | (SEQ ID NO: 378) | 27 |
| TNGVCY | D2-8.2.4 | (SEQ ID NO: 379) | 28 |

TABLE 14-continued

All hexamers that can be extracted from human D segments

| Hexamer | Segment | SEQ ID | # |
|---|---|---|---|
| LMVYAI | D2-8.3.4 | (SEQ ID NO: 380) | 29 |
| yWCMLY | D2-8.1.5 | (SEQ ID NO: 387) | 30 |
| NGVCYT | D2-8.2.5 | (SEQ ID NO: 388) | 31 |
| RILyWW | D2-15.1.1 | (SEQ ID NO: 398) | 32 |
| GYCSGG | D2-15.2.1 | (SEQ ID NO: 399) | 33 |
| DIVVVV | D2-15.3.1 | (SEQ ID NO: 400) | 34 |
| ILyWWy | D2-15.1.2 | (SEQ ID NO: 406) | 35 |
| YCSGGS | D2-15.2.2 | (SEQ ID NO: 407) | 36 |
| IVVVVA | D2-15.3.2 | (SEQ ID NO: 408) | 37 |
| LyWWyL | D2-15.1.3 | (SEQ ID NO: 415) | 38 |
| CSGGSC | D2-15.2.3 | (SEQ ID NO: 416) | 39 |
| VVVVAA | D2-15.3.3 | (SEQ ID NO: 417) | 40 |
| yWWyLL | D2-15.1.4 | (SEQ ID NO: 424) | 41 |
| SGGSCY | D2-15.2.4 | (SEQ ID NO: 425) | 42 |
| VVVAAT | D2-15.3.4 | (SEQ ID NO: 426) | 43 |
| WWyLLL | D2-15.1.5 | (SEQ ID NO: 433) | 44 |
| GGSCYS | D2-15.2.5 | (SEQ ID NO: 434) | 45 |
| SILWWw | D2-21.1.1 | (SEQ ID NO: 448) | 46 |
| AYCGGD | D2-21.2.1 | (SEQ ID NO: 449) | 47 |
| HIVVVT | D2-21.3.1 | (SEQ ID NO: 450) | 48 |
| ILWWwL | D2-21.1.2 | (SEQ ID NO: 456) | 49 |
| YCGGDC | D2-21.2.2 | (SEQ ID NO: 457) | 50 |
| IVVVTA | D2-21.3.2 | (SEQ ID NO: 458) | 51 |
| LWWwLL | D2-21.1.3 | (SEQ ID NO: 465) | 52 |
| CGGDCY | D2-21.2.3 | (SEQ ID NO: 466) | 53 |
| VVVTAI | D2-21.3.3 | (SEQ ID NO: 467) | 54 |
| WWwLLF | D2-21.1.4 | (SEQ ID NO: 474) | 55 |
| GGDCYS | D2-21.2.4 | (SEQ ID NO: 475) | 56 |
| VLRFLE | D3-3.1.1 | (SEQ ID NO: 489) | 57 |
| YDFWS | D3-3.2.1 | (SEQ ID NO: 490) | 58 |
| ITIFGV | D3-3.3.1 | (SEQ ID NO: 491) | 59 |
| LRFLEW | D3-3.1.2 | (SEQ ID NO: 498) | 60 |
| YDFWSG | D3-3.2.2 | (SEQ ID NO: 499) | 61 |
| TIFGVV | D3-3.3.2 | (SEQ ID NO: 500) | 62 |
| RFLEWL | D3-3.1.3 | (SEQ ID NO: 507) | 63 |
| DFWSGY | D3-3.2.3 | (SEQ ID NO: 508) | 64 |
| IFGVVI | D3-3.3.3 | (SEQ ID NO: 509) | 65 |
| FLEWLL | D3-3.1.4 | (SEQ ID NO: 516) | 66 |
| FWSGYY | D3-3.2.4 | (SEQ ID NO: 517) | 67 |
| FGVVII | D3-3.3.4 | (SEQ ID NO: 518) | 68 |
| LEWLLY | D3-3.1.5 | (SEQ ID NO: 525) | 69 |
| WSGYYT | D3-3.2.5 | (SEQ ID NO: 526) | 70 |
| VLRYFD | D3-9.1.1 | (SEQ ID NO: 539) | 71 |
| YDILT | D3-9.2.1 | (SEQ ID NO: 540) | 72 |
| ITIFyL | D3-9.3.1 | (SEQ ID NO: 541) | 73 |
| LRYFDW | D3-9.1.2 | (SEQ ID NO: 548) | 74 |
| YDILTG | D3-9.2.2 | (SEQ ID NO: 549) | 75 |
| TIFyLV | D3-9.3.2 | (SEQ ID NO: 550) | 76 |
| RYFDWL | D3-9.1.3 | (SEQ ID NO: 557) | 77 |
| DILTGY | D3-9.2.3 | (SEQ ID NO: 558) | 78 |
| IFyLVI | D3-9.3.3 | (SEQ ID NO: 559) | 79 |
| YFDWLL | D3-9.1.4 | (SEQ ID NO: 566) | 80 |
| ILTGYY | D3-9.2.4 | (SEQ ID NO: 567) | 81 |
| FyLVII | D3-9.3.4 | (SEQ ID NO: 568) | 82 |
| FDWLLy | D3-9.1.5 | (SEQ ID NO: 575) | 83 |
| LTGYYN | D3-9.2.5 | (SEQ ID NO: 576) | 84 |
| VLLWFG | D3-10.1.1 | (SEQ ID NO: 590) | 85 |
| YYYGSG | D3-10.2.1 | (SEQ ID NO: 591) | 86 |
| ITMVRG | D3-10.3.1 | (SEQ ID NO: 592) | 87 |
| LLWFGE | D3-10.1.2 | (SEQ ID NO: 599) | 88 |
| YYGSGS | D3-10.2.2 | (SEQ ID NO: 600) | 89 |
| TMVRGV | D3-10.3.2 | (SEQ ID NO: 601) | 90 |
| LWFGEL | D3-10.1.3 | (SEQ ID NO: 608) | 91 |
| YGSGSY | D3-10.2.3 | (SEQ ID NO: 609) | 92 |
| MVRGVI | D3-10.3.3 | (SEQ ID NO: 610) | 93 |
| WFGELL | D3-10.1.4 | (SEQ ID NO: 617) | 94 |
| GSGSYY | D3-10.2.4 | (SEQ ID NO: 618) | 95 |
| VRGVII | D3-10.3.4 | (SEQ ID NO: 619) | 96 |
| FGELLy | D3-10.1.5 | (SEQ ID NO: 624) | 97 |
| SGSYYN | D3-10.2.5 | (SEQ ID NO: 625) | 98 |
| VLwLRL | D3-16.1.1 | (SEQ ID NO: 638) | 99 |
| YYDYVW | D3-16.2.1 | (SEQ ID NO: 639) | 100 |
| IMITFG | D3-16.3.1 | (SEQ ID NO: 640) | 101 |
| LwLRLG | D3-16.1.2 | (SEQ ID NO: 647) | 102 |
| YDYVWG | D3-16.2.2 | (SEQ ID NO: 648) | 103 |
| MITFGG | D3-16.3.2 | (SEQ ID NO: 649) | 104 |
| wLRLGE | D3-16.1.3 | (SEQ ID NO: 656) | 105 |

TABLE 14-continued

All hexamers that can be extracted from human D segments

| | | | |
|---|---|---|---|
| DYVWGS | D3-16.2.3 | (SEQ ID NO: 657) | 106 |
| ITFGGV | D3-16.3.3 | (SEQ ID NO: 658) | 107 |
| LRLGEL | D3-16.1.4 | (SEQ ID NO: 665) | 108 |
| YVWGSY | D3-16.2.4 | (SEQ ID NO: 666) | 109 |
| TFGGVI | D3-16.3.4 | (SEQ ID NO: 667) | 110 |
| RLGELS | D3-16.1.5 | (SEQ ID NO: 674) | 111 |
| VWGSYR | D3-16.2.5 | (SEQ ID NO: 675) | 112 |
| FGGVIV | D3-16.3.5 | (SEQ ID NO: 676) | 113 |
| LGELSL | D3-16.1.6 | (SEQ ID NO: 683) | 114 |
| WGSYRY | D3-16.2.6 | (SEQ ID NO: 684) | 115 |
| GGVIVI | D3-16.3.6 | (SEQ ID NO: 685) | 116 |
| GELSLY | D3-16.1.7 | (SEQ ID NO: 692) | 117 |
| GSYRYT | D3-16.2.7 | (SEQ ID NO: 693) | 118 |
| VLLwyy | D3-22.1.1 | (SEQ ID NO: 707) | 119 |
| YYYDSS | D3-22.2.1 | (SEQ ID NO: 708) | 120 |
| ITMIVV | D3-22.3.1 | (SEQ ID NO: 709) | 121 |
| LLwyyW | D3-22.1.2 | (SEQ ID NO: 716) | 122 |
| YYDSSG | D3-22.2.2 | (SEQ ID NO: 717) | 123 |
| TMIVVV | D3-22.3.2 | (SEQ ID NO: 718) | 124 |
| LwyyWL | D3-22.1.3 | (SEQ ID NO: 725) | 125 |
| YDSSGY | D3-22.2.3 | (SEQ ID NO: 726) | 126 |
| MIVVVI | D3-22.3.3 | (SEQ ID NO: 727) | 127 |
| wyyWLL | D3-22.1.4 | (SEQ ID NO: 733) | 128 |
| DSSGYY | D3-22.2.4 | (SEQ ID NO: 734) | 129 |
| IVVVIT | D3-22.3.4 | (SEQ ID NO: 735) | 130 |
| yyWLLL | D3-22.1.5 | (SEQ ID NO: 742) | 131 |
| SSGYYY | D3-22.2.5 | (SEQ ID NO: 743) | 132 |
| wLRWyL | D4-23.1.1 | (SEQ ID NO: 769) | 133 |
| DYGGNS | D4-23.2.1 | (SEQ ID NO: 770) | 134 |
| VDTAMV | D5-5.1.1 | (SEQ ID NO: 784) | 135 |
| WIQLWL | D5-5.2.1 | (SEQ ID NO: 785) | 136 |
| GYSYGY | D5-5.3.1 | (SEQ ID NO: 786) | 137 |
| VDIVAT | D5-12.1.1 | (SEQ ID NO: 802) | 138 |
| WIyWLR | D5-12.2.1 | (SEQ ID NO: 803) | 139 |
| GYSGYD | D5-12.3.1 | (SEQ ID NO: 804) | 140 |
| DIVATI | D5-12.1.2 | (SEQ ID NO: 811) | 141 |
| IyWLRL | D5-12.2.2 | (SEQ ID NO: 812) | 142 |
| YSGYDY | D5-12.3.2 | (SEQ ID NO: 813) | 143 |
| VEMATI | D5-24.1.1 | (SEQ ID NO: 829) | 144 |
| yRWLQL | D5-24.2.1 | (SEQ ID NO: 830) | 145 |
| RDGYNY | D5-24.3.1 | (SEQ ID NO: 831) | 146 |
| EYSSSS | D6-6.1.1 | (SEQ ID NO: 847) | 147 |
| GYSSSW | D6-13.1.1 | (SEQ ID NO: 859) | 148 |
| GIAAAG | D6-13.2.1 | (SEQ ID NO: 860) | 149 |
| VyQQLV | D6-13.3.1 | (SEQ ID NO: 861) | 150 |
| YSSSWY | D6-13.1.2 | (SEQ ID NO: 867) | 151 |
| GYSSGW | D6-19.1.1 | (SEQ ID NO: 878) | 152 |
| GIAVAG | D6-19.2.1 | (SEQ ID NO: 879) | 153 |
| VyQWLV | D6-19.3.1 | (SEQ ID NO: 880) | 154 |
| YSSGWY | D6-19.1.2 | (SEQ ID NO: 887) | 155 |

Example 3

CDR3 of Length 6-20

Insertion of D segments into synthetic HC CDR3s can lead to greater stability and lower immunogenicity. Libraries are designed at the amino-acid level by joining a VH to an optional filler of some length which is joined to a D segment an optional second filler and a JH. For libraries of length six or eight, a full-length JH may follow VH and a short filler. Table 77 shows the frequency of D segments in a sampling of 1419 Abs selected from FAB-310 or FAB-410 for binding to one target or another. In the sample, 1099 Abs had no detectable D segment (i.e., less that 70% match). Where D segments are used, the D segments D1-1.3, D1-26.3, D2-2.2, D2-8.2, D2-15.2, D2-21.2, D3-16.2, D3-22.2, D3-3.2, D3-9.1, D3-9.2, D3-10.2, D3-16.2, D4-4.2, D4-4.3, D4-11.2, D4-4.2, D4-17.2, D4-23.2, D5-5.3, D5-12.3, D5-18.3, D6-6.1, D6-6.2, D6-13.1, D6-13.2, D6-19.1, D6-19.2, and D7-27.1 are preferred.

Once the parental amino-acid sequence has been designed, it can be diversified in several ways: error-prone PCR, wobbling, and dobbling. Table 14 shows a number of hexamers that can be derived from human D regions. In one embodiment, the hexamers that contain cysteine residues are excluded. In one embodiment, the fragments of D regions that contain stops are excluded. In one embodiment, any TAG codon found in the D region is replaced by a codon picked from the set comprising TCG, TTG, TGG, CAG, AAG, TAT, and GAG. In one embodiment, any TAA codon found in the D region is replaced by a codon picked form the set comprising TCA, TTA, CAA, AAA, TAT, and GAA. In one embodiment, any TGA of the D region is replaced by a codon picked from the set comprising TGG, TCA, TTA, AGA, and GGA.

Table 21 shows exemplary parental amino-acid sequences for CDR3s from 6 to 20 amino acids. These parental sequences can be combined with diversity in HC CDR1 and CDR2 to form a library. The utility is likely to improve if the CDR3 regions are diversified by, for example, wobbling, dobbling, or error-prone PCR of the CDR3s. In Table 21, sequence 6a comprises the end of VH from 3-23 fused to whole JH1. Sequence 6b contains the end of 3-23 joined to a Y joined to D4-17 (RF 2) joined to the FR4 region of JH1. Sequence 6c contains the end of 3-23 followed by D5-5 (RF 3) followed by the FR4 part of JH1. Sequence 6d contains the end of 3-23 joined to SY joined to the whole JH4. Table 21 shows the level of doping that would be appropriate for the wobbling of the CDR3; other levels could be used as well. Other D regions or fragments of D regions could be used. Other JH sequences could be used.

TABLE 21

Parental amino-acid sequences for HC CDR3s of 6-20 AAs.

| Length | Parental sequence | level of doping | Comment | SEQ ID NO: |
|---|---|---|---|---|
| 6a | yycakAEYFQHwgqgtlvtvss | 70:10:10:10 | JH1(whole) | 226 |
| 6b | yycakYDYGDYwgqgtlvtvss | 70:10:10:10 | Y::D4-17(2)::FR4 of JH1 | 227 |
| 6c | yycakGYSYGYwgqgtlvtvss | 70:10:10:10 | D5-5(3)::FR4 of JH1 | 228 |
| 6d | yycakSYYFDYwgqgtlvtvss | 70:10:10:10 | SY::JH4(whole) | 229 |
| 8a | yycakYYAEYFQHwgqgtlvtvss | 73:9:9:9 | YY:JH1(whole) | 230 |
| 8b | yycakYGYSSSWYwgqgtlvtvss | 73:9:9:9 | Y::D6-13(1)::FR4 of JH1 | 231 |
| 8c | yycakYGDYYFDYwgqgtlvtvss | 73:9:9:9 | D4-17(2)[2-5]::JH4(whole) | 232 |
| 10a | yycakYYYDSSGYYYwgqgtlvtvss | 73:9:9:9 | D3-22(2)::Fr4 of JH1 | 233 |
| 10b | yycakGYcSSTScYTwgqgtlvtvss | 73:9:9:9 | D2-2(2)::Fr4 of JH1 | 234 |
| 10c | yycakYYSSAEYFQHwgqgtlvtvss | 73:9:9:9 | YYSS::JH1(whole) (SEQ ID NO: 942) | 235 |
| 10d | yycakGYSYGYYFDYwgqgtlvtvss | 73:9:9:9 | D5-5(3)::JH4(whole) | 236 |
| 12a | yycakYYYDSSGYYYQHwgqgtlvtvss | 85:5:5:5 | D3-22(2)::QH::Fr4 of JH1 | 237 |
| 12b | yycakGYcSSTScYTQHwgqgtlvtvss | 85:5:5:5 | D2-2(2)::QH::Fr4 of JH1 | 238 |
| 12c | yycakYDGSYSAEYFQHwgqgtlvtvss | 85:5:5:5 | YDGSYS::JH1(whole) (SEQ ID NO: 943) | 239 |
| 12d | yycakYYDYVWGSYRYTwgqgtlvtvss | 85:5:5:5 | D3-16(2)::Fr of JH1 | 240 |
| 12e | yycakGYSYGYYVVYFDLwgrgtlvtvss | 85:5:5:5 | D5-5(3)::JH2(whole) | 241 |
| 14a | yycakYYYDSSGYYYYFQHwgqgtlvtvss | 73:9:9:9 | D3-22(2)::YFQH::Fr of JH1 (SEQ ID NO: 944) | 242 |
| 14b | yycakGYcSSTScYTYFQHwgqgtlvtvss | 73:9:9:9 | D2-2(2)::YFQH::Fr of JH1 (SEQ ID NO: 944) | 243 |
| 14c | yycakSYGYcSSTScYTQHwgqgtlvtvss | 73:9:9:9 | SY::D2-2(2)::QH::Fr of JH1 | 244 |
| 14d | yycakSYRYSGYSAEYFQHwgqgtlvtvss | 73:9:9:9 | SYRYSGYS::JH1(whole) (SEQ ID NO: 945) | 245 |
| 14e | yycakAYcGGDcYSNWFDPwgqgtlvtvss | 73:9:9:9 | D2-21(2)::JH5(whole) | 246 |
| 15a | yycakSDGYYYDSSGYYYDYwgqgtlvtvss | 73:9:9:9 | SD::D3-22.2::JH4(101 ff) | 930 |
| 15b | yycakGSGYCSGGSCYSFDYwgqgtlvtvss | 73:9:9:9 | GS::D2-15.2::JH4(100 ff) | 931 |
| 15c | yycakGGRGYSSGWYRAFDIwgqgtmvtvss | 73:9:9:9 | GGR::D6-19.1::R::JH3(all) | 932 |
| 16a | yycakYYYDSSGYYYAEYFQHwgqgtlvtvss | 73:9:9:9 | D3-22(2)::JH1(whole) | 247 |
| 16b | yycakGYcSSTScYTAEYFQHwgqgtlvtvss | 73:9:9:9 | D2-2(2)::JH1(whole) | 248 |
| 16c | yycakSYDSYRSYGSAEYFQHwgqgtlvtvss | 73:9:9:9 | SYDSYRSYGS::JH1(whole) (SEQ ID NO: 946) | 249 |
| 16d | yycakSYSYGYcSSTScYTQHwgqgtlvtvss | 73:9:9:9 | SYSY::D2-2(2)::QH::Fr JH1 (SEQ ID NO: 947) | 250 |
| 17a | yycakSRPGYSSSWYYYYGMDVwgqgttvtvss | 73:9:9:9 | SRP::6-13.1::JH6(-1Y) | 933 |
| 18a | yycakGYCSGGSCYSYYYYGMDVwgqgttvtvss | 73:9:9:9 | 2-15.2::JH6(-1Y) | 221 |

TABLE 21-continued

Parental amino-acid sequences for HC CDR3s of 6-20 AAs.

| Length | Parental sequence | level of doping | Comment | SEQ ID NO: |
|---|---|---|---|---|
| 18b | yycakDGYCSGGSCYSYYYGMDVwgqgttvtvss | 73:9:9:9 | D::2-15.2::JH6(-2Ys) | 222 |
| 19a | yycakDGYYYDSSGYYYRGYYFDYwgqgtlvtvss | 73:9:9:9 | D::D3-22.2::RGY::JH4(all) | 223 |
| 20a | yycakYSSYYYYDSSGYYYAEYFQHwgqgtlvtvss | 73:9:9:9 | YSSY::D3-22(2)::JH1(whole) (SEQ ID NO: 948) | 251 |
| 20b | yycakSYYSGYcSSTScYTAEYFQHwgqgtlvtvss | 73:9:9:9 | SYYS::D2-2(2)::JH1(whole) (SEQ ID NO: 949) | 252 |
| 20c | yycakSGYcSSTScYTYYSAEYFQHwgqgtlvtvss | 73:9:9:9 | S::D2-2(2)::YYS::JH1(whole) | 253 |
| 20d | yycakYYYYDYVWGSYRYTSNVVFDPwgqgtlvtvss | 73:9:9:9 | Y::D3-16(2)::S::JH5(whole) | 254 |
| 20e | yycakYYYYDYVWGSYRYTSSYFDYwgqgtlvtvss | 73:9:9:9 | Y::D3-16(2)::SS::JH4(whole) | 255 |

TABLE 22

HC display cassette
The amino-acid sequence shown in Table 22 is SEQ ID NO: 892.
The DNA sequence shown in Table 22 is SEQ ID NO: 893.

```
!       Signal for VH-CH1-IIIstump
!       1   2   3   4   5   6   7   8   9  10  11  12  13  14  15
!       M   K   Y   L   L   P   T   A   A   A   G   L   L   L   L
  946   atg aaa tac cta ttg cct acg gca gcc gct gga ttg tta tta ctc
!
!      16  17  18  19  20  21  22
!       A   A   Q   P   A   M   A
  991  gcG GCC cag ccG GCC atg gcc
!       SfiI.............
!               NgoMI...(1/2)
!                     NcoI....
!
! VH
!                                  FR1(DP47/V3-23)----------------
!                                   1   2   3   4   5   6   7   8
!                                   E   V   Q   L   L   E   S   G
 1012                              gaa|gtt|CAA|TTG|tta|gag|tct|ggt|
!                                          | MfeI  |
!
!      --------------FR1----------------------------------
!       9  10  11  12  13  14  15  16  17  18  19  20  21  22  23
!       G   G   L   V   Q   P   G   G   S   L   R   L   S   C   A
 1036  |ggc|ggt|ctt|gtt|cag|cct|ggt|ggt|tct|tta|cgt|ctt|tct|tgc|gct|
!
!      ----FR1------------------>|...CDR1............|---FR2------
!      24  25  26  27  28  29  30  31  32  33  34  35  36  37  38
!       A   S   G   F   T   F   S   S   Y   A   M   S   W   V   R
 1081  |gct|TCC|GGA|ttc|act|ttc|tct|tct|tcG|TAC|Gct|atg|tct|tgg|gtt|cgC|
!           | BspEI |                 | BsiWI|                    |BstXI.
!
!      -------FR2--------------------------->|...CDR2.........
!      39  40  41  42  43  44  45  46  47  48  49  50  51  52  52a
!       Q   A   P   G   K   G   L   E   W   V   S   A   I   S   G
 1126  |CAa|gct|ccT|GGt|aaa|ggt|ttg|gag|tgg|gtt|tct|gct|atc|tct|ggt|
!      ...BstXI       |
!
!      .....CDR2.................................................|---FR3---
!      53  54  55  56  57  58  59  60  61  62  63  64  65  66  67
!       S   G   G   S   T   Y   Y   A   D   S   V   K   G   R   F
 1171  |tct|ggt|ggc|agt|act|tac|tat|gct|gac|tcc|gtt|aaa|ggt|cgc|ttc|
!
!      --------FR3---------------------------------
!      68  69  70  71  72  73  74  75  76  77  78  79  80  81  82
!       T   I   S   R   D   N   S   K   N   T   L   Y   L   Q   M
```

TABLE 22-continued

HC display cassette
The amino-acid sequence shown in Table 22 is SEQ ID NO: 892.
The DNA sequence shown in Table 22 is SEQ ID NO: 893.

```
1216 |act|atc|TCT|AGA|gac|aac|tct|aag|aat|act|ctc|tac|ttg|cag|atg|
              | XbaI |

---FR3--------------------------------------------------->|
      82a 82b 82c  83  84  85  86  87  88  89  90  91  92  93  94
       N   S   L   R   A   E   D   T   A   V   Y   Y   C   A   K
1261 |aac|agC|TTA|AGg|gct|gag|gac|acT|GCA|Gtc|tac|tat|tgc|gct|aaa|
          |AflII |                | PstI |(2/2)

........CDR3..........................|----FR4--------
      95  96  97  98 98a 98b 98c  99 100 101 102 103 104 105 106
       D   Y   E   G   T   G   Y   A   F   D   I   W   G   Q   G
1306 |gac|tat|gaa|ggt|act|ggt|tat|gct|ttc|gaC|ATA|TGg|ggt|caa|ggt|
                                              | NdeI |

--------------FR4---------->|
      107 108 109 110 111 112 113
       T   M   V   T   V   S   S
1351 |act|atG|GTC|ACC|gtc|tct|agt
             | BstEII |   c tcg ag = XhoI.

! CH1
!    A   S   T   K   G   P   S   V   F   P   L   A   P   S   S
1372 gcc tcc acc aag ggc cca tcg gtc ttc ccG CTA GCa ccc tcc tcc
                                             NheI....

151 152 153 154 155 156 157 158 159 160 161 162 163 164 165
      K   S   T   S   G   G   T   A   A   L   G   C   L   V   K
1417 aag agc acc tct ggg ggc aca gcg gcc ctg ggc tgc ctg gtc aag 166 167 168 169 170 171 172 173 174 175 176 177 178 179 180
      D   Y   F   P   E   P   V   T   V   S   W   N   S   G   A
1462 gac tac ttc ccc gaa ccg gtg acg gtg tcg tgg aac tca ggc gcc 181 182 183 184 185 186 187 188 189 190 191 192 193 194 195
      L   T   S   G   V   H   T   F   P   A   V   L   Q   S   S
1507 ctg acc agc ggc gtc cac acc ttc ccg gct gtc cta cag tcc tca 196 197 198 199 200 201 202 203 204 205 206 207 208 209 210
      G   L   Y   S   L   S   S   V   V   T   V   P   S   S   S
1552 gga ctc tac tcc ctc agc agc gta gtg acc gtg ccc tCC Agc agc
                                                     BstXI........

211 212 213 214 215 216 217 218 219 220 221 222 223 224 225
      L   G   T   Q   T   Y   I   C   N   V   N   H   K   P   S
1597 tTG Ggc acc cag acc tac atc tgc aac gtg aat cac aag ccc agc
     BstXI........

226 227 228 229 230 231 232 233 234 235 236 237 238
      N   T   K   V   D   K   K   V   E   P   K   S   C
1642 aac acc aag gtg gac aaG AAA GTT GAG CCC AAA TCT TGT 139 140 141 His tag..............  cMyc tag.....................
      A   A   A   H   H   H   H   H   H   G   A   A   E   Q   K   L   I
1681 GCG GCC GCa cat cat cat cac cat cac ggg gcc gca gaa caa aaa ctc atc
     NotI......
      EagI....

.........................
       S   E   E   D   L   N   G   A   A   E   A   S   S   A   S   N   A   S
1732 tca gaa gag gat ctg aat ggg GCC gca gaG GCt agt tct gct agt aAC GCG Tct
                                 BglI..........(3/4)            MluI....

! Domain 3 (IIIstump)-------------------------------------------
       S   G   D   F   D   Y   E   K   M   A   N   A   N   K   G   A
1786 tcc ggt gat ttt gat tat gaa aag atg gca aac gct aat aag ggg gct M   T   E   N   A   D   E   N   A   L   Q   S   D   A   K   G
1834 atg acc gaa aat gcc gat gaa aac gcg cta cag tct gac gct aaa ggc K   L   D   S   V   A   T   D   Y   G   A   A   I   D   G   F
1882 aaa ctt gat tct gtc gct act gat tac ggt gct gct atc gat ggt ttc I   G   D   V   S   G   L   A   N   G   N   G   A   T   G   D
1930 att ggt gac gtt tcc ggc ctt gct aat ggt aat ggt gct act ggt gat
```

TABLE 22-continued

HC display cassette
The amino-acid sequence shown in Table 22 is SEQ ID NO: 892.
The DNA sequence shown in Table 22 is SEQ ID NO: 893.

```
!       F   A   G   S   N   S   Q   M   A   Q   V   G   D   G   D   N
1978  ttt gct ggc tct aat tcc caa atg gct caa gtc ggt gac ggt gat aat
!
!       S   P   L   M   N   N   F   R   Q   Y   L   P   S   L   P   Q
2026  tca cct tta atg aat aat ttc cgt caa tat tta cct tcc ctc cct caa
!
!       S   V   E   C   R   P   F   V   F   G   A   G   K   P   Y   E
2074  tcg gtt gaa tgt cgc cct ttt gtc ttt ggc gct ggt aaa cca tat gaa
!
!       F   S   I   D   C   D   K   I   N   L   F   R
2122  ttt tct att gat tgt gac aaa ata aac tta ttc cgt
!                                                       End Domain 3
!
!       G   V   F   A   F   L   L   Y   V   A   T   F   M   Y   V   F140
2158  ggt gtc ttt gcg ttt ctt tta tat gtt gcc acc ttt atg tat gta ttt
!       start transmembrane segment
!
!       S   T   F   A   N   I   L
2206  tct acg ttt gct aac ata ctg
!
!       R   N   K   E   S     (SEQ ID NO: 892)
2227  cgt aat aag gag tct TAA tga aAC GCG Tga tga GAATTC (SEQ ID NO: 893)
!       Intracellular anchor.            MluI....      EcoRI.
```

TABLE 25

The DNA sequence of DY3F85LC containing a sample germline
O12 kappa light chain. The antibody sequences shown are
of the form of actual antibody, but have not been identified
as binding to a particular antigen.
On each line, everything after an exclamation
point (!) is commentary.
The DNA of DY3F85LC is SEQ ID NO: 950

```
!----------------------------------------------------------------
   1 AATGCTACTA CTATTAGTAG AATTGATGCC ACCTTTTCAG CTCGCGCCCC AAATGAAAAT

61 ATAGCTAAAC AGGTTATTGA CCATTTGCGA AATGTATCTA ATGGTCAAAC TAAATCTACT

121 CGTTCGCAGA ATTGGGAATC AACTGTTATA TGGAATGAAA CTTCCAGACA CCGTACTTTA

181 GTTGCATATT TAAAACATGT TGAGCTACAG CATTATATTC AGCAATTAAG CTCTAAGCCA

241 TCCGCAAAAA TGACCTCTTA TCAAAGGAG CAATTAAAGG TACTCTCTAA TCCTGACCTG

301 TTGGAGTTTG CTTCCGGTCT GGTTCGCTTT GAAGCTCGAA TTAAAACGCG ATATTTGAAG

361 TCTTTCGGGC TTCCTCTTAA TCTTTTTGAT GCAATCCGCT TTGCTTCTGA CTATAATAGT

421 CAGGGTAAAG ACCTGATTTT TGATTTATGG TCATTCTCGT TTTCTGAACT GTTTAAAGCA

481 TTTGAGGGGG ATTCAATGAA TATTTATGAC GATTCCGCAG TATTGGACGC TATCCAGTCT

541 AAACATTTTA CTATTACCCC CTCTGGCAAA ACTTCTTTTG CAAAAGCCTC TCGCTATTTT

601 GGTTTTTATC GTCGTCTGGT AAACGAGGGT TATGATAGTG TTGCTCTTAC TATGCCTCGT

661 AATTCCTTTT GGCGTTATGT ATCTGCATTA GTTAATGTG GTATTCCTAA ATCTCAACTG

721 ATGAATCTTT CTACCTGTAA TAATGTTGTT CCGTTAGTTC GTTTTATTAA CGTAGATTTT

781 TCTTCCCAAC GTCCTGACTG GTATAATGAG CCAGTTCTTA AAATCGCATA AGGTAATTCA

841 CAATGATTAA AGTTGAAATT AAACCATCTC AAGCCCAATT TACTACTCGT TCTGGTGTTT

901 CTCGTCAGGG CAAGCCTTAT TCACTGAATG AGCAGCTTTG TTACGTTGAT TTGGGTAATG

961 AATATCCGGT TCTTGTCAAG ATTACTCTTG ATGAAGGTCA GCCAGCCTAT GCGCCTGGTC

1021 TGTACACCGT TCATCTGTCC TCTTTCAAAG TTGGTCAGTT CGGTTCCCTT ATGATTGACC

1081 GTCTGCGCCT CGTTCCGGCT AAGTAACATG GAGCAGGTCG CGGATTTCGA CACAATTTAT
```

TABLE 25-continued

The DNA sequence of DY3F85LC containing a sample germline
O12 kappa light chain. The antibody sequences shown are
of the form of actual antibody, but have not been identified
as binding to a particular antigen.
On each line, everything after an exclamation
point (!) is commentary.
The DNA of DY3F85LC is SEQ ID NO: 950

```
1141 CAGGCGATGA TACAAATCTC CGTTGTACTT TGTTTCGCGC TTGGTATAAT CGCTGGGGGT

1201 CAAAGATGAG TGTTTTAGTG TATTCTTTTG CCTCTTTCGT TTTAGGTTGG TGCCTTCGTA

1261 GTGGCATTAC GTATTTTACC CGTTTAATGG AAACTTCCTC ATGAAAAAGT CTTTAGTCCT

1321 CAAAGCCTCT GTAGCCGTTG CTACCCTCGT TCCGATGCTG TCTTTCGCTG CTGAGGGTGA

1381 CGATCCCGCA AAAGCGGCCT TTAACTCCCT GCAAGCCTCA GCGACCGAAT ATATCGGTTA

1441 TGCGTGGGCG ATGGTTGTTG TCATTGTCGG CGCAACTATC GGTATCAAGC TGTTTAAGAA

1501 ATTCACCTCG AAAGCAAGCT GATAAACCGA TACAATTAAA GGCTCCTTTT GGAGCCTTTT

1561 TTTTGGAGAT TTTCAACGTG AAAAAATTAT TATTCGCAAT TCCTTTAGTT GTTCCTTTCT

1621 ATTCTCACTC CGCTGAAACT GTTGAAAGTT GTTTAGCAAA ATCCCATACA GAAAATTCAT

1681 TTACTAACGT CTGGAAAGAC GACAAAACTT TAGATCGTTA CGCTAACTAT GAGGGCTGTC

1741 TGTGGAATGC TACAGGCGTT GTAGTTTGTA CTGGTGACGA AACTCAGTGT TACGGTACAT

1801 GGGTTCCTAT TGGGCTTGCT ATCCCTGAAA ATGAGGGTGG TGGCTCTGAG GGTGGCGGTT

1861 CTGAGGGTGG CGGTTCTGAG GGTGGCGGTA CTAAACCTCC TGAGTACGGT GATACACCTA

1921 TTCCGGGCTA TACTTATATC AACCCTCTCG ACGGCACTTA TCCGCCTGGT ACTGAGCAAA

1981 ACCCCGCTAA TCCTAATCCT TCTCTTGAGG AGTCTCAGCC TCTTAATACT TTCATGTTTC

2041 AGAATAATAG GTTCCGAAAT AGGCAGGGGG CATTAACTGT TTATACGGGC ACTGTTACTC

2101 AAGGCACTGA CCCCGTTAAA ACTTATTACC AGTACACTCC TGTATCATCA AAAGCCATGT

2161 ATGACGCTTA CTGGAACGGT AAATTCAGAG ACTGCGCTTT CCATTCTGGC TTTAATGAGG

2221 ATTTATTTGT TTGTGAATAT CAAGGCCAAT CGTCTGACCT GCCTCAACCT CCTGTCAATG

2281 CTGGCGGCGG CTCTGGTGGT GGTTCTGGTG GCGGCTCTGA GGGTGGTGGC TCTGAGGGTG

2341 GCGGTTCTGA GGGTGGCGGC TCTGAGGGAG GCGGTTCCGG TGGTGGCTCT GGTTCCGGTG

2401 ATTTTGATTA TGAAAAGATG GCAAACGCTA ATAAGGGGGC TATGACCGAA AATGCCGATG

2461 AAAACGCGCT ACAGTCTGAC GCTAAAGGCA AACTTGATTC TGTCGCTACT GATTACGGTG

2521 CTGCTATCGA TGGTTTCATT GGTGACGTTT CCGGCCTTGC TAATGGTAAT GGTGCTACTG

2581 GTGATTTTGC TGGCTCTAAT TCCCAAATGG CTCAAGTCGG TGACGGTGAT AATTCACCTT

2641 TAATGAATAA TTTCCGTCAA TATTTACCTT CCCTCCCTCA ATCGGTTGAA TGTCGCCCTT

2701 TTGTCTTTGG CGCTGGTAAA CCATATGAAT TTTCTATTGA TTGTGACAAA ATAAACTTAT

2761 TCCGTGGTGT CTTTGCGTTT CTTTTATATG TTGCCACCTT TATGTATGTA TTTTCTACGT

2821 TTGCTAACAT ACTGCGTAAT AAGGAGTCTT AATCATGCCA GTTCTTTTGG GTATTCCGTT

2881 ATTATTGCGT TTCCTCGGTT TCCTTCTGGT AACTTTGTTC GGCTATCTGC TTACTTTTCT

2941 TAAAAAGGGC TTCGGTAAGA TAGCTATTGC TATTTCATTG TTTCTTGCTC TTATTATTGG

3001 GCTTAACTCA ATTCTTGTGG GTTATCTCTC TGATATTAGC GCTCAATTAC CCTCTGACTT

3061 TGTTCAGGGT GTTCAGTTAA TTCTCCCGTC TAATGCGCTT CCCTGTTTTT ATGTTATTCT

3121 CTCTGTAAAG GCTGCTATTT TCATTTTTGA CGTTAAACAA AAAATCGTTT CTTATTTGGA

3181 TTGGGATAAA TAATATGGCT GTTTATTTTG TAACTGGCAA ATTAGGCTCT GGAAAGACGC

3241 TCGTTAGCGT TGGTAAGATT CAGGATAAAA TTGTAGCTGG GTGCAAAATA GCAACTAATC
```

TABLE 25-continued

The DNA sequence of DY3F85LC containing a sample germline
O12 kappa light chain. The antibody sequences shown are
of the form of actual antibody, but have not been identified
as binding to a particular antigen.
On each line, everything after an exclamation
point (!) is commentary.
The DNA of DY3F85LC is SEQ ID NO: 950

```
3301 TTGATTTAAG GCTTCAAAAC CTCCCGCAAG TCGGGAGGTT CGCTAAAACG CCTCGCGTTC

3361 TTAGAATACC GGATAAGCCT TCTATATCTG ATTTGCTTGC TATTGGGCGC GGTAATGATT

3421 CCTACGATGA AAATAAAAAC GGCTTGCTTG TTCTCGATGA GTGCGGTACT TGGTTTAATA

3481 CCCGTTCTTG GAATGATAAG GAAAGACAGC CGATTATTGA TTGGTTTCTA CATGCTCGTA

3541 AATTAGGATG GGATATTATT TTTCTTGTTC AGGACTTATC TATTGTTGAT AAACAGGCGC

3601 GTTCTGCATT AGCTGAACAT GTTGTTTATT GTCGTCGTCT GGACAGAATT ACTTTACCTT

3661 TTGTCGGTAC TTTATATTCT CTTATTACTG GCTCGAAAAT GCCTCTGCCT AAATTACATG

3721 TTGGCGTTGT TAAATATGGC GATTCTCAAT TAAGCCCTAC TGTTGAGCGT GGCTTTATA

3781 CTGGTAAGAA TTTGTATAAC GCATATGATA CTAAACAGGC TTTTTCTAGT AATTATGATT

3841 CCGGTGTTTA TTCTTATTTA ACGCCTTATT TATCACACGG TCGGTATTTC AAACCATTAA

3901 ATTTAGGTCA GAAGATGAAA TTAACTAAAA TATATTTGAA AAAGTTTTCT CGCGTTCTTT

3961 GTCTTGCGAT TGGATTTGCA TCAGCATTTA CATATAGTTA TATAACCCAA CCTAAGCCGG

4021 AGGTTAAAAA GGTAGTCTCT CAGACCTATG ATTTTGATAA ATTCACTATT GACTCTTCTC

4081 AGCGTCTTAA TCTAAGCTAT CGCTATGTTT TCAAGGATTC TAAGGGAAAA TTAATTAATA

4141 GCGACGATTT ACAGAAGCAA GGTTATTCAC TCACATATAT TGATTATGT ACTGTTTCCA

4201 TTAAAAAAGG TAATTCAAAT GAAATTGTTA AATGTAATTA ATTTTGTTTT CTTGATGTTT

4261 GTTTCATCAT CTTCTTTTGC TCAGGTAATT GAAATGAATA ATTCGCCTCT GCGCGATTTT

4321 GTAACTTGGT ATTCAAAGCA ATCAGGCGAA TCCGTTATTG TTTCTCCCGA TGTAAAAGGT

4381 ACTGTTACTG TATATTCATC TGACGTTAAA CCTGAAAATC TACGCAATTT CTTTATTTCT

4441 GTTTTACGTG CAAATAATTT TGATATGGTA GGTTCTAACC CTTCCATAAT TCAGAAGTAT

4501 AATCCAAACA ATCAGGATTA TATTGATGAA TTGCCATCAT CTGATAATCA GGAATATGAT

4561 GATAATTCCG CTCCTTCTGG TGGTTTCTTT GTTCCGCAAA ATGATAATGT TACTCAAACT

4621 TTTAAAATTA ATAACGTTCG GGCAAAGGAT TTAATACGAG TTGTCGAATT GTTTGTAAAG

4681 TCTAATACTT CTAAATCCTC AAATGTATTA TCTATTGACG GCTCTAATCT ATTAGTTGTT

4741 AGTGCTCCTA AAGATATTTT AGATAACCTT CCTCAATTCC TTTCAACTGT TGATTTGCCA

4801 ACTGACCAGA TATTGATTGA GGGTTTGATA TTTGAGGTTC AGCAAGGTGA TGCTTTAGAT

4861 TTTTCATTTG CTGCTGGCTC TCAGCGTGGC ACTGTTGCAG GCGGTGTTAA TACTGACCGC

4921 CTCACCTCTG TTTTATCTTC TGCTGGTGGT TCGTTCGGTA TTTTTAATGG CGATGTTTTA

4981 GGGCTATCAG TTCGCGCATT AAAGACTAAT AGCCATTCAA AAATATTGTC TGTGCCACGT

5041 ATTCTTACGC TTTCAGGTCA GAAGGGTTCT ATCTCTGTTG GCCAGAATGT CCCTTTTATT

5101 ACTGGTCGTG TGACTGGTGA ATCTGCCAAT GTAAATAATC CATTTCAGAC GATTGAGCGT

5161 CAAAATGTAG GTATTTCCAT GAGCGTTTTT CCTGTTGCAA TGGCTGGCGG TAATATTGTT

5221 CTGGATATTA CCAGCAAGGC CGATAGTTTG AGTTCTTCTA CTCAGGCAAG TGATGTTATT

5281 ACTAATCAAA GAAGTATTGC TACAACGGTT AATTTGCGTG ATGGACAGAC TCTTTTACTC

5341 GGTGGCCTCA CTGATTATAA AAACACTTCT CAGGATTCTG CGTACCGTT CCTGTCTAAA

5401 ATCCCTTTAA TCGGCCTCCT GTTTAGCTCC CGCTCTGATT CTAACGAGGA AAGCACGTTA
```

TABLE 25-continued

The DNA sequence of DY3F85LC containing a sample germline
O12 kappa light chain. The antibody sequences shown are
of the form of actual antibody, but have not been identified
as binding to a particular antigen.
On each line, everything after an exclamation
point (!) is commentary.
The DNA of DY3F85LC is SEQ ID NO: 950

```
5461 TACGTGCTCG TCAAAGCAAC CATAGTACGC GCCCTGTAGC GGCGCATTAA GCGCGGCGGG

5521 TGTGGTGGTT ACGCGCAGCG TGACCGCTAC ACTTGCCAGC GCCCTAGCGC CCGCTCCTTT

5581 CGCTTTCTTC CCTTCCTTTC TCGCCACGTT CGCCGGCTTT CCCCGTCAAG CTCTAAATCG

5641 GGGGCTCCCT TAGGGTTCC GATTTAGTGC TTTACGGCAC CTCGACCCCA AAAAACTTGA

5701 TTTGGGTGAT GGTTCACGTA GTGGGCCATC GCCCTGATAG ACGGTTTTTC GCCCTTTGAC

5761 GTTGGAGTCC ACGTTCTTTA ATAGTGGACT CTTGTTCCAA ACTGGAACAA CACTCAACCC

5821 TATCTCGGGC TATTCTTTTG ATTTATAAGG GATTTTGCCG ATTTCGGAAC CACCATCAAA

5881 CAGGATTTTC GCCTGCTGGG GCAAACCAGC GTGGACCGCT TGCTGCAACT CTCTCAGGGC

5941 CAGGCGGTGA AGGGCAATCA GCTGTTGCCC GTCTCACTGG TGAAAAGAAA AACCACCCTG

6001 GATCCAAGCT TGCAGGTGGC ACTTTTCGGG GAAATGTGCG CGGAACCCCT ATTTGTTTAT

6061 TTTTCTAAAT ACATTCAAAT ATGTATCCGC TCATGAGACA ATAACCCTGA TAAATGCTTC

6121 AATAATATTG AAAAAGGAAG AGTATGAGTA TTCAACATTT CCGTGTCGCC CTTATTCCCT

6181 TTTTTGCGGC ATTTTGCCTT CCTGTTTTTG CTCACCCAGA AACGCTGGTG AAAGTAAAAG

6241 ATGCTGAAGA TCAGTTGGGC GCACTAGTGG GTTACATCGA ACTGGATCTC AACAGCGGTA

6301 AGATCCTTGA GAGTTTTCGC CCCGAAGAAC GTTTTCCAAT GATGAGCACT TTTAAAGTTC

6361 TGCTATGTGG CGCGGTATTA TCCCGTATTG ACGCCGGGCA AGAGCAACTC GGTCGCCGCA

6421 TACACTATTC TCAGAATGAC TTGGTTGAGT ACTCACCAGT CACAGAAAAG CATCTTACGG

6481 ATGGCATGAC AGTAAGAGAA TTATGCAGTG CTGCCATAAC CATGAGTGAT AACACTGCGG

6541 CCAACTTACT TCTGACAACG ATCGGAGGAC CGAAGGAGCT AACCGCTTTT TTGCACAACA

6601 TGGGGGATCA TGTAACTCGC CTTGATCGTT GGGAACCGGA GCTGAATGAA GCCATACCAA

6661 ACGACGAGCG TGACACCACG ATGCCTGTAG CAATGGCAAC AACGTTGCGC AAACTATTAA

6721 CTGGCGAACT ACTTACTCTA GCTTCCCGGC AACAATTAAT AGACTGGATG GAGGCGGATA

6781 AAGTTGCAGG ACCACTTCTG CGCTCGGCCC TTCCGGCTGG CTGGTTTATT GCTGATAAAT

6841 CTGGAGCCGG TGAGCGTGGG TCTCGCGGTA TCATTGCAGC ACTGGGGCCA GATGGTAAGC

6901 CCTCCCGTAT CGTAGTTATC TACACGACGG GGAGTCAGGC AACTATGGAT GAACGAAATA

6961 GACAGATCGC TGAGATAGGT GCCTCACTGA TTAAGCATTG GTAACTGTCA GACCAAGTTT

7021 ACTCATATAT ACTTTAGATT GATTTAAAAC TTCATTTTTA ATTTAAAAGG ATCTAGGTGA

7081 AGATCCTTTT TGATAATCTC ATGACCAAAA TCCCTTAACG TGAGTTTTCG TTCCACTGTA

7141 CGTAAGACCC CCAAGCTTGT CGACTGAATG GCGAATGGCG CTTTGCCTGG TTTCCGGCAC

7201 CAGAAGCGGT GCCGGAAAGC TGGCTGGAGT GCGATCTTCC TGACGCTCGA GCGCAACGCA
!                                                    XhoI...

7261 ATTAATGTGA GTTAGCTCAC TCATTAGGCA CCCCAGGCTT TACACTTTAT GCTTCCGGCT

7321 CGTATGTTGT GTGGAATTGT GAGCGGATAA CAATTTCACA CAGGAAACAG CTATGACCAT

7381 GATTACGCCA AGCTTTGGAG CCTTTTTTTT GGAGATTTTC AAC
```

TABLE 30

| DNA sequence of DY3FHC87 (SEQ ID NO: 894) |
|---|
| 1 aatgctacta ctattagtag aattgatgcc accttttcag ctcgcgcccc aaatgaaaat |
| 61 atagctaaac aggttattga ccatttgcga aatgtatcta atggtcaaac taaatctact |
| 121 cgttcgcaga attgggaatc aactgttata tggaatgaaa cttccagaca ccgtacttta |
| 181 gttgcatatt taaaacatgt tgagctacag cattatattc agcaattaag ctctaagcca |
| 241 tccgcaaaaa tgacctctta tcaaaaggag caattaaagg tactctctaa tcctgacctg |
| 301 ttggagtttg cttccggtct ggttcgcttt gaagctcgaa ttaaaacgcg atatttgaag |
| 361 tctttcgggc ttcctcttaa tcttttttgat gcaatccgct ttgcttctga ctataatagt |
| 421 cagggtaaag acctgatttt tgatttatgg tcattctcgt tttctgaact gtttaaagca |
| 481 tttgagggggg attcaatgaa tatttatgac gattccgcag tattggacgc tatccagtct |
| 541 aaacatttta ctattacccc ctctggcaaa acttcttttg caaaagcctc tcgctatttt |
| 601 ggttttatc gtcgtctggt aaacgagggt tatgatagtg ttgctcttac tatgcctcgt |
| 661 aattcctttt ggcgttatgt atctgcatta gttgaatgtg gtattcctaa atctcaactg |
| 721 atgaatcttt ctacctgtaa taatgttgtt ccgttagttc gttttattaa cgtagatttt |
| 781 tcttcccaac gtcctgactg gtataatgag ccagttctta aaatcgcata aggtaattca |
| 841 caatgattaa agttgaaatt aaaccatctc aagcccaatt tactactcgt tctggtgttt |
| 901 ctcgtcaggg caagccttat tcactgaatg agcagctttg ttacgttgat ttgggtaatg |
| 961 aatatccggt tcttgtcaag attactcttg atgaaggtca gccagcctat gcgcctggtc |
| 1021 tgtacaccgt tcatctgtcc tctttcaaag ttggtcagtt cggttccctt atgattgacc |
| 1081 gtctgcgcct cgttccggct aagtaacatg gagcaggtcg cggatttcga cacaatttat |
| 1141 caggcgatga tacaaatctc cgttgtactt tgtttcgcgc ttggtataat cgctgggggt |
| 1201 caaagatgag tgttttagtg tattcttttg cctctttcgt tttaggttgg tgccttcgta |
| 1261 gtggcattac gtatttacc cgtttaatgg aaacttcctc atgaaaaagt ctttagtcct |
| 1321 caaagcctct gtagccgttg ctaccctcgt tccgatgctg tctttcgctg ctgagggtga |
| 1381 cgatcccgca aaagcggcct ttaactccct gcaagcctca gcgaccgaat atatcggtta |
| 1441 tgcgtgggcg atggttgttg tcattgtcgg cgcaactatc ggtatcaagc tgtttaagaa |
| 1501 attcacctcg aaagcaagct gataaaccga tacaattaaa ggctcctttt ggagcctttt |
| 1561 tttttggaga ttttcaacgt gaaaaaatta ttattcgcaa ttcctttagt tgttcctttc |
| 1621 tattctcact ccgctgaaac tgttgaaagt tgtttagcaa atcccatac agaaaattca |
| 1681 tttactaacg tctggaaaga cgacaaaact ttagatcgtt acgctaacta tgagggctgt |
| 1741 ctgtggaatg ctacaggcgt tgtagtttgt actggtgacg aaactcagtg ttacggtaca |
| 1801 tgggttccta ttgggcttgc tatccctgaa aatgagggtg gtggctctga gggtggcggt |
| 1861 tctgagggtg cggttctga gggtggcggt actaaacctc ctgagtacgg tgatacacct |
| 1921 attccgggct atacttatat caaccctctc gacggcactt atccgcctgg tactgagcaa |
| 1981 aaccccgcta tcctaatcc ttctcttgag gagtctcagc ctcttaatac tttcatgttt |
| 2041 cagaataata ggttccgaaa taggcagggg gcattaactg tttatacggg cactgttact |
| 2101 caaggcactg accccgttaa aacttattac cagtacactc ctgtatcatc aaaagccatg |
| 2161 tatgacgctt actggaacgg taaattcaga gactgcgctt ccattctgg ctttaatgag |
| 2221 gatttatttg tttgtgaata tcaaggccaa tcgtctgacc tgcctcaacc tcctgtcaat |
| 2281 gctggcggcg gctctggtgg tggttctggt ggcggctctg agggtggtgg ctctgagggt |

TABLE 30-continued

DNA sequence of DY3FHC87 (SEQ ID NO: 894)

```
2341 ggcggttctg agggtggcgg ctctgaggga ggcggttccg gtggtggctc tggttccggt
2401 gattttgatt atgaaaagat ggcaaacgct aataagggg ctatgaccga aaatgccgat
2461 gaaaacgcgc tacagtctga cgctaaaggc aaacttgatt ctgtcgctac tgattacggt
2521 gctgctatcg atggtttcat tggtgacgtt ccggccttg ctaatggtaa tggtgctact
2581 ggtgattttg ctggctctaa ttcccaaatg gctcaagtcg gtgacggtga taattcacct
2641 ttaatgaata atttccgtca atatttacct tccctccctc aatcggttga atgtcgccct
2701 tttgtctttg gcgctggtaa accatatgaa ttttctattg attgtgacaa aataaactta
2761 ttccgtggtg tctttgcgtt tcttttatat gttgccacct ttatgtatgt attttctacg
2821 tttgctaaca tactgcgtaa taaggagtct taatcatgcc agttcttttg ggtattccgt
2881 tattattgcg tttcctcggt ttccttctgg taactttgtt cggctatctg cttacttttc
2941 ttaaaaaggg cttcggtaag atagctattg ctatttcatt gtttcttgct cttattattg
3001 ggcttaactc aattcttgtg ggttatctct ctgatattag cgctcaatta ccctctgact
3061 ttgttcaggg tgttcagtta attctcccgt ctaatgcgct tccctgtttt tatgttattc
3121 tctctgtaaa ggctgctatt ttcatttttg acgttaaaca aaaaatcgtt tcttatttgg
3181 attgggataa ataatatggc tgtttatttt gtaactggca aattaggctc tggaaagacg
3241 ctcgttagcg ttggtaagat tcaggataaa attgtagctg ggtgcaaaat agcaactaat
3301 cttgatttaa ggcttcaaaa cctcccgcaa gtcgggaggt tcgctaaaac gcctcgcgtt
3361 cttagaatac cggataagcc ttctatatct gatttgcttg ctattgggcg cggtaatgat
3421 tcctacgatg aaaataaaaa cggcttgctt gttctcgatg agtgcggtac ttggtttaat
3481 acccgttctt ggaatgataa ggaaagacag ccgattattg attggtttct acatgctcgt
3541 aaattaggat gggatattat ttttcttgtt caggacttat ctattgttga taaacaggcg
3601 cgttctgcat tagctgaaca tgttgtttat tgtcgtcgtc tggacagaat tactttacct
3661 tttgtcggta ctttatattc tcttattact ggctcgaaaa tgcctctgcc taaattacat
3721 gttggcgttg ttaaatatgg cgattctcaa ttaagcccta ctgttgagcg ttggctttat
3781 actggtaaga atttgtataa cgcatatgat actaaacagg cttttttctag taattatgat
3841 tccggtgttt attcttattt aacgccttat ttatcacacg gtcggtattt caaaccatta
3901 aatttaggtc agaagatgaa attaactaaa atatatttga aaagttttc tcgcgttctt
3961 tgtcttgcga ttggatttgc atcagcattt acatatagtt ataacccca acctaagccg
4021 gaggttaaaa aggtagtctc tcagacctat gattttgata aattcactat tgactcttct
4081 cagcgtctta atctaagcta tcgctatgtt ttcaaggatt ctaagggaaa attaattaat
4141 agcgacgatt tacagaagca aggttattca ctcacatata ttgatttatg tactgtttcc
4201 attaaaaaag gtaattcaaa tgaaattgtt aaatgtaatt aattttgttt tcttgatgtt
4261 tgtttcatca tcttcttttg ctcaggtaat tgaaatgaat aattcgcctc tgcgcgattt
4321 tgtaacttgg tattcaaagc aatcaggcga atccgttatt gtttctcccg atgtaaaagg
4381 tactgttact gtatattcat ctgacgttaa acctgaaaat ctacgcaatt tctttatttc
4441 tgttttacgt gcaaataatt ttgatatggt aggttctaac ccttccataa ttcagaagta
4501 taatccaaac aatcaggatt atattgatga attgccatca tctgataatc aggaatatga
4561 tgataattcc gctccttctg gtggtttctt tgttccgcaa aatgataatg ttactcaaac
4621 ttttaaaatt aataacgttc gggcaaagga tttaatacga gttgtcgaat tgtttgtaaa
```

TABLE 30-continued

DNA sequence of DY3FHC87 (SEQ ID NO: 894)

```
4681 gtctaatact tctaaatcct caaatgtatt atctattgac ggctctaatc tattagttgt
4741 tagtgctcct aaagatattt tagataacct tcctcaattc ctttcaactg ttgatttgcc
4801 aactgaccag atattgattg agggtttgat atttgaggtt cagcaaggtg atgctttaga
4861 ttttttcattt gctgctggct ctcagcgtgg cactgttgca ggcggtgtta atactgaccg
4921 cctcacctct gttttatctt ctgctggtgg ttcgttcggt attttttaatg gcgatgtttt
4981 agggctatca gttcgcgcat taaagactaa tagccattca aaaatattgt ctgtgccacg
5041 tattcttacg ctttcaggtc agaagggttc tatctctgtt ggccagaatg tcccttttat
5101 tactggtcgt gtgactggtg aatctgccaa tgtaaataat ccatttcaga cgattgagcg
5161 tcaaaatgta ggtatttcca tgagcgtttt tcctgttgca atggctggcg gtaatattgt
5221 tctggatatt accagcaagg ccgatagttt gagttcttct actcaggcaa gtgatgttat
5281 tactaatcaa agaagtattg ctacaacggt taatttgcgt gatggacaga ctctttttact
5341 cggtggcctc actgattata aaaacacttc tcaggattct ggcgtaccgt tcctgtctaa
5401 aatcccttta atcggcctcc tgtttagctc ccgctctgat tctaacgagg aaagcacgtt
5461 atacgtgctc gtcaaagcaa ccatagtacg cgccctgtag cggcgcatta agcgcggcgg
5521 gtgtggtggt tacgcgcagc gtgaccgcta cacttgccag cgccctagcg cccgctcctt
5581 tcgctttctt cccttccttt ctcgccacgt tcgccggctt tccccgtcaa gctctaaatc
5641 gggggctccc tttagggttc cgatttagtg ctttacggca cctcgacccc aaaaaacttg
5701 atttgggtga tggttcacgt agtgggccat cgccctgata cacggttttt cgccctttga
5761 cgttggagtc cacgttcttt aatagtggac tcttgttcca aactggaaca acactcaacc
5821 ctatctcggg ctattctttt gatttataag ggattttgcc gatttcggaa ccaccatcaa
5881 acaggatttt cgcctgctgg ggcaaaccag cgtggaccgc ttgctgcaac tctctcaggg
5941 ccaggcggtg aagggcaatc agctgttgcc cgtctcactg gtgaaaagaa aaaccaccct
6001 ggatccaagc ttgcaggtgg cacttttcgg ggaaatgtgc gcggaacccc tatttgttta
6061 tttttctaaa tacattcaaa tatgtatccg ctcatgagac aataaccctg ataaatgctt
6121 caataatatt gaaaaaggaa gagtatgagt attcaacatt tccgtgtcgc ccttattccc
6181 ttttttgcgg cattttgcct tcctgttttt gctcacccag aaacgctggt gaaagtaaaa
6241 gatgctgaag atcagttggg cgcactagtg ggttacatcg aactggatct caacagcggt
6301 aagatccttg agagttttcg ccccgaagaa cgttttccaa tgatgagcac ttttaaagtt
6361 ctgctatgtg gcgcggtatt atcccgtatt gacgccgggc aagagcaact cggtcgccgc
6421 atacactatt ctcagaatga cttggttgag tactcaccag tcacagaaaa gcatcttacg
6481 gatggcatga cagtaagaga attatgcagt gctgccataa ccatgagtga taacactgcg
6541 gccaacttac ttctgacaac gatcggagga ccgaaggagc taaccgcttt tttgcacaac
6601 atgggggatc atgtaactcg ccttgatcgt tgggaaccgg agctgaatga agccatacca
6661 aacgacgagc gtgacaccac gatgcctgta gcaatggcaa caacgttgcg caaactatta
6721 actggcgaac tacttactct agcttcccgg caacaattaa tagactggat ggaggcggat
6781 aaagttgcag gaccacttct gcgctcggcc cttccggctg gctggtttat tgctgataaa
6841 tctggagccg gtgagcgtgg gtctcgcggt atcattgcag cactggggcc agatggtaag
6901 ccctcccgta tcgtagttat ctacacgacg gggagtcagg caactatgga tgaacgaaat
6961 agacagatcg ctgagatagg tgcctcactg attaagcatt ggtaactgtc agaccaagtt
```

TABLE 30-continued

DNA sequence of DY3FHC87 (SEQ ID NO: 894)

```
7021 tactcatata tactttagat tgatttaaaa cttcattttt aatttaaaag gatctaggtg
7081 aagatccttt ttgataatct catgaccaaa atcccttaac gtgagttttc gttccactgt
7141 acgtaagacc cccaagcttg tcgactgaat ggcgaatggc gctttgcctg gtttccggca
7201 ccagaagcgg tgccggaaag ctggctggag tgcgatcttc ctgacgctcg agcgcaacgc
7261 aattaatgtg agttagctca ctcattaggc accccaggct ttacacttta tgcttccggc
7321 tcgtatgttg tgtggaattg tgagcggata acaatttcac acaggaaaca gctatgacca
7381 tgattacgcc aagctttgga ccttttttt tggagatttt caacatgaaa tacctattgc
7441 ctacggcagc cgctggattg ttattactcg cGGCCcagcc GGCCatggcc gaagttcaat
7501 tgttagagtc tggtggcggt cttgttcagc ctggtggttc tttacgtctt tcttgcgctg
7561 cttccggatt cactttctct tcgtacgcta tgtcttgggt tcgccaagct cctggtaaag
7621 gtttggagtg ggtttctgct atctctggtt ctggtggcag tacttactat gctgactccg
7681 ttaaaggtcg cttcactatc tctagagaca actctaagaa tactctctac ttgcagatga
7741 acagcttaag ggctgaggac actgcagtct actattgcgc taaagcctat cgtccttctt
7801 atcatgacat atggggtcaa ggtactatgg tcaccgtctc tagtgcctcc accaagggcc
7861 catcggtctt ccccgctagca ccctcctcca gagcacctc tggggcaca gcggccctgg
7921 gctgcctggt caaggactac ttccccgaac cggtgacggt gtcgtggaac tcaggcgccc
7981 tgaccagcgg cgtccacacc ttcccggctg tcctacagtc ctcaggactc tactccctca
8041 gcagcgtagt gaccgtgccc tccagcagct gggcaccca gacctacatc tgcaacgtga
8101 atcacaagcc cagcaacacc aaggtggaca gaaagttga gcccaaatct tgtgcggccg
8161 cacatcatca tcaccatcac ggggccgcag aacaaaaact catctcagaa gaggatctga
8221 atggggccgc agaggctagc tctgctagtg gcgacttcga ctacgagaaa atggctaatg
8281 ccaacaaagg cgccatgact gagaacgctg acgagaatgc tttgcaaagc gatgccaagg
8341 gtaagttaga cagcgtcgcg accgactatg gcgccgccat cgacggcttt atcggcgatg
8401 tcagtggttt ggccaacggc aacggagcca ccggagactt cgcaggttcg aattctcaga
8461 tggcccaggt tggagatggg gacaacagtc gcttatgaa caactttaga cagtaccttc
8521 cgtctcttcc gcagagtgtc gagtgccgtc cattcgtttt cggtgccggc aagcttacg
8581 agttcagcat cgactgcgat aagatcaatc ttttccgcgg cgttttcgct ttcttgctat
8641 acgtcgctac tttcatgtac gttttcagca ctttcgccaa tattttacgc aacaaagaaa
8701 gctagtgatc tcctaggaag cccgcctaat gagcgggctt tttttttctg gtatgcatcc
8761 tgaggccgat actgtcgtcg tcccctcaaa ctggcagatg cacggttacg atgcgcccat
8821 ctacaccaac gtgacctatc ccattacggt caatccgccg tttgttccca cggagaatcc
8881 gacgggttgt tactcgctca catttaatgt tgatgaaagc tggctacagg aaggccagac
8941 gcgaattatt tttgatggcg ttcctattgg ttaaaaaatg agctgattta caaaaatttt
9001 aatgcgaatt ttaacaaaat attaacgttt acaatttaaa tatttgctta caatcttcc
9061 ctgttttttgg ggcttttctg attatcaacc ggggtacata tgattgacat gctagtttta
9121 cgattaccgt tcatcgattc tcttgtttgc tccagactct caggcaatga cctgatagcc
9181 tttgtagatc tctcaaaaat agctaccctc tccggcatta atttatcagc tagaacggtt
9241 gaatatcata ttgatggtga tttgactgtc tccggccttt ctcaccctt tgaatcttta
9301 cctacacatt actcaggcat tgcatttaaa atatatgagg gttctaaaaa tttttatcct
```

TABLE 30-continued

| DNA sequence of DY3FHC87 (SEQ ID NO: 894) |
|---|
| 9361 tgcgttgaaa taaaggcttc tcccgcaaaa gtattacagg gtcataatgt ttttggtaca |
| 9421 accgatttag ctttatgctc tgaggcttta ttgcttaatt ttgctaattc tttgccttgc |
| 9481 ctgtatgatt tattggatgt t |

TABLE 35

| DNA sequence of pMID21: 5957 bp (SEQ ID NO: 895) |
|---|
| 1 gacgaaaggg cctcgtgata cgcctatttt tataggttaa tgtcatgata ataatggttt |
| 61 cttagacgtc aggtggcact tttcggggaa atgtgcgcgg aaccccctatt tgtttatttt |
| 121 tctaaataca ttcaaatatg tatccgctca tgagacaata accctgataa atgcttcaat |
| 181 aatattgaaa aaggaagagt atgagtattc aacatttccg tgtcgccctt attcccttt |
| 241 ttgcggcatt ttgccttcct gttttgctc acccagaaac gctggtgaaa gtaaaagatg |
| 301 ctgaagatca gttgggtgcc cgagtgggtt acatcgaact ggatctcaac agcggtaaga |
| 361 tccttgagag ttttcgcccc gaagaacgtt ttccaatgat gagcactttt aaagttctgc |
| 421 tatgtggcgc ggtattatcc cgtattgacg ccgggcaaga gcaactcggt cgccgcatac |
| 481 actattctca gaatgacttg gttgagtact caccagtcac agaaaagcat cttacggatg |
| 541 gcatgacagt aagagaatta tgcagtgctg ccataaccat gagtgataac actgcggcca |
| 601 acttacttct gacaacgatc ggaggaccga aggagctaac cgcttttttg cacaacatgg |
| 661 gggatcatgt aactcgcctt gatcgttggg aaccggagct gaatgaagcc ataccaaacg |
| 721 acgagcgtga caccacgatg cctgtagcaa tggcaacaac gttgcgcaaa ctattaactg |
| 781 gcgaactact tactctagct tcccggcaac aattaataga ctggatggag gcggataaag |
| 841 ttgcaggacc acttctgcgc tcggcccttc cggctggctg gtttattgct gataaatctg |
| 901 gagccggtga gcgtgggtct cgcggtatca ttgcagcact ggggccagat ggtaagccct |
| 961 cccgtatcgt agttatctac acgacgggga gtcaggcaac tatggatgaa cgaaatagac |
| 1021 agatcgctga gataggtgcc tcactgatta agcattggta actgtcagac caagtttact |
| 1081 catatatact ttagattgat ttaaaacttc atttttaatt taaaaggatc taggtgaaga |
| 1141 tcctttttga taatctcatg accaaaatcc cttaacgtga gttttcgttc cactgagcgt |
| 1201 cagaccccgt agaaaagatc aaaggatctt cttgagatcc ttttttttctg cgcgtaatct |
| 1261 gctgcttgca acaaaaaaa ccaccgctac cagcggtggt ttgtttgccg gatcaagagc |
| 1321 taccaactct ttttccgaag gtaactggct tcagcagagc gcagatacca aatactgttc |
| 1381 ttctagtgta gccgtagtta ggccaccact tcaagaactc tgtagcaccg cctacatacc |
| 1441 tcgctctgct aatcctgtta ccagtggctg ctgccagtgg cgataagtcg tgtcttaccg |
| 1501 ggttggactc aagacgatag ttaccggata aggcgcagcg gtcgggctga acggggggtt |
| 1561 cgtgcataca gcccagcttg gagcgaacga cctacaccga actgagatac ctacagcgtg |
| 1621 agctatgaga aagcgccacg cttcccgaag ggagaaaggc ggacaggtat ccggtaagcg |
| 1681 gcagggtcgg aacaggagag cgcacgaggg agcttccagg gggaaacgcc tggtatcttt |
| 1741 atagtcctgt cgggtttcgc cacctctgac ttgagcgtcg atttttgtga tgctcgtcag |
| 1801 gggggcggag cctatggaaa aacgccagca acgcggcctt tttacggttc ctggccttt |
| 1861 gctggccttt tgctcacatg ttctttcctg cgttatcccc tgattctgtg ataaccgta |
| 1921 ttaccgcctt tgagtgagct gataccgctc gccgcagccg aacgaccgag cgcagcgagt |

TABLE 35-continued

DNA sequence of pMID21: 5957 bp (SEQ ID NO: 895)

```
1981 cagtgagcga ggaagcggaa gagcgcccaa tacgcaaacc gcctctcccc gcgcgttggc
2041 cgattcatta atgcagctgg cacgacaggt ttcccgactg gaaagcgggc agtgagcgca
2101 acgcaattaa tgtgagttag ctcactcatt aggcacccca ggctttacac tttatgcttc
2161 cggctcgtat gttgtgtgga attgtgagcg gataacaatt tcacacagga aacagctatg
2221 accatgatta cgccaagctt tggagccttt ttttggaga ttttcaacgt gaaaaaatta
2281 ttattcgcaa ttcctttagt tgttcctttc tattctcaca gtgcacaggt ccaactgcag
2341 gagctcgaga tcaaacgtgg aactgtggct gcaccatctg tcttcatctt cccgccatct
2401 gatgagcagt tgaaatctgg aactgcctct gttgtgtgcc tgctgaataa cttctatccc
2461 agagaggcca aagtacagtg gaaggtggat aacgccctcc aatcgggtaa ctcccaggag
2521 agtgtcacag agcaggacag caaggacagc acctacagcc tcagcagcac cctgacgctg
2581 agcaaagcag actacgagaa acacaaagtc tacgcctgcg aagtcaccca tcagggcctg
2641 agttcaccgg tgacaaagag cttcaacagg ggagagtgtt aataaggcgc gcctaaccat
2701 ctatttcaag gaacagtctt aatgaaaaag cttttattca tgatcccgtt agttgtaccg
2761 ttcgtggccc agccggcctc tgctgaagtt caattgttag agtctggtgg cggtcttgtt
2821 cagcctggtg gttctttacg tctttcttgc gctgcttccg gagcttcaga tctgtttgcc
2881 tttttgtggg gtggtgcaga tcgcgttacg gagatcgacc gactgcttga gcaaaagcca
2941 cgcttaactg ctgatcaggc atgggatgtt attcgccaaa ccagtcgtca ggatcttaac
3001 ctgaggcttt ttttacctac tctgcaagca gcgacatctg gtttgacaca gagcgatccg
3061 cgtcgtcagt ggtagaaaac attaacacgt tgggatggca tcaatttgct taatgatgat
3121 ggtaaaacct ggcagcagcc aggctctgcc atcctgaacg tttggctgac cagtatgttg
3181 aagcgtaccg tagtggctgc cgtacctatg ccatttgata agtggtacag cgccagtggc
3241 tacgaaacaa cccaggacgg cccaactggt tcgctgaata taagtgttgg agcaaaaatt
3301 ttgtatgagg cggtgcaggg agacaaatca ccaatcccac aggcggttga tctgtttgct
3361 gggaaaccac agcaggaggt tgtgttggct gcgctggaag atacctggga gactctttcc
3421 aaacgctatg gcaataatgt gagtaactgg aaaacaccgg caatggcctt aacgttccgg
3481 gcaaataatt tctttggtgt accgcaggcc gcagcggaag aaacgcgtca tcaggcggag
3541 tatcaaaacc gtggaacaga aaacgatatg attgttttct caccaacgac aagcgatcgt
3601 cctgtgcttg cctgggatgt ggtcgcaccc ggtcagagtg ggtttattgc tcccgatgga
3661 acagttgata agcactatga agatcagctg aaaatgtacg aaaatttttgg ccgtaagtcg
3721 ctctggttaa cgaagcagga tgtggaggcg cataaggagt tctagagaca actctaagaa
3781 tactctctac ttgcagatga acagcttaag tctgagcatt cggtccgggc aacattctcc
3841 aaactgacca gacgacacaa acggcttacg ctaaatcccg cgcatgggat ggtaaagagg
3901 tggcgtcttt gctggcctgg actcatcaga tgaaggccaa aaattggcag gagtggacac
3961 agcaggcagc gaaacaagca ctgaccatca actggtacta tgctgatgta aacggcaata
4021 ttggttatgt tcatactggt gcttatccag atcgtcaatc aggccatgat ccgcgattac
4081 ccgttcctgg tacgggaaaa tgggactgga aagggctatt gccttttgaa atgaaccccta
4141 aggtgtataa cccccagcag ctagccatat tctctcggtc accgtctcaa gcgcctccac
4201 caagggccca tcggtcttcc cgctagcacc ctcctccaag agcacctctg ggggcacagc
4261 ggccctgggc tgcctggtca aggactactt ccccgaaccg gtgacggtgt cgtggaactc
```

TABLE 35-continued

DNA sequence of pMID21: 5957 bp (SEQ ID NO: 895)

```
4321 aggcgccctg accagcggcg tccacacctt cccggctgtc ctacagtcta gcggactcta
4381 ctccctcagc agcgtagtga ccgtgccctc ttctagcttg ggcacccaga cctacatctg
4441 caacgtgaat cacaagccca gcaacaccaa ggtggacaag aaagttgagc ccaaatcttg
4501 tgcggccgca catcatcatc accatcacgg ggccgcagaa caaaaactca tctcagaaga
4561 ggatctgaat ggggccgcag aggctagttc tgctagtaac gcgtcttccg gtgattttga
4621 ttatgaaaag atggcaaacg ctaataaggg ggctatgacc gaaaatgccg atgaaaacgc
4681 gctacagtct gacgctaaag gcaaacttga ttctgtcgct actgattacg gtgctgctat
4741 cgatggtttc attggtgacg tttccggcct tgctaatggt aatggtgcta ctggtgattt
4801 tgctggctct aattcccaaa tggctcaagt cggtgacggt gataattcac ctttaatgaa
4861 taatttccgt caatatttac cttccctccc tcaatcggtt gaatgtcgcc cttttgtctt
4921 tggcgctggt aaaccatatg aattttctat tgattgtgac aaaataaact tattccgtgg
4981 tgtctttgcg tttcttttat atgttgccac ctttatgtat gtattttcta cgtttgctaa
5041 catactgcgt aataaggagt cttaatgaaa cgcgtgatga gaattcactg gccgtcgttt
5101 tacaacgtcg tgactgggaa aaccctggcg ttacccaact taatcgcctt gcagcacatc
5161 cccctttcgc cagctggcgt aatagcgaag aggcccgcac cgatcgccct tcccaacagt
5221 tgcgcagcct gaatggcgaa tggcgcctga tgcggtattt tctccttacg catctgtgcg
5281 gtatttcaca ccgcatacgt caaagcaacc atagtacgcg ccctgtagcg gcgcattaag
5341 cgcggcgggt gtggtggtta cgcgcagcgt gaccgctaca cttgccagcg ccttagcgcc
5401 cgctcctttc gctttcttcc cttcctttct cgccacgttc gccggctttc cccgtcaagc
5461 tctaaatcgg gggctccctt tagggttccg atttagtgct ttacggcacc tcgaccccaa
5521 aaaacttgat ttgggtgatg ttcacgtag tgggccatcg ccctgataga cggtttttcg
5581 ccctttgacg ttggagtcca cgttctttaa tagtggactc ttgttccaaa ctggaacaac
5641 actcaactct atctcgggct attcttttga tttataaggg attttgccga tttcggtcta
5701 ttggttaaaa aatgagctga tttaacaaaa atttaacgcg aattttaaca aaatattaac
5761 gtttacaatt ttatggtgca gtctcagtac aatctgctct gatgccgcat agttaagcca
5821 gccccgacac ccgccaacac ccgctgacgc gccctgacgg gcttgtctgc tcccggcatc
5881 cgcttacaga caagctgtga ccgtctccgg gagctgcatg tgtcagaggt tttcaccgtc
5941 atcaccgaaa cgcgcga
```

TABLE 36 pM21J containing IIIss::A27::Ckappa
Number of bases 5225 (SEQ ID NO: 921)

```
GACGAAAGGG CCTCGTGATA CGCCTATTTT TATAGGTTAA TGTCATGATA ATAATGGTTT    60
CTTAGACGTC AGGTGGCACT TTTCGGGGAA ATGTGCGCGG AACCCCTATT TGTTTATTTT   120
TCTAAATACA TTCAAATATG TATCCGCTCA TGAGACAATA ACCCTGATAA ATGCTTCAAT   180
AATATTGAAA AAGGAAGAGT ATGAGTATTC AACATTTCCG TGTCGCCCTT ATTCCCTTTT   240
TTGCGGCATT TTGCCTTCCT GTTTTTGCTC ACCCAGAAAC GCTGGTGAAA GTAAAAGATG   300
CTGAAGATCA GTTGGGTGCC CGAGTGGGTT ACATCGAACT GGATCTCAAC AGCGGTAAGA   360
TCCTTGAGAG TTTTCGCCCC GAAGAACGTT TTCCAATGAT GAGCACTTTT AAAGTTCTGC   420
```

TABLE 36-continued pM21J containing IIIss::A27::Ckappa
Number of bases 5225 (SEQ ID NO: 921)

| | | | | | |
|---|---|---|---|---|---|
| TATGTGGCGC | GGTATTATCC | CGTATTGACG | CCGGGCAAGA | GCAACTCGGT | CGCCGCATAC | 480 |
| ACTATTCTCA | GAATGACTTG | GTTGAGTACT | CACCAGTCAC | AGAAAAGCAT | CTTACGGATG | 540 |
| GCATGACAGT | AAGAGAATTA | TGCAGTGCTG | CCATAACCAT | GAGTGATAAC | ACTGCGGCCA | 600 |
| ACTTACTTCT | GACAACGATC | GGAGGACCGA | AGGAGCTAAC | CGCTTTTTTG | CACAACATGG | 660 |
| GGGATCATGT | AACTCGCCTT | GATCGTTGGG | AACCGGAGCT | GAATGAAGCC | ATACCAAACG | 720 |
| ACGAGCGTGA | CACCACGATG | CCTGTAGCAA | TGGCAACAAC | GTTGCGCAAA | CTATTAACTG | 780 |
| GCGAACTACT | TACTCTAGCT | TCCCGGCAAC | AATTAATAGA | CTGGATGGAG | GCGGATAAAG | 840 |
| TTGCAGGACC | ACTTCTGCGC | TCGGCCCTTC | CGGCTGGCTG | GTTTATTGCT | GATAAATCTG | 900 |
| GAGCCGGTGA | GCGTGGGTCT | CGCGGTATCA | TTGCAGCACT | GGGGCCAGAT | GGTAAGCCCT | 960 |
| CCCGTATCGT | AGTTATCTAC | ACGACGGGGA | GTCAGGCAAC | TATGGATGAA | CGAAATAGAC | 1020 |
| AGATCGCTGA | GATAGGTGCC | TCACTGATTA | AGCATTGGTA | ACTGTCAGAC | CAAGTTTACT | 1080 |
| CATATATACT | TTAGATTGAT | TTAAAACTTC | ATTTTTAATT | TAAAAGGATC | TAGGTGAAGA | 1140 |
| TCCTTTTTGA | TAATCTCATG | ACCAAAATCC | CTTAACGTGA | GTTTTCGTTC | CACTGAGCGT | 1200 |
| CAGACCCCGT | AGAAAAGATC | AAAGGATCTT | CTTGAGATCC | TTTTTTTCTG | CGCGTAATCT | 1260 |
| GCTGCTTGCA | AACAAAAAAA | CCACCGCTAC | CAGCGGTGGT | TTGTTTGCCG | GATCAAGAGC | 1320 |
| TACCAACTCT | TTTTCCGAAG | GTAACTGGCT | TCAGCAGAGC | GCAGATACCA | AATACTGTTC | 1380 |
| TTCTAGTGTA | GCCGTAGTTA | GGCCACCACT | TCAAGAACTC | TGTAGCACCG | CCTACATACC | 1440 |
| TCGCTCTGCT | AATCCTGTTA | CCAGTGGCTG | CTGCCAGTGG | CGATAAGTCG | TGTCTTACCG | 1500 |
| GGTTGGACTC | AAGACGATAG | TTACCGGATA | AGGCGCAGCG | GTCGGGCTGA | ACGGGGGGTT | 1560 |
| CGTGCATACA | GCCCAGCTTG | GAGCGAACGA | CCTACACCGA | ACTGAGATAC | CTACAGCGTG | 1620 |
| AGCTATGAGA | AAGCGCCACG | CTTCCCGAAG | GGAGAAAGGC | GGACAGGTAT | CCGGTAAGCG | 1680 |
| GCAGGGTCGG | AACAGGAGAG | CGCACGAGGG | AGCTTCCAGG | GGGAAACGCC | TGGTATCTTT | 1740 |
| ATAGTCCTGT | CGGGTTTCGC | CACCTCTGAC | TTGAGCGTCG | ATTTTTGTGA | TGCTCGTCAG | 1800 |
| GGGGGCGGAG | CCTATGGAAA | AACGCCAGCA | ACGCGGCCTT | TTTACGGTTC | CTGGCCTTTT | 1860 |
| GCTGGCCTTT | TGCTCACATG | TTCTTTCCTG | CGTTATCCCC | TGATTCTGTG | GATAACCGTA | 1920 |
| TTACCGCCTT | TGAGTGAGCT | GATACCGCTC | GCCGCAGCCG | AACGACCGAG | CGCAGCGAGT | 1980 |
| CAGTGAGCGA | GGAAGCGGAA | GAGCGCCCAA | TACGCAAACC | GCCTCTCCCC | GCGCGTTGGC | 2040 |
| CGATTCATTA | ATGCAGCTGG | CACGACAGGT | TTCCCGACTG | GAAAGCGGGC | AGTGAGCGCA | 2100 |
| ACGCAATTAA | TGTGAGTTAG | CTCACTCATT | AGGCACCCCA | GGCTTTACAC | TTTATGCTTC | 2160 |
| CGGCTCGTAT | GTTGTGTGGA | ATTGTGAGCG | GATAACAATT | TCACACAGGA | AACAGCTATG | 2220 |
| ACCATGATTA | CGCCAAGCTT | TGGAGCCTTT | TTTTTGGAGA | TTTTCAACAT | GAAGAAACTG | 2280 |
| CTGTCTGCTA | TCCCACTAGT | TGTCCCTTTC | TATTCTCATA | GTGAAATCGT | TCTGACCCAG | 2340 |
| TCCCCGGGGA | CCCTGTCTCT | GTCTCCGGGT | GAACGTGCTA | CGCTGAGCTG | TCGTGCTTCT | 2400 |
| CAATCCGTTA | GCTCCTCTTA | TTTAGCTTGG | TATCAGCAAA | AGCCGGGTCA | AGCTCCGCGG | 2460 |
| CTGTTGATCT | ATGGTGCCTC | TAGTCGTGCT | ACTGGCATCC | CTGATCGTTT | CTCTGGCTCT | 2520 |
| GGCTCCGGAA | CCGATTTCAC | TCTGACCATT | TCTCGTCTCG | AGCCGGAAGA | TTTCGCTGTC | 2580 |
| TACTATTGTC | AACAGTATGG | TTCTAGTCCG | CTGACTTTCG | GTGGCGGTAC | CAAAGTCGAA | 2640 |
| ATCAAGCGTG | GAACTGTGGC | TGCACCATCT | GTCTTCATCT | TCCCGCCATC | TGATGAGCAG | 2700 |

TABLE 36-continued pM21J containing IIIss::A27::Ckappa
Number of bases 5225 (SEQ ID NO: 921)

| | | | | | |
|---|---|---|---|---|---|
| TTGAAATCTG | GAACTGCCTC | TGTTGTGTGC | CTGCTGAATA | ACTTCTATCC | CAGAGAGGCC | 2760 |
| AAAGTACAGT | GGAAGGTGGA | TAACGCCCTC | CAATCGGGTA | ACTCCCAGGA | GAGTGTCACA | 2820 |
| GAGCAGGACA | GCAAGGACAG | CACCTACAGC | CTCAGCAGCA | CCCTGACTCT | GTCCAAAGCA | 2880 |
| GACTACGAGA | AACACAAAGT | CTACGCCTGC | GAAGTCACCC | ATCAGGGCCT | GAGTTCACCG | 2940 |
| GTGACAAAGA | GCTTCAACAG | GGGAGAGTGT | TAATAAGGCG | CGCCAATTTA | ACCATCTATT | 3000 |
| TCAAGGAACA | GTCTTAATGA | AGAAGCTCCT | CTTTGCTATC | CCGCTCGTCG | TTCCTTTTGT | 3060 |
| GGCCCAGCCG | GCCATGGCCG | AAGTTCAATT | GTTAGAGTCT | GGTGGCGGTC | TTGTTCAGCC | 3120 |
| TGGTGGTTCT | TTACGTCTTT | CTTGCGCTGC | TTCCGGATTC | ACTTTCTCTC | GTTACAAGAT | 3180 |
| GAAGTGGGTT | CGCCAAGCTC | CTGGTAAAGG | TTTGGAGTGG | GTTTCTGTTA | TCTATCCTTC | 3240 |
| TGGTGGCGGT | ACTGGTTATG | CTGACTCCGT | TAAAGGTCGC | TTCACTATCT | CTAGAGACAA | 3300 |
| CTCTAAGAAT | ACTCTCTACT | TGCAGATGAA | CAGCTTAAGG | GCTGAGGACA | CTGCAGTCTA | 3360 |
| CTATTGTGCG | AGAGTCAATT | ACTATGATAG | TAGTGGTTAC | GGTCCTATAG | CTCCTGGACT | 3420 |
| TGACTACTGG | GGCCAGGGAA | CCCTGGTCAC | CGTCTCAAGC | GCCTCCACCA | AGGGTCCGTC | 3480 |
| GGTCTTCCCG | CTAGCACCCT | CCTCCAAGAG | CACCTCTGGG | GGCACAGCGG | CCCTGGGCTG | 3540 |
| CCTGGTCAAG | GACTACTTCC | CCGAACCGGT | GACGGTGTCG | TGGAACTCAG | GCGCCCTGAC | 3600 |
| CAGCGGCGTC | CACACCTTCC | CGGCTGTCCT | ACAGTCTAGC | GGACTCTACT | CCCTCAGCAG | 3660 |
| CGTAGTGACC | GTGCCCTCTT | CTAGCTTGGG | CACCCAGACC | TACATCTGCA | ACGTGAATCA | 3720 |
| CAAGCCCAGC | AACACCAAGG | TGGACAAGAA | AGTTGAGCCC | AAATCTTGTG | CGGCCGCACA | 3780 |
| TCATCATCAC | CATCACGGGG | CCGCAGAACA | AAAACTCATC | TCAGAAGAGG | ATCTGAATGG | 3840 |
| GGCCGCAGAG | GCTAGTTCTG | CTAGTAACGC | GTCTTCCGGT | GATTTTGATT | ATGAAAAGAT | 3900 |
| GGCAAACGCT | AATAAGGGGG | CTATGACCGA | AAATGCCGAT | GAAAACGCGC | TACAGTCTGA | 3960 |
| CGCTAAAGGC | AAACTTGATT | CTGTCGCTAC | TGATTACGGT | GCTGCTATCG | ATGGTTTCAT | 4020 |
| TGGTGACGTT | TCCGGCCTTG | CTAATGGTAA | TGGTGCTACT | GGTGATTTTG | CTGGCTCTAA | 4080 |
| TTCCCAAATG | GCTCAAGTCG | GTGACGGTGA | TAATTCACCT | TTAATGAATA | ATTTCCGTCA | 4140 |
| ATATTTACCT | TCCCTCCCTC | AATCGGTTGA | ATGTCGCCCT | TTTGTCTTTG | GCGCTGGTAA | 4200 |
| ACCATATGAA | TTTTCTATTG | ATTGTGACAA | AATAAACTTA | TTCCGTGGTG | TCTTTGCGTT | 4260 |
| TCTTTTATAT | GTTGCCACCT | TTATGTATGT | ATTTTCTACG | TTTGCTAACA | TACTGCGTAA | 4320 |
| TAAGGAGTCT | TAATGAAACG | CGTGATGAGA | ATTCACTGGC | CGTCGTTTTA | CAACGTCGTG | 4380 |
| ACTGGGAAAA | CCCTGGCGTT | ACCCAACTTA | ATCGCCTTGC | AGCACATCCC | CCTTTCGCCA | 4440 |
| GCTGGCGTAA | TAGCGAAGAG | GCCCGCACCG | ATCGCCCTTC | CCAACAGTTG | CGCAGCCTGA | 4500 |
| ATGGCGAATG | GCGCCTGATG | CGGTATTTTC | TCCTTACGCA | TCTGTGCGGT | ATTTCACACC | 4560 |
| GCATACGTCA | AAGCAACCAT | AGTACGCGCC | CTGTAGCGGC | GCATTAAGCG | CGGCGGGTGT | 4620 |
| GGTGGTTACG | CGCAGCGTGA | CCGCTACACT | TGCCAGCGCC | TTAGCGCCCG | CTCCTTTCGC | 4680 |
| TTTCTTCCCT | TCCTTTCTCG | CCACGTTCGC | CGGCTTTCCC | CGTCAAGCTC | TAAATCGGGG | 4740 |
| GCTCCCTTTA | GGGTTCCGAT | TTAGTGCTTT | ACGGCACCTC | GACCCCAAAA | AACTTGATTT | 4800 |
| GGGTGATGGT | TCACGTAGTG | GGCCATCGCC | CTGATAGACG | GTTTTTCGCC | CTTTGACGTT | 4860 |
| GGAGTCCACG | TTCTTTAATA | GTGGACTCTT | GTTCCAAACT | GGAACAACAC | TCAACTCTAT | 4920 |
| CTCGGGCTAT | TCTTTTGATT | TATAAGGGAT | TTTGCCGATT | TCGGTCTATT | GGTTAAAAAA | 4980 |
| TGAGCTGATT | TAACAAAAAT | TTAACGCGAA | TTTTAACAAA | ATATTAACGT | TTACAATTTT | 5040 |

TABLE 36-continued pM21J containing IIIss::A27::Ckappa
Number of bases 5225 (SEQ ID NO: 921)

```
ATGGTGCAGT CTCAGTACAA TCTGCTCTGA TGCCGCATAG TTAAGCCAGC CCCGACACCC   5100
GCCAACACCC GCTGACGCGC CCTGACGGGC TTGTCTGCTC CCGGCATCCG CTTACAGACA   5160
AGCTGTGACC GTCTCCGGGA GCTGCATGTG TCAGAGGTTT TCACCGTCAT CACCGAAACG   5220
CGCGA                                                                5225
```

TABLE 40 pLCSK23 (SEQ ID NO: 896)

```
   1 GACGAAAGGG CCTGCTCTGC CAGTGTTACA ACCAATTAAC CAATTCTGAT TAGAAAAACT
  61 CATCGAGCAT CAAATGAAAC TGCAATTTAT TCATATCAGG ATTATCAATA CCATATTTTT
 121 GAAAAAGCCG TTTCTGTAAT GAAGGAGAAA ACTCACCGAG GCAGTTCCAT AGGATGGCAA
 181 GATCCTGGTA TCGGTCTGCG ATTCCGACTC GTCCAACATC AATACAACCT ATTAATTTCC
 241 CCTCGTCAAA AATAAGGTTA TCAAGTGAGA AATCACCATG AGTGACGACT GAATCCGGTG
 301 AGAATGGCAA AAGCTTATGC ATTTCTTTCC AGACTTGTTC AACAGGCCAG CCATTACGCT
 361 CGTCATCAAA ATCACTCGCA TCAACCAAAC CGTTATTCAT TCGTGATTGC GCCTGAGCGA
 421 GACGAAATAC GCGATCGCTG TTAAAAGGAC AATTACAAAC AGGAATTGAA TGCAACCGGC
 481 GCAGGAACAC TGCCAGCGCA TCAACAATAT TTTCACCTGA ATCAGGATAT TCTTCTAATA
 541 CCTGGAATGC TGTTTTCCCG GGGATCGCAG TGGTGAGTAA CCATGCATCA TCAGGAGTAC
 601 GGATAAAATG CTTGATGGTC GGAAGAGGCA TAAATTCCGT CAGCCAGTTT AGTCTGACCA
 661 TCTCATCTGT AACATCATTG GCAACGCTAC CTTTGCCATG TTTCAGAAAC AACTCTGGCG
 721 CATCGGGCTT CCCATACAAT CGATAGATTG TCGCACCTGA TTGCCCGACA TTATCGCGAG
 781 CCCATTTATA CCCATATAAA TCAGCATCCA TGTTGGAATT TAATCGCGGC CTCGAGCAAG
 841 ACGTTTCCCG TTGAATATGG CTCATAACAC CCCTTGTATT ACTGTTTATG TAAGCAGACA
 901 GTTTTATTGT TCATGATGAT ATATTTTTAT CTTGTGCAAT GTAACATCAG AGATTTTGAG
 961 ACACAACGTG CTTTCCCCC CCCCCCCTG CAGGTCTCGG CTATTCCTG TCAGACCAAG
1021 TTTACTCATA TATACTTTAG ATTGATTTAA AACTTCATTT TTAATTTAAA AGGATCTAGG
1081 TGAAGATCCT TTTTGATAAT CTCATGACCA AAATCCCTTA ACGTGAGTTT TCGTTCCACT
1141 GAGCGTCAGA CCCCGTAGAA AAGATCAAAG GATCTTCTTG AGATCCTTTT TTTCTGCGCG
1201 TAATCTGCTG CTTGCAAACA AAAAAACCAC CGCTACCAGC GGTGGTTTGT TGCCGGATC
1261 AAGAGCTACC AACTCTTTTT CCGAAGGTAA CTGGCTTCAG CAGAGCGCAG ATACCAAATA
1321 CTGTTCTTCT AGTGTAGCCG TAGTTAGGCC ACCACTTCAA GAACTCTGTA GCACCGCCTA
1381 CATACCTCGC TCTGCTAATC CTGTTACCAG TGGCTGCTGC CAGTGGCGAT AAGTCGTGTC
1441 TTACCGGGTT GGACTCAAGA CGATAGTTAC CGGATAAGGC GCAGCGGTCG GGCTGAACGG
1501 GGGGTTCGTG CATACAGCCC AGCTTGGAGC GAACGACCTA CACCGAACTG AGATACCTAC
1561 AGCGTGAGCT ATGAGAAAGC GCCACGCTTC CCGAAGGGAG AAAGGCGGAC AGGTATCCGG
1621 TAAGCGGCAG GGTCGGAACA GGAGAGCGCA CGAGGGAGCT TCCAGGGGGA AACGCCTGGT
1681 ATCTTTATAG TCCTGTCGGG TTTCGCCACC TCTGACTTGA GCGTCGATTT TGTGATGCT
1741 CGTCAGGGGG GCGGAGCCTA TGGAAAAACG CCAGCAACGC GGCCTTTTTA CGGTTCCTGG
1801 CCTTTTGCTG GCCTTTTGCT CACATGTTCT TTCCTGCGTT ATCCCCTGAT TCTGTGGATA
```

TABLE 40-continued pLCSK23 (SEQ ID NO: 896)

```
1861 ACCGTATTAC CGCCTTTGAG TGAGCTGATA CCGCTCGCCG CAGCCGAACG ACCGAGCGCA

1921 GCGAGTCAGT GAGCGAGGAA GCGGAAGAGC GCCCAATACG CAAACCGCCT CTCCCCGCGC

1981 GTTGGCCGAT TCATTAATGC AGCTGGCACG ACAGGTTTCC CGACTGGAAA GCGGGCAGTG

2041 AGCGCAACGC AATTAATGTG AGTTAGCTCA CTCATTAGGC ACCCCAGGCT TTACACTTTA

2101 TGCTTCCGGC TCGTATGTTG TGTGGAATTG TGAGCGGATA ACAATTTCAC ACAGGAAACA

2161 GCTATGACCA TGATTACGCC AAGCTTTGGA GCCTTTTTTT TGGAGATTTT CAACATGAAG

2221 AAGCTCCTCT TTGCTATCCC GCTCGTCGTT CCTTTTGTGG CCCAGCCGGC CATGGCCGAC

2281 ATCCAGATGA CCCAGTCTCC ATCCTCCCTG TCTGCATCTG TAGGAGACAG AGTCACCATC

2341 ACTTGCCGGG CAAGTCAGAG CATTAGCAGC TATTTAAATT GGTATCAGCA GAAACCAGGG

2401 AAAGCCCCTA AGCTCCTGAT CTATGCTGCA TCCAGTTTGC AAAGTGGGGT CCCATCAAGG

2461 TTCAGTGGCA GTGGATCTGG GACAGATTTC ACTCTCACCA TCAGCAGTCT GCAACCTGAA

2521 GATTTTGCAA CTTACTACTG TCAACAGAGT TACAGTACCC CTTTCACTTT CGGCCCTGGG

2581 ACCAAAGTGG ATATCAAACG TGGtACcGTG GCTGCACCAT CTGTCTTCAT CTTCCCGCCA

2641 TCTGATGAGC AGTTGAAATC TGGAACTGCC TCTGTTGTGT GCCTGCTGAA TAACTTCTAT

2701 CCCAGAGAGG CCAAAGTACA GTGGAAGGTG GATAACGCCC TCCAATCGGG TAACTCCCAG

2761 GAGAGTGTCA CAGAGCAGGA CAGCAAGGAC AGCACCTACA GCCTCAGCAG CACCCTGACG

2821 CTGAGCAAAG CAGACTACGA GAAACACAAA GTCTACGCCT GCGAAGTCAC CCATCAGGGC

2881 CTGAGTTCAC CGGTGACAAA GAGCTTCAAC AGGGGAGAGT GTGCGGCCGC TGGTAAGCCT

2941 ATCCCTAACC CTCTCCTCGG TCTCGATTCT ACGTGATAAC TTCACCGGTC AACGCGTGAT

3001 GAGAATTCAC TGGCCGTCGT TTTACAACGT CGTGACTGGG AAAACCCTGG CGTTACCCAA

3061 CTTAATCGCC TTGCAGCACA TCCCCCTTTC GCCAGCTGGC GTAATAGCGA AGAGGCCCGC

3121 ACCGATCGCC CTTCCCAACA GTTGCGCAGC CTGAATGGCG AATGGCGCCT GATGCGGTAT

3181 TTTCTCCTTA CGCATCTGTG CGGTATTTCA CACCGCATAC GTCAAAGCAA CCATAGTCTC

3241 AGTACAATCT GCTCTGATGC CGCATAGTTA AGCCAGCCCC GACACCCGCC AACACCCGCT

3301 GACGCGCCCT GACGGCTTG TCTGCTCCCG GCATCCGCTT ACAGACAAGC TGTGACCGTC

3361 TCCGGGAGCT GCATGTGTCA GAGGTTTTCA CCGTCATCAC CGAAACGCGC GA
```

Example 4

Dobbling of CDRs

The following examples exemplify the use of dobbling in constructing synthetic libraries. The parental 3-23 heavy chain (HC) is diversified in CDR1, 2, and 3. This diversity is combined with a synthetically diversified A27 light chain (LC). The diversity will be as follows:

Example 4.1

HC CDR1

The following dobbling diversity allows 5,832 variants. See Table 50. At position 31, Ser is the germline (GL) amino-acid type. Hence we make Ser three times more likely then the other types. Since 18 types are allowed, Ser will be allowed 15% of the time and all the others are allowed at 5%. Thus, if there is no selection for the AA type at 31, we are more likely to isolate an Ab with Ser. Similarly, at 33 the GL AA type is Ala and we make Ala 3 times as likely (15%) as all the others (5%). At 35 Ser is the GL AA type and we make it three times as likely as the others. At all three positions, we have excluded Cys and Met. We exclude Cys because we do not want gratuitus disulfides or exposed unpaired cysteines that could adversely affect the solubility and reactivity of the Ab. We exclude Met because exposed methionines side groups are subject to oxidation which can alter binding properties and shelf life. We could make the germline amino-acid type 2, 3, 4, 5, 6, 8, or 10 times more likely than the other AA types.

TABLE 50

Diversity for CDR1 in 3-23

| Position | Parental AA | Allowed |
|---|---|---|
| 31 | S (three-times more likely as the others) | ADEFGHKLNPQRSTVWY |
| 33 | A (3-X more likely) | ADEFGHKLNPQRSTVWY |
| 35 | S (3-X more likely) | ADEFGHKLNPQRSTVWY |

Throughout this disclosure, the shown "Allowed" amino acids are the amino acids that can be used at a given position. For example, in Table 50, at position 31, allowed amino acids "ADEFGHKLNPQRSTVWY" are shown. This indicates that amino acids A, D, E, F, G, H, K, L, N, P, Q, R, S, T, V, W, and Y are all allowed at position 31.

Example 4.2

HC CDR2

In CDR2, we allow diversity at positions 50, 52, 52a, 56, and 58. At 50, 52, 56, and 58 we allow all amino-acid types except Cys and Met and we make the GL AA types more likely by three fold. We could make the GL AA type 2, 3, 4, 5, 6, 8, or 10 times more likely than the other AA types.

TABLE 51

HC CDR2: Diversity = 419,904

| Position | Parental AA | Allowed |
|---|---|---|
| 50 | A (3-X more likely) | ADEFGHKLNPQRSTVWY |
| 52 | S (3-X more likely) | ADEFGHKLNPQRSTVWY |
| 52a | G (3-X more likely) | GPSY |
| 56 | S (3-X more likely) | ADEFGHKLNPQRSTVWY |
| 58 | Y (3-X more likely) | ADEFGHKLNPQRSTVWY |

Combined CDR1 and CDR2 diversity=2.45 E 9

Example 4.3

HC CDR3, Lengths 3, 4, 5

Very short CDR3 can be made by dobbling. Table 7 shows several parental sequences for CDR3 length 3. At 94 many VH3s have Arg and we have allowed this change, but Lys is made 3-X as likely. At 95, F is found at this position in JH1. We also allow Ser, Tyr, Asp, and Arg to allow small, large, plus charge, and minus charge. At 96, JH1 has Q. Since Q is very similar to Glu, we allow Glu as an acidic alternative plus Arg, Ser, Tyr, and Leu. At 97, H is is the germline AA from JH1. We allow minus charge (D), plus charge (R), small polar (S), large hydrophobic (Y), and aliphatic (L). The parental sequence makes up 4.5% of the library, but this is combined with a large diversity in CDR1 and CDR2. The dobbling allows 360 sequences in all. The least likely sequences occur at 1 in 1792. The most likely (parental) sequence occurs about 1 in 22.

TABLE 60

A dobbled HC CDR3 of length 3 (V-3JH1 of Table 7) ('KFQH' disclosed as SEQ ID NO: 951)

| Position | Parental amino acid (source) | Allowed |
|---|---|---|
| 94 | K (VH 3-23) | KR (3:1) |
| 95 | F (JH1) | FSYDR (3:1:1:1:1) |
| 96 | Q (JH1) | QERSYL (3:1:1:1:1:1) |
| 97 | H (JH1) | HDRSYL (3:1:1:1:1:1) |
| 103 | W (JH1) | W |

Table 61 shows a dobbled HC CDR3 of length 3. Here K94 is fixed as is W103. We have made the "parental" D segment amino acid five times as likely as the other allowed AA types.

TABLE 61

A dobbled HC CDR3 of length 3 from a D fragment (V-3D1-1.1.2-JH1 of Table 7). ('KTTG' disclosed as SEQ ID NO: 952)

| Position | Parental | Allowed |
|---|---|---|
| 94 | K (V 3-23) | K |
| 95 | T (D1-1.1.2) | TYRDL (5:1:1:1:1) |
| 96 | T (D1-1.1.2) | TYRDL (5:1:1:1:1) |
| 97 | G (D1-1.1.2) | GSYRDL (5:1:1:1:1:1) |
| 103 | W (JH1) | W |

In this example (Table 62, using V-4JH2 from Table 8), 94 is fixed as Lys. At 95, JH2 has Tyr and we have allowed Ser, Asp, Arg, and Leu so that size, charge, and hydrophobicity can alter to suit the antigen. JH2 has Phe at 96 and we have allowed Ser, Tyr, Asp, Arg, and Leu. At 97, JH2 has Asp and we have allowed Arg, Ser, Tyr, and Leu. At 98, JH2 has Leu and we have allowed Ser, Tyr, Asp, and Arg. This pattern allows 750 distinct sequences, of which the parental is the most likely (1 in 18). The least likely sequences occur at 1 in 4608 or 256 times less likely than the most likely.

TABLE 62

HC CDR3 length 4 from JH2 (V-4JH2 in Table 7) ('KYFDL' disclosed as SEQ ID NO: 953)

| Position | Parental AA (source) | Allowed |
|---|---|---|
| 94 | K (VH 3-23) | K |
| 95 | Y (JH2) | YSDRL (4:1:1:1:1) |
| 96 | F (JH2) | FSYDRL (4:1:1:1:1:1) |
| 97 | D (JH2) | DRSYL (4:1:1:1:1) |
| 98 | L (JH2) | LSYDR (4:1:1:1:1) |
| 103 | W (JH2) | W |

In Table 63, there is a dobbling of V-4D3-10.1a-JH2 from Table 8. At 94, we allow Lys and Arg with Lys (the parental) four times as likely as Arg. At 95, D3-10.1a (i.e., D3-10 in the first reading frame and starting a AA 1) has Leu; we allow SYDR as well with Leu 4-X as likely as each of the other AA types. At 96, D3-10.1a has Leu again and we allow the same menu. At 97, D3-10.1a has Trp and we allow Ser, Tyr, Asp, and Arg with Trp 4-X as likely. At 98, D3-10.1a has Phe and we allow Ser, Tyr, Asp, and Arg as well.

TABLE 63

HC CDR3 of length four from V-4D3-10.1a in Table 8 ('KLLWF' disclosed as SEQ ID NO: 954)

| Position | Parental AA (source) | Allowed |
|---|---|---|
| 94 | K (VH 3-23) | KR (4:1) |
| 95 | L (D3-10.1a) | LSYDR (4:1:1:1:1) |
| 96 | L (D3-10.1a) | LSYDR (4:1:1:1:1) |
| 97 | W (D3-10.1a) | WSYDR (4:1:1:1:1) |
| 98 | F (D3-10.1a) | FSYDR (4:1:1:1:1) |
| 103 | W | W |

Example 4.4

HC CDR3 Length 10 to 20

HC CDR3
Two sublibraries, both with CDR3 of length 16:

TABLE 52

Library 1: Diversity = 5 E 11, the "parental" sequence occurs at 1 in 1.5 E6. ('KYYYDSSGYYYAEYFQHW' disclosed as SEQ ID NO: 955)

| Position | "Parental" AA (source) | Allowed |
|---|---|---|
| 94 | K (3-X more likely) (3-23) | KR (3:1) |
| 95 | Y (3-X more likely) (D2-21(2)) | YSRDL (3:1:1:1:1) |
| 96 | Y (3-X more likely) (D2-21(2)) | YSRDL (3:1:1:1:1) |
| 97 | Y (3-X more likely) (D2-21(2)) | YSRDL (3:1:1:1:1) |
| 98 | D (3-X more likely) (D2-21(2)) | DYSRL (3:1:1:1:1) |
| 99 | S (3-X more likely) (D2-21(2)) | SYRDL (3:1:1:1:1) |
| 100 | S (3-X more likely) (D2-21(2)) | SYRDL (3:1:1:1:1) |
| 101 | G (3-X more likely) (D2-21(2)) | GASYRDL (3:1:1:1:1:1) |
| 102 | Y (3-X more likely) (D2-21(2)) | YSRDL (3:1:1:1:1) |
| 102a | Y (3-X more likely) (D2-21(2)) | YSRDL (3:1:1:1:1) |
| 102b | Y (3-X more likely) (D2-21(2)) | YSRDL (3:1:1:1:1) |
| 102c | A (3-X more likely) (JH1) | ASYRD (3:1:1:1:1) |
| 102d | E (3-X more likely) (JH1) | ERSYL (3:1:1:1:1) |
| 102e | Y (3-X more likely) (JH1) | YSRDL (3:1:1:1:1) |
| 102f | F (3-X more likely) (JH1) | FYSRD (3:1:1:1:1) |
| 102g | Q (3-X more likely) (JH1) | QERSY (3:1:1:1:1) |
| 102h | H (3-X more likely) (JH1) | HERSYL (3:1:1:1:1:1) |
| 103 | W (JH1, fixed) | W |

TABLE 53

Library 2: CDR3 length 16; Diversity is 3.0 E 10 and the parental sequence occurs once in 3.7 E 5. ('KGYCSSTSCYTAEYFQHW' disclosed as SEQ ID NO: 956)

| Position | "Parental" AA (source) | Allowed |
|---|---|---|
| 94 | K (3-X more likely) (3-23) | KR (3:1) |
| 95 | G (3-X more likely) (D2-2(2)) | GSYDRL (3:1:1:1:1:1) |
| 96 | Y (3-X more likely) (D2-2(2)) | YSDRL (3:1:1:1:1) |
| 97 | C (fixed) (D2-2(2)) | C |
| 98 | S (3-X more likely) (D2-2(2)) | SYRDL (3:1:1:1:1) |
| 99 | S (3-X more likely) (D2-2(2)) | SYRDL (3:1:1:1:1) |
| 100 | T (3-X more likely) (D2-2(2)) | TYRDL (3:1:1:1:1) |
| 101 | S (3-X more likely) (D2-2(2)) | SYRDL (3:1:1:1:1) |
| 102 | C (fixed) (D2-2(2)) | C |
| 102a | Y (3-X more likely) (D2-2(2)) | YSDRL |

TABLE 53-continued

Library 2: CDR3 length 16; Diversity is 3.0 E 10 and the parental sequence occurs once in 3.7 E 5. ('KGYCSSTSCYTAEYFQHW' disclosed as SEQ ID NO: 956)

| Position | "Parental" AA (source) | | Allowed (3:1:1:1:1) |
|---|---|---|---|
| 102b | T (3-X more likely) | (D2-2(2)) | TYRDL (3:1:1:1:1) |
| 102c | A (3-X more likely) | (JH1) | ASYDRL (3:1:1:1:1:1) |
| 102d | E (3-X more likely) | (JH1) | ERSYL (3:1:1:1:1) |
| 102e | Y (3-X more likely) | (JH1) | YSDRL (3:1:1:1:1) |
| 102f | F (3-X more likely) | (JH1) | FYSRDL (3:1:1:1:1:1) |
| 102g | Q (3-X more likely) | (JH1) | QERSYL (3:1:1:1:1:1) |
| 102h | H (3-X more likely) | (JH1) | HDRSYL (3:1:1:1:1:1) |
| 103 | W ((JH1)) | | W |

Table 65 shows a dobbling variegation of SEQ ID NO:898. The total diversity allowed is 2.1 E 13. A synthesis that produces 1. E 8, 3. E 8, 5. E 8, 1. E 9, or 5. E 9 will sample the diversity adequately. The design of SEQ ID NO:898 was discussed above. In dobbling SEQ ID NO:898, is to allow the parental AA type at three-fold above other AA types at most positions. At positions where the parental is Tyr, then we use Tyr and Ser at equal amounts with Leu at one half that frequency. The Cys residues are fixed. Each parental AA type is allowed to go to one of Arg, Asp, Ser, Tyr, or Leu (Leu might be omitted if the parental is hydrophobic, such as Phe). The parental sequence will occur once in 1. E 8 members. The least likely sequences will occur once in 9.5 E 16. It is not important that the library actually contain the parental sequence, only that it contains many sequences that resemble the parent. Thus, a library that contains 1. E 7, 5. E7, 1.E8, 3. E8, 1. E 9, or 5. E 9, when combined with diversity in HC CDR1, HC CDR2, LC CDR1, LC CDR2, and LC CDR3 will provide a library that will contain many valuable Abs.

TABLE 65

Dobbling of Design 1 with SEQ ID NO: 898 as parent ('KDYGYCSSTSCYTYGYSYAEYFQHW' disclosed as SEQ ID NO: 957)

| Position | Parental (source) | Allowed |
|---|---|---|
| 94 | K (VH 3-23) | K |
| 95 | D (No source) | DSYL (3:1:1:1) |
| 96 | Y (No source) | YSL (2:2:1) |
| 97 | G (D2-2.2) | GSYDRL (3:1:1:1:1:1) |
| 98 | Y (D2-2.2) | YSL (2:2:1) |
| 99 | C (D2-2.2) | C |
| 100 | S (D2-2.2) | SYDRL (3:1:1:1:1) |
| 101 | S (D2-2.2) | SYDRL (3:1:1:1:1) |

TABLE 65-continued

Dobbling of Design 1 with SEQ ID NO: 898 as parent ('KDYGYCSSTSCYTYGYSYAEYFQHW' disclosed as SEQ ID NO: 957)

| Position | Parental (source) | Allowed |
|---|---|---|
| 102 | T (D2-2.2) | TYDRL (3:1:1:1:1) |
| 102a | S (D2-2.2) | SYDRL (3:1:1:1:1) |
| 102b | C (D2-2.2) | C |
| 102c | Y (D2-2.2) | YSL (2:2:1) |
| 102d | T (D2-2.2) | TYDRL (3:1:1:1:1) |
| 102e | Y (No source) | YDSL (3:1:1:1) |
| 102f | G (No source) | GSYRD (3:1:1:1:1) |
| 102g | Y (No source) | YSL (2:2:1) |
| 102h | S (No source) | SYDRL (3:1:1:1) |
| 102i | Y (No source) | YSL (2:2:1) |
| 102j | A (JH1) | ASYDR (3:1:1:1:1) |
| 102k | E (JH1) | ERSYL (3:1:1:1:1) |
| 102l | Y (JH1) | YSL (2:2:1) |
| 102m | F (JH1) | FSYDR (3:1:1:1:1) |
| 102n | Q (JH1) | QYSDRL (3:1:1:1:1:1) |
| 102p | H (JH1) | HSYDRL (3:1:1:1:1:1) |
| 103 | W (JH1, FR4) | W |

Example 4.5

Dobbling of yycakGSGYCSGGSCYSFDYwgqgtlvtvss (SEQ ID NO:931)

Table 80 shows the dobbling of SEQ ID NO:931, an example of an HC CDR3 of length 15. Position 94 is part of FR3 and is held constant. Positions 95 and 96 have "parental" amino-acid types picked from the highly used set of (YGDRS) and are G95 and S96. The next ten positions are taken from D2-15.2 (a moderately highly used D segment containing a disulfide-closed loop). The final three positions are from the JH4 positions 100, 101, and 102 as shown in Table 3. At each position, we make the parental amino-acid type three times more likely than the other allowed types. The Cys residues are fixed. At 102e, Phe is three times more likely as are YGSRD (i.e., Phe is three times more likely as are any of amino acids Y, G, S, R, or D). The diversity allowed is 1.46 E 9. The parental sequence is expected at 1 in 6.9 E 4. Each of the singly substituted sequences is about ⅓ as likely; the doubly substituted ones are ⅑ as likely and so on. The sequences that are composed entirely of other AA types occur at only 1 in 1.1 E 11.

Each of the other sequences in Table 21 can be dobbled in the same way.

TABLE 80

Dobbling of yycakGS<u>GYCSGGSCYS</u>FDYwgqgtlvtvss
(SEQ ID NO: 931)
('KGSGYCSGGSCYSFDYW' disclosed as SEQ ID NO: 958)

| Position | Parental (source) | Allowed |
|---|---|---|
| 94 | K (VH 3-23) | K |
| 95 | G (No source) | GYSRD (3:1:1:1:1) |
| 96 | S (No source) | SGYRD (3:1:1:1:1) |
| 97 | G (D2-15.2) | GYSRD (3:1:1:1:1) |
| 98 | Y (D2-15.2) | YGSRD (3:1:1:1:1) |
| 99 | C (D2-15.2) | C |
| 100 | S (D2-15.2) | SGYRD (3:1:1:1:1) |
| 101 | G (D2-15.2) | GYSRD (3:1:1:1:1) |
| 102 | G (D2-15.2) | GYSRD (3:1:1:1:1) |
| 102a | S (D2-15.2) | SGYRD (3:1:1:1:1) |
| 102b | C (D2-15.2) | C |
| 102c | Y (D2-15.2) | YGSRD (3:1:1:1:1) |
| 102d | S (D2-15.2) | SGYRD (3:1:1:1:1) |
| 102e | F (JH4) | FYGSRD (3:1:1:1:1:1) |
| 102f | D (JH4) | DGSRY (3:1:1:1:1) |
| 102g | Y (JH4) | YGSRD (3:1:1:1:1) |
| 103 | W (JH4, FR4) | W |

Example 5

Synthetic Light Chain Diversity

To make whole antibodies, we need to combine a library of heavy chains with a library of light chains (LC). In natural Abs, it is often observed that HC does most of the binding and many libraries have given little attention to the LC or have obtained LC diversity from human donors. To have enough diversity to give good binders to almost any target, we have designed a diversification program that exceeds what the human immune system usually provides. Nevertheless, the program is designed to yield fully functional LC that have the same kind of changes as seen in natural Abs, only a few more. Vkappa III A27 was picked as the LC.

From a library that comprises donated kappa and lambda LCs, a collection of 1266 Abs were typed. Among VKIIIs, A27 is most often seen (Table 66) and pairs well with HC 3-23.

The CDRs of A27 contain 12, 7, and 9 amino acids. Putting diversity at all of these positions might not work well: a) there might be many unstable or non-functional members, and b) diversity at some positions might not help improve binding. We have reduced the number of variable positions from 28 to 16.

We have studied the 3D structure of 1QLR which has an A27 LC. The 1GLR structure is publicly available in the RCDB Protein Data Base. From this, the residues marked in Table 68 look useful to vary. The T56 is about 10 Å from a H is in HC CDR3. Variation at 56 may be useful. G24 is only about 7 Å from an atom in HC CDR3. Germline is R24; thus, variation at 24 may be useful.

Table 69 shows a display cassette that we designed for use in pMID21. Thus, the restriction enzymes picked do not have other sites in pMID21. SpeI is in the iii signal sequence and allows the entire LC to be inserted or removed. XmaI, PpuMI, EcoO109I, and BlpI precede CDR1. SacII is in FR2, separating CDR1 from CDR2. Alternatively, an AvrII site could be inserted at the same position. BspEI and XhoI sites are in FR3 and a KpnI site is in FR4.

We gathered 155 A27 sequences and analyzed what happens in the CDRs. Table 70 shows the analysis. In Table 70, we show what is found in the Abs from our library and what we would put at each position.

TABLE 68 where to vary A27

| ! | | | | | | | |
|---|---|---|---|---|---|---|---|
| ! | 22 | 3 | 3 | 5 | 5 | 89 | 9 |
| ! | 45 | 0a | 4 | 0 | 5 | 90 | 5 |
| !1QLR | GASQSVS_NYLA | | | DASSRAT | | QQYGSSPLT | |
| !A27 | RASQSVSSSYLA | | | GASSRAT | | QQYGSSPLT | |
| | ** **** * | | | * * * | | ****** | |

GASQSVS is (SEQID NO: 922)
NYLA (SEQ ID NO: 959)
DASSRAT is (SEQID NO: 923)
QQYGSSPLY is (SEQID NO: 924)
QQYGSSPLT (SEQ ID NO: 966)
RASQSVSSSYLA is (SEQ ID NO: 925)
GASSRAT is (SEQ ID NO: 926)

Table 68 shows where the CDRs of A27 would be variegated.

TABLE 67

Compare VKIII AA seqs

```
VK3 is (SEQ ID NO: 927)
A27 is (SEQ ID NO: 960)
A11 is (SEQ ID NO: 961)
L2  is (SEQ ID NO: 962)
L16 is (SEQ ID NO: 962)
L6  is (SEQ ID NO: 963)
L20 is (SEQ ID NO: 964)
L25 is (SEQ ID NO: 965)

FR1...........CDR1........FR2............CDR2...FR3.........................................CDR3.....FR4........
                    1         2         3         4         5         6         7         8         9         1
    123456789012345678901a2345678901234567890123456789012345678901234567890123456789012345678901234567890123456789
VK3 DIVLTQSPATLSLSPGERATLSCRASQSVSSSYLAWYQQKPGQAPRLLIYGASSRATGVPARFSGSGSGTDFTLTISSLEPEDFAVYYCQQHYTTPPTFGQGTKVEIKRT
A27 E-G-------------------------------------------------------I-D------------------R----------------YGSS-
A11 E---------------------------------------------------------I-D------------------R----------------YGSS-
L2  E--M--------------------G--------#N---------------------L-------T----E---------QS---------------YNNW-
L16 E--M--------------------V--------#N---------------------------T-----E---------QS---------------YNNW-
L6  E--------------------------------#-------------------------D--N----------------------------------RSNW-
L20 E----------------------------------#------G-------------D--N----P---------------------------------RSNWH
L25 E--M--------------------------------------------------S----T------Q---------------D-NL-

VK3 differs from A27 by E1D, G9A, I58V, D60A, R77S.

A27 and L6 differ by G9A(FR1), Δ31a(in CDR1), G50D(CDR2), S53N(CDR2), G92S(CDR3), S93N(CDR3), S94W(CDR3)
VK3 from U.S. Pat. No. 7,264,963.
```

CDR1

R24, A25, and S26 are too far from the combining site to help and were held constant. The side group of V29 is buried; this position was held constant as Val. At the other positions, we allowed Y or S and a charge flip-flop (RE or RD, depending on where the sample had more of E or D at the position in question) plus other types that were frequently seen. We used an Excel spread sheet to determine that this pattern of variegation would give the parental sequence at 0.8% if the "other" AAs were substituted at 5%, at 0.1% if the "other" AAs were substituted at 6.5%, and at 0.02% if "other" was at 9%. In the sample of 155, 17 have one AA deleted (including 1QLR); thus, we will arrange to have S30a deleted in ~8% of the members.

CDR2

From inspection of 1QLR, we see that CDR2 is somewhat remote from the combining site. There have even been suggestions that we keep the residues in this CDR constant. Studying the 3D structure suggests that variegation at G50, S53, and T56 could be useful. S53 is the most variable in the sample of 155, but this does not prove that these changes are useful. In 1QLR, G50 has been mutated to R50. The side group of T56 is pointed toward HC CDR3 and is about 11 Å from an atom in HC CDR3.

CDR3

Q89 and Q90 are buried and nature does not vary them often; these residues are not varied. Y91 is packed against HC CDR3 and changes here would alter the combining site and do occur. At G92, $\phi=-80$ and $\psi=-15$ so putting in a non-Gly is feasible; nature does make it in 47/155 cases. S93 is very often varied or deleted. S94 is highly exposed and is highly varied. P95 is exposed and varied. L96 packs against HC CDR3: changes here will affect the binding site and do occur in nature. T97 is buried and has been held constant/the amino acid is not varied.

The parental sequence appears at 0.000246 or 1 in 4.06 E3. The allowed diversity is about 2.1 E 12. With two 8% deletions, 84.6% of the members will be full length, 7.4% will have short CDR1 and full-length CDR3, 7.4% will have full-length CDR1 and short CDR3, and 0.6% will have both deletions.

Other germlines were not in the sample.

TABLE 66

Distribution of VLs in 1266 selected LCs.

| Kappas | | | | Lambdas | | | |
|---|---|---|---|---|---|---|---|
| O12 | VKI | 313 | | 1a | VL1 | 9 | |
| O18 | VKI | 1 | | 1e | VL1 | 7 | |
| A20 | VKI | 26 | | 1c | VL1 | 55 | |
| A30 | VKI | 26 | | 1g | VL1 | 46 | |
| L14 | VKI | 2 | | 1b | VL1 | 1 | 118 |
| L1 | VKI | 5 | | 2c | VL2 | 18 | |
| L15 | VKI | 1 | | 2e | VL2 | 23 | |
| L5 | VKI | 83 | | 2a2 | VL2 | 79 | |
| L8 | VKI | 10 | | 2d | VL2 | 1 | 121 |
| L12 | VKI | 77 | 544 | 3r | VL3 | 56 | |
| O11 | VKII | 4 | | 3j | VL3 | 4 | |
| A17 | VKII | 17 | | 3l | VL3 | 31 | |
| A19 | VKII | 31 | 52 | 3h | VL3 | 22 | 113 |
| A27 | VKIII | 155 | | 4a | VL4 | 1 | 1 |
| L2 | VKIII | 31 | | 5c | VL5 | 1 | 1 |
| L6 | VKIII | 88 | | 6a | VL6 | 8 | 8 |
| L25 | VKIII | 16 | 290 | 10a | VL10 | 6 | 6 |
| B3 | VKIV | 12 | 12 | Number of lambdas | | | 368 |
| Number of kappas | | | 898 | Total Abs in sample | | | 1266 |

TABLE 69

A Display gene for A27 in pM21J.

```
! IIIsignal::A27::Ckappa
The amino-acid sequence of Table 69 is (SEQ ID NO: 928).
The DNA sequence of Table 69 is (SEQ ID NO: 929).
!       signal sequence------------------------------------
!       1   2   3   4   5   6   7   8   9   10  11  12  13  14  15
!       M   K   K   L   L   S   A   I   P   L   V   V   P   F   Y
    1 |atg|aaG|aaA|ctg|ctg|tct|gct|atc|ccA|CTA|GTt|gtc|cct|ttc|tat|
                                         SpeI....
!
!
!       Signal------- FR1---------------------------------
!       16  17  18  19  20  21  22  23  24  25  26  27  28  29  30
!       S   H   S   E1  I   V3  L   T5  Q   S7  P   G9  T   L   S12
   46   |tct|cat|agt|gaa|atc|gtt|ctg|acc|cag|tcC|CCG|GGG|aCC|Ctg|tct|
                                              XmaI....
!                                             PpuMI....
!                                             EcoO109I.(1/2)
!
!       FR1-------------------------------- CDR1----------
!       31  32  33  34  35  36  37  38  39  40  41  42  43  44  45
!       L13 S   P   G   E   R   A   T   L   S   C23 R24 A   S   Q
   91   |ctg|tct|ccg|ggt|gaa|cgt|gct|acG|CTg|AGC|tgt|cgt|gct|tct|caa|
                                         BlpI.....
!
!       CDR1------------------------ FR2------------------
!       46  47  48  49  50  51  52  53  54  55  56  57  58  59  60
!       S28 V   S   S   S30a Y   L   A34 W   Y   Q   Q   K   P   G
  136   |tcc|gtt|agC|TCC|TCt|tat|tta|gct|tgg|tat|cag|caa|aag|ccg|ggt|
                     BseRI...
!
!       FR2----------------------- CDR2-------------------
!       61  62  63  64  65  66  67  68  69  70  71  72  73  74  75
!       Q   A   P   R45 L   L   I   Y   G50 A   S   S   R   A   T56
  181   |caa|gct|CCG|CGG|ctg|ttg|atc|tat|ggt|gcc|tct|agt|cgt|gct|act|
                     SacII..
!
```

TABLE 69-continued

A Display gene for A27 in pM21J.

```
!       FR3--------------------------------------------------------
!       76  77  78  79  80  81  82  83  84  85  86  87  88  89  90
!       G   I   P   D60 R   F   S   G   S65 G   S   G   T   D   F
    226 |ggc|atc|cct|gat|cgt|ttc|tct|ggc|tct|ggc|TCC|GGA|acc|gat|ttc|
!                                                   BspEI..
!
!       FR3--------------------------------------------------------
!       91  92  93  94  95  96  97  98  99  100 101 102 103 104 105
!       T   L   T   I   S   R   L   E   P   E   D   F   A   V   Y
    271 |act|ctg|acc|att|tct|CGT|CTC|GAG|ccg|gaa|gat|ttc|gct|gtc|tac|
!                                   BsmBI..
!                                       XhoI...
!
!       FR3---- CDR3----------------------------- FR4-----------
!       106 107 108 109 110 111 112 113 114 115 116 117 118 119 120
!       Y   C   Q89 Q   Y   G   S   S   P95 L   T   F   G   G   G
    316 |tat|tgt|caa|cag|tat|ggt|tct|agt|ccg|ctg|act|ttc|ggt|ggc|GGT|
!                                                                     KpnI...
!
!       FR4-------------------
!       121 122 123 124 125 126
!       T   K   V   E   I   K
    361 |ACC|aaa|gtc|gaa|atc|aag
!       KpnI.
!
!       Ckappa----------------------------------------------------
!       R   G   T   V   A   A   P   S   V   F   I   F   P   P   S
    379 cgt gga act gtg gCT GCA Cca tct GTC TTC atc ttc ccg cca tct
!                           BsgI....       BbsI...
!
!       D   E   Q   L   K   S   G   T   A   S   V   V   C   L   L
    424 gat gag cag ttg aaa tct gga act gcc tct gtt gtg tgc ctg ctg
!
!       N   N   F   Y   P   R   E   A   K   V   Q   W   K   V   D
    469 aat aac ttc tat ccc aga gag gcc aaa gta cag tgg aag gtg gat
!
!       N   A   L   Q   S   G   N   S   Q   E   S   V   T   E   Q
    514 aac gcc ctc caa tcg ggt aac tcc cag gag agt gtc aca gag cag
!
!       D   S   K   D   S   T   Y   S   L   S   S   T   L   T   L
    559 gac agc aag gac agc acc tac agc ctc agc agc acc ctg act ctg
!
!       S   K   A   D   Y   E   K   H   K   V   Y   A   C   E   V
    604 tcc aaa gca gac tac gag aaa cac aaa GTC TAC gcc tgc gaa gtc
!
!       T   H   Q   G   L   S   S   P   V   T   K   S   F   N   R
    649 acc cat cAG GGC CTg agt tCA CCG GTG aca aag agc ttc aac agg
!               AlwNI......        SgrAI.....
!               EcoO109I.(2/2)     AgeI....
!
!       G   E   C   .   .
    694 gga gag tgt taa taa
!
    709                     GG CGCGCCaatt
!                              AscI.....
!                               BssHII.
```

TABLE 70

Tally of mutations in CDRs of A27 Abs

CDR1 ('RASQSVSSSYLA' disclosed as SEQ ID NO: 925)

| | | |
|---|---|---|
| R24 | 1, 3G, 1T, 151-, | Fix |
| A25 | 2, 3T, 152-, | Fix |
| S26 | 3, 1R, 154-, | Fix |
| Q27 | 4, 3E, 1H, 1L, 1P, 4R, 145-, | 9% ERYSL |
| S28 | 5, 1A, 2F, 2G, 1I, 2L, 5N, 1P, 1R, 10T, 1V, 1Y, 128-, | 9% NTYERL |
| V29 | 6, 1F, 19I, 6L, 129-, | Fix |
| S30 | 7, 2A, 2D, 8G, 2H, 1I, 11N, 9R, 6T, 4V, 2Y, 108-, | 9% DNRTY |
| S30a | 8, 1A, 2F, 6G, 1H, 6N, 1P, 10R, 6T, 3Y, 119-, (8% delete 30a) | 9% GNRTYD |
| S31 | 9, 1A, 5D, 3F, 4G, 1H, 2I, 4K, 1L, 31N, 19R, 7T, 7Y, 70-, | 9% DFGNRTY |
| Y32 | 10, 5F, 1K, 14L, 4N, 4Q, 2R, 8S, 3V, 1W, 113-, | 9% FDLNQRSY |
| L33 | 11, 16A, 1F, 4I, 1N, 1S, 8V, 1Y, 123-, | Fix |

TABLE 70-continued

| | | |
|---|---|---|
| A34 | 12, 2G, 2L, 1N, 1S, 4V, 128-, | 9% SY |
| — | 13, 2A, 1G, | |
| — | 14, 1S, | |
| — | 15, 1S, | |
| — | 16, 1Y, | |
| — | 17, 1L, | |
| — | 18, 1A, | |

Note: one antibody had an insertion of six AAs in CDR1! Two other Abs had a single insertion. Seventeen Abs have a one AA deletion in CDR1.

CDR2 ('GASSRAT' disclosed as SEQ ID NO: 926)

| | | |
|---|---|---|
| G50 | 1, 10A, 11D, 1H, 2R, 2S, 1V, 7Y, 121-, | 9% DRSYL |
| A51 | 2, 7G, 21, 6S, 7T, 2V, 131-, | Fix |
| S52 | 3, 6A, 3F, 1G, 1T, 144-, | Fix |
| S53 | 4, 1A, 1G, 1H, 5I, 2K, 16N, 7R, 16T, 106-, | 9% NTSYER |
| R54 | 5, 1A, 1I, 1N, 1S, 3T, 1Y, 147-, | Fix |
| A55 | 6, 2P, 7R, 4S, 2V, 140-, | Fix |
| T56 | 7, 10A[1], 1G, 1H, 2P, 4S, 137-, | 9% ERSY |
| — | 8, 1A, 6T, | |

Note, there are seven antibodies with an insertion of one AA.

CDR3 (showing "_" means that the Ab has a deletion in CDR3)
('QQYGSSPLT' disclosed as SEQ ID NO: 966)

| | | |
|---|---|---|
| Q89 | 1, 5H, 1L, 2M, 147-, | Fix |
| Q90 | 2, 1E, 1F, 13H, 2K, 2L, 4R, 1S, 1Y, 130-, | Fix |
| Y91 | 3, 2A, 8F, 2G, 2H, 1L, 1P, 13R, 4S, 122-, | 9% FERS |
| G92 | 4, 10A, 3D, 2H, 1I, 1L, 2N, 6R, 12S, 2V, 3Y, 108-, 5_, | 9% ADRSTY |
| S93 | 5, 1A, 2D, 2F, 6G, 2H, 3I, 2K, 2M, 14N, 1P, 1Q, 8R, 17T, 2Y, 86-, 6_, (8% have 93 deleted) | 9% DFNRTY |
| S94 | 6, 3A, 6F, 1I, 3L, 3P, 2R, 2T, 11W, 117-, 7_, | 9% WERYS |
| P95 | 7, 2A, 1E, 1G, 1K, 3L, 1M, 7R, 3S, 3T, 1V, 108-, 24_, | 9% ERYS |
| L96 | 8, 2A, 2E, 3F, 3G, 1H, 1I, 3K, 7L, 2M, 24P[2], 6Q, 28R, 3S, 3T, 7V, 2Y, 58-, | 9% ERPYS |
| T97 | 9, 2A, 1F, 2G, 3I, 1K, 2L, 3M, 1N, 1R, 6S, 3V, 2Y, 128-, | Fix |
| — | 10, 1A, 1S, 34-, | |
| — | 11, 1S, 7-, | |
| — | 12, 1A, | |

There is one Ab with an insertion of 3 AAs.
Five have deletions of 4 AAs, 1 has a 3 AA deletion, 1 has a 2 AA deletion, and 17 have a one AA deletion.

[1] Seven of these come from the imsertions.
[2] Some of these appear because of insertions.

TABLE 71

Allowed diversity in CDR1, 2, and 3 of A27::JK4. ('RASQSVSSSYLA' disclosed as SEQ ID NO: 925; 'GASSRAT' disclosed as SEQ ID NO: 926; 'QQYGSSPLT' disclosed as SEQ ID NO: 966)

| Position | parental | allowed | |
|---|---|---|---|
| CDR1 | | | |
| 42 (24) | R | fixed | |
| 43 (25) | A | fixed | |
| 44 (26) | S | fixed | |
| 45 (27) | Q | ERYSL | 55% Q 9% other |
| 46 (28) | S | NTYERL | 46% S 9% other |
| 47 (29) | V | fixed | |
| 48 (30) | S | DNRTY | 55% S 9% other |
| 49 (30a) | S | GNRTYD | 46% S 9% other |
| | | 8% have 30a deleted | |
| 50 (31) | S | DFGNRTY | 44% S 8% other |
| 51 (32) | Y | FDLNQRSY | 44% Y 7% other |
| 52 (33) | L | fixed | |
| 53 (34) | A | SY | 70% A 15% other |
| CDR2 | | | |
| 69 (50) | G | DRSYL | 55% G 9% other |
| 70 (51) | A | Fixed | |
| 71 (52) | S | Fixed | |
| 72 (53) | S | NTSYER | 52% S 8% other |
| 73 (54) | R | Fixed | |
| 74 (55) | A | Fixed | |
| 75 (56) | T | ERSY | 64% T 9% other |
| CDR3 | | | |
| 108 (89) | Q | fixed | |
| 109 (90) | Q | fixed | |
| 110 (91) | Y | FERS | 64% Y 9% other |
| 111 (92) | G | ADRSTY | 52% G 8% other |
| 112 (93) | S | DFNRTY | 52% S 8% other |
| 113 (94) | S | WERYS | 55% S 9% other |
| 114 (95) | P | ERYS | 64% P 9% other |
| | | 8% have P95 deleted | |
| 115 (96) | L | ERPYS | 55% L 9% other |
| 116 (97) | T | fixed | |

The parental sequence appears at 5.32 E-5 or 1 in 1.88 E 4.

Sequences with a single substitution have a probability between 1.1 E-5 and 7.5 E-6.

Sequences that have none of the parental AAs occurs at 1 in 6.7 E 16.

The allowed diversity is about 2.35 E 12.

TABLE 75

Frequencies of amino acids in HC CDR3s.

| AA | Number | % | Rel up | Rel down |
|---|---|---|---|---|
| Y | 3428 | 15.64 | 50.41 | 1.00 |
| G | 3244 | 14.80 | 47.71 | 0.95 |
| D | 2622 | 11.96 | 38.56 | 0.76 |
| S | 1777 | 8.11 | 26.13 | 0.52 |
| R | 1337 | 6.10 | 19.66 | 0.39 |
| F | 1328 | 6.06 | 19.53 | 0.39 |
| A | 1213 | 5.53 | 17.84 | 0.35 |
| V | 1141 | 5.20 | 16.78 | 0.33 |
| L | 816 | 3.72 | 12.00 | 0.24 |
| I | 745 | 3.40 | 10.96 | 0.22 |
| P | 726 | 3.31 | 10.68 | 0.21 |
| T | 586 | 2.67 | 8.62 | 0.17 |
| W | 566 | 2.58 | 8.32 | 0.17 |
| M | 560 | 2.55 | 8.24 | 0.16 |
| N | 462 | 2.11 | 6.79 | 0.13 |
| E | 363 | 1.66 | 5.34 | 0.11 |
| K | 355 | 1.62 | 5.22 | 0.10 |
| H | 327 | 1.49 | 4.81 | 0.10 |
| Q | 259 | 1.18 | 3.81 | 0.08 |
| C | 68 | 0.31 | 1.00 | 0.02 |
| Total | 21923 | | | |

TABLE 76

Length distribution of HC CDR3

| Length | Number of Antibodies | Sum | Median |
|---|---|---|---|
| 1 | 0 | | |
| 2 | 0 | | |
| 3 | 2 | 2 | |
| 4 | 21 | 23 | |
| 5 | 16 | 39 | |
| 6 | 100 | 139 | |
| 7 | 36 | 175 | |
| 8 | 78 | 253 | |
| 9 | 155 | 408 | |
| 10 | 153 | 561 | |
| 11 | 134 | 695 | 11.12 |
| 12 | 123 | 818 | |
| 13 | 133 | 951 | |
| 14 | 92 | 1043 | |
| 15 | 87 | 1130 | |
| 16 | 71 | 1201 | |
| 17 | 59 | 1260 | |
| 18 | 41 | 1301 | |
| 19 | 40 | 1341 | |
| 20 | 22 | 1363 | |
| 21 | 21 | 1384 | |
| 22 | 15 | 1399 | |
| 23 | 7 | 1406 | |
| 24 | 7 | 1413 | |
| 25 | 1 | 1414 | |
| 26 | 1 | 1415 | |
| 27 | 3 | 1418 | |
| 28 | 0 | 1418 | |
| 29 | 0 | 1418 | |
| 30 | 1 | 1419 | |
| | 1419 | 709.5 | |

TABLE 77

Utilization of D-segments (cut off at 0.70 match)

| | | | SEQ ID NO: |
|---|---|---|---|
| 3-22.2 | 38 | YYYDSSGYYY | 88 |
| 4-17.2 | 27 | DYGDY | 195 |
| 3-3.2 | 25 | YYDFWSGYYT | 177 |
| 6-19.1 | 25 | GYSSGWY | 218 |
| 7-27.1 | 19 | LTG | 221 |
| 5-5.3 | 18 | GYSYGY | 786 |
| 6-13.1 | 18 | GYSSSWY | 215 |
| 5-12.3 | 13 | GYSGYDY | 205 |
| 6-13.2 | 10 | GIAAAG | 216 |
| 1-26.3 | 9 | YSGSYY | 284 |
| 2-15.2 | 9 | GYCSGGSCYS | 136 |
| 4-4.3 | 9 | TTVT | 190 |
| 3-10.2 | 8 | YYYGSGSYYN | 81 |
| 1-1.3 | 7 | YNWND | 262 |
| 4-4.2 | 7 | DYSNY | 754 |
| 2-2.2 | 6 | GYCSSTSCYT | 70 |
| 3-16.2 | 6 | YYDYVWGSYRYT | 104 |
| 6-6.1 | 6 | EYSSSS | 212 |
| 6-19.2 | 6 | GIAVAG | 219 |
| 3-9.1 | 5 | VLRYFDWLL@ | 179 |
| 4-23.2 | 5 | DYGGNS | 198 |
| 6-6.2 | 5 | SIAAR | 213 |
| 1-7.3 | 4 | YNWNY | 270 |
| 2-2.3 | 4 | DIVVVPAAI | 168 |
| 4-23.3 | 4 | TTVVT | 199 |
| 1-7.1 | 3 | GITGT | 268 |
| 1-26.1 | 3 | GIVGAT | 282 |
| 7-27.3 | 3 | NWG | 223 |
| 3-10.1 | 2 | VLLWFGELL@ | 182 |
| 3-10.2 | 2 | ITMVRGVII | 183 |
| 5-5.1 | 2 | VDTAMV | 200 |
| 5-5.2 | 2 | WIQLWL | 201 |
| 5-12.1 | 2 | VDIVATI | 203 |
| 5-24.3 | 2 | RDGYNY | 211 |
| 1-1.1 | 1 | GTTGT | 260 |
| 2-21.3 | 1 | HIVVVTAI | 175 |
| 3-3.3 | 1 | ITIFGVVII | 178 |
| 5-24.2 | 1 | *RWLQL | 210 |

TABLE 77-continued

Utilization of D-segments (cut off at 0.70 match)

| Name | Number | Sequence | SEQ ID NO: |
|---|---|---|---|
| 6-6.3 | 1 | V*QLV | 214 |
| 6-19.3 | 1 | V*QWLV | 220 |

TABLE 78

D segment utilization (0.667 cutoff)

| Name | Number | Sequence | SEQ ID NO: | % |
|---|---|---|---|---|
| None | 935 | | | 0.517 |
| 7-27.1 | 158 | LTG | 221 | 0.087 |
| 7-27.3 | 98 | NWG | 223 | 0.054 |
| 5-5.3 | 72 | GYSYGY | 786 | 0.040 |
| 1-26.3 | 67 | YSGSYY | 166 | 0.037 |
| 3-22.2 | 46 | YYYDSSGYYY | 187 | 0.025 |
| 4-17.2 | 38 | DYGDY | 195 | 0.021 |
| 3-3.2 | 37 | YYDFWSGYYT | 177 | 0.020 |
| 7-27.2 | 37 | @LG | 222 | 0.020 |
| 6-19.1 | 33 | GYSSGWY | 218 | 0.018 |
| 6-13.2 | 31 | GIAAAG | 860 | 0.017 |
| 6-13.1 | 22 | GYSSSWY | 215 | 0.012 |
| 6-6.1 | 18 | EYSSSS | 847 | 0.010 |
| 6-19.2 | 18 | GIAVAG | 879 | 0.010 |
| 4-23.2 | 17 | DYGGNS | 198 | 0.009 |
| 5-12.3 | 17 | GYSGYDY | 205 | 0.009 |
| 5-24.3 | 14 | RDGYNY | 211 | 0.008 |
| 2-15.2 | 13 | GYCSGGSCYS | 136 | 0.007 |
| 1-26.1 | 11 | GIVGAT | 164 | 0.006 |
| 4-4.3 | 11 | TTVT | 190 | 0.006 |
| 1-1.3 | 9 | YNWND | 262 | 0.005 |
| 2-2.2 | 9 | GYCSSTSCYT | 70 | 0.005 |
| 3-16.2 | 9 | YYDYVWGSYRYT | 104 | 0.005 |
| 2-2.3 | 8 | DIVVVPAAI | 168 | 0.004 |
| 3-10.2 | 8 | YYYGSGSYYN | 81 | 0.004 |
| 4-4.2 | 8 | DYSNY | 192 | 0.004 |
| 1-7.3 | 7 | YNWNY | 270 | 0.004 |
| 3-3.3 | 6 | ITIFGVVII | 178 | 0.003 |
| 6-6.2 | 6 | SIAAR | 213 | 0.003 |
| 3-9.1 | 5 | VLRYFDWLL@ | 179 | 0.003 |
| 3-10.2 | 5 | ITMVRGVII | 183 | 0.003 |
| 6-19.3 | 5 | V*QWLV | 220 | 0.003 |
| 1-7.1 | 4 | GITGT | 268 | 0.002 |
| 4-23.3 | 4 | TTVVT | 768 | 0.002 |
| 1-1.1 | 3 | GTTGT | 156 | 0.002 |
| 5-5.1 | 3 | VDTAMV | 200 | 0.002 |
| 5-24.2 | 3 | *RWLQL | 210 | 0.002 |
| 3-10.1 | 2 | VLLWFGELL@ | 182 | 0.001 |
| 5-5.2 | 2 | WIQLWL | 201 | 0.001 |
| 5-12.1 | 2 | VDIVATI | 203 | 0.001 |
| 1-26.2 | 1 | V*WELL | 165 | 0.001 |
| 2-21.2 | 1 | AYCGGDCYS | 174 | 0.001 |
| 2-21.3 | 1 | HIVVVTAI | 175 | 0.001 |
| 3-3.1 | 1 | VLRFLEWLLY | 176 | 0.001 |
| 3-16.2 | 1 | IMITFGGVIVI | 185 | 0.001 |
| 6-6.3 | 1 | V*QLV | 214 | 0.001 |
| 6-13.3 | 1 | V*QQLV | 217 | 0.001 |

TABLE 78

Utilization of JH segments

| | |
|---|---|
| JH1 | 17 |
| JH2 | 31 |
| JH3 | 452 |
| JH4 | 636 |
| JH5 | 32 |
| JH6 | 251 |

Example 6

Wobbled DNA for HC CDR3 16d

Table 400 shows a segment of DNA from an XbaI site in FR3 to a BstEII site in FR4. The HC CDR3 consists of SYSY::D2-2(2)::QH ('SYSY' disclosed as SEQ ID NO: 947) followed by the FR4 region of JH1. The QH is found in the germline of JH1. In V-D-J joining, immune cells often edit the ends of V, D, and J. Thus the construction corresponds to what is very possible in actual immunoglobulin gene construction and maturation. By wobbling the synthesis, we obtain a large collection of genes that resemble what would come from joining 3-23 to either a D region or to a little edited JH1 followed by some mutations. In library 16d, there are two cysteines that presumably form a disulfide, these are not wobbled.

Table 500 shows the expected distribution of amino-acid types at each position in the 16d library. The wobble doping was set at 73:9:9:9. The most likely sequence is the one shown in Table 21 and should be present at a frequency of 4.8 E-5. Only 55% of the sequences are stop free and 74% are free of ochre or opel. If the library is expressed in supE cells, this is the important number. It would be valuable to remove the sequences with stop codons as discussed elsewhere herein. One can see that those positions that start as S are predicted to have S 54% of the time and Y 5.4% while those that start as Y have Y 44% of the time and S 7.2%. At each position there are 7-9 AA types that appear at >1%. There are 14 variegated positions. The sequences that will be most effectively sampled number about $8^{14}$=4.3 E 12.

TABLE 400

Cassette for display of wobbled HC CDR3 16d

```
!       --------FR3-----------------------------------------
!        68  69  70  71  72  73  74  75  76  77  78  79  80  81  82
!         T   I   S   R   D   N   S   K   N   T   L   Y   L   Q   M
  1216 |act|atc|TCT|AGA|gac|aac|tct|aag|aat|act|ctc|tac|ttg|cag|atg|
!                   | XbaI  |
!
!       ---FR3----------------------------------------------->|
!        82a 82b 82c 83  84  85  86  87  88  89  90  91  92  93  94
!         N   S   L   R   A   E   D   T   A   V   Y   Y   C   A   K
  1261 |aac|agC|TTA|AGg|gct|gag|gac|act|gca|gtc|tac|tat|tgc|gct|aaa|
!              |AflII  |
!
!       e = 0.73 A + 0.09 C + 0.09 G + 0.09 T
!       q = 0.09 A + 0.73 C + 0.09 G + 0.09 T
!       j = 0.09 A + 0.09 C + 0.73 G + 0.09 T
!       z = 0.09 A + 0.09 C + 0.09 G + 0.73 T
!       The values 0.73 and 0.09 are picked so that 0.73 + 3 * 0.09 = 1.0
!       Other ratios could be used.
!
!                                     102 102 102 102 102 102 102 102
!        95  96  97  98  99  100 101 102  a   b   c   d   e   f   g   h
!         S   Y   S   Y   G   Y   c   S   S   T   S   c   Y   T   Q   H
         zqz zez zqz zez jjz zez TGT zqz zqz eqz zqz TGT zez eqz qej qez
!
!       --------------FR4----------------------->|
!        103 104 105 106 107 108 109 110 111 112 113
!         W   G   Q   G   T   L   V   T   V   S   S   (SEQ ID NO: 968)
        |TGg|ggt|caa|ggt|act|ttG|GTC|ACC|gtc|tct|agt   (SEQ ID NO: 967)
!                              | BstEII |
!
```

TABLE 500

Expected distribution of AA types in wobbled HC CDR3 16d

| S | Y | S | Y | G | Y | c | S | S | T | S | c | Y | T | Q | H |
|---|---|---|---|---|---|---|---|---|---|---|---|---|---|---|---|
| zqz | zez | zqz | zez | jjz | zez | tgt | zqz | zqz | eqz | zqz | tgt | zez | eqz | qej | qez |

"." = TGA or TAA;

"b" = TAG

Amino acid disclosed as SEQ ID NO: 970

DNA sequence disclosed as SEQ ID NO: 969

Nominal base purity = 0.7300 others = 0.0900

|    | s(zqz) |         | y(zez) |         | s(zqz) |         | y(zez) |         | g(jjz) |         | y(zez) |         | C(TGT) |       | s(zqz) |         | s(zqz) |         | t(eqz) |         |
|----|--------|---------|--------|---------|--------|---------|--------|---------|--------|---------|--------|---------|--------|-------|--------|---------|--------|---------|--------|---------|
| 1  | s | 5.4-01 | y | 4.4-01 | s | 5.4-01 | y | 4.4-01 | g | 5.3-01 | y | 4.4-01 | c | 1.000 | s | 5.4-01 | s | 5.4-01 | t | 5.3-01 |
| 2  | p | 6.6-02 | s | 7.2-02 | p | 6.6-02 | s | 7.2-02 | r | 7.8-02 | s | 7.2-02 |   |       | p | 6.6-02 | p | 6.6-02 | s | 1.2-01 |
| 3  | a | 6.6-02 | f | 5.4-02 | a | 6.6-02 | f | 5.4-02 | a | 6.6-02 | f | 5.4-02 |   |       | a | 6.6-02 | a | 6.6-02 | a | 6.6-02 |
| 4  | t | 6.6-02 | h | 5.4-02 | t | 6.6-02 | h | 5.4-02 | v | 6.6-02 | h | 5.4-02 |   |       | t | 6.6-02 | t | 6.6-02 | p | 6.6-02 |
| 5  | f | 5.4-02 | n | 5.4-02 | f | 5.4-02 | n | 5.4-02 | s | 6.2-02 | n | 5.4-02 |   |       | f | 5.4-02 | f | 5.4-02 | i | 6.0-02 |
| 6  | c | 5.4-02 | c | 5.4-02 | c | 5.4-02 | c | 5.4-02 | c | 5.4-02 | c | 5.4-02 |   |       | c | 5.4-02 | c | 5.4-02 | n | 5.4-02 |
| 7  | y | 5.4-02 | d | 5.4-02 | y | 5.4-02 | d | 5.4-02 | d | 5.4-02 | d | 5.4-02 |   |       | y | 5.4-02 | y | 5.4-02 | r | 2.0-02 |
| 8  | l | 2.0-02 | — | 5.4-02 | l | 2.0-02 | — | 5.4-02 | e | 1.2-02 | — | 5.4-02 |   |       | l | 2.0-02 | l | 2.0-02 | k | 1.2-02 |
| 9  | — | 1.2-02 | b | 4.8-02 | — | 1.2-02 | b | 4.8-02 | l | 9.6-03 | b | 4.8-02 |   |       | — | 1.2-02 | — | 1.2-02 | l | 9.6-03 |
| 10 | r | 9.6-03 | l | 2.0-02 | r | 9.6-03 | l | 2.0-02 | l | 8.1-03 | l | 2.0-02 |   |       | r | 9.6-03 | r | 9.6-03 | g | 8.1-03 |
| 11 | g | 8.1-03 | k | 1.2-02 | g | 8.1-03 | k | 1.2-02 | p | 8.1-03 | k | 1.2-02 |   |       | g | 8.1-03 | g | 8.1-03 | v | 8.1-03 |
| 12 | v | 8.1-03 | q | 1.2-02 | v | 8.1-03 | q | 1.2-02 | i | 7.4-03 | q | 1.2-02 |   |       | v | 8.1-03 | v | 8.1-03 | f | 6.6-03 |
| 13 | i | 7.4-03 | e | 1.2-02 | i | 7.4-03 | e | 1.2-02 | — | 6.6-03 | e | 1.2-02 |   |       | i | 7.4-03 | i | 7.4-03 | c | 6.6-03 |
| 14 | h | 6.6-03 | r | 9.6-03 | h | 6.6-03 | r | 9.6-03 | f | 6.6-03 | r | 9.6-03 |   |       | h | 6.6-03 | h | 6.6-03 | h | 6.6-03 |
| 15 | n | 6.6-03 | t | 8.1-03 | n | 6.6-03 | t | 8.1-03 | h | 6.6-03 | t | 8.1-03 |   |       | n | 6.6-03 | n | 6.6-03 | d | 6.6-03 |
| 16 | d | 6.6-03 | v | 8.1-03 | d | 6.6-03 | v | 8.1-03 | y | 6.6-03 | v | 8.1-03 |   |       | d | 6.6-03 | d | 6.6-03 | y | 6.6-03 |
| 17 | w | 5.9-03 | a | 8.1-03 | w | 5.9-03 | a | 8.1-03 | n | 6.6-03 | a | 8.1-03 |   |       | w | 5.9-03 | w | 5.9-03 | m | 5.9-03 |
| 18 | b | 5.9-03 | g | 8.1-03 | b | 5.9-03 | g | 8.1-03 | w | 5.9-03 | g | 8.1-03 |   |       | b | 5.9-03 | b | 5.9-03 | q | 1.5-03 |
| 19 | q | 1.5-03 | p | 8.1-03 | q | 1.5-03 | p | 8.1-03 | q | 1.5-03 | p | 8.1-03 |   |       | q | 1.5-03 | q | 1.5-03 | e | 1.5-03 |
| 20 | k | 1.5-03 | i | 7.4-03 | k | 1.5-03 | i | 7.4-03 | k | 1.5-03 | i | 7.4-03 |   |       | k | 1.5-03 | k | 1.5-03 | — | 1.5-03 |
| 21 | e | 1.5-03 | w | 5.9-03 | e | 1.5-03 | w | 5.9-03 | m | 7.3-04 | w | 5.9-03 |   |       | e | 1.5-03 | e | 1.5-03 | w | 7.3-04 |
| 22 | m | 7.3-04 | m | 7.3-04 | m | 7.3-04 | m | 7.3-04 | b | 7.3-04 | m | 7.3-04 |   |       | m | 7.3-04 | m | 7.3-04 | b | 7.3-04 |

-continued

| | s(zqz) | | C(TGT) | | y(zez) | | t(eqz) | | q(qej) | | h(qez) |
|---|---|---|---|---|---|---|---|---|---|---|---|
| 1 | s | 5.4-01 | c | 1.000 | y | 4.4-01 | t | 5.3-01 | q | 4.4-01 | h | 4.4-01 |
| 2 | p | 6.6-02 | | | s | 7.2-02 | s | 1.2-01 | h | 9.6-02 | q | 9.6-02 |
| 3 | a | 6.6-02 | | | f | 5.4-02 | a | 6.6-02 | l | 7.2-02 | l | 6.7-02 |
| 4 | t | 6.6-02 | | | h | 5.4-02 | p | 6.6-02 | r | 7.2-02 | r | 6.7-02 |
| 5 | f | 5.4-02 | | | n | 5.4-02 | i | 6.0-02 | p | 6.6-02 | p | 6.6-02 |
| 6 | c | 5.4-02 | | | c | 5.4-02 | n | 5.4-02 | e | 5.4-02 | n | 5.4-02 |
| 7 | y | 5.4-02 | | | d | 5.4-02 | r | 2.0-02 | k | 5.4-02 | d | 5.4-02 |
| 8 | l | 2.0-02 | | | — | 5.4-02 | k | 1.2-02 | b | 4.8-02 | y | 5.4-02 |
| 9 | — | 1.2-02 | | | b | 4.8-02 | l | 9.6-03 | d | 1.2-02 | s | 1.5-02 |
| 10 | r | 9.6-03 | | | l | 2.0-02 | g | 8.1-03 | y | 1.2-02 | k | 1.2-02 |
| 11 | g | 8.1-03 | | | k | 1.2-02 | v | 8.1-03 | n | 1.2-02 | e | 1.2-02 |
| 12 | v | 8.1-03 | | | q | 1.2-02 | f | 6.6-03 | s | 9.6-03 | g | 8.1-03 |
| 13 | i | 7.4-03 | | | e | 1.2-02 | c | 6.6-03 | t | 8.1-03 | t | 8.1-03 |
| 14 | h | 6.6-03 | | | r | 9.6-03 | h | 6.6-03 | v | 8.1-03 | v | 8.1-03 |
| 15 | n | 6.6-03 | | | t | 8.1-03 | d | 6.6-03 | a | 8.1-03 | a | 8.1-03 |
| 16 | d | 6.6-03 | | | v | 8.1-03 | y | 6.6-03 | g | 8.1-03 | i | 7.4-03 |
| 17 | w | 5.9-03 | | | a | 8.1-03 | m | 5.9-03 | — | 6.6-03 | — | 6.6-03 |
| 18 | b | 5.9-03 | | | g | 8.1-03 | q | 1.5-03 | w | 5.9-03 | c | 6.6-03 |
| 19 | q | 1.5-03 | | | p | 8.1-03 | e | 1.5-03 | m | 5.9-03 | f | 6.6-03 |
| 20 | k | 1.5-03 | | | i | 7.4-03 | — | 1.5-03 | i | 2.2-03 | b | 5.9-03 |
| 21 | e | 1.5-03 | | | w | 5.9-03 | w | 7.3-04 | f | 1.5-03 | w | 7.3-04 |
| 22 | m | 7.3-04 | | | m | 7.3-04 | b | 7.3-04 | c | 1.5-03 | m | 7.3-04 |

| | | Most likely sequence has frequency = | | 4.8E−05 | |
| | | Fraction stop-free = | | 5.5E−01 | |
| | | Fraction (TAA&TGA)-free = | | 7.4E−01 | |

| | | | F % | F % | F % |
|---|---|---|---|---|---|
| D1 | | 1-1 | 0.42 | 0.14 | 2.90 |
| | | 1-7 | 0.42 | 0.28 | 1.24 |
| | | 1-20 | 0.00 | 0.00 | 0.00 |
| | | 1-26 | 0.00 | 0.97 | 1.80 |
| D2 | | 2-2 | 0.55 | 4.30 | 1.21 |
| | | 2-8 | 0.00 | 0.67 | 0.41 |
| | | 2-15 | 0.28 | 4.03 | 0.94 |
| | | 2-21 | 0.00 | 2.22 | 0.94 |
| D3 | | 3-3 | 0.94 | 4.44 | 3.70 |
| | | 3-9 | 0.67 | 1.82 | 0.00 |
| | | 3-10 | 0.67 | 5.78 | 1.55 |
| | | 3-16 | 1.08 | 2.49 | 0.67 |
| | | 3-22 | 0.14 | 7.87 | 0.81 |
| D4 | | 4-4 | 0.28 | 0.69 | 0.28 |
| | | 4-11 | 0.00 | 0.00 | 0.00 |
| | | 4-17 | 0.00 | 4.03 | 2.76 |
| | | 4-23 | 0.14 | 1.41 | 0.54 |
| D5 | | 5-5 | 1.34 | 0.40 | 4.30 |
| | | 5-12 | 1.08 | 0.00 | 1.95 |
| | | 5-18 | 0.00 | 0.00 | 0.00 |
| | | 5-24 | 0.67 | 1.55 | 1.82 |
| D6 | | 6-6 | 1.21 | 1.55 | 0.13 |
| | | 6-13 | 4.84 | 2.62 | 0.27 |
| | | 6-19 | 6.66 | 1.95 | 0.54 |
| D7 | | 7-27 | 0.27 | 0.13 | 0.27 |
| | Total fractional % | | 21.65 | 49.34 | 29.01 |

TABLE 800

LC K1(O12)::JK1

```
!Amino acid disclosed as SEQ ID NO: 972
DNA sequence disclosed as SEQ ID NO: 971
!   ..Leader seq. ->|-------- FR1 ---------------------------->
!                    1    2    3    4    5    6    7    8    9   10   11
!     G   V   H   S   A   Q   D   I   Q   M   T   Q   S   P   S   S   L
!  1 |ggT|GTA|CAc|aGT|GCT|Cag|gat|att|cag|atg|act|caa|tct|ccC|TCG|AGt|ctg|
!     BsrGI... ApaLI...                               XhoI....
!
! -------- FR1 ---------------------------->|--- CDR1 ->
!   12   13   14   15   16   17   18   19   20   21   22   23   24   25   26
!    S    A    S    V    G    D    R    V    T    I    T    C    R    A    S
```

TABLE 800-continued

```
                          LC K1(O12)::JK1
     46 |tct|gct|tct|gtc|gGC|GAT|CGC|gtt|act|att|act|tgt|cgt|gct|tcc|
                         SgfI......
!
!          ---- CDR1 --------------------->|---- FR2 ----------------->
!          27   28   29   30   31   32   33   34   35   36   37   38   39   40   41
!          Q    S    I    S    S    Y    L    N    W    Y    Q    Q    K    P    G
     91 |cag|tcc|att|tct|agc|tat|ctg|aat|tGG|TAC|Cag|caa|aag|ccg|ggt|
                                           KpnI....
!
!          ------ FR2 ------------------->|-- CDR2 ------------------>|
!          42   43   44   45   46   47   48   49   50   51   52   53   54   55   56
!          K    A    P    K    L    L    I    Y    A    A    S    S    L    Q    S
    136 |aag|gct|ccg|aaa|ctg|tta|atc|tat|gcc|gct|tct|agt|ctg|cag|tct|
!
!          ---------- FR3 ---------------------------------------------->
!          57   58   59   60   61   62   63   64   65   66   67   68   69   70   71
!          G    V    P    S    R    F    S    G    S    G    S    T    D    F
    181 |ggt|gtt|ccg|TCT|AGA|ttc|tct|ggc|tct|ggt|tct|ggt|act|gat|ttt|
                         XbaI...
!
!          ---------- FR3 ---------------------------------------------->
!          72   73   74   75   76   77   78   79   80   81   82   83   84   85   86
!          T    L    T    I    S    S    L    Q    P    E    D    F    A    T    Y
    226 |act|ctg|act|att|tcc|tct|ctg|caa|ccg|gag|gac|ttt|gct|acc|tat|
!
!          - FR3->|---- CDR3 ----------------------->|--- FR4 ------>
!          87   88   89   90   91   92   93   94   95   96   97   98   99  100  101
!          Y    C    Q    Q    S    Y    S    T    P    W    T    F    G    Q    G
    271 |tac|tgc|caa|cag|tct|tat|agt|act|ccg|tgg|act|ttc|ggt|caa|ggc|
!
!          ---- FR4 --------------->|---- Ckappa--------------------->
!          102  103  104  105  106  107  108  109  110  111  112  113  114  115  116
!          T    K    V    E    I    K    R    T    V    A    A    P    S    V    F
    316 |act|aaa|gtt|gag|att|aag|CGT|ACG|gtg|gct|gct|ccg|tct|gtc|ttc|
                                    BsiWI..
```

TABLE 900

CDR1 diversity (SEQ ID NO: 973)

| Position | 24 | 25 | 26 | 27 | 28 | 29 | 30 | 31 | 32 | 33 | 34 | Diversity |
|---|---|---|---|---|---|---|---|---|---|---|---|---|
| O12 | R | A | S | Q | S | I | S | S | Y | L | N | |
| diversity | 2 | 2 | 1 | 1 | 3 | 1 | 2 | 2 | 4 | 1 | 3 | 576 |
| allowed | Q | M | | | D | | R | N | D | | A | |
| | | | | | G | | | W | | G | |
| | | | | | | | | | A | | | |

TABLE 1000

Big CDR1 diversity

| | Position | | | | | | | | | | Diversity |
|---|---|---|---|---|---|---|---|---|---|---|---|
| | 24 | 25 | 26 | 27 | 28 | 29 | 30 | 31 | 32 | 33 | 34 | |
| O12 | R | A | S | Q | S | I | S | S | Y | L | N | |
| diversity | 3 | 2 | 4 | 1 | 5 | 1 | 4 | 5 | 5 | 1 | 6 | 72000 |
| allowed | Q | M | E | | D | | R | N | D | | A | |
| | E | | R | | G | | E | W | E | | G | |
| | | | Y | | R | | Y | R | A | | D | |
| | | | | | Y | | | | Y | | R | |
| | | | | | | | | | | | Y | |

TABLE 1100

CDR2 diversity

| POSITION | 50 | 51 | 52 | 53 | 54 | 55 | 56 | Diversity |
|---|---|---|---|---|---|---|---|---|
| O12 | A | A | S | S | L | Q | S | |
| diversity | 2 | 1 | 1 | 3 | 1 | 2 | 2 | 24 |
| allowed | D | | | N | | E | T | |
| | | | | T | | | | |

TABLE 1200

Big CDR2 diversity

| POSITION | 50 | 51 | 52 | 53 | 54 | 55 | 56 | Diversity |
|---|---|---|---|---|---|---|---|---|
| O12 | A | A | S | S | L | Q | S | |
| diversity | 4 | 1 | 4 | 6 | 1 | 4 | 5 | 1920 |
| allowed | D | | E | N | | E | T | |
| | R | | R | T | | R | Y | |
| | Y | | Y | E | | Y | R | |
| | | | | R | | | E | |
| | | | | Y | | | | |

TABLE 1300

CDR3 diversity

| Position | 93 | 94 | 95 | 96 | 97 | 98 | 99 | 100 | 101 | div. tot. |
|---|---|---|---|---|---|---|---|---|---|---|
| O12 | Q | Q | S | Y | S | S | P | W | T | |
| diversity | 2 | 2 | 6 | 3 | 3 | 5 | 2 | 1 | 1 | 2160 |
| allowed | L | K | Y | D | N | T | S | | | |
| | | | H | N | Y | L | | | | |
| | | | F | | | Y | | | | |

TABLE 1300-continued

CDR3 diversity

| Position | 93 | 94 | 95 | 96 | 97 | 98 | 99 | 100 | 101 | div. tot. |
|---|---|---|---|---|---|---|---|---|---|---|
| | | | A | | F | | | | | |
| | | | D | | | | | | | |

TABLE 1400

Big CDR3 diversity

| Position | 93 | 94 | 95 | 96 | 97 | 98 | 99 | 100 | 101 | div. tot. |
|---|---|---|---|---|---|---|---|---|---|---|
| O12 | Q | Q | S | Y | S | S | P | W | T | |
| diversity | 6 | 1 | 7 | 7 | 6 | 5 | 2 | 6 | 1 | 105840 |
| allowed | L | | Y | D | N | T | S | F | | |
| | E | | Y | N | Y | L | | Y | | |
| | R | | H | R | D | Y | | H | | |
| | Y | | F | A | R | F | | L | | |
| | A | | A | D | A | E | | I | | |
| | | | | R | S | | R | | | |

Example 7

Further Examples of synthetic HC CDR3s

A collection of 22,063 Fabs with distinct CDR3 which had been selected from the FAB-310 or FAB-410 library and which were ELISA positive for at least one antigen were examined. The utilization of JH chains is shown in Table 1001; the FR4 part of each JH is shown bold. Table 1010 shows the utilization of amino acids in the HC CDR3s. Table 1020 shows the length distribution of CDR3. The median length is 11.5.

Table 1030 shows the utilization of D segments in the CDR3s. A D segment was identified is 70% of the amino acids matched; there were 5,654 cases (25.6%). The most used Ds were 3-3.2 (743, sequence: YYDFWSGYYT (SEQ ID NO: 177)), 3-22.2 (617, sequence: YYYDSSGYYY (SEQ ID NO: 88)), 6-19.1 (441, sequence: GYSSGWY (SEQ ID NO: 218)), 6-13.1 (399, sequence: GYSSSWY (SEQ ID NO: 215)), and 4-17.2 (392, sequence: DYGDY (SEQ ID NO: 760)). Of the Ds containing paired Cys residues, 2-15.2 (sequence: GYCSGGSCYS (SEQ ID NO: 136)) was the most used; there were 139 examples which is 0.6% of the collection.

When V or V::D is joined to J, there is often editing of the 3' end of V or V::D and the 5' end of J. Inspection of many CDR3-FR4 sequences shows that there is often a portion of JH making up part of CDR3. Often there are mutations in the CDR3 residues corresponding to JH residues 1-9. Herein the portion of CDR3 that is thought to derive from JH is called the "J stump". The JH used in a heavy chain is determined by comparing each of the residues of the six JH chains from position 6 to 20 to fusion of the last four amino acids of CDR3 to FR4. The JH that has the fewest mismatches is selected. The CDR3 sequence is examined for a J stump by working backward in the selected JH from position 9 toward the first position of the selected JH comparing to CDR3 until the search is terminated by a) the end of JH, b) the end of CDR3, or c) two consecutive mismatches. If one of the chains ends and the last compared position is a match, then it is included in J stump. If not, it is not. Table 1070 shows several examples. The CDR is written above, the JH is below, and the J stump is underlined. In 1070 A, we start at 9, V matches V, and we continue to position 6 with matches. The search stops at 4 because of the double mismatch. GMDV (SEQ ID NO: 974) goes into the J stump pile and GL goes into the "Leadin" pile. In 1070 B, the search ends with the end of JH6. The underscored residues go into the J stump pile and EPIWG (SEQ ID NO: 975) goes into the Leadin pile. In 1070 E, the search terminates because of the end of JH4, but the final residue tested (D in the CDR vs Y in JH4) is a mismatch and so the J stump is FDS and DSGVVAAAD (SEQ ID NO: 976) goes into the Leadin pile.

Table 1015 shows the amino-acid distribution of CDR3s that have no D segments from which the J stump has been removed. Note that the frequency of Tyr is much lower than when the whole CDR3s were compiled. This indicates that Tyr comes into CDR3s to a large extent through incorporation of D segments and J stumps. These Tyrs are not randomly inserted, but occur in a sequence that has been selected throughout mammalian evolution. It is a feature of the present invention that high levels (more than 20%) of Tyr should be inserted into libraries through the incorporation of Ds and J stumps that contain Tyr. At leadin or DJ filler positions, Tyr is allowed, but at no more than 20%.

```
                    TABLE 1070

Examples of assignment of J stump

A)
   6          GLGMDV                (SEQ ID NO: 977)
   JH6        YYYYYGMDVWGQGTTVTVSS  (SEQ ID NO:   3)
              123456789

B)
   13         EPIWGYYYYGMDV         (SEQ ID NO: 978)
   JH6            YYYYYGMDVWGQGTTVTVSS (SEQ ID NO: 3)

C)
   9          DFFTSYFDY             (SEQ ID NO: 979)
   JH4        -----YFDYWGQGTLVTVSS  (SEQ ID NO:   1)

D)
   12         DRGVSLLGAFDI          (SEQ ID NO: 980)
   JH3        -----AFDIWGQGTMVTVSS  (SEQ ID NO:   2)

E)
   12         DSGVVAAADFDS          (SEQ ID NO: 981)
   JH4        -----YFDYWGQGTLVTVSS  (SEQ ID NO:   1)
                    6789
```

Table 1082 shows the distribution of amino-acid usage in the J stumps of each JH. Since the most common JHs are JH3, JH4, and JH6, these are the preferred JHs on which to build libraries. Table 1082 shows that most examples of JH3 retain the tetrapeptide sequence AFDI (SEQ ID NO: 986) in CDR3. With JH4, a majority retain DY and a large fraction retain the sequence FDY in CDR3. With JH6, a large majority retain the sequence DV, a majority retain the sequence MDV, and a substantial fraction retain the sequence GMDV (SEQ ID NO: 974). A non-negligible fraction retain the sequence YGMDV (SEQ ID NO: 982), YYGMDV (SEQ ID NO: 983), or YYYG-MDV (SEQ ID NO: 984).

Included in libraries of the present invention are libraries such as 5.001 (Table 1097). Library 5.001 contains LC and HC CDR1-2 as described elsewhere in the present application. The library contains a HC VH (such as 3-23) followed by 6, 7, or 8 amino acids allowing [GSRDLY] in proportion shown in Table 1097. In the J stump, the parental amino acid is present at 3, 4, 5, 6, 7, 8, 10 times as likely as "other" amino-acid types. The "other" amino-acid types comprise Y, S, D, R, G. Thus at A6, we allow 7/12 A, plus 1/12 each of Y, S, D, R, and G. At F7, we allow 7/12 F plus 1/12 each of Y, S, D, R, and G. At D8, we allow 7/11 D plus 1/11 of Y, S, R, and G. At I9, we allow 7/12 I plus 1/12 Y, S, R, D, G. The parental amino acid could be 5, 6, 7, 8, 10 time more likely than the other amino-acid types.

Included in the libraries of the present invention is library 5.002 in Table 1097. This library comprises CDR3 of length 13, 14, and 15 and no D segment. There are 6, 7, or 8 leadin residues allowing G, S, R, D, L, or Y in the ratios 1:0.57:0.46: 0.42:0.36:0.35 or reasonable approximation thereto. The CDR3 is completed with a portion of JH6: YYYGMDV (SEQ ID NO: 984). The DNA that encodes the parental sequence YYYGMDV (SEQ ID NO: 984) is synthesized with the parental amino acid at 5, 6, 7, 8, or 10 times more likely than the others.

Included in the library of the present invention is library 5.003 in Table 1097. FR3 is followed by 4, 5, or 6 leadin residues allowing G, S, R, D, L, Y in the ratio 1.0:0.57:0.46: 0.42:0.36:0.35. Next comes D segment 3-3.2; the DNA that encodes this region favors the parental amino acid by 5-fold and allows as other amino acids Y, G, D, R, S. There is no DJ filler and the final four amino acids come from the J stump of JH3. The DNA encoding the J stump are synthesized with the parental amino acid 5-fold more likely than the others: YSGRD.

Library 5.004 in Table 1097 is a part of the present invention. There are 2, 3, or 4 leadin residues allowing GSRDLY in the ratios shown. The DNA encoding the sequence GYSS-GWY (SEQ ID NO: 218) is synthesized so that the parental amino acid is 6-X as likely as the others, two DJ-filler residues are allowed with GSRDLY allowed in the ratios 1.0:0.57: 0.46:0.42:0.36:0.35. The DNA to encode AFDI (SEQ ID NO: 986) is synthesized with the parental amino acid 6-x as likely as the others.

Library 5.005 is part of the present invention. Library 5.005 comprises members with CDR3 lengths 11-14. After FR3, there are 0, 1, or 2 leadin residues allowing GSRDLY in the ratios shown followed by DNA that encodes the parental sequence GYSSGWY (SEQ ID NO: 218) with variability that allows YGSRD such that the parental amino acid is 6-X as likely as the other allowed types. Following the D region there is zero or one DJ filler residues allowing GSRDLY in the ratios shown. Finally is JH3 with variability in the J stump (sequence: YFDY (SEQ ID NO: 985)) which allows YGSRD with the parental amino acid 6-X as likely as the other allowed types.

Library 5.006 in Table 1097 is part of the present invention. The CDR3 may be of length 19-25. There are zero to three leadin residues allowing GSRDLY in the ratios shown. Following the leadin is the D region 2-2.2. The DNA encoding 2-2.2 is synthesized so that the parental amino acid is 6-X as likely as the others (viz. YGSRD) except that the two Cys residues are fixed. Following 2-2.2 are zero to three DJ filler residues allowing GSRDLY in the ratios shown. The DNA that encodes the first nine residues of JH6 allows the parental amino acid plus YSGDR with the parental type being 6× more likely than the others.

TABLE 1001

Utilization of JHs

| JH | Number | % | 11111111112<br>12345678901234567890 | SEQ ID<br>NO: |
|---|---|---|---|---|
| JH1 | 1356 | 6.15 | ---AEYFQHWGQGTLVTVSS | 66 |
| JH2 | 1720 | 7.80 | ---YWYFDLWGRGTLVTVSS | 67 |
| JH3 | 5601 | 25.39 | -----AFDIWGQGTMVTVSS | 2 |

TABLE 1001-continued

Utilization of JHs

| JH | Number | % | 11111111112<br>12345678901234567890 | SEQ ID<br>NO: |
|---|---|---|---|---|
| JH4 | 7658 | 34.71 | -----YFDYWGQGTLVTVSS | 1 |
| JH5 | 1062 | 4.81 | ----NWFDPWGQGTLVTVSS | 68 |
| JH6 | 4666 | 21.15 | YYYYYGMDVWGQGTTVTVSS | 3 |
| Total | 22063 | | | |

TABLE 1010

Utilization of Amino acids in HC CDR3

| AA | Number | % | Rel up | Rel dwn |
|---|---|---|---|---|
| Y | 42863 | 15.47 | 35.87 | 1.00 |
| G | 37512 | 13.54 | 31.39 | 0.88 |
| D | 34051 | 12.29 | 28.49 | 0.79 |
| S | 23068 | 8.33 | 19.30 | 0.54 |
| F | 17813 | 6.43 | 14.91 | 0.42 |
| A | 15150 | 5.47 | 12.68 | 0.35 |
| R | 14090 | 5.09 | 11.79 | 0.33 |
| V | 13834 | 4.99 | 11.58 | 0.32 |
| L | 12351 | 4.46 | 10.34 | 0.29 |
| I | 10014 | 3.61 | 8.38 | 0.23 |
| P | 9514 | 3.43 | 7.96 | 0.22 |
| W | 9340 | 3.37 | 7.82 | 0.22 |
| T | 7544 | 2.72 | 6.31 | 0.18 |
| M | 6093 | 2.20 | 5.10 | 0.14 |
| E | 6042 | 2.18 | 5.06 | 0.14 |
| N | 5901 | 2.13 | 4.94 | 0.14 |
| H | 4403 | 1.59 | 3.68 | 0.10 |
| K | 3147 | 1.14 | 2.63 | 0.07 |
| Q | 3097 | 1.12 | 2.59 | 0.07 |
| C | 1195 | 0.43 | 1.00 | 0.03 |
| | 277022 | | | |

TABLE 1015

Frequency of amino acids in Leadin of CDR3s lacking D regions

| AA | Number | percent | rel up | rel dn |
|---|---|---|---|---|
| G | 23134 | 18.24 | 46.45 | 1.000 |
| S | 13555 | 10.69 | 27.22 | 0.586 |
| R | 10562 | 8.33 | 21.21 | 0.457 |
| D | 9704 | 7.65 | 19.49 | 0.419 |
| L | 8255 | 6.51 | 16.58 | 0.357 |
| Y | 8099 | 6.39 | 16.26 | 0.350 |
| A | 7188 | 5.67 | 14.43 | 0.311 |
| V | 6599 | 5.20 | 13.25 | 0.285 |
| P | 5768 | 4.55 | 11.58 | 0.249 |
| W | 4804 | 3.79 | 9.65 | 0.208 |
| T | 4769 | 3.76 | 9.58 | 0.206 |
| E | 4497 | 3.55 | 9.03 | 0.194 |
| N | 3733 | 2.94 | 7.50 | 0.161 |
| F | 3616 | 2.85 | 7.26 | 0.156 |
| I | 3464 | 2.73 | 6.96 | 0.150 |
| H | 2787 | 2.20 | 5.60 | 0.120 |
| K | 2460 | 1.94 | 4.94 | 0.106 |
| Q | 2124 | 1.67 | 4.27 | 0.092 |
| M | 1225 | 0.97 | 2.46 | 0.053 |
| C | 498 | 0.39 | 1.00 | 0.022 |
| | 126841 | | | |

TABLE 1020

Lengths of HC CDR3s

| Length | Number | % |
|---|---|---|
| 1 | 0 | 0.00 |
| 2 | 6 | 0.03 |
| 3 | 36 | 0.16 |
| 4 | 153 | 0.69 |
| 5 | 121 | 0.55 |
| 6 | 669 | 3.03 |
| 7 | 756 | 3.43 |
| 8 | 1066 | 4.83 |
| 9 | 2227 | 10.09 |
| 10 | 2701 | 12.24 |
| 11 | 2240 | 10.15 |
| 12 | 2071 | 9.39 |
| 13 | 2006 | 9.09 |
| 14 | 1594 | 7.22 |
| 15 | 1396 | 6.33 |
| 16 | 1254 | 5.68 |
| 17 | 1102 | 4.99 |
| 18 | 783 | 3.55 |
| 19 | 588 | 2.67 |
| 20 | 474 | 2.15 |
| 21 | 285 | 1.29 |
| 22 | 237 | 1.07 |
| 23 | 133 | 0.60 |
| 24 | 81 | 0.37 |
| 25 | 32 | 0.15 |
| 26 | 25 | 0.11 |
| 27 | 11 | 0.05 |
| 28 | 6 | 0.03 |
| 29 | 2 | 0.01 |
| 30 | 3 | 0.01 |
| 31 | 2 | 0.01 |
| 32 | 1 | 0.00 |
| 33 | 1 | 0.00 |
| 34 | 0 | 0.00 |
| 35 | 0 | 0.00 |
| 36 | 1 | 0.00 |
| | 22063 | |

TABLE 1030

Utilization of D segments.

| Id | Number | Sequence | SEQ ID NO: |
|---|---|---|---|
| 1-1.1 | 29 | GTTGT | 156 |
| 1-1.2 | 6 | VQLER | 157 |
| 1-1.3 | 151 | YNWND | 158 |
| 1-7.1 | 34 | GITGT | 159 |
| 1-7.2 | 0 | V*LEL | 160 |
| 1-7.3 | 65 | YNWNY | 161 |
| 1-20.1 | 0 | GITGT | 268 |
| 1-20.2 | 0 | V*LER | 162 |
| 1-20.3 | 0 | YNWND | 163 |
| 1-26.1 | 48 | GIVGAT | 164 |
| 1-26.2 | 3 | V*WELL | 165 |
| 1-26.3 | 220 | YSGSYY | 166 |
| 2-2.1 | 0 | RIL**YQLLY | 177 & 167 |
| 2-2.2 | 102 | GYCSSTSCYT | 70 |
| 2-2.3 | 37 | DIVVVPAAI | 168 |
| 2-8.1 | 0 | RILY@WCMLY | 169 & 392 |
| 2-8.2 | 23 | GYCTNGVCYT | 115 |
| 2-8.3 | 1 | DIVLMVYAI | 170 |
| 2-15.1 | 0 | RIL*WW*LLL | 171 |
| 2-15.2 | 139 | GYCSGGSCYS | 136 |
| 2-15.3 | 12 | DIVVVAAT | 172 |
| 2-21.1 | 0 | SILWW$LLF | 173 |
| 2-21.2 | 24 | AYCGGDCYS | 174 |
| 2-21.3 | 6 | HIVVVTAI | 175 |
| 3-3.1 | 28 | VLRFLEWLLY | 176 |
| 3-3.2 | 743 | YYDFWSGYYT | 177 |
| 3-3.3 | 15 | ITIFGVVII | 178 |
| 3-9.1 | 41 | VLRYFDWLL@ | 179 |
| 3-9.2 | 8 | YYDILTGYYN | 180 |
| 3-9.3 | 0 | ITIF*LVII | 181 & 579 |
| 3-10.1 | 26 | VLLWFGELL@ | 182 |
| 3-10.2 | 136 | YYYGSGSYYN | 81 |
| 3-10.2 | 32 | ITMVRGVII | 183 |
| 3-16.1 | 0 | VL$LRLGELSLY | 184 |
| 3-16.2 | 109 | YYDYVWGSYRYT | 104 |
| 3-16.2 | 8 | IMITFGGVIVI | 185 |
| 3-22.1 | 0 | VLL***WLLL | 186 |
| 3-22.2 | 617 | YYYDSSGYYY | 187 |
| 3-22.3 | 2 | ITMIVVVIT | 188 |
| 4-4.1 | 0 | $LQ@L | 189 |
| 4-4.2 | 75 | DYSNY | 192 |
| 4-4.3 | 165 | TTVT | 190 |
| 4-11.1 | 0 | $LQ@L | 191 |
| 4-11.2 | 0 | DYSNY | 192 |
| 4-11.3 | 0 | TTVT | 193 |
| 4-17.1 | 0 | $LR@L | 194 |
| 4-17.2 | 392 | DYGDY | 195 |
| 4-17.3 | 0 | TTVT | 196 |
| 4-23.1 | 0 | $LRW@L | 197 |
| 4-23.2 | 60 | DYGGNS | 198 |
| 4-23.3 | 16 | TTVVT | 199 |
| 5-5.1 | 25 | VDTAMV | 200 |

TABLE 1030-continued

Utilization of D segments.

| Id | Number | Sequence | SEQ ID NO: |
|---|---|---|---|
| 5-5.2 | 29 | WIQLWL | 201 |
| 5-5.3 | 292 | GYSYGY | 202 |
| 5-12.1 | 13 | VDIVATI | 203 |
| 5-12.2 | 0 | WI*WLRL | 204 |
| 5-12.3 | 200 | GYSGYDY | 205 |
| 5-18.1 | 0 | VDTAMV | 206 |
| 5-18.2 | 0 | WIQLWL | 207 |
| 5-18.3 | 0 | GYSYGY | 208 |
| 5-24.1 | 9 | VEMATI | 209 |
| 5-24.2 | 21 | *RWLQL | 210 |
| 5-24.3 | 44 | RDGYNY | 211 |
| 6-6.1 | 87 | EYSSSS | 212 |
| 6-6.2 | 122 | SIAAR | 213 |
| 6-6.3 | 1 | V*QLV | 214 |
| 6-13.1 | 399 | GYSSSWY | 215 |
| 6-13.2 | 170 | GIAAAG | 216 |
| 6-13.3 | 0 | V*QQLV | 217 |
| 6-19.1 | 441 | GYSSGWY | 218 |
| 6-19.2 | 104 | GIAVAG | 219 |
| 6-19.3 | 3 | V*QWLV | 220 |
| 7-27.1 | 257 | LTG | 221 |
| 7-27.2 | 0 | @LG | 222 |
| 7-27.3 | 64 | NWG | 223 |
| none | 16409 | | |

TABLE 1040

JH vs Length

| Length | JH1 | JH2 | JH3 | JH4 | JH5 | JH6 |
|---|---|---|---|---|---|---|
| 1 | 0 | 0 | 0 | 0 | 0 | 0 |
| 2 | 1 | 4 | 0 | 1 | 0 | 0 |
| 3 | 20 | 2 | 3 | 9 | 0 | 2 |
| 4 | 75 | 3 | 10 | 45 | 8 | 12 |
| 5 | 47 | 6 | 10 | 38 | 8 | 12 |
| 6 | 273 | 14 | 43 | 280 | 26 | 33 |
| 7 | 88 | 27 | 194 | 337 | 30 | 80 |
| 8 | 134 | 43 | 243 | 503 | 41 | 102 |
| 9 | 121 | 70 | 855 | 886 | 61 | 234 |
| 10 | 116 | 693 | 623 | 979 | 68 | 222 |
| 11 | 105 | 81 | 675 | 1003 | 84 | 292 |
| 12 | 107 | 84 | 552 | 905 | 121 | 302 |
| 13 | 87 | 274 | 538 | 672 | 113 | 322 |
| 14 | 48 | 81 | 480 | 532 | 105 | 348 |
| 15 | 50 | 83 | 372 | 421 | 80 | 390 |
| 16 | 28 | 54 | 316 | 322 | 87 | 447 |
| 17 | 27 | 49 | 239 | 334 | 69 | 384 |
| 18 | 11 | 64 | 174 | 140 | 49 | 345 |
| 19 | 8 | 28 | 104 | 99 | 41 | 308 |
| 20 | 4 | 23 | 59 | 56 | 20 | 312 |
| 21 | 0 | 13 | 40 | 30 | 24 | 178 |
| 22 | 3 | 14 | 31 | 30 | 13 | 146 |
| 23 | 1 | 3 | 22 | 12 | 7 | 88 |
| 24 | 0 | 5 | 9 | 12 | 4 | 51 |
| 25 | 1 | 0 | 1 | 3 | 1 | 26 |
| 26 | 0 | 0 | 5 | 5 | 0 | 15 |
| 27 | 0 | 1 | 2 | 1 | 1 | 6 |
| 28 | 1 | 0 | 0 | 2 | 0 | 3 |
| 29 | 0 | 0 | 0 | 0 | 0 | 2 |
| 30 | 0 | 0 | 0 | 0 | 0 | 3 |
| 31 | 0 | 0 | 1 | 0 | 0 | 1 |
| 32 | 0 | 1 | 0 | 0 | 0 | 0 |
| 33 | 0 | 0 | 0 | 1 | 0 | 0 |
| 34 | 0 | 0 | 0 | 0 | 0 | 0 |
| 35 | 0 | 0 | 0 | 0 | 0 | 0 |
| 36 | 0 | 0 | 0 | 0 | 1 | 0 |

TABLE 1050

Utilization of amino acids in Leadin with no D segment

| AA | Number | % | Rel up | Rel dn |
|---|---|---|---|---|
| G | 23134 | 18.24 | 46.45 | 1.00 |
| S | 13555 | 10.69 | 27.22 | 0.59 |
| R | 10562 | 8.33 | 21.21 | 0.46 |
| D | 9704 | 7.65 | 19.49 | 0.42 |
| L | 8255 | 6.51 | 16.58 | 0.36 |
| Y | 8099 | 6.39 | 16.26 | 0.35 |
| A | 7188 | 5.67 | 14.43 | 0.31 |
| V | 6599 | 5.20 | 13.25 | 0.29 |
| P | 5768 | 4.55 | 11.58 | 0.25 |
| W | 4804 | 3.79 | 9.65 | 0.21 |
| T | 4769 | 3.76 | 9.58 | 0.21 |
| E | 4497 | 3.55 | 9.03 | 0.19 |
| N | 3733 | 2.94 | 7.50 | 0.16 |
| F | 3616 | 2.85 | 7.26 | 0.16 |
| I | 3464 | 2.73 | 6.96 | 0.15 |
| H | 2787 | 2.20 | 5.60 | 0.12 |
| K | 2460 | 1.94 | 4.94 | 0.11 |
| Q | 2124 | 1.67 | 4.27 | 0.09 |
| M | 1225 | 0.97 | 2.46 | 0.05 |
| C | 498 | 0.39 | 1.00 | 0.02 |
| | 126841 | | | |

TABLE 1080

Dipepides in HC CDR3s

| | |
|---|---|
| YY | 13565 |
| FD | 11637 |
| DY | 8337 |
| SG | 5979 |
| GY | 5805 |
| YG | 5461 |
| DI | 5448 |
| AF | 4975 |
| DV | 4968 |
| GG | 4575 |
| SS | 4491 |
| MD | 4436 |
| GS | 4047 |
| GM | 3501 |
| YF | 3438 |
| YD | 3430 |
| RG | 3118 |
| SY | 2770 |
| GA | 2611 |

TABLE 1080-continued

| Dipepides in HC CDR3s | |
|---|---|
| YS | 2576 |
| DA | 2285 |
| DS | 2087 |
| WY | 2079 |
| GD | 2017 |
| GR | 1985 |
| GL | 1800 |
| DL | 1777 |
| DF | 1763 |
| GW | 1725 |
| WS | 1675 |
| AA | 1671 |
| LD | 1651 |
| EG | 1610 |
| AG | 1606 |
| RY | 1558 |
| DP | 1547 |
| GV | 1500 |
| RR | 1498 |
| LG | 1387 |
| GF | 1386 |
| VG | 1366 |
| GP | 1339 |
| WF | 1282 |
| FW | 1277 |
| NY | 1271 |
| PY | 1209 |
| GT | 1194 |
| WG | 1177 |
| SR | 1162 |
| TG | 1142 |
| FG | 1073 |
| RS | 1072 |
| SW | 1014 |
| DW | 1003 |
| LR | 990 |
| DG | 989 |
| PG | 976 |
| LL | 974 |
| AY | 962 |
| DR | 923 |
| VR | 882 |
| YM | 877 |
| AR | 872 |
| VV | 869 |
| YR | 865 |
| VA | 857 |
| RA | 844 |
| SP | 820 |
| GN | 812 |
| HY | 809 |
| SD | 805 |
| GI | 804 |
| NW | 785 |
| LS | 760 |
| LY | 757 |
| TY | 749 |
| PR | 742 |
| GE | 737 |
| SA | 736 |
| SF | 728 |
| PF | 725 |
| ND | 693 |
| ST | 684 |
| GH | 683 |
| YP | 676 |
| WL | 675 |
| SN | 667 |
| TS | 652 |
| RD | 648 |
| YA | 648 |
| SL | 644 |
| RP | 643 |
| YL | 638 |
| IA | 634 |
| RL | 627 |
| EL | 622 |
| YN | 607 |
| AV | 605 |
| AP | 600 |
| AT | 592 |
| PL | 591 |
| TT | 589 |
| ID | 588 |
| DD | 583 |
| AS | 570 |
| KG | 566 |
| VD | 556 |
| VP | 551 |
| LT | 540 |
| LF | 539 |
| VL | 539 |
| FY | 534 |
| PD | 533 |
| RV | 531 |
| RF | 525 |
| AL | 521 |
| PS | 510 |
| EY | 508 |
| LW | 508 |
| PA | 505 |
| LP | 500 |
| VS | 497 |
| IR | 493 |
| YV | 493 |
| VY | 478 |
| IG | 476 |
| VT | 475 |
| TR | 472 |
| DN | 471 |
| SI | 469 |
| AD | 462 |
| LA | 459 |
| PP | 451 |
| RT | 451 |
| DT | 448 |
| RW | 447 |
| GQ | 446 |
| QG | 446 |
| TD | 446 |
| TA | 437 |
| TF | 426 |
| GK | 422 |
| YW | 421 |
| HD | 420 |
| IL | 417 |
| LV | 406 |
| IS | 402 |
| NG | 398 |
| RN | 398 |
| SV | 397 |
| TV | 397 |
| TP | 390 |
| NA | 389 |
| NS | 388 |
| ER | 387 |
| HG | 386 |
| VW | 381 |
| QL | 378 |
| RI | 374 |
| WN | 365 |
| YT | 365 |
| CS | 360 |
| DH | 359 |
| EA | 359 |
| WD | 353 |
| ES | 350 |
| FR | 349 |
| YC | 343 |
| PT | 337 |
| TL | 326 |
| KR | 325 |
| VF | 324 |
| MG | 314 |
| PN | 313 |
| RE | 312 |

TABLE 1080-continued

Dipepides in HC CDR3s

| | |
|---|---|
| IV | 311 |
| KS | 310 |
| SC | 310 |
| FL | 309 |
| FF | 306 |
| CY | 303 |
| SH | 302 |
| LK | 300 |
| IT | 298 |
| LE | 298 |
| FS | 296 |
| ED | 294 |
| RK | 294 |
| HF | 292 |
| VI | 290 |
| RH | 287 |
| MV | 285 |
| KY | 284 |
| AI | 282 |
| HS | 281 |
| YH | 281 |
| LN | 278 |
| PV | 276 |
| QY | 276 |
| WA | 271 |
| QH | 267 |
| FQ | 264 |
| LI | 257 |
| EV | 255 |
| AM | 253 |
| DQ | 250 |
| HR | 250 |
| PH | 248 |
| AN | 242 |
| WR | 242 |
| NF | 240 |
| PI | 239 |
| TN | 239 |
| TI | 238 |
| PW | 229 |
| IP | 228 |
| QR | 227 |
| EW | 225 |
| YI | 221 |
| FE | 220 |
| IY | 220 |
| EP | 219 |
| NR | 217 |
| DM | 214 |
| FA | 212 |
| AE | 210 |
| IF | 210 |
| QW | 208 |
| YE | 208 |
| FP | 201 |
| TM | 201 |
| WE | 201 |
| WP | 201 |
| AH | 199 |
| NP | 198 |
| VN | 198 |
| HA | 196 |
| LH | 196 |
| AW | 193 |
| HP | 192 |
| HL | 191 |
| RQ | 191 |
| TW | 186 |
| EN | 185 |
| LQ | 182 |
| SE | 180 |
| VK | 180 |
| ET | 178 |
| DK | 177 |
| NL | 177 |
| KD | 176 |
| SK | 176 |
| YK | 176 |
| EF | 174 |
| FN | 174 |
| HN | 171 |
| FH | 165 |
| YQ | 165 |
| KN | 164 |
| MA | 163 |
| NN | 160 |
| KA | 159 |
| SQ | 157 |
| PE | 156 |
| WV | 154 |
| EI | 153 |
| TH | 153 |
| FV | 152 |
| AK | 151 |
| TK | 151 |
| WT | 151 |
| PK | 150 |
| KK | 148 |
| IW | 145 |
| VH | 145 |
| VE | 141 |
| EE | 138 |
| DE | 136 |
| KL | 136 |
| PQ | 136 |
| QP | 135 |
| SM | 134 |
| QD | 133 |
| QS | 131 |
| VQ | 130 |
| QQ | 129 |
| WW | 129 |
| NT | 128 |
| DC | 118 |
| KT | 118 |
| QA | 118 |
| NK | 113 |
| KW | 112 |
| EK | 109 |
| FT | 108 |
| KV | 108 |
| MR | 105 |
| TE | 104 |
| HH | 103 |
| IQ | 103 |
| II | 102 |
| HI | 101 |
| KP | 101 |
| MY | 100 |
| RM | 99 |
| AQ | 98 |
| EQ | 96 |
| QT | 96 |
| LM | 95 |
| HV | 94 |
| IK | 93 |
| PM | 93 |
| QN | 93 |
| CG | 91 |
| QF | 91 |
| FI | 90 |
| HW | 90 |
| WH | 90 |
| QV | 89 |
| WI | 89 |
| KH | 88 |
| MI | 88 |
| MS | 87 |
| TQ | 86 |
| NV | 85 |
| EM | 84 |
| HK | 84 |
| IN | 83 |
| NH | 82 |
| NI | 82 |
| HT | 81 |

TABLE 1080-continued

| Dipepides in HC CDR3s | |
|---|---|
| WK | 79 |
| KF | 77 |
| VM | 73 |
| MT | 71 |
| IH | 69 |
| EH | 68 |
| IE | 67 |
| QK | 65 |
| WQ | 65 |
| GC | 64 |
| KE | 61 |
| KI | 61 |
| CT | 58 |
| FK | 58 |
| IM | 57 |
| KQ | 57 |
| ML | 55 |
| QE | 55 |
| NE | 53 |
| NQ | 53 |
| CF | 51 |
| MP | 50 |
| CP | 49 |
| RC | 47 |
| HE | 46 |
| VC | 46 |
| QI | 45 |
| MN | 44 |
| MF | 43 |
| HQ | 41 |
| CD | 38 |
| CL | 38 |
| NC | 38 |
| HM | 37 |
| FM | 36 |

TABLE 1080-continued

| Dipepides in HC CDR3s | |
|---|---|
| ME | 36 |
| MK | 35 |
| QM | 35 |
| NM | 34 |
| KM | 32 |
| TC | 31 |
| CR | 29 |
| CV | 25 |
| HC | 25 |
| WM | 25 |
| AC | 24 |
| FC | 24 |
| CA | 23 |
| CH | 21 |
| CN | 21 |
| MW | 21 |
| PC | 19 |
| LC | 17 |
| IC | 16 |
| MM | 16 |
| MH | 15 |
| WC | 15 |
| EC | 12 |
| CK | 10 |
| CW | 10 |
| MQ | 10 |
| CI | 9 |
| CC | 8 |
| CM | 8 |
| CQ | 6 |
| QC | 6 |
| CE | 5 |
| KC | 5 |
| MC | 3 |

TABLE 1060 a Lengths of HC CDR3s vs which D segments occur (if any) for lengths 3-17

| Name | Sequence | SEQ ID NO: | Length | | | | | | | | | | | | | | |
|---|---|---|---|---|---|---|---|---|---|---|---|---|---|---|---|---|---|
| | | | 3 | 4 | 5 | 6 | 7 | 8 | 9 | 10 | 11 | 12 | 13 | 14 | 15 | 16 | 17 |
| 1-1.1 | GTTGT | 156 | 0 | 0 | 0 | 0 | 0 | 0 | 2 | 2 | 3 | 6 | 2 | 3 | 3 | 4 | 0 |
| 1-1.2 | VQLER | 157 | 0 | 0 | 0 | 0 | 0 | 0 | 0 | 0 | 1 | 0 | 1 | 0 | 1 | 2 | 1 |
| 1-1.3 | YNWND | 158 | 0 | 0 | 0 | 0 | 0 | 2 | 6 | 14 | 16 | 19 | 16 | 14 | 17 | 16 | 9 |
| 1-7.1 | GITGT | 159 | 0 | 0 | 0 | 0 | 0 | 0 | 0 | 1 | 2 | 7 | 6 | 4 | 4 | 0 | 4 |
| 1-7.3 | YNWNY | 161 | 0 | 0 | 0 | 0 | 1 | 0 | 2 | 5 | 7 | 8 | 8 | 6 | 5 | 9 | 4 |
| 1-26.1 | GIVGAT | 164 | 0 | 0 | 0 | 1 | 0 | 0 | 2 | 4 | 10 | 4 | 6 | 9 | 3 | 2 | 2 |
| 1-26.2 | V*WELL | 165 | 0 | 0 | 0 | 0 | 0 | 0 | 0 | 0 | 1 | 0 | 1 | 0 | 0 | 0 | 1 |
| 1-26.3 | YSGSYY | 166 | 0 | 0 | 0 | 0 | 1 | 0 | 2 | 10 | 14 | 24 | 24 | 27 | 21 | 26 | 13 |
| 2-2.2 | GYCSSTSCYT | 70 | 0 | 0 | 0 | 0 | 0 | 0 | 0 | 0 | 0 | 2 | 2 | 9 | 15 | 15 | 11 |
| 2-2.3 | DIVVVPAAI | 168 | 0 | 0 | 0 | 0 | 0 | 0 | 0 | 0 | 0 | 0 | 1 | 3 | 2 | 5 | 5 |
| 2-8.2 | GYCTNGVCYT | 115 | 0 | 0 | 0 | 0 | 0 | 0 | 0 | 0 | 0 | 1 | 0 | 2 | 4 | 3 | 4 |
| 2-8.3 | DIVLMVYAI | 170 | 0 | 0 | 0 | 0 | 0 | 0 | 0 | 0 | 0 | 0 | 1 | 0 | 0 | 0 | 0 |
| 2-15.2 | GYCSGGSCYS | 136 | 0 | 0 | 0 | 0 | 0 | 0 | 0 | 0 | 1 | 3 | 5 | 12 | 10 | 25 | 22 |
| 2-15.3 | DIVVVAAT | 172 | 0 | 0 | 0 | 0 | 0 | 0 | 0 | 0 | 0 | 1 | 1 | 2 | 3 | 1 |  |
| 2-21.2 | AYCGGDCYS | 174 | 0 | 0 | 0 | 0 | 0 | 0 | 0 | 0 | 0 | 1 | 1 | 3 | 5 | 2 | 5 |
| 2-21.3 | HIVVVTAI | 175 | 0 | 0 | 0 | 0 | 0 | 0 | 0 | 0 | 0 | 1 | 2 | 0 | 2 | 0 | 1 |

TABLE 1060-continued

| | | | | | | | | | | | | | | | | |
|---|---|---|---|---|---|---|---|---|---|---|---|---|---|---|---|---|
| 3-3.1 | VLRFLEWLLY | 176 | 0 | 0 | 0 | 0 | 0 | 0 | 0 | 0 | 0 | 0 | 1 | 2 | 2 | 2 | 3 |
| 3-3.2 | YYDFWSGYYT | 177 | 0 | 0 | 0 | 0 | 0 | 0 | 1 | 5 | 8 | 22 | 38 | 44 | 72 | 69 |
| 3-3.3 | ITIFGVVII | 178 | 0 | 0 | 0 | 0 | 0 | 0 | 0 | 0 | 0 | 0 | 1 | 0 | 2 | 5 |
| 3-9.1 | VLRYFDWLL@ | 179 | 0 | 0 | 0 | 0 | 0 | 0 | 0 | 1 | 0 | 0 | 4 | 5 | 5 | 5 |
| 3-9.2 | YYDILTGYYN | 180 | 0 | 0 | 0 | 0 | 0 | 0 | 0 | 0 | 0 | 0 | 0 | 0 | 2 | 1 |
| 3-10.1 | VLLWFGELL@ | 182 | 0 | 0 | 0 | 0 | 0 | 0 | 2 | 1 | 2 | 4 | 2 | 3 | 5 |
| 3-10.2 | YYYGSGSYYN | 81 | 0 | 0 | 0 | 0 | 0 | 0 | 2 | 4 | 7 | 10 | 13 | 15 | 18 | 14 |
| 3-10.2 | ITMVRGVII | 183 | 0 | 0 | 0 | 0 | 0 | 0 | 0 | 0 | 3 | 1 | 2 | 7 | 5 | 2 |
| 3-16.2 | YYDYVWGSYRYT | 104 | 0 | 0 | 0 | 0 | 0 | 0 | 0 | 0 | 0 | 0 | 1 | 7 | 7 | 7 |
| 3-16.2 | IMITFGGVIVI | 185 | 0 | 0 | 0 | 0 | 0 | 0 | 0 | 0 | 0 | 0 | 0 | 1 | 0 | 2 |
| 3-22.2 | YYYDSSGYYY | 187 | 0 | 0 | 0 | 0 | 0 | 0 | 0 | 6 | 30 | 45 | 56 | 59 | 108 | 101 |
| 3-22.3 | ITMIVVVIT | 188 | 0 | 0 | 0 | 0 | 0 | 0 | 0 | 0 | 0 | 0 | 0 | 0 | 0 | 0 |
| 4-4.2 | DYSNY | 192 | 0 | 0 | 0 | 0 | 3 | 3 | 4 | 6 | 14 | 4 | 7 | 4 | 10 | 6 |
| 4-4.3 | TTVT | 190 | 0 | 0 | 0 | 2 | 4 | 11 | 19 | 23 | 19 | 25 | 19 | 10 | 11 | 9 |
| 4-17.2 | DYGDY | 195 | 0 | 0 | 2 | 6 | 12 | 8 | 38 | 40 | 48 | 47 | 50 | 40 | 29 | 21 | 10 |
| 4-23.2 | DYGGNS | 198 | 0 | 0 | 0 | 0 | 0 | 2 | 7 | 4 | 5 | 17 | 4 | 8 | 5 | 1 | 1 |
| 4-23.3 | TTVVT | 199 | 0 | 0 | 0 | 0 | 0 | 0 | 2 | 0 | 1 | 1 | 2 | 1 | 2 | 0 | 0 |
| 5-5.1 | VDTAMV | 200 | 0 | 0 | 0 | 0 | 0 | 0 | 0 | 1 | 4 | 8 | 1 | 3 | 2 | 0 | 1 |
| 5-5.2 | WIQLWL | 201 | 0 | 0 | 0 | 0 | 0 | 0 | 0 | 3 | 2 | 0 | 3 | 1 | 4 | 3 | 3 |
| 5-5.3 | GYSYGY | 202 | 0 | 0 | 0 | 0 | 1 | 6 | 9 | 20 | 43 | 29 | 27 | 22 | 32 | 26 | 27 |
| 5-12.1 | VDIVATI | 203 | 0 | 0 | 0 | 0 | 0 | 0 | 0 | 2 | 0 | 1 | 2 | 4 | 0 | 2 | 1 |
| 5-12.3 | GYSGYDY | 205 | 0 | 0 | 0 | 0 | 4 | 10 | 13 | 15 | 19 | 15 | 22 | 27 | 16 | 15 | 9 |
| 5-24.1 | VEMATI | 209 | 0 | 0 | 0 | 0 | 0 | 0 | 1 | 1 | 0 | 0 | 6 | 0 | 0 | 0 | 0 |
| 5-24.2 | *RHLQL | 210 | 0 | 0 | 0 | 0 | 1 | 0 | 3 | 1 | 3 | 2 | 2 | 1 | 2 | 2 | 2 |
| 5-24.3 | RDGYNY | 211 | 0 | 0 | 0 | 0 | 0 | 0 | 0 | 1 | 8 | 12 | 6 | 7 | 3 | 2 | 1 |
| 6-6.1 | EYSSSS | 212 | 0 | 0 | 0 | 0 | 0 | 0 | 0 | 9 | 7 | 16 | 19 | 13 | 2 | 4 | 2 |
| 6-6.2 | SIAAR | 213 | 0 | 0 | 0 | 1 | 1 | 0 | 17 | 8 | 7 | 13 | 17 | 6 | 16 | 16 | 7 |
| 6-6.3 | V*QLV | 214 | 0 | 0 | 0 | 0 | 0 | 0 | 0 | 0 | 0 | 0 | 0 | 0 | 1 | 0 | 0 |
| 6-13.1 | GYSSSWY | 215 | 0 | 0 | 0 | 0 | 0 | 1 | 6 | 11 | 35 | 40 | 56 | 44 | 50 | 42 | 35 |
| 6-13.2 | GIAAAG | 216 | 0 | 0 | 0 | 0 | 1 | 2 | 18 | 14 | 15 | 20 | 20 | 15 | 16 | 14 | 11 |
| 6-19.1 | GYSSGWY | 218 | 0 | 0 | 0 | 0 | 1 | 1 | 4 | 27 | 57 | 58 | 48 | 52 | 45 | 35 | 30 |
| 6-19.2 | GIAVAG | 219 | 0 | 0 | 0 | 0 | 1 | 1 | 0 | 7 | 8 | 20 | 8 | 13 | 16 | 8 | 10 |
| 6-19.3 | V*QWLV | 220 | 0 | 0 | 0 | 0 | 0 | 0 | 0 | 0 | 1 | 1 | 0 | 0 | 0 | 0 | 0 |
| 7-27.1 | LTG | 221 | 0 | 0 | 1 | 0 | 2 | 8 | 12 | 7 | 14 | 11 | 17 | 17 | 24 | 24 | 31 |
| 7-27.3 | NWG | 223 | 0 | 0 | 0 | 1 | 2 | 11 | 6 | 5 | 10 | 6 | 7 | 5 | 7 | 1 | 0 |
| none | | | 36 | 153 | 118 | 660 | 726 | 1007 | 2063 | 2463 | 1851 | 1596 | 1502 | 1075 | 874 | 681 | 609 |

TABLE 1060-continued b Lengths of HC CDR3s vs which D segments occur (if any) for lengths 18-32

| Name | Sequence | SEQ ID NO: | Length | | | | | | | | | | | | | | |
|---|---|---|---|---|---|---|---|---|---|---|---|---|---|---|---|---|---|
| | | | 18 | 19 | 20 | 21 | 22 | 23 | 24 | 25 | 26 | 27 | 28 | 29 | 30 | 31 | 32 |
| 1-1.1 | GTTGT | 156 | 0 | 1 | 0 | 0 | 1 | 1 | 1 | 0 | 0 | 0 | 0 | 0 | 0 | 0 | 0 |
| 1-1.2 | VQLER | 157 | 0 | 0 | 0 | 0 | 0 | 0 | 0 | 0 | 0 | 0 | 0 | 0 | 0 | 0 | 0 |
| 1-1.3 | YNHND | 158 | 6 | 5 | 3 | 4 | 1 | 1 | 1 | 0 | 0 | 1 | 0 | 0 | 0 | 0 | 0 |
| 1-7.1 | GITGT | 159 | 2 | 2 | 1 | 0 | 0 | 0 | 1 | 0 | 0 | 0 | 0 | 0 | 0 | 0 | 0 |
| 1-7.3 | YNWNY | 161 | 5 | 2 | 1 | 1 | 0 | 0 | 0 | 0 | 0 | 0 | 0 | 1 | 0 | 0 | 0 |
| 1-26.1 | GIVGAT | 164 | 0 | 0 | 3 | 0 | 1 | 0 | 0 | 1 | 0 | 0 | 0 | 0 | 0 | 0 | 0 |
| 1-26.2 | V*WELL | 165 | 0 | 0 | 0 | 0 | 0 | 0 | 0 | 0 | 0 | 0 | 0 | 0 | 0 | 0 | 0 |
| 1-26.3 | YSGSYY | 166 | 14 | 11 | 9 | 8 | 6 | 3 | 3 | 0 | 3 | 1 | 0 | 0 | 0 | 0 | 0 |
| 2-2.2 | GYCSSTSCYT | 70 | 11 | 7 | 2 | 10 | 11 | 4 | 2 | 0 | 0 | 0 | 1 | 0 | 0 | 0 | 0 |
| 2-2.3 | DIVVVPAAI | 168 | 2 | 6 | 3 | 4 | 3 | 2 | 1 | 0 | 0 | 0 | 0 | 0 | 0 | 0 | 0 |
| 2-8.2 | GYCTNGVCYT | 115 | 3 | 0 | 1 | 1 | 3 | 1 | 0 | 0 | 0 | 0 | 0 | 0 | 0 | 0 | 0 |
| 2-8.3 | DIVLMVYAI | 170 | 0 | 0 | 0 | 0 | 0 | 0 | 0 | 0 | 0 | 0 | 0 | 0 | 0 | 0 | 0 |
| 2-15.2 | GYCSGGSCYS | 136 | 20 | 10 | 7 | 4 | 8 | 9 | 3 | 0 | 0 | 0 | 0 | 0 | 0 | 0 | 0 |
| 2-15.3 | DIVVVAAT | 172 | 0 | 1 | 1 | 1 | 0 | 0 | 0 | 0 | 1 | 0 | 0 | 0 | 0 | 0 | 0 |
| 2-21.2 | AYCGGDCYS | 174 | 1 | 3 | 1 | 1 | 1 | 0 | 0 | 0 | 0 | 0 | 0 | 0 | 0 | 0 | 0 |
| 2-21.3 | HIVVVTAI | 175 | 0 | 0 | 0 | 0 | 0 | 0 | 0 | 0 | 0 | 0 | 0 | 0 | 0 | 0 | 0 |
| 3-3.1 | VLRFLEWLLY | 176 | 6 | 2 | 4 | 3 | 2 | 0 | 0 | 0 | 1 | 0 | 0 | 0 | 0 | 0 | 0 |
| 3-3.2 | YYDFWSGYYT | 177 | 82 | 97 | 104 | 67 | 61 | 32 | 23 | 7 | 3 | 4 | 0 | 0 | 2 | 1 | 0 |
| 3-3.3 | ITIFGVVII | 178 | 3 | 2 | 0 | 0 | 2 | 0 | 0 | 0 | 0 | 0 | 0 | 0 | 0 | 0 | 0 |
| 3-9.1 | VLRYFDWLL@ | 179 | 7 | 2 | 2 | 6 | 1 | 2 | 1 | 0 | 0 | 0 | 0 | 0 | 0 | 0 | 0 |
| 3-9.2 | YYDILTGYYN | 180 | 3 | 2 | 0 | 0 | 0 | 0 | 0 | 0 | 0 | 0 | 0 | 0 | 0 | 0 | 0 |
| 3-10.1 | VLLWFGELL@ | 182 | 3 | 4 | 0 | 0 | 0 | 0 | 0 | 0 | 0 | 0 | 0 | 0 | 0 | 0 | 0 |
| 3-10.2 | YYYGSGSYYN | 81 | 15 | 10 | 8 | 7 | 6 | 3 | 2 | 1 | 1 | 0 | 0 | 0 | 0 | 0 | 0 |
| 3-10.2 | ITMVRGVII | 183 | 3 | 3 | 6 | 0 | 0 | 0 | 0 | 0 | 0 | 0 | 0 | 0 | 0 | 0 | 0 |
| 3-16.2 | YYDYVWGSYRYT | 104 | 11 | 11 | 14 | 10 | 18 | 13 | 5 | 2 | 2 | 0 | 0 | 0 | 1 | 0 | 0 |
| 3-16.2 | IMITFGGVIVI | 185 | 1 | 3 | 1 | 0 | 0 | 0 | 0 | 0 | 0 | 0 | 0 | 0 | 0 | 0 | 0 |
| 3-22.2 | YYYDSSGYYY | 187 | 77 | 54 | 28 | 22 | 18 | 8 | 1 | 2 | 1 | 1 | 0 | 0 | 0 | 0 | 0 |
| 3-22.3 | ITMIVVIT | 188 | 1 | 1 | 0 | 0 | 0 | 0 | 0 | 0 | 0 | 0 | 0 | 0 | 0 | 0 | 0 |
| 4-4.2 | DYSNY | 192 | 7 | 2 | 2 | 1 | 1 | 0 | 1 | 0 | 0 | 0 | 0 | 0 | 0 | 0 | 0 |
| 4-4.3 | TTVT | 190 | 4 | 2 | 2 | 1 | 3 | 0 | 0 | 0 | 0 | 0 | 1 | 0 | 0 | 0 | 0 |
| 4-17.2 | DYGDY | 195 | 17 | 7 | 8 | 3 | 2 | 1 | 1 | 0 | 1 | 0 | 1 | 0 | 0 | 0 | 0 |
| 4-23.2 | DYGGNS | 198 | 3 | 1 | 0 | 2 | 0 | 0 | 0 | 0 | 0 | 0 | 0 | 0 | 0 | 0 | 0 |
| 4-23.3 | TTVVT | 199 | 2 | 2 | 1 | 1 | 1 | 0 | 0 | 0 | 0 | 0 | 0 | 0 | 0 | 0 | 0 |
| 5-5.1 | VDTAMV | 200 | 0 | 1 | 1 | 2 | 1 | 0 | 0 | 0 | 0 | 0 | 0 | 0 | 0 | 0 | 0 |
| 5-5.2 | WIQLWL | 201 | 3 | 3 | 1 | 0 | 1 | 0 | 0 | 0 | 0 | 1 | 0 | 0 | 0 | 1 | 0 |
| 5-5.3 | GYSYGY | 202 | 13 | 18 | 7 | 2 | 2 | 6 | 0 | 0 | 2 | 0 | 0 | 0 | 0 | 0 | 0 |
| 5-12.1 | VDIVATI | 203 | 0 | 0 | 0 | 1 | 0 | 0 | 0 | 0 | 0 | 0 | 0 | 0 | 0 | 0 | 0 |

TABLE 1060-continued

| | | | | | | | | | | | | | | | | |
|---|---|---|---|---|---|---|---|---|---|---|---|---|---|---|---|---|
| 5-12.3 | GYSGYDY | 205 | 11 | 10 | 6 | 6 | 0 | 2 | 0 | 0 | 0 | 0 | 0 | 0 | 0 | 0 |
| 5-24.1 | VEMATI | 209 | 0 | 1 | 0 | 0 | 0 | 0 | 0 | 0 | 0 | 0 | 0 | 0 | 0 | 0 |
| 5-24.2 | *RWLQL | 210 | 2 | 0 | 0 | 0 | 0 | 0 | 0 | 0 | 0 | 0 | 0 | 0 | 0 | 0 |
| 5-24.3 | RDGYNY | 211 | 2 | 2 | 0 | 0 | 0 | 0 | 0 | 0 | 0 | 0 | 0 | 0 | 0 | 0 |
| 6-6.1 | EYSSSS | 212 | 9 | 3 | 1 | 1 | 0 | 0 | 0 | 1 | 0 | 0 | 0 | 0 | 0 | 0 |
| 6-6.2 | SIAAR | 213 | 2 | 3 | 2 | 6 | 0 | 0 | 0 | 0 | 0 | 0 | 0 | 0 | 0 | 0 |
| 6-6.3 | V*QLV | 214 | 0 | 0 | 0 | 0 | 0 | 0 | 0 | 0 | 0 | 0 | 0 | 0 | 0 | 0 |
| 6-13.1 | GYSSSWY | 215 | 24 | 22 | 17 | 4 | 5 | 1 | 3 | 2 | 0 | 0 | 1 | 0 | 0 | 0 |
| 6-13.2 | GIAAAG | 216 | 10 | 4 | 2 | 5 | 2 | 1 | 0 | 0 | 0 | 0 | 0 | 0 | 0 | 0 |
| 6-19.1 | GYSSGWY | 218 | 23 | 25 | 13 | 7 | 7 | 3 | 0 | 2 | 1 | 0 | 1 | 0 | 0 | 0 |
| 6-19.2 | GIAVAG | 219 | 6 | 2 | 2 | 0 | 0 | 0 | 2 | 0 | 0 | 0 | 0 | 0 | 0 | 0 |
| 6-19.3 | V*QWLV | 220 | 0 | 1 | 0 | 0 | 0 | 0 | 0 | 0 | 0 | 0 | 0 | 0 | 0 | 0 |
| 7-27.1 | LTG | 221 | 29 | 23 | 12 | 9 | 7 | 4 | 3 | 1 | 0 | 1 | 0 | 0 | 0 | 0 |
| 7-27.3 | NWG | 223 | 1 | 0 | 0 | 0 | 2 | 0 | 0 | 0 | 0 | 0 | 0 | 0 | 0 | 0 |
| none | | | 339 | 217 | 198 | 85 | 60 | 36 | 27 | 13 | 9 | 2 | 1 | 1 | 0 | 0 | 1 |

TABLE 1082

Tally of J stumps

| | A | C | D | E | F | G | H | I | K | L | M | N | P | Q | R | S | T | V | W | Y | — |
|---|---|---|---|---|---|---|---|---|---|---|---|---|---|---|---|---|---|---|---|---|---|
| JH1 | ---AEYFQHWGQGTLVTVSS 6.15% (SEQ ID NO: 66) | | | | | | | | | | | | | | | | | | | | |
| 4 | 41 | 0 | 0 | 0 | 0 | 0 | 0 | 0 | 0 | 0 | 0 | 0 | 0 | 0 | 0 | 0 | 0 | 0 | 0 | 0 | 605 |
| 5 | 1 | 0 | 1 | 64 | 0 | 6 | 0 | 1 | 0 | 0 | 0 | 0 | 1 | 2 | 1 | 1 | 0 | 0 | 0 | 0 | 568 |
| 6 | 0 | 0 | 0 | 0 | 0 | 1 | 1 | 0 | 0 | 3 | 0 | 2 | 1 | 0 | 1 | 1 | 0 | 0 | 0 | 211 | 425 |
| 7 | 1 | 0 | 1 | 0 | 363 | 3 | 1 | 0 | 0 | 8 | 0 | 0 | 1 | 0 | 1 | 6 | 0 | 3 | 0 | 6 | 252 |
| 8 | 8 | 0 | 59 | 23 | 4 | 17 | 11 | 3 | 5 | 19 | 0 | 8 | 3 | 221 | 11 | 6 | 8 | 5 | 0 | 4 | 231 |
| 9 | 2 | 1 | 13 | 2 | 13 | 3 | 447 | 19 | 2 | 6 | 3 | 20 | 1 | 2 | 0 | 20 | 3 | 5 | 4 | 9 | 71 |
| JH2 | ---YWYFDLWGRGTLVTVSS 7.80% (SEQ ID NO: 67) | | | | | | | | | | | | | | | | | | | | |
| 4 | 0 | 0 | 0 | 0 | 0 | 0 | 0 | 0 | 0 | 0 | 0 | 0 | 0 | 0 | 0 | 0 | 0 | 0 | 0 | 159 | 1519 |
| 5 | 0 | 0 | 2 | 0 | 2 | 11 | 0 | 0 | 1 | 0 | 1 | 0 | 0 | 7 | 1 | 1 | 1 | 929 | 21 | 701 |
| 6 | 3 | 2 | 9 | 0 | 40 | 5 | 7 | 4 | 1 | 9 | 0 | 7 | 1 | 0 | 1 | 11 | 2 | 0 | 1 | 1083 | 492 |
| 7 | 1 | 6 | 1 | 0 | 1209 | 2 | 6 | 23 | 0 | 89 | 30 | 1 | 2 | 1 | 1 | 12 | 0 | 11 | 1 | 42 | 240 |
| 8 | 31 | 2 | 1241 | 90 | 4 | 38 | 30 | 3 | 1 | 0 | 1 | 29 | 3 | 4 | 2 | 2 | 3 | 19 | 0 | 15 | 160 |
| 9 | 3 | 1 | 9 | 3 | 34 | 2 | 26 | 17 | 5 | 1064 | 36 | 17 | 30 | 38 | 33 | 20 | 8 | 83 | 1 | 177 | 71 |
| JH3 | -----AFDIWGQGTMVTVSS 25.4% (SEQ ID NO: 2) | | | | | | | | | | | | | | | | | | | | |
| 6 | 4374 | 0 | 0 | 0 | 0 | 0 | 0 | 0 | 0 | 0 | 0 | 0 | 0 | 0 | 0 | 0 | 0 | 0 | 0 | 0 | 1074 |
| 7 | 1 | 4 | 0 | 1 | 4612 | 2 | 0 | 8 | 0 | 56 | 3 | 2 | 1 | 1 | 0 | 29 | 2 | 15 | 12 | 74 | 625 |
| 8 | 23 | 0 | 4765 | 51 | 0 | 28 | 14 | 0 | 3 | 0 | 0 | 15 | 2 | 1 | 1 | 2 | 2 | 6 | 0 | 4 | 531 |
| 9 | 7 | 5 | 5 | 0 | 73 | 2 | 1 | 4439 | 4 | 64 | 64 | 43 | 2 | 1 | 11 | 54 | 49 | 113 | 2 | 18 | 491 |
| JH4 | -----YFDYWGQGTLVTVSS 34.7% (SEQ ID NO: 1) | | | | | | | | | | | | | | | | | | | | |
| 6 | 0 | 0 | 0 | 0 | 0 | 0 | 0 | 0 | 0 | 0 | 0 | 0 | 0 | 0 | 0 | 0 | 0 | 0 | 0 | 1975 | 5683 |
| 7 | 9 | 1 | 10 | 7 | 3950 | 31 | 6 | 26 | 0 | 109 | 4 | 5 | 24 | 4 | 5 | 35 | 7 | 28 | 16 | 59 | 3322 |
| 8 | 26 | 0 | 5991 | 32 | 0 | 91 | 19 | 2 | 1 | 6 | 1 | 21 | 7 | 0 | 8 | 13 | 3 | 6 | 2 | 14 | 1410 |
| 9 | 5 | 18 | 17 | 0 | 119 | 2 | 0 | 0 | 14 | 0 | 2 | 64 | 15 | 16 | 10 | 216 | 11 | 3 | 6 | 6317 | 823 |
| JH5 | ----NWFDPWGQGTLVTVSS 4.8% (SEQ ID NO: 68) | | | | | | | | | | | | | | | | | | | | |
| 5 | 0 | 0 | 0 | 0 | 0 | 0 | 0 | 0 | 0 | 0 | 0 | 274 | 0 | 0 | 0 | 0 | 0 | 0 | 0 | 0 | 764 |
| 6 | 2 | 1 | 0 | 0 | 0 | 1 | 0 | 0 | 0 | 0 | 0 | 0 | 0 | 0 | 0 | 0 | 0 | 0 | 644 | 0 | 390 |
| 7 | 1 | 1 | 0 | 0 | 768 | 2 | 1 | 1 | 0 | 13 | 0 | 0 | 0 | 0 | 0 | 1 | 0 | 2 | 0 | 4 | 244 |
| 8 | 2 | 0 | 810 | 3 | 0 | 1 | 0 | 0 | 0 | 0 | 0 | 1 | 0 | 0 | 0 | 0 | 1 | 1 | 0 | 1 | 218 |
| 9 | 3 | 0 | 3 | 0 | 3 | 0 | 3 | 0 | 0 | 4 | 0 | 4 | 814 | 1 | 0 | 14 | 2 | 0 | 0 | 0 | 187 |
| JH6 | YYYYYGMDVWGQGTTVTVSS 21.1% (SEQ ID NO: 3) | | | | | | | | | | | | | | | | | | | | |
| 1 | 0 | 0 | 0 | 0 | 0 | 0 | 0 | 0 | 0 | 0 | 0 | 0 | 0 | 0 | 0 | 0 | 0 | 0 | 0 | 690 | 3967 |
| 2 | 4 | 0 | 15 | 0 | 16 | 31 | 12 | 2 | 1 | 4 | 0 | 8 | 7 | 4 | 14 | 18 | 7 | 4 | 1 | 1694 | 2815 |

TABLE 1082-continued

Tally of J stumps

| A | C | D | E | F | G | H | I | K | L | M | N | P | Q | R | S | T | V | W | Y | — |
|---|---|---|---|---|---|---|---|---|---|---|---|---|---|---|---|---|---|---|---|---|
| 3 | 3 | 0 | 19 | 3 | 14 | 23 | 16 | 1 | 5 | 9 | 0 | 16 | 9 | 5 | 12 | 20 | 4 | 1 | 4 | 2440 | 2053 |
| 4 | 4 | 0 | 14 | 2 | 31 | 16 | 25 | 3 | 2 | 10 | 0 | 13 | 6 | 5 | 15 | 35 | 5 | 5 | 4 | 2815 | 1647 |
| 5 | 2 | 1 | 9 | 1 | 23 | 19 | 21 | 1 | 1 | 3 | 1 | 15 | 3 | 1 | 7 | 26 | 3 | 0 | 1 | 3350 | 11 |
| 6 | 69 | 5 | 14 | 1 | 4 | 3057 | 8 | 1 | 0 | 0 | 0 | 8 | 7 | 5 | 4 | 15 | 3 | 7 | 0 | 657 | 792 |
| 7 | 3 | 0 | 1 | 0 | 4 | 5 | 0 | 18 | 2 | 108 | 3866 | 0 | 2 | 2 | 3 | 1 | 7 | 18 | 3 | 1 | 613 |
| 8 | 7 | 0 | 4064 | 5 | 1 | 17 | 4 | 1 | 0 | 2 | 0 | 11 | 2 | 0 | 0 | 3 | 2 | 3 | 2 | 6 | 527 |
| 9 | 9 | 0 | 1 | 0 | 6 | 1 | 1 | 19 | 0 | 7 | 2 | 1 | 1 | 0 | 1 | 4 | 0 | 4092 | 0 | 1 | 511 |

TABLE 1097

HC CDR3 libraries

| Library | CDR3 Length | Leadin | D region sequence | DJ fill sequence | J stump sequence | FR4 sequence |
|---|---|---|---|---|---|---|
| 5.001 | 10, 11, 12 | 6, 7, or 8 X<br>X = (1.0G, .57S, .46R, .42D, .36L, .35Y) | none | none | AFDI (diversity in text) (SEQ ID NO: 986) | WGQGTMVTVSS (JH4) (SEQ ID NO: 987) |
| 5.002 | 13, 14, 15 | 6, 7, 8 X<br>X = (1.0G, .57S, .46R, .42D, .36L, .35Y) | none | none | YYYGMDV (diversity in text) (SEQ ID NO: 984) | WGQGTTVTVSS (jh6) (SEQ ID NO: 988) |
| 5.003 | 18, 19, 20 | 4, 5, 6 X = (1.0G, .57S, .46R, .42D, .36L, .35Y) | YYDFWSGYYT (3-3.2) (SEQ ID NO: 177) | none | YFDY (SEQ ID NO: 985) | WGQGTLVTVSS (JH3) (SEQ ID NO: 989) |
| 5.004 | 15, 16, 17 | 2, 3, 4 X = (1.0G, .57S, .46R, .42D, .36L, .35Y) | GYSSGWY (6-19.1) (SEQ ID NO: 218) | 2X, X = (1.0G, .57S, .46R, .42D, .36L, .35Y) | AFDI (SEQ ID NO: 986) | WGQGTMVTVSS (JH4) (SEQ ID NO: 987) |
| 5.005 | 11-14 | 0, 1, 2 X (1.0G, .57S, .46R, .42D, .36L, .35Y) | GYSSGWY (6-19.1) (SEQ ID NO: 218) | 0, 1 X = (1.0G, .57S, .46R, .42D, .36L, .35Y) | YFDY (SEQ ID NO: 985) | WGQGTLVTVSS (JH3) (SEQ ID NO: 989) |
| 5.006 | 19-25 | 0, 1, 2, 3 X (1.0G, .57S, .46R, .42D, .36L, .35Y) | GYCSGGSCYS (2-2.2) (Cys residues constant) (SEQ ID NO: 136) | 0, 1, 2, 3 X = (1.0G, .57S, .46R, .42D, .36L, .35Y) | YYYYYGMDV (parent AA 8X others) (SEQ ID NO: 990) | WGQGTTVTVSS (jh6) (SEQ ID NO: 988) |

REFERENCES

The contents of all cited references including literature references, issued patents, published or non-published patent applications cited throughout this application as well as those listed below are hereby expressly incorporated by reference in their entireties. In case of conflict, the present application, including any definitions herein, will control.

U.S. Published Application 2005-0119455A1
Sidhu et al., *J Mol. Biol.* 2004 338:299-310.

EQUIVALENTS

A number of embodiments of the invention have been described. Nevertheless, it will be understood that various modifications may be made without departing from the spirit and scope of the invention. Accordingly, other embodiments are within the scope of the following claims.

---

The invention claimed is:

1. A library of vectors or genetic packages, comprising variegated DNA sequences each encoding an antibody heavy chain (HC) variable region that comprises a HC CDR1, a HC CDR2, and a HC CDR3, wherein the HC CDR3 regions encoded by the variegated DNA sequences are three amino acids in length and:
the first residue of HC CDR3 varies among F, S, Y, D, and R in a 3:1:1:1:1 ratio, respectively;
the second residue of HC CDR3 varies among Q, E, R, S, Y, and L in a 3:1:1:1:1:1 ratio, respectively; and
the third residue of HC CDR3 varies among H, D, R, S, Y, and L in a 3:1:1:1:1:1 ratio, respectively.

2. The library of claim 1, wherein a FR3 is located at the amino terminus of the CDR3, and the last residue of the FR3 varies between K and R in a 3:1 ratio, respectively.

3. A library of vectors or genetic packages, comprising variegated DNA sequences each encoding an antibody heavy chain (HC) variable region that comprises a HC CDR1, a HC CDR2, and a HC CDR3, wherein the HC CDR3 regions encoded by the variegated DNA sequences are three amino acids in length and:
the first residue of HC CDR3 varies among T, Y, R, D, and L in a 5:1:1:1:1 ratio, respectively;
the second residue of HC CDR3 varies among T, Y, R, D, and L in a 5:1:1:1:1 ratio, respectively; and
the third residue of HC CDR3 varies among G, S, Y, R, D, and L in a 5:1:1:1:1:1 ratio, respectively.

4. A library of vectors or genetic packages, comprising variegated DNA sequences each encoding an antibody heavy chain (HC) variable region that comprises a HC CDR1, a HC CDR2, and a HC CDR3, wherein the HC CDR3 regions encoded by the variegated DNA sequences are four amino acids in length set forth as $X_1X_2X_3X_4$ (SEQ ID NO:996), wherein:
residue $X_1$ of HC CDR3 varies among Y, S, D R, and L in a 4:1:1:1:1 ratio, respectively;
residue $X_2$ of HC CDR3 varies among F, S, Y, D, R, and L in a 4:1:1:1:1:1 ratio, respectively;
residue $X_3$ of HC CDR3 varies among D, R, S, Y, and L in a 4:1:1:1:1 ratio, respectively; and
residue $X_4$ of HC CDR3 varies among L, S, Y, D, and R in a 4:1:1:1:1 ratio, respectively.

5. A library of vectors or genetic packages, comprising variegated DNA sequences each encoding an antibody heavy chain (HC) variable region that comprises a HC CDR1, a HC CDR2, and a HC CDR3, wherein the HC CDR3 regions encoded by the variegated DNA sequences are four amino acids in length set forth as $X_1X_2X_3X_4$ (SEQ ID NO:997), wherein:
residue $X_1$ of HC CDR3 varies among L, S, Y, D, and R in a 4:1:1:1:1 ratio, respectively;
residue $X_2$ of HC CDR3 varies among L, S, Y, D, and R in a 4:1:1:1:1 ratio, respectively;
residue $X_3$ of HC CDR3 varies among W, S, Y, D, and R in a 4:1:1:1:1 ratio, respectively; and
residue $X_4$ of HC CDR3 varies among F, S, Y, D, and R in a 4:1:1:1:1 ratio, respectively.

6. The library of claim 5, wherein a FR3 is located at the amino terminus of the HC CDR3, and the last residue of the FR3 varies between K and R in a 4:1 ratio, respectively.

7. A library of vectors or genetic packages, comprising variegated DNA sequences each encoding an antibody heavy chain (HC) variable region that comprises a HC CDR1, a HC CDR2, and a HC CDR3, wherein the HC CDR3 regions encoded by the variegated DNA sequences are sixteen amino acids in length set forth as $X_1X_2X_3X_4X_5X_6X_7X_8X_9X_{10}X_{11}X_{12}X_{13}X_{14}X_{15}X_{16}$ (SEQ ID NO:998), wherein:
residue $X_1$ of HC CDR3 varies among Y, S, R, D, and L in a 3:1:1:1:1 ratio, respectively;
residue $X_2$ of HC CDR3 varies among Y, S, R, D, and L in a 3:1:1:1:1 ratio, respectively;
residue $X_3$ of HC CDR3 varies among Y, S, R, D, and L in a 3:1:1:1:1 ratio, respectively;
residue $X_4$ of HC CDR3 varies among D, Y, S, R, and L in a 3:1:1:1:1 ratio, respectively;

residue $X_5$ of HC CDR3 varies among S, Y, R, D, and L in a 3:1:1:1:1 ratio, respectively;

residue $X_6$ of HC CDR3 varies among S, Y, R, D, and L in a 3:1:1:1:1 ratio, respectively;

residue $X_7$ of HC CDR3 varies among G, A, S, Y, R, D, and L in a 3:1:1:1:1:1:1 ratio, respectively;

residue $X_8$ of HC CDR3 varies among Y, S, R, D, and L in a 3:1:1:1:1 ratio, respectively;

residue $X_9$ of HC CDR3 varies among Y, S, R, D, and L in a 3:1:1:1:1 ratio, respectively;

residue $X_{10}$ of HC CDR3 varies among Y, S, R, D, and L in a 3:1:1:1:1 ratio, respectively;

residue $X_{11}$ of HC CDR3 varies among A, S, Y, R, and D in a 3:1:1:1:1 ratio, respectively;

residue $X_{12}$ of HC CDR3 varies among E, R, S, Y, and L in a 3:1:1:1:1 ratio, respectively;

residue $X_{13}$ of HC CDR3 varies among Y, S, R, D, and L in a 3:1:1:1:1 ratio, respectively;

residue $X_{14}$ of HC CDR3 varies among F, Y, S, R, and D in a 3:1:1:1:1 ratio, respectively;

residue $X_{15}$ of HC CDR3 varies among Q, E, R, S, and Y in a 3:1:1:1:1 ratio, respectively; and residue $X_{16}$ of HC CDR3 varies among H, E, R, S, Y, and L in a 3:1:1:1:1:1 ratio, respectively.

8. The library of claim 7, wherein a FR3 is located at the amino terminus of the HC CDR3, and the last residue of the FR3 varies between K and R in a 3:1 ratio, respectively.

9. A library of vectors or genetic packages, comprising variegated DNA sequences each encoding an antibody heavy chain (HC) variable region that comprises a HC CDR1, a HC CDR2, and a HC CDR3, wherein the HC CDR3 regions encoded by the variegated DNA sequences are sixteen amino acids in length set forth as $X_1X_2X_3X_4X_5X_6X_7X_8X_9X_{10}X_{11}X_{12}X_{13}X_{14}X_{15}X_{16}$ (SEQ ID NO:999), wherein:

residue $X_1$ of HC CDR3 varies among G, S, Y, D, R, and L in a 3:1:1:1:1:1 ratio, respectively;

residue $X_2$ of HC CDR3 varies among Y, S, D, R, and L in a 3:1:1:1:1 ratio, respectively;

residue $X_3$ of HC CDR3 is C;

residue $X_4$ of HC CDR3 varies among S, Y, R, D, and L in a 3:1:1:1:1 ratio, respectively;

residue $X_5$ of HC CDR3 varies among S, Y, R, D, and L in a 3:1:1:1:1 ratio, respectively;

residue $X_6$ of HC CDR3 varies among T, Y, R, D, and L in a 3:1:1:1:1 ratio, respectively;

residue $X_7$ of HC CDR3 varies among S, Y, R, D, and L in a 3:1:1:1:1 ratio, respectively;

residue $X_8$ of HC CDR3 is C;

residue $X_9$ of HC CDR3 varies among Y, S, D, R, and L in a 3:1:1:1:1 ratio, respectively;

residue $X_{10}$ of HC CDR3 varies among T, Y, R, D, and L in a 3:1:1:1:1 ratio, respectively;

residue $X_{11}$ of HC CDR3 varies among A, S, Y, D, R, and L in a 3:1:1:1:1:1 ratio, respectively;

residue $X_{12}$ of HC CDR3 varies among E, R, S, Y, and L in a 3:1:1:1:1 ratio, respectively;

residue $X_{13}$ of HC CDR3 varies among Y, S, D, R, and L in a 3:1:1:1:1 ratio, respectively;

residue $X_{14}$ of HC CDR3 varies among F, Y, S, R, D, and L in a 3:1:1:1:1:1 ratio, respectively;

residue $X_{15}$ of HC CDR3 varies among Q, E, R, S, Y, and L in a 3:1:1:1:1:1 ratio, respectively; and residue $X_{16}$ of HC CDR3 varies among H, D, R, S, Y, and L in a 3:1:1:1:1:1 ratio, respectively.

10. The library of claim 9, wherein a FR3 is located at the amino terminus of the HC CDR3, and the last residue of the FR3 varies between K and R in a 3:1 ratio, respectively.

11. A library of vectors or genetic packages, comprising variegated DNA sequences each encoding an antibody heavy chain (HC) variable region that comprises a HC CDR1, a HC CDR2, and a HC CDR3, wherein the HC CDR3 is between 1 and 35 amino acids in length, wherein at least one position of the CDR3 is selected from the group consisting of Tyr, Gly, Asp, Ser, and Arg residues, and wherein more than about 20% of the HC CDR3 regions encoded by the variegated DNA sequences contain Tyr; the library further comprising variegated DNA sequences that encode an A27 light chain (LC), wherein CDR3 of the LC comprises $X_{91}X_{92}X_{93}X_{94}X_{95}X_{96}$ (SEQ ID NO:1001) and is diversified, and wherein position $X_{91}$ is about 64% Y, and about 9% each of F, E, R, and S;

position $X_{92}$ is about 52% G and about 8% each of A, D, R, S, T, and Y;

position $X_{93}$ is about 52% S and about 8% each of D, F, N, R, T, and Y;

position $X_{94}$ is about 55% S and about 9% each of W, E, R, Y, and S;

position $X_{95}$ is about 64% P and about 9% each of E, R, Y, and S, and about 8% with no amino acid; and position $X_{96}$ is about 55% L and about 9% each of E, R, P, Y, and S.

12. A library of vectors or genetic packages, comprising variegated DNA sequences each encoding an antibody heavy chain (HC) variable region that comprises a HC CDR1, a HC CDR2, and a HC CDR3, wherein the HC CDR3 is between 1 and 35 amino acids in length, wherein at least one position of the CDR3 is selected from the group consisting of Tyr, Gly, Asp, Ser, and Arg residues, and wherein more than about 20% of the HC CDR3 regions encoded by the variegated DNA sequences contain Tyr; the library further comprising variegated DNA sequences encoding light chains having diversity at LC CDR1, LC CDR2, and LC CDR3; and where in (i) the CDR1 comprises $X_{27}X_{28}X_{29}X_{30}X_{30a}X_{31}X_{32}X_{33}X_{34}$ (SEQ ID NO:1000) and is diversified, and wherein position $X_{27}$ is about 55% Q, and about 9% each of E, R, Y, S, and L;

position $X_{28}$ is about 46% S and about 9% each of N, T, Y, E, R, and L;

position $X_{30}$ is about 55% S and about 9% each of D, N, R, T, and Y;

position $X_{30a}$ is about 46% S and about 9% each of G, N, R, T, Y, and D, and about 8% with no amino acid;

position $X_{31}$ is about 44% S and about 8% each of D, F, G, N, R, T, and Y;

position $X_{32}$ is about 44% Y and about 7% each of F, D, L, N, Q, R, S, and Y; and position $X_{34}$ is about 70% A and about 15% each of S and Y, ( ii) the CDR2 is diversified, and wherein position 50 is about 55% G, and about 9% each of D, R, S, Y, and L;

position 53 is about 52% S and about 8% each of N, T, S, Y, E, and R; and position 56 is about 64% T and about 9% each of E, R, S, and Y; or (iii) the CDR3 comprises $X_{91}X_{92}X_{93}X_{94}X_{95}X_{96}$ (SEQ ID NO:1001) and is diversified, and wherein position $X_{91}$ is about 64% Y, and about 9% each of F, E, R, and S;

position $X_{92}$ is about 52% G and about 8% each of A, D, R, S, T, and Y;

position $X_{93}$ is about 52% S and about 8% each of D, F, N, R, T, and Y;

position $X_{94}$ is about 55% S and about 9% each of W, E, R, Y, and S;

position $X_{95}$ is about 64% P and about 9% each of E, R, Y, and S, and about 8% with no amino acid; and position $X_{96}$ is about 55% L and about 9% each of E, R, P, Y, and S.

13. The library of claim 11, wherein about 50% of all the positions of the HC CDR3 regions encoded by the variegated DNA sequences are Tyr, Gly, Asp, Ser, or Arg.

14. The library of claim 11, wherein an Arg residue is present in a filler region between HC V and HC D, between HC D and HC J, or between HC V and HC J.

15. The library of claim 11, wherein a framework region (FR) 3 is located at the amino terminus of the HC CDR3, and a FR4 portion of a JH region is located at the carboxy terminus of the HC CDR3.

16. The library of claim 15, wherein the FR3 is a 3-23 VH FR3.

17. The library of claim 11, wherein HC D regions and HC J stumps of the HC CDR3 consist of more than about 20% of Tyr residues.

18. The library of claim 11, wherein CDR1 of the LC comprises $X_{27}X_{28}X_{29}X_{30}X_{30a}X_{31}X_{32}X_{33}X_{34}$ (SEQ ID NO:1000) and is diversified, and wherein position $X_{27}$ is about 55% Q, and about 9% each of E, R, Y, S, and L;

position $X_{28}$ is about 46% S and about 9% each of N, T, Y, E, R, and L;

position $X_{30}$ is about 55% S and about 9% each of D, N, R, T, and Y;

position $X_{30a}$ is about 46% S and about 9% each of G, N, R, T, Y, and D, and about 8% with no amino acid;

position $X_{31}$ is about 44% S and about 8% each of D, F, G, N, R, T, and Y;

position $X_{32}$ is about 44% Y and about 7% each of F, D, L, N, Q, R, S, and Y; and position $X_{34}$ is about 70% A and about 15% each of S and Y.

19. The library of claim 11, wherein CDR2 of the LC is diversified, and wherein position 50 is about 55% G, and about 9% each of D, R, S, Y, and L;

position 53 is about 52% S and about 8% each of N, T, S, Y, E, and R; and position 56 is about 64% T and about 9% each of E, R, S, and Y.

20. The library of claim 18, wherein the library further comprises LC CDR2 diversity of:

position 50 being about 55% G, and about 9% each of D, R, S, Y, and L;

position 53 being about 52% S and about 8% each of N, T, S, Y, E, and R; and position 56 being about 64% T and about 9% each of E, R, S, and Y.

21. The library of claim 12, wherein about 50% of all the positions of the HC CDR3 regions encoded by the variegated DNA sequences are Tyr, Gly, Asp, Ser, or Arg.

22. The library of claim 12, wherein an Arg residue is present in a filler region between HC V and HC D, between HC D and HC J, or between HC V and HC J.

23. The library of claim 12, wherein a framework region (FR) 3 is located at the amino terminus of the HC CDR3, and a FR4 portion of a JH region is located at the carboxy terminus of the HC CDR3.

24. The library of claim 23, wherein the FR3 is a 3-23 VH FR3.

25. The library of claim 12, wherein HC D regions and HC J stumps of the HC CDR3 consist of more than about 20% of Tyr residues.

* * * * *

SEQUENCE LISTING

```
<160> NUMBER OF SEQ ID NOS: 1001

<210> SEQ ID NO 1
<211> LENGTH: 15
<212> TYPE: PRT
<213> ORGANISM: Homo sapiens

<400> SEQUENCE: 1

Tyr Phe Asp Tyr Trp Gly Gln Gly Thr Leu Val Thr Val Ser Ser
1               5                   10                  15

<210> SEQ ID NO 2
<211> LENGTH: 15
<212> TYPE: PRT
<213> ORGANISM: Homo sapiens

<400> SEQUENCE: 2

Ala Phe Asp Ile Trp Gly Gln Gly Thr Met Val Thr Val Ser Ser
1               5                   10                  15

<210> SEQ ID NO 3
<211> LENGTH: 20
<212> TYPE: PRT
<213> ORGANISM: Homo sapiens

<400> SEQUENCE: 3

Tyr Tyr Tyr Tyr Tyr Gly Met Asp Val Trp Gly Gln Gly Thr Thr Val
1               5                   10                  15

Thr Val Ser Ser
            20

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95
```

```
Thr Phe Gly Pro Gly Thr Lys Val Asp Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Thr Pro Phe
                85                  90                  95

Thr Phe Gly Pro Gly Thr Lys Val Asp Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
```

```
                1               5                  10                 15
Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                  70                 75                  80

Glu Asp Phe Ala Thr Tyr Tyr Cys Gln Gln Glu Tyr Ser Thr Pro Phe
                85                 90                 95

Thr Phe Gly Pro Gly Thr Lys Val Asp Ile Lys
                100                105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Ile Ser Arg Tyr
                20                 25                 30

Leu Asn Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                  70                 75                  80

Glu Asp Phe Ala Thr Tyr Tyr Cys Gln Gln Ser Tyr Ser Thr Pro Phe
                85                 90                 95

Thr Phe Gly Pro Gly Thr Lys Val Asp Ile Lys
                100                105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Ile Ser Glu Tyr
                20                 25                 30

Leu Asn Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                  70                 75                  80

Glu Asp Phe Ala Thr Tyr Tyr Cys Gln Gln Ser Tyr Arg Thr Pro Phe
```

```
Thr Phe Gly Pro Gly Thr Lys Val Asp Ile Lys
                100                 105
```

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
                100                 105
```

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
                100                 105
```

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Pro Leu
                85                  90                  95

Thr Phe Gly Gly Gly Thr Lys Val Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Asn Trp Pro Leu
                85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Asn Trp Pro Leu
                85                  90                  95

Thr Phe Gly Gly Gly Thr Lys Val Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Glu Asn Trp Pro Leu
                85                  90                  95

Thr Phe Gly Gly Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Gly Trp Pro Leu
                85                  90                  95

Thr Phe Gly Gly Gly Thr Lys Val Glu Ile Lys
            100                 105

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 22
<211> LENGTH: 108
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Ser Ser Pro
                85                  90                  95

Phe Thr Phe Gly Pro Gly Thr Lys Val Asp Ile Lys
            100                 105

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser

```
                     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Arg Ser Ser Pro
                 85                  90                  95

Phe Thr Phe Gly Pro Gly Thr Lys Val Asp Ile Lys
            100                 105

<210> SEQ ID NO 25
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Asp Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Glu Ser Ser Pro
                 85                  90                  95

Phe Thr Phe Gly Pro Gly Thr Lys Val Asp Ile Lys
            100                 105

<210> SEQ ID NO 26
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Pro
                 85                  90                  95

Phe Thr Phe Gly Pro Gly Thr Lys Val Asp Ile Lys
            100                 105

<210> SEQ ID NO 27
<211> LENGTH: 107
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 27

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105
```

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Ile
                85                  90                  95

Thr Phe Gly Gln Gly Thr Arg Leu Glu Ile Lys
            100                 105
```

<210> SEQ ID NO 29
<211> LENGTH: 4
<212> TYPE: PRT
<213> ORGANISM: Mus sp.

<400> SEQUENCE: 29

```
Asn Trp Asp Tyr
1
```

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 30

Thr Ala Val Tyr Tyr Cys Ala Lys
1               5

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Ala Val Tyr Tyr Cys Ala Lys Phe Gln His Trp Gly Gln Gly Thr
1               5                   10                  15

Leu Val Thr Val Ser Ser
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Ala Val Tyr Tyr Cys Ala Lys Phe Asp Leu Trp Gly Arg Gly Thr
1               5                   10                  15

Leu Val Thr Val Ser Ser
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ala Val Tyr Tyr Cys Ala Lys Phe Asp Ile Trp Gly Gln Gly Thr
1               5                   10                  15

Met Val Thr Val Ser Ser
            20

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Ala Val Tyr Tyr Cys Ala Lys Phe Asp Tyr Trp Gly Gln Gly Thr
1               5                   10                  15

Leu Val Thr Val Ser Ser
            20

<210> SEQ ID NO 35
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Thr Ala Val Tyr Tyr Cys Ala Lys Phe Asp Pro Trp Gly Gln Gly Thr
1               5                   10                  15

Leu Val Thr Val Ser Ser
            20

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Ala Val Tyr Tyr Cys Ala Lys Met Asp Val Trp Gly Gln Gly Thr
1               5                   10                  15

Thr Val Thr Val Ser Ser
            20

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ala Val Tyr Tyr Cys Ala Lys Gly Thr Thr Trp Gly Gln Gly Thr
1               5                   10                  15

Leu Val Thr Val Ser Ser
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ala Val Tyr Tyr Cys Ala Lys Thr Thr Gly Trp Gly Gln Gly Thr
1               5                   10                  15

Leu Val Thr Val Ser Ser
            20

<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Ala Val Tyr Tyr Cys Ala Lys Ile Phe Gly Trp Gly Arg Gly Thr
1               5                   10                  15

Leu Val Thr Val Ser Ser
            20
```

```
<210> SEQ ID NO 40
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Ala Val Tyr Tyr Cys Ala Lys Tyr Phe Gln His Trp Gly Gln Gly
1               5                   10                  15

Thr Leu Val Thr Val Ser Ser
            20

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ala Val Tyr Tyr Cys Ala Lys Tyr Phe Asp Leu Trp Gly Arg Gly
1               5                   10                  15

Thr Leu Val Thr Val Ser Ser
            20

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Ala Val Tyr Tyr Cys Ala Lys Ala Phe Asp Ile Trp Gly Gln Gly
1               5                   10                  15

Thr Met Val Thr Val Ser Ser
            20

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Ala Val Tyr Tyr Cys Ala Lys Tyr Phe Asp Tyr Trp Gly Gln Gly
1               5                   10                  15

Thr Leu Val Thr Val Ser Ser
            20

<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Thr Ala Val Tyr Tyr Cys Ala Lys Trp Phe Asp Pro Trp Gly Gln Gly
1               5                   10                  15

Thr Leu Val Thr Val Ser Ser
            20

<210> SEQ ID NO 45
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Ala Val Tyr Tyr Cys Ala Lys Gly Met Asp Val Trp Gly Gln Gly
1               5                   10                  15

Thr Thr Val Thr Val Ser Ser
            20

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Ala Val Tyr Tyr Cys Ala Lys Leu Leu Trp Phe Trp Gly Arg Gly
1               5                   10                  15

Thr Leu Val Thr Val Ser Ser
            20

<210> SEQ ID NO 47
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Ala Val Tyr Tyr Cys Ala Lys Glu Tyr Phe Gln His Trp Gly Gln
1               5                   10                  15

Gly Thr Leu Val Thr Val Ser Ser
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ala Val Tyr Tyr Cys Ala Lys Trp Tyr Phe Asp Leu Trp Gly Arg
1               5                   10                  15

Gly Thr Leu Val Thr Val Ser Ser
            20

<210> SEQ ID NO 49
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 49

Thr Ala Val Tyr Tyr Cys Ala Lys Tyr Ala Phe Asp Ile Trp Gly Gln
1               5                   10                  15

Gly Thr Met Val Thr Val Ser Ser
            20

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Ala Val Tyr Tyr Cys Ala Lys Ser Tyr Phe Asp Tyr Trp Gly Gln
1               5                   10                  15

Gly Thr Leu Val Thr Val Ser Ser
            20

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ala Val Tyr Tyr Cys Ala Lys Asn Trp Phe Asp Pro Trp Gly Gln
1               5                   10                  15

Gly Thr Leu Val Thr Val Ser Ser
            20

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ala Val Tyr Tyr Cys Ala Lys Tyr Gly Met Asp Val Trp Gly Gln
1               5                   10                  15

Gly Thr Thr Val Thr Val Ser Ser
            20

<210> SEQ ID NO 53
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ala Val Tyr Tyr Cys Ala Lys Asp Ile Val Leu Met Trp Gly Arg
1               5                   10                  15

Gly Thr Leu Val Thr Val Ser Ser
```

20

<210> SEQ ID NO 54
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Glu Asp Thr Ala Val Tyr Tyr Cys Ala Lys Asp Ile Val Leu Met
1               5                   10                  15

Trp Gly Gln Gly Thr Thr Val Thr Val Ser Ser
            20                  25

<210> SEQ ID NO 55
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(48)
<223> OTHER INFORMATION: a, c, g or t
<220> FEATURE:
<223> OTHER INFORMATION: see specification as filed for detailed
      description of substitutions and preferred embodiments

<400> SEQUENCE: 55
gctgaggata ctgcagttta ttactgcgct aagnnnnnnn nnnnnnnntg gggccagggt      60
actacggtca ccgtctccag t                                                81

<210> SEQ ID NO 56
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(31)
<223> OTHER INFORMATION: Any amino acid

<400> SEQUENCE: 56

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Xaa Trp
            20                  25                  30

Gly Gln Gly Thr Thr Val Thr Val Ser Ser
        35                  40

<210> SEQ ID NO 57
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS

```
<222> LOCATION: (10)..(135)
<220> FEATURE:
<221> NAME/KEY: modified_base
<222> LOCATION: (94)..(95)
<223> OTHER INFORMATION: a, c, g, t, unknown or other
<220> FEATURE:
<221> NAME/KEY: modified_base
<222> LOCATION: (97)..(98)
<223> OTHER INFORMATION: a, c, g, t, unknown or other
<220> FEATURE:
<221> NAME/KEY: modified_base
<222> LOCATION: (100)..(101)
<223> OTHER INFORMATION: a, c, g, t, unknown or other

<400> SEQUENCE: 57 ttcactatc tct aga gac aac tct aag aat act ctc tac ttg cag atg aac      51
          Ser Arg Asp Asn Ser Lys Asn Thr Leu Tyr Leu Gln Met Asn
          1               5                   10 agc tta agg gct gag gat act gca gtt tat tac tgc gct arg nnk nnk        99
Ser Leu Arg Ala Glu Asp Thr Ala Val Tyr Tyr Cys Ala Xaa Xaa Xaa
15                  20                  25                  30 nnk tgg ggc cag ggt act acg gtc acc gtc tcc agt                       135
Xaa Trp Gly Gln Gly Thr Thr Val Thr Val Ser Ser
                35                  40

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(24)
<223> OTHER INFORMATION: a, c, g, t, unknown or other
<220> FEATURE:
<221> NAME/KEY: modified_base
<222> LOCATION: (26)..(27)
<223> OTHER INFORMATION: a, c, g, t, unknown or other
<220> FEATURE:
<221> NAME/KEY: modified_base
<222> LOCATION: (29)..(30)
<223> OTHER INFORMATION: a, c, g, t, unknown or other

<400> SEQUENCE: 58
tgcagtttat tactgcgcta rgnnknnknn ktggggccag ggtactac                   48

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tggggccagg gtactacggt caccgtctcc agt                                   33

<210> SEQ ID NO 60
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
```

```
<221> NAME/KEY: MOD_RES
<222> LOCATION: (29)..(32)
<223> OTHER INFORMATION: Any amino acid

<400> SEQUENCE: 60

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Xaa
            20                  25                  30

Trp Gly Gln Gly Thr Thr Val Thr Val Ser Ser
        35                  40

<210> SEQ ID NO 61
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(138)
<220> FEATURE:
<221> NAME/KEY: modified_base
<222> LOCATION: (94)..(95)
<223> OTHER INFORMATION: a, c, g, t, unknown or other
<220> FEATURE:
<221> NAME/KEY: modified_base
<222> LOCATION: (97)..(98)
<223> OTHER INFORMATION: a, c, g, t, unknown or other
<220> FEATURE:
<221> NAME/KEY: modified_base
<222> LOCATION: (100)..(101)
<223> OTHER INFORMATION: a, c, g, t, unknown or other
<220> FEATURE:
<221> NAME/KEY: modified_base
<222> LOCATION: (103)..(104)
<223> OTHER INFORMATION: a, c, g, t, unknown or other

<400> SEQUENCE: 61 ttcactatc tct aga gac aac tct aag aat act ctc tac ttg cag atg aac        51
          Ser Arg Asp Asn Ser Lys Asn Thr Leu Tyr Leu Gln Met Asn
          1               5                   10 agc tta agg gct gag gat act gca gtt tat tac tgc gct arg nnk nnk         99
Ser Leu Arg Ala Glu Asp Thr Ala Val Tyr Tyr Cys Ala Xaa Xaa Xaa
15                  20                  25                  30 nnk nnk tgg ggc cag ggt act acg gtc acc gtc tcc agt                    138
Xaa Xaa Trp Gly Gln Gly Thr Thr Val Thr Val Ser Ser
            35                  40

<210> SEQ ID NO 62
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
```

```
<222> LOCATION: (31)..(32)
<223> OTHER INFORMATION: a, c, g, t, unknown or other

<400> SEQUENCE: 62
gcagtttatt actgcgctar gnnknnknnk nnktggggcc agggtactac              50

<210> SEQ ID NO 63
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(33)
<223> OTHER INFORMATION: Any amino acid

<400> SEQUENCE: 63

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Xaa
            20                  25                  30

Xaa Trp Gly Gln Gly Thr Thr Val Thr Val Ser Ser
        35                  40

<210> SEQ ID NO 64
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(141)
<220> FEATURE:
<221> NAME/KEY: modified_base
<222> LOCATION: (94)..(95)
<223> OTHER INFORMATION: a, c, g, t, unknown or other
<220> FEATURE:
<221> NAME/KEY: modified_base
<222> LOCATION: (97)..(98)
<223> OTHER INFORMATION: a, c, g, t, unknown or other
<220> FEATURE:
<221> NAME/KEY: modified_base
<222> LOCATION: (100)..(101)
<223> OTHER INFORMATION: a, c, g, t, unknown or other
<220> FEATURE:
<221> NAME/KEY: modified_base
<222> LOCATION: (103)..(104)
<223> OTHER INFORMATION: a, c, g, t, unknown or other
<220> FEATURE:
<221> NAME/KEY: modified_base
<222> LOCATION: (106)..(107)
<223> OTHER INFORMATION: a, c, g, t, unknown or other

<400> SEQUENCE: 64 ttcactatc tct aga gac aac tct aag aat act ctc tac ttg cag atg aac      51
          Ser Arg Asp Asn Ser Lys Asn Thr Leu Tyr Leu Gln Met Asn
          1               5                   10 agc tta agg gct gag gat act gca gtt tat tac tgc gct arg nnk nnk        99
Ser Leu Arg Ala Glu Asp Thr Ala Val Tyr Tyr Cys Ala Xaa Xaa Xaa
15                  20                  25                  30 nnk nnk nnk tgg ggc cag ggt act acg gtc acc gtc tcc agt              141
Xaa Xaa Xaa Trp Gly Gln Gly Thr Thr Val Thr Val Ser Ser
```

<210> SEQ ID NO 65
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (34)..(35)
<223> OTHER INFORMATION: a, c, g, t, unknown or other

<400> SEQUENCE: 65
gcagtttatt actgcgctar gnnknnknnk nnknnktggg gccagggtac tac            53

<210> SEQ ID NO 66
<211> LENGTH: 17
<212> TYPE: PRT
<213> ORGANISM: Homo sapiens

<400> SEQUENCE: 66

Ala Glu Tyr Phe Gln His Trp Gly Gln Gly Thr Leu Val Thr Val Ser
1               5                   10                  15
Ser

<210> SEQ ID NO 67
<211> LENGTH: 17
<212> TYPE: PRT
<213> ORGANISM: Homo sapiens

<400> SEQUENCE: 67

Tyr Trp Tyr Phe Asp Leu Trp Gly Arg Gly Thr Leu Val Thr Val Ser
1               5                   10                  15
Ser

<210> SEQ ID NO 68
<211> LENGTH: 16
<212> TYPE: PRT
<213> ORGANISM: Homo sapiens

<400> SEQUENCE: 68

Asn Trp Phe Asp Pro Trp Gly Gln Gly Thr Leu Val Thr Val Ser Ser
1               5                   10                  15

<210> SEQ ID NO 69
<211> LENGTH: 39
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (18)..(19)
<223> OTHER INFORMATION: Any amino acid

<400> SEQUENCE: 69

Tyr Tyr Cys Ala Xaa Xaa Xaa Gly Tyr Cys Ser Xaa Xaa Ser Cys Tyr
1               5                   10                  15

Thr Xaa Xaa Tyr Ser Tyr Ala Glu Tyr Phe Gln His Trp Gly Gln Gly
            20                  25                  30

Thr Leu Val Thr Val Ser Ser
            35

<210> SEQ ID NO 70
<211> LENGTH: 10
<212> TYPE: PRT
<213> ORGANISM: Homo sapiens

<400> SEQUENCE: 70

Gly Tyr Cys Ser Ser Thr Ser Cys Tyr Thr
1               5                   10

<210> SEQ ID NO 71
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (35)..(36)
<223> OTHER INFORMATION: Any amino acid
<220> FEATURE:
<221> NAME/KEY: MOD_RES
<222> LOCATION: (41)..(42)
<223> OTHER INFORMATION: Any amino acid

<400> SEQUENCE: 71

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Gly Tyr
            20                  25                  30

Cys Ser Xaa Xaa Ser Cys Tyr Thr Xaa Xaa Tyr Ser Tyr Ala Glu Tyr
            35                  40                  45

Phe Gln His Trp Gly Gln Gly Thr Leu Val Thr Val Ser Ser
            50                  55                  60

<210> SEQ ID NO 72
<211> LENGTH: 195
<212> TYPE: DNA
```

-continued

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(195)
<220> FEATURE:
<221> NAME/KEY: modified_base
<222> LOCATION: (94)..(95)
<223> OTHER INFORMATION: a, c, g, t, unknown or other
<220> FEATURE:
<221> NAME/KEY: modified_base
<222> LOCATION: (97)..(98)
<223> OTHER INFORMATION: a, c, g, t, unknown or other
<220> FEATURE:
<221> NAME/KEY: modified_base
<222> LOCATION: (112)..(113)
<223> OTHER INFORMATION: a, c, g, t, unknown or other
<220> FEATURE:
<221> NAME/KEY: modified_base
<222> LOCATION: (115)..(116)
<223> OTHER INFORMATION: a, c, g, t, unknown or other
<220> FEATURE:
<221> NAME/KEY: modified_base
<222> LOCATION: (130)..(131)
<223> OTHER INFORMATION: a, c, g, t, unknown or other
<220> FEATURE:
<221> NAME/KEY: modified_base
<222> LOCATION: (133)..(134)
<223> OTHER INFORMATION: a, c, g, t, unknown or other

<400> SEQUENCE: 72 ttcactatc tct aga gac aac tct aag aat act ctc tac ttg cag atg aac      51
           Ser Arg Asp Asn Ser Lys Asn Thr Leu Tyr Leu Gln Met Asn
             1               5                  10 agc tta agg gct gag gat act gca gtt tat tac tgc gct arg nnk nnk        99
Ser Leu Arg Ala Glu Asp Thr Ala Val Tyr Tyr Cys Ala Xaa Xaa Xaa
 15              20                  25                  30 ggt tat tgt tcc nnk nnk tct tgc tat act nnk nnk tat tcc tac gct       147
Gly Tyr Cys Ser Xaa Xaa Ser Cys Tyr Thr Xaa Xaa Tyr Ser Tyr Ala
                 35                  40                  45 gaa tat ttc cag cac tgg ggc cag ggt act ctg gtc acc gtc tcc agt       195
Glu Tyr Phe Gln His Trp Gly Gln Gly Thr Leu Val Thr Val Ser Ser
         50                  55                  60

<210> SEQ ID NO 73
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (58)..(59)
<223> OTHER INFORMATION: a, c, g, t, unknown or other
<220> FEATURE:
```

```
<221> NAME/KEY: modified_base
<222> LOCATION: (61)..(62)
<223> OTHER INFORMATION: a, c, g, t, unknown or other

<400> SEQUENCE: 73
gcagtttatt actgcgctar gnnknnkggt tattgttccn nknnktcttg ctatactnnk    60
nnktattcct acgctgaata tttccagcac tggggccagg gtactct                107

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gcagtttatt actgcgct                                                 18

<210> SEQ ID NO 75
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agagtaccct ggccccagac gtccataccg taatagt                            37

<210> SEQ ID NO 76
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
actattacgg tatggacgtc tggggccagg gtactct                            37

<210> SEQ ID NO 77
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ttcactatct ctagagacaa ctctaagaat actctctact tgcagatgaa cagcttaagg    60
gctgaggata ctgcagttta ttactgcgct                                    90

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
actggagacg gtgaccagag taccctggcc cca                                33

<210> SEQ ID NO 79
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tggggccagg gtactctggt caccgtctcc agt                                33

<210> SEQ ID NO 80
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (18)..(19)
<223> OTHER INFORMATION: Any amino acid

<400> SEQUENCE: 80

Tyr Tyr Cys Ala Xaa Xaa Xaa Tyr Tyr Tyr Gly Xaa Gly Ser Xaa Tyr
1               5                   10                  15

Asn Xaa Xaa Ser Tyr Tyr Ala Glu Tyr Phe Gln His Trp Gly Gln Gly
            20                  25                  30

Thr Leu Val Thr Val Ser Ser
        35

<210> SEQ ID NO 81
<211> LENGTH: 10
<212> TYPE: PRT
<213> ORGANISM: Homo sapiens

<400> SEQUENCE: 81

Tyr Tyr Tyr Gly Ser Gly Ser Tyr Tyr Asn
1               5                   10

<210> SEQ ID NO 82
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
```

<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (41)..(42)
<223> OTHER INFORMATION: Any amino acid

<400> SEQUENCE: 82

```
Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Tyr Tyr
            20                  25                  30

Tyr Gly Xaa Gly Ser Xaa Tyr Asn Xaa Xaa Ser Tyr Tyr Ala Glu Tyr
        35                  40                  45

Phe Gln His Trp Gly Gln Gly Thr Leu Val Thr Val Ser Ser
    50                  55                  60
```

<210> SEQ ID NO 83
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(195)
<220> FEATURE:
<221> NAME/KEY: modified_base
<222> LOCATION: (94)..(95)
<223> OTHER INFORMATION: a, c, g, t, unknown or other
<220> FEATURE:
<221> NAME/KEY: modified_base
<222> LOCATION: (97)..(98)
<223> OTHER INFORMATION: a, c, g, t, unknown or other
<220> FEATURE:
<221> NAME/KEY: modified_base
<222> LOCATION: (112)..(113)
<223> OTHER INFORMATION: a, c, g, t, unknown or other
<220> FEATURE:
<221> NAME/KEY: modified_base
<222> LOCATION: (121)..(122)
<223> OTHER INFORMATION: a, c, g, t, unknown or other
<220> FEATURE:
<221> NAME/KEY: modified_base
<222> LOCATION: (130)..(131)
<223> OTHER INFORMATION: a, c, g, t, unknown or other
<220> FEATURE:
<221> NAME/KEY: modified_base
<222> LOCATION: (133)..(134)
<223> OTHER INFORMATION: a, c, g, t, unknown or other

<400> SEQUENCE: 83

```
ttcactatc tct aga gac aac tct aag aat act ctc tac ttg cag atg aac      51
          Ser Arg Asp Asn Ser Lys Asn Thr Leu Tyr Leu Gln Met Asn
          1               5                   10 agc tta agg gct gag gat act gca gtt tat tac tgc gct arg nnk nnk        99
Ser Leu Arg Ala Glu Asp Thr Ala Val Tyr Tyr Cys Ala Xaa Xaa Xaa
15                  20                  25                  30 tac tac tat ggt nnk ggc tct nnk tac aat nnk nnk tct tat tac gct       147
Tyr Tyr Tyr Gly Xaa Gly Ser Xaa Tyr Asn Xaa Xaa Ser Tyr Tyr Ala
                35                  40                  45 gag tac ttt caa cat tgg ggc cag ggt act ctg gtc acc gtc tcc agt       195
Glu Tyr Phe Gln His Trp Gly Gln Gly Thr Leu Val Thr Val Ser Ser
            50                  55                  60
```

<210> SEQ ID NO 84
<211> LENGTH: 107

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (49)..(50)
<223> OTHER INFORMATION: a, c, g, t, unknown or other
<220> FEATURE:
<221> NAME/KEY: modified_base
<222> LOCATION: (58)..(59)
<223> OTHER INFORMATION: a, c, g, t, unknown or other
<220> FEATURE:
<221> NAME/KEY: modified_base
<222> LOCATION: (61)..(62)
<223> OTHER INFORMATION: a, c, g, t, unknown or other

<400> SEQUENCE: 84
gcagtttatt actgcgctar gnnknnktac tactatggtn nkggctctnn ktacaatnnk    60
nnktcttatt acgctgagta ctttcaacat tggggccagg gtactct                 107

<210> SEQ ID NO 85
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Arg or Lys
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Tyr or Ser
<220> FEATURE:
<221> NAME/KEY: MOD_RES
<222> LOCATION: (11)..(12)
<223> OTHER INFORMATION: Tyr or Ser
<220> FEATURE:
<221> NAME/KEY: MOD_RES
<222> LOCATION: (14)..(14)
<223> OTHER INFORMATION: Tyr or Ser
<220> FEATURE:
<221> NAME/KEY: MOD_RES
<222> LOCATION: (16)..(16)
<223> OTHER INFORMATION: Tyr or Ser
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (20)..(20)
<223> OTHER INFORMATION: Tyr or Ser
<220> FEATURE:
<221> NAME/KEY: MOD_RES
<222> LOCATION: (21)..(21)
```

<223> OTHER INFORMATION: Any amino acid
<220> FEATURE:
<221> NAME/KEY: MOD_RES
<222> LOCATION: (22)..(22)
<223> OTHER INFORMATION: Tyr or Ser
<220> FEATURE:
<221> NAME/KEY: MOD_RES
<222> LOCATION: (24)..(24)
<223> OTHER INFORMATION: Tyr or Ser
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (27)..(27)
<223> OTHER INFORMATION: Tyr or Ser

<400> SEQUENCE: 85

Ala Val Tyr Tyr Cys Ala Xaa Xaa Xaa Tyr Xaa Xaa Gly Xaa Gly Xaa
1               5                   10                  15

Xaa Tyr Asn Xaa Xaa Xaa Tyr Xaa Ala Xaa Xaa Phe Gln His Trp Gly
            20                  25                  30

Gln Gly Thr Leu
        35

<210> SEQ ID NO 86
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (49)..(50)
<223> OTHER INFORMATION: a, c, g, t, unknown or other
<220> FEATURE:
<221> NAME/KEY: modified_base
<222> LOCATION: (61)..(62)
<223> OTHER INFORMATION: a, c, g, t, unknown or other
<220> FEATURE:
<221> NAME/KEY: modified_base
<222> LOCATION: (76)..(77)
<223> OTHER INFORMATION: a, c, g, t, unknown or other
<220> FEATURE:
<221> NAME/KEY: modified_base
<222> LOCATION: (108)..(108)
<223> OTHER INFORMATION: a, c, g, t, unknown or other

<400> SEQUENCE: 86
gcagtttatt actgcgctar gnnktmctac tmctmtggtt mcggctmtnn ktacaattmt      60
nnktmctatt mcgctnnktm ctttcaacat tggggccagg gtactct                   107

<210> SEQ ID NO 87
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (9)..(9)

-continued

```
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(15)
<223> OTHER INFORMATION: Tyr or Ser
<220> FEATURE:
<221> NAME/KEY: MOD_RES
<222> LOCATION: (19)..(19)
<223> OTHER INFORMATION: Tyr or Ser
<220> FEATURE:
<221> NAME/KEY: MOD_RES
<222> LOCATION: (22)..(22)
<223> OTHER INFORMATION: Tyr or Ser
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(30)
<223> OTHER INFORMATION: Tyr or Ser
<220> FEATURE:
<221> NAME/KEY: MOD_RES
<222> LOCATION: (32)..(34)
<223> OTHER INFORMATION: Tyr or Ser
<220> FEATURE:
<221> NAME/KEY: MOD_RES
<222> LOCATION: (36)..(37)
<223> OTHER INFORMATION: Tyr or Ser

<400> SEQUENCE: 87

Tyr Tyr Cys Ala Xaa Tyr Tyr Ser Xaa Ser Tyr Tyr Xaa Tyr Xaa Tyr
1               5                   10                  15

Asp Ser Xaa Gly Tyr Xaa Tyr Xaa Tyr Tyr Ser Xaa Tyr Xaa Tyr Xaa
            20                  25                  30

Xaa Xaa Ala Xaa Xaa Phe Gln His Trp Gly Gln Gly Thr Leu Val Thr
        35                  40                  45

Val Ser Ser
    50

<210> SEQ ID NO 88
<211> LENGTH: 10
<212> TYPE: PRT
<213> ORGANISM: Homo sapiens

<400> SEQUENCE: 88

Tyr Tyr Tyr Asp Ser Ser Gly Tyr Tyr Tyr
1               5                   10

<210> SEQ ID NO 89
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (32)..(32)
<223> OTHER INFORMATION: Any amino acid
```

```
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (38)..(38)
<223> OTHER INFORMATION: Tyr or Ser
<220> FEATURE:
<221> NAME/KEY: MOD_RES
<222> LOCATION: (42)..(42)
<223> OTHER INFORMATION: Tyr or Ser
<220> FEATURE:
<221> NAME/KEY: MOD_RES
<222> LOCATION: (45)..(45)
<223> OTHER INFORMATION: Tyr or Ser
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (53)..(53)
<223> OTHER INFORMATION: Tyr or Ser
<220> FEATURE:
<221> NAME/KEY: MOD_RES
<222> LOCATION: (55)..(57)
<223> OTHER INFORMATION: Tyr or Ser
<220> FEATURE:
<221> NAME/KEY: MOD_RES
<222> LOCATION: (59)..(60)
<223> OTHER INFORMATION: Tyr or Ser

<400> SEQUENCE: 89

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Tyr Tyr Ser Xaa
            20                  25                  30

Ser Tyr Tyr Xaa Tyr Xaa Tyr Asp Ser Xaa Gly Tyr Xaa Tyr Xaa Tyr
        35                  40                  45

Tyr Ser Xaa Tyr Xaa Tyr Xaa Xaa Xaa Ala Xaa Xaa Phe Gln His Trp
    50                  55                  60

Gly Gln Gly Thr Leu Val Thr Val Ser Ser
65                  70

<210> SEQ ID NO 90
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(231)
<220> FEATURE:
<221> NAME/KEY: modified_base
<222> LOCATION: (103)..(104)
<223> OTHER INFORMATION: a, c, g, t, unknown or other
<220> FEATURE:
<221> NAME/KEY: modified_base
<222> LOCATION: (115)..(116)
<223> OTHER INFORMATION: a, c, g, t, unknown or other
<220> FEATURE:
<221> NAME/KEY: modified_base
<222> LOCATION: (148)..(149)
<223> OTHER INFORMATION: a, c, g, t, unknown or other
<220> FEATURE:
<221> NAME/KEY: modified_base
```

<222> LOCATION: (160)..(161)
<223> OTHER INFORMATION: a, c, g, t, unknown or other

<400> SEQUENCE: 90

```
ttcactatc tct aga gac aac tct aag aat act ctc tac ttg cag atg aac      51
          Ser Arg Asp Asn Ser Lys Asn Thr Leu Tyr Leu Gln Met Asn
            1               5                  10 agc tta agg gct gag gat act gca gtt tat tac tgc gct arg tac tat        99
Ser Leu Arg Ala Glu Asp Thr Ala Val Tyr Tyr Cys Ala Xaa Tyr Tyr
 15              20                  25                  30 tcc nnk tct tac tat nnk tat tmt tac gat agt tmt ggt tac tmc tat       147
Ser Xaa Ser Tyr Tyr Xaa Tyr Xaa Tyr Asp Ser Xaa Gly Tyr Xaa Tyr
             35                  40                  45 nnk tac tat agc nnk tat tmc tac tmc tmt tmc gct tmt tmc ttc caa       195
Xaa Tyr Tyr Ser Xaa Tyr Xaa Tyr Xaa Xaa Xaa Ala Xaa Xaa Phe Gln
         50                  55                  60 cac tgg ggc cag ggt act ctg gtc acc gtc tcc agt                       231
His Trp Gly Gln Gly Thr Leu Val Thr Val Ser Ser
 65                  70
```

<210> SEQ ID NO 91
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (31)..(32)
<223> OTHER INFORMATION: a, c, g, t, unknown or other
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (76)..(77)
<223> OTHER INFORMATION: a, c, g, t, unknown or other
<220> FEATURE:
<221> NAME/KEY: modified_base
<222> LOCATION: (88)..(89)
<223> OTHER INFORMATION: a, c, g, t, unknown or other

<400> SEQUENCE: 91

```
gcagtttatt actgcgctar gtactattcc nnktcttact atnnktattm ttacgatagt      60
tmtggttact mctatnnkta ctatagcnnk tattmctact mctmttmcgc ttmttmcttc     120
caacactggg gccagggtac tct                                             143
```

<210> SEQ ID NO 92
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(7)
<223> OTHER INFORMATION: Tyr or Ser
<220> FEATURE:
<221> NAME/KEY: MOD_RES
<222> LOCATION: (9)..(9)
<223> OTHER INFORMATION: Tyr or Ser
<220> FEATURE:

```
<221> NAME/KEY: MOD_RES
<222> LOCATION: (11)..(12)
<223> OTHER INFORMATION: Tyr or Ser
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Tyr or Ser
<220> FEATURE:
<221> NAME/KEY: MOD_RES
<222> LOCATION: (16)..(16)
<223> OTHER INFORMATION: Tyr or Ser
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(21)
<223> OTHER INFORMATION: Tyr or Ser
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (24)..(24)
<223> OTHER INFORMATION: Tyr or Ser

<400> SEQUENCE: 92

Tyr Tyr Cys Ala Xaa Xaa Xaa Gly Xaa Cys Xaa Xaa Xaa Xaa Cys Xaa
1               5                   10                  15

Thr Xaa Xaa Tyr Xaa Tyr Xaa Xaa Tyr Phe Gln His Trp Gly Gln Gly
            20                  25                  30

Thr Leu Val Thr Val Ser Ser
        35

<210> SEQ ID NO 93
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(30)
<223> OTHER INFORMATION: Tyr or Ser
<220> FEATURE:
<221> NAME/KEY: MOD_RES
<222> LOCATION: (32)..(32)
<223> OTHER INFORMATION: Tyr or Ser
<220> FEATURE:
<221> NAME/KEY: MOD_RES
<222> LOCATION: (34)..(35)
<223> OTHER INFORMATION: Tyr or Ser
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (37)..(37)
<223> OTHER INFORMATION: Tyr or Ser
<220> FEATURE:
<221> NAME/KEY: MOD_RES
<222> LOCATION: (39)..(39)
<223> OTHER INFORMATION: Tyr or Ser
```

```
<220> FEATURE:
<221> NAME/KEY: MOD_RES
<222> LOCATION: (41)..(42)
<223> OTHER INFORMATION: Any amino acid
<220> FEATURE:
<221> NAME/KEY: MOD_RES
<222> LOCATION: (44)..(44)
<223> OTHER INFORMATION: Tyr or Ser
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (47)..(47)
<223> OTHER INFORMATION: Tyr or Ser

<400> SEQUENCE: 93

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Gly Xaa
            20                  25                  30

Cys Xaa Xaa Xaa Xaa Cys Xaa Thr Xaa Xaa Tyr Xaa Tyr Xaa Xaa Tyr
        35                  40                  45

Phe Gln His Trp Gly Gln Gly Thr Leu Val Thr Val Ser Ser
    50                  55                  60

<210> SEQ ID NO 94
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(195)
<220> FEATURE:
<221> NAME/KEY: modified_base
<222> LOCATION: (115)..(116)
<223> OTHER INFORMATION: a, c, g, t, unknown or other
<220> FEATURE:
<221> NAME/KEY: modified_base
<222> LOCATION: (130)..(131)
<223> OTHER INFORMATION: a, c, g, t, unknown or other
<220> FEATURE:
<221> NAME/KEY: modified_base
<222> LOCATION: (133)..(134)
<223> OTHER INFORMATION: a, c, g, t, unknown or other
<220> FEATURE:
<221> NAME/KEY: modified_base
<222> LOCATION: (145)..(146)
<223> OTHER INFORMATION: a, c, g, t, unknown or other

<400> SEQUENCE: 94 ttcactatc tct aga gac aac tct aag aat act ctc tac ttg cag atg aac       51
          Ser Arg Asp Asn Ser Lys Asn Thr Leu Tyr Leu Gln Met Asn
          1               5                   10 agc tta agg gct gag gat act gca gtt tat tac tgc gct arg tmc tmt        99
Ser Leu Arg Ala Glu Asp Thr Ala Val Tyr Tyr Cys Ala Xaa Xaa Xaa
15                  20                  25                  30 ggt tmt tgc tmc tmt nnk tmt tgt tmc acc nnk nnk tat tmt tac nnk       147
Gly Xaa Cys Xaa Xaa Xaa Xaa Cys Xaa Thr Xaa Xaa Tyr Xaa Tyr Xaa
                35                  40                  45 tmt tat ttc cag cac tgg ggc cag ggt act ctg gtc acc gtc tcc agt       195
Xaa Tyr Phe Gln His Trp Gly Gln Gly Thr Leu Val Thr Val Ser Ser
            50                  55                  60

<210> SEQ ID NO 95
```

```
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, g, t, unknown or other
<220> FEATURE:
<221> NAME/KEY: modified_base
<222> LOCATION: (58)..(59)
<223> OTHER INFORMATION: a, c, g, t, unknown or other
<220> FEATURE:
<221> NAME/KEY: modified_base
<222> LOCATION: (61)..(62)
<223> OTHER INFORMATION: a, c, g, t, unknown or other
<220> FEATURE:
<221> NAME/KEY: modified_base
<222> LOCATION: (73)..(74)
<223> OTHER INFORMATION: a, c, g, t, unknown or other

<400> SEQUENCE: 95
gcagtttatt actgcgctar gtmctmtggt tmttgctmct mtnnktmttg ttmcaccnnk      60
nnktattmtt acnnktmtta tttccagcac tggggccagg gtactct                  107

<210> SEQ ID NO 96
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(6)
<223> OTHER INFORMATION: Tyr or Ser
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Tyr or Ser
<220> FEATURE:
<221> NAME/KEY: MOD_RES
<222> LOCATION: (12)..(12)
<223> OTHER INFORMATION: Tyr or Ser
<220> FEATURE:
<221> NAME/KEY: MOD_RES
<222> LOCATION: (14)..(15)
<223> OTHER INFORMATION: Tyr or Ser
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(19)
<223> OTHER INFORMATION: Tyr or Ser
<220> FEATURE:
<221> NAME/KEY: MOD_RES
<222> LOCATION: (22)..(22)
<223> OTHER INFORMATION: Tyr or Ser
<220> FEATURE:
<221> NAME/KEY: MOD_RES
<222> LOCATION: (24)..(24)
<223> OTHER INFORMATION: Tyr or Ser
<220> FEATURE:
<221> NAME/KEY: MOD_RES
```

```
<222> LOCATION: (25)..(25)
<223> OTHER INFORMATION: Any amino acid
<220> FEATURE:
<221> NAME/KEY: MOD_RES
<222> LOCATION: (26)..(26)
<223> OTHER INFORMATION: Tyr or Ser
<220> FEATURE:
<221> NAME/KEY: MOD_RES
<222> LOCATION: (29)..(29)
<223> OTHER INFORMATION: Tyr or Ser
<220> FEATURE:
<221> NAME/KEY: MOD_RES
<222> LOCATION: (31)..(31)
<223> OTHER INFORMATION: Tyr or Ser
<220> FEATURE:
<221> NAME/KEY: MOD_RES
<222> LOCATION: (33)..(33)
<223> OTHER INFORMATION: Tyr or Ser
<220> FEATURE:
<221> NAME/KEY: MOD_RES
<222> LOCATION: (37)..(37)
<223> OTHER INFORMATION: Tyr or Ser

<400> SEQUENCE: 96

Tyr Tyr Cys Ala Xaa Xaa Tyr Xaa Xaa Tyr Gly Xaa Cys Xaa Xaa Xaa
1               5                   10                  15

Ser Cys Xaa Thr Tyr Xaa Ser Xaa Xaa Xaa Tyr Ser Xaa Tyr Xaa Ser
            20                  25                  30

Xaa Tyr Ala Glu Xaa Phe Gln His Trp Gly Gln Gly Thr Leu Val Thr
        35                  40                  45

Val Ser Ser
    50

<210> SEQ ID NO 97
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(29)
<223> OTHER INFORMATION: Tyr or Ser
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (32)..(32)
<223> OTHER INFORMATION: Tyr or Ser
<220> FEATURE:
<221> NAME/KEY: MOD_RES
<222> LOCATION: (35)..(35)
<223> OTHER INFORMATION: Tyr or Ser
<220> FEATURE:
<221> NAME/KEY: MOD_RES
<222> LOCATION: (37)..(38)
<223> OTHER INFORMATION: Tyr or Ser
<220> FEATURE:
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (42)..(42)
<223> OTHER INFORMATION: Tyr or Ser
<220> FEATURE:
<221> NAME/KEY: MOD_RES
```

```
<222> LOCATION: (45)..(45)
<223> OTHER INFORMATION: Tyr or Ser
<220> FEATURE:
<221> NAME/KEY: MOD_RES
<222> LOCATION: (47)..(47)
<223> OTHER INFORMATION: Tyr or Ser
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (49)..(49)
<223> OTHER INFORMATION: Tyr or Ser
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (54)..(54)
<223> OTHER INFORMATION: Tyr or Ser
<220> FEATURE:
<221> NAME/KEY: MOD_RES
<222> LOCATION: (56)..(56)
<223> OTHER INFORMATION: Tyr or Ser

<400> SEQUENCE: 97

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Tyr Xaa Xaa
            20                  25                  30

Tyr Gly Xaa Cys Xaa Xaa Xaa Ser Cys Xaa Thr Tyr Xaa Ser Xaa Xaa
        35                  40                  45

Xaa Tyr Ser Xaa Tyr Xaa Ser Xaa Tyr Ala Glu Tyr Phe Gln His Trp
    50                  55                  60

Gly Gln Gly Thr Leu Val Thr Val Ser Ser
65                  70

<210> SEQ ID NO 98
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(231)
<220> FEATURE:
<221> NAME/KEY: modified_base
<222> LOCATION: (100)..(101)
<223> OTHER INFORMATION: a, c, g, t, unknown or other
<220> FEATURE:
<221> NAME/KEY: modified_base
<222> LOCATION: (124)..(125)
<223> OTHER INFORMATION: a, c, g, t, unknown or other
<220> FEATURE:
<221> NAME/KEY: modified_base
<222> LOCATION: (151)..(152)
<223> OTHER INFORMATION: a, c, g, t, unknown or other
<220> FEATURE:
<221> NAME/KEY: modified_base
<222> LOCATION: (163)..(164)
<223> OTHER INFORMATION: a, c, g, t, unknown or other

<400> SEQUENCE: 98 ttcactatc tct aga gac aac tct aag aat act ctc tac ttg cag atg aac      51
          Ser Arg Asp Asn Ser Lys Asn Thr Leu Tyr Leu Gln Met Asn
          1               5                   10 agc tta agg gct gag gat act gca gtt tat tac tgc gct arg tmt tac        99
```

```
       Ser Leu Arg Ala Glu Asp Thr Ala Val Tyr Tyr Cys Ala Xaa Xaa Tyr
       15                  20                  25                  30 nnk tmc tac ggc tmt tgc tmt tmc nnk tct tgt tmc acc tat tmt tcc       147
Xaa Xaa Tyr Gly Xaa Cys Xaa Xaa Xaa Ser Cys Xaa Thr Tyr Xaa Ser
                    35                  40                  45 tmt nnk tmc tat tct nnk tac tmc agt tmt tat gct gag tat ttc cag       195
Xaa Xaa Xaa Tyr Ser Xaa Tyr Xaa Ser Xaa Tyr Ala Glu Tyr Phe Gln
            50                  55                  60 cac tgg ggc cag ggt act ctg gtc acc gtc tcc agt                       231
His Trp Gly Gln Gly Thr Leu Val Thr Val Ser Ser
            65                  70

<210> SEQ ID NO 99
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (52)..(53)
<223> OTHER INFORMATION: a, c, g, t, unknown or other
<220> FEATURE:
<221> NAME/KEY: modified_base
<222> LOCATION: (79)..(80)
<223> OTHER INFORMATION: a, c, g, t, unknown or other
<220> FEATURE:
<221> NAME/KEY: modified_base
<222> LOCATION: (91)..(92)
<223> OTHER INFORMATION: a, c, g, t, unknown or other

<400> SEQUENCE: 99
gcagtttatt actgcgctar gtmttacnnk tmctacggct attgctmttm cnnktmttgt      60
tmcacctatt mttcctmtnn ktmctattct nnktactmca gttmttatgc tgagtatttc     120
cagcactggg gccagggtac tct                                             143

<210> SEQ ID NO 100
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(6)
<223> OTHER INFORMATION: Tyr or Ser
<220> FEATURE:
<221> NAME/KEY: MOD_RES
<222> LOCATION: (8)..(9)
<223> OTHER INFORMATION: Tyr or Ser
<220> FEATURE:
<221> NAME/KEY: MOD_RES
<222> LOCATION: (12)..(12)
<223> OTHER INFORMATION: Tyr or Ser
<220> FEATURE:
<221> NAME/KEY: MOD_RES
<222> LOCATION: (14)..(15)
<223> OTHER INFORMATION: Tyr or Ser
<220> FEATURE:
<221> NAME/KEY: MOD_RES
<222> LOCATION: (16)..(16)
```

```
<223> OTHER INFORMATION: Any amino acid
<220> FEATURE:
<221> NAME/KEY: MOD_RES
<222> LOCATION: (17)..(17)
<223> OTHER INFORMATION: Tyr or Ser
<220> FEATURE:
<221> NAME/KEY: MOD_RES
<222> LOCATION: (19)..(19)
<223> OTHER INFORMATION: Tyr or Ser
<220> FEATURE:
<221> NAME/KEY: MOD_RES
<222> LOCATION: (22)..(22)
<223> OTHER INFORMATION: Tyr or Ser
<220> FEATURE:
<221> NAME/KEY: MOD_RES
<222> LOCATION: (24)..(24)
<223> OTHER INFORMATION: Tyr or Ser
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (26)..(26)
<223> OTHER INFORMATION: Tyr or Ser
<220> FEATURE:
<221> NAME/KEY: MOD_RES
<222> LOCATION: (29)..(29)
<223> OTHER INFORMATION: Tyr or Ser
<220> FEATURE:
<221> NAME/KEY: MOD_RES
<222> LOCATION: (31)..(31)
<223> OTHER INFORMATION: Tyr or Ser
<220> FEATURE:
<221> NAME/KEY: MOD_RES
<222> LOCATION: (33)..(33)
<223> OTHER INFORMATION: Tyr or Ser
<220> FEATURE:
<221> NAME/KEY: MOD_RES
<222> LOCATION: (36)..(36)
<223> OTHER INFORMATION: Glu, Lys or Gln
<220> FEATURE:
<221> NAME/KEY: MOD_RES
<222> LOCATION: (37)..(37)
<223> OTHER INFORMATION: Tyr or Ser
<220> FEATURE:
<221> NAME/KEY: MOD_RES
<222> LOCATION: (38)..(38)
<223> OTHER INFORMATION: Phe, Ser or Tyr
<220> FEATURE:
<221> NAME/KEY: MOD_RES
<222> LOCATION: (40)..(40)
<223> OTHER INFORMATION: Tyr, His, Asn or Asp

<400> SEQUENCE: 100

Tyr Tyr Cys Ala Xaa Xaa Tyr Xaa Xaa Tyr Gly Xaa Cys Xaa Xaa Xaa
1               5                   10                  15

Xaa Cys Xaa Thr Tyr Xaa Ser Xaa Xaa Xaa Tyr Ser Xaa Tyr Xaa Ser
            20                  25                  30

Xaa Tyr Ala Xaa Xaa Xaa Gln Xaa Trp Gly Gln Gly Thr Leu Val Thr
            35                  40                  45

Val Ser Ser
        50

<210> SEQ ID NO 101
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
```

```
<223> OTHER INFORMATION: Arg or Lys
<220> FEATURE:
<221> NAME/KEY: MOD_RES
<222> LOCATION: (29)..(29)
<223> OTHER INFORMATION: Tyr or Ser
<220> FEATURE:
<221> NAME/KEY: MOD_RES
<222> LOCATION: (31)..(32)
<223> OTHER INFORMATION: Tyr or Ser
<220> FEATURE:
<221> NAME/KEY: MOD_RES
<222> LOCATION: (35)..(35)
<223> OTHER INFORMATION: Tyr or Ser
<220> FEATURE:
<221> NAME/KEY: MOD_RES
<222> LOCATION: (37)..(38)
<223> OTHER INFORMATION: Tyr or Ser
<220> FEATURE:
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (40)..(40)
<223> OTHER INFORMATION: Tyr or Ser
<220> FEATURE:
<221> NAME/KEY: MOD_RES
<222> LOCATION: (42)..(42)
<223> OTHER INFORMATION: Tyr or Ser
<220> FEATURE:
<221> NAME/KEY: MOD_RES
<222> LOCATION: (45)..(45)
<223> OTHER INFORMATION: Tyr or Ser
<220> FEATURE:
<221> NAME/KEY: MOD_RES
<222> LOCATION: (47)..(47)
<223> OTHER INFORMATION: Tyr or Ser
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (49)..(49)
<223> OTHER INFORMATION: Tyr or Ser
<220> FEATURE:
<221> NAME/KEY: MOD_RES
<222> LOCATION: (52)..(52)
<223> OTHER INFORMATION: Tyr or Ser
<220> FEATURE:
<221> NAME/KEY: MOD_RES
<222> LOCATION: (54)..(54)
<223> OTHER INFORMATION: Tyr or Ser
<220> FEATURE:
<221> NAME/KEY: MOD_RES
<222> LOCATION: (56)..(56)
<223> OTHER INFORMATION: Tyr or Ser
<220> FEATURE:
<221> NAME/KEY: MOD_RES
<222> LOCATION: (59)..(59)
<223> OTHER INFORMATION: Lys, Glu or Gln
<220> FEATURE:
<221> NAME/KEY: MOD_RES
<222> LOCATION: (60)..(60)
<223> OTHER INFORMATION: Tyr or Ser
<220> FEATURE:
<221> NAME/KEY: MOD_RES
<222> LOCATION: (61)..(61)
<223> OTHER INFORMATION: Tyr, Ser or Phe
<220> FEATURE:
<221> NAME/KEY: MOD_RES
<222> LOCATION: (63)..(63)
<223> OTHER INFORMATION: Asn, Asp, His or Tyr

<400> SEQUENCE: 101

Ser Arg Asp Asn Ser Lys Asn Thr Leu Tyr Leu Gln Met Asn Ser Leu
1               5                   10                  15
```

```
Arg Ala Glu Asp Thr Ala Val Tyr Tyr Cys Ala Xaa Xaa Tyr Xaa Xaa
            20                  25                  30

Tyr Gly Xaa Cys Xaa Xaa Xaa Xaa Cys Xaa Thr Tyr Xaa Ser Xaa Xaa
        35                  40                  45

Xaa Tyr Ser Xaa Tyr Xaa Ser Xaa Tyr Ala Xaa Xaa Xaa Gln Xaa Trp
 50                  55                  60

Gly Gln Gly Thr Leu Val Thr Val Ser Ser
 65                  70
```

<210> SEQ ID NO 102
<211> LENGTH: 231
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (10)..(231)
<220> FEATURE:
<221> NAME/KEY: modified_base
<222> LOCATION: (124)..(125)
<223> OTHER INFORMATION: a, c, g, t, unknown or other
<220> FEATURE:
<221> NAME/KEY: modified_base
<222> LOCATION: (151)..(152)
<223> OTHER INFORMATION: a, c, g, t, unknown or other
<220> FEATURE:
<221> NAME/KEY: modified_base
<222> LOCATION: (196)..(196)
<223> OTHER INFORMATION: a, c, g, t, unknown or other

<400> SEQUENCE: 102

```
ttcactatc tct aga gac aac tct aag aat act ctc tac ttg cag atg aac      51
          Ser Arg Asp Asn Ser Lys Asn Thr Leu Tyr Leu Gln Met Asn
            1               5                  10 agc tta agg gct gag gat act gca gtt tat tac tgc gct arg tmt tac         99
Ser Leu Arg Ala Glu Asp Thr Ala Val Tyr Tyr Cys Ala Xaa Xaa Tyr
 15              20                  25                  30 tmc tmc tac ggc tmt tgc tmt tmc nnk tmt tgt tmc acc tat tmt tcc        147
Xaa Xaa Tyr Gly Xaa Cys Xaa Xaa Xaa Xaa Cys Xaa Thr Tyr Xaa Ser
                 35                  40                  45 tmt nnk tmc tat tct tmt tac tmc agt tmt tat gct vag tmt thc cag        195
Xaa Xaa Xaa Tyr Ser Xaa Tyr Xaa Ser Xaa Tyr Ala Xaa Xaa Xaa Gln
             50                  55                  60 nac tgg ggc cag ggt act ctg gtc acc gtc tcc agt                        231
Xaa Trp Gly Gln Gly Thr Leu Val Thr Val Ser Ser
 65                  70
```

<210> SEQ ID NO 103
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(6)
<223> OTHER INFORMATION: Tyr or Ser
<220> FEATURE:
<221> NAME/KEY: MOD_RES
<222> LOCATION: (7)..(7)
<223> OTHER INFORMATION: Any amino acid
<220> FEATURE:

```
<221> NAME/KEY: MOD_RES
<222> LOCATION: (8)..(8)
<223> OTHER INFORMATION: Tyr or Ser
<220> FEATURE:
<221> NAME/KEY: MOD_RES
<222> LOCATION: (10)..(10)
<223> OTHER INFORMATION: Tyr or Ser
<220> FEATURE:
<221> NAME/KEY: MOD_RES
<222> LOCATION: (11)..(11)
<223> OTHER INFORMATION: Tyr, His, Asn or Asp
<220> FEATURE:
<221> NAME/KEY: MOD_RES
<222> LOCATION: (12)..(12)
<223> OTHER INFORMATION: Tyr or Ser
<220> FEATURE:
<221> NAME/KEY: MOD_RES
<222> LOCATION: (16)..(17)
<223> OTHER INFORMATION: Tyr or Ser
<220> FEATURE:
<221> NAME/KEY: MOD_RES
<222> LOCATION: (19)..(19)
<223> OTHER INFORMATION: Tyr or Ser
<220> FEATURE:
<221> NAME/KEY: MOD_RES
<222> LOCATION: (21)..(21)
<223> OTHER INFORMATION: Tyr or Ser
<220> FEATURE:
<221> NAME/KEY: MOD_RES
<222> LOCATION: (23)..(23)
<223> OTHER INFORMATION: Tyr or Ser
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (25)..(25)
<223> OTHER INFORMATION: Tyr or Ser
<220> FEATURE:
<221> NAME/KEY: MOD_RES
<222> LOCATION: (27)..(29)
<223> OTHER INFORMATION: Tyr or Ser
<220> FEATURE:
<221> NAME/KEY: MOD_RES
<222> LOCATION: (31)..(31)
<223> OTHER INFORMATION: Tyr or Ser
<220> FEATURE:
<221> NAME/KEY: MOD_RES
<222> LOCATION: (33)..(33)
<223> OTHER INFORMATION: Tyr or Ser
<220> FEATURE:
<221> NAME/KEY: MOD_RES
<222> LOCATION: (35)..(35)
<223> OTHER INFORMATION: Glu, Lys or Gln
<220> FEATURE:
<221> NAME/KEY: MOD_RES
<222> LOCATION: (36)..(36)
<223> OTHER INFORMATION: Tyr or Ser

<400> SEQUENCE: 103

Tyr Tyr Cys Ala Xaa Xaa Xaa Xaa Tyr Xaa Xaa Xaa Val Trp Gly Xaa
1               5                   10                  15

Xaa Arg Xaa Thr Xaa Ser Xaa Xaa Xaa Tyr Xaa Xaa Xaa Tyr Xaa Ser
            20                  25                  30

Xaa Ala Xaa Xaa Phe Gln His Trp Gly Gln Gly Thr Leu Val Thr Val
        35                  40                  45

Ser Ser
    50

<210> SEQ ID NO 104
<211> LENGTH: 12
<212> TYPE: PRT
<213> ORGANISM: Homo sapiens
```

<400> SEQUENCE: 104

Tyr Tyr Asp Tyr Val Trp Gly Ser Tyr Arg Tyr Thr
1               5                   10

<210> SEQ ID NO 105
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(29)
<223> OTHER INFORMATION: Tyr or Ser
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (31)..(31)
<223> OTHER INFORMATION: Tyr or Ser
<220> FEATURE:
<221> NAME/KEY: MOD_RES
<222> LOCATION: (33)..(33)
<223> OTHER INFORMATION: Tyr or Ser
<220> FEATURE:
<221> NAME/KEY: MOD_RES
<222> LOCATION: (34)..(34)
<223> OTHER INFORMATION: Asn, Asp, His or Tyr
<220> FEATURE:
<221> NAME/KEY: MOD_RES
<222> LOCATION: (35)..(35)
<223> OTHER INFORMATION: Tyr or Ser
<220> FEATURE:
<221> NAME/KEY: MOD_RES
<222> LOCATION: (39)..(40)
<223> OTHER INFORMATION: Tyr or Ser
<220> FEATURE:
<221> NAME/KEY: MOD_RES
<222> LOCATION: (42)..(42)
<223> OTHER INFORMATION: Tyr or Ser
<220> FEATURE:
<221> NAME/KEY: MOD_RES
<222> LOCATION: (44)..(44)
<223> OTHER INFORMATION: Tyr or Ser
<220> FEATURE:
<221> NAME/KEY: MOD_RES
<222> LOCATION: (46)..(46)
<223> OTHER INFORMATION: Tyr or Ser
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (48)..(48)
<223> OTHER INFORMATION: Tyr or Ser
<220> FEATURE:
<221> NAME/KEY: MOD_RES
<222> LOCATION: (50)..(52)
<223> OTHER INFORMATION: Tyr or Ser
<220> FEATURE:
<221> NAME/KEY: MOD_RES
<222> LOCATION: (54)..(54)
<223> OTHER INFORMATION: Tyr or Ser
<220> FEATURE:
<221> NAME/KEY: MOD_RES
<222> LOCATION: (56)..(56)
<223> OTHER INFORMATION: Tyr or Ser
<220> FEATURE:

```
<221> NAME/KEY: MOD_RES
<222> LOCATION: (58)..(58)
<223> OTHER INFORMATION: Lys, Glu or Gln
<220> FEATURE:
<221> NAME/KEY: MOD_RES
<222> LOCATION: (59)..(59)
<223> OTHER INFORMATION: Tyr or Ser

<400> SEQUENCE: 105

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Xaa Tyr
            20                  25                  30

Xaa Xaa Xaa Val Trp Gly Xaa Xaa Arg Xaa Thr Xaa Ser Xaa Xaa Xaa
        35                  40                  45

Tyr Xaa Xaa Xaa Tyr Xaa Ser Xaa Ala Xaa Xaa Phe Gln His Trp Gly
    50                  55                  60

Gln Gly Thr Leu Val Thr Val Ser Ser
65                  70

<210> SEQ ID NO 106
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(228)
<220> FEATURE:
<221> NAME/KEY: modified_base
<222> LOCATION: (97)..(98)
<223> OTHER INFORMATION: a, c, g, t, unknown or other
<220> FEATURE:
<221> NAME/KEY: modified_base
<222> LOCATION: (109)..(109)
<223> OTHER INFORMATION: a, c, g, t, unknown or other
<220> FEATURE:
<221> NAME/KEY: modified_base
<222> LOCATION: (148)..(149)
<223> OTHER INFORMATION: a, c, g, t, unknown or other

<400> SEQUENCE: 106 ttcactatc tct aga gac aac tct aag aat act ctc tac ttg cag atg aac      51
          Ser Arg Asp Asn Ser Lys Asn Thr Leu Tyr Leu Gln Met Asn
          1               5                   10 agc tta agg gct gag gat act gca gtt tat tac tgc gct arg tmt nnk        99
Ser Leu Arg Ala Glu Asp Thr Ala Val Tyr Tyr Cys Ala Xaa Xaa Xaa
15              20                  25                  30 tmc tac tmt nat tmt gtt tgg ggt tmt tmc cgt tmt act tmt agt tmc        147
Xaa Tyr Xaa Xaa Xaa Val Trp Gly Xaa Xaa Arg Xaa Thr Xaa Ser Xaa
            35                  40                  45 nnk tmt tac tmc tmt tmc tat tmc agt tmt gct vag tmc ttc cag cat        195
Xaa Xaa Tyr Xaa Xaa Xaa Tyr Xaa Ser Xaa Ala Xaa Xaa Phe Gln His
        50                  55                  60 tgg ggc cag ggt act ctg gtc acc gtc tcc agt                            228
Trp Gly Gln Gly Thr Leu Val Thr Val Ser Ser
                65                  70

<210> SEQ ID NO 107
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (37)..(37)
<223> OTHER INFORMATION: a, c, g, t, unknown or other
<220> FEATURE:
<221> NAME/KEY: modified_base
<222> LOCATION: (76)..(77)
<223> OTHER INFORMATION: a, c, g, t, unknown or other

<400> SEQUENCE: 107
gcagtttatt actgcgctar gtmtnnktmc tactmtnatt mtgtttgggg ttmttmccgt     60
tmtacttmta gttmcnnktm ttactmctmt tmctattmca gttmtgctva gtmcttccag    120
cattggggcc agggtactct                                                140

<210> SEQ ID NO 108
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(6)
<223> OTHER INFORMATION: Tyr or Ser
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(10)
<223> OTHER INFORMATION: Tyr or Ser
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Tyr or Ser
<220> FEATURE:
<221> NAME/KEY: MOD_RES
<222> LOCATION: (14)..(16)
<223> OTHER INFORMATION: Tyr or Ser
<220> FEATURE:
<221> NAME/KEY: MOD_RES
<222> LOCATION: (18)..(18)
<223> OTHER INFORMATION: Tyr or Ser
<220> FEATURE:
<221> NAME/KEY: MOD_RES
<222> LOCATION: (19)..(19)
<223> OTHER INFORMATION: Tyr, His, Asn or Asp
<220> FEATURE:
<221> NAME/KEY: MOD_RES
<222> LOCATION: (20)..(20)
<223> OTHER INFORMATION: Tyr or Ser
<220> FEATURE:
<221> NAME/KEY: MOD_RES
<222> LOCATION: (24)..(25)
<223> OTHER INFORMATION: Tyr or Ser
<220> FEATURE:
<221> NAME/KEY: MOD_RES
<222> LOCATION: (27)..(27)
<223> OTHER INFORMATION: Tyr or Ser
<220> FEATURE:
<221> NAME/KEY: MOD_RES
```

```
<222> LOCATION: (30)..(30)
<223> OTHER INFORMATION: Tyr or Ser
<220> FEATURE:
<221> NAME/KEY: MOD_RES
<222> LOCATION: (32)..(32)
<223> OTHER INFORMATION: Tyr or Ser
<220> FEATURE:
<221> NAME/KEY: MOD_RES
<222> LOCATION: (35)..(35)
<223> OTHER INFORMATION: Glu, Lys or Gln
<220> FEATURE:
<221> NAME/KEY: MOD_RES
<222> LOCATION: (36)..(36)
<223> OTHER INFORMATION: Tyr or Ser

<400> SEQUENCE: 108

Tyr Tyr Cys Ala Xaa Xaa Xaa Xaa Xaa Xaa Xaa Tyr Xaa Xaa Xaa
1               5                   10                  15

Tyr Xaa Xaa Xaa Val Trp Gly Xaa Xaa Arg Xaa Thr Tyr Xaa Ser Xaa
            20                  25                  30

Tyr Ala Xaa Xaa Phe Gln His Trp Gly Gln Gly Thr Leu Val Thr Val
        35                  40                  45

Ser Ser
    50

<210> SEQ ID NO 109
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(29)
<223> OTHER INFORMATION: Tyr or Ser
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (31)..(33)
<223> OTHER INFORMATION: Tyr or Ser
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (35)..(35)
<223> OTHER INFORMATION: Tyr or Ser
<220> FEATURE:
<221> NAME/KEY: MOD_RES
<222> LOCATION: (37)..(39)
<223> OTHER INFORMATION: Tyr or Ser
<220> FEATURE:
<221> NAME/KEY: MOD_RES
<222> LOCATION: (41)..(41)
<223> OTHER INFORMATION: Tyr or Ser
<220> FEATURE:
<221> NAME/KEY: MOD_RES
<222> LOCATION: (42)..(42)
<223> OTHER INFORMATION: Asn, Asp, His or Tyr
<220> FEATURE:
<221> NAME/KEY: MOD_RES
<222> LOCATION: (43)..(43)
<223> OTHER INFORMATION: Tyr or Ser
<220> FEATURE:
<221> NAME/KEY: MOD_RES
```

```
<222> LOCATION: (47)..(48)
<223> OTHER INFORMATION: Tyr or Ser
<220> FEATURE:
<221> NAME/KEY: MOD_RES
<222> LOCATION: (50)..(50)
<223> OTHER INFORMATION: Tyr or Ser
<220> FEATURE:
<221> NAME/KEY: MOD_RES
<222> LOCATION: (53)..(53)
<223> OTHER INFORMATION: Tyr or Ser
<220> FEATURE:
<221> NAME/KEY: MOD_RES
<222> LOCATION: (55)..(55)
<223> OTHER INFORMATION: Tyr or Ser
<220> FEATURE:
<221> NAME/KEY: MOD_RES
<222> LOCATION: (58)..(58)
<223> OTHER INFORMATION: Lys, Glu or Gln
<220> FEATURE:
<221> NAME/KEY: MOD_RES
<222> LOCATION: (59)..(59)
<223> OTHER INFORMATION: Tyr or Ser

<400> SEQUENCE: 109

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Xaa Xaa
            20                  25                  30

Xaa Xaa Xaa Tyr Xaa Xaa Xaa Tyr Xaa Xaa Xaa Val Trp Gly Xaa Xaa
        35                  40                  45

Arg Xaa Thr Tyr Xaa Ser Xaa Tyr Ala Xaa Xaa Phe Gln His Trp Gly
    50                  55                  60

Gln Gly Thr Leu Val Thr Val Ser Ser
65                  70

<210> SEQ ID NO 110
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(228)
<220> FEATURE:
<221> NAME/KEY: modified_base
<222> LOCATION: (97)..(98)
<223> OTHER INFORMATION: a, c, g, t, unknown or other
<220> FEATURE:
<221> NAME/KEY: modified_base
<222> LOCATION: (109)..(110)
<223> OTHER INFORMATION: a, c, g, t, unknown or other
<220> FEATURE:
<221> NAME/KEY: modified_base
<222> LOCATION: (133)..(133)
<223> OTHER INFORMATION: a, c, g, t, unknown or other

<400> SEQUENCE: 110 ttcactatc tct aga gac aac tct aag aat act ctc tac ttg cag atg aac      51
          Ser Arg Asp Asn Ser Lys Asn Thr Leu Tyr Leu Gln Met Asn
          1               5                   10 agc tta agg gct gag gat act gca gtt tat tac tgc gct arg tmt nnk       99
Ser Leu Arg Ala Glu Asp Thr Ala Val Tyr Tyr Cys Ala Xaa Xaa Xaa
 15                  20                  25                  30 tmc tmt tmc nnk tmt tac tmc tmt tmc tac tmt nat tmt gtt tgg ggt      147
Xaa Xaa Xaa Xaa Xaa Tyr Xaa Xaa Xaa Tyr Xaa Xaa Xaa Val Trp Gly
             35                  40                  45 tmt tmc cgt tmt act tat tmc agt tmt tac gct vag tmc ttc cag cat      195
```

Xaa Xaa Arg Xaa Thr Tyr Xaa Ser Xaa Tyr Ala Xaa Xaa Phe Gln His
            50                  55                  60 tgg ggc cag ggt act ctg gtc acc gtc tcc agt                        228
Trp Gly Gln Gly Thr Leu Val Thr Val Ser Ser
        65                  70

<210> SEQ ID NO 111
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(26)
<223> OTHER INFORMATION: a, c, g, t, unknown or other
<220> FEATURE:
<221> NAME/KEY: modified_base
<222> LOCATION: (37)..(38)
<223> OTHER INFORMATION: a, c, g, t, unknown or other
<220> FEATURE:
<221> NAME/KEY: modified_base
<222> LOCATION: (61)..(61)
<223> OTHER INFORMATION: a, c, g, t, unknown or other

<400> SEQUENCE: 111
gcagtttatt actgcgctar gtmtnnktmc tmttmcnnkt mttactmctm ttmctactmt      60
nattmtgttt ggggttmttm ccgttmtact tattmcagtt mttacgctva gtmcttccag     120
cattggggcc agggtactct                                                 140

<210> SEQ ID NO 112
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(8)
<223> OTHER INFORMATION: Tyr or Ser
<220> FEATURE:
<221> NAME/KEY: MOD_RES
<222> LOCATION: (10)..(11)
<223> OTHER INFORMATION: Tyr or Ser
<220> FEATURE:
<221> NAME/KEY: MOD_RES
<222> LOCATION: (13)..(13)
<223> OTHER INFORMATION: Tyr or Ser
<220> FEATURE:
<221> NAME/KEY: MOD_RES
<222> LOCATION: (15)..(15)
<223> OTHER INFORMATION: Tyr or Ser
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (19)..(19)
<223> OTHER INFORMATION: Tyr or Ser
<220> FEATURE:
<221> NAME/KEY: MOD_RES
<222> LOCATION: (20)..(20)

<223> OTHER INFORMATION: Any amino acid
<220> FEATURE:
<221> NAME/KEY: MOD_RES
<222> LOCATION: (21)..(21)
<223> OTHER INFORMATION: Tyr or Ser
<220> FEATURE:
<221> NAME/KEY: MOD_RES
<222> LOCATION: (23)..(23)
<223> OTHER INFORMATION: Tyr or Ser
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (26)..(26)
<223> OTHER INFORMATION: Tyr or Ser

<400> SEQUENCE: 112

Tyr Tyr Cys Ala Xaa Xaa Xaa Xaa Tyr Xaa Xaa Gly Xaa Gly Xaa Xaa
1               5                   10                  15

Tyr Asn Xaa Xaa Xaa Tyr Xaa Ala Xaa Xaa Phe Gln His Trp Gly Gln
            20                  25                  30

Gly Thr Leu Val Thr Val Ser Ser
            35                  40

<210> SEQ ID NO 113
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(23)
<223> OTHER INFORMATION: a, c, g, t, unknown or other
<220> FEATURE:
<221> NAME/KEY: modified_base
<222> LOCATION: (52)..(53)
<223> OTHER INFORMATION: a, c, g, t, unknown or other
<220> FEATURE:
<221> NAME/KEY: modified_base
<222> LOCATION: (64)..(65)
<223> OTHER INFORMATION: a, c, g, t, unknown or other
<220> FEATURE:
<221> NAME/KEY: modified_base
<222> LOCATION: (79)..(80)
<223> OTHER INFORMATION: a, c, g, t, unknown or other

<400> SEQUENCE: 113
gcagtttatt actgcgctar gnnktmctmc tactmctmtg gttmcggctm tnnktacaat      60
tmtnnktmct attmcgctnn ktmctttcaa cattggggcc agggtactct                110

<210> SEQ ID NO 114
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
<222> LOCATION: (6)..(7)
<223> OTHER INFORMATION: Tyr or Ser
<220> FEATURE:
<221> NAME/KEY: MOD_RES
<222> LOCATION: (8)..(8)

```
<223> OTHER INFORMATION: Any amino acid
<220> FEATURE:
<221> NAME/KEY: MOD_RES
<222> LOCATION: (9)..(9)
<223> OTHER INFORMATION: Tyr or Ser
<220> FEATURE:
<221> NAME/KEY: MOD_RES
<222> LOCATION: (11)..(11)
<223> OTHER INFORMATION: Tyr or Ser
<220> FEATURE:
<221> NAME/KEY: MOD_RES
<222> LOCATION: (13)..(13)
<223> OTHER INFORMATION: Ile, Thr, Lys or Arg
<220> FEATURE:
<221> NAME/KEY: MOD_RES
<222> LOCATION: (14)..(14)
<223> OTHER INFORMATION: Tyr, His, Asn or Asp
<220> FEATURE:
<221> NAME/KEY: MOD_RES
<222> LOCATION: (18)..(18)
<223> OTHER INFORMATION: Tyr or Ser
<220> FEATURE:
<221> NAME/KEY: MOD_RES
<222> LOCATION: (19)..(19)
<223> OTHER INFORMATION: Ile, Thr, Lys or Arg
<220> FEATURE:
<221> NAME/KEY: MOD_RES
<222> LOCATION: (20)..(20)
<223> OTHER INFORMATION: Tyr or Ser
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (22)..(23)
<223> OTHER INFORMATION: Tyr or Ser
<220> FEATURE:
<221> NAME/KEY: MOD_RES
<222> LOCATION: (24)..(24)
<223> OTHER INFORMATION: Leu, Ser or Trp
<220> FEATURE:
<221> NAME/KEY: MOD_RES
<222> LOCATION: (25)..(5)
<223> OTHER INFORMATION: Tyr or Ser
<220> FEATURE:
<221> NAME/KEY: MOD_RES
<222> LOCATION: (26)..(26)
<223> OTHER INFORMATION: Phe, Tyr or Ser
<220> FEATURE:
<221> NAME/KEY: MOD_RES
<222> LOCATION: (27)..(27)
<223> OTHER INFORMATION: Tyr, His, Asn or Asp

<400> SEQUENCE: 114

Tyr Tyr Cys Ala Xaa Xaa Xaa Xaa Gly Xaa Cys Xaa Xaa Gly Val
1               5                   10                  15

Cys Xaa Xaa Xaa Xaa Xaa Xaa Xaa Xaa Xaa Xaa Leu Trp Gly Arg Gly
            20                  25                  30

Thr Leu Val Thr Val Ser Ser
        35

<210> SEQ ID NO 115
<211> LENGTH: 10
<212> TYPE: PRT
<213> ORGANISM: Homo sapiens

<400> SEQUENCE: 115

Gly Tyr Cys Thr Asn Gly Val Cys Tyr Thr
1               5                   10

<210> SEQ ID NO 116
<211> LENGTH: 107
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (44)..(44)
<223> OTHER INFORMATION: a, c, g, t, unknown or other
<220> FEATURE:
<221> NAME/KEY: modified_base
<222> LOCATION: (46)..(46)
<223> OTHER INFORMATION: a, c, g, t, unknown or other
<220> FEATURE:
<221> NAME/KEY: modified_base
<222> LOCATION: (62)..(62)
<223> OTHER INFORMATION: a, c, g, t, unknown or other
<220> FEATURE:
<221> NAME/KEY: modified_base
<222> LOCATION: (67)..(68)
<223> OTHER INFORMATION: a, c, g, t, unknown or other
<220> FEATURE:
<221> NAME/KEY: modified_base
<222> LOCATION: (85)..(85)
<223> OTHER INFORMATION: a, c, g, t, unknown or other

<400> SEQUENCE: 116
gcagtttatt actgcgctar gtmctmtnnk tmtggttmct gtananatgg tgtctgctmt      60
anatmcnnkt mttmttbgtm tthtnatctg tggggccagg gtactct                  107

<210> SEQ ID NO 117
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (44)..(44)
<223> OTHER INFORMATION: a, c, g, t, unknown or other
<220> FEATURE:
<221> NAME/KEY: modified_base
<222> LOCATION: (46)..(46)
<223> OTHER INFORMATION: a, c, g, t, unknown or other
<220> FEATURE:
<221> NAME/KEY: modified_base
<222> LOCATION: (62)..(62)
<223> OTHER INFORMATION: a, c, g, t, unknown or other
<220> FEATURE:
<221> NAME/KEY: modified_base
<222> LOCATION: (67)..(68)
<223> OTHER INFORMATION: a, c, g, t, unknown or other
<220> FEATURE:
<221> NAME/KEY: modified_base
<222> LOCATION: (85)..(85)
<223> OTHER INFORMATION: a, c, g, t, unknown or other

<400> SEQUENCE: 117
gcagtttatt actgcgctar gtmctmtnnk tmcggttmct gcananatgg cgtctgctmt      60
anatmcnnkt mttmttbgtm tthtnatctg tggggccagg gtactct                  107

<210> SEQ ID NO 118
<211> LENGTH: 58
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, g, t, unknown or other
<220> FEATURE:
<221> NAME/KEY: modified_base
<222> LOCATION: (44)..(44)
<223> OTHER INFORMATION: a, c, g, t, unknown or other
<220> FEATURE:
<221> NAME/KEY: modified_base
<222> LOCATION: (46)..(46)
<223> OTHER INFORMATION: a, c, g, t, unknown or other

<400> SEQUENCE: 118
gcagtttatt actgcgctar gtmctmtnnk tmcggttmct gcananatgg cgtctgct        58

<210> SEQ ID NO 119
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a, c, g, t, unknown or other
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (46)..(46)
<223> OTHER INFORMATION: a, c, g, t, unknown or other
<220> FEATURE:
<221> NAME/KEY: modified_base
<222> LOCATION: (62)..(62)
<223> OTHER INFORMATION: a, c, g, t, unknown or other
<220> FEATURE:
<221> NAME/KEY: modified_base
<222> LOCATION: (64)..(64)
<223> OTHER INFORMATION: a, c, g, t, unknown or other

<400> SEQUENCE: 119
agagtaccct ggccccacag atnadaakac vaakaakamn ngkatntaka gcagacgcca        60
tntntgcagk aaccg        75

<210> SEQ ID NO 120
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (14)..(14)
<223> OTHER INFORMATION: a, c, g, t, unknown or other
<220> FEATURE:
<221> NAME/KEY: modified_base
<222> LOCATION: (30)..(30)
<223> OTHER INFORMATION: a, c, g, t, unknown or other
<220> FEATURE:
<221> NAME/KEY: modified_base
<222> LOCATION: (35)..(36)

```
<223> OTHER INFORMATION: a, c, g, t, unknown or other
<220> FEATURE:
<221> NAME/KEY: modified_base
<222> LOCATION: (53)..(53)
<223> OTHER INFORMATION: a, c, g, t, unknown or other

<400> SEQUENCE: 120
cggttmctgc ananatggcg tctgctmtan atmcnnktmt tmttbgtmtt htnatctgtg      60
gggccagggt actct                                                      75

<210> SEQ ID NO 121
<211> LENGTH: 49
<212> TYPE: PRT
<213> ORGANISM: Artificial Sequence
<220> FEATURE:
<223> OTHER INFORMATION: Description of Artificial
      Sequence: Synthetic polypeptide
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
<222> LOCATION: (6)..(11)
<223> OTHER INFORMATION: Tyr or Ser
<220> FEATURE:
<221> NAME/KEY: MOD_RES
<222> LOCATION: (13)..(13)
<223> OTHER INFORMATION: Tyr or Ser
<220> FEATURE:
<221> NAME/KEY: MOD_RES
<222> LOCATION: (15)..(15)
<223> OTHER INFORMATION: Ile, Thr, Lys or Arg
<220> FEATURE:
<221> NAME/KEY: MOD_RES
<222> LOCATION: (16)..(16)
<223> OTHER INFORMATION: Tyr, His, Asn or Asp
<220> FEATURE:
<221> NAME/KEY: MOD_RES
<222> LOCATION: (20)..(20)
<223> OTHER INFORMATION: Tyr or Ser
<220> FEATURE:
<221> NAME/KEY: MOD_RES
<222> LOCATION: (21)..(21)
<223> OTHER INFORMATION: Ile, Thr, Lys or Arg
<220> FEATURE:
<221> NAME/KEY: MOD_RES
<222> LOCATION: (22)..(25)
<223> OTHER INFORMATION: Tyr or Ser
<220> FEATURE:
<221> NAME/KEY: MOD_RES
<222> LOCATION: (27)..(28)
<223> OTHER INFORMATION: Tyr or Ser
<220> FEATURE:
<221> NAME/KEY: MOD_RES
<222> LOCATION: (30)..(30)
<223> OTHER INFORMATION: Tyr or Ser
<220> FEATURE:
<221> NAME/KEY: MOD_RES
<222> LOCATION: (32)..(33)
<223> OTHER INFORMATION: Tyr or Ser
<220> FEATURE:
<221> NAME/KEY: MOD_RES
<222> LOCATION: (34)..(34)
<223> OTHER INFORMATION: Leu, Ser or Trp
<220> FEATURE:
<221> NAME/KEY: MOD_RES
<222> LOCATION: (35)..(35)
<223> OTHER INFORMATION: Tyr or Ser
<220> FEATURE:
<221> NAME/KEY: MOD_RES
<222> LOCATION: (36)..(36)
<223> OTHER INFORMATION: Phe, Tyr or Ser
<220> FEATURE:
<221> NAME/KEY: MOD_RES
<222> LOCATION: (37)..(37)
```

<223> OTHER INFORMATION: Tyr, His, Asn or Asp

<400> SEQUENCE: 121

Tyr Tyr Cys Ala Xaa Xaa Xaa Xaa Xaa Xaa Gly Xaa Cys Xaa Xaa
1               5                   10                  15

Gly Val Cys Xaa Xaa Xaa Xaa Xaa Xaa Tyr Xaa Xaa Tyr Xaa Tyr Xaa
            20                  25                  30

Xaa Xaa Xaa Xaa Xaa Leu Trp Gly Arg Gly Thr Leu Val Thr Val Ser
        35                  40                  45

Ser

<210> SEQ ID NO 122
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (50)..(50)
<223> OTHER INFORMATION: a, c, g, t, unknown or other
<220> FEATURE:
<221> NAME/KEY: modified_base
<222> LOCATION: (52)..(52)
<223> OTHER INFORMATION: a, c, g, t, unknown or other
<220> FEATURE:
<221> NAME/KEY: modified_base
<222> LOCATION: (68)..(68)
<223> OTHER INFORMATION: a, c, g, t, unknown or other
<220> FEATURE:
<221> NAME/KEY: modified_base
<222> LOCATION: (115)..(115)
<223> OTHER INFORMATION: a, c, g, t, unknown or other

<400> SEQUENCE: 122
gcagtttatt actgcgctar gtmttmctmc tmttmctmcg gttmttgtan anatggcgtg    60
tgctmtanat mctmctmctm ttattmttmc tattmttact mttmctbgtm cthtnatctg   120
tggggccagg gtactct                                                 137

<210> SEQ ID NO 123
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Arg or Lys
<220> FEATURE:
<221> NAME/KEY: MOD_RES
<222> LOCATION: (6)..(15)
<223> OTHER INFORMATION: Tyr or Ser
<220> FEATURE:
<221> NAME/KEY: MOD_RES
<222> LOCATION: (26)..(34)
<223> OTHER INFORMATION: Tyr or Ser
<220> FEATURE:
<221> NAME/KEY: MOD_RES
<222> LOCATION: (36)..(36)
<223> OTHER INFORMATION: Tyr or Ser
<220> FEATURE:
<221> NAME/KEY: MOD_RES
<222> LOCATION: (38)..(38)
<223> OTHER INFORMATION: Tyr, His, Asn or Asp

<400> SEQUENCE: 123

Tyr Tyr Cys Ala Xaa Xaa Xaa Xaa Xaa Xaa Xaa Xaa Xaa Xaa Xaa Gly
1               5                   10                  15

Tyr Cys Thr Asn Gly Val Cys Tyr Thr Xaa Xaa Xaa Xaa Xaa Xaa Xaa
            20                  25                  30

Xaa Xaa Trp Xaa Phe Xaa Leu Trp Gly Arg Gly Thr Leu Val Thr Val
        35                  40                  45

Ser Ser
    50

<210> SEQ ID NO 124
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gcagtttatt actgcgctar gtmttmctmc tmttmttmct mctmttmctm cggttattgt    60
actaacggcg tttgctatac t                                              81

<210> SEQ ID NO 125
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: a, c, g, t, unknown or other

<400> SEQUENCE: 125
agagtaccct ggccccacag gtngaaakac caakaakaak agkagkagka gkaakaakaa    60
gtatagcaaa cgccgttagt acaata                                         86

<210> SEQ ID NO 126
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (64)..(64)
<223> OTHER INFORMATION: a, c, g, t, unknown or other

<400> SEQUENCE: 126
tattgtacta acggcgtttg ctatacttmt tmttmctmct mctmctmttm ttmttggtmt    60
ttcnacctgt ggggccaggg tactct                                         86

<210> SEQ ID NO 127
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(16)
<223> OTHER INFORMATION: Tyr or Ser
<220> FEATURE:
<221> NAME/KEY: MOD_RES
<222> LOCATION: (25)..(25)
<223> OTHER INFORMATION: Tyr or Ser
<220> FEATURE:
<221> NAME/KEY: MOD_RES
<222> LOCATION: (27)..(33)
<223> OTHER INFORMATION: Tyr or Ser
<220> FEATURE:
<221> NAME/KEY: MOD_RES
<222> LOCATION: (36)..(36)
<223> OTHER INFORMATION: Tyr or Ser

<400> SEQUENCE: 127

Tyr Tyr Cys Ala Xaa Xaa Xaa Xaa Xaa Xaa Xaa Xaa Xaa Xaa Xaa
1               5                   10                  15

Asp Tyr Val Trp Gly Ser Tyr Arg Xaa Thr Xaa Xaa Xaa Xaa Xaa
            20                  25                  30

Xaa Ala Glu Xaa Phe Gln His Trp Gly Gln Gly Thr Leu Val Thr Val
        35                  40                  45

Ser Ser
    50

<210> SEQ ID NO 128
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gcagtttatt actgcgctar gtmttmctmc tmttmttmct mctmttmctm ctmcgattat      60
gtctggggta cttatcgt                                                   78

<210> SEQ ID NO 129
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
agagtaccct ggccccaatg ctggaaakac tcagcgkagk agkagkagka gkaakaagtg      60
kaacgataag taccccagac ataatc                                          86

<210> SEQ ID NO 130
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gattatgtct ggggtactta tcgttmcact tmttmctmct mctmctmctm cgctgagtmt      60
ttccagcatt ggggccaggg tactct                                          86

<210> SEQ ID NO 131
<211> LENGTH: 51
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(16)
<223> OTHER INFORMATION: Tyr or Ser
<220> FEATURE:
<221> NAME/KEY: MOD_RES
<222> LOCATION: (18)..(18)
<223> OTHER INFORMATION: Tyr or Ser
<220> FEATURE:
<221> NAME/KEY: MOD_RES
<222> LOCATION: (22)..(23)
<223> OTHER INFORMATION: Tyr or Ser
<220> FEATURE:
<221> NAME/KEY: MOD_RES
<222> LOCATION: (25)..(25)
<223> OTHER INFORMATION: Tyr or Ser
<220> FEATURE:
<221> NAME/KEY: MOD_RES
<222> LOCATION: (27)..(34)
<223> OTHER INFORMATION: Tyr or Ser
<220> FEATURE:
<221> NAME/KEY: MOD_RES
<222> LOCATION: (37)..(37)
<223> OTHER INFORMATION: Tyr or Ser

<400> SEQUENCE: 131

Tyr Tyr Cys Ala Lys Xaa Xaa Xaa Xaa Xaa Xaa Xaa Xaa Xaa Xaa
1               5                   10                  15

Asp Xaa Val Trp Gly Xaa Xaa Arg Xaa Thr Xaa Xaa Xaa Xaa Xaa
            20                  25                  30

Xaa Xaa Ala Glu Xaa Phe Gln His Trp Gly Gln Gly Thr Leu Val Thr
            35                  40                  45

Val Ser Ser
     50

<210> SEQ ID NO 132
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gcagtttatt actgcgctar gtmttmctmc tmttmttmct mctmttmctm ctmcgactmt   60
gtctggggtt mctmccgttm cacct                                        85

<210> SEQ ID NO 133
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
agagtaccct ggccccaatg ctggaaakac tcagcgkagk agkagkagka gkagkaakag   60
gtgkaacggk agkaacccca gacakagtcg kag                               93

<210> SEQ ID NO 134
<211> LENGTH: 93
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 134
ctmcgactmt gtctggggtt mctmccgttm cacctmttmc tmctmctmct mctmctmcgc    60
tgagtmtttc cagcattggg gccagggtac tct                                 93

<210> SEQ ID NO 135
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(15)
<223> OTHER INFORMATION: Tyr or Ser
<220> FEATURE:
<221> NAME/KEY: MOD_RES
<222> LOCATION: (17)..(17)
<223> OTHER INFORMATION: Tyr or Ser
<220> FEATURE:
<221> NAME/KEY: MOD_RES
<222> LOCATION: (19)..(19)
<223> OTHER INFORMATION: Tyr or Ser
<220> FEATURE:
<221> NAME/KEY: MOD_RES
<222> LOCATION: (22)..(22)
<223> OTHER INFORMATION: Tyr or Ser
<220> FEATURE:
<221> NAME/KEY: MOD_RES
<222> LOCATION: (24)..(24)
<223> OTHER INFORMATION: Tyr or Ser
<220> FEATURE:
<221> NAME/KEY: MOD_RES
<222> LOCATION: (26)..(34)
<223> OTHER INFORMATION: Tyr or Ser
<220> FEATURE:
<221> NAME/KEY: MOD_RES
<222> LOCATION: (37)..(37)
<223> OTHER INFORMATION: Tyr or Ser

<400> SEQUENCE: 135

Tyr Tyr Cys Ala Xaa Xaa Xaa Xaa Xaa Xaa Xaa Xaa Xaa Xaa Gly
1               5                   10                  15

Xaa Cys Xaa Gly Gly Xaa Cys Xaa Ser Xaa Xaa Xaa Xaa Xaa Xaa
            20                  25                  30

Xaa Xaa Ala Glu Xaa Phe Gln His Trp Gly Gln Gly Thr Leu Val Thr
        35                  40                  45

Val Ser Ser
    50

<210> SEQ ID NO 136
<211> LENGTH: 10
<212> TYPE: PRT
<213> ORGANISM: Homo sapiens

<400> SEQUENCE: 136

Gly Tyr Cys Ser Gly Gly Ser Cys Tyr Ser
1               5                   10

<210> SEQ ID NO 137
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gcagtttatt actgcgctar gtmttmttmt tmttmttmtt mttmttmctm cggctmctgt    60
tmcggtggct mctgctmctc ct    82

<210> SEQ ID NO 138
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
agagtaccct ggccccaatg ttggaaakat tcagcgkagk agkagkagka gkagkagkag    60
kagkaggagc agkagccacc gkaacagkag ccgkag    96

<210> SEQ ID NO 139
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gcagtttatt actgcgctar gtmttmttmt tmttmttmtt mttmctmcgg ctmctgttmc    60
ggtggctmct gctmctcct    79

<210> SEQ ID NO 140
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
agagtaccct ggccccaatg ttggaaakat tcagcgkagk agkagkagka gkagkagkag    60
kaggagcagk agccaccgka acagkagccg kag    93

<210> SEQ ID NO 141
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(12)
<223> OTHER INFORMATION: Tyr or Ser
<220> FEATURE:
<221> NAME/KEY: MOD_RES
<222> LOCATION: (14)..(14)
<223> OTHER INFORMATION: Tyr or Ser
<220> FEATURE:
<221> NAME/KEY: MOD_RES
<222> LOCATION: (18)..(19)
<223> OTHER INFORMATION: Tyr or Ser -continued

```
<220> FEATURE:
<221> NAME/KEY: MOD_RES
<222> LOCATION: (21)..(21)
<223> OTHER INFORMATION: Tyr or Ser
<220> FEATURE:
<221> NAME/KEY: MOD_RES
<222> LOCATION: (23)..(33)
<223> OTHER INFORMATION: Tyr or Ser
<220> FEATURE:
<221> NAME/KEY: MOD_RES
<222> LOCATION: (36)..(36)
<223> OTHER INFORMATION: Tyr or Ser

<400> SEQUENCE: 141

Tyr Tyr Cys Ala Xaa Xaa Xaa Xaa Xaa Xaa Xaa Asp Xaa Val Trp
1               5                   10                  15

Gly Xaa Xaa Arg Xaa Thr Xaa Xaa Xaa Xaa Xaa Xaa Xaa Xaa Xaa
            20                  25                  30

Xaa Ala Glu Xaa Phe Gln His Trp Gly Gln Gly Thr Leu Val Thr Val
        35                  40                  45

Ser Ser
    50

<210> SEQ ID NO 142
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gcagtttatt actgcgctar gtmttmttmt tmttmttmtt mcgactmcgt ctggggttmt     60 tmccgtttmta cct                                                       73

<210> SEQ ID NO 143
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
agagtaccct ggccccagtg ctggaagkac tcagcgkagk agkagkagka gkagkagkag     60
kagkagkagk agkaggtaka acggkaakaa ccccagacgk agtcg                    105

<210> SEQ ID NO 144
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(15)
<223> OTHER INFORMATION: Tyr or Ser
<220> FEATURE:
<221> NAME/KEY: MOD_RES
<222> LOCATION: (17)..(17)
<223> OTHER INFORMATION: Tyr or Ser
<220> FEATURE:
<221> NAME/KEY: MOD_RES
```

-continued

```
<222> LOCATION: (21)..(22)
<223> OTHER INFORMATION: Tyr or Ser
<220> FEATURE:
<221> NAME/KEY: MOD_RES
<222> LOCATION: (24)..(24)
<223> OTHER INFORMATION: Tyr or Ser
<220> FEATURE:
<221> NAME/KEY: MOD_RES
<222> LOCATION: (26)..(33)
<223> OTHER INFORMATION: Tyr or Ser
<220> FEATURE:
<221> NAME/KEY: MOD_RES
<222> LOCATION: (36)..(36)
<223> OTHER INFORMATION: Tyr or Ser

<400> SEQUENCE: 144

Tyr Tyr Cys Ala Xaa Xaa Xaa Xaa Xaa Xaa Xaa Xaa Xaa Xaa Xaa Asp
1               5                   10                  15

Xaa Val Trp Gly Xaa Xaa Arg Xaa Thr Xaa Xaa Xaa Xaa Xaa Xaa Xaa
            20                  25                  30

Xaa Ala Glu Xaa Phe Gln His Trp Gly Gln Gly Thr Leu Val Thr Val
        35                  40                  45

Ser Ser
    50

<210> SEQ ID NO 145
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gcagtttatt actgcgctar gtmttmttmt tmttmttmtt mctmctmctm cgactmcgtc    60
tggggttmct mccgttmcac ct                                             82

<210> SEQ ID NO 146
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
agagtaccct ggccccagtg ctggaagkac tcagcgkagk agkagkagka gkagkagkag    60
kagkaggtgk aacggkagka accccagacg kagtcg                              96

<210> SEQ ID NO 147
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(16)
<223> OTHER INFORMATION: Tyr or Ser
<220> FEATURE:
<221> NAME/KEY: MOD_RES
<222> LOCATION: (21)..(34)
<223> OTHER INFORMATION: Tyr or Ser
```

```
<220> FEATURE:
<221> NAME/KEY: MOD_RES
<222> LOCATION: (37)..(37)
<223> OTHER INFORMATION: Tyr or Ser

<400> SEQUENCE: 147

Tyr Tyr Cys Ala Xaa Xaa Xaa Xaa Xaa Xaa Xaa Xaa Xaa Xaa
1               5                   10                  15

Asp Ser Ser Gly Xaa Xaa Xaa Xaa Xaa Xaa Xaa Xaa Xaa Xaa
            20                  25                  30

Xaa Xaa Ala Glu Xaa Phe Gln His Trp Gly Gln Gly Thr Leu Val Thr
        35                  40                  45

Val Ser Ser
    50

<210> SEQ ID NO 148
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Arg or Lys
<220> FEATURE:
<221> NAME/KEY: MOD_RES
<222> LOCATION: (29)..(39)
<223> OTHER INFORMATION: Tyr or Ser
<220> FEATURE:
<221> NAME/KEY: MOD_RES
<222> LOCATION: (44)..(57)
<223> OTHER INFORMATION: Tyr or Ser
<220> FEATURE:
<221> NAME/KEY: MOD_RES
<222> LOCATION: (60)..(60)
<223> OTHER INFORMATION: Tyr or Ser

<400> SEQUENCE: 148

Ser Arg Asp Asn Ser Lys Asn Thr Leu Tyr Leu Gln Met Asn Ser Leu
1               5                   10                  15

Arg Ala Glu Asp Thr Ala Val Tyr Tyr Cys Ala Xaa Xaa Xaa Xaa Xaa
            20                  25                  30

Xaa Xaa Xaa Xaa Xaa Xaa Xaa Asp Ser Ser Gly Xaa Xaa Xaa Xaa Xaa
        35                  40                  45

Xaa Xaa Xaa Xaa Xaa Xaa Xaa Xaa Xaa Ala Glu Xaa Phe Gln His Trp
    50                  55                  60

Gly Gln Gly Thr Leu Val Thr Val Ser Ser
65                  70

<210> SEQ ID NO 149
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(231)

<400> SEQUENCE: 149 ttcactatc tct aga gac aac tct aag aat act ctc tac ttg cag atg aac      51
          Ser Arg Asp Asn Ser Lys Asn Thr Leu Tyr Leu Gln Met Asn
          1               5                   10
```

```
agc tta agg gct gag gat act gca gtt tat tac tgc gct arg tmc tmt      99
Ser Leu Arg Ala Glu Asp Thr Ala Val Tyr Tyr Cys Ala Xaa Xaa Xaa
 15                  20                  25                  30 tmc tmc tmt tmc tmt tmc tmc tmc tmc gac agc tcc ggc tmc tmc tmt     147
Xaa Xaa Xaa Xaa Xaa Xaa Xaa Xaa Xaa Asp Ser Ser Gly Xaa Xaa Xaa
                 35                  40                  45 tmc tmt tmc tmc tmt tmc tmt tmc tmc tmc tmc gct gaa tmc ttc caa    195
Xaa Xaa Xaa Xaa Xaa Xaa Xaa Xaa Xaa Xaa Xaa Ala Glu Xaa Phe Gln
         50                  55                  60 cac tgg ggc cag ggt act ctg gtc acc gtc tcc agt                     231
His Trp Gly Gln Gly Thr Leu Val Thr Val Ser Ser
         65                  70
```

```
<210> SEQ ID NO 150
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gcagtttatt actgcgctar gtmctmttmc tmctmttmct mttmctmctm ctmcgacagc    60
tccggctmct mct                                                       73

<210> SEQ ID NO 151
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cagagtaccc tggccccagt gttggaagka ttcagcgkag kagkagkaak agkaakagka    60
gkaakagkaa kagkagkagc cggagctgtc gkagkag                             97

<210> SEQ ID NO 152
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(16)
<223> OTHER INFORMATION: Tyr or Ser
<220> FEATURE:
<221> NAME/KEY: MOD_RES
<222> LOCATION: (12)..(12)
<223> OTHER INFORMATION: May or may not be present
<220> FEATURE:
<221> NAME/KEY: MOD_RES
<222> LOCATION: (21)..(34)
<223> OTHER INFORMATION: Tyr or Ser
<220> FEATURE:
<221> NAME/KEY: MOD_RES
<222> LOCATION: (31)..(31)
<223> OTHER INFORMATION: May or may not be present
<220> FEATURE:
<221> NAME/KEY: MOD_RES
<222> LOCATION: (37)..(37)
<223> OTHER INFORMATION: Tyr or Ser
```

<400> SEQUENCE: 152

Tyr Tyr Cys Ala Xaa Xaa Xaa Xaa Xaa Xaa Xaa Xaa Xaa Xaa
1               5                   10                  15

Asp Ser Ser Gly Xaa Xaa Xaa Xaa Xaa Xaa Xaa Xaa Xaa
                20                  25                  30

Xaa Xaa Ala Glu Xaa Phe Gln His Trp Gly Gln Gly Thr Leu Val Thr
        35                  40                  45

Val Ser Ser
    50

<210> SEQ ID NO 153
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcagtttatt actgcgctar gtmctmttmc tmctmttmct mttmctmctm ctmcgacagc    60
tccggctmct mct                                                      73

<210> SEQ ID NO 154
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gcagtttatt actgcgctar gtmctmctmc tmttmctmtt mctmctmctm cgacagctcc    60 ggctmctmct                                                          70

<210> SEQ ID NO 155
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cagagtaccc tggccccagt gttggaagka ttcagcgkag kagkagkaak agkaakagka    60
gkaakaakag kagkagccgg agctgtcgka gkag                               94

<210> SEQ ID NO 156
<211> LENGTH: 5
<212> TYPE: PRT
<213> ORGANISM: Homo sapiens

<400> SEQUENCE: 156

Gly Thr Thr Gly Thr
1               5

<210> SEQ ID NO 157
<211> LENGTH: 5
<212> TYPE: PRT
<213> ORGANISM: Homo sapiens

<400> SEQUENCE: 157

Val Gln Leu Glu Arg

```
<210> SEQ ID NO 158
<211> LENGTH: 5
<212> TYPE: PRT
<213> ORGANISM: Homo sapiens

<400> SEQUENCE: 158

Tyr Asn Trp Asn Asp
1               5

<210> SEQ ID NO 159
<211> LENGTH: 5
<212> TYPE: PRT
<213> ORGANISM: Homo sapiens

<400> SEQUENCE: 159

Gly Ile Thr Gly Thr
1               5

<210> SEQ ID NO 160
<211> LENGTH: 3
<212> TYPE: PRT
<213> ORGANISM: Homo sapiens

<400> SEQUENCE: 160

Leu Glu Leu
1

<210> SEQ ID NO 161
<211> LENGTH: 5
<212> TYPE: PRT
<213> ORGANISM: Homo sapiens

<400> SEQUENCE: 161

Tyr Asn Trp Asn Tyr
1               5

<210> SEQ ID NO 162
<211> LENGTH: 3
<212> TYPE: PRT
<213> ORGANISM: Homo sapiens

<400> SEQUENCE: 162

Leu Glu Arg
1

<210> SEQ ID NO 163
<211> LENGTH: 5
<212> TYPE: PRT
<213> ORGANISM: Homo sapiens

<400> SEQUENCE: 163

Tyr Asn Trp Asn Asp
1               5

<210> SEQ ID NO 164
<211> LENGTH: 6
<212> TYPE: PRT
<213> ORGANISM: Homo sapiens

<400> SEQUENCE: 164

Gly Ile Val Gly Ala Thr
1               5
```

```
<210> SEQ ID NO 165
<211> LENGTH: 4
<212> TYPE: PRT
<213> ORGANISM: Homo sapiens

<400> SEQUENCE: 165

Trp Glu Leu Leu
1

<210> SEQ ID NO 166
<211> LENGTH: 6
<212> TYPE: PRT
<213> ORGANISM: Homo sapiens

<400> SEQUENCE: 166

Tyr Ser Gly Ser Tyr Tyr
1               5

<210> SEQ ID NO 167
<211> LENGTH: 5
<212> TYPE: PRT
<213> ORGANISM: Homo sapiens

<400> SEQUENCE: 167

Tyr Gln Leu Leu Tyr
1               5

<210> SEQ ID NO 168
<211> LENGTH: 9
<212> TYPE: PRT
<213> ORGANISM: Homo sapiens

<400> SEQUENCE: 168

Asp Ile Val Val Val Pro Ala Ala Ile
1               5

<210> SEQ ID NO 169
<211> LENGTH: 4
<212> TYPE: PRT
<213> ORGANISM: Homo sapiens

<400> SEQUENCE: 169

Arg Ile Leu Tyr
1

<210> SEQ ID NO 170
<211> LENGTH: 9
<212> TYPE: PRT
<213> ORGANISM: Homo sapiens

<400> SEQUENCE: 170

Asp Ile Val Leu Met Val Tyr Ala Ile
1               5

<210> SEQ ID NO 171
<211> LENGTH: 3
<212> TYPE: PRT
<213> ORGANISM: Homo sapiens

<400> SEQUENCE: 171

Arg Ile Leu
1

<210> SEQ ID NO 172
```

<211> LENGTH: 9
<212> TYPE: PRT
<213> ORGANISM: Homo sapiens

<400> SEQUENCE: 172

Asp Ile Val Val Val Ala Ala Thr
1               5

<210> SEQ ID NO 173
<211> LENGTH: 5
<212> TYPE: PRT
<213> ORGANISM: Homo sapiens

<400> SEQUENCE: 173

Ser Ile Leu Trp Trp
1               5

<210> SEQ ID NO 174
<211> LENGTH: 9
<212> TYPE: PRT
<213> ORGANISM: Homo sapiens

<400> SEQUENCE: 174

Ala Tyr Cys Gly Gly Asp Cys Tyr Ser
1               5

<210> SEQ ID NO 175
<211> LENGTH: 8
<212> TYPE: PRT
<213> ORGANISM: Homo sapiens

<400> SEQUENCE: 175

His Ile Val Val Val Thr Ala Ile
1               5

<210> SEQ ID NO 176
<211> LENGTH: 10
<212> TYPE: PRT
<213> ORGANISM: Homo sapiens

<400> SEQUENCE: 176

Val Leu Arg Phe Leu Glu Trp Leu Leu Tyr
1               5                   10

<210> SEQ ID NO 177
<211> LENGTH: 10
<212> TYPE: PRT
<213> ORGANISM: Homo sapiens

<400> SEQUENCE: 177

Tyr Tyr Asp Phe Trp Ser Gly Tyr Tyr Thr
1               5                   10

<210> SEQ ID NO 178
<211> LENGTH: 9
<212> TYPE: PRT
<213> ORGANISM: Homo sapiens

<400> SEQUENCE: 178

Ile Thr Ile Phe Gly Val Val Ile Ile
1               5

<210> SEQ ID NO 179
<211> LENGTH: 9
<212> TYPE: PRT

<213> ORGANISM: Homo sapiens

<400> SEQUENCE: 179

Val Leu Arg Tyr Phe Asp Trp Leu Leu
1               5

<210> SEQ ID NO 180
<211> LENGTH: 10
<212> TYPE: PRT
<213> ORGANISM: Homo sapiens

<400> SEQUENCE: 180

Tyr Tyr Asp Ile Leu Thr Gly Tyr Tyr Asn
1               5                   10

<210> SEQ ID NO 181
<211> LENGTH: 4
<212> TYPE: PRT
<213> ORGANISM: Homo sapiens

<400> SEQUENCE: 181

Ile Thr Ile Phe
1

<210> SEQ ID NO 182
<211> LENGTH: 9
<212> TYPE: PRT
<213> ORGANISM: Homo sapiens

<400> SEQUENCE: 182

Val Leu Leu Trp Phe Gly Glu Leu Leu
1               5

<210> SEQ ID NO 183
<211> LENGTH: 9
<212> TYPE: PRT
<213> ORGANISM: Homo sapiens

<400> SEQUENCE: 183

Ile Thr Met Val Arg Gly Val Ile Ile
1               5

<210> SEQ ID NO 184
<211> LENGTH: 9
<212> TYPE: PRT
<213> ORGANISM: Homo sapiens

<400> SEQUENCE: 184

Leu Arg Leu Gly Glu Leu Ser Leu Tyr
1               5

<210> SEQ ID NO 185
<211> LENGTH: 11
<212> TYPE: PRT
<213> ORGANISM: Homo sapiens

<400> SEQUENCE: 185

Ile Met Ile Thr Phe Gly Gly Val Ile Val Ile
1               5                   10

<210> SEQ ID NO 186
<211> LENGTH: 4
<212> TYPE: PRT
<213> ORGANISM: Homo sapiens

<400> SEQUENCE: 186

Trp Leu Leu Leu
1

<210> SEQ ID NO 187
<211> LENGTH: 10
<212> TYPE: PRT
<213> ORGANISM: Homo sapiens

<400> SEQUENCE: 187

Tyr Tyr Tyr Asp Ser Ser Gly Tyr Tyr Tyr
1               5                   10

<210> SEQ ID NO 188
<211> LENGTH: 9
<212> TYPE: PRT
<213> ORGANISM: Homo sapiens

<400> SEQUENCE: 188

Ile Thr Met Ile Val Val Val Ile Thr
1               5

<210> SEQ ID NO 189
<211> LENGTH: 2
<212> TYPE: PRT
<213> ORGANISM: Homo sapiens

<400> SEQUENCE: 189

Leu Gln
1

<210> SEQ ID NO 190
<211> LENGTH: 4
<212> TYPE: PRT
<213> ORGANISM: Homo sapiens

<400> SEQUENCE: 190

Thr Thr Val Thr
1

<210> SEQ ID NO 191
<211> LENGTH: 2
<212> TYPE: PRT
<213> ORGANISM: Homo sapiens

<400> SEQUENCE: 191

Leu Gln
1

<210> SEQ ID NO 192
<211> LENGTH: 5
<212> TYPE: PRT
<213> ORGANISM: Homo sapiens

<400> SEQUENCE: 192

Asp Tyr Ser Asn Tyr
1               5

<210> SEQ ID NO 193
<211> LENGTH: 4
<212> TYPE: PRT
<213> ORGANISM: Homo sapiens

<400> SEQUENCE: 193

Thr Thr Val Thr
1

<210> SEQ ID NO 194
<211> LENGTH: 2
<212> TYPE: PRT
<213> ORGANISM: Homo sapiens

<400> SEQUENCE: 194

Leu Arg
1

<210> SEQ ID NO 195
<211> LENGTH: 5
<212> TYPE: PRT
<213> ORGANISM: Homo sapiens

<400> SEQUENCE: 195

Asp Tyr Gly Asp Tyr
1               5

<210> SEQ ID NO 196
<211> LENGTH: 4
<212> TYPE: PRT
<213> ORGANISM: Homo sapiens

<400> SEQUENCE: 196

Thr Thr Val Thr
1

<210> SEQ ID NO 197
<211> LENGTH: 3
<212> TYPE: PRT
<213> ORGANISM: Homo sapiens

<400> SEQUENCE: 197

Leu Arg Trp
1

<210> SEQ ID NO 198
<211> LENGTH: 6
<212> TYPE: PRT
<213> ORGANISM: Homo sapiens

<400> SEQUENCE: 198

Asp Tyr Gly Gly Asn Ser
1               5

<210> SEQ ID NO 199
<211> LENGTH: 5
<212> TYPE: PRT
<213> ORGANISM: Homo sapiens

<400> SEQUENCE: 199

Thr Thr Val Val Thr
1               5

<210> SEQ ID NO 200
<211> LENGTH: 6
<212> TYPE: PRT
<213> ORGANISM: Homo sapiens

<400> SEQUENCE: 200

Val Asp Thr Ala Met Val
1               5

```
<210> SEQ ID NO 201
<211> LENGTH: 6
<212> TYPE: PRT
<213> ORGANISM: Homo sapiens

<400> SEQUENCE: 201

Trp Ile Gln Leu Trp Leu
1               5

<210> SEQ ID NO 202
<211> LENGTH: 6
<212> TYPE: PRT
<213> ORGANISM: Homo sapiens

<400> SEQUENCE: 202

Gly Tyr Ser Tyr Gly Tyr
1               5

<210> SEQ ID NO 203
<211> LENGTH: 7
<212> TYPE: PRT
<213> ORGANISM: Homo sapiens

<400> SEQUENCE: 203

Val Asp Ile Val Ala Thr Ile
1               5

<210> SEQ ID NO 204
<211> LENGTH: 4
<212> TYPE: PRT
<213> ORGANISM: Homo sapiens

<400> SEQUENCE: 204

Trp Leu Arg Leu
1

<210> SEQ ID NO 205
<211> LENGTH: 7
<212> TYPE: PRT
<213> ORGANISM: Homo sapiens

<400> SEQUENCE: 205

Gly Tyr Ser Gly Tyr Asp Tyr
1               5

<210> SEQ ID NO 206
<211> LENGTH: 6
<212> TYPE: PRT
<213> ORGANISM: Homo sapiens

<400> SEQUENCE: 206

Val Asp Thr Ala Met Val
1               5

<210> SEQ ID NO 207
<211> LENGTH: 6
<212> TYPE: PRT
<213> ORGANISM: Homo sapiens

<400> SEQUENCE: 207

Trp Ile Gln Leu Trp Leu
1               5
```

<210> SEQ ID NO 208
<211> LENGTH: 6
<212> TYPE: PRT
<213> ORGANISM: Homo sapiens

<400> SEQUENCE: 208

Gly Tyr Ser Tyr Gly Tyr
1               5

<210> SEQ ID NO 209
<211> LENGTH: 6
<212> TYPE: PRT
<213> ORGANISM: Homo sapiens

<400> SEQUENCE: 209

Val Glu Met Ala Thr Ile
1               5

<210> SEQ ID NO 210
<211> LENGTH: 5
<212> TYPE: PRT
<213> ORGANISM: Homo sapiens

<400> SEQUENCE: 210

Arg Trp Leu Gln Leu
1               5

<210> SEQ ID NO 211
<211> LENGTH: 6
<212> TYPE: PRT
<213> ORGANISM: Homo sapiens

<400> SEQUENCE: 211

Arg Asp Gly Tyr Asn Tyr
1               5

<210> SEQ ID NO 212
<211> LENGTH: 6
<212> TYPE: PRT
<213> ORGANISM: Homo sapiens

<400> SEQUENCE: 212

Glu Tyr Ser Ser Ser Ser
1               5

<210> SEQ ID NO 213
<211> LENGTH: 5
<212> TYPE: PRT
<213> ORGANISM: Homo sapiens

<400> SEQUENCE: 213

Ser Ile Ala Ala Arg
1               5

<210> SEQ ID NO 214
<211> LENGTH: 3
<212> TYPE: PRT
<213> ORGANISM: Homo sapiens

<400> SEQUENCE: 214

Gln Leu Val
1

<210> SEQ ID NO 215
<211> LENGTH: 7

<212> TYPE: PRT
<213> ORGANISM: Homo sapiens

<400> SEQUENCE: 215

Gly Tyr Ser Ser Ser Trp Tyr
1               5

<210> SEQ ID NO 216
<211> LENGTH: 6
<212> TYPE: PRT
<213> ORGANISM: Homo sapiens

<400> SEQUENCE: 216

Gly Ile Ala Ala Ala Gly
1               5

<210> SEQ ID NO 217
<211> LENGTH: 4
<212> TYPE: PRT
<213> ORGANISM: Homo sapiens

<400> SEQUENCE: 217

Gln Gln Leu Val
1

<210> SEQ ID NO 218
<211> LENGTH: 7
<212> TYPE: PRT
<213> ORGANISM: Homo sapiens

<400> SEQUENCE: 218

Gly Tyr Ser Ser Gly Trp Tyr
1               5

<210> SEQ ID NO 219
<211> LENGTH: 6
<212> TYPE: PRT
<213> ORGANISM: Homo sapiens

<400> SEQUENCE: 219

Gly Ile Ala Val Ala Gly
1               5

<210> SEQ ID NO 220
<211> LENGTH: 4
<212> TYPE: PRT
<213> ORGANISM: Homo sapiens

<400> SEQUENCE: 220

Gln Trp Leu Val
1

<210> SEQ ID NO 221
<211> LENGTH: 3
<212> TYPE: PRT
<213> ORGANISM: Homo sapiens

<400> SEQUENCE: 221

Leu Thr Gly
1

<210> SEQ ID NO 222
<211> LENGTH: 2
<212> TYPE: PRT
<213> ORGANISM: Homo sapiens

<400> SEQUENCE: 222

Leu Gly
1

<210> SEQ ID NO 223
<211> LENGTH: 3
<212> TYPE: PRT
<213> ORGANISM: Homo sapiens

<400> SEQUENCE: 223

Asn Trp Gly
1

<210> SEQ ID NO 224
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Glu Asp Thr Ala Val Tyr Tyr Cys Ala Lys Asp Ile Val Leu Met
1               5                   10                  15

Trp Gly Gln Gly Thr Thr Val Thr Val Ser Ser
            20                  25

<210> SEQ ID NO 225
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(48)
<223> OTHER INFORMATION: a, c, g or t
<220> FEATURE:
<223> OTHER INFORMATION: see specification as filed for detailed
      description of substitutions and preferred embodiments

<400> SEQUENCE: 225
gctgaggata ctgcagttta ttactgcgct aagnnnnnnn nnnnnnnntg gggccagggt      60
actacggtca ccgtctccag t                                               81

<210> SEQ ID NO 226
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Tyr Cys Ala Lys Ala Glu Tyr Phe Gln His Trp Gly Gln Gly Thr
1               5                   10                  15

Leu Val Thr Val Ser Ser
            20

<210> SEQ ID NO 227
<211> LENGTH: 22
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 227

Tyr Tyr Cys Ala Lys Tyr Asp Tyr Gly Asp Tyr Trp Gly Gln Gly Thr
1               5                   10                  15

Leu Val Thr Val Ser Ser
            20

<210> SEQ ID NO 228
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Tyr Cys Ala Lys Gly Tyr Ser Tyr Gly Tyr Trp Gly Gln Gly Thr
1               5                   10                  15

Leu Val Thr Val Ser Ser
            20

<210> SEQ ID NO 229
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Tyr Tyr Cys Ala Lys Ser Tyr Tyr Phe Asp Tyr Trp Gly Gln Gly Thr
1               5                   10                  15

Leu Val Thr Val Ser Ser
            20

<210> SEQ ID NO 230
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Tyr Tyr Cys Ala Lys Tyr Tyr Ala Glu Tyr Phe Gln His Trp Gly Gln
1               5                   10                  15

Gly Thr Leu Val Thr Val Ser Ser
            20

<210> SEQ ID NO 231
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Tyr Tyr Cys Ala Lys Tyr Gly Tyr Ser Ser Ser Trp Tyr Trp Gly Gln
1               5                   10                  15

Gly Thr Leu Val Thr Val Ser Ser
            20
```

<210> SEQ ID NO 232
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Tyr Tyr Cys Ala Lys Tyr Gly Asp Tyr Tyr Phe Asp Tyr Trp Gly Gln
1               5                   10                  15

Gly Thr Leu Val Thr Val Ser Ser
            20

<210> SEQ ID NO 233
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Tyr Tyr Cys Ala Lys Tyr Tyr Tyr Asp Ser Ser Gly Tyr Tyr Tyr Trp
1               5                   10                  15

Gly Gln Gly Thr Leu Val Thr Val Ser Ser
            20                  25

<210> SEQ ID NO 234
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Tyr Tyr Cys Ala Lys Gly Tyr Cys Ser Ser Thr Ser Cys Tyr Thr Trp
1               5                   10                  15

Gly Gln Gly Thr Leu Val Thr Val Ser Ser
            20                  25

<210> SEQ ID NO 235
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Tyr Tyr Cys Ala Lys Tyr Tyr Ser Ser Ala Glu Tyr Phe Gln His Trp
1               5                   10                  15

Gly Gln Gly Thr Leu Val Thr Val Ser Ser
            20                  25

<210> SEQ ID NO 236
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

```
Tyr Tyr Cys Ala Lys Gly Ser Gly Tyr Tyr Phe Asp Tyr Trp
1               5                   10                  15

Gly Gln Gly Thr Leu Val Thr Val Ser Ser
            20                  25

<210> SEQ ID NO 237
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Tyr Tyr Cys Ala Lys Tyr Tyr Asp Ser Ser Gly Tyr Tyr Tyr Gln
1               5                   10                  15

His Trp Gly Gln Gly Thr Leu Val Thr Val Ser Ser
            20                  25

<210> SEQ ID NO 238
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Tyr Tyr Cys Ala Lys Gly Tyr Cys Ser Ser Thr Ser Cys Tyr Thr Gln
1               5                   10                  15

His Trp Gly Gln Gly Thr Leu Val Thr Val Ser Ser
            20                  25

<210> SEQ ID NO 239
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Tyr Tyr Cys Ala Lys Tyr Tyr Ser Ser Tyr Ser Ala Glu Tyr Phe Gln
1               5                   10                  15

His Trp Gly Gln Gly Thr Leu Val Thr Val Ser Ser
            20                  25

<210> SEQ ID NO 240
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Tyr Tyr Cys Ala Lys Tyr Tyr Asp Tyr Val Trp Gly Ser Tyr Arg Tyr
1               5                   10                  15

Thr Trp Gly Gln Gly Thr Leu Val Thr Val Ser Ser
            20                  25

<210> SEQ ID NO 241
<211> LENGTH: 28
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 241

Tyr Tyr Cys Ala Lys Gly Tyr Ser Tyr Gly Tyr Tyr Trp Tyr Phe Asp
1               5                   10                  15

Leu Trp Gly Arg Gly Thr Leu Val Thr Val Ser Ser
            20                  25

<210> SEQ ID NO 242
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Tyr Tyr Cys Ala Lys Tyr Tyr Tyr Asp Ser Ser Gly Tyr Tyr Tyr Tyr
1               5                   10                  15

Phe Gln His Trp Gly Gln Gly Thr Leu Val Thr Val Ser Ser
            20                  25                  30

<210> SEQ ID NO 243
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Tyr Tyr Cys Ala Lys Gly Tyr Cys Ser Ser Thr Ser Cys Tyr Thr Tyr
1               5                   10                  15

Phe Gln His Trp Gly Gln Gly Thr Leu Val Thr Val Ser Ser
            20                  25                  30

<210> SEQ ID NO 244
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Tyr Tyr Cys Ala Lys Ser Tyr Gly Tyr Cys Ser Ser Thr Ser Cys Tyr
1               5                   10                  15

Thr Gln His Trp Gly Gln Gly Thr Leu Val Thr Val Ser Ser
            20                  25                  30

<210> SEQ ID NO 245
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Tyr Tyr Cys Ala Lys Ser Tyr Tyr Ser Ser Tyr Ser Ala Glu Tyr
1               5                   10                  15

Phe Gln His Trp Gly Gln Gly Thr Leu Val Thr Val Ser Ser
            20                  25                  30
```

<210> SEQ ID NO 246
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Tyr Tyr Cys Ala Lys Ala Tyr Cys Gly Gly Asp Cys Tyr Ser Asn Trp
1               5                   10                  15

Phe Asp Pro Trp Gly Gln Gly Thr Leu Val Thr Val Ser Ser
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Tyr Tyr Cys Ala Lys Tyr Tyr Tyr Asp Ser Ser Gly Tyr Tyr Tyr Ala
1               5                   10                  15

Glu Tyr Phe Gln His Trp Gly Gln Gly Thr Leu Val Thr Val Ser Ser
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Tyr Tyr Cys Ala Lys Gly Tyr Cys Ser Ser Thr Ser Cys Tyr Thr Ala
1               5                   10                  15

Glu Tyr Phe Gln His Trp Gly Gln Gly Thr Leu Val Thr Val Ser Ser
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Tyr Tyr Cys Ala Lys Ser Tyr Tyr Ser Tyr Ser Ser Tyr Tyr Ser Ala
1               5                   10                  15

Glu Tyr Phe Gln His Trp Gly Gln Gly Thr Leu Val Thr Val Ser Ser
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

```
Tyr Tyr Cys Ala Lys Ser Tyr Ser Gly Tyr Cys Ser Ser Thr Ser
1               5                   10                  15

Cys Tyr Thr Gln His Trp Gly Gln Gly Thr Leu Val Thr Val Ser Ser
            20                  25                  30

<210> SEQ ID NO 251
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Tyr Tyr Cys Ala Lys Tyr Ser Ser Tyr Tyr Tyr Asp Ser Gly
1               5                   10                  15

Tyr Tyr Tyr Ala Glu Tyr Phe Gln His Trp Gly Gln Gly Thr Leu Val
            20                  25                  30

Thr Val Ser Ser
        35

<210> SEQ ID NO 252
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Tyr Tyr Cys Ala Lys Ser Tyr Tyr Ser Gly Tyr Cys Ser Ser Thr Ser
1               5                   10                  15

Cys Tyr Thr Ala Glu Tyr Phe Gln His Trp Gly Gln Gly Thr Leu Val
            20                  25                  30

Thr Val Ser Ser
        35

<210> SEQ ID NO 253
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Tyr Tyr Cys Ala Lys Ser Gly Tyr Cys Ser Ser Thr Ser Cys Tyr Thr
1               5                   10                  15

Tyr Tyr Ser Ala Glu Tyr Phe Gln His Trp Gly Gln Gly Thr Leu Val
            20                  25                  30

Thr Val Ser Ser
        35

<210> SEQ ID NO 254
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Tyr Tyr Cys Ala Lys Tyr Tyr Tyr Tyr Asp Tyr Val Trp Gly Ser Tyr
```

```
                1               5                  10                 15
Arg Tyr Thr Ser Asn Trp Phe Asp Pro Trp Gly Gln Gly Thr Leu Val
                    20                 25                 30
Thr Val Ser Ser
        35

<210> SEQ ID NO 255
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Tyr Tyr Cys Ala Lys Tyr Tyr Tyr Asp Tyr Val Trp Gly Ser Tyr
1               5                  10                 15

Arg Tyr Thr Ser Ser Tyr Phe Asp Tyr Trp Gly Gln Gly Thr Leu Val
                    20                 25                 30

Thr Val Ser Ser
        35

<210> SEQ ID NO 256
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
actggagacg gtgaccgtag taccctggcc cca                                    33

<210> SEQ ID NO 257
<211> LENGTH: 4
<212> TYPE: PRT
<213> ORGANISM: Homo sapiens

<400> SEQUENCE: 257

Gly Thr Thr Gly
1

<210> SEQ ID NO 258
<211> LENGTH: 4
<212> TYPE: PRT
<213> ORGANISM: Homo sapiens

<400> SEQUENCE: 258

Val Gln Leu Glu
1

<210> SEQ ID NO 259
<211> LENGTH: 4
<212> TYPE: PRT
<213> ORGANISM: Homo sapiens

<400> SEQUENCE: 259

Tyr Asn Trp Asn
1

<210> SEQ ID NO 260
<211> LENGTH: 5
<212> TYPE: PRT
<213> ORGANISM: Homo sapiens
```

<400> SEQUENCE: 260

Gly Thr Thr Gly Thr
1               5

<210> SEQ ID NO 261
<211> LENGTH: 5
<212> TYPE: PRT
<213> ORGANISM: Homo sapiens

<400> SEQUENCE: 261

Val Gln Leu Glu Arg
1               5

<210> SEQ ID NO 262
<211> LENGTH: 5
<212> TYPE: PRT
<213> ORGANISM: Homo sapiens

<400> SEQUENCE: 262

Tyr Asn Trp Asn Asp
1               5

<210> SEQ ID NO 263
<211> LENGTH: 4
<212> TYPE: PRT
<213> ORGANISM: Homo sapiens

<400> SEQUENCE: 263

Thr Thr Gly Thr
1

<210> SEQ ID NO 264
<211> LENGTH: 4
<212> TYPE: PRT
<213> ORGANISM: Homo sapiens

<400> SEQUENCE: 264

Gln Leu Glu Arg
1

<210> SEQ ID NO 265
<211> LENGTH: 4
<212> TYPE: PRT
<213> ORGANISM: Homo sapiens

<400> SEQUENCE: 265

Asn Trp Asn Asp
1

<210> SEQ ID NO 266
<211> LENGTH: 4
<212> TYPE: PRT
<213> ORGANISM: Homo sapiens

<400> SEQUENCE: 266

Gly Ile Thr Gly
1

<210> SEQ ID NO 267
<211> LENGTH: 4
<212> TYPE: PRT
<213> ORGANISM: Homo sapiens

<400> SEQUENCE: 267

Val Tyr Leu Glu
1

<210> SEQ ID NO 268
<211> LENGTH: 5
<212> TYPE: PRT
<213> ORGANISM: Homo sapiens

<400> SEQUENCE: 268

Gly Ile Thr Gly Thr
1               5

<210> SEQ ID NO 269
<211> LENGTH: 5
<212> TYPE: PRT
<213> ORGANISM: Homo sapiens

<400> SEQUENCE: 269

Val Tyr Leu Glu Leu
1               5

<210> SEQ ID NO 270
<211> LENGTH: 5
<212> TYPE: PRT
<213> ORGANISM: Homo sapiens

<400> SEQUENCE: 270

Tyr Asn Trp Asn Tyr
1               5

<210> SEQ ID NO 271
<211> LENGTH: 4
<212> TYPE: PRT
<213> ORGANISM: Homo sapiens

<400> SEQUENCE: 271

Ile Thr Gly Thr
1

<210> SEQ ID NO 272
<211> LENGTH: 4
<212> TYPE: PRT
<213> ORGANISM: Homo sapiens

<400> SEQUENCE: 272

Tyr Leu Glu Leu
1

<210> SEQ ID NO 273
<211> LENGTH: 4
<212> TYPE: PRT
<213> ORGANISM: Homo sapiens

<400> SEQUENCE: 273

Asn Trp Asn Tyr
1

<210> SEQ ID NO 274
<211> LENGTH: 5
<212> TYPE: PRT
<213> ORGANISM: Homo sapiens

<400> SEQUENCE: 274

Val Tyr Leu Glu Arg

```
<210> SEQ ID NO 275
<211> LENGTH: 4
<212> TYPE: PRT
<213> ORGANISM: Homo sapiens

<400> SEQUENCE: 275

Tyr Leu Glu Arg
1

<210> SEQ ID NO 276
<211> LENGTH: 4
<212> TYPE: PRT
<213> ORGANISM: Homo sapiens

<400> SEQUENCE: 276

Gly Ile Val Gly
1

<210> SEQ ID NO 277
<211> LENGTH: 4
<212> TYPE: PRT
<213> ORGANISM: Homo sapiens

<400> SEQUENCE: 277

Val Tyr Trp Glu
1

<210> SEQ ID NO 278
<211> LENGTH: 4
<212> TYPE: PRT
<213> ORGANISM: Homo sapiens

<400> SEQUENCE: 278

Tyr Ser Gly Ser
1

<210> SEQ ID NO 279
<211> LENGTH: 5
<212> TYPE: PRT
<213> ORGANISM: Homo sapiens

<400> SEQUENCE: 279

Gly Ile Val Gly Ala
1               5

<210> SEQ ID NO 280
<211> LENGTH: 5
<212> TYPE: PRT
<213> ORGANISM: Homo sapiens

<400> SEQUENCE: 280

Val Tyr Trp Glu Leu
1               5

<210> SEQ ID NO 281
<211> LENGTH: 5
<212> TYPE: PRT
<213> ORGANISM: Homo sapiens

<400> SEQUENCE: 281

Tyr Ser Gly Ser Tyr
1               5
```

```
<210> SEQ ID NO 282
<211> LENGTH: 6
<212> TYPE: PRT
<213> ORGANISM: Homo sapiens

<400> SEQUENCE: 282

Gly Ile Val Gly Ala Thr
1               5

<210> SEQ ID NO 283
<211> LENGTH: 6
<212> TYPE: PRT
<213> ORGANISM: Homo sapiens

<400> SEQUENCE: 283

Val Tyr Trp Glu Leu Leu
1               5

<210> SEQ ID NO 284
<211> LENGTH: 6
<212> TYPE: PRT
<213> ORGANISM: Homo sapiens

<400> SEQUENCE: 284

Tyr Ser Gly Ser Tyr Tyr
1               5

<210> SEQ ID NO 285
<211> LENGTH: 4
<212> TYPE: PRT
<213> ORGANISM: Homo sapiens

<400> SEQUENCE: 285

Ile Val Gly Ala
1

<210> SEQ ID NO 286
<211> LENGTH: 4
<212> TYPE: PRT
<213> ORGANISM: Homo sapiens

<400> SEQUENCE: 286

Tyr Trp Glu Leu
1

<210> SEQ ID NO 287
<211> LENGTH: 4
<212> TYPE: PRT
<213> ORGANISM: Homo sapiens

<400> SEQUENCE: 287

Ser Gly Ser Tyr
1

<210> SEQ ID NO 288
<211> LENGTH: 5
<212> TYPE: PRT
<213> ORGANISM: Homo sapiens

<400> SEQUENCE: 288

Ile Val Gly Ala Thr
1               5

<210> SEQ ID NO 289
```

```
<211> LENGTH: 5
<212> TYPE: PRT
<213> ORGANISM: Homo sapiens

<400> SEQUENCE: 289

Tyr Trp Glu Leu Leu
1               5

<210> SEQ ID NO 290
<211> LENGTH: 5
<212> TYPE: PRT
<213> ORGANISM: Homo sapiens

<400> SEQUENCE: 290

Ser Gly Ser Tyr Tyr
1               5

<210> SEQ ID NO 291
<211> LENGTH: 4
<212> TYPE: PRT
<213> ORGANISM: Homo sapiens

<400> SEQUENCE: 291

Val Gly Ala Thr
1

<210> SEQ ID NO 292
<211> LENGTH: 4
<212> TYPE: PRT
<213> ORGANISM: Homo sapiens

<400> SEQUENCE: 292

Trp Glu Leu Leu
1

<210> SEQ ID NO 293
<211> LENGTH: 4
<212> TYPE: PRT
<213> ORGANISM: Homo sapiens

<400> SEQUENCE: 293

Gly Ser Tyr Tyr
1

<210> SEQ ID NO 294
<211> LENGTH: 4
<212> TYPE: PRT
<213> ORGANISM: Homo sapiens

<400> SEQUENCE: 294

Arg Ile Leu Tyr
1

<210> SEQ ID NO 295
<211> LENGTH: 4
<212> TYPE: PRT
<213> ORGANISM: Homo sapiens

<400> SEQUENCE: 295

Gly Tyr Cys Ser
1

<210> SEQ ID NO 296
<211> LENGTH: 4
<212> TYPE: PRT
```

<213> ORGANISM: Homo sapiens

<400> SEQUENCE: 296

Asp Ile Val Val
1

<210> SEQ ID NO 297
<211> LENGTH: 5
<212> TYPE: PRT
<213> ORGANISM: Homo sapiens

<400> SEQUENCE: 297

Arg Ile Leu Tyr Tyr
1               5

<210> SEQ ID NO 298
<211> LENGTH: 5
<212> TYPE: PRT
<213> ORGANISM: Homo sapiens

<400> SEQUENCE: 298

Gly Tyr Cys Ser Ser
1               5

<210> SEQ ID NO 299
<211> LENGTH: 5
<212> TYPE: PRT
<213> ORGANISM: Homo sapiens

<400> SEQUENCE: 299

Asp Ile Val Val Val
1               5

<210> SEQ ID NO 300
<211> LENGTH: 6
<212> TYPE: PRT
<213> ORGANISM: Homo sapiens

<400> SEQUENCE: 300

Arg Ile Leu Tyr Tyr Tyr
1               5

<210> SEQ ID NO 301
<211> LENGTH: 6
<212> TYPE: PRT
<213> ORGANISM: Homo sapiens

<400> SEQUENCE: 301

Gly Tyr Cys Ser Ser Thr
1               5

<210> SEQ ID NO 302
<211> LENGTH: 6
<212> TYPE: PRT
<213> ORGANISM: Homo sapiens

<400> SEQUENCE: 302

Asp Ile Val Val Val Pro
1               5

<210> SEQ ID NO 303
<211> LENGTH: 4
<212> TYPE: PRT
<213> ORGANISM: Homo sapiens

```
<400> SEQUENCE: 303

Ile Leu Tyr Tyr
1

<210> SEQ ID NO 304
<211> LENGTH: 4
<212> TYPE: PRT
<213> ORGANISM: Homo sapiens

<400> SEQUENCE: 304

Tyr Cys Ser Ser
1

<210> SEQ ID NO 305
<211> LENGTH: 4
<212> TYPE: PRT
<213> ORGANISM: Homo sapiens

<400> SEQUENCE: 305

Ile Val Val Val
1

<210> SEQ ID NO 306
<211> LENGTH: 5
<212> TYPE: PRT
<213> ORGANISM: Homo sapiens

<400> SEQUENCE: 306

Ile Leu Tyr Tyr Tyr
1               5

<210> SEQ ID NO 307
<211> LENGTH: 5
<212> TYPE: PRT
<213> ORGANISM: Homo sapiens

<400> SEQUENCE: 307

Tyr Cys Ser Ser Thr
1               5

<210> SEQ ID NO 308
<211> LENGTH: 5
<212> TYPE: PRT
<213> ORGANISM: Homo sapiens

<400> SEQUENCE: 308

Ile Val Val Val Pro
1               5

<210> SEQ ID NO 309
<211> LENGTH: 6
<212> TYPE: PRT
<213> ORGANISM: Homo sapiens

<400> SEQUENCE: 309

Ile Leu Tyr Tyr Tyr Gln
1               5

<210> SEQ ID NO 310
<211> LENGTH: 6
<212> TYPE: PRT
<213> ORGANISM: Homo sapiens

<400> SEQUENCE: 310
```

Tyr Cys Ser Ser Thr Ser
1               5

<210> SEQ ID NO 311
<211> LENGTH: 6
<212> TYPE: PRT
<213> ORGANISM: Homo sapiens

<400> SEQUENCE: 311

Ile Val Val Val Pro Ala
1               5

<210> SEQ ID NO 312
<211> LENGTH: 4
<212> TYPE: PRT
<213> ORGANISM: Homo sapiens

<400> SEQUENCE: 312

Leu Tyr Tyr Tyr
1

<210> SEQ ID NO 313
<211> LENGTH: 4
<212> TYPE: PRT
<213> ORGANISM: Homo sapiens

<400> SEQUENCE: 313

Cys Ser Ser Thr
1

<210> SEQ ID NO 314
<211> LENGTH: 4
<212> TYPE: PRT
<213> ORGANISM: Homo sapiens

<400> SEQUENCE: 314

Val Val Val Pro
1

<210> SEQ ID NO 315
<211> LENGTH: 5
<212> TYPE: PRT
<213> ORGANISM: Homo sapiens

<400> SEQUENCE: 315

Leu Tyr Tyr Tyr Gln
1               5

<210> SEQ ID NO 316
<211> LENGTH: 5
<212> TYPE: PRT
<213> ORGANISM: Homo sapiens

<400> SEQUENCE: 316

Cys Ser Ser Thr Ser
1               5

<210> SEQ ID NO 317
<211> LENGTH: 5
<212> TYPE: PRT
<213> ORGANISM: Homo sapiens

<400> SEQUENCE: 317

Val Val Val Pro Ala
1               5

```
<210> SEQ ID NO 318
<211> LENGTH: 6
<212> TYPE: PRT
<213> ORGANISM: Homo sapiens

<400> SEQUENCE: 318

Leu Tyr Tyr Tyr Gln Leu
1               5

<210> SEQ ID NO 319
<211> LENGTH: 6
<212> TYPE: PRT
<213> ORGANISM: Homo sapiens

<400> SEQUENCE: 319

Cys Ser Ser Thr Ser Cys
1               5

<210> SEQ ID NO 320
<211> LENGTH: 6
<212> TYPE: PRT
<213> ORGANISM: Homo sapiens

<400> SEQUENCE: 320

Val Val Val Pro Ala Ala
1               5

<210> SEQ ID NO 321
<211> LENGTH: 4
<212> TYPE: PRT
<213> ORGANISM: Homo sapiens

<400> SEQUENCE: 321

Tyr Tyr Tyr Gln
1

<210> SEQ ID NO 322
<211> LENGTH: 4
<212> TYPE: PRT
<213> ORGANISM: Homo sapiens

<400> SEQUENCE: 322

Ser Ser Thr Ser
1

<210> SEQ ID NO 323
<211> LENGTH: 4
<212> TYPE: PRT
<213> ORGANISM: Homo sapiens

<400> SEQUENCE: 323

Val Val Pro Ala
1

<210> SEQ ID NO 324
<211> LENGTH: 5
<212> TYPE: PRT
<213> ORGANISM: Homo sapiens

<400> SEQUENCE: 324

Tyr Tyr Tyr Gln Leu
1               5
```

```
<210> SEQ ID NO 325
<211> LENGTH: 5
<212> TYPE: PRT
<213> ORGANISM: Homo sapiens

<400> SEQUENCE: 325

Ser Ser Thr Ser Cys
1               5

<210> SEQ ID NO 326
<211> LENGTH: 5
<212> TYPE: PRT
<213> ORGANISM: Homo sapiens

<400> SEQUENCE: 326

Val Val Pro Ala Ala
1               5

<210> SEQ ID NO 327
<211> LENGTH: 6
<212> TYPE: PRT
<213> ORGANISM: Homo sapiens

<400> SEQUENCE: 327

Tyr Tyr Tyr Gln Leu Leu
1               5

<210> SEQ ID NO 328
<211> LENGTH: 6
<212> TYPE: PRT
<213> ORGANISM: Homo sapiens

<400> SEQUENCE: 328

Ser Ser Thr Ser Cys Tyr
1               5

<210> SEQ ID NO 329
<211> LENGTH: 6
<212> TYPE: PRT
<213> ORGANISM: Homo sapiens

<400> SEQUENCE: 329

Val Val Pro Ala Ala Ile
1               5

<210> SEQ ID NO 330
<211> LENGTH: 4
<212> TYPE: PRT
<213> ORGANISM: Homo sapiens

<400> SEQUENCE: 330

Tyr Tyr Gln Leu
1

<210> SEQ ID NO 331
<211> LENGTH: 4
<212> TYPE: PRT
<213> ORGANISM: Homo sapiens

<400> SEQUENCE: 331

Ser Thr Ser Cys
1

<210> SEQ ID NO 332
<211> LENGTH: 4
```

```
<212> TYPE: PRT
<213> ORGANISM: Homo sapiens

<400> SEQUENCE: 332

Val Pro Ala Ala
1

<210> SEQ ID NO 333
<211> LENGTH: 5
<212> TYPE: PRT
<213> ORGANISM: Homo sapiens

<400> SEQUENCE: 333

Tyr Tyr Gln Leu Leu
1               5

<210> SEQ ID NO 334
<211> LENGTH: 5
<212> TYPE: PRT
<213> ORGANISM: Homo sapiens

<400> SEQUENCE: 334

Ser Thr Ser Cys Tyr
1               5

<210> SEQ ID NO 335
<211> LENGTH: 5
<212> TYPE: PRT
<213> ORGANISM: Homo sapiens

<400> SEQUENCE: 335

Val Pro Ala Ala Ile
1               5

<210> SEQ ID NO 336
<211> LENGTH: 6
<212> TYPE: PRT
<213> ORGANISM: Homo sapiens

<400> SEQUENCE: 336

Tyr Tyr Gln Leu Leu Tyr
1               5

<210> SEQ ID NO 337
<211> LENGTH: 6
<212> TYPE: PRT
<213> ORGANISM: Homo sapiens

<400> SEQUENCE: 337

Ser Thr Ser Cys Tyr Thr
1               5

<210> SEQ ID NO 338
<211> LENGTH: 4
<212> TYPE: PRT
<213> ORGANISM: Homo sapiens

<400> SEQUENCE: 338

Tyr Gln Leu Leu
1

<210> SEQ ID NO 339
<211> LENGTH: 4
<212> TYPE: PRT
<213> ORGANISM: Homo sapiens
```

<400> SEQUENCE: 339

Thr Ser Cys Tyr
1

<210> SEQ ID NO 340
<211> LENGTH: 4
<212> TYPE: PRT
<213> ORGANISM: Homo sapiens

<400> SEQUENCE: 340

Pro Ala Ala Ile
1

<210> SEQ ID NO 341
<211> LENGTH: 5
<212> TYPE: PRT
<213> ORGANISM: Homo sapiens

<400> SEQUENCE: 341

Tyr Gln Leu Leu Tyr
1               5

<210> SEQ ID NO 342
<211> LENGTH: 5
<212> TYPE: PRT
<213> ORGANISM: Homo sapiens

<400> SEQUENCE: 342

Thr Ser Cys Tyr Thr
1               5

<210> SEQ ID NO 343
<211> LENGTH: 4
<212> TYPE: PRT
<213> ORGANISM: Homo sapiens

<400> SEQUENCE: 343

Gln Leu Leu Tyr
1

<210> SEQ ID NO 344
<211> LENGTH: 4
<212> TYPE: PRT
<213> ORGANISM: Homo sapiens

<400> SEQUENCE: 344

Ser Cys Tyr Thr
1

<210> SEQ ID NO 345
<211> LENGTH: 4
<212> TYPE: PRT
<213> ORGANISM: Homo sapiens

<400> SEQUENCE: 345

Arg Ile Leu Tyr
1

<210> SEQ ID NO 346
<211> LENGTH: 4
<212> TYPE: PRT
<213> ORGANISM: Homo sapiens

<400> SEQUENCE: 346

Gly Tyr Cys Thr
1

<210> SEQ ID NO 347
<211> LENGTH: 4
<212> TYPE: PRT
<213> ORGANISM: Homo sapiens

<400> SEQUENCE: 347

Asp Ile Val Leu
1

<210> SEQ ID NO 348
<211> LENGTH: 5
<212> TYPE: PRT
<213> ORGANISM: Homo sapiens

<400> SEQUENCE: 348

Arg Ile Leu Tyr Tyr
1               5

<210> SEQ ID NO 349
<211> LENGTH: 5
<212> TYPE: PRT
<213> ORGANISM: Homo sapiens

<400> SEQUENCE: 349

Gly Tyr Cys Thr Asn
1               5

<210> SEQ ID NO 350
<211> LENGTH: 5
<212> TYPE: PRT
<213> ORGANISM: Homo sapiens

<400> SEQUENCE: 350

Asp Ile Val Leu Met
1               5

<210> SEQ ID NO 351
<211> LENGTH: 6
<212> TYPE: PRT
<213> ORGANISM: Homo sapiens

<400> SEQUENCE: 351

Arg Ile Leu Tyr Tyr Trp
1               5

<210> SEQ ID NO 352
<211> LENGTH: 6
<212> TYPE: PRT
<213> ORGANISM: Homo sapiens

<400> SEQUENCE: 352

Gly Tyr Cys Thr Asn Gly
1               5

<210> SEQ ID NO 353
<211> LENGTH: 6
<212> TYPE: PRT
<213> ORGANISM: Homo sapiens

<400> SEQUENCE: 353

Asp Ile Val Leu Met Val

```
<210> SEQ ID NO 354
<211> LENGTH: 4
<212> TYPE: PRT
<213> ORGANISM: Homo sapiens

<400> SEQUENCE: 354

Ile Leu Tyr Tyr
1

<210> SEQ ID NO 355
<211> LENGTH: 4
<212> TYPE: PRT
<213> ORGANISM: Homo sapiens

<400> SEQUENCE: 355

Tyr Cys Thr Asn
1

<210> SEQ ID NO 356
<211> LENGTH: 4
<212> TYPE: PRT
<213> ORGANISM: Homo sapiens

<400> SEQUENCE: 356

Ile Val Leu Met
1

<210> SEQ ID NO 357
<211> LENGTH: 5
<212> TYPE: PRT
<213> ORGANISM: Homo sapiens

<400> SEQUENCE: 357

Ile Leu Tyr Tyr Trp
1               5

<210> SEQ ID NO 358
<211> LENGTH: 5
<212> TYPE: PRT
<213> ORGANISM: Homo sapiens

<400> SEQUENCE: 358

Tyr Cys Thr Asn Gly
1               5

<210> SEQ ID NO 359
<211> LENGTH: 5
<212> TYPE: PRT
<213> ORGANISM: Homo sapiens

<400> SEQUENCE: 359

Ile Val Leu Met Val
1               5

<210> SEQ ID NO 360
<211> LENGTH: 6
<212> TYPE: PRT
<213> ORGANISM: Homo sapiens

<400> SEQUENCE: 360

Ile Leu Tyr Tyr Trp Cys
1               5
```

```
<210> SEQ ID NO 361
<211> LENGTH: 6
<212> TYPE: PRT
<213> ORGANISM: Homo sapiens

<400> SEQUENCE: 361

Tyr Cys Thr Asn Gly Val
1               5

<210> SEQ ID NO 362
<211> LENGTH: 6
<212> TYPE: PRT
<213> ORGANISM: Homo sapiens

<400> SEQUENCE: 362

Ile Val Leu Met Val Tyr
1               5

<210> SEQ ID NO 363
<211> LENGTH: 4
<212> TYPE: PRT
<213> ORGANISM: Homo sapiens

<400> SEQUENCE: 363

Leu Tyr Tyr Trp
1

<210> SEQ ID NO 364
<211> LENGTH: 4
<212> TYPE: PRT
<213> ORGANISM: Homo sapiens

<400> SEQUENCE: 364

Cys Thr Asn Gly
1

<210> SEQ ID NO 365
<211> LENGTH: 4
<212> TYPE: PRT
<213> ORGANISM: Homo sapiens

<400> SEQUENCE: 365

Val Leu Met Val
1

<210> SEQ ID NO 366
<211> LENGTH: 5
<212> TYPE: PRT
<213> ORGANISM: Homo sapiens

<400> SEQUENCE: 366

Leu Tyr Tyr Trp Cys
1               5

<210> SEQ ID NO 367
<211> LENGTH: 5
<212> TYPE: PRT
<213> ORGANISM: Homo sapiens

<400> SEQUENCE: 367

Cys Thr Asn Gly Val
1               5

<210> SEQ ID NO 368
```

```
<211> LENGTH: 5
<212> TYPE: PRT
<213> ORGANISM: Homo sapiens

<400> SEQUENCE: 368

Val Leu Met Val Tyr
1               5

<210> SEQ ID NO 369
<211> LENGTH: 6
<212> TYPE: PRT
<213> ORGANISM: Homo sapiens

<400> SEQUENCE: 369

Leu Tyr Tyr Trp Cys Met
1               5

<210> SEQ ID NO 370
<211> LENGTH: 6
<212> TYPE: PRT
<213> ORGANISM: Homo sapiens

<400> SEQUENCE: 370

Cys Thr Asn Gly Val Cys
1               5

<210> SEQ ID NO 371
<211> LENGTH: 6
<212> TYPE: PRT
<213> ORGANISM: Homo sapiens

<400> SEQUENCE: 371

Val Leu Met Val Tyr Ala
1               5

<210> SEQ ID NO 372
<211> LENGTH: 4
<212> TYPE: PRT
<213> ORGANISM: Homo sapiens

<400> SEQUENCE: 372

Tyr Tyr Trp Cys
1

<210> SEQ ID NO 373
<211> LENGTH: 4
<212> TYPE: PRT
<213> ORGANISM: Homo sapiens

<400> SEQUENCE: 373

Thr Asn Gly Val
1

<210> SEQ ID NO 374
<211> LENGTH: 4
<212> TYPE: PRT
<213> ORGANISM: Homo sapiens

<400> SEQUENCE: 374

Leu Met Val Tyr
1

<210> SEQ ID NO 375
<211> LENGTH: 5
<212> TYPE: PRT
```

<213> ORGANISM: Homo sapiens

<400> SEQUENCE: 375

Tyr Tyr Trp Cys Met
1               5

<210> SEQ ID NO 376
<211> LENGTH: 5
<212> TYPE: PRT
<213> ORGANISM: Homo sapiens

<400> SEQUENCE: 376

Thr Asn Gly Val Cys
1               5

<210> SEQ ID NO 377
<211> LENGTH: 5
<212> TYPE: PRT
<213> ORGANISM: Homo sapiens

<400> SEQUENCE: 377

Leu Met Val Tyr Ala
1               5

<210> SEQ ID NO 378
<211> LENGTH: 6
<212> TYPE: PRT
<213> ORGANISM: Homo sapiens

<400> SEQUENCE: 378

Tyr Tyr Trp Cys Met Leu
1               5

<210> SEQ ID NO 379
<211> LENGTH: 6
<212> TYPE: PRT
<213> ORGANISM: Homo sapiens

<400> SEQUENCE: 379

Thr Asn Gly Val Cys Tyr
1               5

<210> SEQ ID NO 380
<211> LENGTH: 6
<212> TYPE: PRT
<213> ORGANISM: Homo sapiens

<400> SEQUENCE: 380

Leu Met Val Tyr Ala Ile
1               5

<210> SEQ ID NO 381
<211> LENGTH: 4
<212> TYPE: PRT
<213> ORGANISM: Homo sapiens

<400> SEQUENCE: 381

Tyr Trp Cys Met
1

<210> SEQ ID NO 382
<211> LENGTH: 4
<212> TYPE: PRT
<213> ORGANISM: Homo sapiens

```
<400> SEQUENCE: 382

Asn Gly Val Cys
1

<210> SEQ ID NO 383
<211> LENGTH: 4
<212> TYPE: PRT
<213> ORGANISM: Homo sapiens

<400> SEQUENCE: 383

Met Val Tyr Ala
1

<210> SEQ ID NO 384
<211> LENGTH: 5
<212> TYPE: PRT
<213> ORGANISM: Homo sapiens

<400> SEQUENCE: 384

Tyr Trp Cys Met Leu
1               5

<210> SEQ ID NO 385
<211> LENGTH: 5
<212> TYPE: PRT
<213> ORGANISM: Homo sapiens

<400> SEQUENCE: 385

Asn Gly Val Cys Tyr
1               5

<210> SEQ ID NO 386
<211> LENGTH: 5
<212> TYPE: PRT
<213> ORGANISM: Homo sapiens

<400> SEQUENCE: 386

Met Val Tyr Ala Ile
1               5

<210> SEQ ID NO 387
<211> LENGTH: 6
<212> TYPE: PRT
<213> ORGANISM: Homo sapiens

<400> SEQUENCE: 387

Tyr Trp Cys Met Leu Tyr
1               5

<210> SEQ ID NO 388
<211> LENGTH: 6
<212> TYPE: PRT
<213> ORGANISM: Homo sapiens

<400> SEQUENCE: 388

Asn Gly Val Cys Tyr Thr
1               5

<210> SEQ ID NO 389
<211> LENGTH: 4
<212> TYPE: PRT
<213> ORGANISM: Homo sapiens

<400> SEQUENCE: 389
```

Trp Cys Met Leu
1

<210> SEQ ID NO 390
<211> LENGTH: 4
<212> TYPE: PRT
<213> ORGANISM: Homo sapiens

<400> SEQUENCE: 390

Gly Val Cys Tyr
1

<210> SEQ ID NO 391
<211> LENGTH: 4
<212> TYPE: PRT
<213> ORGANISM: Homo sapiens

<400> SEQUENCE: 391

Val Tyr Ala Ile
1

<210> SEQ ID NO 392
<211> LENGTH: 5
<212> TYPE: PRT
<213> ORGANISM: Homo sapiens

<400> SEQUENCE: 392

Trp Cys Met Leu Tyr
1               5

<210> SEQ ID NO 393
<211> LENGTH: 5
<212> TYPE: PRT
<213> ORGANISM: Homo sapiens

<400> SEQUENCE: 393

Gly Val Cys Tyr Thr
1               5

<210> SEQ ID NO 394
<211> LENGTH: 4
<212> TYPE: PRT
<213> ORGANISM: Homo sapiens

<400> SEQUENCE: 394

Cys Met Leu Tyr
1

<210> SEQ ID NO 395
<211> LENGTH: 4
<212> TYPE: PRT
<213> ORGANISM: Homo sapiens

<400> SEQUENCE: 395

Val Cys Tyr Thr
1

<210> SEQ ID NO 396
<211> LENGTH: 5
<212> TYPE: PRT
<213> ORGANISM: Homo sapiens

<400> SEQUENCE: 396

Arg Ile Leu Tyr Trp
1               5

<210> SEQ ID NO 397
<211> LENGTH: 5
<212> TYPE: PRT
<213> ORGANISM: Homo sapiens

<400> SEQUENCE: 397

Gly Tyr Cys Ser Gly
1               5

<210> SEQ ID NO 398
<211> LENGTH: 6
<212> TYPE: PRT
<213> ORGANISM: Homo sapiens

<400> SEQUENCE: 398

Arg Ile Leu Tyr Trp Trp
1               5

<210> SEQ ID NO 399
<211> LENGTH: 6
<212> TYPE: PRT
<213> ORGANISM: Homo sapiens

<400> SEQUENCE: 399

Gly Tyr Cys Ser Gly Gly
1               5

<210> SEQ ID NO 400
<211> LENGTH: 6
<212> TYPE: PRT
<213> ORGANISM: Homo sapiens

<400> SEQUENCE: 400

Asp Ile Val Val Val Val
1               5

<210> SEQ ID NO 401
<211> LENGTH: 4
<212> TYPE: PRT
<213> ORGANISM: Homo sapiens

<400> SEQUENCE: 401

Ile Leu Tyr Trp
1

<210> SEQ ID NO 402
<211> LENGTH: 4
<212> TYPE: PRT
<213> ORGANISM: Homo sapiens

<400> SEQUENCE: 402

Tyr Cys Ser Gly
1

<210> SEQ ID NO 403
<211> LENGTH: 5
<212> TYPE: PRT
<213> ORGANISM: Homo sapiens

<400> SEQUENCE: 403

Ile Leu Tyr Trp Trp
1               5

```
<210> SEQ ID NO 404
<211> LENGTH: 5
<212> TYPE: PRT
<213> ORGANISM: Homo sapiens

<400> SEQUENCE: 404

Tyr Cys Ser Gly Gly
1               5

<210> SEQ ID NO 405
<211> LENGTH: 5
<212> TYPE: PRT
<213> ORGANISM: Homo sapiens

<400> SEQUENCE: 405

Ile Val Val Val Val
1               5

<210> SEQ ID NO 406
<211> LENGTH: 6
<212> TYPE: PRT
<213> ORGANISM: Homo sapiens

<400> SEQUENCE: 406

Ile Leu Tyr Trp Trp Tyr
1               5

<210> SEQ ID NO 407
<211> LENGTH: 6
<212> TYPE: PRT
<213> ORGANISM: Homo sapiens

<400> SEQUENCE: 407

Tyr Cys Ser Gly Gly Ser
1               5

<210> SEQ ID NO 408
<211> LENGTH: 6
<212> TYPE: PRT
<213> ORGANISM: Homo sapiens

<400> SEQUENCE: 408

Ile Val Val Val Val Ala
1               5

<210> SEQ ID NO 409
<211> LENGTH: 4
<212> TYPE: PRT
<213> ORGANISM: Homo sapiens

<400> SEQUENCE: 409

Leu Tyr Trp Trp
1

<210> SEQ ID NO 410
<211> LENGTH: 4
<212> TYPE: PRT
<213> ORGANISM: Homo sapiens

<400> SEQUENCE: 410

Cys Ser Gly Gly
1

<210> SEQ ID NO 411
<211> LENGTH: 4
```

```
<212> TYPE: PRT
<213> ORGANISM: Homo sapiens

<400> SEQUENCE: 411

Val Val Val Val
1

<210> SEQ ID NO 412
<211> LENGTH: 5
<212> TYPE: PRT
<213> ORGANISM: Homo sapiens

<400> SEQUENCE: 412

Leu Tyr Trp Trp Tyr
1               5

<210> SEQ ID NO 413
<211> LENGTH: 5
<212> TYPE: PRT
<213> ORGANISM: Homo sapiens

<400> SEQUENCE: 413

Cys Ser Gly Gly Ser
1               5

<210> SEQ ID NO 414
<211> LENGTH: 5
<212> TYPE: PRT
<213> ORGANISM: Homo sapiens

<400> SEQUENCE: 414

Val Val Val Val Ala
1               5

<210> SEQ ID NO 415
<211> LENGTH: 6
<212> TYPE: PRT
<213> ORGANISM: Homo sapiens

<400> SEQUENCE: 415

Leu Tyr Trp Trp Tyr Leu
1               5

<210> SEQ ID NO 416
<211> LENGTH: 6
<212> TYPE: PRT
<213> ORGANISM: Homo sapiens

<400> SEQUENCE: 416

Cys Ser Gly Gly Ser Cys
1               5

<210> SEQ ID NO 417
<211> LENGTH: 6
<212> TYPE: PRT
<213> ORGANISM: Homo sapiens

<400> SEQUENCE: 417

Val Val Val Val Ala Ala
1               5

<210> SEQ ID NO 418
<211> LENGTH: 4
<212> TYPE: PRT
<213> ORGANISM: Homo sapiens
```

<400> SEQUENCE: 418

Tyr Trp Trp Tyr
1

<210> SEQ ID NO 419
<211> LENGTH: 4
<212> TYPE: PRT
<213> ORGANISM: Homo sapiens

<400> SEQUENCE: 419

Ser Gly Gly Ser
1

<210> SEQ ID NO 420
<211> LENGTH: 4
<212> TYPE: PRT
<213> ORGANISM: Homo sapiens

<400> SEQUENCE: 420

Val Val Val Ala
1

<210> SEQ ID NO 421
<211> LENGTH: 5
<212> TYPE: PRT
<213> ORGANISM: Homo sapiens

<400> SEQUENCE: 421

Tyr Trp Trp Tyr Leu
1               5

<210> SEQ ID NO 422
<211> LENGTH: 5
<212> TYPE: PRT
<213> ORGANISM: Homo sapiens

<400> SEQUENCE: 422

Ser Gly Gly Ser Cys
1               5

<210> SEQ ID NO 423
<211> LENGTH: 5
<212> TYPE: PRT
<213> ORGANISM: Homo sapiens

<400> SEQUENCE: 423

Val Val Val Ala Ala
1               5

<210> SEQ ID NO 424
<211> LENGTH: 6
<212> TYPE: PRT
<213> ORGANISM: Homo sapiens

<400> SEQUENCE: 424

Tyr Trp Trp Tyr Leu Leu
1               5

<210> SEQ ID NO 425
<211> LENGTH: 6
<212> TYPE: PRT
<213> ORGANISM: Homo sapiens

<400> SEQUENCE: 425

```
Ser Gly Gly Ser Cys Tyr
1               5

<210> SEQ ID NO 426
<211> LENGTH: 6
<212> TYPE: PRT
<213> ORGANISM: Homo sapiens

<400> SEQUENCE: 426

Val Val Val Ala Ala Thr
1               5

<210> SEQ ID NO 427
<211> LENGTH: 4
<212> TYPE: PRT
<213> ORGANISM: Homo sapiens

<400> SEQUENCE: 427

Trp Trp Tyr Leu
1

<210> SEQ ID NO 428
<211> LENGTH: 4
<212> TYPE: PRT
<213> ORGANISM: Homo sapiens

<400> SEQUENCE: 428

Gly Gly Ser Cys
1

<210> SEQ ID NO 429
<211> LENGTH: 4
<212> TYPE: PRT
<213> ORGANISM: Homo sapiens

<400> SEQUENCE: 429

Val Val Ala Ala
1

<210> SEQ ID NO 430
<211> LENGTH: 5
<212> TYPE: PRT
<213> ORGANISM: Homo sapiens

<400> SEQUENCE: 430

Trp Trp Tyr Leu Leu
1               5

<210> SEQ ID NO 431
<211> LENGTH: 5
<212> TYPE: PRT
<213> ORGANISM: Homo sapiens

<400> SEQUENCE: 431

Gly Gly Ser Cys Tyr
1               5

<210> SEQ ID NO 432
<211> LENGTH: 5
<212> TYPE: PRT
<213> ORGANISM: Homo sapiens

<400> SEQUENCE: 432

Val Val Ala Ala Thr
```

```
1               5

<210> SEQ ID NO 433
<211> LENGTH: 6
<212> TYPE: PRT
<213> ORGANISM: Homo sapiens

<400> SEQUENCE: 433

Trp Trp Tyr Leu Leu Leu
1               5

<210> SEQ ID NO 434
<211> LENGTH: 6
<212> TYPE: PRT
<213> ORGANISM: Homo sapiens

<400> SEQUENCE: 434

Gly Gly Ser Cys Tyr Ser
1               5

<210> SEQ ID NO 435
<211> LENGTH: 4
<212> TYPE: PRT
<213> ORGANISM: Homo sapiens

<400> SEQUENCE: 435

Trp Tyr Leu Leu
1

<210> SEQ ID NO 436
<211> LENGTH: 4
<212> TYPE: PRT
<213> ORGANISM: Homo sapiens

<400> SEQUENCE: 436

Gly Ser Cys Tyr
1

<210> SEQ ID NO 437
<211> LENGTH: 4
<212> TYPE: PRT
<213> ORGANISM: Homo sapiens

<400> SEQUENCE: 437

Val Ala Ala Thr
1

<210> SEQ ID NO 438
<211> LENGTH: 5
<212> TYPE: PRT
<213> ORGANISM: Homo sapiens

<400> SEQUENCE: 438

Trp Tyr Leu Leu Leu
1               5

<210> SEQ ID NO 439
<211> LENGTH: 5
<212> TYPE: PRT
<213> ORGANISM: Homo sapiens

<400> SEQUENCE: 439

Gly Ser Cys Tyr Ser
1               5
```

<210> SEQ ID NO 440
<211> LENGTH: 4
<212> TYPE: PRT
<213> ORGANISM: Homo sapiens

<400> SEQUENCE: 440

Tyr Leu Leu Leu
1

<210> SEQ ID NO 441
<211> LENGTH: 4
<212> TYPE: PRT
<213> ORGANISM: Homo sapiens

<400> SEQUENCE: 441

Ser Cys Tyr Ser
1

<210> SEQ ID NO 442
<211> LENGTH: 4
<212> TYPE: PRT
<213> ORGANISM: Homo sapiens

<400> SEQUENCE: 442

Ser Ile Leu Trp
1

<210> SEQ ID NO 443
<211> LENGTH: 4
<212> TYPE: PRT
<213> ORGANISM: Homo sapiens

<400> SEQUENCE: 443

Ala Tyr Cys Gly
1

<210> SEQ ID NO 444
<211> LENGTH: 4
<212> TYPE: PRT
<213> ORGANISM: Homo sapiens

<400> SEQUENCE: 444

His Ile Val Val
1

<210> SEQ ID NO 445
<211> LENGTH: 5
<212> TYPE: PRT
<213> ORGANISM: Homo sapiens

<400> SEQUENCE: 445

Ser Ile Leu Trp Trp
1               5

<210> SEQ ID NO 446
<211> LENGTH: 5
<212> TYPE: PRT
<213> ORGANISM: Homo sapiens

<400> SEQUENCE: 446

Ala Tyr Cys Gly Gly
1               5

<210> SEQ ID NO 447

```
<211> LENGTH: 5
<212> TYPE: PRT
<213> ORGANISM: Homo sapiens

<400> SEQUENCE: 447

His Ile Val Val Val
1               5

<210> SEQ ID NO 448
<211> LENGTH: 6
<212> TYPE: PRT
<213> ORGANISM: Homo sapiens

<400> SEQUENCE: 448

Ser Ile Leu Trp Trp Trp
1               5

<210> SEQ ID NO 449
<211> LENGTH: 6
<212> TYPE: PRT
<213> ORGANISM: Homo sapiens

<400> SEQUENCE: 449

Ala Tyr Cys Gly Gly Asp
1               5

<210> SEQ ID NO 450
<211> LENGTH: 6
<212> TYPE: PRT
<213> ORGANISM: Homo sapiens

<400> SEQUENCE: 450

His Ile Val Val Val Thr
1               5

<210> SEQ ID NO 451
<211> LENGTH: 4
<212> TYPE: PRT
<213> ORGANISM: Homo sapiens

<400> SEQUENCE: 451

Ile Leu Trp Trp
1

<210> SEQ ID NO 452
<211> LENGTH: 4
<212> TYPE: PRT
<213> ORGANISM: Homo sapiens

<400> SEQUENCE: 452

Tyr Cys Gly Gly
1

<210> SEQ ID NO 453
<211> LENGTH: 5
<212> TYPE: PRT
<213> ORGANISM: Homo sapiens

<400> SEQUENCE: 453

Ile Leu Trp Trp Trp
1               5

<210> SEQ ID NO 454
<211> LENGTH: 5
<212> TYPE: PRT
```

<213> ORGANISM: Homo sapiens

<400> SEQUENCE: 454

Tyr Cys Gly Gly Asp
1               5

<210> SEQ ID NO 455
<211> LENGTH: 5
<212> TYPE: PRT
<213> ORGANISM: Homo sapiens

<400> SEQUENCE: 455

Ile Val Val Val Thr
1               5

<210> SEQ ID NO 456
<211> LENGTH: 6
<212> TYPE: PRT
<213> ORGANISM: Homo sapiens

<400> SEQUENCE: 456

Ile Leu Trp Trp Trp Leu
1               5

<210> SEQ ID NO 457
<211> LENGTH: 6
<212> TYPE: PRT
<213> ORGANISM: Homo sapiens

<400> SEQUENCE: 457

Tyr Cys Gly Gly Asp Cys
1               5

<210> SEQ ID NO 458
<211> LENGTH: 6
<212> TYPE: PRT
<213> ORGANISM: Homo sapiens

<400> SEQUENCE: 458

Ile Val Val Val Thr Ala
1               5

<210> SEQ ID NO 459
<211> LENGTH: 4
<212> TYPE: PRT
<213> ORGANISM: Homo sapiens

<400> SEQUENCE: 459

Leu Trp Trp Trp
1

<210> SEQ ID NO 460
<211> LENGTH: 4
<212> TYPE: PRT
<213> ORGANISM: Homo sapiens

<400> SEQUENCE: 460

Cys Gly Gly Asp
1

<210> SEQ ID NO 461
<211> LENGTH: 4
<212> TYPE: PRT
<213> ORGANISM: Homo sapiens

<400> SEQUENCE: 461

Val Val Val Thr
1

<210> SEQ ID NO 462
<211> LENGTH: 5
<212> TYPE: PRT
<213> ORGANISM: Homo sapiens

<400> SEQUENCE: 462

Leu Trp Trp Trp Leu
1               5

<210> SEQ ID NO 463
<211> LENGTH: 5
<212> TYPE: PRT
<213> ORGANISM: Homo sapiens

<400> SEQUENCE: 463

Cys Gly Gly Asp Cys
1               5

<210> SEQ ID NO 464
<211> LENGTH: 5
<212> TYPE: PRT
<213> ORGANISM: Homo sapiens

<400> SEQUENCE: 464

Val Val Val Thr Ala
1               5

<210> SEQ ID NO 465
<211> LENGTH: 6
<212> TYPE: PRT
<213> ORGANISM: Homo sapiens

<400> SEQUENCE: 465

Leu Trp Trp Trp Leu Leu
1               5

<210> SEQ ID NO 466
<211> LENGTH: 6
<212> TYPE: PRT
<213> ORGANISM: Homo sapiens

<400> SEQUENCE: 466

Cys Gly Gly Asp Cys Tyr
1               5

<210> SEQ ID NO 467
<211> LENGTH: 6
<212> TYPE: PRT
<213> ORGANISM: Homo sapiens

<400> SEQUENCE: 467

Val Val Val Thr Ala Ile
1               5

<210> SEQ ID NO 468
<211> LENGTH: 4
<212> TYPE: PRT
<213> ORGANISM: Homo sapiens

<400> SEQUENCE: 468

```
Trp Trp Trp Leu
1

<210> SEQ ID NO 469
<211> LENGTH: 4
<212> TYPE: PRT
<213> ORGANISM: Homo sapiens

<400> SEQUENCE: 469

Gly Gly Asp Cys
1

<210> SEQ ID NO 470
<211> LENGTH: 4
<212> TYPE: PRT
<213> ORGANISM: Homo sapiens

<400> SEQUENCE: 470

Val Val Thr Ala
1

<210> SEQ ID NO 471
<211> LENGTH: 5
<212> TYPE: PRT
<213> ORGANISM: Homo sapiens

<400> SEQUENCE: 471

Trp Trp Trp Leu Leu
1               5

<210> SEQ ID NO 472
<211> LENGTH: 5
<212> TYPE: PRT
<213> ORGANISM: Homo sapiens

<400> SEQUENCE: 472

Gly Gly Asp Cys Tyr
1               5

<210> SEQ ID NO 473
<211> LENGTH: 5
<212> TYPE: PRT
<213> ORGANISM: Homo sapiens

<400> SEQUENCE: 473

Val Val Thr Ala Ile
1               5

<210> SEQ ID NO 474
<211> LENGTH: 6
<212> TYPE: PRT
<213> ORGANISM: Homo sapiens

<400> SEQUENCE: 474

Trp Trp Trp Leu Leu Phe
1               5

<210> SEQ ID NO 475
<211> LENGTH: 6
<212> TYPE: PRT
<213> ORGANISM: Homo sapiens

<400> SEQUENCE: 475

Gly Gly Asp Cys Tyr Ser
1               5
```

```
<210> SEQ ID NO 476
<211> LENGTH: 4
<212> TYPE: PRT
<213> ORGANISM: Homo sapiens

<400> SEQUENCE: 476

Trp Trp Leu Leu
1

<210> SEQ ID NO 477
<211> LENGTH: 4
<212> TYPE: PRT
<213> ORGANISM: Homo sapiens

<400> SEQUENCE: 477

Gly Asp Cys Tyr
1

<210> SEQ ID NO 478
<211> LENGTH: 4
<212> TYPE: PRT
<213> ORGANISM: Homo sapiens

<400> SEQUENCE: 478

Val Thr Ala Ile
1

<210> SEQ ID NO 479
<211> LENGTH: 5
<212> TYPE: PRT
<213> ORGANISM: Homo sapiens

<400> SEQUENCE: 479

Trp Trp Leu Leu Phe
1               5

<210> SEQ ID NO 480
<211> LENGTH: 5
<212> TYPE: PRT
<213> ORGANISM: Homo sapiens

<400> SEQUENCE: 480

Gly Asp Cys Tyr Ser
1               5

<210> SEQ ID NO 481
<211> LENGTH: 4
<212> TYPE: PRT
<213> ORGANISM: Homo sapiens

<400> SEQUENCE: 481

Trp Leu Leu Phe
1

<210> SEQ ID NO 482
<211> LENGTH: 4
<212> TYPE: PRT
<213> ORGANISM: Homo sapiens

<400> SEQUENCE: 482

Asp Cys Tyr Ser
1
```

```
<210> SEQ ID NO 483
<211> LENGTH: 4
<212> TYPE: PRT
<213> ORGANISM: Homo sapiens

<400> SEQUENCE: 483

Val Leu Arg Phe
1

<210> SEQ ID NO 484
<211> LENGTH: 4
<212> TYPE: PRT
<213> ORGANISM: Homo sapiens

<400> SEQUENCE: 484

Tyr Tyr Asp Phe
1

<210> SEQ ID NO 485
<211> LENGTH: 4
<212> TYPE: PRT
<213> ORGANISM: Homo sapiens

<400> SEQUENCE: 485

Ile Thr Ile Phe
1

<210> SEQ ID NO 486
<211> LENGTH: 5
<212> TYPE: PRT
<213> ORGANISM: Homo sapiens

<400> SEQUENCE: 486

Val Leu Arg Phe Leu
1               5

<210> SEQ ID NO 487
<211> LENGTH: 5
<212> TYPE: PRT
<213> ORGANISM: Homo sapiens

<400> SEQUENCE: 487

Tyr Tyr Asp Phe Trp
1               5

<210> SEQ ID NO 488
<211> LENGTH: 5
<212> TYPE: PRT
<213> ORGANISM: Homo sapiens

<400> SEQUENCE: 488

Ile Thr Ile Phe Gly
1               5

<210> SEQ ID NO 489
<211> LENGTH: 6
<212> TYPE: PRT
<213> ORGANISM: Homo sapiens

<400> SEQUENCE: 489

Val Leu Arg Phe Leu Glu
1               5

<210> SEQ ID NO 490
<211> LENGTH: 6
```

```
<212> TYPE: PRT
<213> ORGANISM: Homo sapiens

<400> SEQUENCE: 490

Tyr Tyr Asp Phe Trp Ser
1               5

<210> SEQ ID NO 491
<211> LENGTH: 6
<212> TYPE: PRT
<213> ORGANISM: Homo sapiens

<400> SEQUENCE: 491

Ile Thr Ile Phe Gly Val
1               5

<210> SEQ ID NO 492
<211> LENGTH: 4
<212> TYPE: PRT
<213> ORGANISM: Homo sapiens

<400> SEQUENCE: 492

Leu Arg Phe Leu
1

<210> SEQ ID NO 493
<211> LENGTH: 4
<212> TYPE: PRT
<213> ORGANISM: Homo sapiens

<400> SEQUENCE: 493

Tyr Asp Phe Trp
1

<210> SEQ ID NO 494
<211> LENGTH: 4
<212> TYPE: PRT
<213> ORGANISM: Homo sapiens

<400> SEQUENCE: 494

Thr Ile Phe Gly
1

<210> SEQ ID NO 495
<211> LENGTH: 5
<212> TYPE: PRT
<213> ORGANISM: Homo sapiens

<400> SEQUENCE: 495

Leu Arg Phe Leu Glu
1               5

<210> SEQ ID NO 496
<211> LENGTH: 5
<212> TYPE: PRT
<213> ORGANISM: Homo sapiens

<400> SEQUENCE: 496

Tyr Asp Phe Trp Ser
1               5

<210> SEQ ID NO 497
<211> LENGTH: 5
<212> TYPE: PRT
<213> ORGANISM: Homo sapiens
```

<400> SEQUENCE: 497

Thr Ile Phe Gly Val
1               5

<210> SEQ ID NO 498
<211> LENGTH: 6
<212> TYPE: PRT
<213> ORGANISM: Homo sapiens

<400> SEQUENCE: 498

Leu Arg Phe Leu Glu Trp
1               5

<210> SEQ ID NO 499
<211> LENGTH: 6
<212> TYPE: PRT
<213> ORGANISM: Homo sapiens

<400> SEQUENCE: 499

Tyr Asp Phe Trp Ser Gly
1               5

<210> SEQ ID NO 500
<211> LENGTH: 6
<212> TYPE: PRT
<213> ORGANISM: Homo sapiens

<400> SEQUENCE: 500

Thr Ile Phe Gly Val Val
1               5

<210> SEQ ID NO 501
<211> LENGTH: 4
<212> TYPE: PRT
<213> ORGANISM: Homo sapiens

<400> SEQUENCE: 501

Arg Phe Leu Glu
1

<210> SEQ ID NO 502
<211> LENGTH: 4
<212> TYPE: PRT
<213> ORGANISM: Homo sapiens

<400> SEQUENCE: 502

Asp Phe Trp Ser
1

<210> SEQ ID NO 503
<211> LENGTH: 4
<212> TYPE: PRT
<213> ORGANISM: Homo sapiens

<400> SEQUENCE: 503

Ile Phe Gly Val
1

<210> SEQ ID NO 504
<211> LENGTH: 5
<212> TYPE: PRT
<213> ORGANISM: Homo sapiens

<400> SEQUENCE: 504

```
Arg Phe Leu Glu Trp
1               5

<210> SEQ ID NO 505
<211> LENGTH: 5
<212> TYPE: PRT
<213> ORGANISM: Homo sapiens

<400> SEQUENCE: 505

Asp Phe Trp Ser Gly
1               5

<210> SEQ ID NO 506
<211> LENGTH: 5
<212> TYPE: PRT
<213> ORGANISM: Homo sapiens

<400> SEQUENCE: 506

Ile Phe Gly Val Val
1               5

<210> SEQ ID NO 507
<211> LENGTH: 6
<212> TYPE: PRT
<213> ORGANISM: Homo sapiens

<400> SEQUENCE: 507

Arg Phe Leu Glu Trp Leu
1               5

<210> SEQ ID NO 508
<211> LENGTH: 6
<212> TYPE: PRT
<213> ORGANISM: Homo sapiens

<400> SEQUENCE: 508

Asp Phe Trp Ser Gly Tyr
1               5

<210> SEQ ID NO 509
<211> LENGTH: 6
<212> TYPE: PRT
<213> ORGANISM: Homo sapiens

<400> SEQUENCE: 509

Ile Phe Gly Val Val Ile
1               5

<210> SEQ ID NO 510
<211> LENGTH: 4
<212> TYPE: PRT
<213> ORGANISM: Homo sapiens

<400> SEQUENCE: 510

Phe Leu Glu Trp
1

<210> SEQ ID NO 511
<211> LENGTH: 4
<212> TYPE: PRT
<213> ORGANISM: Homo sapiens

<400> SEQUENCE: 511

Phe Trp Ser Gly
1
```

```
<210> SEQ ID NO 512
<211> LENGTH: 4
<212> TYPE: PRT
<213> ORGANISM: Homo sapiens

<400> SEQUENCE: 512

Phe Gly Val Val
1

<210> SEQ ID NO 513
<211> LENGTH: 5
<212> TYPE: PRT
<213> ORGANISM: Homo sapiens

<400> SEQUENCE: 513

Phe Leu Glu Trp Leu
1               5

<210> SEQ ID NO 514
<211> LENGTH: 5
<212> TYPE: PRT
<213> ORGANISM: Homo sapiens

<400> SEQUENCE: 514

Phe Trp Ser Gly Tyr
1               5

<210> SEQ ID NO 515
<211> LENGTH: 5
<212> TYPE: PRT
<213> ORGANISM: Homo sapiens

<400> SEQUENCE: 515

Phe Gly Val Val Ile
1               5

<210> SEQ ID NO 516
<211> LENGTH: 6
<212> TYPE: PRT
<213> ORGANISM: Homo sapiens

<400> SEQUENCE: 516

Phe Leu Glu Trp Leu Leu
1               5

<210> SEQ ID NO 517
<211> LENGTH: 6
<212> TYPE: PRT
<213> ORGANISM: Homo sapiens

<400> SEQUENCE: 517

Phe Trp Ser Gly Tyr Tyr
1               5

<210> SEQ ID NO 518
<211> LENGTH: 6
<212> TYPE: PRT
<213> ORGANISM: Homo sapiens

<400> SEQUENCE: 518

Phe Gly Val Val Ile Ile
1               5
```

```
<210> SEQ ID NO 519
<211> LENGTH: 4
<212> TYPE: PRT
<213> ORGANISM: Homo sapiens

<400> SEQUENCE: 519

Leu Glu Trp Leu
1

<210> SEQ ID NO 520
<211> LENGTH: 4
<212> TYPE: PRT
<213> ORGANISM: Homo sapiens

<400> SEQUENCE: 520

Trp Ser Gly Tyr
1

<210> SEQ ID NO 521
<211> LENGTH: 4
<212> TYPE: PRT
<213> ORGANISM: Homo sapiens

<400> SEQUENCE: 521

Gly Val Val Ile
1

<210> SEQ ID NO 522
<211> LENGTH: 5
<212> TYPE: PRT
<213> ORGANISM: Homo sapiens

<400> SEQUENCE: 522

Leu Glu Trp Leu Leu
1               5

<210> SEQ ID NO 523
<211> LENGTH: 5
<212> TYPE: PRT
<213> ORGANISM: Homo sapiens

<400> SEQUENCE: 523

Trp Ser Gly Tyr Tyr
1               5

<210> SEQ ID NO 524
<211> LENGTH: 5
<212> TYPE: PRT
<213> ORGANISM: Homo sapiens

<400> SEQUENCE: 524

Gly Val Val Ile Ile
1               5

<210> SEQ ID NO 525
<211> LENGTH: 6
<212> TYPE: PRT
<213> ORGANISM: Homo sapiens

<400> SEQUENCE: 525

Leu Glu Trp Leu Leu Tyr
1               5

<210> SEQ ID NO 526
```

```
<211> LENGTH: 6
<212> TYPE: PRT
<213> ORGANISM: Homo sapiens

<400> SEQUENCE: 526

Trp Ser Gly Tyr Tyr Thr
1               5

<210> SEQ ID NO 527
<211> LENGTH: 4
<212> TYPE: PRT
<213> ORGANISM: Homo sapiens

<400> SEQUENCE: 527

Glu Trp Leu Leu
1

<210> SEQ ID NO 528
<211> LENGTH: 4
<212> TYPE: PRT
<213> ORGANISM: Homo sapiens

<400> SEQUENCE: 528

Ser Gly Tyr Tyr
1

<210> SEQ ID NO 529
<211> LENGTH: 4
<212> TYPE: PRT
<213> ORGANISM: Homo sapiens

<400> SEQUENCE: 529

Val Val Ile Ile
1

<210> SEQ ID NO 530
<211> LENGTH: 5
<212> TYPE: PRT
<213> ORGANISM: Homo sapiens

<400> SEQUENCE: 530

Glu Trp Leu Leu Tyr
1               5

<210> SEQ ID NO 531
<211> LENGTH: 5
<212> TYPE: PRT
<213> ORGANISM: Homo sapiens

<400> SEQUENCE: 531

Ser Gly Tyr Tyr Thr
1               5

<210> SEQ ID NO 532
<211> LENGTH: 4
<212> TYPE: PRT
<213> ORGANISM: Homo sapiens

<400> SEQUENCE: 532

Trp Leu Leu Tyr
1

<210> SEQ ID NO 533
<211> LENGTH: 4
<212> TYPE: PRT
```

<213> ORGANISM: Homo sapiens

<400> SEQUENCE: 533

Gly Tyr Tyr Thr
1

<210> SEQ ID NO 534
<211> LENGTH: 4
<212> TYPE: PRT
<213> ORGANISM: Homo sapiens

<400> SEQUENCE: 534

Val Leu Arg Tyr
1

<210> SEQ ID NO 535
<211> LENGTH: 4
<212> TYPE: PRT
<213> ORGANISM: Homo sapiens

<400> SEQUENCE: 535

Tyr Tyr Asp Ile
1

<210> SEQ ID NO 536
<211> LENGTH: 5
<212> TYPE: PRT
<213> ORGANISM: Homo sapiens

<400> SEQUENCE: 536

Val Leu Arg Tyr Phe
1               5

<210> SEQ ID NO 537
<211> LENGTH: 5
<212> TYPE: PRT
<213> ORGANISM: Homo sapiens

<400> SEQUENCE: 537

Tyr Tyr Asp Ile Leu
1               5

<210> SEQ ID NO 538
<211> LENGTH: 5
<212> TYPE: PRT
<213> ORGANISM: Homo sapiens

<400> SEQUENCE: 538

Ile Thr Ile Phe Tyr
1               5

<210> SEQ ID NO 539
<211> LENGTH: 6
<212> TYPE: PRT
<213> ORGANISM: Homo sapiens

<400> SEQUENCE: 539

Val Leu Arg Tyr Phe Asp
1               5

<210> SEQ ID NO 540
<211> LENGTH: 6
<212> TYPE: PRT
<213> ORGANISM: Homo sapiens

```
<400> SEQUENCE: 540

Tyr Tyr Asp Ile Leu Thr
1               5

<210> SEQ ID NO 541
<211> LENGTH: 6
<212> TYPE: PRT
<213> ORGANISM: Homo sapiens

<400> SEQUENCE: 541

Ile Thr Ile Phe Tyr Leu
1               5

<210> SEQ ID NO 542
<211> LENGTH: 4
<212> TYPE: PRT
<213> ORGANISM: Homo sapiens

<400> SEQUENCE: 542

Leu Arg Tyr Phe
1

<210> SEQ ID NO 543
<211> LENGTH: 4
<212> TYPE: PRT
<213> ORGANISM: Homo sapiens

<400> SEQUENCE: 543

Tyr Asp Ile Leu
1

<210> SEQ ID NO 544
<211> LENGTH: 4
<212> TYPE: PRT
<213> ORGANISM: Homo sapiens

<400> SEQUENCE: 544

Thr Ile Phe Tyr
1

<210> SEQ ID NO 545
<211> LENGTH: 5
<212> TYPE: PRT
<213> ORGANISM: Homo sapiens

<400> SEQUENCE: 545

Leu Arg Tyr Phe Asp
1               5

<210> SEQ ID NO 546
<211> LENGTH: 5
<212> TYPE: PRT
<213> ORGANISM: Homo sapiens

<400> SEQUENCE: 546

Tyr Asp Ile Leu Thr
1               5

<210> SEQ ID NO 547
<211> LENGTH: 5
<212> TYPE: PRT
<213> ORGANISM: Homo sapiens

<400> SEQUENCE: 547
```

Thr Ile Phe Tyr Leu
1               5

<210> SEQ ID NO 548
<211> LENGTH: 6
<212> TYPE: PRT
<213> ORGANISM: Homo sapiens

<400> SEQUENCE: 548

Leu Arg Tyr Phe Asp Trp
1               5

<210> SEQ ID NO 549
<211> LENGTH: 6
<212> TYPE: PRT
<213> ORGANISM: Homo sapiens

<400> SEQUENCE: 549

Tyr Asp Ile Leu Thr Gly
1               5

<210> SEQ ID NO 550
<211> LENGTH: 6
<212> TYPE: PRT
<213> ORGANISM: Homo sapiens

<400> SEQUENCE: 550

Thr Ile Phe Tyr Leu Val
1               5

<210> SEQ ID NO 551
<211> LENGTH: 4
<212> TYPE: PRT
<213> ORGANISM: Homo sapiens

<400> SEQUENCE: 551

Arg Tyr Phe Asp
1

<210> SEQ ID NO 552
<211> LENGTH: 4
<212> TYPE: PRT
<213> ORGANISM: Homo sapiens

<400> SEQUENCE: 552

Asp Ile Leu Thr
1

<210> SEQ ID NO 553
<211> LENGTH: 4
<212> TYPE: PRT
<213> ORGANISM: Homo sapiens

<400> SEQUENCE: 553

Ile Phe Tyr Leu
1

<210> SEQ ID NO 554
<211> LENGTH: 5
<212> TYPE: PRT
<213> ORGANISM: Homo sapiens

<400> SEQUENCE: 554

Arg Tyr Phe Asp Trp
1               5

<210> SEQ ID NO 555
<211> LENGTH: 5
<212> TYPE: PRT
<213> ORGANISM: Homo sapiens

<400> SEQUENCE: 555

Asp Ile Leu Thr Gly
1               5

<210> SEQ ID NO 556
<211> LENGTH: 5
<212> TYPE: PRT
<213> ORGANISM: Homo sapiens

<400> SEQUENCE: 556

Ile Phe Tyr Leu Val
1               5

<210> SEQ ID NO 557
<211> LENGTH: 6
<212> TYPE: PRT
<213> ORGANISM: Homo sapiens

<400> SEQUENCE: 557

Arg Tyr Phe Asp Trp Leu
1               5

<210> SEQ ID NO 558
<211> LENGTH: 6
<212> TYPE: PRT
<213> ORGANISM: Homo sapiens

<400> SEQUENCE: 558

Asp Ile Leu Thr Gly Tyr
1               5

<210> SEQ ID NO 559
<211> LENGTH: 6
<212> TYPE: PRT
<213> ORGANISM: Homo sapiens

<400> SEQUENCE: 559

Ile Phe Tyr Leu Val Ile
1               5

<210> SEQ ID NO 560
<211> LENGTH: 4
<212> TYPE: PRT
<213> ORGANISM: Homo sapiens

<400> SEQUENCE: 560

Tyr Phe Asp Trp
1

<210> SEQ ID NO 561
<211> LENGTH: 4
<212> TYPE: PRT
<213> ORGANISM: Homo sapiens

<400> SEQUENCE: 561

Ile Leu Thr Gly
1

```
<210> SEQ ID NO 562
<211> LENGTH: 4
<212> TYPE: PRT
<213> ORGANISM: Homo sapiens

<400> SEQUENCE: 562

Phe Tyr Leu Val
1

<210> SEQ ID NO 563
<211> LENGTH: 5
<212> TYPE: PRT
<213> ORGANISM: Homo sapiens

<400> SEQUENCE: 563

Tyr Phe Asp Trp Leu
1               5

<210> SEQ ID NO 564
<211> LENGTH: 5
<212> TYPE: PRT
<213> ORGANISM: Homo sapiens

<400> SEQUENCE: 564

Ile Leu Thr Gly Tyr
1               5

<210> SEQ ID NO 565
<211> LENGTH: 5
<212> TYPE: PRT
<213> ORGANISM: Homo sapiens

<400> SEQUENCE: 565

Phe Tyr Leu Val Ile
1               5

<210> SEQ ID NO 566
<211> LENGTH: 6
<212> TYPE: PRT
<213> ORGANISM: Homo sapiens

<400> SEQUENCE: 566

Tyr Phe Asp Trp Leu Leu
1               5

<210> SEQ ID NO 567
<211> LENGTH: 6
<212> TYPE: PRT
<213> ORGANISM: Homo sapiens

<400> SEQUENCE: 567

Ile Leu Thr Gly Tyr Tyr
1               5

<210> SEQ ID NO 568
<211> LENGTH: 6
<212> TYPE: PRT
<213> ORGANISM: Homo sapiens

<400> SEQUENCE: 568

Phe Tyr Leu Val Ile Ile
1               5

<210> SEQ ID NO 569
<211> LENGTH: 4
```

<212> TYPE: PRT
<213> ORGANISM: Homo sapiens

<400> SEQUENCE: 569

Phe Asp Trp Leu
1

<210> SEQ ID NO 570
<211> LENGTH: 4
<212> TYPE: PRT
<213> ORGANISM: Homo sapiens

<400> SEQUENCE: 570

Leu Thr Gly Tyr
1

<210> SEQ ID NO 571
<211> LENGTH: 4
<212> TYPE: PRT
<213> ORGANISM: Homo sapiens

<400> SEQUENCE: 571

Tyr Leu Val Ile
1

<210> SEQ ID NO 572
<211> LENGTH: 5
<212> TYPE: PRT
<213> ORGANISM: Homo sapiens

<400> SEQUENCE: 572

Phe Asp Trp Leu Leu
1               5

<210> SEQ ID NO 573
<211> LENGTH: 5
<212> TYPE: PRT
<213> ORGANISM: Homo sapiens

<400> SEQUENCE: 573

Leu Thr Gly Tyr Tyr
1               5

<210> SEQ ID NO 574
<211> LENGTH: 5
<212> TYPE: PRT
<213> ORGANISM: Homo sapiens

<400> SEQUENCE: 574

Tyr Leu Val Ile Ile
1               5

<210> SEQ ID NO 575
<211> LENGTH: 6
<212> TYPE: PRT
<213> ORGANISM: Homo sapiens

<400> SEQUENCE: 575

Phe Asp Trp Leu Leu Tyr
1               5

<210> SEQ ID NO 576
<211> LENGTH: 6
<212> TYPE: PRT
<213> ORGANISM: Homo sapiens

<400> SEQUENCE: 576

Leu Thr Gly Tyr Tyr Asn
1               5

<210> SEQ ID NO 577
<211> LENGTH: 4
<212> TYPE: PRT
<213> ORGANISM: Homo sapiens

<400> SEQUENCE: 577

Asp Trp Leu Leu
1

<210> SEQ ID NO 578
<211> LENGTH: 4
<212> TYPE: PRT
<213> ORGANISM: Homo sapiens

<400> SEQUENCE: 578

Thr Gly Tyr Tyr
1

<210> SEQ ID NO 579
<211> LENGTH: 4
<212> TYPE: PRT
<213> ORGANISM: Homo sapiens

<400> SEQUENCE: 579

Leu Val Ile Ile
1

<210> SEQ ID NO 580
<211> LENGTH: 5
<212> TYPE: PRT
<213> ORGANISM: Homo sapiens

<400> SEQUENCE: 580

Asp Trp Leu Leu Tyr
1               5

<210> SEQ ID NO 581
<211> LENGTH: 5
<212> TYPE: PRT
<213> ORGANISM: Homo sapiens

<400> SEQUENCE: 581

Thr Gly Tyr Tyr Asn
1               5

<210> SEQ ID NO 582
<211> LENGTH: 4
<212> TYPE: PRT
<213> ORGANISM: Homo sapiens

<400> SEQUENCE: 582

Trp Leu Leu Tyr
1

<210> SEQ ID NO 583
<211> LENGTH: 4
<212> TYPE: PRT
<213> ORGANISM: Homo sapiens

<400> SEQUENCE: 583

Gly Tyr Tyr Asn
1

<210> SEQ ID NO 584
<211> LENGTH: 4
<212> TYPE: PRT
<213> ORGANISM: Homo sapiens

<400> SEQUENCE: 584

Val Leu Leu Trp
1

<210> SEQ ID NO 585
<211> LENGTH: 4
<212> TYPE: PRT
<213> ORGANISM: Homo sapiens

<400> SEQUENCE: 585

Tyr Tyr Tyr Gly
1

<210> SEQ ID NO 586
<211> LENGTH: 4
<212> TYPE: PRT
<213> ORGANISM: Homo sapiens

<400> SEQUENCE: 586

Ile Thr Met Val
1

<210> SEQ ID NO 587
<211> LENGTH: 5
<212> TYPE: PRT
<213> ORGANISM: Homo sapiens

<400> SEQUENCE: 587

Val Leu Leu Trp Phe
1               5

<210> SEQ ID NO 588
<211> LENGTH: 5
<212> TYPE: PRT
<213> ORGANISM: Homo sapiens

<400> SEQUENCE: 588

Tyr Tyr Tyr Gly Ser
1               5

<210> SEQ ID NO 589
<211> LENGTH: 5
<212> TYPE: PRT
<213> ORGANISM: Homo sapiens

<400> SEQUENCE: 589

Ile Thr Met Val Arg
1               5

<210> SEQ ID NO 590
<211> LENGTH: 6
<212> TYPE: PRT
<213> ORGANISM: Homo sapiens

<400> SEQUENCE: 590

Val Leu Leu Trp Phe Gly

```
1               5

<210> SEQ ID NO 591
<211> LENGTH: 6
<212> TYPE: PRT
<213> ORGANISM: Homo sapiens

<400> SEQUENCE: 591

Tyr Tyr Tyr Gly Ser Gly
1               5

<210> SEQ ID NO 592
<211> LENGTH: 6
<212> TYPE: PRT
<213> ORGANISM: Homo sapiens

<400> SEQUENCE: 592

Ile Thr Met Val Arg Gly
1               5

<210> SEQ ID NO 593
<211> LENGTH: 4
<212> TYPE: PRT
<213> ORGANISM: Homo sapiens

<400> SEQUENCE: 593

Leu Leu Trp Phe
1

<210> SEQ ID NO 594
<211> LENGTH: 4
<212> TYPE: PRT
<213> ORGANISM: Homo sapiens

<400> SEQUENCE: 594

Tyr Tyr Gly Ser
1

<210> SEQ ID NO 595
<211> LENGTH: 4
<212> TYPE: PRT
<213> ORGANISM: Homo sapiens

<400> SEQUENCE: 595

Thr Met Val Arg
1

<210> SEQ ID NO 596
<211> LENGTH: 5
<212> TYPE: PRT
<213> ORGANISM: Homo sapiens

<400> SEQUENCE: 596

Leu Leu Trp Phe Gly
1               5

<210> SEQ ID NO 597
<211> LENGTH: 5
<212> TYPE: PRT
<213> ORGANISM: Homo sapiens

<400> SEQUENCE: 597

Tyr Tyr Gly Ser Gly
1               5
```

```
<210> SEQ ID NO 598
<211> LENGTH: 5
<212> TYPE: PRT
<213> ORGANISM: Homo sapiens

<400> SEQUENCE: 598

Thr Met Val Arg Gly
1               5

<210> SEQ ID NO 599
<211> LENGTH: 6
<212> TYPE: PRT
<213> ORGANISM: Homo sapiens

<400> SEQUENCE: 599

Leu Leu Trp Phe Gly Glu
1               5

<210> SEQ ID NO 600
<211> LENGTH: 6
<212> TYPE: PRT
<213> ORGANISM: Homo sapiens

<400> SEQUENCE: 600

Tyr Tyr Gly Ser Gly Ser
1               5

<210> SEQ ID NO 601
<211> LENGTH: 6
<212> TYPE: PRT
<213> ORGANISM: Homo sapiens

<400> SEQUENCE: 601

Thr Met Val Arg Gly Val
1               5

<210> SEQ ID NO 602
<211> LENGTH: 4
<212> TYPE: PRT
<213> ORGANISM: Homo sapiens

<400> SEQUENCE: 602

Leu Trp Phe Gly
1

<210> SEQ ID NO 603
<211> LENGTH: 4
<212> TYPE: PRT
<213> ORGANISM: Homo sapiens

<400> SEQUENCE: 603

Tyr Gly Ser Gly
1

<210> SEQ ID NO 604
<211> LENGTH: 4
<212> TYPE: PRT
<213> ORGANISM: Homo sapiens

<400> SEQUENCE: 604

Met Val Arg Gly
1

<210> SEQ ID NO 605
```

```
<211> LENGTH: 5
<212> TYPE: PRT
<213> ORGANISM: Homo sapiens

<400> SEQUENCE: 605

Leu Trp Phe Gly Glu
1               5

<210> SEQ ID NO 606
<211> LENGTH: 5
<212> TYPE: PRT
<213> ORGANISM: Homo sapiens

<400> SEQUENCE: 606

Tyr Gly Ser Gly Ser
1               5

<210> SEQ ID NO 607
<211> LENGTH: 5
<212> TYPE: PRT
<213> ORGANISM: Homo sapiens

<400> SEQUENCE: 607

Met Val Arg Gly Val
1               5

<210> SEQ ID NO 608
<211> LENGTH: 6
<212> TYPE: PRT
<213> ORGANISM: Homo sapiens

<400> SEQUENCE: 608

Leu Trp Phe Gly Glu Leu
1               5

<210> SEQ ID NO 609
<211> LENGTH: 6
<212> TYPE: PRT
<213> ORGANISM: Homo sapiens

<400> SEQUENCE: 609

Tyr Gly Ser Gly Ser Tyr
1               5

<210> SEQ ID NO 610
<211> LENGTH: 6
<212> TYPE: PRT
<213> ORGANISM: Homo sapiens

<400> SEQUENCE: 610

Met Val Arg Gly Val Ile
1               5

<210> SEQ ID NO 611
<211> LENGTH: 4
<212> TYPE: PRT
<213> ORGANISM: Homo sapiens

<400> SEQUENCE: 611

Trp Phe Gly Glu
1

<210> SEQ ID NO 612
<211> LENGTH: 4
<212> TYPE: PRT
```

<213> ORGANISM: Homo sapiens

<400> SEQUENCE: 612

Gly Ser Gly Ser
1

<210> SEQ ID NO 613
<211> LENGTH: 4
<212> TYPE: PRT
<213> ORGANISM: Homo sapiens

<400> SEQUENCE: 613

Val Arg Gly Val
1

<210> SEQ ID NO 614
<211> LENGTH: 5
<212> TYPE: PRT
<213> ORGANISM: Homo sapiens

<400> SEQUENCE: 614

Trp Phe Gly Glu Leu
1               5

<210> SEQ ID NO 615
<211> LENGTH: 5
<212> TYPE: PRT
<213> ORGANISM: Homo sapiens

<400> SEQUENCE: 615

Gly Ser Gly Ser Tyr
1               5

<210> SEQ ID NO 616
<211> LENGTH: 5
<212> TYPE: PRT
<213> ORGANISM: Homo sapiens

<400> SEQUENCE: 616

Val Arg Gly Val Ile
1               5

<210> SEQ ID NO 617
<211> LENGTH: 6
<212> TYPE: PRT
<213> ORGANISM: Homo sapiens

<400> SEQUENCE: 617

Trp Phe Gly Glu Leu Leu
1               5

<210> SEQ ID NO 618
<211> LENGTH: 6
<212> TYPE: PRT
<213> ORGANISM: Homo sapiens

<400> SEQUENCE: 618

Gly Ser Gly Ser Tyr Tyr
1               5

<210> SEQ ID NO 619
<211> LENGTH: 6
<212> TYPE: PRT
<213> ORGANISM: Homo sapiens

```
<400> SEQUENCE: 619

Val Arg Gly Val Ile Ile
1               5

<210> SEQ ID NO 620
<211> LENGTH: 4
<212> TYPE: PRT
<213> ORGANISM: Homo sapiens

<400> SEQUENCE: 620

Phe Gly Glu Leu
1

<210> SEQ ID NO 621
<211> LENGTH: 4
<212> TYPE: PRT
<213> ORGANISM: Homo sapiens

<400> SEQUENCE: 621

Arg Gly Val Ile
1

<210> SEQ ID NO 622
<211> LENGTH: 5
<212> TYPE: PRT
<213> ORGANISM: Homo sapiens

<400> SEQUENCE: 622

Phe Gly Glu Leu Leu
1               5

<210> SEQ ID NO 623
<211> LENGTH: 5
<212> TYPE: PRT
<213> ORGANISM: Homo sapiens

<400> SEQUENCE: 623

Arg Gly Val Ile Ile
1               5

<210> SEQ ID NO 624
<211> LENGTH: 6
<212> TYPE: PRT
<213> ORGANISM: Homo sapiens

<400> SEQUENCE: 624

Phe Gly Glu Leu Leu Tyr
1               5

<210> SEQ ID NO 625
<211> LENGTH: 6
<212> TYPE: PRT
<213> ORGANISM: Homo sapiens

<400> SEQUENCE: 625

Ser Gly Ser Tyr Tyr Asn
1               5

<210> SEQ ID NO 626
<211> LENGTH: 4
<212> TYPE: PRT
<213> ORGANISM: Homo sapiens

<400> SEQUENCE: 626
```

Gly Glu Leu Leu
1

<210> SEQ ID NO 627
<211> LENGTH: 4
<212> TYPE: PRT
<213> ORGANISM: Homo sapiens

<400> SEQUENCE: 627

Gly Val Ile Ile
1

<210> SEQ ID NO 628
<211> LENGTH: 5
<212> TYPE: PRT
<213> ORGANISM: Homo sapiens

<400> SEQUENCE: 628

Gly Glu Leu Leu Tyr
1               5

<210> SEQ ID NO 629
<211> LENGTH: 5
<212> TYPE: PRT
<213> ORGANISM: Homo sapiens

<400> SEQUENCE: 629

Gly Ser Tyr Tyr Asn
1               5

<210> SEQ ID NO 630
<211> LENGTH: 4
<212> TYPE: PRT
<213> ORGANISM: Homo sapiens

<400> SEQUENCE: 630

Glu Leu Leu Tyr
1

<210> SEQ ID NO 631
<211> LENGTH: 4
<212> TYPE: PRT
<213> ORGANISM: Homo sapiens

<400> SEQUENCE: 631

Ser Tyr Tyr Asn
1

<210> SEQ ID NO 632
<211> LENGTH: 4
<212> TYPE: PRT
<213> ORGANISM: Homo sapiens

<400> SEQUENCE: 632

Val Leu Trp Leu
1

<210> SEQ ID NO 633
<211> LENGTH: 4
<212> TYPE: PRT
<213> ORGANISM: Homo sapiens

<400> SEQUENCE: 633

Tyr Tyr Asp Tyr
1

<210> SEQ ID NO 634
<211> LENGTH: 4
<212> TYPE: PRT
<213> ORGANISM: Homo sapiens

<400> SEQUENCE: 634

Ile Met Ile Thr
1

<210> SEQ ID NO 635
<211> LENGTH: 5
<212> TYPE: PRT
<213> ORGANISM: Homo sapiens

<400> SEQUENCE: 635

Val Leu Trp Leu Arg
1               5

<210> SEQ ID NO 636
<211> LENGTH: 5
<212> TYPE: PRT
<213> ORGANISM: Homo sapiens

<400> SEQUENCE: 636

Tyr Tyr Asp Tyr Val
1               5

<210> SEQ ID NO 637
<211> LENGTH: 5
<212> TYPE: PRT
<213> ORGANISM: Homo sapiens

<400> SEQUENCE: 637

Ile Met Ile Thr Phe
1               5

<210> SEQ ID NO 638
<211> LENGTH: 6
<212> TYPE: PRT
<213> ORGANISM: Homo sapiens

<400> SEQUENCE: 638

Val Leu Trp Leu Arg Leu
1               5

<210> SEQ ID NO 639
<211> LENGTH: 6
<212> TYPE: PRT
<213> ORGANISM: Homo sapiens

<400> SEQUENCE: 639

Tyr Tyr Asp Tyr Val Trp
1               5

<210> SEQ ID NO 640
<211> LENGTH: 6
<212> TYPE: PRT
<213> ORGANISM: Homo sapiens

<400> SEQUENCE: 640

Ile Met Ile Thr Phe Gly
1               5

<210> SEQ ID NO 641
<211> LENGTH: 4
<212> TYPE: PRT
<213> ORGANISM: Homo sapiens

<400> SEQUENCE: 641

Leu Trp Leu Arg
1

<210> SEQ ID NO 642
<211> LENGTH: 4
<212> TYPE: PRT
<213> ORGANISM: Homo sapiens

<400> SEQUENCE: 642

Tyr Asp Tyr Val
1

<210> SEQ ID NO 643
<211> LENGTH: 4
<212> TYPE: PRT
<213> ORGANISM: Homo sapiens

<400> SEQUENCE: 643

Met Ile Thr Phe
1

<210> SEQ ID NO 644
<211> LENGTH: 5
<212> TYPE: PRT
<213> ORGANISM: Homo sapiens

<400> SEQUENCE: 644

Leu Trp Leu Arg Leu
1               5

<210> SEQ ID NO 645
<211> LENGTH: 5
<212> TYPE: PRT
<213> ORGANISM: Homo sapiens

<400> SEQUENCE: 645

Tyr Asp Tyr Val Trp
1               5

<210> SEQ ID NO 646
<211> LENGTH: 5
<212> TYPE: PRT
<213> ORGANISM: Homo sapiens

<400> SEQUENCE: 646

Met Ile Thr Phe Gly
1               5

<210> SEQ ID NO 647
<211> LENGTH: 6
<212> TYPE: PRT
<213> ORGANISM: Homo sapiens

<400> SEQUENCE: 647

Leu Trp Leu Arg Leu Gly
1               5

<210> SEQ ID NO 648
<211> LENGTH: 6

```
<212> TYPE: PRT
<213> ORGANISM: Homo sapiens

<400> SEQUENCE: 648

Tyr Asp Tyr Val Trp Gly
1               5

<210> SEQ ID NO 649
<211> LENGTH: 6
<212> TYPE: PRT
<213> ORGANISM: Homo sapiens

<400> SEQUENCE: 649

Met Ile Thr Phe Gly Gly
1               5

<210> SEQ ID NO 650
<211> LENGTH: 4
<212> TYPE: PRT
<213> ORGANISM: Homo sapiens

<400> SEQUENCE: 650

Trp Leu Arg Leu
1

<210> SEQ ID NO 651
<211> LENGTH: 4
<212> TYPE: PRT
<213> ORGANISM: Homo sapiens

<400> SEQUENCE: 651

Asp Tyr Val Trp
1

<210> SEQ ID NO 652
<211> LENGTH: 4
<212> TYPE: PRT
<213> ORGANISM: Homo sapiens

<400> SEQUENCE: 652

Ile Thr Phe Gly
1

<210> SEQ ID NO 653
<211> LENGTH: 5
<212> TYPE: PRT
<213> ORGANISM: Homo sapiens

<400> SEQUENCE: 653

Trp Leu Arg Leu Gly
1               5

<210> SEQ ID NO 654
<211> LENGTH: 5
<212> TYPE: PRT
<213> ORGANISM: Homo sapiens

<400> SEQUENCE: 654

Asp Tyr Val Trp Gly
1               5

<210> SEQ ID NO 655
<211> LENGTH: 5
<212> TYPE: PRT
<213> ORGANISM: Homo sapiens
```

<400> SEQUENCE: 655

Ile Thr Phe Gly Gly
1               5

<210> SEQ ID NO 656
<211> LENGTH: 6
<212> TYPE: PRT
<213> ORGANISM: Homo sapiens

<400> SEQUENCE: 656

Trp Leu Arg Leu Gly Glu
1               5

<210> SEQ ID NO 657
<211> LENGTH: 6
<212> TYPE: PRT
<213> ORGANISM: Homo sapiens

<400> SEQUENCE: 657

Asp Tyr Val Trp Gly Ser
1               5

<210> SEQ ID NO 658
<211> LENGTH: 6
<212> TYPE: PRT
<213> ORGANISM: Homo sapiens

<400> SEQUENCE: 658

Ile Thr Phe Gly Gly Val
1               5

<210> SEQ ID NO 659
<211> LENGTH: 4
<212> TYPE: PRT
<213> ORGANISM: Homo sapiens

<400> SEQUENCE: 659

Leu Arg Leu Gly
1

<210> SEQ ID NO 660
<211> LENGTH: 4
<212> TYPE: PRT
<213> ORGANISM: Homo sapiens

<400> SEQUENCE: 660

Tyr Val Trp Gly
1

<210> SEQ ID NO 661
<211> LENGTH: 4
<212> TYPE: PRT
<213> ORGANISM: Homo sapiens

<400> SEQUENCE: 661

Thr Phe Gly Gly
1

<210> SEQ ID NO 662
<211> LENGTH: 5
<212> TYPE: PRT
<213> ORGANISM: Homo sapiens

<400> SEQUENCE: 662

Leu Arg Leu Gly Glu
1               5

<210> SEQ ID NO 663
<211> LENGTH: 5
<212> TYPE: PRT
<213> ORGANISM: Homo sapiens

<400> SEQUENCE: 663

Tyr Val Trp Gly Ser
1               5

<210> SEQ ID NO 664
<211> LENGTH: 5
<212> TYPE: PRT
<213> ORGANISM: Homo sapiens

<400> SEQUENCE: 664

Thr Phe Gly Gly Val
1               5

<210> SEQ ID NO 665
<211> LENGTH: 6
<212> TYPE: PRT
<213> ORGANISM: Homo sapiens

<400> SEQUENCE: 665

Leu Arg Leu Gly Glu Leu
1               5

<210> SEQ ID NO 666
<211> LENGTH: 6
<212> TYPE: PRT
<213> ORGANISM: Homo sapiens

<400> SEQUENCE: 666

Tyr Val Trp Gly Ser Tyr
1               5

<210> SEQ ID NO 667
<211> LENGTH: 6
<212> TYPE: PRT
<213> ORGANISM: Homo sapiens

<400> SEQUENCE: 667

Thr Phe Gly Gly Val Ile
1               5

<210> SEQ ID NO 668
<211> LENGTH: 4
<212> TYPE: PRT
<213> ORGANISM: Homo sapiens

<400> SEQUENCE: 668

Arg Leu Gly Glu
1

<210> SEQ ID NO 669
<211> LENGTH: 4
<212> TYPE: PRT
<213> ORGANISM: Homo sapiens

<400> SEQUENCE: 669

Val Trp Gly Ser

```
<210> SEQ ID NO 670
<211> LENGTH: 4
<212> TYPE: PRT
<213> ORGANISM: Homo sapiens

<400> SEQUENCE: 670

Phe Gly Gly Val
1

<210> SEQ ID NO 671
<211> LENGTH: 5
<212> TYPE: PRT
<213> ORGANISM: Homo sapiens

<400> SEQUENCE: 671

Arg Leu Gly Glu Leu
1               5

<210> SEQ ID NO 672
<211> LENGTH: 5
<212> TYPE: PRT
<213> ORGANISM: Homo sapiens

<400> SEQUENCE: 672

Val Trp Gly Ser Tyr
1               5

<210> SEQ ID NO 673
<211> LENGTH: 5
<212> TYPE: PRT
<213> ORGANISM: Homo sapiens

<400> SEQUENCE: 673

Phe Gly Gly Val Ile
1               5

<210> SEQ ID NO 674
<211> LENGTH: 6
<212> TYPE: PRT
<213> ORGANISM: Homo sapiens

<400> SEQUENCE: 674

Arg Leu Gly Glu Leu Ser
1               5

<210> SEQ ID NO 675
<211> LENGTH: 6
<212> TYPE: PRT
<213> ORGANISM: Homo sapiens

<400> SEQUENCE: 675

Val Trp Gly Ser Tyr Arg
1               5

<210> SEQ ID NO 676
<211> LENGTH: 6
<212> TYPE: PRT
<213> ORGANISM: Homo sapiens

<400> SEQUENCE: 676

Phe Gly Gly Val Ile Val
1               5
```

<210> SEQ ID NO 677
<211> LENGTH: 4
<212> TYPE: PRT
<213> ORGANISM: Homo sapiens

<400> SEQUENCE: 677

Leu Gly Glu Leu
1

<210> SEQ ID NO 678
<211> LENGTH: 4
<212> TYPE: PRT
<213> ORGANISM: Homo sapiens

<400> SEQUENCE: 678

Trp Gly Ser Tyr
1

<210> SEQ ID NO 679
<211> LENGTH: 4
<212> TYPE: PRT
<213> ORGANISM: Homo sapiens

<400> SEQUENCE: 679

Gly Gly Val Ile
1

<210> SEQ ID NO 680
<211> LENGTH: 5
<212> TYPE: PRT
<213> ORGANISM: Homo sapiens

<400> SEQUENCE: 680

Leu Gly Glu Leu Ser
1               5

<210> SEQ ID NO 681
<211> LENGTH: 5
<212> TYPE: PRT
<213> ORGANISM: Homo sapiens

<400> SEQUENCE: 681

Trp Gly Ser Tyr Arg
1               5

<210> SEQ ID NO 682
<211> LENGTH: 5
<212> TYPE: PRT
<213> ORGANISM: Homo sapiens

<400> SEQUENCE: 682

Gly Gly Val Ile Val
1               5

<210> SEQ ID NO 683
<211> LENGTH: 6
<212> TYPE: PRT
<213> ORGANISM: Homo sapiens

<400> SEQUENCE: 683

Leu Gly Glu Leu Ser Leu
1               5

<210> SEQ ID NO 684

```
<211> LENGTH: 6
<212> TYPE: PRT
<213> ORGANISM: Homo sapiens

<400> SEQUENCE: 684

Trp Gly Ser Tyr Arg Tyr
1               5

<210> SEQ ID NO 685
<211> LENGTH: 6
<212> TYPE: PRT
<213> ORGANISM: Homo sapiens

<400> SEQUENCE: 685

Gly Gly Val Ile Val Ile
1               5

<210> SEQ ID NO 686
<211> LENGTH: 4
<212> TYPE: PRT
<213> ORGANISM: Homo sapiens

<400> SEQUENCE: 686

Gly Glu Leu Ser
1

<210> SEQ ID NO 687
<211> LENGTH: 4
<212> TYPE: PRT
<213> ORGANISM: Homo sapiens

<400> SEQUENCE: 687

Gly Ser Tyr Arg
1

<210> SEQ ID NO 688
<211> LENGTH: 4
<212> TYPE: PRT
<213> ORGANISM: Homo sapiens

<400> SEQUENCE: 688

Gly Val Ile Val
1

<210> SEQ ID NO 689
<211> LENGTH: 5
<212> TYPE: PRT
<213> ORGANISM: Homo sapiens

<400> SEQUENCE: 689

Gly Glu Leu Ser Leu
1               5

<210> SEQ ID NO 690
<211> LENGTH: 5
<212> TYPE: PRT
<213> ORGANISM: Homo sapiens

<400> SEQUENCE: 690

Gly Ser Tyr Arg Tyr
1               5

<210> SEQ ID NO 691
<211> LENGTH: 5
<212> TYPE: PRT
```

<213> ORGANISM: Homo sapiens

<400> SEQUENCE: 691

Gly Val Ile Val Ile
1               5

<210> SEQ ID NO 692
<211> LENGTH: 6
<212> TYPE: PRT
<213> ORGANISM: Homo sapiens

<400> SEQUENCE: 692

Gly Glu Leu Ser Leu Tyr
1               5

<210> SEQ ID NO 693
<211> LENGTH: 6
<212> TYPE: PRT
<213> ORGANISM: Homo sapiens

<400> SEQUENCE: 693

Gly Ser Tyr Arg Tyr Thr
1               5

<210> SEQ ID NO 694
<211> LENGTH: 4
<212> TYPE: PRT
<213> ORGANISM: Homo sapiens

<400> SEQUENCE: 694

Glu Leu Ser Leu
1

<210> SEQ ID NO 695
<211> LENGTH: 4
<212> TYPE: PRT
<213> ORGANISM: Homo sapiens

<400> SEQUENCE: 695

Ser Tyr Arg Tyr
1

<210> SEQ ID NO 696
<211> LENGTH: 4
<212> TYPE: PRT
<213> ORGANISM: Homo sapiens

<400> SEQUENCE: 696

Val Ile Val Ile
1

<210> SEQ ID NO 697
<211> LENGTH: 5
<212> TYPE: PRT
<213> ORGANISM: Homo sapiens

<400> SEQUENCE: 697

Glu Leu Ser Leu Tyr
1               5

<210> SEQ ID NO 698
<211> LENGTH: 5
<212> TYPE: PRT
<213> ORGANISM: Homo sapiens

```
<400> SEQUENCE: 698

Ser Tyr Arg Tyr Thr
1               5

<210> SEQ ID NO 699
<211> LENGTH: 4
<212> TYPE: PRT
<213> ORGANISM: Homo sapiens

<400> SEQUENCE: 699

Leu Ser Leu Tyr
1

<210> SEQ ID NO 700
<211> LENGTH: 4
<212> TYPE: PRT
<213> ORGANISM: Homo sapiens

<400> SEQUENCE: 700

Tyr Arg Tyr Thr
1

<210> SEQ ID NO 701
<211> LENGTH: 4
<212> TYPE: PRT
<213> ORGANISM: Homo sapiens

<400> SEQUENCE: 701

Val Leu Leu Trp
1

<210> SEQ ID NO 702
<211> LENGTH: 4
<212> TYPE: PRT
<213> ORGANISM: Homo sapiens

<400> SEQUENCE: 702

Tyr Tyr Tyr Asp
1

<210> SEQ ID NO 703
<211> LENGTH: 4
<212> TYPE: PRT
<213> ORGANISM: Homo sapiens

<400> SEQUENCE: 703

Ile Thr Met Ile
1

<210> SEQ ID NO 704
<211> LENGTH: 5
<212> TYPE: PRT
<213> ORGANISM: Homo sapiens

<400> SEQUENCE: 704

Val Leu Leu Trp Tyr
1               5

<210> SEQ ID NO 705
<211> LENGTH: 5
<212> TYPE: PRT
<213> ORGANISM: Homo sapiens

<400> SEQUENCE: 705
```

Tyr Tyr Tyr Asp Ser
1               5

<210> SEQ ID NO 706
<211> LENGTH: 5
<212> TYPE: PRT
<213> ORGANISM: Homo sapiens

<400> SEQUENCE: 706

Ile Thr Met Ile Val
1               5

<210> SEQ ID NO 707
<211> LENGTH: 6
<212> TYPE: PRT
<213> ORGANISM: Homo sapiens

<400> SEQUENCE: 707

Val Leu Leu Trp Tyr Tyr
1               5

<210> SEQ ID NO 708
<211> LENGTH: 6
<212> TYPE: PRT
<213> ORGANISM: Homo sapiens

<400> SEQUENCE: 708

Tyr Tyr Tyr Asp Ser Ser
1               5

<210> SEQ ID NO 709
<211> LENGTH: 6
<212> TYPE: PRT
<213> ORGANISM: Homo sapiens

<400> SEQUENCE: 709

Ile Thr Met Ile Val Val
1               5

<210> SEQ ID NO 710
<211> LENGTH: 4
<212> TYPE: PRT
<213> ORGANISM: Homo sapiens

<400> SEQUENCE: 710

Leu Leu Trp Tyr
1

<210> SEQ ID NO 711
<211> LENGTH: 4
<212> TYPE: PRT
<213> ORGANISM: Homo sapiens

<400> SEQUENCE: 711

Tyr Tyr Asp Ser
1

<210> SEQ ID NO 712
<211> LENGTH: 4
<212> TYPE: PRT
<213> ORGANISM: Homo sapiens

<400> SEQUENCE: 712

Thr Met Ile Val
1

```
<210> SEQ ID NO 713
<211> LENGTH: 5
<212> TYPE: PRT
<213> ORGANISM: Homo sapiens

<400> SEQUENCE: 713

Leu Leu Trp Tyr Tyr
1               5

<210> SEQ ID NO 714
<211> LENGTH: 5
<212> TYPE: PRT
<213> ORGANISM: Homo sapiens

<400> SEQUENCE: 714

Tyr Tyr Asp Ser Ser
1               5

<210> SEQ ID NO 715
<211> LENGTH: 5
<212> TYPE: PRT
<213> ORGANISM: Homo sapiens

<400> SEQUENCE: 715

Thr Met Ile Val Val
1               5

<210> SEQ ID NO 716
<211> LENGTH: 6
<212> TYPE: PRT
<213> ORGANISM: Homo sapiens

<400> SEQUENCE: 716

Leu Leu Trp Tyr Tyr Trp
1               5

<210> SEQ ID NO 717
<211> LENGTH: 6
<212> TYPE: PRT
<213> ORGANISM: Homo sapiens

<400> SEQUENCE: 717

Tyr Tyr Asp Ser Ser Gly
1               5

<210> SEQ ID NO 718
<211> LENGTH: 6
<212> TYPE: PRT
<213> ORGANISM: Homo sapiens

<400> SEQUENCE: 718

Thr Met Ile Val Val Val
1               5

<210> SEQ ID NO 719
<211> LENGTH: 4
<212> TYPE: PRT
<213> ORGANISM: Homo sapiens

<400> SEQUENCE: 719

Leu Trp Tyr Tyr
1
```

```
<210> SEQ ID NO 720
<211> LENGTH: 4
<212> TYPE: PRT
<213> ORGANISM: Homo sapiens

<400> SEQUENCE: 720

Tyr Asp Ser Ser
1

<210> SEQ ID NO 721
<211> LENGTH: 4
<212> TYPE: PRT
<213> ORGANISM: Homo sapiens

<400> SEQUENCE: 721

Met Ile Val Val
1

<210> SEQ ID NO 722
<211> LENGTH: 5
<212> TYPE: PRT
<213> ORGANISM: Homo sapiens

<400> SEQUENCE: 722

Leu Trp Tyr Tyr Trp
1               5

<210> SEQ ID NO 723
<211> LENGTH: 5
<212> TYPE: PRT
<213> ORGANISM: Homo sapiens

<400> SEQUENCE: 723

Tyr Asp Ser Ser Gly
1               5

<210> SEQ ID NO 724
<211> LENGTH: 5
<212> TYPE: PRT
<213> ORGANISM: Homo sapiens

<400> SEQUENCE: 724

Met Ile Val Val Val
1               5

<210> SEQ ID NO 725
<211> LENGTH: 6
<212> TYPE: PRT
<213> ORGANISM: Homo sapiens

<400> SEQUENCE: 725

Leu Trp Tyr Tyr Trp Leu
1               5

<210> SEQ ID NO 726
<211> LENGTH: 6
<212> TYPE: PRT
<213> ORGANISM: Homo sapiens

<400> SEQUENCE: 726

Tyr Asp Ser Ser Gly Tyr
1               5

<210> SEQ ID NO 727
<211> LENGTH: 6
```

```
<212> TYPE: PRT
<213> ORGANISM: Homo sapiens

<400> SEQUENCE: 727

Met Ile Val Val Ile
1               5

<210> SEQ ID NO 728
<211> LENGTH: 4
<212> TYPE: PRT
<213> ORGANISM: Homo sapiens

<400> SEQUENCE: 728

Trp Tyr Tyr Trp
1

<210> SEQ ID NO 729
<211> LENGTH: 4
<212> TYPE: PRT
<213> ORGANISM: Homo sapiens

<400> SEQUENCE: 729

Asp Ser Ser Gly
1

<210> SEQ ID NO 730
<211> LENGTH: 5
<212> TYPE: PRT
<213> ORGANISM: Homo sapiens

<400> SEQUENCE: 730

Trp Tyr Tyr Trp Leu
1               5

<210> SEQ ID NO 731
<211> LENGTH: 5
<212> TYPE: PRT
<213> ORGANISM: Homo sapiens

<400> SEQUENCE: 731

Asp Ser Ser Gly Tyr
1               5

<210> SEQ ID NO 732
<211> LENGTH: 5
<212> TYPE: PRT
<213> ORGANISM: Homo sapiens

<400> SEQUENCE: 732

Ile Val Val Val Ile
1               5

<210> SEQ ID NO 733
<211> LENGTH: 6
<212> TYPE: PRT
<213> ORGANISM: Homo sapiens

<400> SEQUENCE: 733

Trp Tyr Tyr Trp Leu Leu
1               5

<210> SEQ ID NO 734
<211> LENGTH: 6
<212> TYPE: PRT
<213> ORGANISM: Homo sapiens
```

<400> SEQUENCE: 734

Asp Ser Ser Gly Tyr Tyr
1               5

<210> SEQ ID NO 735
<211> LENGTH: 6
<212> TYPE: PRT
<213> ORGANISM: Homo sapiens

<400> SEQUENCE: 735

Ile Val Val Val Ile Thr
1               5

<210> SEQ ID NO 736
<211> LENGTH: 4
<212> TYPE: PRT
<213> ORGANISM: Homo sapiens

<400> SEQUENCE: 736

Tyr Tyr Trp Leu
1

<210> SEQ ID NO 737
<211> LENGTH: 4
<212> TYPE: PRT
<213> ORGANISM: Homo sapiens

<400> SEQUENCE: 737

Ser Ser Gly Tyr
1

<210> SEQ ID NO 738
<211> LENGTH: 4
<212> TYPE: PRT
<213> ORGANISM: Homo sapiens

<400> SEQUENCE: 738

Val Val Val Ile
1

<210> SEQ ID NO 739
<211> LENGTH: 5
<212> TYPE: PRT
<213> ORGANISM: Homo sapiens

<400> SEQUENCE: 739

Tyr Tyr Trp Leu Leu
1               5

<210> SEQ ID NO 740
<211> LENGTH: 5
<212> TYPE: PRT
<213> ORGANISM: Homo sapiens

<400> SEQUENCE: 740

Ser Ser Gly Tyr Tyr
1               5

<210> SEQ ID NO 741
<211> LENGTH: 5
<212> TYPE: PRT
<213> ORGANISM: Homo sapiens

<400> SEQUENCE: 741

Val Val Val Ile Thr
1               5

<210> SEQ ID NO 742
<211> LENGTH: 6
<212> TYPE: PRT
<213> ORGANISM: Homo sapiens

<400> SEQUENCE: 742

Tyr Tyr Trp Leu Leu Leu
1               5

<210> SEQ ID NO 743
<211> LENGTH: 6
<212> TYPE: PRT
<213> ORGANISM: Homo sapiens

<400> SEQUENCE: 743

Ser Ser Gly Tyr Tyr Tyr
1               5

<210> SEQ ID NO 744
<211> LENGTH: 4
<212> TYPE: PRT
<213> ORGANISM: Homo sapiens

<400> SEQUENCE: 744

Tyr Trp Leu Leu
1

<210> SEQ ID NO 745
<211> LENGTH: 4
<212> TYPE: PRT
<213> ORGANISM: Homo sapiens

<400> SEQUENCE: 745

Val Val Ile Thr
1

<210> SEQ ID NO 746
<211> LENGTH: 5
<212> TYPE: PRT
<213> ORGANISM: Homo sapiens

<400> SEQUENCE: 746

Tyr Trp Leu Leu Leu
1               5

<210> SEQ ID NO 747
<211> LENGTH: 5
<212> TYPE: PRT
<213> ORGANISM: Homo sapiens

<400> SEQUENCE: 747

Ser Gly Tyr Tyr Tyr
1               5

<210> SEQ ID NO 748
<211> LENGTH: 4
<212> TYPE: PRT
<213> ORGANISM: Homo sapiens

<400> SEQUENCE: 748

Trp Leu Leu Leu
1

<210> SEQ ID NO 749
<211> LENGTH: 4
<212> TYPE: PRT
<213> ORGANISM: Homo sapiens

<400> SEQUENCE: 749

Gly Tyr Tyr Tyr
1

<210> SEQ ID NO 750
<211> LENGTH: 4
<212> TYPE: PRT
<213> ORGANISM: Homo sapiens

<400> SEQUENCE: 750

Trp Leu Gln Tyr
1

<210> SEQ ID NO 751
<211> LENGTH: 4
<212> TYPE: PRT
<213> ORGANISM: Homo sapiens

<400> SEQUENCE: 751

Asp Tyr Ser Asn
1

<210> SEQ ID NO 752
<211> LENGTH: 4
<212> TYPE: PRT
<213> ORGANISM: Homo sapiens

<400> SEQUENCE: 752

Thr Thr Val Thr
1

<210> SEQ ID NO 753
<211> LENGTH: 5
<212> TYPE: PRT
<213> ORGANISM: Homo sapiens

<400> SEQUENCE: 753

Trp Leu Gln Tyr Leu
1               5

<210> SEQ ID NO 754
<211> LENGTH: 5
<212> TYPE: PRT
<213> ORGANISM: Homo sapiens

<400> SEQUENCE: 754

Asp Tyr Ser Asn Tyr
1               5

<210> SEQ ID NO 755
<211> LENGTH: 4
<212> TYPE: PRT
<213> ORGANISM: Homo sapiens

<400> SEQUENCE: 755

Leu Gln Tyr Leu
1

```
<210> SEQ ID NO 756
<211> LENGTH: 4
<212> TYPE: PRT
<213> ORGANISM: Homo sapiens

<400> SEQUENCE: 756

Tyr Ser Asn Tyr
1

<210> SEQ ID NO 757
<211> LENGTH: 4
<212> TYPE: PRT
<213> ORGANISM: Homo sapiens

<400> SEQUENCE: 757

Trp Leu Arg Trp
1

<210> SEQ ID NO 758
<211> LENGTH: 4
<212> TYPE: PRT
<213> ORGANISM: Homo sapiens

<400> SEQUENCE: 758

Asp Tyr Gly Asp
1

<210> SEQ ID NO 759
<211> LENGTH: 5
<212> TYPE: PRT
<213> ORGANISM: Homo sapiens

<400> SEQUENCE: 759

Trp Leu Arg Trp Leu
1               5

<210> SEQ ID NO 760
<211> LENGTH: 5
<212> TYPE: PRT
<213> ORGANISM: Homo sapiens

<400> SEQUENCE: 760

Asp Tyr Gly Asp Tyr
1               5

<210> SEQ ID NO 761
<211> LENGTH: 4
<212> TYPE: PRT
<213> ORGANISM: Homo sapiens

<400> SEQUENCE: 761

Leu Arg Trp Leu
1

<210> SEQ ID NO 762
<211> LENGTH: 4
<212> TYPE: PRT
<213> ORGANISM: Homo sapiens

<400> SEQUENCE: 762

Tyr Gly Asp Tyr
1

<210> SEQ ID NO 763
```

```
<211> LENGTH: 4
<212> TYPE: PRT
<213> ORGANISM: Homo sapiens

<400> SEQUENCE: 763

Trp Leu Arg Trp
1

<210> SEQ ID NO 764
<211> LENGTH: 4
<212> TYPE: PRT
<213> ORGANISM: Homo sapiens

<400> SEQUENCE: 764

Asp Tyr Gly Gly
1

<210> SEQ ID NO 765
<211> LENGTH: 4
<212> TYPE: PRT
<213> ORGANISM: Homo sapiens

<400> SEQUENCE: 765

Thr Thr Val Val
1

<210> SEQ ID NO 766
<211> LENGTH: 5
<212> TYPE: PRT
<213> ORGANISM: Homo sapiens

<400> SEQUENCE: 766

Trp Leu Arg Trp Tyr
1               5

<210> SEQ ID NO 767
<211> LENGTH: 5
<212> TYPE: PRT
<213> ORGANISM: Homo sapiens

<400> SEQUENCE: 767

Asp Tyr Gly Gly Asn
1               5

<210> SEQ ID NO 768
<211> LENGTH: 5
<212> TYPE: PRT
<213> ORGANISM: Homo sapiens

<400> SEQUENCE: 768

Thr Thr Val Val Thr
1               5

<210> SEQ ID NO 769
<211> LENGTH: 6
<212> TYPE: PRT
<213> ORGANISM: Homo sapiens

<400> SEQUENCE: 769

Trp Leu Arg Trp Tyr Leu
1               5

<210> SEQ ID NO 770
<211> LENGTH: 6
<212> TYPE: PRT
```

<213> ORGANISM: Homo sapiens

<400> SEQUENCE: 770

Asp Tyr Gly Gly Asn Ser
1               5

<210> SEQ ID NO 771
<211> LENGTH: 4
<212> TYPE: PRT
<213> ORGANISM: Homo sapiens

<400> SEQUENCE: 771

Leu Arg Trp Tyr
1

<210> SEQ ID NO 772
<211> LENGTH: 4
<212> TYPE: PRT
<213> ORGANISM: Homo sapiens

<400> SEQUENCE: 772

Tyr Gly Gly Asn
1

<210> SEQ ID NO 773
<211> LENGTH: 4
<212> TYPE: PRT
<213> ORGANISM: Homo sapiens

<400> SEQUENCE: 773

Thr Val Val Thr
1

<210> SEQ ID NO 774
<211> LENGTH: 5
<212> TYPE: PRT
<213> ORGANISM: Homo sapiens

<400> SEQUENCE: 774

Leu Arg Trp Tyr Leu
1               5

<210> SEQ ID NO 775
<211> LENGTH: 5
<212> TYPE: PRT
<213> ORGANISM: Homo sapiens

<400> SEQUENCE: 775

Tyr Gly Gly Asn Ser
1               5

<210> SEQ ID NO 776
<211> LENGTH: 4
<212> TYPE: PRT
<213> ORGANISM: Homo sapiens

<400> SEQUENCE: 776

Arg Trp Tyr Leu
1

<210> SEQ ID NO 777
<211> LENGTH: 4
<212> TYPE: PRT
<213> ORGANISM: Homo sapiens

```
<400> SEQUENCE: 777

Gly Gly Asn Ser
1

<210> SEQ ID NO 778
<211> LENGTH: 4
<212> TYPE: PRT
<213> ORGANISM: Homo sapiens

<400> SEQUENCE: 778

Val Asp Thr Ala
1

<210> SEQ ID NO 779
<211> LENGTH: 4
<212> TYPE: PRT
<213> ORGANISM: Homo sapiens

<400> SEQUENCE: 779

Trp Ile Gln Leu
1

<210> SEQ ID NO 780
<211> LENGTH: 4
<212> TYPE: PRT
<213> ORGANISM: Homo sapiens

<400> SEQUENCE: 780

Gly Tyr Ser Tyr
1

<210> SEQ ID NO 781
<211> LENGTH: 5
<212> TYPE: PRT
<213> ORGANISM: Homo sapiens

<400> SEQUENCE: 781

Val Asp Thr Ala Met
1               5

<210> SEQ ID NO 782
<211> LENGTH: 5
<212> TYPE: PRT
<213> ORGANISM: Homo sapiens

<400> SEQUENCE: 782

Trp Ile Gln Leu Trp
1               5

<210> SEQ ID NO 783
<211> LENGTH: 5
<212> TYPE: PRT
<213> ORGANISM: Homo sapiens

<400> SEQUENCE: 783

Gly Tyr Ser Tyr Gly
1               5

<210> SEQ ID NO 784
<211> LENGTH: 6
<212> TYPE: PRT
<213> ORGANISM: Homo sapiens

<400> SEQUENCE: 784
```

Val Asp Thr Ala Met Val
1               5

<210> SEQ ID NO 785
<211> LENGTH: 6
<212> TYPE: PRT
<213> ORGANISM: Homo sapiens

<400> SEQUENCE: 785

Trp Ile Gln Leu Trp Leu
1               5

<210> SEQ ID NO 786
<211> LENGTH: 6
<212> TYPE: PRT
<213> ORGANISM: Homo sapiens

<400> SEQUENCE: 786

Gly Tyr Ser Tyr Gly Tyr
1               5

<210> SEQ ID NO 787
<211> LENGTH: 4
<212> TYPE: PRT
<213> ORGANISM: Homo sapiens

<400> SEQUENCE: 787

Asp Thr Ala Met
1

<210> SEQ ID NO 788
<211> LENGTH: 4
<212> TYPE: PRT
<213> ORGANISM: Homo sapiens

<400> SEQUENCE: 788

Ile Gln Leu Trp
1

<210> SEQ ID NO 789
<211> LENGTH: 4
<212> TYPE: PRT
<213> ORGANISM: Homo sapiens

<400> SEQUENCE: 789

Tyr Ser Tyr Gly
1

<210> SEQ ID NO 790
<211> LENGTH: 5
<212> TYPE: PRT
<213> ORGANISM: Homo sapiens

<400> SEQUENCE: 790

Asp Thr Ala Met Val
1               5

<210> SEQ ID NO 791
<211> LENGTH: 5
<212> TYPE: PRT
<213> ORGANISM: Homo sapiens

<400> SEQUENCE: 791

Ile Gln Leu Trp Leu
1               5

<210> SEQ ID NO 792
<211> LENGTH: 5
<212> TYPE: PRT
<213> ORGANISM: Homo sapiens

<400> SEQUENCE: 792

Tyr Ser Tyr Gly Tyr
1               5

<210> SEQ ID NO 793
<211> LENGTH: 4
<212> TYPE: PRT
<213> ORGANISM: Homo sapiens

<400> SEQUENCE: 793

Thr Ala Met Val
1

<210> SEQ ID NO 794
<211> LENGTH: 4
<212> TYPE: PRT
<213> ORGANISM: Homo sapiens

<400> SEQUENCE: 794

Gln Leu Trp Leu
1

<210> SEQ ID NO 795
<211> LENGTH: 4
<212> TYPE: PRT
<213> ORGANISM: Homo sapiens

<400> SEQUENCE: 795

Ser Tyr Gly Tyr
1

<210> SEQ ID NO 796
<211> LENGTH: 4
<212> TYPE: PRT
<213> ORGANISM: Homo sapiens

<400> SEQUENCE: 796

Val Asp Ile Val
1

<210> SEQ ID NO 797
<211> LENGTH: 4
<212> TYPE: PRT
<213> ORGANISM: Homo sapiens

<400> SEQUENCE: 797

Trp Ile Tyr Trp
1

<210> SEQ ID NO 798
<211> LENGTH: 4
<212> TYPE: PRT
<213> ORGANISM: Homo sapiens

<400> SEQUENCE: 798

Gly Tyr Ser Gly
1

```
<210> SEQ ID NO 799
<211> LENGTH: 5
<212> TYPE: PRT
<213> ORGANISM: Homo sapiens

<400> SEQUENCE: 799

Val Asp Ile Val Ala
1               5

<210> SEQ ID NO 800
<211> LENGTH: 5
<212> TYPE: PRT
<213> ORGANISM: Homo sapiens

<400> SEQUENCE: 800

Trp Ile Tyr Trp Leu
1               5

<210> SEQ ID NO 801
<211> LENGTH: 5
<212> TYPE: PRT
<213> ORGANISM: Homo sapiens

<400> SEQUENCE: 801

Gly Tyr Ser Gly Tyr
1               5

<210> SEQ ID NO 802
<211> LENGTH: 6
<212> TYPE: PRT
<213> ORGANISM: Homo sapiens

<400> SEQUENCE: 802

Val Asp Ile Val Ala Thr
1               5

<210> SEQ ID NO 803
<211> LENGTH: 6
<212> TYPE: PRT
<213> ORGANISM: Homo sapiens

<400> SEQUENCE: 803

Trp Ile Tyr Trp Leu Arg
1               5

<210> SEQ ID NO 804
<211> LENGTH: 6
<212> TYPE: PRT
<213> ORGANISM: Homo sapiens

<400> SEQUENCE: 804

Gly Tyr Ser Gly Tyr Asp
1               5

<210> SEQ ID NO 805
<211> LENGTH: 4
<212> TYPE: PRT
<213> ORGANISM: Homo sapiens

<400> SEQUENCE: 805

Asp Ile Val Ala
1

<210> SEQ ID NO 806
<211> LENGTH: 4
```

<212> TYPE: PRT
<213> ORGANISM: Homo sapiens

<400> SEQUENCE: 806

Ile Tyr Trp Leu
1

<210> SEQ ID NO 807
<211> LENGTH: 4
<212> TYPE: PRT
<213> ORGANISM: Homo sapiens

<400> SEQUENCE: 807

Tyr Ser Gly Tyr
1

<210> SEQ ID NO 808
<211> LENGTH: 5
<212> TYPE: PRT
<213> ORGANISM: Homo sapiens

<400> SEQUENCE: 808

Asp Ile Val Ala Thr
1               5

<210> SEQ ID NO 809
<211> LENGTH: 5
<212> TYPE: PRT
<213> ORGANISM: Homo sapiens

<400> SEQUENCE: 809

Ile Tyr Trp Leu Arg
1               5

<210> SEQ ID NO 810
<211> LENGTH: 5
<212> TYPE: PRT
<213> ORGANISM: Homo sapiens

<400> SEQUENCE: 810

Tyr Ser Gly Tyr Asp
1               5

<210> SEQ ID NO 811
<211> LENGTH: 6
<212> TYPE: PRT
<213> ORGANISM: Homo sapiens

<400> SEQUENCE: 811

Asp Ile Val Ala Thr Ile
1               5

<210> SEQ ID NO 812
<211> LENGTH: 6
<212> TYPE: PRT
<213> ORGANISM: Homo sapiens

<400> SEQUENCE: 812

Ile Tyr Trp Leu Arg Leu
1               5

<210> SEQ ID NO 813
<211> LENGTH: 6
<212> TYPE: PRT
<213> ORGANISM: Homo sapiens

<400> SEQUENCE: 813

Tyr Ser Gly Tyr Asp Tyr
1               5

<210> SEQ ID NO 814
<211> LENGTH: 4
<212> TYPE: PRT
<213> ORGANISM: Homo sapiens

<400> SEQUENCE: 814

Ile Val Ala Thr
1

<210> SEQ ID NO 815
<211> LENGTH: 4
<212> TYPE: PRT
<213> ORGANISM: Homo sapiens

<400> SEQUENCE: 815

Tyr Trp Leu Arg
1

<210> SEQ ID NO 816
<211> LENGTH: 4
<212> TYPE: PRT
<213> ORGANISM: Homo sapiens

<400> SEQUENCE: 816

Ser Gly Tyr Asp
1

<210> SEQ ID NO 817
<211> LENGTH: 5
<212> TYPE: PRT
<213> ORGANISM: Homo sapiens

<400> SEQUENCE: 817

Ile Val Ala Thr Ile
1               5

<210> SEQ ID NO 818
<211> LENGTH: 5
<212> TYPE: PRT
<213> ORGANISM: Homo sapiens

<400> SEQUENCE: 818

Tyr Trp Leu Arg Leu
1               5

<210> SEQ ID NO 819
<211> LENGTH: 5
<212> TYPE: PRT
<213> ORGANISM: Homo sapiens

<400> SEQUENCE: 819

Ser Gly Tyr Asp Tyr
1               5

<210> SEQ ID NO 820
<211> LENGTH: 4
<212> TYPE: PRT
<213> ORGANISM: Homo sapiens

<400> SEQUENCE: 820

Val Ala Thr Ile
1

<210> SEQ ID NO 821
<211> LENGTH: 4
<212> TYPE: PRT
<213> ORGANISM: Homo sapiens

<400> SEQUENCE: 821

Trp Leu Arg Leu
1

<210> SEQ ID NO 822
<211> LENGTH: 4
<212> TYPE: PRT
<213> ORGANISM: Homo sapiens

<400> SEQUENCE: 822

Gly Tyr Asp Tyr
1

<210> SEQ ID NO 823
<211> LENGTH: 4
<212> TYPE: PRT
<213> ORGANISM: Homo sapiens

<400> SEQUENCE: 823

Val Glu Met Ala
1

<210> SEQ ID NO 824
<211> LENGTH: 4
<212> TYPE: PRT
<213> ORGANISM: Homo sapiens

<400> SEQUENCE: 824

Tyr Arg Trp Leu
1

<210> SEQ ID NO 825
<211> LENGTH: 4
<212> TYPE: PRT
<213> ORGANISM: Homo sapiens

<400> SEQUENCE: 825

Arg Asp Gly Tyr
1

<210> SEQ ID NO 826
<211> LENGTH: 5
<212> TYPE: PRT
<213> ORGANISM: Homo sapiens

<400> SEQUENCE: 826

Val Glu Met Ala Thr
1               5

<210> SEQ ID NO 827
<211> LENGTH: 5
<212> TYPE: PRT
<213> ORGANISM: Homo sapiens

<400> SEQUENCE: 827

Tyr Arg Trp Leu Gln

-continued

```
1               5

<210> SEQ ID NO 828
<211> LENGTH: 5
<212> TYPE: PRT
<213> ORGANISM: Homo sapiens

<400> SEQUENCE: 828

Arg Asp Gly Tyr Asn
1               5

<210> SEQ ID NO 829
<211> LENGTH: 6
<212> TYPE: PRT
<213> ORGANISM: Homo sapiens

<400> SEQUENCE: 829

Val Glu Met Ala Thr Ile
1               5

<210> SEQ ID NO 830
<211> LENGTH: 6
<212> TYPE: PRT
<213> ORGANISM: Homo sapiens

<400> SEQUENCE: 830

Tyr Arg Trp Leu Gln Leu
1               5

<210> SEQ ID NO 831
<211> LENGTH: 6
<212> TYPE: PRT
<213> ORGANISM: Homo sapiens

<400> SEQUENCE: 831

Arg Asp Gly Tyr Asn Tyr
1               5

<210> SEQ ID NO 832
<211> LENGTH: 4
<212> TYPE: PRT
<213> ORGANISM: Homo sapiens

<400> SEQUENCE: 832

Glu Met Ala Thr
1

<210> SEQ ID NO 833
<211> LENGTH: 4
<212> TYPE: PRT
<213> ORGANISM: Homo sapiens

<400> SEQUENCE: 833

Arg Trp Leu Gln
1

<210> SEQ ID NO 834
<211> LENGTH: 4
<212> TYPE: PRT
<213> ORGANISM: Homo sapiens

<400> SEQUENCE: 834

Asp Gly Tyr Asn
1
```

```
<210> SEQ ID NO 835
<211> LENGTH: 5
<212> TYPE: PRT
<213> ORGANISM: Homo sapiens

<400> SEQUENCE: 835

Glu Met Ala Thr Ile
1               5

<210> SEQ ID NO 836
<211> LENGTH: 5
<212> TYPE: PRT
<213> ORGANISM: Homo sapiens

<400> SEQUENCE: 836

Arg Trp Leu Gln Leu
1               5

<210> SEQ ID NO 837
<211> LENGTH: 5
<212> TYPE: PRT
<213> ORGANISM: Homo sapiens

<400> SEQUENCE: 837

Asp Gly Tyr Asn Tyr
1               5

<210> SEQ ID NO 838
<211> LENGTH: 4
<212> TYPE: PRT
<213> ORGANISM: Homo sapiens

<400> SEQUENCE: 838

Met Ala Thr Ile
1

<210> SEQ ID NO 839
<211> LENGTH: 4
<212> TYPE: PRT
<213> ORGANISM: Homo sapiens

<400> SEQUENCE: 839

Trp Leu Gln Leu
1

<210> SEQ ID NO 840
<211> LENGTH: 4
<212> TYPE: PRT
<213> ORGANISM: Homo sapiens

<400> SEQUENCE: 840

Gly Tyr Asn Tyr
1

<210> SEQ ID NO 841
<211> LENGTH: 4
<212> TYPE: PRT
<213> ORGANISM: Homo sapiens

<400> SEQUENCE: 841

Glu Tyr Ser Ser
1

<210> SEQ ID NO 842
```

```
<211> LENGTH: 4
<212> TYPE: PRT
<213> ORGANISM: Homo sapiens

<400> SEQUENCE: 842

Ser Ile Ala Ala
1

<210> SEQ ID NO 843
<211> LENGTH: 4
<212> TYPE: PRT
<213> ORGANISM: Homo sapiens

<400> SEQUENCE: 843

Val Tyr Gln Leu
1

<210> SEQ ID NO 844
<211> LENGTH: 5
<212> TYPE: PRT
<213> ORGANISM: Homo sapiens

<400> SEQUENCE: 844

Glu Tyr Ser Ser Ser
1               5

<210> SEQ ID NO 845
<211> LENGTH: 5
<212> TYPE: PRT
<213> ORGANISM: Homo sapiens

<400> SEQUENCE: 845

Ser Ile Ala Ala Arg
1               5

<210> SEQ ID NO 846
<211> LENGTH: 5
<212> TYPE: PRT
<213> ORGANISM: Homo sapiens

<400> SEQUENCE: 846

Val Tyr Gln Leu Val
1               5

<210> SEQ ID NO 847
<211> LENGTH: 6
<212> TYPE: PRT
<213> ORGANISM: Homo sapiens

<400> SEQUENCE: 847

Glu Tyr Ser Ser Ser Ser
1               5

<210> SEQ ID NO 848
<211> LENGTH: 4
<212> TYPE: PRT
<213> ORGANISM: Homo sapiens

<400> SEQUENCE: 848

Tyr Ser Ser Ser
1

<210> SEQ ID NO 849
<211> LENGTH: 4
<212> TYPE: PRT
```

<213> ORGANISM: Homo sapiens

<400> SEQUENCE: 849

Ile Ala Ala Arg
1

<210> SEQ ID NO 850
<211> LENGTH: 4
<212> TYPE: PRT
<213> ORGANISM: Homo sapiens

<400> SEQUENCE: 850

Tyr Gln Leu Val
1

<210> SEQ ID NO 851
<211> LENGTH: 5
<212> TYPE: PRT
<213> ORGANISM: Homo sapiens

<400> SEQUENCE: 851

Tyr Ser Ser Ser Ser
1               5

<210> SEQ ID NO 852
<211> LENGTH: 4
<212> TYPE: PRT
<213> ORGANISM: Homo sapiens

<400> SEQUENCE: 852

Ser Ser Ser Ser
1

<210> SEQ ID NO 853
<211> LENGTH: 4
<212> TYPE: PRT
<213> ORGANISM: Homo sapiens

<400> SEQUENCE: 853

Gly Tyr Ser Ser
1

<210> SEQ ID NO 854
<211> LENGTH: 4
<212> TYPE: PRT
<213> ORGANISM: Homo sapiens

<400> SEQUENCE: 854

Gly Ile Ala Ala
1

<210> SEQ ID NO 855
<211> LENGTH: 4
<212> TYPE: PRT
<213> ORGANISM: Homo sapiens

<400> SEQUENCE: 855

Val Tyr Gln Gln
1

<210> SEQ ID NO 856
<211> LENGTH: 5
<212> TYPE: PRT
<213> ORGANISM: Homo sapiens

```
<400> SEQUENCE: 856

Gly Tyr Ser Ser Ser
1               5

<210> SEQ ID NO 857
<211> LENGTH: 5
<212> TYPE: PRT
<213> ORGANISM: Homo sapiens

<400> SEQUENCE: 857

Gly Ile Ala Ala Ala
1               5

<210> SEQ ID NO 858
<211> LENGTH: 5
<212> TYPE: PRT
<213> ORGANISM: Homo sapiens

<400> SEQUENCE: 858

Val Tyr Gln Gln Leu
1               5

<210> SEQ ID NO 859
<211> LENGTH: 6
<212> TYPE: PRT
<213> ORGANISM: Homo sapiens

<400> SEQUENCE: 859

Gly Tyr Ser Ser Ser Trp
1               5

<210> SEQ ID NO 860
<211> LENGTH: 6
<212> TYPE: PRT
<213> ORGANISM: Homo sapiens

<400> SEQUENCE: 860

Gly Ile Ala Ala Ala Gly
1               5

<210> SEQ ID NO 861
<211> LENGTH: 6
<212> TYPE: PRT
<213> ORGANISM: Homo sapiens

<400> SEQUENCE: 861

Val Tyr Gln Gln Leu Val
1               5

<210> SEQ ID NO 862
<211> LENGTH: 4
<212> TYPE: PRT
<213> ORGANISM: Homo sapiens

<400> SEQUENCE: 862

Ile Ala Ala Ala
1

<210> SEQ ID NO 863
<211> LENGTH: 4
<212> TYPE: PRT
<213> ORGANISM: Homo sapiens

<400> SEQUENCE: 863
```

Tyr Gln Gln Leu
1

<210> SEQ ID NO 864
<211> LENGTH: 5
<212> TYPE: PRT
<213> ORGANISM: Homo sapiens

<400> SEQUENCE: 864

Tyr Ser Ser Ser Trp
1               5

<210> SEQ ID NO 865
<211> LENGTH: 5
<212> TYPE: PRT
<213> ORGANISM: Homo sapiens

<400> SEQUENCE: 865

Ile Ala Ala Ala Gly
1               5

<210> SEQ ID NO 866
<211> LENGTH: 5
<212> TYPE: PRT
<213> ORGANISM: Homo sapiens

<400> SEQUENCE: 866

Tyr Gln Gln Leu Val
1               5

<210> SEQ ID NO 867
<211> LENGTH: 6
<212> TYPE: PRT
<213> ORGANISM: Homo sapiens

<400> SEQUENCE: 867

Tyr Ser Ser Ser Trp Tyr
1               5

<210> SEQ ID NO 868
<211> LENGTH: 4
<212> TYPE: PRT
<213> ORGANISM: Homo sapiens

<400> SEQUENCE: 868

Ser Ser Ser Trp
1

<210> SEQ ID NO 869
<211> LENGTH: 4
<212> TYPE: PRT
<213> ORGANISM: Homo sapiens

<400> SEQUENCE: 869

Ala Ala Ala Gly
1

<210> SEQ ID NO 870
<211> LENGTH: 4
<212> TYPE: PRT
<213> ORGANISM: Homo sapiens

<400> SEQUENCE: 870

Gln Gln Leu Val
1

```
<210> SEQ ID NO 871
<211> LENGTH: 5
<212> TYPE: PRT
<213> ORGANISM: Homo sapiens

<400> SEQUENCE: 871

Ser Ser Ser Trp Tyr
1               5

<210> SEQ ID NO 872
<211> LENGTH: 4
<212> TYPE: PRT
<213> ORGANISM: Homo sapiens

<400> SEQUENCE: 872

Ser Ser Trp Tyr
1

<210> SEQ ID NO 873
<211> LENGTH: 4
<212> TYPE: PRT
<213> ORGANISM: Homo sapiens

<400> SEQUENCE: 873

Gly Ile Ala Val
1

<210> SEQ ID NO 874
<211> LENGTH: 4
<212> TYPE: PRT
<213> ORGANISM: Homo sapiens

<400> SEQUENCE: 874

Val Tyr Gln Trp
1

<210> SEQ ID NO 875
<211> LENGTH: 5
<212> TYPE: PRT
<213> ORGANISM: Homo sapiens

<400> SEQUENCE: 875

Gly Tyr Ser Ser Gly
1               5

<210> SEQ ID NO 876
<211> LENGTH: 5
<212> TYPE: PRT
<213> ORGANISM: Homo sapiens

<400> SEQUENCE: 876

Gly Ile Ala Val Ala
1               5

<210> SEQ ID NO 877
<211> LENGTH: 5
<212> TYPE: PRT
<213> ORGANISM: Homo sapiens

<400> SEQUENCE: 877

Val Tyr Gln Trp Leu
1               5
```

```
<210> SEQ ID NO 878
<211> LENGTH: 6
<212> TYPE: PRT
<213> ORGANISM: Homo sapiens

<400> SEQUENCE: 878

Gly Tyr Ser Ser Gly Trp
1               5

<210> SEQ ID NO 879
<211> LENGTH: 6
<212> TYPE: PRT
<213> ORGANISM: Homo sapiens

<400> SEQUENCE: 879

Gly Ile Ala Val Ala Gly
1               5

<210> SEQ ID NO 880
<211> LENGTH: 6
<212> TYPE: PRT
<213> ORGANISM: Homo sapiens

<400> SEQUENCE: 880

Val Tyr Gln Trp Leu Val
1               5

<210> SEQ ID NO 881
<211> LENGTH: 4
<212> TYPE: PRT
<213> ORGANISM: Homo sapiens

<400> SEQUENCE: 881

Tyr Ser Ser Gly
1

<210> SEQ ID NO 882
<211> LENGTH: 4
<212> TYPE: PRT
<213> ORGANISM: Homo sapiens

<400> SEQUENCE: 882

Ile Ala Val Ala
1

<210> SEQ ID NO 883
<211> LENGTH: 4
<212> TYPE: PRT
<213> ORGANISM: Homo sapiens

<400> SEQUENCE: 883

Tyr Gln Trp Leu
1

<210> SEQ ID NO 884
<211> LENGTH: 5
<212> TYPE: PRT
<213> ORGANISM: Homo sapiens

<400> SEQUENCE: 884

Tyr Ser Ser Gly Trp
1               5

<210> SEQ ID NO 885
<211> LENGTH: 5
```

```
<212> TYPE: PRT
<213> ORGANISM: Homo sapiens

<400> SEQUENCE: 885

Ile Ala Val Ala Gly
1               5

<210> SEQ ID NO 886
<211> LENGTH: 5
<212> TYPE: PRT
<213> ORGANISM: Homo sapiens

<400> SEQUENCE: 886

Tyr Gln Trp Leu Val
1               5

<210> SEQ ID NO 887
<211> LENGTH: 6
<212> TYPE: PRT
<213> ORGANISM: Homo sapiens

<400> SEQUENCE: 887

Tyr Ser Ser Gly Trp Tyr
1               5

<210> SEQ ID NO 888
<211> LENGTH: 4
<212> TYPE: PRT
<213> ORGANISM: Homo sapiens

<400> SEQUENCE: 888

Ser Ser Gly Trp
1

<210> SEQ ID NO 889
<211> LENGTH: 4
<212> TYPE: PRT
<213> ORGANISM: Homo sapiens

<400> SEQUENCE: 889

Ala Val Ala Gly
1

<210> SEQ ID NO 890
<211> LENGTH: 4
<212> TYPE: PRT
<213> ORGANISM: Homo sapiens

<400> SEQUENCE: 890

Gln Trp Leu Val
1

<210> SEQ ID NO 891
<211> LENGTH: 5
<212> TYPE: PRT
<213> ORGANISM: Homo sapiens

<400> SEQUENCE: 891

Ser Ser Gly Trp Tyr
1               5

<210> SEQ ID NO 892
<211> LENGTH: 432
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 892

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Asp Tyr Glu Gly Thr Gly Tyr Ala
        115                 120                 125

Phe Asp Ile Trp Gly Gln Gly Thr Met Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Ala Ala His His His His His His Gly Ala
                245                 250                 255

Ala Glu Gln Lys Leu Ile Ser Glu Glu Asp Leu Asn Gly Ala Ala Glu
            260                 265                 270

Ala Ser Ser Ala Ser Asn Ala Ser Ser Gly Asp Phe Asp Tyr Glu Lys
        275                 280                 285

Met Ala Asn Ala Asn Lys Gly Ala Met Thr Glu Asn Ala Asp Glu Asn
    290                 295                 300

Ala Leu Gln Ser Asp Ala Lys Gly Lys Leu Asp Ser Val Ala Thr Asp
305                 310                 315                 320

Tyr Gly Ala Ala Ile Asp Gly Phe Ile Gly Asp Val Ser Gly Leu Ala
                325                 330                 335

Asn Gly Asn Gly Ala Thr Gly Asp Phe Ala Gly Ser Asn Ser Gln Met
            340                 345                 350

Ala Gln Val Gly Asp Gly Asp Asn Ser Pro Leu Met Asn Asn Phe Arg
        355                 360                 365

Gln Tyr Leu Pro Ser Leu Pro Gln Ser Val Glu Cys Arg Pro Phe Val
    370                 375                 380

Phe Gly Ala Gly Lys Pro Tyr Glu Phe Ser Ile Asp Cys Asp Lys Ile
```

```
                385                 390                 395                 400
Asn Leu Phe Arg Gly Val Phe Ala Phe Leu Leu Tyr Val Ala Thr Phe
                    405                 410                 415
Met Tyr Val Phe Ser Thr Phe Ala Asn Ile Leu Arg Asn Lys Glu Ser
                420                 425                 430

<210> SEQ ID NO 893
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1296)

<400> SEQUENCE: 893 atg aaa tac cta ttg cct acg gca gcc gct gga ttg tta tta ctc gcg     48
Met Lys Tyr Leu Leu Pro Thr Ala Ala Ala Gly Leu Leu Leu Leu Ala
1               5                   10                  15 gcc cag ccg gcc atg gcc gaa gtt caa ttg tta gag tct ggt ggc ggt     96
Ala Gln Pro Ala Met Ala Glu Val Gln Leu Leu Glu Ser Gly Gly Gly
            20                  25                  30 ctt gtt cag cct ggt ggt tct tta cgt ctt tct tgc gct gct tcc gga    144
Leu Val Gln Pro Gly Gly Ser Leu Arg Leu Ser Cys Ala Ala Ser Gly
        35                  40                  45 ttc act ttc tct tcg tac gct atg tct tgg gtt cgc caa gct cct ggt    192
Phe Thr Phe Ser Ser Tyr Ala Met Ser Trp Val Arg Gln Ala Pro Gly
    50                  55                  60 aaa ggt ttg gag tgg gtt tct gct atc tct ggt tct ggt ggc agt act    240
Lys Gly Leu Glu Trp Val Ser Ala Ile Ser Gly Ser Gly Gly Ser Thr
65                  70                  75                  80 tac tat gct gac tcc gtt aaa ggt cgc ttc act atc tct aga gac aac    288
Tyr Tyr Ala Asp Ser Val Lys Gly Arg Phe Thr Ile Ser Arg Asp Asn
                85                  90                  95 tct aag aat act ctc tac ttg cag atg aac agc tta agg gct gag gac    336
Ser Lys Asn Thr Leu Tyr Leu Gln Met Asn Ser Leu Arg Ala Glu Asp
            100                 105                 110 act gca gtc tac tat tgc gct aaa gac tat gaa ggt act ggt tat gct    384
Thr Ala Val Tyr Tyr Cys Ala Lys Asp Tyr Glu Gly Thr Gly Tyr Ala
        115                 120                 125 ttc gac ata tgg ggt caa ggt act atg gtc acc gtc tct agt gcc tcc    432
Phe Asp Ile Trp Gly Gln Gly Thr Met Val Thr Val Ser Ser Ala Ser
    130                 135                 140 acc aag ggc cca tcg gtc ttc ccg cta gca ccc tcc tcc aag agc acc    480
Thr Lys Gly Pro Ser Val Phe Pro Leu Ala Pro Ser Ser Lys Ser Thr
145                 150                 155                 160 tct ggg ggc aca gcg gcc ctg ggc tgc ctg gtc aag gac tac ttc ccc    528
Ser Gly Gly Thr Ala Ala Leu Gly Cys Leu Val Lys Asp Tyr Phe Pro
                165                 170                 175 gaa ccg gtg acg gtg tcg tgg aac tca ggc gcc ctg acc agc ggc gtc    576
Glu Pro Val Thr Val Ser Trp Asn Ser Gly Ala Leu Thr Ser Gly Val
            180                 185                 190 cac acc ttc ccg gct gtc cta cag tcc tca gga ctc tac tcc ctc agc    624
His Thr Phe Pro Ala Val Leu Gln Ser Ser Gly Leu Tyr Ser Leu Ser
        195                 200                 205 agc gta gtg acc gtg ccc tcc agc agc ttg ggc acc cag acc tac atc    672
Ser Val Val Thr Val Pro Ser Ser Ser Leu Gly Thr Gln Thr Tyr Ile
    210                 215                 220 tgc aac gtg aat cac aag ccc agc aac acc aag gtg gac aag aaa gtt    720
```

```
                Cys Asn Val Asn His Lys Pro Ser Asn Thr Lys Val Asp Lys Lys Val
                225                 230                 235                 240 gag ccc aaa tct tgt gcg gcc gca cat cat cat cac cat cac ggg gcc      768
Glu Pro Lys Ser Cys Ala Ala Ala His His His His His His Gly Ala
                245                 250                 255 gca gaa caa aaa ctc atc tca gaa gag gat ctg aat ggg gcc gca gag      816
Ala Glu Gln Lys Leu Ile Ser Glu Glu Asp Leu Asn Gly Ala Ala Glu
                260                 265                 270 gct agt tct gct agt aac gcg tct tcc ggt gat ttt gat tat gaa aag      864
Ala Ser Ser Ala Ser Asn Ala Ser Ser Gly Asp Phe Asp Tyr Glu Lys
                275                 280                 285 atg gca aac gct aat aag ggg gct atg acc gaa aat gcc gat gaa aac      912
Met Ala Asn Ala Asn Lys Gly Ala Met Thr Glu Asn Ala Asp Glu Asn
                290                 295                 300 gcg cta cag tct gac gct aaa ggc aaa ctt gat tct gtc gct act gat      960
Ala Leu Gln Ser Asp Ala Lys Gly Lys Leu Asp Ser Val Ala Thr Asp
305                 310                 315                 320 tac ggt gct gct atc gat ggt ttc att ggt gac gtt tcc ggc ctt gct     1008
Tyr Gly Ala Ala Ile Asp Gly Phe Ile Gly Asp Val Ser Gly Leu Ala
                325                 330                 335 aat ggt aat ggt gct act ggt gat ttt gct ggc tct aat tcc caa atg     1056
Asn Gly Asn Gly Ala Thr Gly Asp Phe Ala Gly Ser Asn Ser Gln Met
                340                 345                 350 gct caa gtc ggt gac ggt gat aat tca cct tta atg aat aat ttc cgt     1104
Ala Gln Val Gly Asp Gly Asp Asn Ser Pro Leu Met Asn Asn Phe Arg
                355                 360                 365 caa tat tta cct tcc ctc cct caa tcg gtt gaa tgt cgc cct ttt gtc     1152
Gln Tyr Leu Pro Ser Leu Pro Gln Ser Val Glu Cys Arg Pro Phe Val
370                 375                 380 ttt ggc gct ggt aaa cca tat gaa ttt tct att gat tgt gac aaa ata     1200
Phe Gly Ala Gly Lys Pro Tyr Glu Phe Ser Ile Asp Cys Asp Lys Ile
385                 390                 395                 400 aac tta ttc cgt ggt gtc ttt gcg ttt ctt tta tat gtt gcc acc ttt     1248
Asn Leu Phe Arg Gly Val Phe Ala Phe Leu Leu Tyr Val Ala Thr Phe
                405                 410                 415 atg tat gta ttt tct acg ttt gct aac ata ctg cgt aat aag gag tct     1296
Met Tyr Val Phe Ser Thr Phe Ala Asn Ile Leu Arg Asn Lys Glu Ser
                420                 425                 430 taatgaaacg cgtgatgaga attc                                          1320

<210> SEQ ID NO 894
<211> LENGTH: 9501
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 894
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttata tggaatgaaa cttccagaca ccgtacttta     180
gttgcatatt taaaacatgt tgagctacag cattatattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tctttttgat gcaatccgct ttgcttctga ctataatagt     420
cagggtaaag acctgatttt tgatttatgg tcattctcgt tttctgaact gtttaaagca     480
```

-continued

```
tttgagggggg attcaatgaa tatttatgac gattccgcag tattggacgc tatccagtct    540
aaacatttta ctattacccc ctctggcaaa acttcttttg caaaagcctc tcgctatttt    600
ggtttttatc gtcgtctggt aaacgagggt tatgatagtg ttgctcttac tatgcctcgt    660
aattccttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagccttt   1560
tttttggaga ttttcaacgt gaaaaaatta ttattcgcaa ttcctttagt tgttcctttc   1620
tattctcact ccgctgaaac tgttgaaagt tgtttagcaa atcccatac agaaaattca   1680
tttactaacg tctggaaaga cgacaaaact ttagatcgtt acgctaacta tgagggctgt   1740
ctgtggaatg ctacaggcgt tgtagtttgt actggtgacg aaactcagtg ttacggtaca   1800
tgggttccta ttgggcttgc tatccctgaa atgaggggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg accccgttaa aacttattac cagtacactc ctgtatcatc aaaagccatg   2160
tatgacgctt actggaacgg taaattcaga gactgcgctt ccattctggc tttaatgag   2220
gatttatttg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataagggg ctatgaccga aaatgccgat   2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg tgacggtga taattcacct   2640
ttaatgaata atttccgtca atatttacct tccctccctc aatcggttga atgtcgccct   2700
tttgtctttg cgctggtaa accatatgaa ttttctattg attgtgacaa aataaactta   2760
ttccgtggtg tctttgcgtt tctttttatat gttgccacct ttatgtatgt attttctacg   2820
```

```
tttgctaaca tactgcgtaa taaggagtct taatcatgcc agttcttttg ggtattccgt    2880
tattattgcg tttcctcggt ttccttctgg taactttgtt cggctatctg cttacttttc    2940
ttaaaaaggg cttcggtaag atagctattg ctatttcatt gtttcttgct cttattattg    3000
ggcttaactc aattcttgtg ggttatctct ctgatattag cgctcaatta ccctctgact    3060
ttgttcaggg tgttcagtta attctcccgt ctaatgcgct tccctgtttt tatgttattc    3120
tctctgtaaa ggctgctatt ttcattttg acgttaaaca aaaaatcgtt tcttatttgg     3180
attgggataa ataatatggc tgtttatttt gtaactggca aattaggctc tggaaagacg    3240
ctcgttagcg ttggtaagat tcaggataaa attgtagctg ggtgcaaaat agcaactaat    3300
cttgatttaa ggcttcaaaa cctcccgcaa gtcgggaggt tcgctaaaac gcctcgcgtt    3360
cttagaatac cggataagcc ttctatatct gatttgcttg ctattgggcg cggtaatgat    3420
tcctacgatg aaaataaaaa cggcttgctt gttctcgatg agtgcggtac ttggtttaat    3480
acccgttctt ggaatgataa ggaaagacag ccgattattg attggtttct acatgctcgt    3540
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta ctttatattc tcttattact ggctcgaaaa tgcctctgcc taaattacat    3720
gttggcgttg ttaaatatgg cgattctcaa ttaagcccta ctgttgagcg ttggctttat    3780
actggtaaga atttgtataa cgcatatgat actaaacagg cttttctag taattatgat     3840
tccggtgttt attcttattt aacgccttat ttatcacacg gtcggtattt caaaccatta    3900
aatttaggtc agaagatgaa attaactaaa atatatttga aaagttttc tcgcgttctt     3960
tgtcttgcga ttggatttgc atcagcattt acatatagtt atataaccca acctaagccg    4020
gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt tcttgatgtt    4260
tgtttcatca tcttcttttg ctcaggtaat tgaaatgaat aattcgcctc tgcgcgattt    4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gcaaataatt ttgatatggt aggttctaac ccttccataa ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgtttgtaaa    4680
gtctaatact tctaaatcct caaatgtatt atctattgac ggctctaatc tattagttgt    4740
tagtgctcct aaagatattt tagataacct tcctcaattc ctttcaactg ttgatttgcc    4800
aactgaccag atattgattg agggtttgat atttgaggtt cagcaaggtg atgctttaga    4860
tttttcattt gctgctggct ctcagcgtgg cactgttgca ggcggtgtta atactgaccg    4920
cctcacctct gttttatctt ctgctggtgg ttcgttcggt atttttaatg gcgatgtttt    4980
agggctatca gttcgcgcat taaagactaa tagccattca aaaatattgt ctgtgccacg    5040
tattcttacg ctttcaggtc agaagggttc tatctctgtt ggccagaatg tcccttttat    5100
tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
```

-continued

```
tctggatatt accagcaagg ccgatagttt gagttcttct actcaggcaa gtgatgttat   5280
tactaatcaa agaagtattg ctacaacggt taatttgcgt gatggacaga ctcttttact   5340
cggtggcctc actgattata aaaacacttc tcaggattct ggcgtaccgt tcctgtctaa   5400
aatcccttta atcggcctcc tgtttagctc ccgctctgat tctaacgagg aaagcacgtt   5460
atacgtgctc gtcaaagcaa ccatagtacg cgccctgtag cggcgcatta agcgcggcgg   5520
gtgtggtggt tacgcgcagc gtgaccgcta cacttgccag cgccctagcg cccgctcctt   5580
tcgctttctt cccttccttt ctcgccacgt tcgccggctt tccccgtcaa gctctaaatc   5640
gggggctccc tttagggttc cgatttagtg ctttacggca cctcgacccc aaaaaacttg   5700
atttgggtga tggttcacgt agtgggccat cgccctgata cggttttt cgcccttga    5760 cgttggagtc cacgttcttt aatagtggac tcttgttcca aactgaaca acactcaacc   5820 ctatctcggg ctattctttt gatttataag ggattttgcc gatttcggaa ccaccatcaa   5880
acaggatttt cgcctgctgg ggcaaaccag cgtggaccgc ttgctgcaac tctctcaggg   5940
ccaggcggtg aagggcaatc agctgttgcc cgtctcactg gtgaaaagaa aaaccaccct   6000
ggatccaagc ttgcaggtgg cacttttcgg ggaaatgtgc gcggaacccc tatttgttta   6060
tttttctaaa tacattcaaa tatgtatccg ctcatgagac aataaccctg ataaatgctt   6120
caataatatt gaaaaggaa gagtatgagt attcaacatt tccgtgtcgc ccttattccc    6180
ttttttgcgg cattttgcct tcctgttttt gctcacccag aaacgctggt gaaagtaaaa   6240
gatgctgaag atcagttggg cgcactagtg ggttacatcg aactggatct caacagcggt   6300
aagatccttg agagttttcg ccccgaagaa cgttttccaa tgatgagcac ttttaaagtt   6360
ctgctatgtg gcgcggtatt atcccgtatt gacgccgggc aagagcaact cggtcgccgc   6420
atacactatt ctcagaatga cttggttgag tactcaccag tcacagaaaa gcatcttacg   6480
gatggcatga cagtaagaga attatgcagt gctgccataa ccatgagtga taacactgcg   6540
gccaacttac ttctgacaac gatcggagga ccgaaggagc taaccgcttt tttgcacaac   6600 atggggatc atgtaactcg ccttgatcgt tgggaaccgg agctgaatga agccatacca    6660
aacgacgagc gtgacaccac gatgcctgta gcaatggcaa caacgttgcg caaactatta   6720
actggcgaac tacttactct agcttcccgg caacaattaa tagactggat ggaggcggat   6780
aaagttgcag gaccacttct gcgctcggcc cttccggctg gctggtttat tgctgataaa   6840
tctggagccg gtgagcgtgg gtctcgcggt atcattgcag cactggggcc agatggtaag   6900
ccctcccgta tcgtagttat ctacacgacg gggagtcagg caactatgga tgaacgaaat   6960
agacagatcg ctgagatagg tgcctcactg attaagcatt ggtaactgtc agaccaagtt   7020
tactcatata ctttagat tgatttaaaa cttcattttt aatttaaaag gatctaggtg    7080
aagatccttt ttgataatct catgaccaaa atcccttaac gtgagttttc gttccactgt   7140
acgtaagacc cccaagcttg tcgactgaat ggcgaatggc gctttgcctg gtttccggca   7200
ccagaagcgg tgccggaaag ctggctggag tgcgatcttc ctgacgctcg agcgcaacgc   7260
aattaatgtg agttagctca ctcattaggc accccaggct ttacacttta tgcttccggc   7320
tcgtatgttg tgtggaattg tgagcggata acaatttcac acaggaaaca gctatgacca   7380
tgattacgcc aagctttgga gcctttttt tggagatttt caacatgaaa tacctattgc    7440
ctacggcagc cgctggattg ttattactcg cgcccagcc ggccatggcc gaagttcaat     7500
tgttagagtc tggtggcggt cttgttcagc ctggtggttc tttacgtctt tcttgcgctg   7560
```

```
cttccggatt cactttctct tcgtacgcta tgtcttgggt tcgccaagct cctggtaaag   7620
gtttggagtg ggtttctgct atctctggtt ctggtggcag tacttactat gctgactccg   7680
ttaaaggtcg cttcactatc tctagagaca actctaagaa tactctctac ttgcagatga   7740
acagcttaag ggctgaggac actgcagtct actattgcgc taaagcctat cgtccttctt   7800
atcatgacat atggggtcaa ggtactatgg tcaccgtctc tagtgcctcc accaagggcc   7860
catcggtctt cccgctagca ccctcctcca gagcacctc tggggcaca gcggccctgg    7920 gctgcctggt caaggactac ttccccgaac cggtgacggt gtcgtggaac tcaggcgccc   7980
tgaccagcgg cgtccacacc ttcccggctg tcctacagtc ctcaggactc tactccctca   8040
gcagcgtagt gaccgtgccc tccagcagct gggcaccca gacctacatc tgcaacgtga    8100
atcacaagcc cagcaacacc aaggtggaca agaaagttga gcccaaatct tgtgcggccg   8160
cacatcatca tcaccatcac ggggccgcag aacaaaaact catctcagaa gaggatctga   8220
atggggccgc agaggctagc tctgctagtg gcgacttcga ctacgagaaa atggctaatg   8280
ccaacaaagg cgccatgact gagaacgctg acagaatgc tttgcaaagc gatgccaagg    8340
gtaagttaga cagcgtcgcg accgactatg gcgccgccat cgacggcttt atcggcgatg   8400
tcagtggttt ggccaacggc aacggagcca ccggagactt cgcaggttcg aattctcaga   8460
tggcccaggt tggagatggg gacaacagtc gcttatgaa caactttaga cagtaccttc    8520
cgtctcttcc gcagagtgtc gagtgccgtc cattcgtttt cggtgccggc aagcttacg    8580 agttcagcat cgactgcgat aagatcaatc ttttccgcgg cgttttcgct ttcttgctat   8640
acgtcgctac tttcatgtac gttttcagca cttttcgccaa tattttacgc aacaaagaaa   8700
gctagtgatc tcctaggaag cccgcctaat gagcgggctt ttttttttctg gtatgcatcc   8760 tgaggccgat actgtcgtcg tcccctcaaa ctggcagatg cacggttacg atgcgcccat   8820
ctacaccaac gtgacctatc ccattacggt caatccgccg tttgttccca cggagaatcc   8880
gacgggttgt tactcgctca catttaatgt tgatgaaagc tggctacagg aaggccagac   8940
gcgaattatt tttgatggcg ttcctattgg ttaaaaaatg agctgattta acaaaaattt   9000
aatgcgaatt ttaacaaaat attaacgttt acaatttaaa tatttgctta tacaatcttc   9060
ctgttttggg ggcttttctg attatcaacc ggggtacata tgattgacat gctagtttta   9120
cgattaccgt tcatcgattc tcttgtttgc tccagactct caggcaatga cctgatagcc   9180
tttgtagatc tctcaaaaat agctaccctc tccggcatta atttatcagc tagaacggtt   9240
gaatatcata ttgatggtga tttgactgtc tccggccttt ctcacccttt tgaatcttta   9300
cctacacatt actcaggcat tgcatttaaa atatatgagg gttctaaaaa ttttttatcct   9360 tgcgttgaaa taaaggcttc tcccgcaaaa gtattacagg gtcataatgt ttttggtaca   9420
accgatttag ctttatgctc tgaggcttta ttgcttaatt ttgctaattc tttgccttgc   9480
ctgtatgatt tattggatgt t                                              9501
```

<210> SEQ ID NO 895
<211> LENGTH: 5957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 895

```
gacgaaaggg cctcgtgata cgcctatttt tataggttaa tgtcatgata ataatggttt     60
```

-continued

| | |
|---|---|
| cttagacgtc aggtggcact tttcggggaa atgtgcgcgg aaccccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgcc cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc atttttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca aacaaaaaaa ccaccgctac cagcggtggt ttgtttgccg atcaagagc | 1320 |
| taccaactct ttttccgaag gtaactggct tcagcagagc gcagatacca atactgttc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg tcgggctga acggggggtt | 1560 |
| cgtgcataca gcccagcttg gagcgaacga cctacaccga actgagatac ctacagcgtg | 1620 |
| agctatgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg attttttgtga tgctcgtcag | 1800 |
| gggggcggag cctatggaaa aacgccagca acgcggcctt tttacggttc ctggccttt | 1860 |
| gctggccttt tgctcacatg ttctttcctg cgttatcccc tgattctgtg ataaccgta | 1920 |
| ttaccgcctt tgagtgagct gataccgctc gccgcagccg aacgaccgag cgcagcgagt | 1980 |
| cagtgagcga ggaagcggaa gagcgcccaa tacgcaaacc gcctctcccc gcgcgttggc | 2040 |
| cgattcatta atgcagctgg cacgacaggt ttcccgactg gaaagcgggc agtgagcgca | 2100 |
| acgcaattaa tgtgagttag ctcactcatt aggcaccccca ggctttacac tttatgcttc | 2160 |
| cggctcgtat gttgtgtgga attgtgagcg ataacaatt tcacacagga aacagctatg | 2220 |
| accatgatta cgccaagctt tggagccttt ttttttggaga ttttcaacgt gaaaaaatta | 2280 |
| ttattcgcaa ttcctttagt tgttcctttc tattctcaca gtgcacaggt ccaactgcag | 2340 |
| gagctcgaga tcaaacgtgg aactgtggct gcaccatctg tcttcatctt cccgccatct | 2400 |
| gatgagcagt tgaaatctgg aactgcctct gttgtgtgcc tgctgaataa cttctatccc | 2460 |

```
agagaggcca aagtacagtg gaaggtggat aacgccctcc aatcgggtaa ctcccaggag    2520
agtgtcacag agcaggacag caaggacagc acctacagcc tcagcagcac cctgacgctg    2580
agcaaagcag actacgagaa acacaaagtc tacgcctgcg aagtcaccca tcagggcctg    2640
agttcaccgg tgacaaagag cttcaacagg ggagagtgtt aataaggcgc gcctaaccat    2700
ctatttcaag gaacagtctt aatgaaaaag cttttattca tgatcccgtt agttgtaccg    2760
ttcgtggccc agccggcctc tgctgaagtt caattgttag agtctggtgg cggtcttgtt    2820
cagcctggtg gttctttacg tctttcttgc gctgcttccg gagcttcaga tctgtttgcc    2880
tttttgtggg gtggtgcaga tcgcgttacg gagatcgacc gactgcttga gcaaaagcca    2940
cgcttaactg ctgatcaggc atgggatgtt attcgccaaa ccagtcgtca ggatcttaac    3000
ctgaggcttt ttttacctac tctgcaagca gcgacatctg gtttgacaca gagcgatccg    3060
cgtcgtcagt tggtagaaac attaacacgt tgggatggca tcaatttgct taatgatgat    3120
ggtaaaacct ggcagcagcc aggctctgcc atcctgaacg tttggctgac cagtatgttg    3180
aagcgtaccg tagtggctgc cgtacctatg ccatttgata agtggtacag cgccagtggc    3240
tacgaaacaa cccaggacgg cccaactggt tcgctgaata taagtgttgg agcaaaaatt    3300
ttgtatgagg cggtgcaggg agacaaatca ccaatcccac aggcggttga tctgtttgct    3360
gggaaaccac agcaggaggt tgtgttggct gcgctggaag atacctggga gactcttttcc   3420 aaacgctatg gcaataatgt gagtaactgg aaaacaccgg caatggcctt aacgttccgg    3480
gcaaataatt tctttggtgt accgcaggcc gcagcggaag aaacgcgtca tcaggcggag    3540
tatcaaaacc gtggaacaga aaacgatatg attgttttct caccaacgac aagcgatcgt    3600
cctgtgcttg cctgggatgt ggtcgcaccc ggtcagagtg ggtttattgc tcccgatgga    3660
acagttgata agcactatga agatcagctg aaaatgtacg aaaattttgg ccgtaagtcg    3720
ctctggttaa cgaagcagga tgtggaggcg cataaggagt tctagagaca actctaagaa    3780
tactctctac ttgcagatga acagcttaag tctgagcatt cggtccgggc aacattctcc    3840
aaactgacca gacgacacaa acggcttacg ctaaatcccg cgcatgggat ggtaaagagg    3900
tggcgtcttt gctggcctgg actcatcaga tgaaggccaa aaattggcag gagtggacac    3960
agcaggcagc gaaacaagca ctgaccatca actggtacta tgctgatgta aacggcaata    4020
ttggttatgt tcatactggt gcttatccag atcgtcaatc aggccatgat ccgcgattac    4080
ccgttcctgg tacgggaaaa tgggactgga aagggctatt gccttttgaa atgaacccta    4140
aggtgtataa cccccagcag ctagccatat tctctcggtc accgtctcaa gcgcctccac    4200
caagggccca tcggtcttcc cgctagcacc ctcctccaag agcacctctg ggggcacagc    4260
ggccctgggc tgcctggtca aggactactt ccccgaaccg gtgacggtgt cgtggaactc    4320
aggcgccctg accagcggcg tccacacctt cccggctgtc ctacagtcta gcggactcta    4380
ctccctcagc agcgtagtga ccgtgccctc ttctagcttg gcacccagac ctacatctg    4440 caacgtgaat cacaagccca gcaacaccaa ggtggacaag aaagttgagc ccaaatcttg    4500
tgcggccgca catcatcatc accatcacgg ggccgcagaa caaaaactca tctcagaaga    4560
ggatctgaat ggggccgcag aggctagttc tgctagtaac gcgtcttccg gtgattttga    4620
ttatgaaaag atggcaaacg ctaataaggg ggctatgacc gaaaatgccg atgaaaacgc    4680
gctacagtct gacgctaaag gcaaacttga ttctgtcgct actgattacg gtgctgctat    4740
cgatggtttc attggtgacg tttccggcct tgctaatggt aatggtgcta ctggtgattt    4800
```

```
tgctggctct aattcccaaa tggctcaagt cggtgacggt gataattcac ctttaatgaa    4860
taatttccgt caatatttac cttccctccc tcaatcggtt gaatgtcgcc cttttgtctt    4920
tggcgctggt aaaccatatg aattttctat tgattgtgac aaaataaact tattccgtgg    4980
tgtctttgcg tttctttat atgttgccac ctttatgtat gtattttcta cgtttgctaa     5040
catactgcgt aataaggagt cttaatgaaa cgcgtgatga gaattcactg gccgtcgttt    5100
tacaacgtcg tgactgggaa aaccctggcg ttacccaact taatcgcctt gcagcacatc    5160 ccccttttcgc cagctggcgt aatagcgaag aggcccgcac cgatcgccct tcccaacagt    5220
tgcgcagcct gaatggcgaa tggcgcctga tgcggtattt tctccttacg catctgtgcg    5280
gtatttcaca ccgcatacgt caaagcaacc atagtacgcg ccctgtagcg cgcattaag    5340 cgcggcgggt gtggtggtta cgcgcagcgt gaccgctaca cttgccagcg ccttagcgcc    5400
cgctcctttc gctttcttcc cttcctttct cgccacgttc gccggctttc cccgtcaagc    5460
tctaaatcgg gggctccctt tagggttccg atttagtgct ttacggcacc tcgaccccaa    5520
aaaacttgat ttgggtgatg gttcacgtag tgggccatcg ccctgataga cggttttcg    5580 ccctttgacg ttggagtcca cgttctttaa tagtggactc ttgttccaaa ctggaacaac    5640
actcaactct atctcgggct attctttga tttataaggg attttgccga tttcggtcta    5700
ttggttaaaa aatgagctga tttaacaaaa attaacgcg aatttaaca aaatattaac      5760 gtttacaatt ttatggtgca gtctcagtac aatctgctct gatgccgcat agttaagcca    5820
gccccgacac ccgccaacac ccgctgacgc gccctgacgg gcttgtctgc tcccggcatc    5880
cgcttacaga caagctgtga ccgtctccgg gagctgcatg tgtcagaggt tttcaccgtc    5940
atcaccgaaa cgcgcga                                                   5957
```

<210> SEQ ID NO 896
<211> LENGTH: 3412
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 896

```
gacgaaaggg cctgctctgc cagtgttaca accaattaac caattctgat tagaaaaact     60
catcgagcat caaatgaaac tgcaatttat tcatatcagg attatcaata ccatattttt    120 gaaaagccg tttctgtaat gaaggagaaa actcaccgag gcagttccat aggatggcaa    180
gatcctggta tcggtctgcg attccgactc gtccaacatc aatacaacct attaatttcc    240
cctcgtcaaa aataaggtta tcaagtgaga atcaccatg agtgacgact gaatccggtg    300
agaatggcaa aagcttatgc atttctttcc agacttgttc aacaggccag ccattacgct    360
cgtcatcaaa atcactcgca tcaaccaaac cgttattcat tcgtgattgc gcctgagcga    420
gacgaaatac gcgatcgctg ttaaaaggac aattacaaac aggaattgaa tgcaaccggc    480
gcaggaacac tgccagcgca tcaacaatat tttcacctga atcaggatat tcttctaata    540
cctggaatgc tgttttcccg gggatcgcag tggtgagtaa ccatgcatca tcaggagtac    600
ggataaaatg cttgatggtc ggaagaggca taaattccgt cagccagttt agtctgacca    660
tctcatctgt aacatcattg gcaacgctac ctttgccatg tttcagaaac aactctggcg    720
catcgggctt cccatacaat cgatagattg tcgcacctga ttgcccgaca ttatcgcgag    780
cccatttata cccatataaa tcagcatcca tgttggaatt taatcgcggc ctcgagcaag    840
```

```
acgtttcccg ttgaatatgg ctcataacac cccttgtatt actgtttatg taagcagaca    900
gttttattgt tcatgatgat atattttat cttgtgcaat gtaacatcag agattttgag    960
acacaacgtg gctttccccc ccccccctg caggtctcgg gctattcctg tcagaccaag   1020
tttactcata tatactttag attgatttaa aacttcattt ttaatttaaa aggatctagg   1080
tgaagatcct ttttgataat ctcatgacca aaatcccta acgtgagttt tcgttccact   1140
gagcgtcaga ccccgtagaa aagatcaaag gatcttcttg agatccttt tttctgcgcg   1200
taatctgctg cttgcaaaca aaaaaaccac cgctaccagc ggtggtttgt ttgccggatc   1260
aagagctacc aactcttttt ccgaaggtaa ctggcttcag cagagcgcag ataccaaata   1320
ctgttcttct agtgtagccg tagttaggcc accacttcaa gaactctgta gcaccgccta   1380
catacctcgc tctgctaatc ctgttaccag tggctgctgc cagtggcgat aagtcgtgtc   1440
ttaccgggtt ggactcaaga cgatagttac cggataaggc gcagcggtcg ggctgaacgg   1500
ggggttcgtg catacagccc agcttggagc gaacgaccta caccgaactg agatacctac   1560
agcgtgagct atgagaaagc gccacgcttc ccgaagggag aaaggcggac aggtatccgg   1620
taagcggcag ggtcggaaca ggagagcgca cgagggagct tccaggggga aacgcctggt   1680
atctttatag tcctgtcggg tttcgccacc tctgacttga gcgtcgattt ttgtgatgct   1740
cgtcaggggg gcggagccta tggaaaaacg ccagcaacgc ggccttttta cggttcctgg   1800
ccttttgctg gccttttgct cacatgttct ttcctgcgtt atcccctgat tctgtggata   1860
accgtattac cgcctttgag tgagctgata ccgctcgccg cagccgaacg accgagcgca   1920
gcgagtcagt gagcgaggaa gcggaagagc gcccaatacg caaaccgcct ctccccgcgc   1980
gttggccgat tcattaatgc agctggcacg acaggtttcc cgactggaaa gcgggcagtg   2040
agcgcaacgc aattaatgtg agttagctca ctcattaggc accccaggct ttacacttta   2100
tgcttccggc tcgtatgttg tgtggaattg tgagcggata acaatttcac acaggaaaca   2160
gctatgacca tgattacgcc aagctttgga gcctttttt tggagatttt caacatgaag   2220
aagctcctct ttgctatccc gctcgtcgtt cctttgtgg cccagccggc catggccgac   2280
atccagatga cccagtctcc atcctccctg tctgcatctg taggagacag agtcaccatc   2340
acttgccggg caagtcagag cattagcagc tatttaaatt ggtatcagca gaaaccaggg   2400
aaagccccta agctcctgat ctatgctgca tccagtttgc aaagtggggt cccatcaagg   2460
ttcagtggca gtggatctgg gacagatttc actctcacca tcagcagtct gcaacctgaa   2520
gattttgcaa cttactactg tcaacagagt tacagtaccc cttcactttt cggccctggg   2580
accaaagtgg atatcaaacg tggtaccgtg gctgcaccat ctgtcttcat cttcccgcca   2640
tctgatgagc agttgaaatc tggaactgcc tctgttgtgt gcctgctgaa taacttctat   2700
cccagagagg ccaaagtaca gtggaaggtg gataacgccc tccaatcggg taactcccag   2760
gagagtgtca cagagcagga cagcaaggac agcacctaca gcctcagcag cacctgacg   2820
ctgagcaaag cagactacga gaaacacaaa gtctacgcct gcgaagtcac ccatcagggc   2880
ctgagttcac cggtgacaaa gagcttcaac aggggagagt gtgcggccgc tggtaagcct   2940
atccctaacc ctctcctcgg tctcgattct acgtgataac ttcaccggtc aacgcgtgat   3000
gagaattcac tggccgtcgt tttacaacgt cgtgactggg aaaaccctgg cgttacccaa   3060
cttaatcgcc ttgcagcaca tccccctttc gccagctggc gtaatagcga agaggcccgc   3120
accgatcgcc cttcccaaca gttgcgcagc ctgaatggcg aatggcgcct gatgcggtat   3180
tttctcctta cgcatctgtg cggtatttca caccgcatac gtcaaagcaa ccatagtctc   3240
```

```
agtacaatct gctctgatgc cgcatagtta agccagcccc gacacccgcc aacacccgct    3300
gacgcgccct gacaggcttg tctgctcccg gcatccgctt acagacaagc tgtgaccgtc    3360
tccgggagct gcatgtgtca gaggttttca ccgtcatcac cgaaacgcgc ga            3412
```

<210> SEQ ID NO 897
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 897

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg Gly Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Ala Ala Ala Gly Lys Pro Ile Pro Asn
    210                 215                 220

Pro Leu Leu Gly Leu Asp Ser Thr
225                 230
```

<210> SEQ ID NO 898
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 898

```
Tyr Tyr Cys Ala Lys Asp Tyr Gly Tyr Cys Ser Ser Thr Ser Cys Tyr
1               5                   10                  15

Thr Lys Leu Tyr Ser Tyr Ala Glu Tyr Phe Gln His Trp Gly Gln Gly
            20                  25                  30
```

```
<210> SEQ ID NO 899
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 899

Tyr Tyr Cys Ala Lys Gly Ser Tyr Tyr Gly Ser Gly Ser Tyr Tyr
1               5                   10                  15

Asn Met Asp Ser Tyr Tyr Ala Glu Tyr Phe Gln His Trp Gly Gln Gly
            20                  25                  30

Thr Leu Val Thr Val Ser Ser
        35

<210> SEQ ID NO 900
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 900

Tyr Tyr Cys Ala Lys Glu Tyr Tyr Tyr Gly Ser Gly Ser Tyr Tyr
1               5                   10                  15

Asn Ser Thr Thr Thr Ser Ala Glu Tyr Phe Gln His Trp Gly Gln Gly
            20                  25                  30

Thr Leu Val Thr Val Ser Ser
        35

<210> SEQ ID NO 901
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 901

Tyr Tyr Cys Ala Lys Tyr Tyr Ser Phe Ser Tyr Tyr Pro Tyr Tyr
1               5                   10                  15

Asp Ser Ser Gly Tyr Tyr Tyr Ala Tyr Tyr Ser Asp Tyr Ser Tyr Ser
            20                  25                  30

Tyr Tyr Ala Glu Tyr Phe Gln His Trp Gly Gln Gly Thr Leu Val Thr
        35                  40                  45

Val Ser Ser
    50

<210> SEQ ID NO 902
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 902

Tyr Tyr Cys Ala Lys Ser Ser Gly Tyr Cys Ser Ser Thr Ser Cys Tyr
```

```
                   1               5                  10                  15
Thr Asn Pro Tyr Tyr Tyr Ala Glu Tyr Phe Gln His Trp Gly Gln Gly
                  20                  25                  30

Thr Leu Val Thr Val Ser Ser
          35

<210> SEQ ID NO 903
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 903

Tyr Tyr Cys Ala Lys Ser Tyr Gln Tyr Gly Tyr Cys Ser Ser Thr
1               5                  10                  15

Ser Cys Tyr Thr Tyr Tyr Ser Tyr Trp Ser Tyr Ser Ser Tyr Ser
                  20                  25                  30

Tyr Tyr Ala Glu Tyr Phe Gln His Trp Gly Gln Gly Thr Leu Val Thr
              35                  40                  45

Val Ser Ser
        50

<210> SEQ ID NO 904
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 904

Tyr Tyr Cys Ala Lys Tyr Tyr Ser Tyr Gly Tyr Cys Ser Ser Thr
1               5                  10                  15

Ser Cys Tyr Thr Tyr Ser Ser Pro Ser Tyr Ser Tyr Ser Ser
                  20                  25                  30

Tyr Tyr Ala Glu Tyr Phe Gln His Trp Gly Gln Gly Thr Leu Val Thr
              35                  40                  45

Val Ser Ser
        50

<210> SEQ ID NO 905
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 905

Tyr Tyr Cys Ala Lys Ser Pro Ser Tyr Tyr Asp Tyr Val Trp Gly Ser
1               5                  10                  15

Tyr Arg Tyr Thr Ser Ser Tyr Thr Tyr Tyr Ser Tyr Ser Tyr Ser Ser
                  20                  25                  30

Tyr Ala Glu Tyr Phe Gln His Trp Gly Gln Gly Thr Leu Val Thr Val
              35                  40                  45

Ser Ser
    50

<210> SEQ ID NO 906
```

```
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 906

Tyr Tyr Cys Ala Lys Tyr Ala Tyr Ser Ser Glu Ser Tyr Tyr Ser Ser
1               5                   10                  15

Tyr Tyr Asp Tyr Val Trp Gly Ser Tyr Arg Tyr Thr Tyr Ser Ser Tyr
            20                  25                  30

Tyr Ala Glu Tyr Phe Gln His Trp Gly Gln Gly Thr Leu Val Thr Val
        35                  40                  45

Ser Ser
    50

<210> SEQ ID NO 907
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 907

Tyr Tyr Cys Ala Lys Gly Ser Ser Tyr Tyr Gly Ser Gly Ser Tyr
1               5                   10                  15

Tyr Asn Ser Glu Tyr Tyr Ser Ala Glu Tyr Phe Gln His Trp Gly Gln
            20                  25                  30

Gly Thr Leu Val Thr Val Ser Ser
        35                  40

<210> SEQ ID NO 908
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 908

Tyr Tyr Cys Ala Arg Ser Ser Tyr Tyr Ser Tyr Gly Tyr Cys Thr Asn
1               5                   10                  15

Gly Val Cys Tyr Thr Tyr Ser Tyr Ser Tyr Ser Tyr Ser Tyr Ser
            20                  25                  30

Tyr Trp Tyr Phe Asp Leu Trp Gly Arg Gly Thr Leu Val Thr Val Ser
        35                  40                  45

Ser

<210> SEQ ID NO 909
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
gcagtttatt actgcgct                                                 18

<210> SEQ ID NO 910
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910
agagtaccct ggcccca                                                    17

<210> SEQ ID NO 911
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 911
gcagtttatt actgcgctag gtcttcctac tattcctacg gttattgtac aaatggcgtg     60
tgctatacat actcctactc ttattattcc tattcttact cttactggta ctttgatctg    120
tggggccagg gtactct                                                   137

<210> SEQ ID NO 912
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 912

Tyr Tyr Cys Ala Arg Ser Ser Ser Tyr Tyr Ser Tyr Tyr Ser Ser Gly
1               5                   10                  15

Tyr Cys Thr Asn Gly Val Cys Tyr Thr Tyr Ser Ser Tyr Tyr Ser Ser
                20                  25                  30

Tyr Tyr Trp Tyr Phe Asp Leu Trp Gly Arg Gly Thr Leu Val Thr Val
            35                  40                  45

Ser Ser
    50

<210> SEQ ID NO 913
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 913

Tyr Tyr Cys Ala Lys Tyr Ser Tyr Tyr Ser Ser Tyr Tyr Tyr Tyr Ser
1               5                   10                  15

Asp Tyr Val Trp Gly Ser Tyr Arg Tyr Thr Ser Tyr Tyr Ser Tyr Tyr
                20                  25                  30

Tyr Ala Glu Tyr Phe Gln His Trp Gly Gln Gly Thr Leu Val Thr Val
            35                  40                  45

Ser Ser
    50

<210> SEQ ID NO 914
<211> LENGTH: 51
<212> TYPE: PRT
<213> ORGANISM: Artificial Sequence
<220> FEATURE:
```

-continued

<223> OTHER INFORMATION: Description of Artificial Sequence: Synthetic
    polypeptide

<400> SEQUENCE: 914

Tyr Tyr Cys Ala Lys Ser Tyr Tyr Ser Ser Tyr Ser Tyr Tyr
1               5                   10                  15

Asp Tyr Val Trp Gly Ser Tyr Arg Tyr Thr Ser Tyr Ser Ser Ser Ser
            20                  25                  30

Tyr Tyr Ala Glu Tyr Phe Gln His Trp Gly Gln Gly Thr Leu Val Thr
        35                  40                  45

Val Ser Ser
    50

<210> SEQ ID NO 915
<211> LENGTH: 51
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 915

Tyr Tyr Cys Ala Lys Ser Ser Tyr Tyr Ser Tyr Tyr Ser Gly
1               5                   10                  15

Tyr Cys Ser Gly Gly Ser Cys Tyr Ser Ser Tyr Tyr Tyr Ser Ser Tyr
            20                  25                  30

Tyr Ser Ala Glu Tyr Phe Gln Gly Trp Gly Gln Gly Thr Leu Val Thr
        35                  40                  45

Val Ser Ser
    50

<210> SEQ ID NO 916
<211> LENGTH: 50
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 916

Tyr Tyr Cys Ala Lys Tyr Ser Ser Tyr Ser Tyr Tyr Asp Tyr Val Trp
1               5                   10                  15

Gly Ser Tyr Arg Tyr Thr Ser Ser Tyr Ser Tyr Tyr Ser Tyr Tyr
            20                  25                  30

Tyr Ala Glu Tyr Phe Gln Gly Trp Gly Gln Gly Thr Leu Val Thr Val
        35                  40                  45

Ser Ser
    50

<210> SEQ ID NO 917
<211> LENGTH: 50
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 917

Tyr Tyr Cys Ala Lys Ser Ser Tyr Tyr Ser Ser Ser Tyr Tyr Asp
1               5                   10                  15

Tyr Val Trp Gly Ser Tyr Arg Tyr Thr Ser Ser Tyr Tyr Ser Tyr Ser
            20                  25                  30

Tyr Ala Glu Tyr Phe Gln Gly Trp Gly Gln Gly Thr Leu Val Thr Val
        35                  40                  45

Ser Ser
    50

<210> SEQ ID NO 918
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 918

Tyr Tyr Cys Ala Lys Tyr Ser Ser Ser Tyr Ser Tyr Tyr Tyr
1               5                   10                  15

Asp Ser Ser Gly Tyr Tyr Tyr Ser Tyr Ser Ser Ser Tyr Tyr Ser
            20                  25                  30

Tyr Tyr Ala Glu Tyr Phe Gln Gly Trp Gly Gln Gly Thr Leu Val Thr
        35                  40                  45

Val Ser Ser
    50

<210> SEQ ID NO 919
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 919

Tyr Tyr Cys Ala Lys Tyr Ser Ser Tyr Ser Ser Tyr Tyr Tyr Tyr Asp
1               5                   10                  15

Ser Ser Gly Tyr Tyr Tyr Ser Ser Tyr Ser Ser Tyr Ser Tyr Tyr Tyr
            20                  25                  30

Ala Glu Tyr Phe Gln Gly Trp Gly Gln Gly Thr Leu Val Thr Val Ser
        35                  40                  45

Ser

<210> SEQ ID NO 920
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
cagagtaccc tggccccagt gttggaagka ttcagcgkag kagkagkaak agkaakagka      60
gkaakagkaa kagkagkagc cggagctgtc gkagkag                              97

<210> SEQ ID NO 921
<211> LENGTH: 5225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 921
gacgaaaggg cctcgtgata cgcctatttt tataggttaa tgtcatgata ataatggttt      60

| | |
|---|---|
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgcc cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca aacaaaaaaa ccaccgctac cagcggtggt ttgtttgccg gatcaagagc | 1320 |
| taccaactct ttttccgaag gtaactggct tcagcagagc gcagatacca atactgttc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg tcgggctga acgggggggtt | 1560 |
| cgtgcataca gcccagcttg gagcgaacga cctacaccga actgagatac ctacagcgtg | 1620 |
| agctatgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg atttttgtga tgctcgtcag | 1800 |
| ggggggcggag cctatggaaa aacgccagca acgcggcctt tttacggttc ctggccttt | 1860 |
| gctggccttt tgctcacatg ttctttcctg cgttatcccc tgattctgtg ataaccgta | 1920 |
| ttaccgcctt tgagtgagct gataccgctc gccgcagccg aacgaccgag cgcagcgagt | 1980 |
| cagtgagcga ggaagcggaa gagcgcccaa tacgcaaacc gcctctcccc gcgcgttggc | 2040 |
| cgattcatta atgcagctgg cacgacaggt ttcccgactg gaaagcgggc agtgagcgca | 2100 |
| acgcaattaa tgtgagttag ctcactcatt aggcacccca ggctttacac tttatgcttc | 2160 |
| cggctcgtat gttgtgtgga attgtgagcg ataacaatt tcacacagga aacagctatg | 2220 |
| accatgatta cgccaagctt tggagccttt ttttttggaga ttttcaacat gaagaaactg | 2280 |
| ctgtctgcta tcccactagt tgtccctttc tattctcata gtgaaatcgt tctgaccag | 2340 |
| tccccgggga ccctgtctct gtctccgggt gaacgtgcta cgctgagctg tcgtgcttct | 2400 |

```
caatccgtta gctcctctta tttagcttgg tatcagcaaa agccgggtca agctccgcgg    2460
ctgttgatct atggtgcctc tagtcgtgct actggcatcc ctgatcgttt ctctggctct    2520
ggctccggaa ccgatttcac tctgaccatt tctcgtctcg agccggaaga tttcgctgtc    2580
tactattgtc aacagtatgg ttctagtccg ctgactttcg gtggcggtac caaagtcgaa    2640
atcaagcgtg gaactgtggc tgcaccatct gtcttcatct tcccgccatc tgatgagcag    2700
ttgaaatctg gaactgcctc tgttgtgtgc ctgctgaata acttctatcc cagagaggcc    2760
aaagtacagt ggaaggtgga taacgccctc caatcgggta actcccagga gagtgtcaca    2820
gagcaggaca gcaaggacag cacctacagc ctcagcagca ccctgactct gtccaaagca    2880
gactacgaga acacaaagt ctacgcctgc gaagtcaccc atcagggcct gagttcaccg    2940
gtgacaaaga gcttcaacag gggagagtgt taataaggcg cgccaattta accatctatt    3000
tcaaggaaca gtcttaatga agaagctcct ctttgctatc ccgctcgtcg ttccttttgt    3060
ggcccagccg gccatggccg aagttcaatt gttagagtct ggtggcggtc ttgttcagcc    3120
tggtggttct ttacgtcttt cttgcgctgc ttccggattc actttctctc gttacaagat    3180
gaagtgggtt cgccaagctc ctggtaaagg tttggagtgg gtttctgtta tctatccttc    3240
tggtggcggt actggttatg ctgactccgt taaaggtcgc ttcactatct ctagagacaa    3300
ctctaagaat actctctact gcagatgaa cagcttaagg gctgaggaca ctgcagtcta    3360
ctattgtgcg agagtcaatt actatgatag tagtggttac ggtcctatag ctcctggact    3420
tgactactgg ggccagggaa ccctggtcac cgtctcaagc gcctccacca agggtccgtc    3480
ggtcttcccg ctagcaccct cctccaagag cacctctggg ggcacagcgg ccctgggctg    3540
cctggtcaag gactacttcc ccgaaccggt gacggtgtcg tggaactcag gcgccctgac    3600
cagcggcgtc cacaccttcc cggctgtcct acagtctagc ggactctact ccctcagcag    3660
cgtagtgacc gtgccctctt ctagcttggg cacccagacc tacatctgca acgtgaatca    3720
caagcccagc aacaccaagg tggacaagaa agttgagccc aaatcttgtg cggccgcaca    3780
tcatcatcac catcacgggg ccgcagaaca aaaactcatc tcagaagagg atctgaatgg    3840
ggccgcagag ctagttctg ctagtaacgc gtcttccggt gattttgatt atgaaaagat    3900
ggcaaacgct aataagggg ctatgaccga aaatgccgat gaaaacgcgc tacagtctga    3960
cgctaaaggc aaacttgatt ctgtcgctac tgattacggt gctgctatcg atggtttcat    4020
tggtgacgtt tccggccttg ctaatggtaa tggtgctact ggtgattttg ctggctctaa    4080
ttcccaaatg gctcaagtcg gtgacggtga taattcacct ttaatgaata atttccgtca    4140
atatttacct tccctccctc aatcggttga atgtcgccct tttgtctttg gcgctggtaa    4200
accatatgaa ttttctattg attgtgacaa aataaactta ttccgtggtg tctttgcgtt    4260
tcttttatat gttgccacct ttatgtatgt attttctacg tttgctaaca tactgcgtaa    4320
taaggagtct taatgaaacg cgtgatgaga attcactggc cgtcgtttta caacgtcgtg    4380
actgggaaaa ccctggcgtt acccaactta atcgccttgc agcacatccc cctttcgcca    4440
gctggcgtaa tagcgaagag gcccgcaccg atcgcccttc ccaacagttg cgcagcctga    4500
atggcgaatg cgcctgatg cggtattttc tccttacgca tctgtgcggt atttcacacc    4560
gcatacgtca agcaaccat agtacgcgcc ctgtagcggc gcattaagcg cggcgggtgt    4620
ggtggttacg cgcagcgtga ccgctacact tgccagcgcc ttagcgcccg ctcctttcgc    4680
tttcttccct tcctttctcg ccacgttcgc cggcttccc cgtcaagctc taaatcgggg    4740
gctcccttta gggttccgat ttagtgcttt acggcacctc gaccccaaaa aacttgattt    4800
```

```
gggtgatggt tcacgtagtg ggccatcgcc ctgatagacg gttttcgcc ctttgacgtt    4860 ggagtccacg ttctttaata gtggactctt gttccaaact ggaacaacac tcaactctat    4920
ctcgggctat tcttttgatt tataagggat tttgccgatt tcggtctatt ggttaaaaaa    4980
tgagctgatt taacaaaaat ttaacgcgaa ttttaacaaa atattaacgt ttacaatttt    5040
atggtgcagt ctcagtacaa tctgctctga tgccgcatag ttaagccagc cccgacaccc    5100
gccaacaccc gctgacgcgc cctgacgggc ttgtctgctc ccggcatccg cttacagaca    5160
agctgtgacc gtctccggga gctgcatgtg tcagaggttt tcaccgtcat caccgaaacg    5220
cgcga                                                                5225
```

<210> SEQ ID NO 922
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

Gly Ala Ser Gln Ser Val Ser
1               5

<210> SEQ ID NO 923
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

Asp Ala Ser Ser Arg Ala Thr
1               5

<210> SEQ ID NO 924
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Gln Gln Tyr Gly Ser Ser Pro Leu Tyr
1               5

<210> SEQ ID NO 925
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Arg Ala Ser Gln Ser Val Ser Ser Ser Tyr Leu Ala
1               5                   10

<210> SEQ ID NO 926
<211> LENGTH: 7
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 926

Gly Ala Ser Ser Arg Ala Thr
1               5

<210> SEQ ID NO 927
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 927

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln His Tyr Thr Thr Pro
                85                  90                  95

Pro Thr Phe Gly Gln Gly Thr Lys Val Glu Ile Lys Arg Thr
            100                 105                 110

<210> SEQ ID NO 928
<211> LENGTH: 234
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 928

Met Lys Lys Leu Leu Ser Ala Ile Pro Leu Val Val Pro Phe Tyr Ser
1               5                   10                  15

His Ser Glu Ile Val Leu Thr Gln Ser Pro Gly Thr Leu Ser Leu Ser
            20                  25                  30

Pro Gly Glu Arg Ala Thr Leu Ser Cys Arg Ala Ser Gln Ser Val Ser
        35                      40                  45

Ser Ser Tyr Leu Ala Trp Tyr Gln Gln Lys Pro Gly Gln Ala Pro Arg
50                  55                      60

Leu Leu Ile Tyr Gly Ala Ser Ser Arg Ala Thr Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Tyr Gly Ser
            100                 105                 110

Ser Pro Leu Thr Phe Gly Gly Gly Thr Lys Val Glu Ile Lys Arg Gly
            115                 120                 125

Thr Val Ala Ala Pro Ser Val Phe Ile Phe Pro Pro Ser Asp Glu Gln
            130                 135                 140

Leu Lys Ser Gly Thr Ala Ser Val Val Cys Leu Leu Asn Asn Phe Tyr

```
                145                 150                 155                 160
Pro Arg Glu Ala Lys Val Gln Trp Lys Val Asp Asn Ala Leu Gln Ser
                    165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 929
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(702)

<400> SEQUENCE: 929 atg aag aaa ctg ctg tct gct atc cca cta gtt gtc cct ttc tat tct      48
Met Lys Lys Leu Leu Ser Ala Ile Pro Leu Val Val Pro Phe Tyr Ser
1               5                   10                  15 cat agt gaa atc gtt ctg acc cag tcc ccg ggg acc ctg tct ctg tct      96
His Ser Glu Ile Val Leu Thr Gln Ser Pro Gly Thr Leu Ser Leu Ser
            20                  25                  30 ccg ggt gaa cgt gct acg ctg agc tgt cgt gct tct caa tcc gtt agc     144
Pro Gly Glu Arg Ala Thr Leu Ser Cys Arg Ala Ser Gln Ser Val Ser
        35                  40                  45 tcc tct tat tta gct tgg tat cag caa aag ccg ggt caa gct ccg cgg     192
Ser Ser Tyr Leu Ala Trp Tyr Gln Gln Lys Pro Gly Gln Ala Pro Arg
    50                  55                  60 ctg ttg atc tat ggt gcc tct agt cgt gct act ggc atc cct gat cgt     240
Leu Leu Ile Tyr Gly Ala Ser Ser Arg Ala Thr Gly Ile Pro Asp Arg
65                  70                  75                  80 ttc tct ggc tct ggc tcc gga acc gat ttc act ctg acc att tct cgt     288
Phe Ser Gly Ser Gly Ser Gly Thr Asp Phe Thr Leu Thr Ile Ser Arg
                85                  90                  95 ctc gag ccg gaa gat ttc gct gtc tac tat tgt caa cag tat ggt tct     336
Leu Glu Pro Glu Asp Phe Ala Val Tyr Tyr Cys Gln Gln Tyr Gly Ser
            100                 105                 110 agt ccg ctg act ttc ggt ggc ggt acc aaa gtc gaa atc aag cgt gga     384
Ser Pro Leu Thr Phe Gly Gly Gly Thr Lys Val Glu Ile Lys Arg Gly
        115                 120                 125 act gtg gct gca cca tct gtc ttc atc ttc ccg cca tct gat gag cag     432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat     480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg     528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc     576
Gly Asn Ser Gln Glu Ser Val Thr Glu Gln Asp Ser Lys Asp Ser Thr
            180                 185                 190
```

```
tac agc ctc agc agc acc ctg act ctg tcc aaa gca gac tac gag aaa         624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agt tca ccg         672
His Lys Val Tyr Ala Cys Glu Val Thr His Gln Gly Leu Ser Ser Pro
    210                 215                 220 gtg aca aag agc ttc aac agg gga gag tgt taataaggcg cgccaatt             720
Val Thr Lys Ser Phe Asn Arg Gly Glu Cys
225                 230
```

<210> SEQ ID NO 930
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 930

```
Tyr Tyr Cys Ala Lys Ser Asp Gly Tyr Tyr Asp Ser Ser Gly Tyr
1               5                   10                  15

Tyr Tyr Asp Tyr Trp Gly Gln Gly Thr Leu Val Thr Val Ser Ser
            20                  25                  30
```

<210> SEQ ID NO 931
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 931

```
Tyr Tyr Cys Ala Lys Gly Ser Gly Tyr Cys Ser Gly Gly Ser Cys Tyr
1               5                   10                  15

Ser Phe Asp Tyr Trp Gly Gln Gly Thr Leu Val Thr Val Ser Ser
            20                  25                  30
```

<210> SEQ ID NO 932
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 932

```
Tyr Tyr Cys Ala Lys Gly Gly Arg Gly Tyr Ser Ser Gly Trp Tyr Arg
1               5                   10                  15

Ala Phe Asp Ile Trp Gly Gln Gly Thr Met Val Thr Val Ser Ser
            20                  25                  30
```

<210> SEQ ID NO 933
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 933

```
Tyr Tyr Cys Ala Lys Ser Arg Pro Gly Tyr Ser Ser Ser Trp Tyr Tyr
1               5                   10                  15

Tyr Tyr Gly Met Asp Val Trp Gly Gln Gly Thr Thr Val Thr Val Ser
            20                  25                  30
```

Ser

<210> SEQ ID NO 934
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 934

His His His His His His
1               5

<210> SEQ ID NO 935
<211> LENGTH: 11
<212> TYPE: PRT
<213> ORGANISM: Homo sapiens

<400> SEQUENCE: 935

Arg Ala Ser Gln Ser Ile Ser Ser Tyr Leu Asn
1               5                   10

<210> SEQ ID NO 936
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Arg

<400> SEQUENCE: 936

Tyr Tyr Cys Ala Xaa
1               5

<210> SEQ ID NO 937
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 937

Tyr Gly Tyr Ser Tyr
1               5

<210> SEQ ID NO 938
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 938

Tyr Tyr Cys Ala
1

<210> SEQ ID NO 939
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 939

Trp Gly Gln Gly
1

<210> SEQ ID NO 940
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Tyr or Ser
<220> FEATURE:
<221> NAME/KEY: MOD_RES
<222> LOCATION: (9)..(10)
<223> OTHER INFORMATION: Tyr or Ser
<220> FEATURE:
<221> NAME/KEY: MOD_RES
<222> LOCATION: (12)..(12)
<223> OTHER INFORMATION: Tyr or Ser
<220> FEATURE:
<221> NAME/KEY: MOD_RES
<222> LOCATION: (14)..(14)
<223> OTHER INFORMATION: Tyr or Ser
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (18)..(18)
<223> OTHER INFORMATION: Tyr or Ser
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: Tyr or Ser
<220> FEATURE:
<221> NAME/KEY: MOD_RES
<222> LOCATION: (22)..(22)
<223> OTHER INFORMATION: Tyr or Ser
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (25)..(25)
<223> OTHER INFORMATION: Tyr or Ser

<400> SEQUENCE: 940

Tyr Tyr Cys Ala Lys Xaa Xaa Tyr Xaa Xaa Gly Xaa Gly Xaa Xaa Tyr
1               5                   10                  15

Asn Xaa Xaa Xaa Tyr Xaa Ala Xaa Xaa Phe Gln His Trp Gly Gln Gly
            20                  25                  30

Thr Leu Val Thr Val Ser Ser
        35

<210> SEQ ID NO 941

```
<211> LENGTH: 4
<212> TYPE: PRT
<213> ORGANISM: Homo sapiens

<400> SEQUENCE: 941

Ser Gly Trp Tyr
1

<210> SEQ ID NO 942
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 942

Tyr Tyr Ser Ser
1

<210> SEQ ID NO 943
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 943

Tyr Asp Gly Ser Tyr Ser
1               5

<210> SEQ ID NO 944
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 944

Tyr Phe Gln His
1

<210> SEQ ID NO 945
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 945

Ser Tyr Arg Tyr Ser Gly Tyr Ser
1               5

<210> SEQ ID NO 946
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 946

Ser Tyr Asp Ser Tyr Arg Ser Tyr Gly Ser
1               5                   10
```

<210> SEQ ID NO 947
<211> LENGTH: 4
<212> TYPE: PRT
<213> ORGANISM: artificial sequence
<220> FEATURE:
<223> OTHER INFORMATION: synthetic polypeptide

<400> SEQUENCE: 947

Ser Tyr Ser Tyr
1

<210> SEQ ID NO 948
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 948

Tyr Ser Ser Tyr
1

<210> SEQ ID NO 949
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 949

Ser Tyr Tyr Ser
1

<210> SEQ ID NO 950
<211> LENGTH: 7423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 950
aatgctacta ctattagtag aattgatgcc acctttcag ctcgcgcccc aaatgaaaat      60
atagctaaac aggttattga ccatttgcga aatgtatcta atggtcaaac taaatctact     120
cgttcgcaga attgggaatc aactgttata tggaatgaaa cttccagaca ccgtactta      180 gttgcatatt taaacatgt tgagctacag cattatattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tcttttgat gcaatccgct ttgcttctga ctataatagt     420
cagggtaaag acctgatttt tgattatgg tcattctcgt tttctgaact gtttaaagca     480
tttgaggggg attcaatgaa tatttatgac gattccgcag tattggacgc tatccagtct     540
aaacatttta ctattacccc ctctggcaaa acttcttttg caaaagcctc tcgctatttt     600 ggttttatc gtcgtctggt aaacgagggt tatgatagtg ttgctcttac tatgcctcgt     660
aattcctttt ggcgttatgt atctgcatta gttgaatgtg gtattcctaa atctcaactg     720
atgaatcttt ctacctgtaa taatgttgtt ccgttagttc gttttattaa cgtagatttt     780
tcttcccaac gtcctgactg gtataatgag ccagttctta aaatcgcata aggtaattca     840

```
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctggggt    1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca cgaccgaat atatcggtta    1440
tgcgtgggcg atggttgttg tcattgtcgg cgcaactatc ggtatcaagc tgtttaagaa   1500
attcacctcg aaagcaagct gataaaccga tacaattaaa ggctccttt ggagcctttt    1560
ttttggagat tttcaacgtg aaaaaattat tattcgcaat ccctttagtt gttcctttct   1620
attctcactc cgctgaaact gttgaaagtt gtttagcaaa atcccataca gaaaattcat   1680
ttactaacgt ctggaaagac gacaaaactt tagatcgtta cgctaactat gagggctgtc   1740
tgtggaatgc tacaggcgtt gtagtttgta ctggtgacga aactcagtgt tacggtacat   1800
ggttcctat tgggcttgct atccctgaaa atgagggtgg tggctctgag ggtggcggtt    1860
ctgagggtgg cggttctgag ggtggcggta ctaaacctcc tgagtacggt gatacaccta   1920
ttccgggcta tacttatatc aaccctctcg acggcactta tccgcctggt actgagcaaa   1980
accccgctaa tcctaatcct tctcttgagg agtctcagcc tcttaatact ttcatgtttc   2040
agaataatag gttccgaaat aggcaggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgagg   2220
atttatttgt ttgtgaatat caaggccaat cgtctgacct gcctcaacct cctgtcaatg   2280
ctggcggcgg ctctggtggt ggttctggtg gcggctctga gggtggtggc tctgagggtg   2340
gcggttctga gggtggcggc tctgagggag gcggttccgg tggtggctct ggttccggtg   2400
attttgatta tgaaaagatg gcaaacgcta ataaggggc tatgaccgaa atgccgatg     2460
aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
ttgtctttgg cgctggtaaa ccatatgaat tttctattga ttgtgacaaa ataaacttat   2760
tccgtggtgt ctttgcgttt cttttatatg ttgccacctt tatgtatgta ttttctacgt   2820
ttgctaacat actgcgtaat aaggagtctt aatcatgcca gttcttttgg gtattccgtt   2880
attattgcgt ttcctcggtt tccttctggt aactttgttc ggctatctgc ttacttttct   2940
taaaaagggc ttcggtaaga tagctattgc tatttcattg tttcttgctc ttattattgg   3000
gcttaactca attcttgtgg gttatctctc tgatattagc gctcaattac cctctgactt   3060
tgttcagggt gttcagttaa ttctcccgtc taatgcgctt ccctgttttt atgttattct   3120
ctctgtaaag gctgctattt tcattttga cgttaaacaa aaaatcgttt cttatttgga   3180
```

```
ttgggataaa taatatggct gtttatttg taactggcaa attaggctct ggaaagacgc      3240
tcgttagcgt tggtaagatt caggataaaa ttgtagctgg gtgcaaaata gcaactaatc      3300
ttgatttaag gcttcaaaac ctcccgcaag tcgggaggtt cgctaaaacg cctcgcgttc      3360
ttagaatacc ggataagcct tctatatctg atttgcttgc tattgggcgc ggtaatgatt      3420
cctacgatga aaataaaaac ggcttgcttg ttctcgatga gtgcggtact tggtttaata      3480
cccgttcttg gaatgataag gaaagacagc cgattattga ttggtttcta catgctcgta      3540
aattaggatg ggatattatt tttcttgttc aggacttatc tattgttgat aaacaggcgc      3600
gttctgcatt agctgaacat gttgtttatt gtcgtcgtct ggacagaatt actttacctt      3660
ttgtcggtac tttatattct cttattactg gctcgaaaat gcctctgcct aaattacatg      3720
ttggcgttgt taaatatggc gattctcaat taagccctac tgttgagcgt tggctttata      3780
ctggtaagaa tttgtataac gcatatgata ctaaacaggc tttttctagt aattatgatt      3840
ccggtgttta ttcttattta acgccttatt tatcacacgg tcggtatttc aaaccattaa      3900
atttaggtca gaagatgaaa ttaactaaaa tatatttgaa aaagttttct cgcgttcttt      3960
gtcttgcgat tggatttgca tcagcattta catatagtta tataacccaa cctaagccgg      4020
aggttaaaaa ggtagtctct cagacctatg attttgataa attcactatt gactcttctc      4080
agcgtcttaa tctaagctat cgctatgttt tcaaggattc taagggaaaa ttaattaata      4140
gcgacgattt acagaagcaa ggttattcac tcacatatat tgatttatgt actgtttcca      4200
ttaaaaaagg taattcaaat gaaattgtta aatgtaatta attttgtttt cttgatgttt      4260
gtttcatcat cttcttttgc tcaggtaatt gaaatgaata attcgcctct gcgcgatttt      4320
gtaacttggt attcaaagca atcaggcgaa tccgttattg tttctcccga tgtaaaaggt      4380
actgttactg tatattcatc tgacgttaaa cctgaaaatc tacgcaattt ctttatttct      4440
gttttacgtg caaataattt tgatatggta ggttctaacc cttccataat tcagaagtat      4500
aatccaaaca atcaggatta tattgatgaa ttgccatcat ctgataatca ggaatatgat      4560
gataattccg ctccttctgg tggtttcttt gttccgcaaa atgataatgt tactcaaact      4620
tttaaaatta ataacgttcg ggcaaaggat ttaatacgag ttgtcgaatt gtttgtaaag      4680
tctaatactt ctaaatcctc aaatgtatta tctattgacg gctctaatct attagttgtt      4740
agtgctccta aagatatttt agataaccct cctcaattcc tttcaactgt tgatttgcca      4800
actgaccaga tattgattga gggtttgata tttgaggttc agcaaggtga tgctttagat      4860
ttttcatttg ctgctggctc tcagcgtggc actgttgcag gcggtgttaa tactgaccgc      4920
ctcacctctg ttttatcttc tgctggtggt tcgttcggta ttttttaatgg cgatgtttta      4980
gggctatcag ttcgcgcatt aaagactaat agccattcaa aaatattgtc tgtgccacgt      5040
attcttacgc tttcaggtca gaagggttct atctctgttg gccagaatgt ccctttatt      5100
actggtcgtg tgactggtga atctgccaat gtaaataatc catttcagac gattgagcgt      5160
caaaatgtag gtatttccat gagcgttttt cctgttgcaa tggctggcgg taatattgtt      5220
ctggatatta ccagcaaggc cgatagtttg agttcttcta ctcaggcaag tgatgttatt      5280
actaatcaaa gaagtattgc tacaacggtt aatttgcgtg atggacagac tcttttactc      5340
ggtggcctca ctgattataa aaacacttct caggattctg gcgtaccgtt cctgtctaaa      5400
atccctttaa tcggcctcct gtttagctcc cgctctgatt ctaacgagga aagcacgtta      5460
tacgtgctcg tcaaagcaac catagtacgc gccctgtagc ggcgcattaa gcgcggcggg      5520
tgtggtggtt acgcgcagcg tgaccgctac acttgccagc gccctagcgc ccgctccttt      5580
```

```
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gatccaagct tgcaggtggc acttttcggg gaaatgtgcg cggaaccccct atttgtttat    6060 ttttctaaat acattcaaat atgtatccgc tcatgagaca ataaccctga taaatgcttc    6120
aataatattg aaaaggaag agtatgagta ttcaacattt ccgtgtcgcc cttattccct    6180
tttttgcggc attttgcctt cctgttttg ctcacccaga aacgctggtg aaagtaaaag    6240
atgctgaaga tcagttgggc gcactagtgg gttacatcga actggatctc aacagcggta    6300
agatccttga gagtttttcgc cccgaagaac gttttccaat gatgagcact tttaaagttc    6360
tgctatgtgg cgcggtatta tcccgtattg acgccgggca agagcaactc ggtcgccgca    6420
tacactattc tcagaatgac ttggttgagt actcaccagt cacagaaaag catcttacgg    6480
atggcatgac agtaagagaa ttatgcagtg ctgccataac catgagtgat aacactgcgg    6540
ccaacttact tctgacaacg atcggaggac cgaaggagct aaccgctttt ttgcacaaca    6600
tgggggatca tgtaactcgc cttgatcgtt gggaaccgga gctgaatgaa gccataccaa    6660
acgacgagcg tgacaccacg atgcctgtag caatggcaac aacgttgcgc aaactattaa    6720
ctggcgaact acttactcta gcttcccggc aacaattaat agactggatg gaggcggata    6780
aagttgcagg accacttctg cgctcggccc ttccggctgg ctggtttatt gctgataaat    6840
ctggagccgg tgagcgtggg tctcgcggta tcattgcagc actggggcca gatggtaagc    6900
cctcccgtat cgtagttatc tacacgacgg ggagtcaggc aactatggat gaacgaaata    6960
gacagatcgc tgagataggt gcctcactga ttaagcattg gtaactgtca gaccaagttt    7020
actcatatat actttagatt gatttaaaac ttcatttta atttaaaagg atctaggtga    7080
agatcctttt tgataatctc atgaccaaaa tcccttaacg tgagttttcg ttccactgta    7140
cgtaagaccc ccaagcttgt cgactgaatg gcgaatggcg ctttgcctgg tttccggcac    7200
cagaagcggt gccggaaagc tggctggagt gcgatcttcc tgacgctcga gcgcaacgca    7260
attaatgtga gttagctcac tcattaggca ccccaggctt tacactttat gcttccggct    7320
cgtatgttgt gtggaattgt gagcggataa caatttcaca caggaaacag ctatgaccat    7380
gattacgcca agctttggag cctttttttt ggagattttc aac                      7423
```

<210> SEQ ID NO 951
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 951

Lys Phe Gln His
1

<210> SEQ ID NO 952

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 952

Lys Thr Thr Gly
1

<210> SEQ ID NO 953
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 953

Lys Tyr Phe Asp Leu
1               5

<210> SEQ ID NO 954
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 954

Lys Leu Leu Trp Phe
1               5

<210> SEQ ID NO 955
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 955

Lys Tyr Tyr Tyr Asp Ser Ser Gly Tyr Tyr Ala Glu Tyr Phe Gln
1               5                   10                  15

His Trp

<210> SEQ ID NO 956
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 956

Lys Gly Tyr Cys Ser Ser Thr Ser Cys Tyr Thr Ala Glu Tyr Phe Gln
1               5                   10                  15

His Trp

<210> SEQ ID NO 957
<211> LENGTH: 25
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 957

Lys Asp Tyr Gly Tyr Cys Ser Ser Thr Ser Cys Tyr Thr Tyr Gly Tyr
1               5                   10                  15

Ser Tyr Ala Glu Tyr Phe Gln His Trp
            20                  25

<210> SEQ ID NO 958
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 958

Lys Gly Ser Gly Tyr Cys Ser Gly Gly Ser Cys Tyr Ser Phe Asp Tyr
1               5                   10                  15

Trp

<210> SEQ ID NO 959
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 959

Asn Tyr Leu Ala
1

<210> SEQ ID NO 960
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 960

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 961
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 961

```
Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
                20                  25                  30

Tyr Leu Ala Trp Tyr Gln Gln Lys Pro Gly Leu Ala Pro Arg Leu Leu
            35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 962
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 962

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 963
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 963

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 964

<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 964

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 965
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 965

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 966
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 966

Gln Gln Tyr Gly Ser Ser Pro Leu Thr
1               5

<210> SEQ ID NO 967
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

```
<221> NAME/KEY: modified_base
<222> LOCATION: (91)..(108)
<223> OTHER INFORMATION: a, c, t or g
<220> FEATURE:
<221> NAME/KEY: modified_base
<222> LOCATION: (112)..(123)
<223> OTHER INFORMATION: a, c, t or g
<220> FEATURE:
<221> NAME/KEY: modified_base
<222> LOCATION: (127)..(138)
<223> OTHER INFORMATION: a, c, t or g

<400> SEQUENCE: 967
actatctcta gagacaactc taagaatact ctctacttgc agatgaacag cttaagggct      60
gaggacactg cagtctacta ttgcgctaaa nnnnnnnnnn nnnnnnnntg tnnnnnnnnn     120
nnntgtnnnn nnnnnnnntg gggtcaaggt actttggtca ccgtctctag t             171

<210> SEQ ID NO 968
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 968

Thr Ile Ser Arg Asp Asn Ser Lys Asn Thr Leu Tyr Leu Gln Met Asn
1               5                   10                  15

Ser Leu Arg Ala Glu Asp Thr Ala Val Tyr Tyr Cys Ala Lys Ser Tyr
            20                  25                  30

Ser Tyr Gly Tyr Cys Ser Ser Thr Ser Cys Tyr Thr Gln His Trp Gly
        35                  40                  45

Gln Gly Thr Leu Val Thr Val Ser Ser
    50                  55

<210> SEQ ID NO 969
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(18)
<223> OTHER INFORMATION: a, c, t or g
<220> FEATURE:
<221> NAME/KEY: modified_base
<222> LOCATION: (22)..(33)
<223> OTHER INFORMATION: a, c, t or g
<220> FEATURE:
<221> NAME/KEY: modified_base
<222> LOCATION: (37)..(48)
<223> OTHER INFORMATION: a, c, t or g

<400> SEQUENCE: 969
nnnnnnnnnn nnnnnnnntg tnnnnnnnnn nnntgtnnnn nnnnnnnn                  48

<210> SEQ ID NO 970
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 970
```

```
Ser Tyr Ser Tyr Gly Tyr Cys Ser Ser Thr Ser Cys Tyr Thr Gln His
1               5                   10                  15
```

<210> SEQ ID NO 971
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(366)

<400> SEQUENCE: 971

```
ggt gta cac agt gct cag gat att cag atg act caa tct ccc tcg agt      48
Gly Val His Ser Ala Gln Asp Ile Gln Met Thr Gln Ser Pro Ser Ser
1               5                   10                  15 ctg tct gct tct gtc ggc gat cgc gtt act att act tgt cgt gct tcc      96
Leu Ser Ala Ser Val Gly Asp Arg Val Thr Ile Thr Cys Arg Ala Ser
                20                  25                  30 cag tcc att tct agc tat ctg aat tgg tac cag caa aag ccg ggt aag     144
Gln Ser Ile Ser Ser Tyr Leu Asn Trp Tyr Gln Gln Lys Pro Gly Lys
            35                  40                  45 gct ccg aaa ctg tta atc tat gcc gct tct agt ctg cag tct ggt gtt     192
Ala Pro Lys Leu Leu Ile Tyr Ala Ala Ser Ser Leu Gln Ser Gly Val
        50                  55                  60 ccg tct aga ttc tct ggc tct ggt tct ggt act gat ttt act ctg act     240
Pro Ser Arg Phe Ser Gly Ser Gly Ser Gly Thr Asp Phe Thr Leu Thr
65                  70                  75                  80 att tcc tct ctg caa ccg gag gac ttt gct acc tat tac tgc caa cag     288
Ile Ser Ser Leu Gln Pro Glu Asp Phe Ala Thr Tyr Tyr Cys Gln Gln
                85                  90                  95 tct tat agt act ccg tgg act ttc ggt caa ggc act aaa gtt gag att     336
Ser Tyr Ser Thr Pro Trp Thr Phe Gly Gln Gly Thr Lys Val Glu Ile
                100                 105                 110 aag cgt acg gtg gct gct ccg tct gtc ttc                             366
Lys Arg Thr Val Ala Ala Pro Ser Val Phe
            115                 120
```

<210> SEQ ID NO 972
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 972

```
Gly Val His Ser Ala Gln Asp Ile Gln Met Thr Gln Ser Pro Ser Ser
1               5                   10                  15

Leu Ser Ala Ser Val Gly Asp Arg Val Thr Ile Thr Cys Arg Ala Ser
                20                  25                  30

Gln Ser Ile Ser Ser Tyr Leu Asn Trp Tyr Gln Gln Lys Pro Gly Lys
            35                  40                  45

Ala Pro Lys Leu Leu Ile Tyr Ala Ala Ser Ser Leu Gln Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Thr Pro Trp Thr Phe Gly Gln Gly Thr Lys Val Glu Ile
```

```
                100                 105                 110
Lys Arg Thr Val Ala Ala Pro Ser Val Phe
        115                 120

<210> SEQ ID NO 973
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Gln
<220> FEATURE:
<221> NAME/KEY: MOD_RES
<222> LOCATION: (2)..(2)
<223> OTHER INFORMATION: Ala or Met
<220> FEATURE:
<221> NAME/KEY: MOD_RES
<222> LOCATION: (5)..(5)
<223> OTHER INFORMATION: Ser, Asp or Gly
<220> FEATURE:
<221> NAME/KEY: MOD_RES
<222> LOCATION: (7)..(7)
<223> OTHER INFORMATION: Ser or Arg
<220> FEATURE:
<221> NAME/KEY: MOD_RES
<222> LOCATION: (8)..(8)
<223> OTHER INFORMATION: Ser or Asn
<220> FEATURE:
<221> NAME/KEY: MOD_RES
<222> LOCATION: (9)..(9)
<223> OTHER INFORMATION: Tyr, Asp, Trp or Ala
<220> FEATURE:
<221> NAME/KEY: MOD_RES
<222> LOCATION: (11)..(11)
<223> OTHER INFORMATION: Asn, Ala or Gly

<400> SEQUENCE: 973

Xaa Xaa Ser Gln Xaa Ile Xaa Xaa Xaa Leu Xaa
1               5                   10

<210> SEQ ID NO 974
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 974

Gly Met Asp Val
1

<210> SEQ ID NO 975
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 975

Glu Pro Ile Trp Gly
1               5

<210> SEQ ID NO 976
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 976

Asp Ser Gly Val Val Ala Ala Ala Asp
1               5

<210> SEQ ID NO 977
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 977

Gly Leu Gly Met Asp Val
1               5

<210> SEQ ID NO 978
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 978

Glu Pro Ile Trp Gly Tyr Tyr Tyr Tyr Gly Met Asp Val
1               5                   10

<210> SEQ ID NO 979
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 979

Asp Phe Phe Thr Ser Tyr Phe Asp Tyr
1               5

<210> SEQ ID NO 980
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 980

Asp Arg Gly Val Ser Leu Leu Gly Ala Phe Asp Ile
1               5                   10

<210> SEQ ID NO 981
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 981

Asp Ser Gly Val Val Ala Ala Ala Asp Phe Asp Ser
1               5                   10
```

```
<210> SEQ ID NO 982
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 982

Tyr Gly Met Asp Val
1               5

<210> SEQ ID NO 983
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 983

Tyr Tyr Gly Met Asp Val
1               5

<210> SEQ ID NO 984
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 984

Tyr Tyr Tyr Gly Met Asp Val
1               5

<210> SEQ ID NO 985
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 985

Tyr Phe Asp Tyr
1

<210> SEQ ID NO 986
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 986

Ala Phe Asp Ile
1

<210> SEQ ID NO 987
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 987

Trp Gly Gln Gly Thr Met Val Thr Val Ser Ser
1               5                   10

<210> SEQ ID NO 988
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 988

Trp Gly Gln Gly Thr Thr Val Thr Val Ser Ser
1               5                   10

<210> SEQ ID NO 989
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 989

Trp Gly Gln Gly Thr Leu Val Thr Val Ser Ser
1               5                   10

<210> SEQ ID NO 990
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 990

Tyr Tyr Tyr Tyr Tyr Gly Met Asp Val
1               5

<210> SEQ ID NO 991
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 991

Tyr Tyr Cys Ala Arg Ser Ser Arg Ser Gly Tyr Cys Thr Asn Gly Val
1               5                   10                  15

Cys Tyr Thr Ser Lys Ser Tyr Trp Tyr Phe Asp Leu Trp Gly Arg Gly
            20                  25                  30

Thr Leu Val Thr Val Ser Ser
        35

<210> SEQ ID NO 992
<211> LENGTH: 17
<212> TYPE: PRT
<213> ORGANISM: artificial sequence
<220> FEATURE:
<223> OTHER INFORMATION: synthetic polypeptide
<220> FEATURE:
<221> NAME/KEY: misc_feature
<222> LOCATION: (1)..(1)
<223> OTHER INFORMATION: can be any amino acid
```

```
<220> FEATURE:
<221> NAME/KEY: MOD_RES
<222> LOCATION: (2)..(2)
<223> OTHER INFORMATION: Tyr or Ser
<220> FEATURE:
<221> NAME/KEY: MOD_RES
<222> LOCATION: (4)..(5)
<223> OTHER INFORMATION: Tyr or Ser
<220> FEATURE:
<221> NAME/KEY: MOD_RES
<222> LOCATION: (7)..(7)
<223> OTHER INFORMATION: Tyr or Ser
<220> FEATURE:
<221> NAME/KEY: MOD_RES
<222> LOCATION: (9)..(9)
<223> OTHER INFORMATION: Tyr or Ser
<220> FEATURE:
<221> NAME/KEY: misc_feature
<222> LOCATION: (10)..(10)
<223> OTHER INFORMATION: can be any amino acid
<220> FEATURE:
<221> NAME/KEY: MOD_RES
<222> LOCATION: (13)..(13)
<223> OTHER INFORMATION: Tyr or Ser
<220> FEATURE:
<221> NAME/KEY: misc_feature
<222> LOCATION: (14)..(14)
<223> OTHER INFORMATION: can be any amino acid
<220> FEATURE:
<221> NAME/KEY: MOD_RES
<222> LOCATION: (15)..(15)
<223> OTHER INFORMATION: Tyr or Ser
<220> FEATURE:
<221> NAME/KEY: MOD_RES
<222> LOCATION: (17)..(17)
<223> OTHER INFORMATION: Tyr or Ser

<400> SEQUENCE: 992

Xaa Xaa Tyr Xaa Xaa Gly Xaa Gly Xaa Xaa Tyr Asn Xaa Xaa Xaa Tyr
1               5                   10                  15

Xaa

<210> SEQ ID NO 993
<211> LENGTH: 29
<212> TYPE: PRT
<213> ORGANISM: artificial sequence
<220> FEATURE:
<223> OTHER INFORMATION: synthetic polypeptide
<220> FEATURE:
<221> NAME/KEY: MISC_FEATURE
<222> LOCATION: (4)..(4)
<223> OTHER INFORMATION: can be any amino acid
<220> FEATURE:
<221> NAME/KEY: MISC_FEATURE
<222> LOCATION: (8)..(8)
<223> OTHER INFORMATION: can be any amino acid
<220> FEATURE:
<221> NAME/KEY: mod_res
<222> LOCATION: (10)..(10)
<223> OTHER INFORMATION: Tyr or Ser
<220> FEATURE:
<221> NAME/KEY: mod_res
<222> LOCATION: (14)..(14)
<223> OTHER INFORMATION: Tyr or Ser
<220> FEATURE:
<221> NAME/KEY: mod_res
<222> LOCATION: (17)..(17)
<223> OTHER INFORMATION: Tyr or Ser
<220> FEATURE:
<221> NAME/KEY: MISC_FEATURE
<222> LOCATION: (19)..(19)
<223> OTHER INFORMATION: can be any amino acid
<220> FEATURE:
<221> NAME/KEY: MISC_FEATURE
<222> LOCATION: (23)..(23)
<223> OTHER INFORMATION: can be any amino acid
```

-continued

```
<220> FEATURE:
<221> NAME/KEY: mod_res
<222> LOCATION: (25)..(25)
<223> OTHER INFORMATION: Tyr or Ser
<220> FEATURE:
<221> NAME/KEY: mod_res
<222> LOCATION: (27)..(29)
<223> OTHER INFORMATION: Tyr or Ser

<400> SEQUENCE: 993

Tyr Tyr Ser Xaa Ser Tyr Tyr Xaa Tyr Xaa Tyr Asp Ser Xaa Gly Tyr
1               5                   10                  15

Xaa Tyr Xaa Tyr Tyr Ser Xaa Tyr Xaa Tyr Xaa Xaa Xaa
            20                  25

<210> SEQ ID NO 994
<211> LENGTH: 18
<212> TYPE: PRT
<213> ORGANISM: artificial sequence
<220> FEATURE:
<223> OTHER INFORMATION: synthetic polypeptide
<220> FEATURE:
<221> NAME/KEY: misc_feature
<222> LOCATION: (1)..(1)
<223> OTHER INFORMATION: can be any amino acid
<220> FEATURE:
<221> NAME/KEY: mod_res
<222> LOCATION: (2)..(3)
<223> OTHER INFORMATION: Tyr or Ser
<220> FEATURE:
<221> NAME/KEY: mod_res
<222> LOCATION: (5)..(6)
<223> OTHER INFORMATION: Tyr or Ser
<220> FEATURE:
<221> NAME/KEY: mod_res
<222> LOCATION: (8)..(8)
<223> OTHER INFORMATION: Tyr or Ser
<220> FEATURE:
<221> NAME/KEY: mod_res
<222> LOCATION: (10)..(10)
<223> OTHER INFORMATION: Tyr or Ser
<220> FEATURE:
<221> NAME/KEY: misc_feature
<222> LOCATION: (11)..(11)
<223> OTHER INFORMATION: can be any amino acid
<220> FEATURE:
<221> NAME/KEY: mod_res
<222> LOCATION: (14)..(14)
<223> OTHER INFORMATION: Tyr or Ser
<220> FEATURE:
<221> NAME/KEY: misc_feature
<222> LOCATION: (15)..(15)
<223> OTHER INFORMATION: can be any amino acid
<220> FEATURE:
<221> NAME/KEY: mod_res
<222> LOCATION: (16)..(16)
<223> OTHER INFORMATION: Tyr or Ser
<220> FEATURE:
<221> NAME/KEY: mod_res
<222> LOCATION: (18)..(18)
<223> OTHER INFORMATION: Tyr or Ser

<400> SEQUENCE: 994

Xaa Xaa Xaa Tyr Xaa Xaa Gly Xaa Gly Xaa Xaa Tyr Asn Xaa Xaa Xaa
1               5                   10                  15

Tyr Xaa

<210> SEQ ID NO 995
<211> LENGTH: 29
<212> TYPE: PRT
<213> ORGANISM: Artificial Sequence
<220> FEATURE:
<223> OTHER INFORMATION: synthetic polypeptide
```

```
<220> FEATURE:
<221> NAME/KEY: mod_res
<222> LOCATION: (1)..(11)
<223> OTHER INFORMATION: Tyr or Ser
<220> FEATURE:
<221> NAME/KEY: mod_res
<222> LOCATION: (16)..(29)
<223> OTHER INFORMATION: Tyr or Ser

<400> SEQUENCE: 995

Xaa Xaa Xaa Xaa Xaa Xaa Xaa Xaa Xaa Xaa Xaa Asp Ser Ser Gly Xaa
1               5                   10                  15

Xaa Xaa Xaa Xaa Xaa Xaa Xaa Xaa Xaa Xaa Xaa Xaa Xaa
            20                  25

<210> SEQ ID NO 996
<211> LENGTH: 4
<212> TYPE: PRT
<213> ORGANISM: artificial sequence
<220> FEATURE:
<223> OTHER INFORMATION: synthetic polynucleotide
<220> FEATURE:
<221> NAME/KEY: MOD_RES
<222> LOCATION: (1)..(1)
<223> OTHER INFORMATION: Tyr, Ser, Asp, Arg, or Leu
<220> FEATURE:
<221> NAME/KEY: MOD_RES
<222> LOCATION: (2)..(2)
<223> OTHER INFORMATION: Phe, Ser, Tyr, Asp, Arg, or Leu
<220> FEATURE:
<221> NAME/KEY: MOD_RES
<222> LOCATION: (3)..(4)
<223> OTHER INFORMATION: Asp, Arg, Ser, Tyr, or Leu

<400> SEQUENCE: 996

Xaa Xaa Xaa Xaa
1

<210> SEQ ID NO 997
<211> LENGTH: 4
<212> TYPE: PRT
<213> ORGANISM: artificial sequence
<220> FEATURE:
<223> OTHER INFORMATION: synthetic polynucleotide
<220> FEATURE:
<221> NAME/KEY: mod_res
<222> LOCATION: (1)..(2)
<223> OTHER INFORMATION: Leu, Ser, Tyr, Asp, or Arg
<220> FEATURE:
<221> NAME/KEY: mod_res
<222> LOCATION: (3)..(3)
<223> OTHER INFORMATION: Trp, Ser, Tyr, Asp, or Arg
<220> FEATURE:
<221> NAME/KEY: mod_res
<222> LOCATION: (4)..(4)
<223> OTHER INFORMATION: Phe, Ser, Tyr, Asp or Arg

<400> SEQUENCE: 997

Xaa Xaa Xaa Xaa
1

<210> SEQ ID NO 998
<211> LENGTH: 16
<212> TYPE: PRT
<213> ORGANISM: artificial sequence
<220> FEATURE:
<223> OTHER INFORMATION: synthetic polynucleotide
<220> FEATURE:
<221> NAME/KEY: MOD_RES
<222> LOCATION: (1)..(6)
<223> OTHER INFORMATION: Tyr, Ser, Arg, Asp, or Leu
<220> FEATURE:
```

```
<221> NAME/KEY: MOD_RES
<222> LOCATION: (7)..(7)
<223> OTHER INFORMATION: Gly, Ala, Ser, Tyr, Arg, Asp, or Leu
<220> FEATURE:
<221> NAME/KEY: MOD_RES
<222> LOCATION: (8)..(10)
<223> OTHER INFORMATION: Tyr, Ser, Arg, Asp, or Leu
<220> FEATURE:
<221> NAME/KEY: MOD_RES
<222> LOCATION: (11)..(11)
<223> OTHER INFORMATION: Ala, Ser, Tyr, Arg, or Asp
<220> FEATURE:
<221> NAME/KEY: MOD_RES
<222> LOCATION: (12)..(12)
<223> OTHER INFORMATION: Glu, Arg, Ser, Tyr, or Leu
<220> FEATURE:
<221> NAME/KEY: MOD_RES
<222> LOCATION: (13)..(13)
<223> OTHER INFORMATION: Tyr, Ser, Arg, Asp, or Leu
<220> FEATURE:
<221> NAME/KEY: MOD_RES
<222> LOCATION: (14)..(14)
<223> OTHER INFORMATION: Phe, Tyr, Ser, Arg, or Asp
<220> FEATURE:
<221> NAME/KEY: MOD_RES
<222> LOCATION: (15)..(15)
<223> OTHER INFORMATION: Gln, Glu, Arg, Ser, or Tyr
<220> FEATURE:
<221> NAME/KEY: MOD_RES
<222> LOCATION: (16)..(16)
<223> OTHER INFORMATION: His, Glu, Arg, Ser, Tyr, or Leu

<400> SEQUENCE: 998

Xaa Xaa Xaa Xaa Xaa Xaa Xaa Xaa Xaa Xaa Xaa Xaa Xaa Xaa Xaa Xaa
1               5                   10                  15

<210> SEQ ID NO 999
<211> LENGTH: 16
<212> TYPE: PRT
<213> ORGANISM: artificial sequence
<220> FEATURE:
<223> OTHER INFORMATION: synthetic polynucleotide
<220> FEATURE:
<221> NAME/KEY: mod_res
<222> LOCATION: (1)..(1)
<223> OTHER INFORMATION: Gly, Ser, Tyr, Asp, Arg, or Leu
<220> FEATURE:
<221> NAME/KEY: mod_res
<222> LOCATION: (2)..(2)
<223> OTHER INFORMATION: Tyr, Ser, Asp, Arg, or Leu
<220> FEATURE:
<221> NAME/KEY: mod_res
<222> LOCATION: (4)..(5)
<223> OTHER INFORMATION: Ser, Tyr, Arg, Asp, or Leu
<220> FEATURE:
<221> NAME/KEY: mod_res
<222> LOCATION: (6)..(6)
<223> OTHER INFORMATION: Thr, Tyr, Arg, Asp, or Leu
<220> FEATURE:
<221> NAME/KEY: mod_res
<222> LOCATION: (7)..(7)
<223> OTHER INFORMATION: Ser, Tyr, Arg, Asp, or Leu
<220> FEATURE:
<221> NAME/KEY: mod_res
<222> LOCATION: (9)..(9)
<223> OTHER INFORMATION: Tyr, Ser, Asp, Arg, or Leu
<220> FEATURE:
<221> NAME/KEY: mod_res
<222> LOCATION: (10)..(10)
<223> OTHER INFORMATION: Thr, Tyr, Arg, Asp, or Leu
<220> FEATURE:
<221> NAME/KEY: mod_res
<222> LOCATION: (11)..(11)
<223> OTHER INFORMATION: Ala, Ser, Tyr, Asp, Arg, or Leu
<220> FEATURE:
<221> NAME/KEY: mod_res
<222> LOCATION: (12)..(12)
```

```
<223> OTHER INFORMATION: Glu, Arg, Ser, Tyr, or Leu
<220> FEATURE:
<221> NAME/KEY: mod_res
<222> LOCATION: (13)..(13)
<223> OTHER INFORMATION: Tyr, Ser, Asp, Arg, or Leu
<220> FEATURE:
<221> NAME/KEY: mod_res
<222> LOCATION: (14)..(14)
<223> OTHER INFORMATION: Phe, Tyr, Ser, Arg, Asp, or Leu
<220> FEATURE:
<221> NAME/KEY: mod_res
<222> LOCATION: (15)..(15)
<223> OTHER INFORMATION: Gln, Glu, Arg, Ser, Tyr, or Leu
<220> FEATURE:
<221> NAME/KEY: mod_res
<222> LOCATION: (16)..(16)
<223> OTHER INFORMATION: His, Asp, Arg, Ser, Tyr, or Leu

<400> SEQUENCE: 999

Xaa Xaa Cys Xaa Xaa Xaa Xaa Cys Xaa Xaa Xaa Xaa Xaa Xaa Xaa Xaa
1               5                   10                  15

<210> SEQ ID NO 1000
<211> LENGTH: 9
<212> TYPE: PRT
<213> ORGANISM: artificial sequence
<220> FEATURE:
<223> OTHER INFORMATION: synthetic polynucleotide
<220> FEATURE:
<221> NAME/KEY: mod_res
<222> LOCATION: (1)..(1)
<223> OTHER INFORMATION: Gln, Glu, Arg, Tyr, Ser or Leu
<220> FEATURE:
<221> NAME/KEY: mod_res
<222> LOCATION: (2)..(2)
<223> OTHER INFORMATION: Ser, Asn, Thr, Tyr, Glu, Arg, or Leu
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: mod_res
<222> LOCATION: (4)..(4)
<223> OTHER INFORMATION: Ser, Asp, Asn, Arg, Thr, or Tyr
<220> FEATURE:
<221> NAME/KEY: mod_res
<222> LOCATION: (5)..(5)
<223> OTHER INFORMATION: Ser, Gly, Asn, Arg, Thr, Tyr, or Asp
<220> FEATURE:
<221> NAME/KEY: mod_res
<222> LOCATION: (6)..(6)
<223> OTHER INFORMATION: Ser, Asp, Phe, Gly, Asn, Arg, Thr, or Tyr
<220> FEATURE:
<221> NAME/KEY: mod_res
<222> LOCATION: (7)..(7)
<223> OTHER INFORMATION: Tyr, Phe, Asp, Leu, Asn, Gln, Arg, Ser or Tyr
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: mod_res
<222> LOCATION: (9)..(9)
<223> OTHER INFORMATION: Ala, Ser, or Tyr

<400> SEQUENCE: 1000

Xaa Xaa Xaa Xaa Xaa Xaa Xaa Xaa Xaa
1               5

<210> SEQ ID NO 1001
<211> LENGTH: 6
<212> TYPE: PRT
<213> ORGANISM: artificial sequence
<220> FEATURE:
<223> OTHER INFORMATION: synthetic polynucleotide
```

```
<220> FEATURE:
<221> NAME/KEY: res_mod
<222> LOCATION: (1)..(1)
<223> OTHER INFORMATION: Tyr, Phe, Glu, Arg, or Ser
<220> FEATURE:
<221> NAME/KEY: res_mod
<222> LOCATION: (2)..(2)
<223> OTHER INFORMATION: Gly, Ala, Asp, Arg, Ser, Thr, or Tyr
<220> FEATURE:
<221> NAME/KEY: res_mod
<222> LOCATION: (3)..(3)
<223> OTHER INFORMATION: Ser, Asp, Phe, Asn, Arg, Thr, or Tyr
<220> FEATURE:
<221> NAME/KEY: res_mod
<222> LOCATION: (4)..(4)
<223> OTHER INFORMATION: Ser, Trp, Glu, Arg, Tyr, or Ser
<220> FEATURE:
<221> NAME/KEY: res_mod
<222> LOCATION: (5)..(5)
<223> OTHER INFORMATION: Pro, Glu, Arg, Tyr, Ser or no amino acid
<220> FEATURE:
<221> NAME/KEY: res_mod
<222> LOCATION: (6)..(6)
<223> OTHER INFORMATION: Ley, Glu, Arg, Pro, Tyr, or Ser

<400> SEQUENCE: 1001

Xaa Xaa Xaa Xaa Xaa Xaa
1               5
```